US012478067B2

(12) United States Patent
Tsuruda et al.

(10) Patent No.: US 12,478,067 B2
(45) Date of Patent: Nov. 25, 2025

(54) HETEROCYCLIC COMPOUND AND HARMFUL ARTHROPOD PEST CONTROL COMPOSITION CONTAINING SAME

(71) Applicant: SUMITOMO CHEMICAL COMPANY, LIMITED, Chuo-ku (JP)

(72) Inventors: Takeshi Tsuruda, Takarazuka (JP); Yoshihiko Nokura, Takarazuka (JP); Yasumasa Saito, Takarazuka (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 939 days.

(21) Appl. No.: 17/598,744

(22) PCT Filed: Mar. 27, 2020

(86) PCT No.: PCT/JP2020/014004
§ 371 (c)(1),
(2) Date: Sep. 27, 2021

(87) PCT Pub. No.: WO2020/203763
PCT Pub. Date: Oct. 8, 2020

(65) Prior Publication Data

US 2022/0217979 A1 Jul. 14, 2022

(30) Foreign Application Priority Data

Mar. 29, 2019 (JP) ................................ 2019-066002
Dec. 26, 2019 (JP) ................................ 2019-235932

(51) Int. Cl.
*A01N 43/90* (2006.01)
*A01N 43/54* (2006.01)
(Continued)

(52) U.S. Cl.
CPC ............ *A01N 43/90* (2013.01); *A01N 43/54* (2013.01); *A01P 7/00* (2021.08); *C07D 401/04* (2013.01);
(Continued)

(58) Field of Classification Search
CPC . A01P 7/00; A01P 7/04; C07D 401/04; C07D 471/04; C07D 519/00
See application file for complete search history.

(56) References Cited

U.S. PATENT DOCUMENTS

2003/0229050 A1 12/2003 Lahm et al.
2004/0142984 A1 7/2004 Lahm et al.
(Continued)

FOREIGN PATENT DOCUMENTS

CA 3 029 722 A1 1/2018
EA 201791815 A1 11/2017
(Continued)

OTHER PUBLICATIONS

Combined Chinese Office Action and Search Report issued May 10, 2022 in Chinese Patent Application No. 202080039608.9 (with English translation), 12 pages.
Indian Examination Report issued on Feb. 1, 2023 in Indian Patent Application No. 202147042844, 6 pages.
Ukrainian Office Action issued Jun. 18, 2024 in Ukrainian Application No. a202105454 with English translation, 6 pgs.
Indonesian Office Action issued on Apr. 3, 2023 in Indonesian Patent Application No. P00202108009 (with English translation), 4 pages.
Russian Office Action and Search Report issued Jun. 15, 2023 in Russian Patent Application No. 2021128126/10(059425) (with English language translation), 17 pages.
(Continued)

*Primary Examiner* — Joseph K McKane
*Assistant Examiner* — Ashli Ariana Chicks
(74) *Attorney, Agent, or Firm* — Oblon, McClelland, Maier & Neustadt, L.L.P.

(57) ABSTRACT

A compound of formula (I) or an N-oxide thereof, a composition for controlling harmful arthropods including the compound, and a method for controlling harmful arthropods by applying the compound, (I)

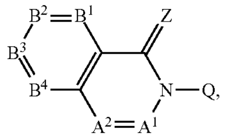

Q1

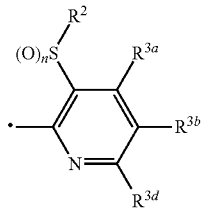

where Q represents a group represented by formula Q1 etc., Z represents an oxygen atom etc., $A^1$ represents $CR^{4a}$ etc., $A^2$ represents a nitrogen atom etc., $B^1$ represents a nitrogen atom or $CR^{6a}$ etc., $B^2$ represents $CR^1$ etc., $B^3$ represents a nitrogen atom or $CR^{6c}$ etc., $B^4$ represents a nitrogen atom or $CR^{6d}$ etc., $R^1$ represents a C1-C6 chain hydrocarbon group etc., $R^2$ represents a C1-C6 alkyl group etc., $R^{3a}$, $R^{3b}$ and $R^{3d}$ are identical to or different from each other and each represents a C1-C6 chain hydrocarbon group etc., $R^{4a}$, $R^{6a}$, $R^{6c}$ and $R^{6d}$ are identical to or different from each other and each represents a C1-C6 chain hydrocarbon group etc., and n is 0, 1 or 2.

17 Claims, No Drawings

(51) Int. Cl.

| | |
|---|---|
| ***A01P 7/00*** | (2006.01) |
| ***C07D 401/04*** | (2006.01) |
| ***C07D 471/04*** | (2006.01) |
| ***C07D 519/00*** | (2006.01) |

(52) U.S. Cl.
CPC ......... *C07D 471/04* (2013.01); *C07D 519/00* (2013.01)

(56) References Cited

U.S. PATENT DOCUMENTS

| | | | |
|---|---|---|---|
| 2006/0079561 | A1 | 4/2006 | Lahm et al. |
| 2018/0022760 | A1 | 1/2018 | Kudo et al. |
| 2019/0327970 | A1 | 10/2019 | Tanaka et al. |

FOREIGN PATENT DOCUMENTS

| | | | | |
|---|---|---|---|---|
| JP | 2015-117194 | A | 6/2015 | |
| JP | 2018-76354 | A | 5/2018 | |
| WO | WO 01/70671 | A2 | 9/2001 | |
| WO | WO 2016/129684 | A1 | 8/2016 | |
| WO | WO 2018/008727 | A1 | 1/2018 | |
| WO | WO-2019131575 | A1 * | 7/2019 | .............. A01M 1/20 |
| WO | WO 2021/033141 | A1 | 2/2021 | |

OTHER PUBLICATIONS

Extended European Search Report issued Nov. 7, 2022 in European Patent Application No. 20784877.1, 8 pages.
International Search Report and Written Opinion issued Jun. 16, 2020 in PCT/JP2020/014004, 7 pages.

* cited by examiner

HETEROCYCLIC COMPOUND AND HARMFUL ARTHROPOD PEST CONTROL COMPOSITION CONTAINING SAME

CROSS-REFERENCE TO RELATED APPLICATIONS

The present application is a 35 U.S.C. § 371 national stage patent application of International patent application PCT/JP2020/014004, filed on Mar. 27, 2020, which is based on and claims the benefits of priority to Japanese Application No. 2019-066002, filed on Mar. 29, 2019 and Japanese Application No. 2019-235932, filed Dec. 26, 2019. The entire contents of all of the above applications are incorporated herein by reference.

TECHNICAL FIELD

This application claims priority to and the benefit of Japanese Patent Application No. 2019-066002 filed Mar. 29, 2019, and Japanese Patent Application No. 2019-235932 filed Dec. 26, 2019, the entire contents of which are incorporated herein by reference.

The present invention is related to a certain class of heterocyclic compound and a composition for controlling harmful arthropods comprising the same.

BACKGROUND ART

To date, in order to control harmful arthropods, some compounds have been studied. For example, a certain class of compound has been known to have an effect on controlling pests (see Patent Document 1).

CITATION LIST

Patent Document

Patent Document 1: WO 2016/129684

SUMMARY OF THE INVENTION

Problems to be Solved by Invention

An object of the present invention is to provide a compound having an excellent efficacy for controlling harmful arthropods.

Means to Solve Problems

The present inventors have intensively studied to find compounds having an excellent efficacy for controlling harmful arthropods, and as a result, found that a compound represented by the below-mentioned formula (I) has an excellent efficacy for controlling harmful arthropods.

That is, the present invention includes the followings.

[1] A compound represented by formula (I):

(I)

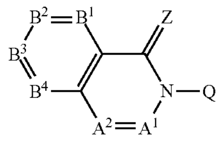

[wherein

Q represents a group represented by formula Q1, or a group represented by formula Q2,

Q1

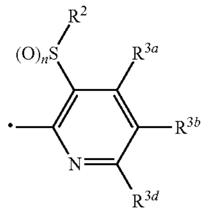

Q2

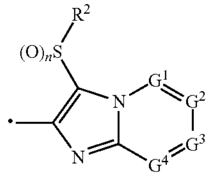

Z represents an oxygen atom or a sulfur atom, a combination of $A^1$ and $A^2$ represents a combination in which $A^1$ represents $CR^{4a}$, and $A^2$ represents a nitrogen atom or $CR^{4b}$; or a combination in which $A^1$ represents a nitrogen atom, and $A^2$ represents a nitrogen atom or $CR^{4b}$, a combination of $B^1$, $B^2$, $B^3$ and $B^4$ represents, a combination in which $B^1$ represents a nitrogen atom or $CR^{6a}$, $B^2$ represents $CR^1$, $B^3$ represents a nitrogen atom or $CR^{6c}$, and $B^4$ represents a nitrogen atom or $CR^{6d}$;

a combination in which $B^1$ represents a nitrogen atom or $CR^{6a}$, $B^2$ represents a nitrogen atom or $CR^{6b}$, $B^3$ represents $CR^1$, and $B^4$ represents a nitrogen atom or $CR^{6d}$;

a combination in which $B^1$ represents a nitrogen atom or $CR^{6a}$, $B^2$ represents a nitrogen atom or $CR^{6b}$, $B^3$ represents $CR^{6c}$, and $B^4$ represents $CR^1$;

a combination in which $B^1$ represents a nitrogen atom or $CR^{6a}$, $B^2$ represents $CR^{6b}$, $B^3$ represents a nitrogen atom, and $B^4$ represents $CR^1$; or a combination in which $B^1$ represents $CR^{6a}$, $B^2$ represents a nitrogen atom, $B^3$ represents a nitrogen atom, and $B^4$ represents $CR^1$, $R^1$ represents a C1-C6 chain hydrocarbon group having one or more substituents selected from the group consisting of cyano group and halogen atom, a C3-C4 cycloalkyl group optionally having one or more substituents selected from the group consisting of cyano group and halogen atom, $S(O)_mR^8$, $OR^8$, halogen atom or $OS(O)_2R^8$, m represents 0, 1 or 2, $R^8$ represents a C1-C6 chain hydrocarbon group having one or more substituents selected from the group consisting of cyano group and halogen atom; or a C3-C4 cycloalkyl group optionally having one or more substituents selected from the group consisting of cyano group and halogen atom, $R^{4a}$, $R^{4b}$, $R^{6a}$, $R^{6b}$, $R^{6c}$ and $R^{6d}$ are identical to or different from each other and each represents a C1-C6 chain hydrocarbon group optionally having one or more halogen atoms, a C3-C7 cycloalkyl group optionally having one or more halogen atoms, a C1-C6 alkoxy group optionally having one or more halogen atoms, $NR^9R^{10}$, $C(O)R^7$, $C(O)NR^{19}R^{20}$, $NR^9C(O)R^{18}$, $NR^9C(O)OR^{18}$, $NR^9C(O)NR^{19}R^{20}$, cyano group, halogen atom or a hydrogen atom, $R^9$ and $R^{19}$ are identical to or different from each other and each represents a C1-C6 chain hydrocarbon group optionally having one or more halogen atoms, or a hydrogen atom, $R^{10}$ represents a C1-C6 chain hydrocarbon group optionally having one or more substituents selected from Group F, a C3-C7 cycloalkyl group optionally having one or more substituents selected from Group J, a C3-C7 cycloalkenyl group optionally having one or more substituents selected from Group J, a phenyl group optionally having one or more substituents selected from Group D, a six(6) membered aromatic heterocyclic group optionally having one or more substituents selected from Group D, a hydrogen atom, or $S(O)_2R^{21}$, $R^{21}$ represents a C1-C6 chain hydrocarbon group optionally having one or more halogen atoms, a C3-C7 cycloalkyl group optionally having one or more halogen atoms, or a phenyl group optionally having one or more substituents selected from Group D, $R^7$, $R^{18}$, and $R^{20}$ are identical to or different from each other and each represents a C1-C6 chain hydrocarbon group optionally having one or more substituents selected from Group F, a C3-C7 cycloalkyl group optionally having one or more substituents selected from Group J, or a hydrogen atom, n represents 0, 1 or 2, $R^2$ represents a C1-C6 chain hydrocarbon group optionally having one or more halogen atoms, a cyclopropyl group, or a cyclopropylmethyl group, $G^1$ represents a nitrogen atom or $CR^{3a}$, $G^2$ represents a nitrogen atom or $CR^{3b}$, $G^3$ represents a nitrogen atom or $CR^{3c}$, $G^4$ represents a nitrogen atom or $CR^{3d}$, $R^{3a}$, $R^{3b}$, $R^{3c}$ and $R^{3d}$ are identical to or different from each other and each represents a C1-C6 chain hydrocarbon group optionally having one or more substituents selected from Group B, a C3-C7 cycloalkyl group optionally having one or more substituents selected from Group E, a phenyl group optionally having one or more substituents selected from Group H, a five(5) or six(6) membered aromatic heterocyclic group optionally having one or more substituents selected from Group H, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{31}R^{32}$, $NR^{24}NR^{11}C(O)NR^{31}R^{32}$, $N{=}CHNR^{31}R^{32}$, $N{=}S(O)R^{15}R^{16}$, $C(O)R^{13}$, $C(O)OR^{17}$, $C(O)NR^{31}R^{32}$, $C(O)NR^{11}S(O)_2R^{23}$, $CR^{30}{=}NOR^{17}$, $NR^{11}CR^{24}{=}NOR^{17}$, $S(O)_qR^{23}$, a cyano group, a nitro group, a hydrogen atom, or a halogen atom, p represents 0 or 1, q represents 0 or 1, $R^{30}$ represents a C1-C6 chain hydrocarbon group optionally having one or more halogen atoms, a halogen atom $OR^{35}$, $NR^{36}R^{37}$, or a hydrogen atom, $R^{35}$ represents a C1-C6 chain hydrocarbon group optionally having one or more halogen atoms, $R^{17}$ represents a C1-C6 chain hydrocarbon group optionally having one or more halogen atoms, a phenyl group optionally having one or more substituents selected from Group D, or a hydrogen atom, $R^{11}$, $R^{24}$, $R^{36}$ and $R^{37}$ are identical to or different from each other and each represents a C1-C6 chain hydrocarbon group optionally having one or more halogen atoms, or a hydrogen atom, $R^{12}$ represents a C1-C6 chain hydrocarbon group optionally having one or more substituents selected from Group F, a C3-C7 cycloalkyl group optionally having one or more substituents selected from Group J, a C3-C7 cycloalkenyl group optionally having one or more substituents selected from Group J, a phenyl group optionally having one or more substituents selected from Group D, a six(6) membered aromatic heterocyclic group optionally having one or more substituents selected from Group D, a hydrogen atom, or $S(O)_2R^{23}$, $R^{23}$ represents a C1-C6 chain hydrocarbon group optionally having one or more halogen atoms, or a phenyl group optionally having one or more substituents selected from Group D, $R^{11a}$ and $R^{12a}$ combined together with a nitrogen atom to which they are attached represent a three(3) to seven(7) membered nonaromatic heterocyclic group optionally having one or more substituents selected from Group E, $R^{13}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, a five(5) or six(6) membered aromatic heterocyclic group optionally having one or more substituents selected from Group D, or a hydrogen atom, $R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group {the phenyl moiety in the phenyl C1-C3 alkyl group may have optionally one or more substituents selected from Group D}, $R^{15}$ and $R^{16}$ are identical to or different from each other and each represents a C1-C6 alkyl group optionally having one or more halogen atoms, $R^{31}$ represents a C1-C6 alkyl group optionally having one or more halogen atoms, or a hydrogen atom, $R^{32}$ represents a C1-C6 chain hydrocarbon group optionally having one or more substituents selected from Group F, a C3-C7 cycloalkyl group optionally having one or more substituents selected from Group J, or a hydrogen atom, when Q represents a group represented by formula Q1, $R^{3b}$ and $R^{3d}$ combined together with two carbon atoms to which they are attached may form a benzene ring, a pyrrole ring, a furan ring, a thiophene ring, a pyrazole ring, an imidazole ring, an oxazole ring, an isoxazole ring, a thiazole ring, an isothiazole ring, an oxadiazole ring, a thiadiazole ring, a pyridine ring, a pyridazine ring, a pyrimidine ring, a pyrazine ring {the benzene ring, the pyrrole ring, the furan ring, the thiophene ring, the pyrazole ring, the imidazole ring, the oxazole ring, the isoxazole ring, the thiazole ring, the isothiazole ring, the pyridine ring, the pyridazine ring, the pyrimidine ring, and the pyrazine ring each may have optionally one or more substituents selected from Group H}, or a triazole ring optionally having one or more substituents selected from Group I, Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a C1-C6 alkylamino group optionally having one or more halogen atoms, a di(C1-C4 alkyl) amino group optionally having one or more halogen atoms, a C2-C6 alkylcarbonyl group optionally having one or more halogen atoms, a C2-C6 alkoxycarbonyl group optionally having one or more halogen atoms, a C2-C6 alkoxycarbonyloxy group optionally having one or more halogen atoms, an aminocarbonyl group, a C1-C6 alkylaminocarbonyl group optionally having one or more halogen atoms, a di(C1-C4 alkyl)aminocarbonyl group optionally having one or more halogen atoms, a C2-C6 alkoxycarbonylamino group optionally having one or more halogen atoms, a (C2-C6 alkoxycarbonyl)(C1-C6 alkyl) amino group optionally having one or more halogen atoms, a cyano group, an amino group, a nitro group, a hydroxy group, and a halogen atom, Group D: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a C1-C6 alkylamino group optionally having one or more halogen atoms, a di(C1-C4 alkyl)amino group optionally having one or more halogen atoms, a C2-C6 alkylcarbonyl group optionally having one or more halogen atoms, a C2-C6 alkoxycarbonyl group optionally having one or more halogen atoms, a C2-C6 alkoxycarbonyloxy group optionally having one or more halogen atoms, an aminocarbonyl group, a C1-C6 alkylaminocarbonyl group optionally having one or more halogen atoms, a di(C1-C4 alkyl)aminocarbonyl group optionally having one or more halogen atoms, a C2-C6 alkoxycarbonylamino group optionally having one or more halogen atoms, a (C2-C6 alkoxycarbonyl)(C1-C6 alkyl) amino group optionally having one or more halogen atoms, a cyano group, an amino group, a nitro group, a hydroxy group, and a halogen atom, Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylamino group optionally having one or more halogen atoms, a di(C1-C4 alkyl) amino group optionally having one or more halogen atoms, a C2-C6 alkylcarbonyl group optionally having one or more halogen atoms, a C2-C6 alkoxycarbonyl group optionally having one or more halogen atoms, a C2-C6 alkoxycarbonyloxy group optionally having one or more halogen atoms, an aminocarbonyl group, a C1-C6 alkylaminocarbonyl group optionally having one or more halogen atoms, a di(C1-C4 alkyl)aminocarbonyl group optionally having one or more halogen atoms, a C2-C6 alkoxycarbonylamino group optionally having one or more halogen atoms, a (C2-C6 alkoxycarbonyl)(C1-C6 alkyl) amino group optionally having one or more halogen atoms, a cyano group, an amino group, a nitro group, a hydroxy group, an oxo group, and a halogen atom, Group F: a group consisting of a C3-C7 cycloalkyl group optionally having one or more halogen atoms, a phenyl group optionally having one or more substituents selected from Group D, a five(5) or six(6) membered aromatic heterocyclic group optionally having one or more substituents selected from Group D, a C1-C6 alkoxy group optionally having one or more halogen atoms, a C1-C6 alkylamino group optionally having one or more halogen atoms, a di(C1-C4 alkyl)amino group optionally having one or more halogen atoms, a cyano group, an amino group, a nitro group, a hydroxy group, and a halogen atom, Group H: a group consisting of a C1-C6 chain hydrocarbon group optionally having one or more halogen atoms, a C3-C6 cycloalkyl group optionally having one or more halogen atoms, a phenyl group optionally having one or more substituents selected from Group D, a five(5) or six(6) membered aromatic heterocyclic group optionally having one or more substituents selected from Group D, a C1-C6 alkoxy group optionally having one or more halogen atoms, a C1-C6 alkylamino group optionally having one or more halogen atoms, a di(C1-C4 alkyl)amino group optionally having one or more halogen atoms, a C2-C6 alkylcarbonyl group optionally having one or more halogen atoms, a C2-C6 alkoxycarbonyl group optionally having one or more halogen atoms, a C2-C6 alkoxycarbonyloxy group optionally having one or more halogen atoms, an aminocarbonyl group, a (C1-C6 alkyl)aminocarbonyl group optionally having one or more halogen atoms, a di(C1-C4 alkyl)aminocarbonyl group optionally having one or more halogen atoms, a C2-C6 alkoxycarbonylamino group optionally having one or more halogen atoms, a (C2-C6 alkoxycarbonyl)(C1-C6 alkyl) amino group optionally having one or more halogen atoms, a cyano group, an amino group, a nitro group, a hydroxy group, and a halogen atom, Group I: a group consisting of a C2-C6 chain hydrocarbon group optionally having one or more halogen atoms, a C3-C6 cycloalkyl group optionally having one or more halogen atoms, a phenyl group optionally having one or more substituents selected from Group D, a five(5) or six(6) membered aromatic heterocyclic group optionally having one or more substituents selected from Group D, a C2-C6 alkylcarbonyl group optionally having one or more halogen atoms, a C2-C6 alkoxycarbonyl group optionally having one or more halogen atoms, an aminocarbonyl group, a (C1-C6 alkyl)aminocarbonyl group optionally having one or more halogen atoms, and a di(C1-C4 alkyl)aminocarbonyl group optionally having one or more halogen atoms, Group J: a group consisting of a C1-C6 alkyl group optionally having one or more halogen atoms, a C1-C6 alkoxy group optionally having one or more halogen atoms, a C2-C6 alkoxycarbonyl group optionally having one or more halogen atoms, an amino group, a cyano group, and a halogen atom] (hereinafter, which is referred to as "present compound P" or "compound P of the present invention") or N-oxide thereof (hereinafter, a compound represented by formula (I) or N-oxide thereof is collectively referred to as "present compound X" or "compound X of the present invention").

[2] The compound according to [1] wherein a combination of $A^1$ and $A^2$ represents a combination in which $A^1$ represents $CR^{4a}$, and $A^2$ represents a nitrogen atom or $CR^{4b}$; or a combination in which $A^1$ represents a nitrogen atom, and $A^2$ represents $CR^{4b}$, $R^1$ represents a C1-C6 chain hydrocarbon group having one or more substituents selected from the group consisting of cyano group and halogen atom, a C3-C4 cycloalkyl group optionally having one or more substituents selected from the group consisting of cyano group and halogen atom, $S(O)_mR^8$, $OR^8$, or $OS(O)_2R^8$ (hereinafter, which is referred to as "present compound N" or "compound N of the present invention") or N-oxide thereof (hereinafter, a compound represented by formula (I) or N-oxide thereof is collectively referred to as "present compound" or "compound of the present invention")

[3] The compound according to [1] or [2] or N-oxide thereof, wherein $R^{3a}$ represents a hydrogen atom, $R^{3b}$, $R^{3c}$ and $R^{3d}$ are identical to or different from each other and each represents a C1-C6 alkyl group, a C2-C6 alkenyl group, a C3-C7 cycloalkyl group {the C1-C6 alkyl group, the C2-C6 alkenyl group, and the C3-C7 cycloalkyl group each may have optionally one or more substituents selected from the group consisting of halogen atom and cyano group}, a phenyl group, a triazolyl group, a pyridyl group, a pyrimidinyl group {the phenyl group, the triazolyl group, the pyridyl group, and the pyrimidinyl group each may have optionally one or more substituents selected from Group J}, $OR^{12}$, $CR^{30}{=}NOR^{17}$, a hydrogen atom, or a halogen atom, and when Q represents a group represented by formula Q1, and $R^{3b}$ and $R^{3d}$ combined together with two carbon atoms to which they are attached may form a benzene ring {the benzene ring may have optionally one or more substituents selected from a group consisting of C1-C6 alkyl group optionally having one or more halogen atoms, and a halogen atom}.

[4] The compound according to [1] or [2] or N-oxide thereof, wherein $R^{3a}$ and $R^{3d}$ represent a hydrogen atom, $R^{3b}$ and $R^{3c}$ are identical to or different from each other and each represents a C1-C6 alkyl group optionally having one or more halogen atoms, a cyclopropyl group, a hydrogen atom, or a halogen atom, and when Q represents a group represented by formula Q1, $R^{3b}$ and $R^{3d}$ combined together with two carbon atoms to which they are attached may form a benzene ring {the benzene ring may have optionally one or more substituents selected from a group consisting of C1-C6 alkyl group optionally having one or more halogen atoms, and halogen atom}.

[5] The compound according to any one of [1] to [4] or N-oxide thereof, wherein Q represents a group represented by formula Q1.

[6] The compound according to [1] or [2] or N-oxide thereof, wherein Q represents a group represented by formula Q1, and $R^{3a}$ and $R^{3d}$ represent a hydrogen atom.

[7] The compound according to any one of [1] to [4] or N-oxide thereof, wherein Q represents a group represented by formula Q2.

[8] The compound according to any one of [1] to [7] or N-oxide thereof, wherein $B^1$ represents CH, a combination of $B^2$, $B^3$ and $B^4$ represents a combination in which $B^2$ represents $CR^1$, $B^3$ represents $CR^{6c}$, and $B^4$ represents $CR^{6d}$; a combination in which $B^2$ represents $CR^{6b}$, $B^3$ represents $CR^1$, and $B^4$ represents $CR^{6d}$; or a combination in which $B^2$ represents $CR^{6b}$, $B^3$ represents $CR^{6c}$, and $B^4$ represents $CR^1$.

[9] The compound according to any one of [1] to [4], [7] or [8] or N-oxide thereof, wherein $G^1$ represents a nitrogen atom or CH, $G^2$ represents $CR^{3b}$, $G^3$ represents $CR^{3c}$, and $G^4$ represents a nitrogen atom or CH.

[10] The compound according to any one of [1] to [4], [6] or [7] or N-oxide thereof, wherein $G^1$ represents CH, $G^2$ represents $CR^{3b}$, $G^3$ represents $CR^{3c}$, and $G^4$ represents CH.

[11] The compound according to any one of [1] to [10] or N-oxide thereof, wherein $R^1$ represents a C1-C6 alkyl group having one or more substituents selected from a group consisting of halogen atom and cyano group; a cyclopropyl group optionally having one or more substituents selected from the group consisting of cyano group and halogen atom; $S(O)_mR^8$; a halogen atom; or $OR^8$.

[12] The compound according to any one of [1] to [10] or N-oxide thereof, wherein $R^1$ represents a C1-C6 alkyl group having one or more substituents selected from a group consisting of halogen atom and cyano group; a cyclopropyl group optionally having one or more substituents selected from the group consisting of cyano group and halogen atom; $S(O)^mR^8$; or $OR^8$.

[13] The compound according to any one of [1] to [12] or N-oxide thereof, wherein $R^2$ represents an ethyl group.

[14] The compound according to any one of [1] to [13] or N-oxide thereof, wherein Z represents an oxygen atom.

[15] A composition for controlling harmful arthropod which comprises the compound according to any one of [1] to [14] or N-oxide thereof.

[16] A composition comprising one or more ingredients selected from the group consisting of the following Group (a), Group (b), Group (c), and Group (d), and the compound according to any one of [1] to [14] or N-oxide thereof (hereinafter, which is referred to as "Present Composition" or "composition of the present invention"):

Group (a): a group consisting of insecticidal ingredients, miticidal ingredients, and nematicidal ingredients;

Group (b): fungicidal ingredients,

Group (c): plant growth modulating ingredients; and

Group (d): repellent ingredients.

[17] A method for controlling harmful arthropod which comprises applying an effective amount of the compound according to any one of [1] to [14] or N-oxide thereof, or an effective amount of the composition according to [16] to a harmful arthropod or a habitat where a harmful arthropod lives.

[18] A seed or vegetative reproductive organ carrying an effective amount of the compound according to any one of [1] to [14] or N-oxide thereof, or an effective amount of the composition according to [16].

[19] A compound represented by formula (II):

(II)

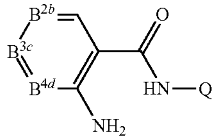

[wherein, a combination of $B^{2b}$, $B^{3c}$ and $B^{4d}$ represents a combination in which $B^{2b}$ represents $CR^1$, $B^{3c}$ represents a nitrogen atom or $CR^{6cc}$, and $B^{4d}$ represents a nitrogen atom or $CR^{6dd}$;

a combination in which $B^{2b}$ represents a nitrogen atom or $CR^{6bb}$, $B^{3c}$ represents $CR^1$, and $B^{4d}$ represents a nitrogen atom or $CR^{6dd}$; or a combination in which $B^{2b}$ represents a nitrogen atom or $CR^{6bb}$, $B^{3c}$ represents a nitrogen atom or $CR^{6cc}$, and $B^{4d}$ represents $CR^1$.

$R^{6bb}$, $R^{6cc}$ and $R^{6dd}$ are identical to or different from each other and each represents a C1-C6 chain hydrocarbon group optionally having one or more halogen atoms, a halogen atom or a hydrogen atom, and the other symbols are the same as described in [1]] (hereinafter, which is referred to as "Intermediate compound C"), or salts thereof.

[20] The compound according to [19] wherein $R^1$ represents a C1-C6 chain hydrocarbon group having one or more substituents selected from the group consisting of cyano group and halogen atom, a C3-C4 cycloalkyl group optionally having one or more substituents selected from the group consisting of cyano group and halogen atom, $S(O)_mR^8$, $OR^8$, or $OS(O)_2R^8$ (hereinafter, which is referred to as "Intermediate compound A") or salts thereof.

[21] A compound represented by formula (III):

(III)

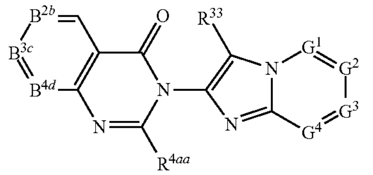

[wherein $R^{33}$ represents a hydrogen atom or halogen atom, a combination of $B^{2b}$, $B^{3c}$ and $B^{4d}$ represents a combination in which $B^{2b}$ represents $CR^1$, $B^{3c}$ represents a nitrogen atom or $CR^{6cc}$, and $B^{4d}$ represents a nitrogen atom or $CR^{6dd}$;

a combination in which $B^{2b}$ represents a nitrogen atom or $CR^{6bb}$, $B^{3c}$ represents $CR^1$, and $B^{4d}$ represents a nitrogen atom or $CR^{6dd}$; or a combination in which $B^{2b}$ represents a nitrogen atom or $CR^{6bb}$, $B^{3c}$ represents a nitrogen atom or $CR^{6cc}$, and $B^{4d}$ represents $CR^1$;

$R^{4aa}$, $R^{6bb}$, $R^{6cc}$ and $R^{6dd}$ are identical to or different from each other and each represents a C1-C6 chain hydrocarbon group optionally having one or more halogen atoms, halogen atom or a hydrogen atom, and the other symbols are the same as defined in [1].], (hereinafter, which is referred to as "Intermediate compound D").

[22] The compound according to [21], wherein $R^1$ represents a C1-C6 chain hydrocarbon group having one or more substituents selected from the group consisting of cyano group and halogen atom, a C3-C4 cycloalkyl group optionally having one or more substituents selected from the group consisting of cyano group and halogen atom, $S(O)_mR^8$, $OR^8$, or $OS(O)_2R^8$ (hereinafter, which is referred to as "Intermediate compound B").

Effect of Invention

The present invention can control harmful arthropod.

MODE FOR CARRYING OUT THE INVENTION

The substituent(s) as described herein is/are explained.

The term "halogen atom" represents fluorine atom, chlorine atom, bromine atom, or iodine atom.

When the substituents have two or more halogen atoms, these halogen atoms may be identical to or different from each other.

The expression of "CX-CY" as used herein represents that the number of carbon atom is from X to Y. For example, the expression of "C1-C6" represents that the number of carbon atom is from 1 to 6.

The term of "chain hydrocarbon group" represents an alkyl group, an alkenyl group, or an alkynyl group.

Example of "alkyl group" include methyl group, ethyl group, propyl group, isopropyl group, 1,1-dimethylpropyl group, 1,2-dimethylpropyl group, 1-ethylpropyl group, butyl group, sec-butyl group, tert-butyl group, pentyl group, and hexyl group.

Example of "alkenyl group" include vinyl group, 1-propenyl group, 2-propenyl group, 1-methyl-1-propenyl group, 1-methyl-2-propenyl group, 1,2-dimethyl-1-propenyl group, 1-ethyl-1-propenyl group, 3-butenyl group, 4-pentenyl group, and 5-hexenyl group.

Example of "alkynyl group" includes ethynyl group, 1-propynyl group, 2-propynyl group, 1-methyl-2-propynyl group, 1,1-dimethyl-2-propynyl group, 1-ethyl-2-propynyl group, 2-butynyl group, 4-pentynyl group, and 5-hexynyl group.

Examples of "alkoxy group" includes methoxy group, ethoxy group, propoxy group, isopropoxy group, butoxy group, tert-butoxy group, pentoxy group, and hexyloxy group.

Examples of "alkenyloxy group" includes 2-propenyloxy group, 2-butenyloxy group, and 5-hexenyloxy group.

Examples of "alkynyloxy group" includes 2-propynyloxy group, 2-butynyloxy group, and 5-hexynyloxy group.

Examples of "fluoroalkyl group" include trifluoromethyl group, 2,2,2-trifluoroethyl group, pentafluoroethyl group, 2,2,3,3,3-pentafluoropropyl group, 1,1,1-trifluoropropan-2-yl group, and heptafluoropropyl group.

Examples of "fluoroalkoxy group" include fluoromethoxy group, difluoromethoxy group, trifluoromethoxy group, 2,2,2-trifluoroethoxy group, perfluoroethoxy group, and perfluoropropoxy group.

Examples of "cycloalkyl group" include cyclopropyl group, cyclobutyl group, cyclopentyl group, cyclohexyl group, and cycloheptyl group.

Examples of "cycloalkenyl group" include cyclopropenyl group, cyclobutenyl group, cyclopentenyl group, cyclohexenyl group, and cycloheptenyl group.

Examples of "three(3) to seven(7) membered nonaromatic heterocyclic group" include aziridine ring, azetidine ring, pyrrolidine ring, imidazoline ring, imidazolidine ring, piperidine ring, tetrahydropyrimidine ring, hexahydropyrimidine ring, piperazine ring, azepane ring, oxazolidine ring, isoxazolidine ring, 1,3-oxazinane ring, morpholine ring, 1,4-oxazepane ring, thiazolidine ring, isothiazolidine ring, 1,3-thiazinane ring, thiomorpholine ring, and 1,4-thiazepane ring.

Examples of the three(3) to seven(7) membered nonaromatic heterocyclic group optionally having one or more substituents selected from Group E include the followings:

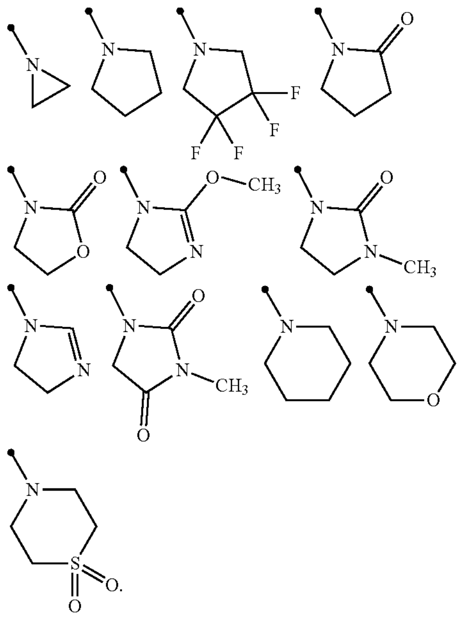

The term of "five(5) or six(6) membered aromatic heterocyclic group" represents five(5) membered aromatic heterocyclic group or six(6) membered aromatic heterocyclic group, and examples of the five(5) membered aromatic heterocyclic group include pyrrolyl group, furyl group, thienyl group, pyrazolyl group, imidazolyl group, triazolyl group, tetrazolyl group, oxazolyl group, isoxazolyl group, thiazolyl group, isothiazolyl group, oxadiazolyl group, and thiadiazolyl group. Examples of six(6) membered aromatic heterocyclic group include pyridyl group, pyridazinyl group, pyrimidinyl group, pyrazinyl group, triazinyl group, and tetrazinyl group.

Examples of "(C3-C6 cycloalkyl)C1-C3 alkyl group optionally having one or more halogen atoms" include cyclopropylmethyl group, (2-fluorocyclopropyl)methyl group, cyclopropyl(fluoro)methyl group, and (2-fluorocyclopropyl) (fluoro)methyl group.

Examples of "phenylC1-C3 alkyl group {the phenyl moiety in the phenyl C1-C3 alkyl group may have optionally one or more substituents selected from Group D}" include benzyl group, 2-fluorobenzyl group, 4-chlorobenzyl group, 4-(trifluromethyl)benzyl group, and 2-[4-(trifluoromethyl) phenyl]ethyl group.

The terms of "alkylsulfanyl group", "alkylsulfinyl group" and "alkylsulfonyl group" represent an alkyl group containing a $S(O)_z$ moiety, respectively.

For example, examples of the "alkylsulfanyl" when z is 0 include methylsulfanyl group, ethylsulfanyl group, propylsulfanyl group, and isopropylsulfanyl group.

For example, examples of the "alkylsulfinyl" when z is 1 include methylsulfinyl group, ethylsulfinyl group, propylsulfinyl group, and isopropylsulfinyl group.

For example, examples of the "alkylsulfonyl" when z is 2 include methylsulfonyl group, ethylsulfonyl group, propylsulfonyl group, and isopropylsulfonyl group.

Examples of "N-oxide of the compound represented by formula (I)" include compounds represented by the following formulae.

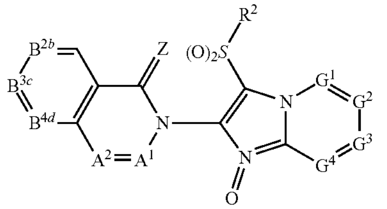

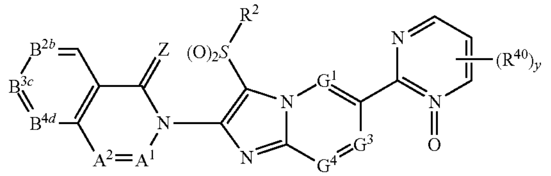

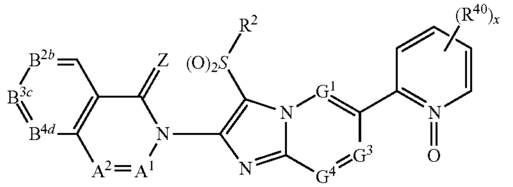

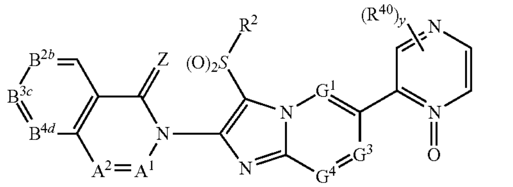

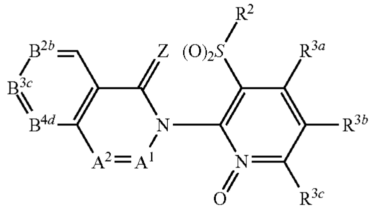

[wherein $R^{40}$ represents any substituents selected from Group H, x is 0, 1, 2, 3 or 4, y is 0, 1, 2 or 3, and the other symbols are the same as defined.]

The present compound X, the intermediate compound C, and the intermediate compound D may be existed as one or more stereoisomers. Examples of the stereoisomer include enantiomer, diastereoisomer, and geometric isomer. Each stereoisomer, and stereoisomer mixture (s) in an arbitrary ratio thereof are included in the present compound X, the intermediate compound C, and the intermediate compound D.

The present compound X, and the intermediate compound C may form acid addition salts. Examples of the acid to form the acid addition salt include inorganic acids such as hydrogen chloride, phosphoric acid, sulfuric acid; and organic acids such as acetic acid, trifluoroacetic acid, benzoic acid, p-toluenesulfonic acid. The acid addition salt may be obtained by mixing the present compound X or the intermediate compound C with an acid.

Examples of the Embodiment of the present compound N include the followings.

[Embodiment 1] The present compound N wherein $R^{3a}$ represents a hydrogen atom, $R^{3b}$, $R^{3c}$ and $R^{3d}$ are identical to or different from each other and each represents a C1-C6 alkyl group, a C2-C6 alkenyl group, a C3-C7 cycloalkyl group {the C1-C6 alkyl group, the C2-C6 alkenyl group, and the C3-C7 cycloalkyl group each may have optionally one or more substituents selected from the group consisting of halogen atom and cyano group}, a phenyl group, a triazolyl group, a pyridyl group, a pyrimidinyl group {the phenyl group, the triazolyl group, the pyridyl group, and the pyrimidinyl group each may have optionally one or more substituents selected from Group J}, $OR^{12}$, $CR^{30}$═$NOR^{17}$, a hydrogen atom, or halogen atom, and when Q represents a group represented by formula Q1, and $R^{3b}$ and $R^{3d}$ combined together with two carbon atoms to which they are attached may form a benzene ring {the benzene ring may have optionally a C1-C6 alkyl group optionally having one or more halogen atoms and halogen atom).

[Embodiment 2] The present compound N wherein $R^{3a}$ and $R^{3d}$ represent a hydrogen atom, $R^{3b}$ and $R^{3c}$ are identical to or different from each other and each represents a C1-C6 alkyl group optionally having one or more halogen atoms, a cyclopropyl group, a hydrogen atom, of a halogen atom, and when Q represents a group represented by formula Q1, $R^{3b}$ and $R^{3d}$ combined together with two carbon atoms to which they are attached may form a benzene ring {the benzene ring may have optionally one or more substituents selected from a group consisting of C1-C6 alkyl group optionally having halogen atoms, and halogen atom.

[Embodiment 3] The present compound N wherein Q represents a group represented by formula Q2.

[Embodiment 4] The compound according to the Embodiment 1 wherein Q represents a group represented by formula Q2.

[Embodiment 5] The compound according to the Embodiment 2 wherein Q represents a group represented by formula Q2.

[Embodiment 6] The present compound N wherein Q represents a group represented by formula Q1.

[Embodiment 7] The compound according to the Embodiment 1 wherein Q represents a group represented by formula Q1.

[Embodiment 8] The compound according to the Embodiment 2 wherein Q represents a group represented by formula Q1.

[Embodiment 9] The present compound N wherein Q represents a group represented by formula Q1, $R^{3a}$ represents a hydrogen atom, $R^{3b}$ and $R^{3d}$ are identical to or different from each other and each represents a C1-C6 alkyl group, a C2-C6 alkenyl group, a C3-C7 cycloalkyl group {the C1-C6 alkyl group, the C2-C6 alkenyl group, and the C3-C7 cycloalkyl group each may have optionally one or more substituents selected from the group consisting of halogen atom and cyano group}, a phenyl group, a triazolyl group, a pyridyl group, a pyrimidinyl group {the phenyl group, the triazolyl group, the pyridyl group, and the pyrimidinyl group each may have optionally one or more substituents selected from Group J}, $OR^{12}$, $CR^{30}$═$NOR^{17}$, a hydrogen atom, or a halogen atom.

[Embodiment 10] The present compound N wherein Q represents a group represented by formula Q1, $R^{3a}$ and $R^{3d}$ represent a hydrogen atom, $R^{3b}$ represents a C1-C6 alkyl group optionally having one or more halogen atoms, a cyclopropyl group, a hydrogen atom, or a halogen atom.

[Embodiment 11] The present compound N wherein Q represents a group represented by formula Q1, $R^{3a}$ represents a hydrogen atom, $R^{3b}$ and $R^{3d}$ combined together with two carbon atoms to which they are attached may form a benzene ring, a pyrrole ring, a furan ring, a thiophene ring, a pyrazole ring, an imidazole ring, an oxazole ring, an isoxazole ring, a thiazole ring, an isothiazole ring, an oxadiazole ring, a thiadiazole ring, a pyridine ring, a pyridazine ring, a pyrimidine ring, a pyrazine ring {the benzene ring, the pyrrole ring, the furan ring, the thiophene ring, the pyrazole ring, the imidazole ring, the oxazole ring, the isoxazole ring, the thiazole ring, the isothiazole ring, the pyridine ring, the pyridazine ring, the pyrimidine ring, and the pyrazine ring each may have optionally one or more substituents selected from Group H}, or a triazole ring optionally having one or more substituents selected from Group I.

[Embodiment 12] The present compound N wherein Q represents a group represented by formula Q1, $R^{3a}$ represents a hydrogen atom, $R^{3b}$ and $R^{3d}$ combined together with two carbon atoms to which they are attached form a benzene ring {the benzene ring may have optionally one or more substituents selected from a group consisting of C1-C6 alkyl group optionally having one or more halogen atoms, and halogen atom}.

[Embodiment 13] The present compound N wherein $G^2$ represents $CR^{3b}$, $G^3$ represents $CR^{3c}$, and a combination of $G^1$ and $G^4$ represents a combination in which $G^1$ represents $CR^{3a}$, and $G^4$ represents a nitrogen atom or $CR^{3d}$; or a combination in which $G^1$ represents a nitrogen atom, and $G^4$ represents $CR^{3d}$.

[Embodiment 14] The present compound N wherein $G^1$ represents CH, $G^2$ represents $CR^{3b}$, $G^3$ represents $GR^{3c}$, and $G^4$ represents CH.

[Embodiment 15] The present compound N wherein $G^1$ represents a nitrogen atom, $G^2$ represents $CR^{3b}$, $G^3$ represents $GR^{3c}$, and $G^4$ represents CH.

[Embodiment 16] The present compound N wherein $G^1$ represents CH, $G^2$ represents $CR^{3b}$, $G^3$ represents $CR^{3c}$, and $G^4$ represents a nitrogen atom.

[Embodiment 17] The compound according to the Embodiment 1 wherein $G^2$ represents $CR^{3b}$, $G^3$ represents $CR^{3c}$, and a combination of $G^1$ and $G^4$ represents a combination in which $G^1$ represents CH, and $G^4$ represents a nitrogen atom or $CR^{3d}$; or a combination in which $G^1$ represents a nitrogen atom, and $G^4$ represents $CR^{3d}$.

[Embodiment 18] The compound according to the Embodiment 2 wherein $G^2$ represents $CR^{3b}$, $G^3$ represents $CR^{3c}$, and a combination of $G^1$ and $G^4$ represents a combination in which $G^1$ represents CH, and $G^4$ represents a nitrogen atom or CH; or a combination in which $G^1$ represents a nitrogen atom, and $G^4$ represents CH.

[Embodiment 19] The compound according to the Embodiment 3 wherein $G^2$ represents $CR^{3b}$, $G^3$ represents $CR^{3c}$, and a combination of $G^1$ and $G^4$ represents a combination in which $G^1$ represents $CR^{3a}$, and $G^4$ represents a nitrogen atom or $CR^{3d}$; or a combination in which $G^1$ represents a nitrogen atom, and $G^4$ represents $CR^{3d}$.

[Embodiment 20] The compound according to the Embodiment 4 wherein $G^2$ represents $CR^{3b}$, $G^3$ represents $CR^{3c}$, and a combination of $G^1$ and $G^4$ represents a combination in which $G^1$ represents CH, and $G^4$ represents a nitrogen atom or $CR^{3d}$; or a combination in which $G^1$ represents a nitrogen atom, and $G^4$ represents $CR^{3d}$.

[Embodiment 21] The compound according to the Embodiment 5 wherein $G^2$ represents $CR^{3b}$, $G^3$ represents $CR^{3c}$, and a combination of $G^1$ and $G^4$ represents a combination in which $G^1$ represents CH, and $G^4$ represents a nitrogen atom or CH; or a combination in which $G^1$ represents a nitrogen atom, and $G^4$ represents $CR^{3d}$.

[Embodiment 22] The compound according to the Embodiment 1 wherein $G^1$ represents CH, $G^2$ represents $CR^{3b}$, $G^3$ represents $CR^{3c}$, and $G^4$ represents CH.

[Embodiment 23] The compound according to the Embodiment 2 wherein $G^1$ represents CH, $G^2$ represents $CR^{3b}$, $G^3$ represents $CR^{3c}$, and $G^4$ represents CH.

[Embodiment 24] The compound according to the Embodiment 3 wherein $G^1$ represents CH, $G^2$ represents $CR^{3b}$, $G^3$ represents $CR^{3c}$, and $G^4$ represents CH.

[Embodiment 25] The compound according to the Embodiment 4 wherein $G^1$ represents CH, $G^2$ represents $CR^{3b}$, $G^3$ represents $CR^{3c}$, and $G^4$ represents CH.

[Embodiment 26] The compound according to the Embodiment 5 wherein $G^1$ represents CH, $G^2$ represents $CR^{3b}$, $G^3$ represents $CR^{3c}$, and $G^4$ represents CH.

[Embodiment 27] The compound according to the Embodiment 1 wherein $G^1$ represents a nitrogen atom, $G^2$ represents $CR^{3b}$, $G^3$ represents $CR^{3c}$, and $G^4$ represents CH.

[Embodiment 28] The compound according to the Embodiment 2 wherein $G^1$ represents a nitrogen atom, $G^2$ represents $CR^{3b}$, $G^3$ represents $CR^{3c}$, and $G^4$ represents CH.

[Embodiment 29] The compound according to the Embodiment 3 wherein $G^1$ represents a nitrogen atom, $G^2$ represents $CR^{3b}$, $G^3$ represents $CR^{3c}$, and $G^4$ represents CH.

[Embodiment 30] The compound according to the Embodiment 4 wherein $G^1$ represents a nitrogen atom, $G^2$ represents $CR^{3b}$, $G^3$ represents $CR^{3c}$, and $G^4$ represents CH.

[Embodiment 31] The compound according to the Embodiment 5 wherein $G^1$ represents a nitrogen atom, $G^2$ represents $CR^{3b}$, $G^3$ represents $CR^{3c}$, and $G^4$ represents CH.

[Embodiment 32] The compound according to the Embodiment 1 wherein $G^1$ represents a nitrogen atom, $G^2$ represents $CR^{3b}$, $G^3$ represents $CR^{3c}$, and $G^4$ represents CH.

[Embodiment 33] The compound according to the Embodiment 2 wherein $G^1$ represents CH, $G^2$ represents $CR^{3b}$, $G^3$ represents $CR^{3c}$, and $G^4$ represents a nitrogen atom.

[Embodiment 34] The compound according to the Embodiment 3 wherein $G^1$ represents CH, $G^2$ represents $CR^{3b}$, $G^3$ represents $CR^{3c}$, and $G^4$ represents a nitrogen atom.

[Embodiment 35] The compound according to the Embodiment 4 wherein $G^1$ represents CH, $G^2$ represents $CR^{3b}$, $G^3$ represents $CR^{3c}$, and $G^4$ represents a nitrogen atom.

[Embodiment 36] The compound according to the Embodiment 5 wherein $G^1$ represents CH, $G^2$ represents $CR^{3b}$, $G^3$ represents $CR^{3c}$, and $G^4$ represents a nitrogen atom.

[Embodiment 37] The present compound N wherein $R^2$ represents a C1-C6 alkyl group.

[Embodiment 38] The present compound N wherein $R^2$ represents an ethyl group.

[Embodiment 39] The compound according to the Embodiment 1 wherein $R^2$ represents a C1-C6 alkyl group.

[Embodiment 40] The compound according to the Embodiment 2 wherein $R^2$ represents a C1-C6 alkyl group.

[Embodiment 41] The compound according to the Embodiment 3 wherein $R^2$ represents a C1-C6 alkyl group.

[Embodiment 42] The compound according to the Embodiment 4 wherein $R^2$ represents a C1-C6 alkyl group.

[Embodiment 43] The compound according to the Embodiment 5 wherein $R^2$ represents a C1-C6 alkyl group.

[Embodiment 44] The compound according to the Embodiment 6 wherein $R^2$ represents a C1-C6 alkyl group.

[Embodiment 45] The compound according to the Embodiment 7 wherein $R^2$ represents a C1-C6 alkyl group.

[Embodiment 46] The compound according to the Embodiment 8 wherein $R^2$ represents a C1-C6 alkyl group.

[Embodiment 47] The compound according to the Embodiment 9 wherein $R^2$ represents a C1-C6 alkyl group.

[Embodiment 48] The compound according to the Embodiment 10 wherein $R^2$ represents a C1-C6 alkyl group.

[Embodiment 49] The compound according to the Embodiment 11 wherein $R^2$ represents a C1-C6 alkyl group.

[Embodiment 50] The compound according to the Embodiment 12 wherein $R^2$ represents a C1-C6 alkyl group.

[Embodiment 51] The compound according to the Embodiment 13 wherein $R^2$ represents a C1-C6 alkyl group.

[Embodiment 52] The compound according to the Embodiment 14 wherein $R^2$ represents a C1-C6 alkyl group.

[Embodiment 53] The compound according to the Embodiment 15 wherein $R^2$ represents a C1-C6 alkyl group.

[Embodiment 54] The compound according to the Embodiment 16 wherein $R^2$ represents a C1-C6 alkyl group.

[Embodiment 55] The compound according to the Embodiment 17 wherein $R^2$ represents a C1-C6 alkyl group.

[Embodiment 56] The compound according to the Embodiment 18 wherein $R^2$ represents a C1-C6 alkyl group.

[Embodiment 57] The compound according to the Embodiment 19 wherein $R^2$ represents a C1-C6 alkyl group.

[Embodiment 58] The compound according to the Embodiment 20 wherein $R^2$ represents a C1-C6 alkyl group.

[Embodiment 59] The compound according to the Embodiment 21 wherein $R^2$ represents a C1-C6 alkyl group.

[Embodiment 60] The compound according to the Embodiment 22 wherein $R^2$ represents a C1-C6 alkyl group.

[Embodiment 61] The compound according to the Embodiment 23 wherein $R^2$ represents a C1-C6 alkyl group.

[Embodiment 62] The compound according to the Embodiment 24 wherein $R^2$ represents a C1-C6 alkyl group.

[Embodiment 63] The compound according to the Embodiment 25 wherein $R^2$ represents a C1-C6 alkyl group.

[Embodiment 64] The compound according to the Embodiment 26 wherein $R^2$ represents a C1-C6 alkyl group.

[Embodiment 65] The compound according to the Embodiment 27 wherein $R^2$ represents a C1-C6 alkyl group.

[Embodiment 66] The compound according to the Embodiment 28 wherein $R^2$ represents a C1-C6 alkyl group.

[Embodiment 67] The compound according to the Embodiment 29 wherein $R^2$ represents a C1-C6 alkyl group.

[Embodiment 68] The compound according to the Embodiment 30 wherein $R^2$ represents a C1-C6 alkyl group.

[Embodiment 69] The compound according to the Embodiment 31 wherein $R^2$ represents a C1-C6 alkyl group.

[Embodiment 70] The compound according to the Embodiment 32 wherein $R^2$ represents a C1-C6 alkyl group.

[Embodiment 71] The compound according to the Embodiment 33 wherein $R^2$ represents a C1-C6 alkyl group.

[Embodiment 72] The compound according to the Embodiment 34 wherein $R^2$ represents a C1-C6 alkyl group.

[Embodiment 73] The compound according to the Embodiment 35 wherein $R^2$ represents a C1-C6 alkyl group.

[Embodiment 74] The compound according to the Embodiment 36 wherein $R^2$ represents a C1-C6 alkyl group.

[Embodiment 75] The compound according to the Embodiment 1 wherein $R^2$ represents an ethyl group.

[Embodiment 76] The compound according to the Embodiment 2 wherein $R^2$ represents an ethyl group.

[Embodiment 77] The compound according to the Embodiment 3 wherein $R^2$ represents an ethyl group.

[Embodiment 78] The compound according to the Embodiment 4 wherein $R^2$ represents an ethyl group.

[Embodiment 79] The compound according to the Embodiment 5 wherein $R^2$ represents an ethyl group.

[Embodiment 80] The compound according to the Embodiment 6 wherein $R^2$ represents an ethyl group.

[Embodiment 81] The compound according to the Embodiment 7 wherein $R^2$ represents an ethyl group.

[Embodiment 82] The compound according to the Embodiment 8 wherein $R^2$ represents an ethyl group.

[Embodiment 83] The compound according to the Embodiment 9 wherein $R^2$ represents an ethyl group.

[Embodiment 84] The compound according to the Embodiment 10 wherein $R^2$ represents an ethyl group.

[Embodiment 85] The compound according to the Embodiment 11 wherein $R^2$ represents an ethyl group.

[Embodiment 86] The compound according to the Embodiment 12 wherein $R^2$ represents an ethyl group.

[Embodiment 87] The compound according to the Embodiment 13 wherein $R^2$ represents an ethyl group.

[Embodiment 88] The compound according to the Embodiment 14 wherein $R^2$ represents an ethyl group.

[Embodiment 89] The compound according to the Embodiment 15 wherein $R^2$ represents an ethyl group.

[Embodiment 90] The compound according to the Embodiment 16 wherein $R^2$ represents an ethyl group.

[Embodiment 91] The compound according to the Embodiment 17 wherein $R^2$ represents an ethyl group.

[Embodiment 92] The compound according to the Embodiment 18 wherein $R^2$ represents an ethyl group.

[Embodiment 93] The compound according to the Embodiment 19 wherein $R^2$ represents an ethyl group.

[Embodiment 94] The compound according to the Embodiment 20 wherein $R^2$ represents an ethyl group.

[Embodiment 95] The compound according to the Embodiment 21 wherein $R^2$ represents an ethyl group.

[Embodiment 96] The compound according to the Embodiment 22 wherein $R^2$ represents an ethyl group.

[Embodiment 97] The compound according to the Embodiment 23 wherein $R^2$ represents an ethyl group.

[Embodiment 98] The compound according to the Embodiment 24 wherein $R^2$ represents an ethyl group.

[Embodiment 99] The compound according to the Embodiment 25 wherein $R^2$ represents an ethyl group.

[Embodiment 100] The compound according to the Embodiment 26 wherein $R^2$ represents an ethyl group.

[Embodiment 101] The compound according to the Embodiment 27 wherein $R^2$ represents an ethyl group.

[Embodiment 102] The compound according to the Embodiment 28 wherein $R^2$ represents an ethyl group.

[Embodiment 103] The compound according to the Embodiment 29 wherein $R^2$ represents an ethyl group.

[Embodiment 104] The compound according to the Embodiment 30 wherein $R^2$ represents an ethyl group.

[Embodiment 105] The compound according to the Embodiment 31 wherein $R^2$ represents an ethyl group.

[Embodiment 106] The compound according to the Embodiment 32 wherein $R^2$ represents an ethyl group.

[Embodiment 107] The compound according to the Embodiment 33 wherein $R^2$ represents an ethyl group.

[Embodiment 108] The compound according to the Embodiment 34 wherein $R^2$ represents an ethyl group.

[Embodiment 109] The compound according to the Embodiment 35 wherein $R^2$ represents an ethyl group.

[Embodiment 110] The compound according to the Embodiment 36 wherein $R^2$ represents an ethyl group.

[Embodiment 111] The compound according to any one of the Embodiment 1 to the Embodiment 110 or the present compound N, wherein $R^1$ represents a C1-C6 alkyl group having one or more substituents selected from a group consisting of halogen atom and cyano group; a cyclopropyl group optionally having one or more substituents selected from the group consisting of cyano group and halogen atom; $S(O)_mR^8$; or $OR^8$, and $R^8$ represents a C1-C6 alkyl group having one or more substituents selected from a group consisting of halogen atom and cyano group.

[Embodiment 112] The compound according to the Embodiment 111 wherein $A^1$ represents $CR^{4a}$, $A^2$ represents a nitrogen atom, $R^{4a}$ represents a C1-C6 alkyl group optionally having one or more halogen atoms, a halogen atom or a hydrogen atom, and $R^{6a}$, $R^{6b}$, $R^{6c}$ and $R^{6d}$ are identical to or different from each other and each represents a halogen atom or a hydrogen atom.

[Embodiment 113] The compound according to the Embodiment 111 wherein $R^{4a}$ represents a C1-C6 alkyl group optionally having one or more halogen atoms, a halogen atom or a hydrogen atom, $B^1$ represents $CR^{6a}$, and a combination of $B^2$, $B^3$ and $B^4$ represents a combination in which $B^2$ represents $CR^1$, $B^3$ represents $CR^{6c}$, and $B^4$ represents a nitrogen atom or $CR^{6d}$; a combination in which $B^2$ represents $CR^{6d}$, $B^3$ represents $CR^1$, and $B^4$ represents a nitrogen atom or $CR^{6d}$; or a combination in which $B^2$ represents $CR^{6b}$, $B^3$ represents $CR^{6c}$, and $B^4$ represents $CR^1$, and $R^{6a}$, $R^{6b}$b, $R^{6c}$ and $R^{6d}$ are identical to or different from each other and each represents a halogen atom or a hydrogen atom.

[Embodiment 114] The compound according to the Embodiment 113 wherein $A^1$ represents $CR^{4a}$, and $A^2$ represents a nitrogen atom.

[Embodiment 115] The compound according to the Embodiment 111 wherein $A^1$ represents CH, $A^2$ represents a nitrogen atom, $B^1$ represents CH, a combination of $B^2$, $B^3$ and $B^4$ represents a combination in which $B^2$ represents $CR^1$, $B^3$ represents CH, and $B^4$ represents a nitrogen atom or CH; a combination in which $B^2$ represents CH, $B^3$ represents $CR^1$, and $B^4$ represents a nitrogen atom or CH; or a combination in which $B^2$ represents CH, $B^3$ represents CH, and $B^4$ represents $CR^1$.

[Embodiment 116] The compound according to the Embodiment 111 wherein $R^{4a}$ and $R^{4b}$ represent a hydrogen atom, $B^1$ represents CH, and a combination of $B^2$, $B^3$ and $B^4$ represents a combination in which $B^2$ represents $CR^1$, $B^3$ represents CH, and $B^4$ represents CH; a combination in which $B^2$ represents CH, $B^3$ represents $CR^1$, and $B^4$ represents CH; or a combination in which $B^2$ represents CH, $B^3$ represents CH, and $B^4$ represents $CR^1$.

[Embodiment 117] The compound according to the Embodiment 111 wherein $A^1$ represents CH, $A^2$ represents a nitrogen atom, $B^1$ represents CH, and a combination of $B^2$, $B^3$ and $B^4$ represents a combination in which $B^2$ represents $CR^1$, $B^3$ represents CH, and $B^4$ represents CH; a combination in which $B^2$ represents CH, $B^3$ represents $CR^1$, and $B^4$ represents CH; or a combination in which $B^2$ represents CH, $B^3$ represents CH, and $B^4$ represents $CR^1$.

[Embodiment 118] The compound according to any one of the Embodiment 1 to the Embodiment 110 or the present compound N, wherein $B^1$ represents CH, a combination of $B^2$, $B^3$ and $B^4$ represents a combination in which $B^2$ represents $CR^1$, $B^3$ represents CH, and $B^4$ represents a nitrogen atom or CH; a combination in which $B^2$ represents CH, $B^3$ represents $CR^1$, and $B^4$ represents a nitrogen atom or CH; or a combination in which $B^2$ represents CH, $B^3$ represents CH, and $B^4$ represents $CR^1$, $R^1$ represents a C1-C3 fluoroalkyl group or $S(O)_mCF_3$, and $R^{4a}$ and $R^{4b}$ represent a hydrogen atom.

[Embodiment 119] The compound according to any one of the Embodiment 1 to the Embodiment 110 or the present compound N, wherein $B^1$ represents CH, a combination of $B^2$, $B^3$ and $B^4$ represents a combination in which $B^2$ represents $CR^1$, $B^3$ represents CH, and $B^4$ represents CH; a combination in which $B^2$ represents CH, $B^3$ represents $CR^1$, and $B^4$ represents CH; or a combination in which $B^2$ represents CH, $B^3$ represents CH, $B^4$ represents $CR^1$, and $R^1$ represents a C1-C3 fluoroalkyl group or $S(O)_mCF_3$, and $R^{4a}$ and $R^{4b}$ represent a hydrogen atom.

[Embodiment 120] The compound according to any one of the Embodiment 1 to the Embodiment 110 or the present compound N, wherein $B^1$ represents CH, a combination of $B^2$, $B^3$ and $B^4$ represents a combination in which $B^2$ represents $CR^1$, $B^3$ represents CH, and $B^4$ represents nitrogen atom or CH; a combination in which $B^2$ represents CH, $B^3$ represents CH, and $B^4$ represents $CR^1$, $R^1$ represents a C1-C3 fluoroalkyl group or $S(O)_mCF_3$, $A^1$ represents CH, and $A^2$ represents a nitrogen atom.

[Embodiment 121] The compound according to any one of the Embodiment 1 to the Embodiment 110 or the present compound N, wherein $B^1$ represents CH, a combination of $B^2$, $B^3$ and $B^4$ represents a combination in which $B^2$ represents $CR^1$, $B^3$ represents CH, and $B^4$ represents CH; a combination in which $B^2$ represents CH, $B^3$ represents $CR^1$, and $B^4$ represents CH; or a combination in which $B^2$ represents CH, $B^3$ represents CH, and $B^4$ represents $CR^1$, $R^1$ represents a C1-C3 fluoroalkyl group or $S(O)_mCF_3$, $A^1$ represents CH, and $A^2$ represents a nitrogen atom.

[Embodiment 122] The compound according to any one of the Embodiment 1 to the Embodiment 110 or the present compound N, wherein $B^1$ represents CH, $B^4$ represents a nitrogen atom, a combination of $B^2$ and $B^3$ represents a combination in which $B^2$ represents $CR^1$, and $B^3$ represents CH; or a combination in which $B^2$ represents CH, and $B^3$ represents $CR^1$, $R^1$ represents a C1-C3 fluoroalkyl group or $S(O)_mCF_3$, $A^1$ represents CH, and $A^2$ represents a nitrogen atom.

[Embodiment 123] The compound according to any one of the Embodiment 1 to the Embodiment 110 or the present compound N, wherein $R^1$ represents a C1-C3 fluoroalkyl group, A-represents CH, $A^2$ represents a nitrogen atom, and $R^{6a}$, $R^{6b}$, $R^{6c}$ and $R^{6d}$ represent a hydrogen atom.

[Embodiment 124] The compound according to any one of the Embodiment 1 to the Embodiment 110 or the present compound N, wherein $B^1$ represents CH, a combination of $B^2$, $B^3$ and $B^4$ represents a combination in which $B^2$ represents $CR^1$, $B^3$ represents CH, and $B^4$ represents a nitrogen atom or CH; a combination in which $B^2$ represents CH, $B^3$ represents $CR^1$, and $B^4$ represents a nitrogen atom or CH; or a combination in which $B^2$ represents CH, $B^3$ represents CH, and $B^4$ represents $CR^1$, $R^1$ represents a C1-C3 fluoroalkyl group, and $R^{4a}$ and $R^{4b}$ represent a hydrogen atom.

[Embodiment 125] The compound according to any one of the Embodiment 1 to the Embodiment 110 or the present compound N, wherein $B^1$ represents CH, a combination of $B^2$, $B^3$ and $B^4$ represents a combination in which $B^2$ represents $CR^1$, $B^3$ represents CH, and $B^4$ represents a nitrogen atom or CH; a combination in which $B^2$ represents CH, $B^3$ represents $CR^1$, and $B^4$ represents a nitrogen atom or CH; or a combination in which $B^2$ represents CH, $B^3$ represents CH, and $B^4$ represents $CR^1$, $R^1$ represents a C1-C3 fluoroalkyl group, $A^1$ represents CH, and $A^2$ represents a nitrogen atom.

[Embodiment 126] The compound according to any one of the Embodiment 1 to the Embodiment 110 or the present compound N, wherein $B^1$ represents CH, a combination of $B^2$, $B^3$ and $B^4$ represents a combination in which $B^2$ represents $CR^1$, $B^3$ represents CH, and $B^4$ represents CH; a combination in which $B^2$ represents CH, $B^3$ represents $CR^1$, and $B^4$ represents CH; or a combination in which $B^2$ represents CH, $B^3$ represents CH, and $B^4$ represents $CR^1$, $R^1$ represents a C1-C3 fluoroalkyl group, and $R^{4a}$, and $R^{4b}$ represent a hydrogen atom.

[Embodiment 127] The compound according to any one of the Embodiment 1 to the Embodiment 110 or the present compound N, wherein $B^1$ represents CH, $B^4$ represents a nitrogen atom, a combination of $B^2$ and $B^3$ represents a combination in which $B^2$ represents $CR^1$, and $B^3$ represents CH; or a combination in which $B^2$ represents CH, and $B^3$ represents $CR^1$, $R^1$ represents a C1-C3 fluoroalkyl group, $A^1$ represents CH, and $A^2$ represents a nitrogen atom.

[Embodiment 128] The compound according to any one of the Embodiment 1 to the Embodiment 110 or the present compound N, wherein $B^1$ represents a CH, a combination of $B^2$, $B^2$ and $B^4$ represents a combination in which $B^2$ represents $CR^1$, $B^3$ represents CH, and $B^4$ represents CH; a combination of $B^2$ represents CH, $B^3$ represents $CR^1$, and $B^4$ represents CH; or a combination in which $B^2$ represents CH, $B^3$ represents CH, and $B^4$ represents $CR^1$, $R^1$ represents a C1-C3 fluoroalkyl group, $A^1$ represents CH, and $A^2$ represents a nitrogen atom.

[Embodiment 129] The compound according to any one of the Embodiment 1 to the Embodiment 110 or the present compound N, wherein Z represents an oxygen atom.

[Embodiment 130] The compound according to the Embodiment 111 wherein Z represents an oxygen atom.

[Embodiment 131] The compound according to the Embodiment 112 wherein Z represents an oxygen atom.

[Embodiment 132] The compound according to the Embodiment 113 wherein Z represents an oxygen atom.

[Embodiment 133] The compound according to the Embodiment 114 wherein Z represents an oxygen atom.

[Embodiment 134] The compound according to the Embodiment 115 wherein Z represents an oxygen atom.

[Embodiment 135] The compound according to the Embodiment 116 wherein Z represents an oxygen atom.

[Embodiment 136] The compound according to the Embodiment 117 wherein Z represents an oxygen atom.

[Embodiment 137] The compound according to the Embodiment 118 wherein Z represents an oxygen atom.

[Embodiment 138] The compound according to the Embodiment 119 wherein Z represents an oxygen atom.

[Embodiment 139] The compound according to the Embodiment 120 wherein Z represents an oxygen atom.

[Embodiment 140] The compound according to the Embodiment 121 wherein Z represents an oxygen atom.

[Embodiment 141] The compound according to the Embodiment 122 wherein Z represents an oxygen atom.

[Embodiment 142] The compound according to the Embodiment 123 wherein Z represents an oxygen atom.

[Embodiment 143] The compound according to the Embodiment 124 wherein Z represents an oxygen atom.

[Embodiment 144] The compound according to the Embodiment 125 wherein Z represents an oxygen atom.

[Embodiment 145] The compound according to the Embodiment 126 wherein Z represents an oxygen atom.

[Embodiment 146] The compound according to the Embodiment 127 wherein Z represents an oxygen atom.

[Embodiment 147] The compound according to the Embodiment 128 wherein Z represents an oxygen atom.

[Embodiment 148] The present compound N wherein Z represents an oxygen atom, $A^1$ represents CH, $A^2$ represents a nitrogen atom, $B^1$ represents CH, a combination of $B^2$, $B^3$ and $B^4$ represents a combination in which $B^2$ represents $CR^1$, $B^3$ represents CH, and $B^4$ represents a nitrogen atom or CH; a combination in which $B^2$ represents CH, $B^3$ represents $CR^1$, and $B^4$ represents a nitrogen atom or CH; or a combination in which $B^2$ represents CH, $B^3$ represents CH, and $B^4$ represents $CR^1$, $R^1$ represents a trifluoromethyl group, $R^2$ represents an ethyl group, $G^1$ represents CH, $G^2$ represents $CR^{3b}$, $G^3$ represents $CR^{3c}$, $G^4$ represents CH, $R^{3b}$ and $R^{3c}$ are identical to or different from each other and each represents a cyclopropyl group, a halogen atom, or a hydrogen atom, and $R^{3c}$ represents a hydrogen atom.

Examples of the Embodiment of the present compound P include the followings.

[Embodiment P1] The present compound P wherein $R^{3a}$ represents a hydrogen atom, $R^{3b}$, $R^{3c}$ and $R^{3d}$ are identical to or different from each other and each represents a C1-C6 alkyl group, a C2-C6 alkenyl group, a C3-C7 cycloalkyl group {the C1-C6 alkyl group, the C2-C6 alkenyl group, and the C3-C7 cycloalkyl group each may have optionally one or more substituents selected from the group consisting of halogen atom and cyano group}, a phenyl group, a triazolyl group, a pyridyl group, a pyrimidinyl group {the phenyl group, the triazolyl group, the pyridyl group, and the pyrimidinyl group each may have optionally one or more substituents selected from Group J}, $OR^{12}$, a hydrogen atom, or halogen atom, when Q represents a group represented by formula Q1, $R^{3b}$ and $R^{3d}$ combined together with two carbon atoms to which they are attached may form a benzene ring {the benzene ring may have optionally one or more substituents selected from a group consisting of C1-C6 alkyl group optionally having one or more halogen atoms, and halogen atom}.

[Embodiment P2] The present compound P wherein $R^{3a}$ and $R^{3d}$ represent a hydrogen atom, $R^{3b}$ and $R^{3c}$ are identical to or different from each other and each represents a C1-C6 alkyl group optionally having one or more halogen atoms, a cyclopropyl group, a hydrogen atom, or a halogen atom, when Q represents a group represented by formula Q1, $R^{3b}$ and $R^{3d}$ combined together with two carbon atoms to which they are attached may form a benzene ring {the benzene ring may have optionally one or more substituents selected from a group consisting of C1-C6 alkyl group optionally having one or more halogen atoms, and halogen atom}.

[Embodiment P3] The present compound P wherein Q represents a group represented by formula Q2.

[Embodiment P4] The compound according to the Embodiment P1 wherein Q represents a group represented by formula Q2.

[Embodiment P5] The compound according to the Embodiment P2 wherein Q represents a group represented by formula Q2.

[Embodiment P6] The present compound P wherein Q represents a group represented by formula Q1.

[Embodiment P7] The compound according to the Embodiment P1 wherein Q represents a group represented by formula Q1.

[Embodiment P8] The compound according to the Embodiment P2 wherein Q represents a group represented by formula Q1.

[Embodiment P9] The present compound P wherein Q represents a group represented by formula Q1, $R^{3a}$ represents a hydrogen atom, $R^{3b}$ and $R^{3d}$ are identical to or different from each other and each represents a C1-C6 alkyl group, a C2-C6 alkenyl group, a C3-C7 cycloalkyl group (the C1-C6 alkyl group, the C2-C6 alkenyl group, and the C3-C7 cycloalkyl group each may have optionally one or more substituents selected from the group consisting of halogen atom and cyano group}, a phenyl group, a triazolyl group, a pyridyl group, a pyrimidinyl group {the phenyl group, the triazolyl group, the pyridyl group, and the pyrimidinyl group each may have optionally one or more substituents selected from Group J}, $OR^{12}$, $CR^{30}$=$NOR^{17}$, a hydrogen atom, or a halogen atom.

[Embodiment P10] The present compound P wherein Q represents a group represented by formula Q1, $R^{3a}$ and $R^{3d}$ represent a hydrogen atom, $R^{3b}$ represents a C1-C6 alkyl group optionally having one or more halogen atoms, a cyclopropyl group, a hydrogen atom, or a halogen atom.

[Embodiment P11] The present compound P wherein Q represents a group represented by formula Q1, $R^{3a}$ represents a hydrogen atom, $R^{3b}$, and $R^{3d}$ combined together with two carbon atoms to which they are attached form a benzene ring, a pyrrole ring, a furan ring, a thiophene ring, a pyrazole ring, an imidazole ring, an oxazole ring, an isoxazole ring, a thiazole ring, an isothiazole ring, an oxadiazole ring, a thiadiazole ring, a pyridine ring, a pyridazine ring, a pyrimidine ring, a pyrazine ring {the benzene ring, the pyrrole ring, the furan ring, the thiophene ring, the pyrazole ring, the imidazole ring, the oxazole ring, the isoxazole ring, the thiazole ring, the isothiazole ring, the pyridine ring, the pyridazine ring, the pyrimidine ring, and the pyrazine ring each may have optionally one or more substituents selected from Group H}, or a triazole ring optionally having one or more substituents selected from Group I.

[Embodiment P12] The present compound P wherein Q represents a group represented by formula Q1, $R^{3a}$ represents a hydrogen atom, $R^{3b}$ and $R^{3d}$ combined together with two carbon atoms to which they are attached form a benzene ring {the benzene ring may have optionally one or more substituents selected from a group consisting of C1-C6 alkyl group optionally having one or more halogen atoms, and halogen atom}.

[Embodiment P13] The present compound P wherein $G^2$ represents $CR^{3b}$, $G^3$ represents $CR^{3c}$, a combination of $G^1$ and $G^4$ represents a combination in which $G^1$ represents $CR^{3a}$, and $G^4$ represents a nitrogen atom or $CR^{3d}$; or a combination in which $G^1$ represents a nitrogen atom, and $G^4$ represents $CR^{3d}$.

[Embodiment P14] The present compound P wherein $G^1$ represents CH, $G^2$ represents $CR^{3b}$, $G^3$ represents $CR^{3c}$, and $G^4$ represents CH.

[Embodiment P15] The present compound P wherein $G^1$ represents a nitrogen atom, $G^2$ represents $CR^{3b}$, $G^3$ represents $CR^{3c}$, and $G^4$ represents CH.

[Embodiment P16] The present compound P wherein $G^1$ represents CH, $G^2$ represents $CR^{3b}$, $G^3$ represents $CR^{3c}$, and $G^4$ represents a nitrogen atom.

[Embodiment P17] The present compound P wherein $G^2$ represents $CR^{3b}$, $G^3$ represents $CR^{3c}C$, a combination of $G^1$ and $G^4$ represents a combination in which $G^1$ represents CH, and $G^4$ represents a nitrogen atom or $CR^{3d}$; or a combination in which $G^1$ represents a nitrogen atom, and $G^4$ represents $CR^{3d}$.

[Embodiment P18] The compound according to the Embodiment P2 wherein $G^2$ represents $CR^{3b}$, $G^3$ represents $CR^{3c}$, a combination of $G^1$ and $G^4$ represents a combination in which $G^1$ represents CH, and $G^4$ represents a nitrogen atom or H; or a combination in which $G^1$ represents a nitrogen atom, and $G^4$ represents CH.

[Embodiment P19] The compound according to the Embodiment P3 wherein $G^2$ represents $CR^{3b}$, $G^3$ represents $CR^{3c}$, a combination of $G^1$ and $G^4$ represents a combination in which $G^1$ represents $CR^{3a}$, and $G^4$ represents a nitrogen atom or $CR^{3d}$; or a combination in which $G^1$ represents a nitrogen atom, and $G^4$ represents $CR^{3d}$.

[Embodiment P20] The compound according to the Embodiment P4 wherein $G^2$ represents $CR^{3b}$, $G^3$ represents $CR^{3c}$, a combination of $G^1$ and $G^4$ represents a combination in which $G^1$ represents CH, and $G^4$ represents a nitrogen atom or $CR^{3d}$; or a combination in which $G^1$ represents a nitrogen atom, and $G^4$ represents $CR^{3d}$.

[Embodiment P21] The compound according to the Embodiment P5 wherein $G^2$ represents $CR^{3b}$, $G^3$ represents $CR^{3c}$, a combination of $G^1$ and $G^4$ represents a combination in which $G^1$ represents CH, and $G^4$ represents a nitrogen atom or CH; or a combination in which $G^1$ represents a nitrogen atom, and $G^4$ represents $CR^{3d}$.

[Embodiment P22] The compound according to the Embodiment P1 wherein $G^1$ represents CH, $G^2$ represents $CR^{3b}$, $G^3$ represents $CR^{3c}$, and $G^4$ represents CH.

[Embodiment P23] The compound according to the Embodiment P2 wherein $G^1$ represents CH, $G^2$ represents $CR^{3b}$, $G^3$ represents $CR^{3c}$, and $G^4$ represents CH.

[Embodiment P24] The compound according to the Embodiment P3 wherein $G^1$ represents CH, $G^2$ represents $CR^{3b}$, $G^3$ represents $CR^{3c}$, and $G^4$ represents CH.

[Embodiment P25] The compound according to the Embodiment P4 wherein $G^1$ represents CH, $G^2$ represents $CR^{3b}$, $G^3$ represents $CR^{3c}$, and $G^4$ represents CH.

[Embodiment P26] The compound according to the Embodiment P5 wherein $G^1$ represents CH, $G^2$ represents $CR^{3b}$, $G^3$ represents $CR^{3c}$, and $G^4$ represents CH.

[Embodiment P27] The compound according to the Embodiment P1 wherein $G^1$ represents a nitrogen atom, $G^2$ represents $CR^{3b}$, $G^3$ represents $CR^{3c}$, and $G^4$ represents CH.

[Embodiment P28] The compound according to the Embodiment P2 wherein $G^1$ represents a nitrogen atom, $G^2$ represents $CR^{3b}$, $G^3$ represents $CR^{3c}$, and $G^4$ represents CH.

[Embodiment P29] The compound according to the Embodiment P3 wherein $G^1$ represents a nitrogen atom, $G^2$ represents $CR^{3b}$, $G^3$ represents $CR^{3c}$, and $G^4$ represents CH.

[Embodiment P30] The compound according to the Embodiment P4 wherein $G^1$ represents a nitrogen atom, $G^2$ represents $CR^{3b}$, $G^3$ represents $CR^{3c}$, and $G^4$ represents CH.

[Embodiment P31] The compound according to the Embodiment P5 wherein $G^1$ represents a nitrogen atom, $G^2$ represents $CR^{3b}$, $G^3$ represents $CR^{3c}$, and $G^4$ represents CH.

[Embodiment P32] The compound according to the Embodiment P1 wherein $G^1$ represents CH, $G^2$ represents $CR^{3b}$, $G^3$ represents $CR^{3c}$, and G represents a nitrogen atom.

[Embodiment P33] The compound according to the Embodiment P2 wherein $G^1$ represents CH, $G^2$ represents $CR^{3b}$, $G^3$ represents $CR^{3c}$, and $G^4$ represents a nitrogen atom.

[Embodiment P34] The compound according to the Embodiment P3 wherein $G^1$ represents CH, $G^2$ represents $CR^{3b}$, $G^3$ represents $CR^{3c}$, and $G^4$ represents a nitrogen atom.

[Embodiment P35] The compound according to the Embodiment P4 wherein $G^1$ represents CH, $G^2$ represents $CR^{3b}$, $G^3$ represents $CR^{3c}$, and $G^4$ represents a nitrogen atom.

[Embodiment P36] The compound according to the Embodiment P5 wherein $G^1$ represents CH, $G^2$ represents $CR^{3b}$, $G^3$ represents $CR^{3c}$, and $G^4$ represents a nitrogen atom.

[Embodiment P37] The present compound P wherein $R^2$ represents a C1-C6 alkyl group.

[Embodiment P38] The present compound P wherein $R^2$ represents an ethyl group.

[Embodiment P39] The compound according to the Embodiment P1 wherein $R^2$ represents a C1-C6 alkyl group.

[Embodiment P40] The compound according to the Embodiment P2 wherein $R^2$ represents a C1-C6 alkyl group.

[Embodiment P41] The compound according to the Embodiment P3 wherein $R^2$ represents a C1-C6 alkyl group.

[Embodiment P42] The compound according to the Embodiment P4 wherein $R^2$ represents a C1-C6 alkyl group.

[Embodiment P43] The compound according to the Embodiment P5 wherein $R^2$ represents a C1-C6 alkyl group.

[Embodiment P44] The compound according to the Embodiment P6 wherein $R^2$ represents a C1-C6 alkyl group.

[Embodiment P45] The compound according to the Embodiment P7 wherein $R^2$ represents a C1-C6 alkyl group.

[Embodiment P46] The compound according to the Embodiment P8 wherein $R^2$ represents a C1-C6 alkyl group.

[Embodiment P47] The compound according to the Embodiment P9 wherein $R^2$ represents a C1-C6 alkyl group.

[Embodiment P48] The compound according to the Embodiment P10 wherein $R^2$ represents a C1-C6 alkyl group.

[Embodiment P49] The compound according to the Embodiment P11 wherein $R^2$ represents a C1-C6 alkyl group.

[Embodiment P50] The compound according to the Embodiment P12 wherein $R^2$ represents a C1-C6 alkyl group.

[Embodiment P51] The compound according to the Embodiment P13 wherein $R^2$ represents a C1-C6 alkyl group.

[Embodiment P52] The compound according to the Embodiment P14 wherein $R^2$ represents a C1-C6 alkyl group.

[Embodiment P53] The compound according to the Embodiment P15 wherein $R^2$ represents a C1-C6 alkyl group.

[Embodiment P54] The compound according to the Embodiment P16 wherein $R^2$ represents a C1-C6 alkyl group.

[Embodiment P55] The compound according to the Embodiment P17 wherein $R^2$ represents a C1-C6 alkyl group.

[Embodiment P56] The compound according to the Embodiment P18 wherein $R^2$ represents a C1-C6 alkyl group.

[Embodiment P57] The compound according to the Embodiment P19 wherein $R^2$ represents a C1-C6 alkyl group.

[Embodiment P58] The compound according to the Embodiment P20 wherein $R^2$ represents a C1-C6 alkyl group.

[Embodiment P59] The compound according to the Embodiment P21 wherein $R^2$ represents a C1-C6 alkyl group.

[Embodiment P60] The compound according to the Embodiment P22 wherein $R^2$ represents a C1-C6 alkyl group.

[Embodiment P61] The compound according to the Embodiment P23 wherein $R^2$ represents a C1-C6 alkyl group.

[Embodiment P62] The compound according to the Embodiment P24 wherein $R^2$ represents a C1-C6 alkyl group.

[Embodiment P63] The compound according to the Embodiment P25 wherein $R^2$ represents a C1-C6 alkyl group.

[Embodiment P64] The compound according to the Embodiment P26 wherein $R^2$ represents a C1-C6 alkyl group.

[Embodiment P65] The compound according to the Embodiment P27 wherein $R^2$ represents a C1-C6 alkyl group.

[Embodiment P66] The compound according to the Embodiment P28 wherein $R^2$ represents a C1-C6 alkyl group.

[Embodiment P67] The compound according to the Embodiment P29 wherein $R^2$ represents a C1-C6 alkyl group.

[Embodiment P68] The compound according to the Embodiment P30 wherein $R^2$ represents a C1-C6 alkyl group.

[Embodiment P69] The compound according to the Embodiment P31 wherein $R^2$ represents a C1-C6 alkyl group.

[Embodiment P70] The compound according to the Embodiment P32 wherein $R^2$ represents a C1-C6 alkyl group.

[Embodiment P71] The compound according to the Embodiment P33 wherein $R^2$ represents a C1-C6 alkyl group.

[Embodiment P72] The compound according to the Embodiment P34 wherein $R^2$ represents a C1-C6 alkyl group.

[Embodiment P73] The compound according to the Embodiment P35 wherein $R^2$ represents a C1-C6 alkyl group.

[Embodiment P74] The compound according to the Embodiment P36 wherein $R^2$ represents a C1-C6 alkyl group.

[Embodiment P75] The compound according to the Embodiment P1 wherein $R^2$ represents an ethyl group.

[Embodiment P76] The compound according to the Embodiment P2 wherein $R^2$ represents an ethyl group.

[Embodiment P77] The compound according to the Embodiment P3 wherein $R^2$ represents an ethyl group.

[Embodiment P78] The compound according to the Embodiment P4 wherein $R^2$ represents an ethyl group.

[Embodiment P79] The compound according to the Embodiment P5 wherein $R^2$ represents an ethyl group.

[Embodiment P80] The compound according to the Embodiment P6 wherein $R^2$ represents an ethyl group.

[Embodiment P81] The compound according to the Embodiment P7 wherein $R^2$ represents an ethyl group.

[Embodiment P82] The compound according to the Embodiment P8 wherein $R^2$ represents an ethyl group.

[Embodiment P83] The compound according to the Embodiment P9 wherein $R^2$ represents an ethyl group.

[Embodiment P84] The compound according to the Embodiment P10 wherein $R^2$ represents an ethyl group.

[Embodiment P85] The compound according to the Embodiment P11 wherein $R^2$ represents an ethyl group.

[Embodiment P86] The compound according to the Embodiment P12 wherein $R^2$ represents an ethyl group.

[Embodiment P87] The compound according to the Embodiment P13 wherein $R^2$ represents an ethyl group.

[Embodiment P88] The compound according to the Embodiment P14 wherein $R^2$ represents an ethyl group.

[Embodiment P89] The compound according to the Embodiment P15 wherein $R^2$ represents an ethyl group.

[Embodiment P90] The compound according to the Embodiment P16 wherein $R^2$ represents an ethyl group.

[Embodiment P91] The compound according to the Embodiment P17 wherein $R^2$ represents an ethyl group.

[Embodiment P92] The compound according to the Embodiment P18 wherein $R^2$ represents an ethyl group.

[Embodiment P93] The compound according to the Embodiment P19 wherein $R^2$ represents an ethyl group.

[Embodiment P94] The compound according to the Embodiment P20 wherein $R^2$ represents an ethyl group.

[Embodiment P95] The compound according to the Embodiment P21 wherein $R^2$ represents an ethyl group.

[Embodiment P96] The compound according to the Embodiment P22 wherein $R^2$ represents an ethyl group.

[Embodiment P97] The compound according to the Embodiment P23 wherein $R^2$ represents an ethyl group.

[Embodiment P98] The compound according to the Embodiment P24 wherein $R^2$ represents an ethyl group.

[Embodiment P99] The compound according to the Embodiment P25 wherein $R^2$ represents an ethyl group.

[Embodiment P100] The compound according to the Embodiment P26 wherein $R^2$ represents an ethyl group.

[Embodiment P101] The compound according to the Embodiment P27 wherein $R^2$ represents an ethyl group.

[Embodiment P102] The compound according to the Embodiment P28 wherein $R^2$ represents an ethyl group.

[Embodiment P103] The compound according to the Embodiment P29 wherein $R^2$ represents an ethyl group.

[Embodiment P104] The compound according to the Embodiment P30 wherein $R^2$ represents an ethyl group.

[Embodiment P105] The compound according to the Embodiment P31 wherein $R^2$ represents an ethyl group.

[Embodiment P106] The compound according to the Embodiment P32 wherein $R^2$ represents an ethyl group.

[Embodiment P107] The compound according to the Embodiment P33 wherein $R^2$ represents an ethyl group.

[Embodiment P108] The compound according to the Embodiment P34 wherein $R^2$ represents an ethyl group.

[Embodiment P109] The compound according to the Embodiment P35 wherein $R^2$ represents an ethyl group.

[Embodiment P110] The compound according to the Embodiment P36 wherein $R^2$ represents an ethyl group.

[Embodiment P111] The compound according to any one of the Embodiment P1 to the Embodiment P110 or the present compound P wherein R1 represents a C1-C6 alkyl group having one or more substituents selected from a group consisting of halogen atom and cyano group; a cyclopropyl group optionally having one or more substituents selected from the group consisting of cyano group and halogen atom; $S(O)_mR^8$; or $OR^8$, $R^8$ represents a C1-C6 alkyl group having one or more substituents selected from a group consisting of halogen atom and cyano group.

[Embodiment P112] The compound according to the Embodiment P111 wherein $A^1$ represents $CR^{4a}$, $A^2$ represents a nitrogen atom, $R^{4a}$ represents a C1-C6 alkyl group optionally having one or more halogen atoms, a halogen atom or a hydrogen atom, $R^{6a}$, $R^{6b}$, $R^{6c}$ and $R^{6d}$ are identical to or different from each other and each represents a halogen atom or a hydrogen atom.

[Embodiment P113] The compound according to the Embodiment P111 wherein $R^{4a}$ represents a C1-C6 alkyl group optionally having one or more halogen atoms, $B^1$ represents $CR^{6a}$, a combination of $B^2$, $B^3$ and $B^4$ represents a combination in which $B^2$ represents $CR^1$, $B^3$ represents $CR^{6c}$, $B^4$ represents a nitrogen atom or $CR^{6d}$; a combination in which $B^2$ represents $CR^{6b}$, $B^3$ represents $CR^1$, and $B^4$ represents a nitrogen atom or $CR^{6d}$; or a combination in which $B^2$ represents $CR^{6b}$, $B^3$ represents $CR^{6c}$, and $B^4$ represents $CR^1$, and $R^{6a}$, $R^{6b}$, $R^{6c}$ and $R^{6d}$ are identical to or different from each other and each represents a halogen atom or a hydrogen atom.

[Embodiment P114] The compound according to the Embodiment P113 wherein $A^1$ represents $CR^{4a}$, and $A^2$ represents a nitrogen atom.

[Embodiment P115] The compound according to the Embodiment P111 wherein $A^1$ represents CH, and $A^2$ represents a nitrogen atom, $B^1$ represents CH, a combination of $B^2$, $B^3$ and $B^4$ represents a combination in which $B^2$ represents $CR^1$, $B^3$ represents CH, and $B^4$ represents a nitrogen atom or CH; a combination in which $B^2$ represents CH, $B^3$ represents $CR^1$, and $B^4$ represents a nitrogen atom or CH; a combination in which $B^2$ represents CH, $B^3$ represents CH, and $B^4$ represents $CR^1$.

[Embodiment P116] The compound according to the Embodiment P111 wherein $R^{4a}$ and $R^{4b}$ represent a hydrogen atom, $B^1$ represents CH, a combination of $B^2$, $B^3$ and $B^4$ represents a combination in which $B^2$ represents $CR^1$, $B^3$ represents CH, and $B^4$ represents CH; a combination in which $B^2$ represents CH, $B^3$ represents $CR^1$, and $B^4$ represents CH; or a combination in which $B^2$ represents CH, $B^3$ represents CH, and $B^4$ represents $CR^1$.

[Embodiment P117] The compound according to the Embodiment P111 wherein $A^1$ represents CH, $A^2$ represents a nitrogen atom, $B^1$ represents CH, a combination of $B^2$, $B^3$ and $B^4$ represents a combination in which $B^2$ represents $CR^1$, $B^3$ represents CH, and $B^4$ represents CH; a combination in which $B^2$ represents CH, $B^3$ represents $CR^1$, and $B^4$ represents CH; or a combination in which $B^2$ represents CH, $B^3$ represents CH, and $B^4$ represents $CR^1$.

[Embodiment P118] The compound according to any one of the Embodiment P1 to the Embodiment P110 or the present compound P wherein $B^1$ represents CH, a combination of $B^2$, $B^3$ and $B^4$ represents a combination in which $B^2$ represents $CR^1$, $B^3$ represents CH, and $B^4$ represents a nitrogen atom or CH; a combination in which $B^2$ represents CH, $B^3$ represents $CR^1$, $B^4$ represents a nitrogen atom or CH; or a combination in which $B^2$ represents CH, $B^3$ represents CH, and $B^4$ represents $CR^1$, $R^1$ represents a C1-C3 fluoroalkyl group, and $R^{4a}$ and $R^{4b}$ represents a hydrogen atom.

[Embodiment P119] The compound according to any one of the Embodiment P1 to the Embodiment P110 or the present compound P wherein $B^1$ represents CH, a combination of $B^2$, $B^3$ and $B^4$ represents a combination in which $B^2$ represents $CR^1$, $B^3$ represents CH, and $B^4$ represents CH; a combination in which $B^2$ represents CH, $B^3$ represents $CR^1$, and $B^4$ represents CH; or a combination in which $B^2$ represents CH, $B^3$ represents CH, and $B^4$ represents $CR^1$, $R^1$ represents a C1-C3 fluoroalkyl group, a C1-C3 fluoroalkoxy group, or $S(O)_mCF_3$, and $R^{4a}$ and $R^{4b}$ represent a hydrogen atom.

[Embodiment P120] The compound according to any one of the Embodiment P1 to the Embodiment P110 or the present compound P wherein $B^1$ represents CH, a combination of $B^2$, $B^3$ and $B^4$ represents a combination in which $B^2$ represents $CR^1$, $B^3$ represents CH, and $B^4$ represents a nitrogen atom or CH; a combination in which $B^2$ represents CH, $B^3$ represents $CR^1$, and $B^4$ represents a nitrogen atom or CH; a combination in which $B^2$ represents CH, $B^3$ represents CH, and $B^4$ represents $CR^1$, $R^1$ represents a C1-C3 fluoroalkyl group, $A^1$ represents CH, and $A^2$ represents a nitrogen atom.

[Embodiment P121] The compound according to any one of the Embodiment P1 to the Embodiment P110 or the present compound P wherein $B^1$ represents CH, a combination of $B^2$, $B^3$ and $B^4$ represents a combination in which $B^2$ represents $CR^1$, $B^3$ represents CH, and $B^4$ represents CH; a combination in which $B^2$ represents CH, $B^3$ represents $CR^1$, and $B^4$ represents CH; a combination in which $B^2$ represents CH, $B^3$ represents CH, and $B^4$ represents $CR^1$, $R^1$ represents a C1-C3 fluoroalkyl group, a C1-C3 fluoroalkoxy group, or $S(O)_mCF_3$, $A^1$ represents CH, and $A^2$ represents a nitrogen atom.

[Embodiment P122] The compound according to any one of the Embodiment P1 to the Embodiment P110 or the present compound P wherein $B^1$ represents CH, $B^4$ represents a nitrogen atom, a combination of $B^2$ and $B^3$ represents a combination in which $B^2$ represents $CR^1$, and $B^3$ represents CH; or a combination in which $B^2$ represents CH, and $B^3$ represents $CR^1$, $R^1$ represents a C1-C3 fluoroalkyl group, $A^1$ represents CH, and $A^2$ represents a nitrogen atom.

[Embodiment P123] The compound according to any one of the Embodiment P1 to the Embodiment P110 or the present compound P wherein $R^1$ represents a C1-C3 fluoroalkyl group, a C1-C3 fluoroalkoxy group, or $S(O)_mCF_3$, $A^1$ represents CH, $A^2$ represents a nitrogen atom, and $R^{6a}$, $R^{6b}$, $R^{6c}$ and $R^{6d}$ represent a hydrogen atom.

[Embodiment P124] The compound according to the Embodiment P111 wherein $A^1$ and $A^2$ represent a nitrogen atom, $R^{6a}$, $R^{6b}$, $R^{6c}$ and $R^{6d}$ are identical to or different from each other and each represents a halogen atom or a hydrogen atom.

[Embodiment P125] The compound according to the Embodiment P124 wherein $B^1$ represents $CR^{6a}$, a combination of $B^2$, $B^3$ and $B^4$ represents a combination in which $B^2$ represents $CR^1$, $B^3$ represents $CR^{6c}$, and $B^4$ represents a nitrogen atom or $CR^{6d}$; a combination in which $B^2$ represents $CR^{6b}$, and $B^3$ represents $CR^1$, and $B^4$ represents a nitrogen atom or $CR^{6d}$; or a combination in which $B^2$ represents $CR^{6b}$, $B^3$ represents $CR^{6c}$, and $B^4$ represents $CR^1$.

[Embodiment P126] The compound according to the Embodiment P124 wherein $B^1$ represents CH, a combination of $B^2$, $B^3$ and $B^4$ represents a combination in which $B^2$ represents $CR^1$, $B^3$ represents CH, and $B^4$ represents a nitrogen atom or CH; a combination in which $B^2$ represents CH, $B^3$ represents $CR^1$, and $B^4$ represents a nitrogen atom or CH; or a combination in which $B^2$ represents CH, $B^3$ represents CH, and $B^4$ represents $CR^1$.

[Embodiment P127] The compound according to the Embodiment P124 wherein B1 represents CH, a combination of $B^2$, $B^3$ and $B^4$ represents a combination in which $B^2$ represents $CR^1$, $B^3$ represents CH, and $B^4$ represents CH; a combination in which $B^2$ represents CH, $B^3$ represents $CR^1$, and $B^4$ represents CH; or a combination in which $B^2$ represents CH, $B^3$ represents CH, and $B^4$ represents $CR^1$.

[Embodiment P128] The compound according to any one of the Embodiment P1 to the Embodiment P110 or the present compound P wherein $A^1$ and $A^2$ represent a nitrogen atom, $B^1$ represents CH, a combination of $B^2$, $B^3$ and $B^4$ represents a combination in which $B^2$ represents $CR^1$, $B^3$ represents CH, and $B^4$ represents a nitrogen atom or CH; a combination in which $B^2$ represents CH, $B^3$ represents $CR^1$, and $B^4$ represents a nitrogen atom or CH; or a combination in which $B^2$ represents CH, $B^3$ represents CH, and $B^4$ represents $CR^1$, and $R^1$ represents a C1-C3 fluoroalkyl group.

[Embodiment P129] The compound according to any one of the Embodiment P1 to the Embodiment P110 or the present compound P wherein $A^1$ and $A^2$ represent a nitrogen atom, $B^1$ represents CH, a combination of $B^2$, $B^3$ and $B^4$ represents a combination in which $B^2$ represents $CR^1$, $B^2$ represents CH, and $B^4$ represents CH; a combination in which $B^2$ represents CH, $B^3$ represents $CR^1$, and $B^4$ represents CH; or a combination in which $B^2$ represents CH, $B^3$ represents CH, and $B^4$ represents $CR^1$, and $R^1$ represents a C1-C3 fluoroalkyl group, a C1-C3 fluoroalkoxy group, or $S(O)_mCF_3$.

[Embodiment P130] The compound according to any one of the Embodiment P1 to the Embodiment P110 or the present compound P wherein $A^1$ and $A^2$ represent a nitrogen atom, $B^1$ represents CH, $B^4$ represents a nitrogen atom, a combination of $B^2$ and $B^3$ represents a combination in which $B^2$ represents $CR^1$, and $B^3$ represents CH; or a combination in which $B^2$ represents CH, and $B^3$ represents $CR^1$, and $R^1$ represents a C1-C3 fluoroalkyl group.

[Embodiment P131] The compound according to any one of the Embodiment P1 to the Embodiment P110 or the present compound P wherein $A^1$ and $A^2$ represent a nitrogen atom, $R^1$ represents a C1-C3 fluoroalkyl group, a C1-C3 fluoroalkoxy group, or $S(O)_mCF_3$, and $R^{6a}$, $R^{6b}$, $R^{6c}$ and $R^{6d}$ represent a hydrogen atom.

[Embodiment P132] The compound according to any one of the Embodiment P1 to the Embodiment 110 or the present compound P wherein z represents an oxygen atom.

[Embodiment P133] The compound according to the Embodiment P111 or the present compound P wherein Z represents an oxygen atom.

[Embodiment P134] The compound according to the Embodiment P112 or the present compound P wherein Z represents an oxygen atom.

[Embodiment P135] The compound according to the Embodiment P113 or the present compound P wherein Z represents an oxygen atom.

[Embodiment P136] The compound according to the Embodiment P114 or the present compound P wherein Z represents an oxygen atom.

[Embodiment P137] The compound according to the Embodiment P115 or the present compound P wherein Z represents an oxygen atom.

[Embodiment P138] The compound according to the Embodiment P116 or the present compound P wherein Z represents an oxygen atom.

[Embodiment P139] The compound according to the Embodiment P117 or the present compound P wherein Z represents an oxygen atom.

[Embodiment P140] The compound according to the Embodiment P118 or the present compound P wherein Z represents an oxygen atom.

[Embodiment P141] The compound according to the Embodiment P119 or the present compound P wherein Z represents an oxygen atom.

[Embodiment P142] The compound according to the Embodiment P120 or the present compound P wherein Z represents an oxygen atom.

[Embodiment P143] The compound according to the Embodiment P121 or the present compound P wherein Z represents an oxygen atom.

[Embodiment P144] The compound according to the Embodiment P122 or the present compound P wherein Z represents an oxygen atom.

[Embodiment P145] The compound according to the Embodiment P123 or the present compound P wherein Z represents an oxygen atom.

[Embodiment P146] The compound according to the Embodiment P124 or the present compound P wherein Z represents an oxygen atom.

[Embodiment P147] The compound according to the Embodiment P125 or the present compound P wherein Z represents an oxygen atom.

[Embodiment P148] The compound according to the Embodiment P126 or the present compound P wherein Z represents an oxygen atom.

[Embodiment P149] The compound according to the Embodiment P127 or the present compound P wherein Z represents an oxygen atom.

[Embodiment P150] The compound according to the Embodiment P128 or the present compound P wherein Z represents an oxygen atom.

[Embodiment P151] The compound according to the Embodiment P129 or the present compound P wherein Z represents an oxygen atom.

[Embodiment P152] The compound according to the Embodiment P130 or the present compound P wherein Z represents an oxygen atom.

[Embodiment P153] The compound according to the Embodiment P131 or the present compound P wherein Z represents an oxygen atom.

[Embodiment P2-1] The present compound P wherein Z represents an oxygen atom, $B^1$ represents CH, a combination of $B^2$, $B^3$ and $B^4$ represents a combination in which $B^2$ represents $CR^1$, $B^3$ represents CH, and $B^4$ represents CH; a combination in which $B^2$ represents CH, $B^3$ represents $CR^1$, $B^4$ represents CH; or a combination in which $B^2$ represents CH, $B^3$ represents CH, and $B^4$ represents $CR^1$, $R^1$ represents a C1-C3 chain hydrocarbon group having one or more halogen atoms, S(O)m$R^8$, $OR^8$, or halogen atom, $R^8$ represents a C1-C3 chain hydrocarbon group having one or more halogen atoms.

[Embodiment P2-2] The compound according to the Embodiment P2-1 wherein a combination of $B^2$, $B^3$ and $B^4$ represents a combination in which $B^2$ represents $CR^1$, $B^3$ represents CH, and $B^4$ represents CH; or a combination in which $B^2$ represents CH, $B^3$ represents $CR^1$, and $B^4$ represents CH.

[Embodiment P2-3] The compound according to the Embodiment P2-1 wherein $A^1$ represents CH, and $A^2$ represents a nitrogen atom or CH.

[Embodiment P2-4] The compound according to the Embodiment P2-2 wherein $A^1$ represents CH, and $A^2$ represents a nitrogen atom or CH.

[Embodiment P2-5] The compound according to the Embodiment P2-1 wherein $A^1$ and $A^2$ represent a nitrogen atom.

[Embodiment P2-6] The compound according to the Embodiment P2-2 wherein $A^1$ and $A^2$ represent a nitrogen atom.

[Embodiment P2-7] The present compound P wherein $R^2$ represents an ethyl group, $R^{3a}$ represents a hydrogen atom, $R^{3b}$, $R^{3c}$ and $R^{3d}$ are identical to or different from each other and each represents a C1-C3 chain hydrocarbon group optionally having one or more halogen atoms, a C3-C4 cycloalkyl group optionally having one or more halogen atoms, a phenyl group, a pyridyl group, a pyrimidinyl group {the phenyl group, the pyridyl group, and the pyrimidinyl group each may have optionally one or more substituents selected from Group P}, $OR^{12}$, a hydrogen atom, or halogen atom, $R^{12}$ represents a C1-C3 chain hydrocarbon group optionally having one or more halogen atoms, a C3-C4 cycloalkyl group optionally having one or more halogen atoms, $G^1$ represents CH, $G^2$ represents $CR^{3b}$, $G^3$ represents $CR^{3c}$, $G^4$ represents $CR^{3d}$ or a nitrogen atom, when Q represents a group represented by formula Q1, $R^{3b}$ and $R^{3d}$ combined together with two carbon atoms to which they are attached may form a benzene ring optionally having one or more substituents selected from Group P, Group P: a group consisting of a C1-C3 alkyl group optionally having one or more halogen atoms, a C1-C3 alkoxy group optionally having one or more halogen atoms, and a halogen atom.

[Embodiment P2-8] The present compound P wherein $R^{3a}$ and $R^{3d}$ represent a hydrogen atom, $R^{3b}$ and $R^{3c}$ are identical to or different from each other and each represents a C1-C3 chain hydrocarbon group optionally having one or more halogen atoms, a C3-C4 cycloalkyl group optionally having one or more halogen atoms, a phenyl group, a pyridyl group, pyrimidinyl group {the phenyl group, the pyridyl group, and the pyrimidinyl group may have optionally one or more substituents selected from Group P}, $OR^{12}$, a hydrogen atom, or halogen atom, $R^{12}$ represents a C1-C3 chain hydrocarbon group optionally having one or more halogen atoms, a C3-C4 cycloalkyl group optionally having one or more halogen atoms, $G^1$ represents CH, $G^2$ represents $CR^{3b}$, $G^3$ represents $CR^{3c}$, $G^4$ represents CH or a nitrogen atom.

[Embodiment P2-9] The compound according to the Embodiment P2-7 wherein Z represents an oxygen atom, $B^1$ represents CH, a combination of $B^2$, $B^3$ and $B^4$ represents a combination in which $B^2$ represents $CR^1$, $B^3$ represents CH, and $B^4$ represents CH; a combination in which $B^2$ represents CH, $B^3$ represents $CR^1$, and $B^4$ represents CH; or a combination in which $B^2$ represents CH, $B^3$ represents CH, and $B^4$ represents $CR^1$, $R^1$ represents a C1-C3 chain hydrocarbon group having one or more halogen atoms, $S(O)_mR^8$, $OR^8$, or halogen atom, $R^8$ represents a C1-C3 chain hydrocarbon group having one or more halogen atoms.

[Embodiment P2-10] The compound according to the Embodiment P2-8 wherein Z represents an oxygen atom, $B^1$ represents CH, a combination of $B^2$, $B^3$ and $B^4$ represents a combination in which $B^2$ represents $CR^1$, $B^3$ represents CH, and $B^4$ represents CH; a combination in which $B^2$ represents CH, $B^3$ represents $CR^1$, and $B^4$ represents CH; or a combination in which $B^2$ represents CH, $B^3$ represents CH, $B^4$ represents $CR^1$, $R^1$ represents a C1-C3 chain hydrocarbon group having one or more halogen atoms, $S(O)_mR^8$, $OR^8$, or halogen atom, and $R^8$ represents a C1-C3 chain hydrocarbon group having one or more halogen atoms.

[Embodiment P2-11] The compound according to the Embodiment P2-7 wherein a combination of $B^2$, $B^3$ and $B^4$ represents a combination in which $B^2$ represents $CR^1$, $B^3$ represents CH, and $B^4$ represents CH; or a combination in which $B^2$ represents CH, $B^3$ represents $CR^1$, and $B^4$ represents CH.

[Embodiment P2-12] The compound according to the Embodiment P2-8 wherein a combination of $B^2$, $B^3$ and $B^4$ represents a combination in which $B^2$ represents $CR^1$, $B^3$ represents CH, and $B^4$ represents CH; or a combination in which $B^2$ represents CH, $B^3$ represents $CR^1$, and $B^4$ represents CH.

[Embodiment P2-13] The compound according to any one of the Embodiment P2-7 wherein $A^1$ represents CH, and $A^2$ represents a nitrogen atom or CH.

[Embodiment P2-14] The compound according to the Embodiment P2-8 wherein $A^1$ represents CH, and $A^2$ represents a nitrogen atom or CH.

[Embodiment P2-15] The compound according to the Embodiment P2-9 wherein $A^1$ represents CH, and $A^2$ represents a nitrogen atom or CH.

[Embodiment P2-16] The compound according to the Embodiment P2-10 wherein $A^1$ represents CH, and $A^2$ represents a nitrogen atom or CH.

[Embodiment P2-17] The compound according to the Embodiment P2-li wherein $A^1$ represents CH, and $A^2$ represents a nitrogen atom or CH.

[Embodiment P2-18] The compound according to the Embodiment P2-7 wherein $A^1$ and $A^2$ represents a nitrogen atom.

[Embodiment P2-19] The compound according to the Embodiment P2-8 wherein $A^1$ and $A^2$ represents a nitrogen atom.

[Embodiment P2-20] The compound according to the Embodiment P2-9 wherein $A^1$ and $A^2$ represents a nitrogen atom.

[Embodiment P2-21] The compound according to the Embodiment P2-10 wherein $A^1$ and $A^2$ represents a nitrogen atom.

[Embodiment P2-22] The compound according to the Embodiment P2-11 wherein $A^1$ and $A^2$ represents a nitrogen atom.

[Embodiment P2-23] The present compound P or the compound according to any one of the Embodiment P2-1 to the Embodiment P2-22 wherein Q represents a group represented by formula Q1.

[Embodiment P2-24] The present compound P or the compound according to any one of the Embodiment P2-1 to the Embodiment P2-22 wherein Q represents a group represented by formula Q2.

[Embodiment P2-25] The present compound P or the compound according to any one of the Embodiment P2-1 to the Embodiment P2-22 wherein Q represents a group represented by formula Q1, and $R^2$ represents an ethyl group.

[Embodiment P2-26] The present compound P or the compound according to any one of the Embodiment P2-1 to the Embodiment P2-22 wherein Q represents a group represented by formula Q2, and $R^2$ represents an ethyl group.

[Embodiment P2-27] The present compound P or the compound according to any one of the Embodiment P2-1 to the Embodiment P2-22 wherein Q represents a group represented by formula Q1, $R^2$ represents an ethyl group, and n is 2.

[Embodiment P2-28] The present compound P or the compound according to any one of the Embodiment P2-1 to the Embodiment P2-22 wherein Q represents a group represented by formula Q2, $R^2$ represents an ethyl group, and n is 2.

[Embodiment P3-1] The present compound P wherein a combination of $B^2$, $B^3$ and $B^4$ represents a combination in which $B^2$ represents $CR^1$, $B^3$ represents CH, and $B^4$ represents CH.

[Embodiment P3-2] The present compound P wherein $A^1$ represents CH, and $A^2$ represents a nitrogen atom or CH.

[Embodiment P3-3] The present compound P wherein $A^1$ and $A^2$ represents a nitrogen atom.

Examples of the Embodiment of the intermediate compound A include the followings.

[Embodiment A1] The intermediate compound A wherein $R^{3a}$ represents a hydrogen atom, $R^{3b}$, $R^{3c}$ and $R^{3d}$ are identical to or different from each other and each represents a C1-C6 alkyl group, a C2-C6 alkenyl group, a C3-C7 cycloalkyl group {the C1-C6 alkyl group, the C2-C6 alkenyl group, and the C3-C7 cycloalkyl group each may have optionally one or more substituents selected from the group consisting of halogen atom and cyano group}, a phenyl group, a triazolyl group, a pyridyl group, a pyrimidinyl group {the phenyl group, the triazolyl group, the pyridyl group, and the pyrimidinyl group each may have optionally one or more substituents selected from Group J}, $OR^{12}$, $CR^{30}$═$NOR^{17}$, a hydrogen atom, or halogen atom, when Q represents a group represented by formula Q1, and $R^{3b}$ and $R^{3d}$ combined together with two carbon atoms to which they are attached may form a benzene ring {the benzene ring may have optionally one or more substituents selected from a group consisting of C1-C6 alkyl group optionally having one or more halogen atoms, and halogen atom}.

[Embodiment A2] The intermediate compound A wherein $R^{3a}$ and $R^{3d}$ represent a hydrogen atom, $R^{3b}$ and $R^{3c}$ are identical to or different from each other and each represents a C1-C6 alkyl group optionally having one or more halogen atoms, a cyclopropyl group, a hydrogen atom, or a halogen atom, when Q represents a group represented by formula Q1, and $R^{3b}$ and $R^{3d}$ combined together with two carbon atoms to which they are attached may form a benzene ring {the benzene ring may have optionally one or more substituents selected from a group consisting of C1-C6 alkyl group optionally having one or more halogen atoms, and halogen atom}.

[Embodiment A3] The compound according to the Embodiment A1 wherein Q represents a group represented by formula Q2.

[Embodiment A4] The compound according to the Embodiment A2 wherein Q represents a group represented by formula Q2.

{Embodiment A5] The compound according to the Embodiment A1 wherein Q represents a group represented by formula Q1.

{Embodiment A6] The compound according to the Embodiment A2 wherein Q represents a group represented by formula 01.

[Embodiment A7] The intermediate compound A wherein Q represents a group represented by formula Q1, $R^{3a}$ represents a hydrogen atom, $R^{3b}$ and $R^{3d}$ are identical to or different from each other and each represents a C1-C6 alkyl group, a C2-C6 alkenyl group, a C3-C7 cycloalkyl group {the C1-C6 alkyl group, the C2-C6 alkenyl group, and the C3-C7 cycloalkyl group each may have optionally one or more substituents selected from the group consisting of halogen atom and cyano group}, a phenyl group, a pyridyl group, a pyrimidinyl group {the phenyl group, the pyridyl group, and the pyrimidinyl group each may have optionally one or more substituents selected from Group J}.

[Embodiment A8] The intermediate compound A wherein Q represents a group represented by formula Q1, $R^{3a}$ and $R^{3d}$ represent a hydrogen atom, $R^{3b}$ represents a C1-C6 alkyl group optionally having one or more halogen atoms, a cyclopropyl group, a hydrogen atom, or a halogen atom.

[Embodiment 9] The intermediate compound A wherein Q represents a group represented by formula Q1, $R^{3a}$ represents a hydrogen atom, $R^{3b}$ and $R^{3d}$ combined together with two carbon atoms to which they are attached form a benzene ring, a pyrrole ring, a furan ring, a thiophene ring, a pyrazole ring, an imidazole ring, an oxazole ring, an isoxazole ring, a thiazole ring, an isothiazole ring, an oxadiazole ring, a thiadiazole ring, a pyridine ring, a pyridazine ring, a pyrimidine ring, a pyrazine ring {the benzene ring, the pyrrole ring, the furan ring, the thiophene ring, the pyrazole ring, the imidazole ring, the oxazole ring, the isoxazole ring, the thiazole ring, the isothiazole ring, the pyridine ring, the pyridazine ring, the pyrimidine ring, and the pyrazine ring each may have optionally one or more substituents selected from Group H}, or a triazole ring optionally having one or more substituents selected from Group I.

[Embodiment A10] The intermediate compound A wherein Q represents a group represented by formula Q1, $R^{3a}$ represents a hydrogen atom, $R^{3b}$ and $R^{3d}$ combined together with two carbon atoms to which they are attached form a benzene ring {the benzene ring may have optionally one or more substituents selected from a group consisting of C1-C6 alkyl group optionally having one or more halogen atoms, and halogen atom}.

[Embodiment A11] The intermediate compound A wherein $G^2$ represents $CR^{3b}$, $G^3$ represents $CR^{3c}$, a combination of $G^1$ and $G^4$ represents a combination in which $G^1$ represents $CR^{3a}$, and $G^4$ represents a nitrogen atom or $CR^{3d}$; or a combination in which $G^1$ represents a nitrogen atom, and $G^4$ represents $CR^{3d}$.

[Embodiment A12] The intermediate compound A wherein $G^1$ represents CH, $G^2$ represents $CR^{3b}$, $G^3$ represents $CR^{3c}$, and $G^4$ represents CH.

[Embodiment A13] The compound according to the Embodiment A1 wherein $G^2$ represents $CR^{3b}$, $G^3$ represents $CR^{3c}$, a combination of $G^1$ and $G^4$ represents a combination in which $G^1$ represents CH, and $G^4$ represents a nitrogen atom or $CR^{3d}$; a combination in which $G^1$ represents a nitrogen atom, and $G^4$ represents $CR^{3d}$.

[Embodiment A14] The compound according to the Embodiment A2 wherein $G^2$ represents $CR^{3b}$, $G^3$ represents $CR^{3c}$, a combination of $G^1$ and $G^4$ represents a combination in which $G^1$ represents CH, and $G^4$ represents a nitrogen atom or CH; or a combination in which $G^1$ represents a nitrogen atom, and $G^4$ represents CH.

[Embodiment A15] The compound according to the Embodiment A3, wherein $G^2$ represents $CR^{3b}$, $G^3$ represents $CR^{3c}$, a combination of $G^1$ and $G^4$ represents a combination in which $G^1$ represents CH, and $G^4$ represents a nitrogen atom or $CR^{3d}$; or a combination in which $G^1$ represents a nitrogen atom, and $G^4$ represents $CR^{3d}$.

[Embodiment A16] The compound according to the Embodiment A4, wherein $G^2$ represents $CR^{3b}$, $G^3$ represents $CR^{3c}$, a combination of $G^1$ and $G^4$ represents a combination in which $G^1$ represents CH, and $G^4$ represents a nitrogen atom or CH; or a combination in which $G^1$ represents a nitrogen atom, and $G^4$ represents CH.

[Embodiment A17] The compound according to the Embodiment A1, wherein $G^1$ represents CH, G represents $CR^{3b}$, $G^3$ represents $CR^{3c}$, and $G^4$ represents CH.

[Embodiment A18] The compound according to the Embodiment A2, wherein $G^1$ represents CH, $G^2$ represents $CR^{3b}$, $G^3$ represents $CR^{3c}$, and $G^4$ represents CH.

[Embodiment A19] The compound according to the Embodiment A3, wherein $G^1$ represents CH, $G^2$ represents $CR^{3b}$, $G^3$ represents $CR^{3c}$, and $G^4$ represents CH.

[Embodiment A20] The compound according to the Embodiment A4, wherein $G^1$ represents CH, $G^2$ represents $CR^{3b}$, $G^3$ represents $CR^{3c}$, and $G^4$ represents CH.

[Embodiment A21] The intermediate compound A, wherein $R^2$ represents a C1-C6 alkyl group.

[Embodiment A22] The intermediate compound A wherein $R^2$ represents an ethyl group.

[Embodiment A23] The compound according to the Embodiment A1, wherein $R^2$ represents a C1-C6 alkyl group.

[Embodiment A24] The compound according to the Embodiment A2, wherein $R^2$ represents a C1-C6 alkyl group.

[Embodiment A25] The compound according to the Embodiment A3, wherein $R^2$ represents a C1-C6 alkyl group.

[Embodiment A26] The compound according to the Embodiment A4, wherein $R^2$ represents a C1-C6 alkyl group.

[Embodiment A27] The compound according to the Embodiment A5, wherein $R^2$ represents a C1-C6 alkyl group.

[Embodiment A28] The compound according to the Embodiment A6, wherein $R^2$ represents a C1-C6 alkyl group.

[Embodiment A29] The compound according to the Embodiment A7, wherein $R^2$ represents a C1-C6 alkyl group.

[Embodiment A30] The compound according to the Embodiment A8, wherein $R^2$ represents a C1-C6 alkyl group.

[Embodiment A31] The compound according to the Embodiment A9, wherein $R^2$ represents a C1-C6 alkyl group.

[Embodiment A32] The compound according to the Embodiment A10, wherein $R^2$ represents a C1-C6 alkyl group.

[Embodiment A33] The compound according to the Embodiment A11, wherein $R^2$ represents a C1-C6 alkyl group.

[Embodiment A34] The compound according to the Embodiment A12, wherein $R^2$ represents a C1-C6 alkyl group.

[Embodiment A35] The compound according to the Embodiment A13, wherein $R^2$ represents a C1-C6 alkyl group.

[Embodiment A36] The compound according to the Embodiment A14, wherein $R^2$ represents a C1-C6 alkyl group.

[Embodiment A37] The compound according to the Embodiment A15, wherein $R^2$ represents a C1-C6 alkyl group.

[Embodiment A38] The compound according to the Embodiment A16, wherein $R^2$ represents a C1-C6 alkyl group.

[Embodiment A39] The compound according to the Embodiment A17, wherein $R^2$ represents a C1-C6 alkyl group.

[Embodiment A40] The compound according to the Embodiment A18, wherein $R^2$ represents a C1-C6 alkyl group.

[Embodiment A41] The compound according to the Embodiment A19, wherein $R^2$ represents a C1-C6 alkyl group.

[Embodiment A42] The compound according to the Embodiment A20, wherein $R^2$ represents a C1-C6 alkyl group.

[Embodiment A43] The compound according to the Embodiment A1, wherein $R^2$ represents an ethyl group.

[Embodiment A44] The compound according to the Embodiment A2, wherein $R^2$ represents an ethyl group.

[Embodiment A45] The compound according to the Embodiment A3, wherein $R^2$ represents an ethyl group.

[Embodiment A46] The compound according to the Embodiment A4, wherein $R^2$ represents an ethyl group.

[Embodiment A47] The compound according to the Embodiment A5, wherein $R^2$ represents an ethyl group.

[Embodiment A48] The compound according to the Embodiment A6, wherein $R^2$ represents an ethyl group.

[Embodiment A49] The compound according to the Embodiment A7, wherein $R^2$ represents an ethyl group.

[Embodiment A50] The compound according to the Embodiment A8, wherein $R^2$ represents an ethyl group.

[Embodiment A51] The compound according to the Embodiment A9, wherein $R^2$ represents an ethyl group.

[Embodiment A52] The compound according to the Embodiment A10, wherein $R^2$ represents an ethyl group.

[Embodiment A53] The compound according to the Embodiment A11, wherein $R^2$ represents an ethyl group.

[Embodiment A54] The compound according to the Embodiment A12, wherein $R^2$ represents an ethyl group.

[Embodiment A55] The compound according to the Embodiment A13, wherein $R^2$ represents an ethyl group.

[Embodiment A56] The compound according to the Embodiment A14, wherein $R^2$ represents an ethyl group.

[Embodiment A57] The compound according to the Embodiment A15, wherein $R^2$ represents an ethyl group.

[Embodiment A58] The compound according to the Embodiment A16, wherein $R^2$ represents an ethyl group.

[Embodiment A59] The compound according to the Embodiment A17, wherein $R^2$ represents an ethyl group.

[Embodiment A60] The compound according to the Embodiment A18, wherein $R^2$ represents an ethyl group.

[Embodiment A61] The compound according to the Embodiment A19, wherein $R^2$ represents an ethyl group.

[Embodiment A62] The compound according to the Embodiment A20, wherein $R^2$ represents an ethyl group.

[Embodiment A63] The compound according to any one of the Embodiment A1 to the Embodiment A62 or the intermediate compound A, wherein a combination of $B^{2b}$, $B^{3c}$ and $B^{4d}$ represents a combination in which $B^{2b}$ represents $CR^1$, $B^3$ represents $CR^{6cc}$, and $B^{4d}$ represents a nitrogen atom or $CR^{6dd}$; a combination in which $B^{2b}$ represents $CR^{6bb}$, $B^{3c}$ represents $CR^1$, and $B^{4d}$ represents a nitrogen atom or $CR^{6cc}$; or a combination in which $B^{2b}$ represents $CR^{6bb}$, $B^{3c}$ represents $CR^{6cc}$, and $B^{4d}$ represents $CR^1$, $R^{6bb}$, $R^{6cc}$ and $R^{6dd}$ are identical to or different from each other and each represents a halogen atom or a hydrogen atom, $R^1$ represents a C1-C6 alkyl group having one or more substituents selected from a group consisting of halogen atom and cyano group; a cyclopropyl group optionally having one or more substituents selected from the group consisting of cyano group and halogen atom; $S(O)_mR^8$; or $OR^8$, $R^8$ represents a C1-C6 alkyl group having one or more substituents selected from a group consisting of halogen atom and cyano group.

[Embodiment A64] The compound according to the Embodiment A1 to the Embodiment A62 or the intermediate compound A, wherein a combination of $B^{2b}$, $B^{3c}$ and $B^{4c}$ represents a combination in which $B^{2b}$ represents $CR^1$, $B^{3c}$ represents $CR^{6cc}$, and $B^{4d}$ represents a nitrogen atom or $CR^{6dd}$; a combination in which $B^{2b}$ represents $CR^{6bb}$, $B^{3c}$ represents $CR^1$, and $B^{4d}$ represents a nitrogen atom or $CR^{6dd}$; or a combination in which $B^{2b}$ represents $CR^{6bb}$, $B^{3c}$ represents $CR^{6cc}$, and $B^{4d}$ represents $CR^1$, $R^{6bb}$, $R^{6cc}$ and $R^{6dd}$ are identical to or different from each other and each represents a halogen atom or a hydrogen atom, and $R^1$ represents C1-C3 fluoroalkyl group or $S(O)_mCF_3$.

[Embodiment A65] The compound according to any one of the Embodiment A1 to the Embodiment A62 or the intermediate compound A, wherein a combination of $B^{2b}$, $B^{3c}$ and $B^{4d}$ represents a combination in which $B^{2b}$ represents $CR^1$, $B^{3c}$ represents CH, and $B^{4d}$ represents CH; a combination in which $B^{2b}$ represents CH, $B^{3c}$ represents $CR^1$, and $B^{4d}$ represents CH; or a combination in which $B^{2b}$ represents CH, $B^{3c}$ represents CH, and $B^{4d}$ represents $CR^1$, $R^1$ represents a C1-C3 fluoroalkyl group or $S(O)_mCF_3$.

[Embodiment A66] The compound according to any one of the Embodiment A1 to the Embodiment A62 or the intermediate compound A, wherein a combination of $B^{2b}$, $B^{3c}$ and $B^{4d}$ represents a combination in which $B^{2b}$ represents $CR^1$, $B^{3c}$ represents CH, and $B^{4d}$ represents a nitrogen atom or CH; a combination in which $B^{2b}$ represents CH, $B^{3c}$ represents $CR^1$, and $B^{4d}$ represents a nitrogen atom or CH; or a combination in which $B^{2b}$ represents CH, $B^{3c}$ represents CH, and $B^{4d}$ represents $CR^1$, $R^1$ represents a C1-C3 fluoroalkyl group.

[Embodiment A67] The compound according to any one of the Embodiment A1 to the Embodiment A62 or the intermediate compound A, wherein a combination of $B^{2b}$, $B^{3c}$ and $B^{4d}$ represents a combination in which $B^{2b}$ represents $CR^1$, $B^{3c}$ represents CH, and $B^{4d}$ represents CH; a combination in which $B^{2b}$ represents CH, $B^{3c}$ represents $CR^1$, and $B^{4d}$ represents CH; or a combination in which $B^{2b}$ represents CH, $B^{3c}$ represents CH, and $B^{4d}$ represents $CR^1$, and $R^1$ represents a C1-C3 fluoroalkyl group.

[Embodiment A68] The compound according to any one of the Embodiment A1 to the Embodiment A62 or the intermediate compound A, wherein $B^{4d}$ represents a nitrogen atom, a combination of $B^{3c}$ and $B^{4d}$ represents a combination in which $B^{2b}$ represents $CR^1$, and $B^{3c}$ represents CH; or a combination in which $B^{2b}$ represents CH, and $B^{3c}$ represents $CR^1$, and $R^1$ represents a C1-C3 fluoroalkyl group.

[Embodiment A69] The intermediate compound A, wherein a combination of $B^{2b}$, $B^{3c}$ and $B^{4d}$ represents a combination in which $B^{2b}$ represents $CR^1$, $B^{3c}$ represents CH, and $B^{4d}$ represents a nitrogen atom or CH; a combination in which $B^{2b}$ represents CH, $B^{3c}$ represents $CR^1$, and $B^{4d}$ represents a nitrogen atom or CH; or a combination in which $B^{2b}$ represents CH, $B^{3c}$ represents CH, and $B^{4d}$ represents $CR^1$, $R^1$ represents a trifluoromethyl group, $R^2$ represents an ethyl group, $G^1$ represents CH, $G^2$ represents $CR^{3b}$, $G^3$ represents $CR^{3c}$, and $G^4$ represents CH, $R^{3b}$ and $R^{3c}$ are identical to or different from each other and each represents a cyclopropyl group, a halogen atom or a hydrogen atom, and $R^{3d}$ represents a hydrogen atom.

Examples of the Embodiment of the intermediate compound B include the followings.

[Embodiment B1] The intermediate compound B, wherein a combination of $B^{2b}$, $B^{3c}$ and $B^{4d}$ represents a combination in which $B^{2b}$ represents $CR^1$, $B^{3c}$ represents $CR^{6cc}$, and $B^{4d}$ represents a nitrogen atom or $CR^{6dd}$; a combination in which $B^{2b}$ represents $CR^{6bb}$, $B^{3c}$ represents $CR^1$, and $B^{4d}$ represents a nitrogen atom or $CR^{6dd}$; or a combination in which $B^{2b}$ represents $CR^{6bb}$, $B^{3c}$ represents $CR^{6cc}$, and $B^{4d}$ represents $CR^1$, a combination $R^{6bb}$, $R^{6cc}$ and $R^{6dd}$ are identical to or different from each other and each represents a halogen atom or a hydrogen atom, $R^1$ represents a C1-C6 alkyl group having one or more substituents selected from a group consisting of halogen atom and cyano group; a cyclopropyl group optionally having one or more substituents selected from the group consisting of cyano group and halogen atom; $S(O)_mR^8$; or $OR^8$, $R^8$ represents a C1-C6 alkyl group having one or more substituents selected from a group consisting of halogen atom and cyano group, and $R^{4aa}$ represents a halogen atom or a hydrogen atom.

[Embodiment B2] The intermediate compound B wherein a combination of $B^{2b}$, $B^{3c}$ and $B^{4d}$ represents a combination in which $B^{2b}$ represents $CR^1$, $B^{3c}$ represents $CR^{6cc}$, and $B^{4d}$ represents a nitrogen atom or $CR^{6dd}$; a combination in which $B^{2b}$ represents $CR^{6bb}$, $B^{3c}$ represents $CR^1$, and $B^{4c}$ represents a nitrogen atom or $CR^{6dd}$; a combination in which $B^{2b}$ represents $CR^{6bb}$, $B^{3c}$ represents $CR^{6cc}$, and $B^{4d}$ represents $CR^1$; $R^{6bb}$, $R^{6cc}$ and $R^{6dd}$ are identical to or different from each other and each represents a halogen atom or a hydrogen atom, $R^1$ represents a C1-C3 fluoroalkyl group or $S(O)_mCF_3$, and $R^{4aa}$ represents a halogen atom or a hydrogen atom.

[Embodiment B3] The intermediate compound B wherein a combination of $B^{2b}$, $B^{3c}$ and $B^{4d}$ represents a combination in which $B^{2b}$ represents $CR^1$, $B^{3c}$ represents CH, and $B^{4d}$ represents CH; a combination in which $B^{2b}$ represents CH, $B^{3c}$ represents $CR^1$, and $B^{4d}$ represents CH; or a combination in which $B^{2b}$ represents CH, $B^{3c}$ represents CH, and $B^{4d}$ represents $CR^1$, and $R^1$ represents a C1-C3 fluoroalkyl group or $S(O)_mCF_3$.

[Embodiment B4] The intermediate compound B wherein a combination of $B^{2b}$, $B^{3c}$ and $B^{4d}$ represents a combination in which $B^{2b}$ represents $CR^1$, $B^{3c}$ represents CH, and $B^{4d}$ represents a nitrogen atom or CH; a combination in which $B^{2b}$ represents CH, $B^{3c}$ represents $CR^1$, and $B^{4d}$ represents a nitrogen atom or CH; or a combination in which $B^{2b}$ represents CH, $B^{3c}$ represents CH, and $B^{4d}$ represents $CR^1$, $R^1$ represents a C1-C3 fluoroalkyl group, and $R^{4aa}$ represents a hydrogen atom.

[Embodiment B5] The intermediate compound B wherein a combination of $B^{2b}$, $B^{3c}$ and $B^{4d}$ represents a combination in which $B^{2b}$ represents $CR^1$, $B^{3c}$ represents CH, and $B^{4d}$ represents CH; a combination in which $B^{2b}$ represents CH, $B^{3c}$ represents $CR^1$, and $B^{4d}$ represents CH; or a combination in which $B^{2b}$ represents CH, $B^{3c}$ represents CH, and $B^{4d}$ represents $CR^1$, $R^1$ represents a C1-C3 fluoroalkyl group, and $R^{4aa}$ represents a hydrogen atom.

[Embodiment B6] The intermediate compound B wherein $B^{4d}$ represents a nitrogen atom, a combination of $B^{3c}$ and $B^{4d}$ represents a combination in which $B^{2b}$ represents $CR^1$, and $B^{3c}$ represents CH; or a combination in which $B^{2b}$ represents CH, and $B^{3c}$ represents $CR^1$, $R^1$ represents a C1-C3 fluoroalkyl group, and $R^{4aa}$ represents a hydrogen atom.

[Embodiment B7] The intermediate compound B wherein $G^2$ represents $CR^{3b}$, $G^3$ represents $CR^{3c}$, a combination of $G^1$ and $G^4$ represents a combination in which $G^1$ represents $CR^{3a}$, and $G^4$ represents $CR^{3d}$; or a combination in which $G^1$ represents a nitrogen atom, and $G^4$ represents $CR^{3d}$.

[Embodiment B8] The intermediate compound B wherein $G^1$ represents CH, $G^2$ represents $CR^{3b}$, $G^3$ represents $CR^{3c}$, and $G^4$ represents CH.

[Embodiment B9] The compound according to the Embodiment B1 wherein $G^2$ represents $CR^{3b}$, $G^3$ represents $CR^{3c}$, a combination of $G^1$ and $G^4$ represents a combination in which $G^1$ represents $CR^{3a}$, and $G^4$ represents $CR^{3d}$; or a combination in which $G^1$ represents a nitrogen atom, and $G^4$ represents $CR^{3d}$.

[Embodiment B10] The compound according to the Embodiment B2 wherein $G^2$ represents $CR^{3b}$, $G^3$ represents $CR^{3c}$, a combination of $G^1$ and $G^4$ represents a combination in which $G^1$ represents $CR^{3a}$, and $G^4$ represents $CR^{3d}$; or a combination in which $G^1$ represents a nitrogen atom, and $G^4$ represents $CR^{3d}$.

[Embodiment B11] The compound according to the Embodiment B3 wherein $G^2$ represents $CR^{3b}$, $G^3$ represents $CR^{3c}$, a combination of $G^1$ and $G^4$ represents, a combination in which $G^1$ represents $CR^{3a}$, and $G^4$ represents $CR^{3d}$; or a combination in which $G^1$ represents a nitrogen atom, and $G^4$ represents $CR^{3d}$.

[Embodiment B12] The compound according to the Embodiment B4 wherein $G^2$ represents $CR^{3b}$, $G^3$ represents $CR^{3c}$, a combination of $G^1$ and $G^4$ represents a combination in which G represents $CR^{3a}$, and $G^4$ represents $CR^{3d}$; or a combination in which $G^1$ represents a nitrogen atom, and $G^4$ represents $CR^{3d}$.

[Embodiment B13] The compound according to the Embodiment B5 wherein $G^2$ represents $CR^{3b}$, $G^3$ represents $CR^{3c}$, a combination of $G^1$ and $G^4$ represents a combination in which $G^1$ represents $CR^{3a}$, and $G^4$ represents $CR^{3d}$; or a combination in which $G^1$ represents a nitrogen atom, and $G^4$ represents $CR^{3d}$.

[Embodiment B14] The compound according to the Embodiment B6 wherein $G^2$ represents $CR^{3b}$, $G^3$ represents $CR^{3c}$, a combination of $G^1$ and $G^4$ represents a combination in which $G^1$ represents $CR^{3a}$, and $G^4$ represents $CR^{3d}$; or a combination in which $G^1$ represents a nitrogen atom, and $G^4$ represents $CR^{3d}$.

[Embodiment B15] The compound according to the Embodiment B1 wherein $G^1$ represents CH, $G^2$ represents $CR^{3b}$, $G^3$ represents $CR^{3c}$, and $G^4$ represents CH.

[Embodiment B16] The compound according to the Embodiment B2 wherein $G^1$ represents CH, $G^2$ represents $CR^{3b}$, $G^3$ represents $CR^{3c}$, and $G^4$ represents CH.

[Embodiment B17] The compound according to the Embodiment B3 wherein $G^1$ represents CH, $G^2$ represents $CR^{3b}$, $G^3$ represents $CR^{3c}$, and $G^4$ represents CH.

[Embodiment B18] The compound according to the Embodiment B4 wherein $G^1$ represents CH, $G^2$ represents $CR^{3b}$, $G^2$ represents $CR^{3c}$, and $G^4$ represents CH.

[Embodiment B19] The compound according to the Embodiment B5 wherein $G^1$ represents CH, $G^2$ represents $CR^{3b}$, $G^3$ represents $CR^{3c}$, and $G^4$ represents CH.

[Embodiment B20] The compound according to the Embodiment B6 wherein $G^1$ represents CH, $G^2$ represents $CR^{3b}$, $G^3$ represents $CR^{3c}$, and $G^4$ represents CH.

[Embodiment B21] The compound according to any one of the Embodiment B1 to the Embodiment B20 or the intermediate compound B, wherein $R^{3a}$ represents a hydrogen atom, $R^{3b}$, $R^{3c}$ and $R^{3d}$ are identical to or different from each other and each represents a C1-C6 alkyl group, a C2-C6 alkenyl group, a C3-C7 cycloalkyl group {the C1-C6 alkyl group, the C2-C6 alkenyl group, and the C3-C7 cycloalkyl group each may have optionally one or more substituents selected from the group consisting of halogen atom and cyano group}, a phenyl group, a triazolyl group, a pyridyl group, a pyrimidinyl group {the phenyl group, the triazolyl group, the pyridyl group, and the pyrimidinyl group each may have optionally one or more substituents selected from Group J}, $OR^{12}$, $CR^{30}{=}NOR^{17}$, a hydrogen atom, or a halogen atom.

[Embodiment B22] The compound according to any one of the Embodiment B1 to the Embodiment 20 or the intermediate compound B, wherein $R^{3a}$ and $R^{3d}$ represent a hydrogen atom, $R^{3b}$ and $R^{3c}$ are identical to or different from each other and each represents a C1-C6 alkyl group optionally having one or more halogen atoms, a cyclopropyl group, a hydrogen atom, or a halogen atom.

[Embodiment B23] The intermediate compound B, wherein a combination of $B^{2b}$, $B^{3c}$ and $B^{4d}$ represents a combination in which $B^{2b}$ represents $CR^1$, $B^{3c}$ represents CH, and $B^{4d}$ represents a nitrogen atom or CH; a combination in which $B^{2b}$ represents CH, $B^{3c}$ represents $CR^1$, and $B^{4d}$ represents a nitrogen atom or CH; or a combination in which $B^{2b}$ represents CH, $B^{3c}$ represents CH, and $B^{4d}$ represents $CR^1$, $R^1$ represents a trifluoromethyl group, $G^1$ represents CH, $G^2$ represents $CR^{3b}$, $G^3$ represents $CR^{3c}$, $G^4$ represents CH, $R^{3b}$ and $R^{3c}$ are identical to or different from each other and each represents a cyclopropyl group, a halogen atom or a hydrogen atom, $R^{3d}$ represents a hydrogen atom, and $R^{4aa}$ represents a hydrogen atom.

[Embodiment B24] The compound according to the Embodiment B21, wherein $R^{33}$ represents a halogen atom.

[Embodiment B25] The compound according to the Embodiment B21, wherein $R^{33}$ represents a hydrogen atom.

[Embodiment B26] The compound according to the Embodiment B22, wherein $R^{33}$ represents a halogen atom.

[Embodiment B27] The compound according to the Embodiment B22, wherein $R^{33}$ represents a hydrogen atom.

[Embodiment B28] The compound according to the Embodiment B23, wherein $R^{33}$ represents a halogen atom.

[Embodiment B29] The compound according to the Embodiment B23, wherein $R^{33}$ represents a hydrogen atom.

Examples of the Embodiment of the intermediate compound C include the followings.

[Embodiment C1] The intermediate compound C, wherein $R^{3a}$ represents a hydrogen atom, $R^{3b}$, $R^{3c}$ and $R^{3d}$ are identical to or different from each other and each represents a C1-C6 alkyl group, a C2-C6 alkenyl group, a C3-C7 cycloalkyl group {the C1-C6 alkyl group, the C2-C6 alkenyl group, and the C3-C7 cycloalkyl group each may have optionally one or more substituents selected from the group consisting of halogen atom and cyano group}, a phenyl group, a triazolyl group, a pyridyl group, a pyrimidinyl group {the phenyl group, the triazolyl group, the pyridyl group, and the pyrimidinyl group each may have optionally one or more substituents selected from Group J}, $OR^{12}$, $CR^{30}{=}NOR^{17}$, a hydrogen atom, or halogen atom, when Q represents a group represented by formula Q1, $R^{3b}$ and $R^{3d}$ combined together with two carbon atoms to which they are attached may form a benzene ring {the benzene ring may have optionally one or more substituents selected from a group consisting of C1-C6 alkyl group optionally having one or more halogen atoms, and halogen atom}.

[Embodiment C2] The intermediate compound C, wherein $R^{3a}$ and $R^{3d}$ represent a hydrogen atom, $R^{3b}$ and $R^{3c}$ are identical to or different from each other and each represents a C1-C6 alkyl group optionally having one or more halogen atoms, a cyclopropyl group, a hydrogen atom, or halogen atom, when Q represents a group represented by formula Q1, $R^{3b}$ and $R^{3d}$ combined together with two carbon atoms to which they are attached may form a benzene ring {the benzene ring may have optionally one or more substituents selected from a group consisting of C1-C6 alkyl group optionally having one or more halogen atoms, and halogen atom}.

[Embodiment C3] The compound according to the Embodiment C1, wherein Q represents a group represented by formula Q2.

[Embodiment C4] The compound according to the Embodiment C2, wherein Q represents a group represented by formula Q2.

[Embodiment C5] The compound according to the Embodiment C1, wherein Q represents a group represented by formula Q1.

[Embodiment C6] The compound according to the Embodiment C2, wherein Q represents a group represented by formula Q1.

[Embodiment C7] The intermediate compound C, wherein Q represents a group represented by formula Q1, $R^{3a}$ represents a hydrogen atom, $R^{3b}$ and $R^{3d}$ are identical to or different from each other and each represents a C1-C6 alkyl group, a C2-C6 alkenyl group, a C3-C7 cycloalkyl group {the C1-C6 alkyl group, the C2-C6 alkenyl group, and the C3-C7 cycloalkyl group may have optionally one or more substituents selected from the group consisting of halogen atom and cyano group}, a phenyl group, a pyridyl group, a pyrimidinyl group {the phenyl group, the pyridyl group, and the pyrimidinyl group each may have optionally one or more substituents selected from Group J}.

[Embodiment C8] The intermediate compound C, wherein Q represents a group represented by formula Q1, $R^{3a}$ and $R^{3d}$ represent a hydrogen atom, $R^{3b}$ represents a C1-C6 alkyl group optionally having one or more halogen atoms, cyclopropyl group, a hydrogen atom, or a halogen atom.

[Embodiment C9] The intermediate compound C, wherein Q represents a group represented by formula Q1, $R^{3a}$ represents a hydrogen atom, $R^{3b}$ and $R^{3d}$ combined together with two carbon atoms to which they are attached form a benzene ring, a pyrrole ring, a furan ring, a thiophene ring, a pyrazole ring, an imidazole ring, an oxazole ring, an isoxazole ring, a thiazole ring, an isothiazole ring, an oxadiazole ring, a thiadiazole ring, a pyridine ring, a pyridazine ring, a pyrimidine ring, a pyrazine ring {the benzene ring, the pyrrole ring, the furan ring, the thiophene ring, the pyrazole ring, the imidazole ring, the oxazole ring, the isoxazole ring, the thiazole ring, the isothiazole ring, the pyridine ring, the pyridazine ring, the pyrimidine ring, and the pyrazine ring each may have optionally one or more substituents selected from Group H}, or a triazole ring optionally having one or more substituents selected from Group I.

[Embodiment C10] The intermediate compound C, wherein Q represents a group represented by formula Q1, $R^{3a}$ represents a hydrogen atom, $R^{3b}$ and $R^{3d}$ combined together with two carbon atoms to which they are attached form benzene ring {the benzene ring may have optionally one or more substituents selected from a group consisting of C1-C6 alkyl group optionally having one or more halogen atoms, and halogen atom}.

[Embodiment C11] The intermediate compound C, wherein Q represents a group represented by formula Q1, $G^2$ represents $CR^{3b}$, $G^3$ represents $CR^{3c}$, a combination of $G^1$ and $G^4$ represents a combination in which $G^1$ represents $CR^{3a}$, and $G^4$ represents a nitrogen atom or $CR^{3d}$; or a combination in which $G^1$ represents a nitrogen atom, and $G^4$ represents $CR^{3d}$.

[Embodiment C12] The intermediate compound C, wherein $G^1$ represents CH, $G^2$ represents $CR^{3b}$, $G^3$ represents $CR^{3c}$, and $G^4$ represents CH.

[Embodiment C13] The compound according to the Embodiment C1, wherein $G^2$ represents $CR^{3b}$, $G^3$ represents $CR^{3c}$, a combination of $G^1$ and $G^4$ represents a combination in which $G^1$ represents CH, and $G^4$ represents a nitrogen atom or $CR^{3d}$; or a combination in which $G^1$ represents a nitrogen atom, and $G^4$ represents $CR^{3d}$.

[Embodiment C14] The compound according to the Embodiment C2, wherein $G^2$ represents $CR^{3b}$, $G^3$ represents $CR^{3c}$, a combination of $G^1$ and $G^4$ represents a combination in which G represents CH, and $G^4$ represents a nitrogen atom or CH; or a combination in which $G^1$ represents a nitrogen atom, and $G^4$ represents CH.

[Embodiment C15] The compound according to the Embodiment C3, wherein $G^2$ represents $CR^{3b}$, $G^3$ represents $CR^{3c}$, a combination of $G^1$ and $G^4$ represents a combination in which $G^1$ represents CH, and $G^4$ represents a nitrogen atom or $CR^{3d}$; or a combination in which $G^1$ represents a nitrogen atom, and $G^4$ represents $CR^{3d}$.

[Embodiment C16] The compound according to the Embodiment C4, wherein $G^2$ represents $CR^{3b}$, $G^3$ represents $CR^{3c}$, a combination of G1 and G4 represents a combination in which $G^1$ represents CH, and $G^4$ represents a nitrogen atom or CH; or a combination in which $G^1$ represents a nitrogen atom, and $G^4$ represents CH.

[Embodiment C17] The compound according to the Embodiment C1, wherein $G^1$ represents CH, $G^2$ represents $CR^{3b}$, $G^3$ represents $CR^{3c}$, and $G^4$ represents CH.

[Embodiment C18] The compound according to the Embodiment C2, wherein $G^1$ represents CH, $G^2$ represents $CR^3n$, $G^3$ represents $CR^{3c}$, and $G^4$ represents CH.

[Embodiment C19] The compound according to the Embodiment C3, wherein $G^1$ represents CH, $G^2$ represents $CR^{3b}$, $G^3$ represents $CR^{3c}$, and $G^4$ represents CH.

[Embodiment C20] The compound according to the Embodiment C4, wherein $G^1$ represents CH, $G^2$ represents $CR^{3b}$, $G^3$ represents $CR^{3c}$, and $G^4$ represents CH.

[Embodiment C21] The intermediate compound C, wherein $R^2$ represents a C1-C6 alkyl group.

[Embodiment C22] The intermediate compound C, wherein $R^2$ represents an ethyl group.

[Embodiment C23] The compound according to the Embodiment C1, wherein $R^2$ represents a C1-C6 alkyl group.

[Embodiment C24] The compound according to the Embodiment C2, wherein $R^2$ represents a C1-C6 alkyl group.

[Embodiment C25] The compound according to the Embodiment C3, wherein $R^2$ represents a C1-C6 alkyl group.

[Embodiment C26] The compound according to the Embodiment C4, wherein $R^2$ represents a C1-C6 alkyl group.

[Embodiment C27] The compound according to the Embodiment C5, wherein $R^2$ represents a C1-C6 alkyl group.

[Embodiment C28] The compound according to the Embodiment C6, wherein $R^2$ represents a C1-C6 alkyl group.

[Embodiment C29] The compound according to the Embodiment C7, wherein $R^2$ represents a C1-C6 alkyl group.

[Embodiment C30] The compound according to the Embodiment C8, wherein $R^2$ represents a C1-C6 alkyl group.

[Embodiment C31] The compound according to the Embodiment C9, wherein $R^2$ represents a C1-C6 alkyl group.

[Embodiment C32] The compound according to the Embodiment C10, wherein $R^2$ represents a C1-C6 alkyl group.

[Embodiment C33] The compound according to the Embodiment C11, wherein $R^2$ represents a C1-C6 alkyl group.

[Embodiment C34] The compound according to the Embodiment C12, wherein $R^2$ represents a C1-C6 alkyl group.

[Embodiment C35] The compound according to the Embodiment C13, wherein $R^2$ represents a C1-C6 alkyl group.

[Embodiment C36] The compound according to the Embodiment C14, wherein $R^2$ represents a C1-C6 alkyl group.

[Embodiment C37] The compound according to the Embodiment C15, wherein $R^2$ represents a C1-C6 alkyl group.

[Embodiment C38] The compound according to the Embodiment C16, wherein $R^2$ represents a C1-C6 alkyl group.

[Embodiment C39] The compound according to the Embodiment C17, wherein $R^2$ represents a C1-C6 alkyl group.

[Embodiment C40] The compound according to the Embodiment C18, wherein $R^2$ represents a C1-C6 alkyl group.

[Embodiment C41] The compound according to the Embodiment C19, wherein $R^2$ represents a C1-C6 alkyl group.

[Embodiment C42] The compound according to the Embodiment C20, wherein $R^2$ represents a C1-C6 alkyl group.

[Embodiment C43] The compound according to the Embodiment C1, wherein $R^2$ represents an ethyl group.

[Embodiment C44] The compound according to the Embodiment C2, wherein $R^2$ represents an ethyl group.

[Embodiment C45] The compound according to the Embodiment C3, wherein $R^2$ represents an ethyl group.

[Embodiment C46] The compound according to the Embodiment C4, wherein $R^2$ represents an ethyl group.

[Embodiment C47] The compound according to the Embodiment C5, wherein $R^2$ represents an ethyl group.

[Embodiment C48] The compound according to the Embodiment C6, wherein $R^2$ represents an ethyl group.

[Embodiment C49] The compound according to the Embodiment C7, wherein $R^2$ represents an ethyl group.

[Embodiment C50] The compound according to the Embodiment C8, wherein $R^2$ represents an ethyl group.

[Embodiment C51] The compound according to the Embodiment C9, wherein $R^2$ represents an ethyl group.

[Embodiment C52] The compound according to the Embodiment C10, wherein $R^2$ represents an ethyl group.

[Embodiment C53] The compound according to the Embodiment C11, wherein $R^2$ represents an ethyl group.

[Embodiment C54] The compound according to the Embodiment C12, wherein $R^2$ represents an ethyl group.

[Embodiment C55] The compound according to the Embodiment C13, wherein $R^2$ represents an ethyl group.

[Embodiment C56] The compound according to the Embodiment C14, wherein $R^2$ represents an ethyl group.

[Embodiment C57] The compound according to the Embodiment C15, wherein $R^2$ represents an ethyl group.

[Embodiment C58] The compound according to the Embodiment C16, wherein $R^2$ represents an ethyl group.

[Embodiment C59] The compound according to the Embodiment C17, wherein $R^2$ represents an ethyl group.

[Embodiment C60] The compound according to the Embodiment C18, wherein $R^2$ represents an ethyl group.

[Embodiment C61] The compound according to the Embodiment C19, wherein $R^2$ represents an ethyl group.

[Embodiment C62] The compound according to the Embodiment C20, wherein $R^2$ represents an ethyl group.

[Embodiment C63] The compound according to any one of the Embodiment C1 to the Embodiment C62 or the intermediate compound C, wherein a combination of $B^{2b}$, $B^{3c}$ and $B^{4d}$ represents a combination in which $B^{2b}$ represents $CR^1$, $B^{3c}$ represents $CR^{6cc}$, and $B^{4d}$ represents a nitrogen atom or $CR^{6dd}$; or a combination in which $B^{2b}$ represents $CR^{6bb}$, $B^{3c}$ represents $CR^1$, and $B^{4d}$ represents a nitrogen atom or $CR^{6dd}$; or a combination in which $B^{2b}$ represents $CR^{6bb}$, $B^{3c}$ represents $CR^{6cc}$, and $B^{4d}$, represents $CR^1$, $R^{6bb}$, $R^{6cc}$ and $R^{6dd}$ are identical to or different from each other and each represents a halogen atom or a hydrogen atom, $R^1$ represents a C1-C6 alkyl group having one or more substituents selected from a group consisting of halogen atom and cyano group; a cyclopropyl group optionally having one or more substituents selected from the group consisting of cyano group and halogen atom; $S(O)_mR^8$; or $OR^8$, $R^8$ represents a C1-C6 alkyl group having one or more substituents selected from a group consisting of halogen atom and cyano group.

[Embodiment C64] The compound according to any one of the Embodiment C1 to the Embodiment C62 or the intermediate compound C, wherein a combination of $B^{2b}$, $B^{3c}$ and $B^{4d}$ represents a combination in which $B^{2b}$ represents $CR^1$, $B^{3c}$ represents $CR^{6cc}$, and $B^{4d}$ represents a nitrogen atom or $CR^{6dd}$; a combination in which $B^{2b}$ represents $CR^{6bb}$, $B^3$ represents $CR^1$, and $B^{4d}$ represents a nitrogen atom or $CR^{6dd}$; or a combination in which $B^{2b}$ represents $CR^{6bb}$, $B^{3c}$ represents $CR^{6cc}$, and $B^{4d}$ represents $CR^1$, $R^{6bb}$, $R^{6cc}$ and $R^{6dd}$ are identical to or different from each other and each represents a halogen atom or a hydrogen atom, and $R^1$ represents a C1-C3 fluoroalkyl group, a C1-C3 fluoroalkoxy group, or $S(O)_mCF_3$.

[Embodiment C65] The compound according to any one of the Embodiment C1 to the Embodiment C62 or the intermediate compound C, wherein a combination of $B^{2b}$, $B^{3c}$ and $B^{4d}$ represents a combination in which $B^{2b}$ represents $CR^1$, $B^{3c}$ represents CH, and $B^{4d}$ represents CH; a combination in which $B^{2b}$ represents CH, $B^{3c}$ represents $CR^1$, and $B^{4d}$ represents CH; or a combination in which $B^{2b}$ represents CH, $B^{3c}$ represents CH, and $B^{4d}$ represents $CR^1$, $R^1$ represents a C1-C3 fluoroalkyl group, a C1-C3 fluoroalkoxy group, or $S(O)_mCF_3$.

[Embodiment C66] The compound according to any one of the Embodiment C1 to the Embodiment C62 or the intermediate compound C, wherein a combination of $B^{2b}$, $B^{3c}$ and $B^{4d}$ represents a combination in which $B^{2b}$ represents $CR^1$, $B^{3c}$ represents CH, $B^{4c}$ represents a nitrogen atom or CH; a combination in which $B^{2b}$ represents CH, $B^{3c}$ represents $CR^1$, and $B^{4d}$ represents a nitrogen atom or CH; or a combination in which $B^{2b}$ represents CH, $B^{3c}$ represents CH, and $B^{4d}$ represents $CR^1$, and $R^1$ represents a C1-C3 fluoroalkyl group, a C1-C3 fluoroalkoxy group, or $S(O)_mCF^3$.

[Embodiment C67] The compound according to any one of the Embodiment C1 to the Embodiment C62 or the intermediate compound C, wherein a combination of $B^{2b}$, $B^{3c}$ and $B^{4d}$ represents a combination in which $B^{2b}$ represents $CR^1$, $B^{3c}$ represents CH, and $B^{4d}$ represents CH; a combination in which $B^{2b}$ represents CH, $B^{3c}$ represents $CR^1$, and $B^{4d}$ represents CH; or a combination in which $B^{2b}$ represents CH, $B^{3c}$ represents CH, and $B^{4d}$ represents $CR^1$, and $R^1$ represents a C1-C3 fluoroalkyl group, a C1-C3 fluoroalkoxy group, or $S(O)_mCF_3$.

[Embodiment C68] The compound according to any one of the Embodiment C1 to the Embodiment C62 or the intermediate compound C, wherein $B^{4d}$ represents a nitrogen atom, a combination of $B^{3c}$ and $B^{4d}$ represents a combination in which $B^{2b}$ represents $CR^1$, and $B^{3c}$ represents CH; or a combination in which $B^{2b}$ represents CH, and $B^{3c}$ represents $CR^1$, $R^1$ represents a C1-C3 fluoroalkyl group, a C1-C3 fluoroalkoxy group, or $S(O)_mCF_3$.

Examples of the Embodiment of the intermediate compound D include the followings.

[Embodiment D1] The intermediate compound D, wherein a combination of $B^{2b}$, $B^{3c}$ and $B^{4d}$ represents a combination in which $B^{2b}$ represents $CR^1$, $B^{3c}$ represents $CR^{6cc}$, and $B^{4d}$ represents a nitrogen atom or $CR^{6dd}$; a combination in which $B^{2b}$ represents $CR^{6bb}$, $B^{3c}$ represents $CR^1$, and $B^{4d}$ represents a nitrogen atom or $CR^{6dd}$; or a combination in which $B^{2b}$ represents $CR^{6bb}$, $B^{3c}$ represents $CR^{6cc}$, and $B^{4d}$ represents $CR^1$, $R^{6bb}$, $R^{6cc}$ and $R^{6dd}$ are identical to or different from each other and each represents a halogen atom or a hydrogen atom, $R^1$ represents a C1-C6 alkyl group having one or more substituents selected from a group consisting of halogen atom and cyano group; a cyclopropyl group optionally having one or more substituents selected from the group consisting of cyano group and halogen atom; $S(O)_mR^8$; or $OR^8$, $R^8$ represents a C1-C6 alkyl group having one or more substituents selected from a group consisting of halogen atom and cyano group, and $R^{4aa}$ represents a halogen atom or a hydrogen atom.

[Embodiment D2] The intermediate compound D, wherein a combination of $B^{2b}$, $B^{3c}$ and $B^{4d}$ represents a combination in which $B^{2b}$ represents $CR^1$, $B^{3c}$ represents $CR^{6cc}$, and $B^{4d}$ represents a nitrogen atom or $CR^{6dd}$; a combination in which $B^{2b}$ represents $CR^{6bb}$, $B^{3c}$ represents $CR^1$, and $B^{4d}$ represents a nitrogen atom or $CR^{6dd}$; or a combination in which $B^{2b}$ represents $CR^{6bb}$, $B^{3c}$ represents $CR^{6cc}$, and $B^{4d}$ represents $CR^1$, $R^{6bb}$, $R^{6cc}$ and $R^{6dd}$ are identical to or different from each other and each represents a halogen atom or a hydrogen atom, $R^1$ represents a C1-C3 fluoroalkyl group, a C1-C3 fluoroalkoxy group, or $S(O)_mCF_3$, and $R^{4aa}$ represents a halogen atom or a hydrogen atom.

[Embodiment D3] The intermediate compound D, wherein a combination of $B^{2b}$, $B^{3c}$ and $B^{4d}$ represents a combination in which $B^{2b}$ represents $CR^1$, $B^{3c}$ represents CH, and $B^{4d}$ represents CH; a combination in which $B^{2b}$ represents CH, $B^{3c}$ represents $CR^1$, and $B^{4d}$ represents CH; or a combination in which $B^{2b}$ represents CH, $B^{3c}$ represents CH, and $B^{4d}$ represents $CR^1$, $R^1$ represents a C1-C3 fluoroalkyl group, a C1-C3 fluoroalkoxy group, or $S(O)_mCF_3$.

[Embodiment D4] The intermediate compound D, wherein a combination of $B^{2b}$, $B^{3c}$ and $B^{4d}$ represents a combination in which $B^{2b}$ represents $CR^1$, $B^{3c}$ represents CH, and $B^{4d}$ represents a nitrogen atom or CH; a combination in which $B^{2b}$ represents CH, $B^{3c}$ represents $CR^1$, and $B^{4d}$ represents a nitrogen atom or CH; or a combination in which $B^{2b}$ represents CH, $B^{3c}$ represents CH, and $B^{4d}$ represents $CR^1$, $R^1$ represents a C1-C3 fluoroalkyl group, a C1-C3 fluoroalkoxy group, or $S(O)_mCF_3$, and $R^{4aa}$ represents a hydrogen atom.

[Embodiment D5] The intermediate compound D, wherein a combination of $B^{2b}$, $B^{3c}$ and $B^{4d}$ represents a combination in which $B^{2b}$ represents $CR^1$, $B^{3c}$ represents CH, and $B^{4d}$ represents CH; a combination in which $B^{2b}$ represents CH, $B^{3c}$ represents $CR^1$, and $B^{4d}$ represents CH; or a combination in which $B^{2b}$ represents CH, $B^{3c}$ represents CH, and $B^{4d}$ represents $CR^1$, $R^1$ represents a C1-C3 fluoroalkyl group, a C1-C3 fluoroalkoxy group, or $S(O)_mCF_3$, and $R^{4aa}$ represents a hydrogen atom.

[Embodiment D6] The intermediate compound D, wherein $B^{4d}$ represents a nitrogen atom, a combination of $B^{3c}$ and $B^{4d}$ represents a combination in which $B^{2b}$ represents $CR^1$, and $B^{3c}$ represents CH; or a combination in which $B^{2b}$ represents CH, and $B^{3c}$ represents $CR^1$, $R^1$ represents a C1-C3 fluoroalkyl group, a C1-C3 fluoroalkoxy group, or $S(O)_mCF_3$, and $R^{4aa}$ represents a hydrogen atom.

[Embodiment D7] The intermediate compound D, wherein $G^2$ represents $CR^{3b}$, $G^3$ represents $CR^{3c}$, and a combination of $G^1$ and $G^4$ represents, $G^1$ represents $CR^{3a}$, and $G^4$ represents $CR^{3d}$; or a combination in which $G^1$ represents a nitrogen atom, and $G^4$ represents $CR^{3d}$.

[Embodiment D8] The intermediate compound D, wherein $G^1$ represents CH, $G^2$ represents $CR^{3b}$, $G^3$ represents $CR^{3c}$, and $G^4$ represents CH.

[Embodiment D9] The compound according to the Embodiment D1, wherein $G^2$ represents $CR^{3b}$, $G^3$ represents $CR^{3c}$, and a combination of $G^1$ and $G^4$ represents a combination in which $G^1$ represents $CR^{3a}$, $G^4$ represents $CR^{3d}$; or a combination in which $G^1$ represents a nitrogen atom, and $G^4$ represents $CR^{3d}$.

[Embodiment D10] The compound according to the Embodiment D2, wherein $G^2$ represents $CR^{3b}$, $G^3$ represents $CR^{3c}$, and a combination of $G^1$ and $G^4$ represents a combination in which $G^1$ represents $CR^{3a}$, and $G^4$ represents $CR^{3d}$; or a combination in which $G^1$ represents a nitrogen atom, and $G^4$ represents $CR^{3d}$.

[Embodiment D11] The compound according to the Embodiment D3, wherein $G^2$ represents $CR^{3b}$, $G^3$ represents $CR^{3c}$, and a combination of $G^1$ and $G^4$ represents a combination in which $G^1$ represents $CR^{3a}$, and $G^4$ represents $CR^{3d}$; or a combination in $G^1$ represents a nitrogen atom, and $G^4$ represents $CR^{3d}$.

[Embodiment D12] The compound according to the Embodiment D4, wherein $G^2$ represents $CR^{3b}$, $G^3$ represents $CR^{3c}$, and a combination of $G^1$ and $G^4$ represents a combination in which $G^1$ represents $CR^{3a}$, and $G^4$ represents $CR^{3d}$; or a combination in which $G^1$ represents a nitrogen atom, and $G^4$ represents $CR^{3d}$.

[Embodiment D13] The compound according to the Embodiment D5, wherein $G^2$ represents $CR^{3b}$, $G^3$ represents $CR^{3c}$, and a combination of $G^1$ and $G^4$ represents a combination in which $G^1$ represents $CR^{3a}$, and $G^4$ represents $CR^{3d}$; or a combination in which $G^1$ represents a nitrogen atom, and $G^4$ represents $CR^{3d}$.

[Embodiment D14] The compound according to the Embodiment D6, wherein $G^2$ represents $CR^{3b}$, $G^3$ represents $CR^{3c}$, and a combination of $G^1$ and $G^4$ represents a combination in which $G^1$ represents $CR^{3a}$, and $G^4$ represents $CR^{3d}$; or a combination in which $G^1$ represents a nitrogen atom, and $G^4$ represents $CR^{3d}$.

[Embodiment D15] The compound according to the Embodiment D1, wherein $G^1$ represents CH, $G^2$ represents $CR^{3b}$, $G^3$ represents $CR^{3c}$, and $G^4$ represents CH.

[Embodiment D16] The compound according to the Embodiment D2, wherein $G^1$ represents CH, $G^2$ represents $CR^{3b}$, $G^3$ represents $CR^{3c}$, and $G^4$ represents CH.

[Embodiment D17] The compound according to the Embodiment D3, wherein $G^1$ represents CH, $G^2$ represents $CR^{3b}$, $G^3$ represents $CR^{3c}$, and $G^4$ represents CH.

[Embodiment D18] The compound according to the Embodiment D4, wherein $G^1$ represents CH, $G^2$ represents $CR^{3b}$, $G^3$ represents $CR^{3c}$, and $G^4$ represents CH.

[Embodiment D19] The compound according to the Embodiment D5, wherein $G^1$ represents CH, G represents $CR^{3b}$, $G^3$ represents $CR^{3c}$, and $G^4$ represents CH.

[Embodiment D20] The compound according to the Embodiment D6, wherein $G^1$ represents CH, $G^2$ represents $CR^{3b}$, $G^3$ represents $CR^{3c}$, and $G^4$ represents CH.

[Embodiment D21] The compound according to any one of the Embodiment D1 to the Embodiment D20 or the intermediate compound D, wherein $R^{3a}$ represents a hydrogen atom, $R^{3b}$, $R^{3c}$ and $R^{3d}$ are identical to or different from each other and each represents a C1-C6 alkyl group, a C2-C6 alkenyl group, a C3-C7 cycloalkyl group {the C1-C6 alkyl group, the C2-C6 alkenyl group, and the C3-C7 cycloalkyl group each may have optionally one or more substituents selected from the group consisting of halogen atom and cyano group}, a phenyl group, a triazolyl group, a pyridyl group, a pyrimidinyl group {the phenyl group, the triazolyl group, the pyridyl group, and the pyrimidinyl group each may have optionally one or more substituents selected from Group J}, $OR^{12}$, $CR^{30}$=$NOR^{17}$, a hydrogen atom, or a halogen atom.

[Embodiment D22] The compound according to any one of the Embodiment D1 to the Embodiment D20 or the intermediate compound D, wherein $R^{3a}$ and $R^{3d}$ represent a hydrogen atom, $R^{3b}$ and $R^{3c}$ are identical to or different from each other and each represents a C1-C6 alkyl group optionally having one or more halogen atoms, a cyclopropyl group, a hydrogen atom, or a halogen atom.

[Embodiment D23] The intermediate compound D, wherein a combination of $B^{2b}$, $B^{3c}$ and $B^{4d}$ represents a combination in which $B^{2b}$ represents $CR^1$, $B^{3c}$ represents CH, $B^{4d}$ represents a nitrogen atom or CH; a combination in which $B^{2b}$ represents CH, $B^{3c}$ represents $CR^1$, $B^{4d}$ represents a nitrogen atom or CH; or a combination in which $B^{2b}$ represents CH, $B^{3c}$ represents CH, and $B^{4d}$ represents $CR^1$, $R^1$ represents a trifluoromethyl group, $G^1$ represents CH, $G^2$ represents $CR^{3b}$, $G^3$ represents $CR^{3c}$, and $G^4$ represents CH, $R^{3b}$ and $R^{3c}$ are identical to or different from each other and each represents a cyclopropyl group, a halogen atom or a hydrogen atom, $R^{3d}$ represents a hydrogen atom, and $R^{4aa}$ represents a hydrogen atom.

[Embodiment D24] The compound according to the Embodiment D21, wherein $R^{33}$ represents a halogen atom.

[Embodiment D25] The compound according to the Embodiment D21, wherein $R^{33}$ represents a hydrogen atom.

[Embodiment D26] The compound according to the Embodiment D22, wherein $R^{33}$ represents a halogen atom.

[Embodiment D27] The compound according to the Embodiment D22, wherein $R^{33}$ represents a hydrogen atom.

[Embodiment D28] The compound according to the Embodiment D23, wherein $R^{33}$ represents a halogen atom.

[Embodiment D29] The compound according to the Embodiment D23, wherein $R^{33}$ represents a hydrogen atom.

Next, a process for preparing a compound X of the present invention is explained.

Process 1

A compound represented by formula (I-b) (hereinafter, referred to as compound (I-b)) or a compound represented by formula (I-c) (hereinafter, referred to as compound (I-c)) can be prepared by reacting a compound represented by formula (I-a) (hereinafter, compound (I-a)) with an oxidizing agent.

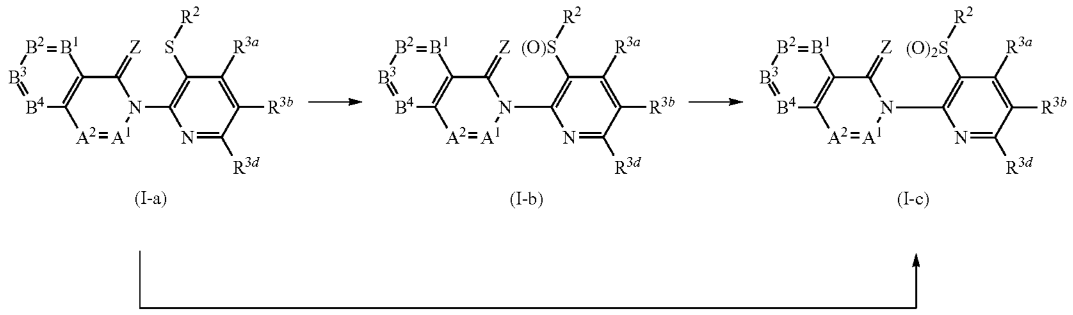

(I-a) (I-b) (I-c)

[wherein the symbols are the same as defined above.]

Firstly, a process for the compound (I-b) from the compound (I-a) is described.

The reaction is usually carried out in a solvent. Examples of the solvent to be used in the reaction include halogenated hydrocarbons such as dichloromethane and chloroform (hereinafter, collectively referred to as halogenated hydrocarbons); nitriles such as acetonitrile (hereinafter collectively referred to nitriles); alcohols such as methanol and ethanol (hereinafter, collectively referred to as alcohols); acetic acid; water; and mixed solvents of two or more kinds of the solvents.

Examples of the oxidizing agent to be used in the reaction include sodium periodate, m-chloroperoxybenzoic acid (hereinafter, referred to as mCPBA) and hydrogen peroxide.

When hydrogen peroxide is used as an oxidizing agent, a base or a catalyst may be added as needed.

Examples of the base include sodium carbonate.

When the base is used in the reaction, the base is usually used within a range of 0.01 to 1 molar ration(s), as opposed to 1 mole of the compound (I-a).

Examples of the catalyst to be used in the reaction include tungstic acid, and sodium tungstate. When the catalyst is used in the reaction, the catalyst is usually used within a range of 0.01 to 0.5 molar rations, as opposed to a mole of the compound (I-a).

In the reaction, the oxidizing agent is usually used within a range of 1 to 1.2 molar ratio(s), as opposed to 1 mole of the compound (I-a).

The reaction temperature of the reaction is usually within a range of −20 to 80° C. The reaction period of the reaction is usually within a range of 0.1 to 12 hours.

When the reaction is completed, water is added to reaction mixtures, and the reaction mixtures are extracted with organic solvent(s), and if necessary, the organic layers are washed with an aqueous solution of a reducing agent (such as sodium sulfite, and sodium thiosulfate) and an aqueous solution of a base (such as sodium hydrogen carbonate). The resulting organic layers are dried and concentrated to obtain the compound (I-b).

Next, a process for preparing the compound (I-c) from the compound (I-b) is described.

The reaction is usually carried out in a solvent. Examples of the solvents to be used in the reaction include halogenated hydrocarbons, nitriles, alcohols, acetic acid, water, and mixed solvents of two or more kinds of the solvents.

Examples of the oxidizing agent to be used in the reaction include mCPBA and peroxide hydrogen.

In the reaction, the oxidizing agent is usually used within a range of 1 to 2 molar ratio(s), as opposed to 1 mole of the compound (I-b).

When peroxide hydrogen is used an oxidizing agent, a base or a catalyst may be added as needed.

Examples of the base to be used in the reaction include sodium carbonate.

When the base is used in the reaction, the base is usually used within a range of 0.01 to 1 molar ration(s), as opposed to 1 mole of the compound (I-b).

Examples of the catalyst to be used in the reaction include sodium tungstate.

When the catalyst is used in the reaction, the base is usually used within a range of 0.01 to 0.5 molar rations, as opposed to 1 mole of the compound (I-b).

The reaction temperature of the reaction is usually within a range of −20 to 120° C. The reaction period of the reaction is usually within a range of 0.1 to 12 hours.

When the reaction is completed, water is added to reaction mixtures, and the reaction mixtures are extracted with organic solvent(s), and if necessary, the organic layers are washed with an aqueous solution of a reducing agent (such as sodium sulfite, and sodium thiosulfate) and an aqueous solution of a base (such as sodium hydrogen carbonate). The resulting organic layers are dried and concentrated to obtain the compound (I-c).

Also, the compound (I-c) can be prepared by reacting the compound (I-a) with an oxidizing agent in one step (one-spot).

The reaction may be carried out by using the oxidizing agent in a ratio of 2 to 5 molar ratios as opposed to 1 mole of the compound (I-a) according to the process for preparing the compound (I-c) from the compound (I-b).

Process 2

A compound represented by formula (II-b) (hereinafter, referred to as compound (II-b)) or a compound represented by formula (II-c) (hereinafter, referred to as compound (II-c)) can be prepared by reacting a compound represented by formula (II-a)) (hereinafter, referred to as compound (II-a)) with an oxidizing agent.

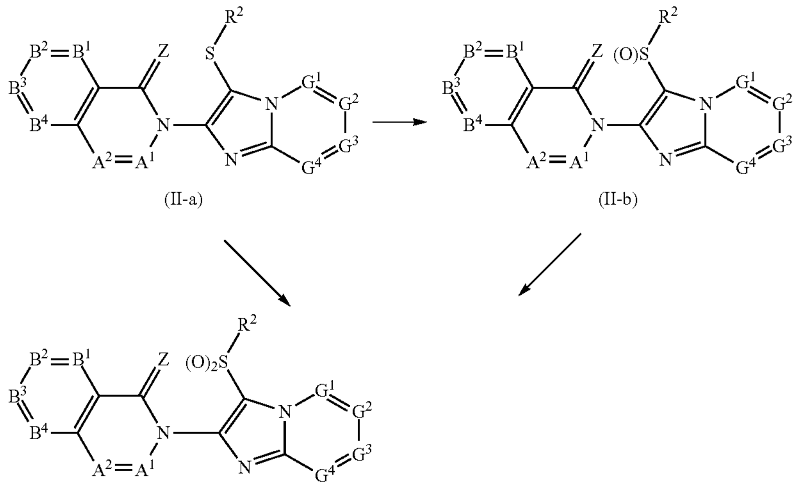

(II-a) (II-b) (II-c)

[wherein the symbols are the same as defined above.]

These reactions can be carried out according to the process 1.

Process 3

A compound represented by formula (I-S) (hereinafter, referred to as compound (I-S)) can be prepared by reacting a compound represented by formula (I-O) (hereinafter, referred to as compound (I-O)) with a sulfurizing agent.

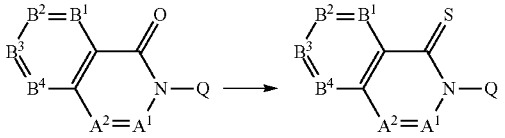

(I-O) (I-S)

[wherein the symbols are the same as defined above.]

The reaction is carried out in the presence or the absence of a solvent. Examples of the solvent to be used in the reaction include ethers such as tetrahydrofuran (hereinafter, referred to as THF), 1,2-dimethoxyethane (hereinafter, referred to as DME), methyl tert-butyl ether (hereinafter, referred to as MTBE) and diethyl ether (hereinafter, collectively referred to as ethers), halogenated hydrocarbons: aromatic hydrocarbons such as toluene and xylene (hereinafter, referred to as aromatic hydrocarbons); nitriles; nitrogen-containing aromatic compounds such as pyridine, picoline, lutidine, and quinoline (hereinafter, collectively referred to as nitrogen-containing aromatic compounds); and mixed solvents of two or more kinds of the solvents.

Examples of the sulfurizing agent to be used in the reaction include diphosphorus pentasulfide, a Lawesson's reagent (2,4-bis-(4-methoxyphenyl)-1,3-dithia-2,4-diphosphetane 2,4-disulfide), and the like.

In the reaction, the sulfurizing agent is usually used within a range of 1 to 3 molar ratio(s), as opposed to 1 mole of the compound (I-O).

The reaction temperature of the reaction is usually within a range of 0 to 200° C. The reaction period of the reaction is usually within a range of 1 to 24 hours.

When the reaction is completed, water is added to reaction mixtures, and the reaction mixtures are extracted with organic solvent(s), and the organic layers are worked up (for example, drying and concentration) to obtain the compound (I-S).

Process 4

The compound (I-O) can be prepared by reacting a compound represented by formula (M-1) (hereinafter, referred to compound (M-1)) with a compound represented by formula (M-2) (hereinafter, referred to as compound (M-2)) in the presence of a base.

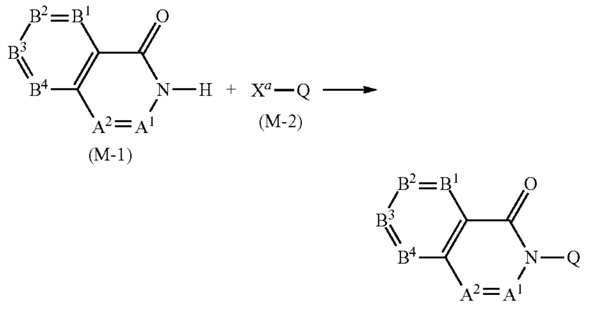

(M-1) (M-2) (I-O)

[wherein, $X^a$ represents a halogen atom, and the other symbols are the same as defined above.]

The reaction is usually carried out in a solvent. Examples of the solvents to be used in the reaction include ethers; aromatic hydrocarbons; nitriles; polar aprotic solvents such as dimethylformamide (hereinafter, referred to as DMF), N-methyl pyrrolidone (hereinafter, referred to as NMP), and dimethyl sulfoxide (hereinafter, referred to DMSO) (hereinafter, collectively referred to as polar aprotic solvents); and mixed solvents of two or more kinds of the solvents.

Examples of the base include organic bases such as triethylamine, diisopropylethylamine, pyridine, and 4-dimethylaminopyridine (hereinafter, collectively referred to as organic bases); alkali metal carbonates such as sodium carbonate, and potassium carbonate (hereinafter, collectively referred to as alkali metal carbonates); and alkali metal hydrides such as sodium hydride (hereinafter, collectively referred to as alkali metal hydrides).

In the reaction, the compound (M-2) is usually used within a range of 0.8 to 1.2 molar ratio(s), and the base is usually used within a range of 1 to 3 molar ratio(s), as opposed to 1 mole of the compound (M-1).

In the reaction, as needed, metal catalyst may be used. Examples of the metal catalyst include copper catalysts such as copper(I) iodide, copper(I) bromide, copper(I) bromide, copper(I) oxide, copper(I) trifluoromethanesulfonate benzene complex, tetrakis(acetonitrile)copper(I) hexafluorophosphate, and copper(I) 2-thiophenecarboxylate; and nickel catalysts such as bis(cyclooctadiene)nickel(0) and nickel(II) chloride; palladium catalysts such as palladium(II) acetate, tetrakis(triphenylphosphine)palladium(0), and tris(dibenzylideneacetone)dipalladium(II).

When the metal catalyst is used in the reaction, the metal catalyst is usually used within a range of 0.01 to 0.5 molar ratios, as opposed to 1 mole of the compound (M-1).

In the reaction, as needed, a ligand may be used. Examples of the ligand include triphenylphosphine, 4,5-bis(dihenylphoshino)-9,9-dimethylxanthene (hereinafter, referred to as Xantphos), 2,2'-bis(diphenylphoshino)-1,1'-binaphthyl, 1,1'-bis(diphenylphoshino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, 1,10-phenanthroline, trans-1,2-cyclohexanediamine, trans-N,N'-dimethylhexane-1,2-diamine, N,N'-diethylenediamine and the like.

When the ligand is used in the reaction, the ligand is used within a range of 0.01 to 0.5 molar ratios, as 1 mole of the compound (M-1).

The reaction temperature is usually within a range of −20 to 150° C. The reaction period of the reaction is usually within a range of 0.5 to 24 hours.

When the reaction is completed, water is added to the reaction mixture, and the reaction mixtures are extracted with organic solvent(s), and the organic solvents are worked up (for example, drying and concentration) to obtain the compound (I-O).

The compound (M-1) is a commercially available compound, or can be prepared according to a well-known method.

Process 5

A compound represented by formula (I-O-a) (hereinafter, referred to as compound (I-O-a)) can be prepared according to the below-mentioned scheme.

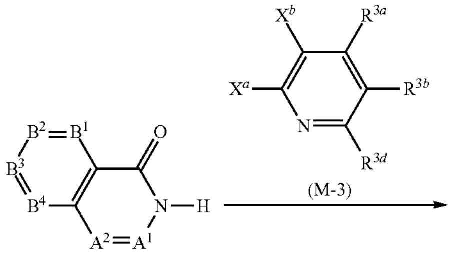

(M-3)

(M-1)

-continued

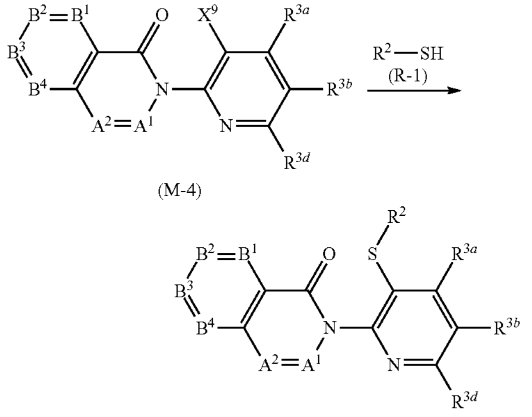

(M-4)

(I-O-a)

[wherein, $X^b$ represents fluorine atom, a chlorine atom, or a bromine atom, and the other symbols are the same as defined above.]

A compound represented by formula (M-4) (hereinafter, referred to as compound (M-4)) can be prepared by using a compound represented by formula (M-3) (hereinafter, referred to as compound (M-3)) in place of the compound (M-2) according to the process 4.

The compound (M-3) is publically known, or can be prepared according to the method described in, for example, WO 2015/187845.

The compound (I-O-a) can be prepared by reacting the compound (M-4) with a compound represented by formula (R-1) (hereinafter, referred to as compound (R-1)) in the presence of a base.

The reaction is usually carried out in a solvent. Examples of the solvents to be used in the reaction include ethers, aromatic hydrocarbons, nitriles, polar aprotic solvents, water, and mixed solvents of two or more kinds of the solvents.

Examples of the bases to be used in the reaction include alkali metal carbonates, alkali metal hydrides, and organic bases.

In the reaction, the compound (R-1) is usually used within a range of 1 to 3 molar ratio(s), and the base is usually used within a range of 1 to 3 molar ratio(s), as opposed to 1 mole of the compound (M-4).

The reaction temperature is usually within a range of −20 to 150° C. The reaction period of the reaction is usually within a range of 0.5 to 24 hours.

When the reaction is completed, water is added to the reaction mixtures, and the reaction mixtures are extracted with organic solvent(s), and the organic solvents are worked up (for example, drying and concentration) to give the compound (I-O-a).

The compound (R-3) is

The compound (R-3) is a commercially available compound, or can be prepared according to a well-known method.

Process 6

A compound represented by formula (II-O-a) (hereinafter, referred to as compound (II-O-a)) can be prepared according to the below-mentioned scheme.

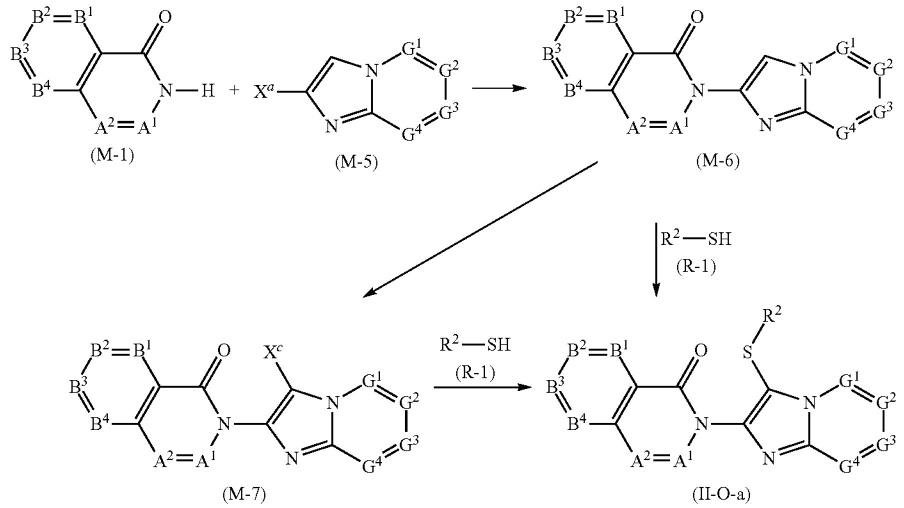

[wherein, $X^c$ represents a chlorine atom, a bromine atom or an iodine atom, and the other symbols are the same as above.]

A compound represented by formula (M-6) (hereinafter, referred to as compound (M-6)) can be prepared by using a compound represented by formula (M-5) (hereinafter, referred to as compound (M-5)) in place of the compound (M-2) according to the process 4.

The compound (M-5) is publically known, or can be prepared according to the method described in, for example, WO 2015/157093, WO 2016/109706, Organic & Biomolecular Chemistry, 2017, 15, 4199, ad Europian Journal of Medicinal Chemistry, 2016, 123, 916.

A compound represented by formula (M-7) (hereinafter, referred to as compound (M-7)) can be prepared by reacting the compound (M-6) with a halogenating agent.

The reaction is usually carried out in a solvent. Examples of the solvent include alcohols, nitriles, ethers, aromatic hydrocarbons, ethers, aromatic hydrocarbons, polar aprotic solvents, halogenated hydrocarbons, water, and mixed solvents of two or more kinds of the solvents.

Examples of the halogenating agent include chlorine, bromine, iodine, N-chlorosuccinimide, N-bromosuccinimide, and N-iodosuccinimide.

In the reaction, the halogenating agent is usually used within a range of 1 to 20 molar ratio(s), as opposed to 1 mole of the compound (M-6).

The reaction temperature of the reaction is usually within a range of −20 to 200° C. The reaction period of the reaction is usually within a range of 0.1 to 72 hours.

When the reaction is completed, water is added to the reaction mixtures, and the reaction mixtures are extracted with organic solvent(s), and the organic solvents are worked up (for example, drying and concentration) to give the compound (M-7).

The compound (II-O-a) can be prepared by reacting the compound (M-6), the compound (R-1) and a halogenating agent.

The reaction is usually carried out in a solvent. Examples of the solvent include alcohols, nitriles, ethers, aromatic hydrocarbons, ethers, aromatic hydrocarbons, polar aprotic solvents, halogenated hydrocarbons, water, and mixed solvents of two or more kinds of the solvents.

Examples of the halogenating agent include chlorine, bromine, iodine, N-chlorosuccinimide, N-bromosuccinimide, and N-iodosuccinimide.

In the reaction, the compound (R-1) is usually used within a range of 1 to 20 molar ratio(s), and the halogenating agent is usually used within a range of 1 to 20 molar ratio(s), as opposed to 1 mole of the compound (M-6).

The reaction temperature of the reaction is usually within a range of −20 to 200° C. The reaction period of the reaction is usually within a range of 0.1 to 72 hours.

When the reaction is completed, water is added to the reaction mixtures, and the reaction mixtures are extracted with organic solvent(s), and the organic solvents are worked up (for example, drying and concentration) to give the compound (II-O-a).

The compound (II-O-a) can be also prepared by reacting the compound (M-7) with the compound (R-1) in the presence of a metal catalyst and a base.

The reaction is usually carried out in a solvent. Examples of the solvents to be used in the reaction include alcohols, nitriles, ethers, aromatic hydrocarbons, polar aprotic solvents, water, and mixed solvents of two or more kinds of the solvents.

Examples of the meal catalyst to be used in the reaction include palladium catalysts such as tetrakis(triphenylphosphine)palladium(0), 1,1'-bis(diphenylphosphino) ferrocene palladium(II) dichloride, tris(dibenzylideneacetone)dipalladium(0), and palladium(II) acetate; nickel catalysts such as bis(cyclooctadiene)nickel(0) and nickel(II) chloride; and copper catalyst such as copper(I) iodide and copper(I) chloride.

Examples of the base to be used in the reaction include alkali metal hydrides, alkali metal carbonates, and organic bases.

A ligand may be used in the reaction. Examples of the ligand to be used in the reaction include triphenylphosphine, Xantphos, 2,2'-bis(diphenylphoshino)-1,1'-binaphthyl, 1,1'-bis(diphenylphoshino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, and 1,10-phenanthroline.

In the reaction, the compound (R5) is usually used within a range of 1 to 20 molar ratio(s), the metal catalyst is usually used within a range of 0.01 to 0.5 molar ratios, the ligand is usually used within a range of 0.01 to 1 molar ratio(s), and the base is usually used within a range of 0.1 to 5 molar ratio(s), as opposed to 1 mole of the compound (M-6).

When a ligand is used in the reaction, the ligand is usually used within a range of 0.01 to 1 molar ratio(s) as opposed to 1 mole of the compound (M-7).

In the reaction, the compound (R-1) is usually used within a range of 1 to 20 molar ratio(s), the metal catalyst is usually used within a range of 0.01 to 0.5 molar ratios, and the base is usually used within a range of 0.1 to 5 molar ratio(s), as opposed to 1 mole of the compound (M-7).

The reaction temperature of the reaction is usually within a range of −20 to 200° C. The reaction period of the reaction is usually within a range of 0.1 to 72 hours.

When the reaction is completed, water is added to the reaction mixtures, and the reaction mixtures are extracted with organic solvent(s), and the organic solvents are worked up (for example, drying and concentration) to give the compound (II-O-a).

Process 7

A compound represented by formula (I-1) (hereinafter, referred to as compound (I-1)) can be prepared according to the below-mentioned scheme.

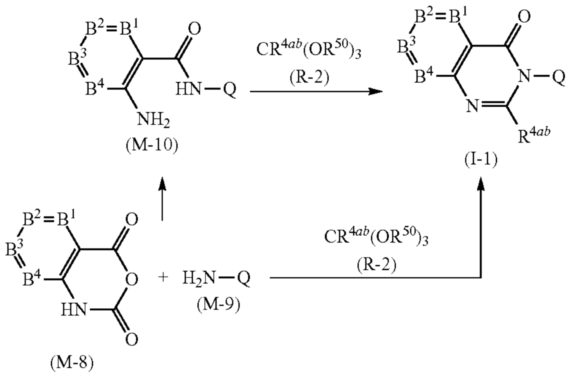

[wherein, $R^{50}$ represents a methyl group or an ethyl group, $R^{4ab}$ represents a C1-C6 chain hydrocarbon group optionally having one or more halogen atoms, a C3-C7 cycloalkyl group optionally having one or more halogen atoms, or a hydrogen atom, and the other symbols are the same as defined above.]

A compound represented by formula (M-10) (hereinafter, referred to as compound (M-10)) can be prepared by reacting a compound represented by formula (M-8) (hereinafter, referred to as compound (M-8)) with a compound represented by formula (M-9) (hereinafter, referred to as compound (M-9)).

The reaction is usually carried out in a solvent. Examples of the solvents to be used in the reaction include alcohols, ethers, aromatic hydrocarbons, nitriles, polar aprotic solvents, and mixed solvents of two or more kinds of the solvents.

A base may be used in the reaction as needed. Examples of the base include organic bases. When the base is used in the reaction, the base is usually used within a range of 1 to 5 molar ratio(s), as opposed to 1 mole of the compound (M-8).

In the reaction, the compound (M-9) is usually used within a range of 1 to 5 molar ratio(s), as opposed to 1 mole of the compound (M-8).

The reaction temperature of the reaction is usually within a range of 0 to 150° C. The reaction period of the reaction is usually within a range of 0.5 to 12 hours.

When the reaction is completed, water is added to the reaction mixtures, and the reaction mixtures are extracted with organic solvent(s), and the organic solvents are worked up (for example, drying and concentration) to give the compound (M-10).

The compound (M-8) can be prepared according to the method described in, for example, Journal of Biological Chemistry, 2016, 291, 14146.

The compound (I-1) can be prepared by reacting the compound (M-10) with a compound represented by formula (R-2) (hereinafter, referred to as compound (R-2)).

The reaction is carried out in the presence or the absence of a solvent. Examples of the solvents to be used in the reaction include ethers, aromatic hydrocarbons, halogenated hydrocarbons, nitriles, polar aprotic solvents and mixed solvents of two or more kinds of the solvents.

In the reaction, the compound (R-2) is usually used within a range of 1 to 50 molar ratio(s), as opposed to 1 mole of the compound (M-10).

An acid or a base may be used in the reaction as needed.

Examples of the acid to be used in the reaction include sulfonic acids such as para-toluenesulfonic acid; carbonic acids such as acetic acid; and polyphosphoric acids.

Examples of the base to be used in the reaction include organic bases.

When the acid or the base is used in the reaction, the acid is usually used within a range of 0.01 to 5 molar ratio(s), and the base is usually used within a range of 1 to 5 molar ratio(s), as opposed to 1 mole of the compound (M-10).

The reaction temperature of the reaction is usually within a range of 0 to 150° C. The reaction period of the reaction is usually within a range of 0.5 to 24 hours.

When the reaction is completed, water is added to reaction mixtures, and the reaction mixtures are extracted with organic solvent(s), and the organic layers are worked up (for example, drying and concentration) to obtain the compound (I-1).

The compound (M-1) is a commercially available compound, or can be prepared according to a well-known method.

Also, the compound (I-1) can be prepared by reacting the compound (M-8), the compound (M-9) and the compound (R-2) in one step (one-spot).

In the reaction, the compound (M-9) is usually used within a range of 1 to 5 molar ratio(s), and the compound (R-2) is usually used within a range of 1 to 50 molar ratio(s), as opposed to 1 mole of the compound (M-8), according to the method for preparing the compound (I-1) from the compound (M-10).

Process 8

A compound represented by formula (I-2) (hereinafter, referred to as compound (I-2) can be prepared by reacting a compound represented by formula (M-11) (hereinafter, referred to as compound (M-11)) with a compound represented by formula (R-3) (hereinafter, referred to as compound (R-3)) in the presence of a base.

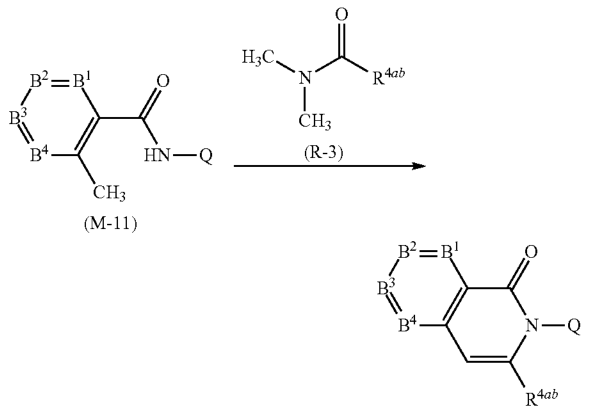

(M-11) (R-3) (I-2)

[wherein the symbols are the same as defined above.]

The reaction is usually carried out in a solvent. Examples of the solvents to be used in the reaction include ethers, aromatic hydrocarbons, and mixed solvents of two or more kinds of the solvents.

Examples of the base to be used in the reaction include butyl lithium, s-butyl lithium, t-butyl lithium, lithium diisopropylamide, lithium bis(trimethylsilyl)amide, sodium bis (trimethylsilyl)amide; and potassium bis(trimethylsilyl)amide.

In the reaction, the compound (R-3) is usually used within a range of 1 to 15 molar ratio(s), and the base is usually used within a range of 1 to 5 molar ratio(s), as opposed to 1 mole of the compound (M-11).

The reaction temperature is usually within a range of −78 to 25° C. The reaction period of the reaction is usually within a range of 0.5 to 12 hours.

When the reaction is completed, water is added to reaction mixtures, and the reaction mixtures are extracted with organic solvent(s), and the organic layers are worked up (for example, drying and concentration) to obtain the compound (I-2).

The compound (R-3) is a commercially available compound, or can be prepared according to a well-known method.

Process 9

A compound represented by formula (I-3) (hereinafter, referred to as compound (I-3)) can be prepared according to the below-mentioned scheme.

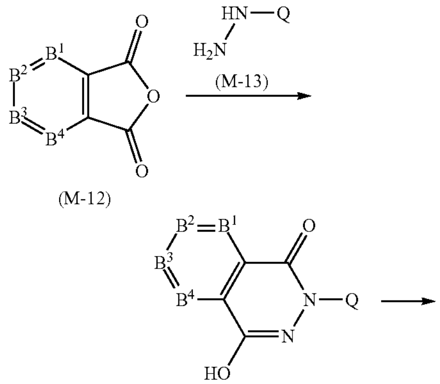

(M-12) (M-13) (M-14)

-continued

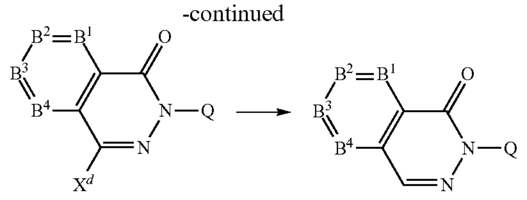

(M-15) (I-3)

[wherein $X^d$ represents a chlorine atom or a bromine atom, and the other symbols are the same as defined above.]

A compound represented by formula (M-14) (hereinafter, referred to as compound (M-14)) can be prepared by reacting a compound represented by formula (M-12) (hereinafter, referred to as compound (M-12)) with a compound represented by formula (M-13) (hereinafter, referred to as compound (M-13)). The reaction can be carried out according to the method described in, for example, Journal of Medicinal Chemistry, 2011, 54, 2102.

A compound represented by formula (M-15) (hereinafter, referred to as compound (M-15)) can be prepared by reacting the compound (M-14) with a halogenating agent.

The reaction is carried out in the presence or the absence of a solvent. Examples of the solvents to be used in the reaction include ethers, aromatic hydrocarbons, halogenated hydrocarbons, and mixed solvents of two or more kinds of the solvents.

Examples of the halogenating agent to be used in the reaction include thionyl chloride, oxalyl chloride, phosphorus oxychloride, phosphorus trichloride, phosphorus pentachloride, thionyl bromide, phosphorus oxybromide, phosphorus tribromide, and phosphorus pentachloride.

In the reaction, the halogenating agent is usually used within a range of 1 to 30 molar ratio(s), as opposed to 1 mole of the compound (M-14).

The reaction temperature is usually within a range of 0 to 100° C. The reaction period of the reaction is usually within a range of 0.1 to 24 hours.

When the reaction is completed, water is added to reaction mixtures, and the reaction mixtures are extracted with organic solvent(s), and the organic layers are worked up (for example, drying and concentration) to obtain the compound (M-15).

The compound (I-3) can be prepared by reacting the compound (M-15) with a hydrogen in the presence of a catalyst.

The reaction is usually carried out in a solvent under 1 to 100 bar of hydrogen atmosphere. Examples of the solvent to be used in the reaction include ethers; esters (such as ethyl acetate, and butyl acetate) (hereinafter, collectively referred to as esters); alcohols; water; and mixed solvents comprising two or more thereof.

Examples of the catalysts to be used in the reaction include palladium carbon.

In the reaction, the catalyst is usually used within a range of 0.001 to 0.5 molar ratios, as opposed to 1 mole of the compound (M-15).

An acid or a base may be used in the reaction as needed. Examples of the acid to be used in the reaction include acetic acid, and hydrochloric acid, and examples of the base to be used in the reaction include tertiary amines such as triethylamine. When the acid is used in the reaction, the acid is usually used within a range of 0.1 to 5 molar ratio(s), as opposed to 1 mole of the compound (M-15). When the base is used in the reaction, the base is usually used within a range of 0.1 to 5 molar ratio(s), as opposed to 1 mole of the compound (M-15).

The reaction temperature is usually within a range of −20 to 100° C. The reaction period of the reaction is usually within a range of 0.1 to 24 hours.

When the reaction is completed, the reaction mixtures are filtered, and as needed, are extracted with organic solvent(s), and the resulting organic layers are worked up (for example, drying and concentration) to obtain the Compound (I-3).

Process 10

An oxide of the compound represented by formula (I) can be prepared by reacting the compound represented by formula (I) with an oxidizing agent. The reaction can be carried out according to the method described in, for example, the process 1, U.S. patent publication No. 2018/0009778 or WO 2016/121970.

Process 11

A compound represented by formula (I-4) (hereinafter, referred to as compound (I-4)) can be prepared by reacting the compound (M-10) with sodium sulfite in the presence of a halogenating agent.

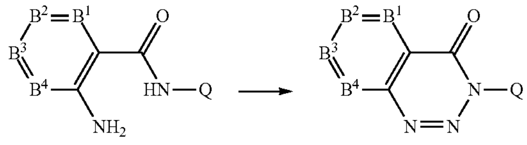

(M-10) (I-4)

The reaction is carried out in the presence or the absence of a solvent. Examples of the solvents to be used in the reaction include nitriles, polar aprotic solvents, and mixed solvents of two or more kinds of the solvents.

Examples of the halogenating agent to be used in the reaction include chlorine, bromine, iodine, N-chlorosuccinimide, N-bromosuccinimide, and N-iodosuccinimide.

In the reaction, the sodium sulfite is usually used within a range of 1 to 10 molar ratios, and the halogenating agent is usually used within a range of 0.1 to 5 molar ratio(s), as opposed to 1 mole of the compound (M-10).

The reaction temperature is usually within a range of 0 to 100° C. The reaction period of the reaction is usually within a range of 0.5 to 12 hours.

When the reaction is completed, water is added to reaction mixtures, and the reaction mixtures are extracted with organic solvent(s), and the organic layers are worked up (for example, drying and concentration) to obtain the compound (I-4).

Next, a process for preparing preparation intermediate compound is described.

Reference Process 1

A compound represented by formula (M-2A-b) and a compound represented by formula (M-2A-c) can be prepared by reacting the compound represented by formula (M-2A-a) (hereinafter, referred to as compound (M-2A-a)) with an oxidizing agent.

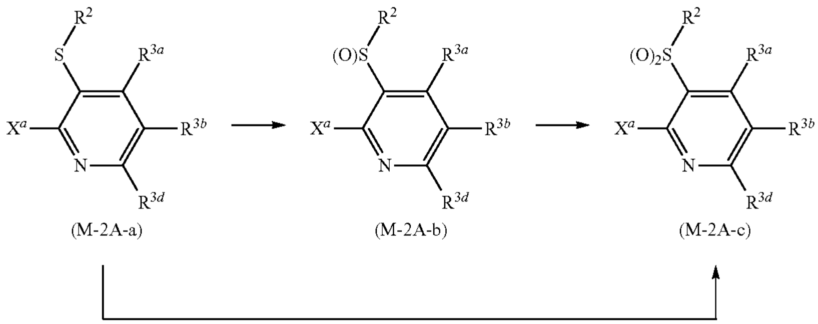

(M-2A-a) (M-2A-b) (M-2A-c)

[wherein the symbols are the same as defined above.]

These reactions can be carried out according to the process 1.

Reference Process 2

The compound (M-2A-a) can be prepared by reacting a compound represented by formula (M-2A-1) (hereinafter, referred to as compound (M-2A-1)) with the compound (R-1) in the presence of a base.

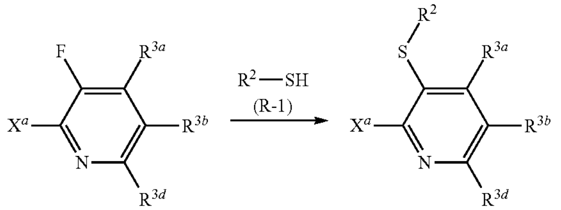

(M-2A-1) (M-2A-a)

[wherein the symbols are the same as defined above.]

The reaction can be carried out according to the method described in the process 5 for preparing the compound (I-O-a) from the compound (M-4).

The compound (M-2A-1) is a commercially available compound, or can be prepared according to a well-known method.

Reference Process 3

A compound represented by formula (M-2B-b) and a compound represented by formula (M-2B-c) can be prepared by reacting a compound represented by formula (M-2B-a) with an oxidizing agent.

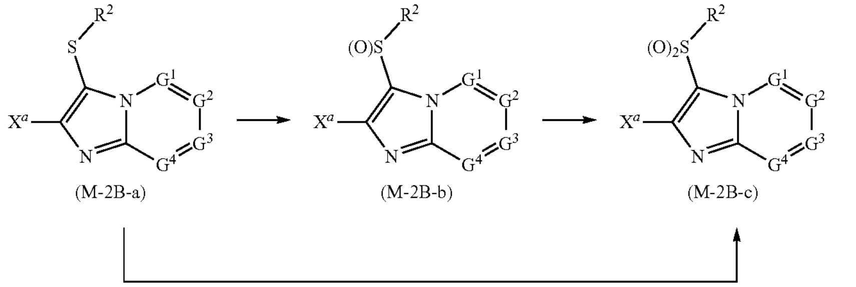

(M-2B-a) (M-2B-b) (M-2B-c)

[wherein the symbols are the same as defined above.]

These reactions can be carried out according to the process 1.

Reference Process 4

A compound represented by formula (M-2B-d) can be prepared according to the below-mentioned scheme.

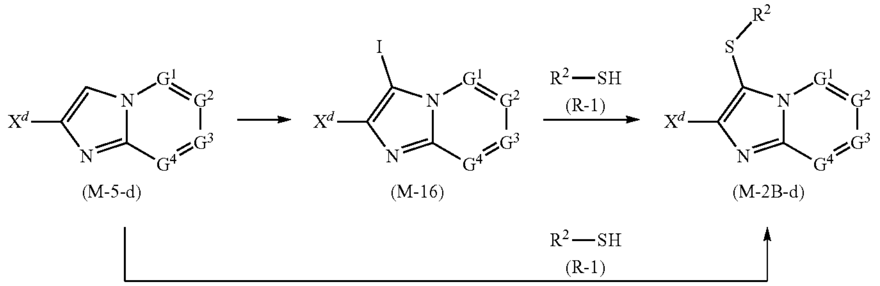

(M-5-d) (M-16) (M-2B-d)

[wherein the symbols are the same as defined above.]

A compound represented by formula (M-16) (hereinafter, referred to as compound (M-16)) can be prepared by reacting a compound represented by formula (M-5-d) (hereinafter, referred to as compound (M-5-d)) with N-iodosuccinimide. The reaction can be carried out according to the method described in the process 6 for preparing the compound (M-7) from the compound (M-6).

The compound (M-2B-d) can be prepared by reacting the compound (M-16) or the compound (M-5-d) with the compound (R-1). These reactions can be carried out according to the method described in the process 6 for preparing the compound (II-O-a) from the compound (M-6) or the compound (M-7).

Reference Process 5

A compound represented by formula (M-2B-f) can be prepared by reacting a compound represented by formula (M-2B-e) (hereinafter, referred to as compound (M-2B-e)) with silver fluoride in the presence of a metal catalyst.

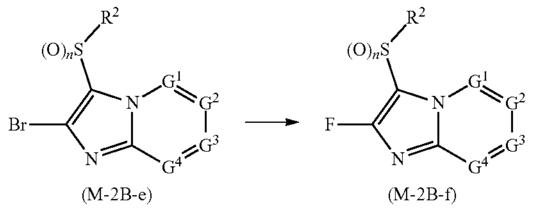

(M-2B-e) (M-2B-f)

[wherein the symbols are the same as defined above.]

The reaction can be carried out according to the method described in, for example, Journal of the American Chemical Society, 2014, 136, 3792.

Reference Process 6

A compound represented by formula (M-2B-g) can be prepared by reacting the compound (M-2B-e) with sodium iodide in the presence of a metal catalyst.

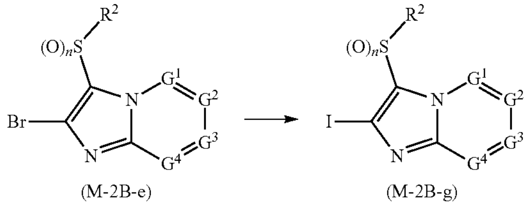

(M-2B-e) (M-2B-g)

[wherein the symbols are the same as defined above.]

The reaction can be carried out according to the method described in, for example, Journal of the American Chemical Society, 2002, 124, 14844.

Reference Process 7

A compound represented by formula (M-4A) (hereinafter, referred to as compound (M-4A)) can be prepared by reacting a compound represented by formula (M-17) (hereinafter, referred to as compound (M-17)) with the compound (R-3) in the presence of a base.

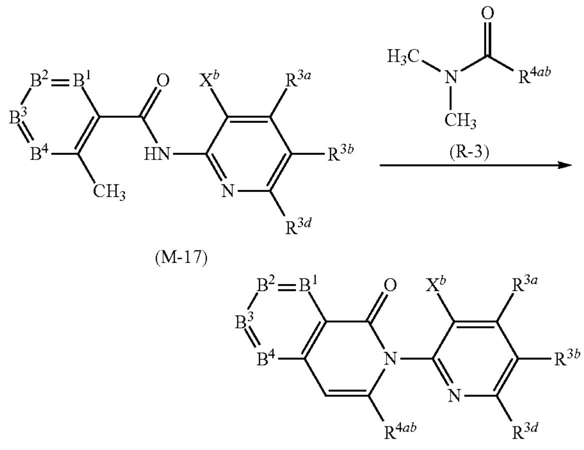
(M-17)
(R-3)
(M-4A)

[wherein the symbols are the same as defined above]

The reaction can be carried out by using the compound (M-17) in place of the compound (M-11) according to the process 8.

Reference Process 8

The compound (M-4B) can be prepared by reacting a compound represented by formula (M-18) (hereinafter, referred to as compound (M-18)) with the compound (R-3) in the presence of a base.

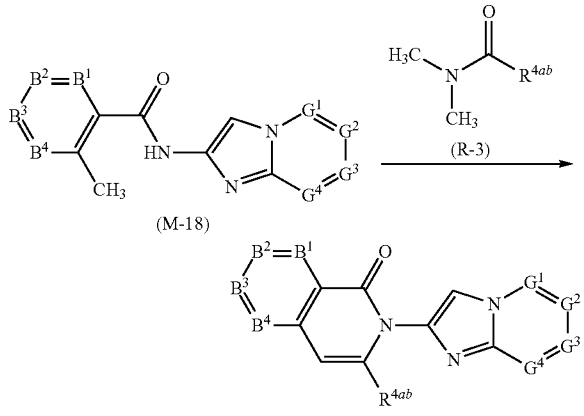
(M-18)
(R-3)
(M-4B)

[wherein the symbols are the same as defined above.]

The reaction can be carried out by using the compound (M-18) in place of the compound (M-11) according to the process 8.

Reference Process 9

The compound (M-11) can be prepared by reacting a compound represented by formula (M-19) (hereinafter, referred to as compound (M-19)) with the compound (M-9) in the presence of a condensation agent.

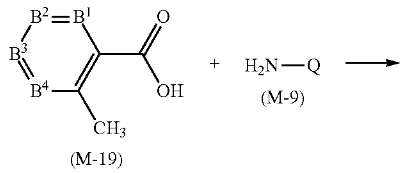
(M-19)
(M-9)

-continued

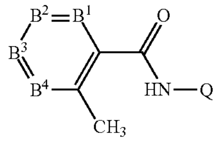
(M-11)

[wherein the symbols are the same as defined above.]

The reaction is usually carried out in a solvent. Examples of the solvents to be used in the reaction include ethers, halogenated hydrocarbons, aromatic hydrocarbons, esters, polar aprotic solvents, nitrogen-containing aromatic hydrocarbons, and mixed solvents of two or more kinds of the solvents.

Examples of the condensation agent include 1-ethyl-3-83-dimetylaminopropyl)carbodiimide (hereinafter, referred to as WSC) and 1,3-dicyclohexylarbodiimide In the reaction, the compound (M-9) is usually used within a range of 0.8 to 1.2 molar ratio(s), and the condensation agent is usually used within a range of 1 to 2 molar ratio(s), as opposed to 1 mole of the compound (M-19).

A catalyst may be added in the reaction as needed. Examples of the catalyst include 1-hydroxybenzotriazole (hereinafter, referred to as HOBt). When the catalyst is used in the reaction, the catalyst is usually used within a range of 0.01 to 1 molar ratio(s), as opposed to 1 mole of the compound (M-19).

The reaction temperature of the reaction is usually within a range of 0 to 200° C. The reaction period of the reaction is usually within a range of 0.1 to 24 hours.

When the reaction is completed, water is added to reaction mixtures, and the reaction mixtures are extracted with organic solvent(s), and the organic layers are worked up (for example, drying and concentration) to obtain the compound (M-11).

The compound (M-19) is a commercially available compound, or can be prepared according to a well-known method.

Reference Process 10

The compound (M-17) can be prepared by reacting the compound (M-19) with a compound represented by formula (M-20) (hereinafter, referred to as compound (M-20)) in the presence of a condensation agent.

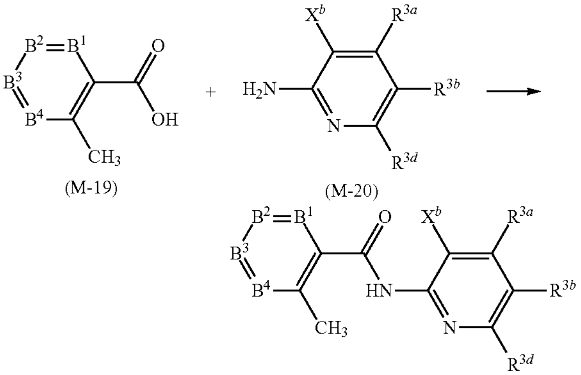
(M-19)
(M-20)
(M-17)

[wherein the symbols are the same as defined above.]

The reaction can be carried out by using the compound (M-20) in place of the compound (M-9) according to the Reference Process 9.

Reference Process 11

The compound (M-18) can be prepared by reacting the compound (M-19) with a compound represented by formula (M-21) (hereinafter, referred to as compound (M-21)) in the presence of a condensation agent.

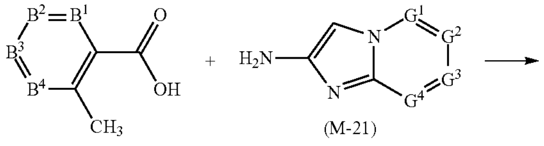

(M-19) (M-21)

-continued

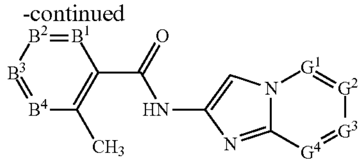

(M-18)

[wherein the symbols are the same as defined above.]

The reaction can be carried out by using the compound (M-21) in place of the compound (M-9) according to the Reference Process 9.

Reference Process 11

A compound represented by formula (M-4C) can be prepared according to the below-mentioned scheme.

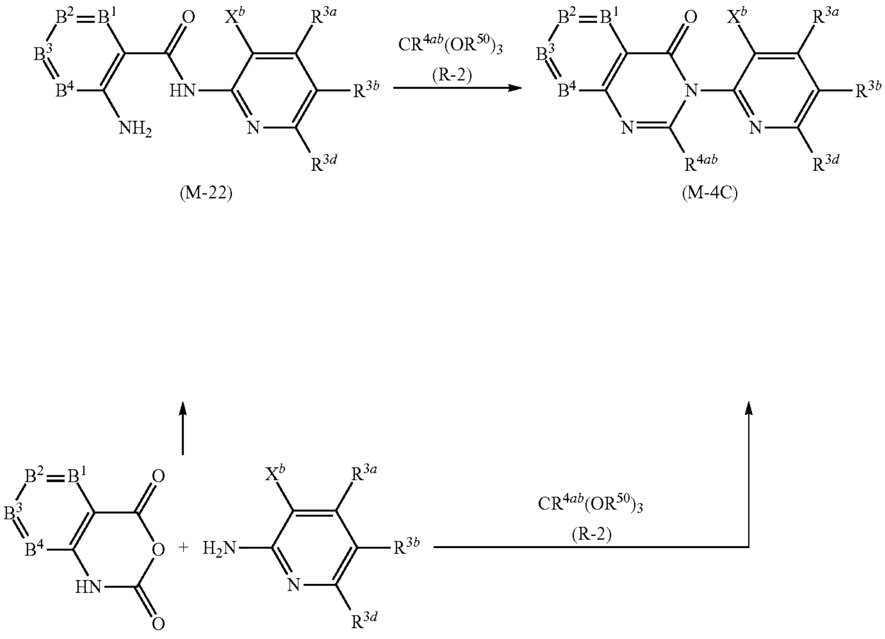

(M-22) (M-4C) (M-8) (M-20)

[wherein the symbols are the same as defined above.]

These reactions can be carried out according to the Process 7.

Reference Process 12

A compound represented by formula (M-4D) can be prepared according to the below-mentioned scheme.

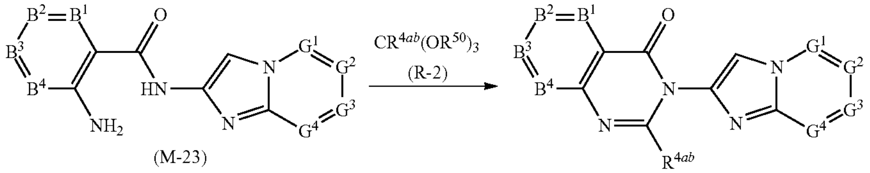

(M-23) (M-4D)

-continued

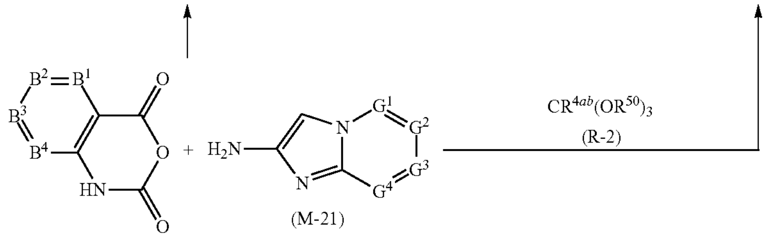

(M-21)

(M-8)

[wherein the symbols are the same as defined above.]

These reactions can be carried out according to the Process 7.

Reference Process 13

The compound (M-12) can be prepared by a dehydration condensation of a compound represented by formula (M-24) (hereinafter, referred to as compound (M-24)).

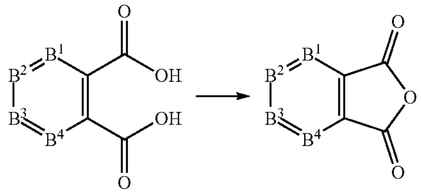

(M-24) (M-12)

[wherein the symbols are the same as defined above.]

The reaction can be carried out according to the method described in, for example, Organic Letters, 2010, 12, 4796.

The compound (M-24) is a commercially available compound, or can be prepared according to a well-known method.

Reference Process 14

A compound represented by formula (M-4E) can be prepared according to the below-mentioned scheme.

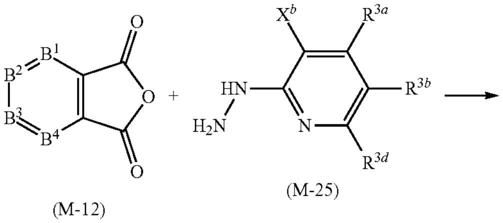

(M-12) (M-25)

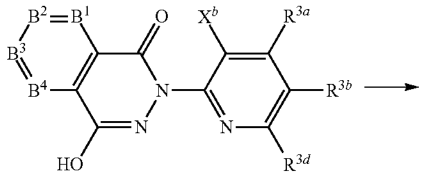

(M-26)

-continued

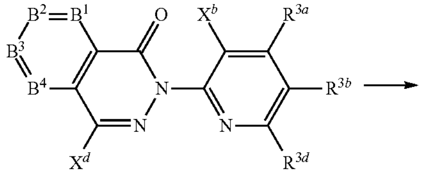

(M-27)

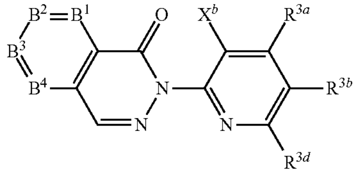

(M-4E)

[wherein the symbols are the same as defined above.]

These reactions can be carried out according to the Process 9.

A compound represented by formula (M-4F) can be prepared according to the below-mentioned scheme.

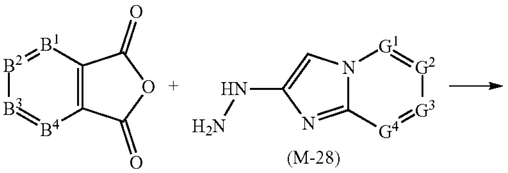

(M-28)

(M-12)

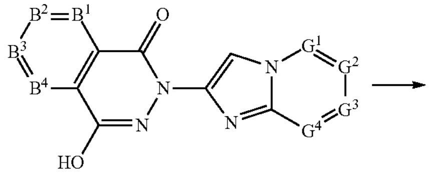

(M-29)

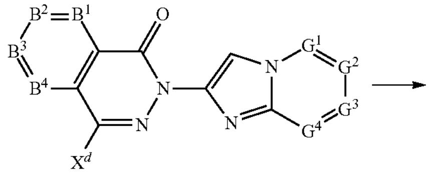

(M-30)

-continued

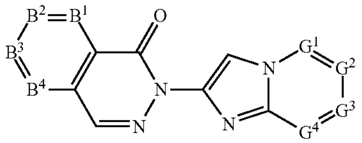

(M-4F)

[wherein the symbols are the same as defined above.]

These reactions can be carried out according to the Process 9.

Reference Process 16

The compound (M-9) can be prepared by reacting the compound (M-2) with ammonia.

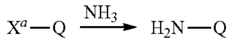

(M-2) (M-9)

[wherein the symbols are the same as defined above.]

The reaction can be carried out according to the method described in, for example, Journal of Medicinal Chemistry, 1980, 23, 1376 or WO 2010/130665.

The compound (M-9) can be prepared by according to the method described in WO 2018/052136.

Reference Process 17

The compound (M-20) can be prepared by reacting the compound (M-3) with ammonia.

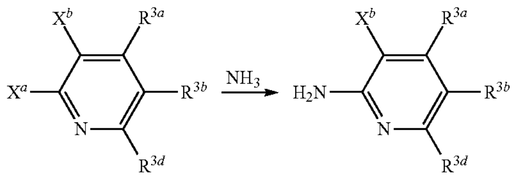

(M-3) (M-20)

[wherein the symbols are the same as defined above.]

The reaction can be carried out according to the Reference Process 16.

Reference Process 18

The compound (M-21) can be prepared by reacting the compound (M-5) with ammonia.

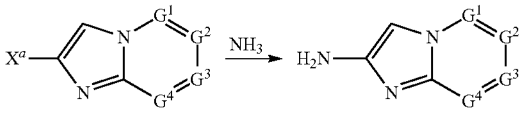

(M-5) (M-21)

[wherein the symbols are the same as defined above.]

The reaction can be carried out according to the Reference Process 16.

Reference Process 19

The compound (M-13) can be prepared by reacting the compound (M-2) with hydrazine monohydrate.

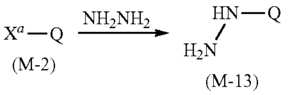

(M-2) (M-13)

[wherein the symbols are the same as defined above.]

The reaction can be carried out according to the method described in, for example WO 2018/008727.

Reference Process 20

The compound (M-25) can be prepared by reacting the compound (M-3) with hydrazine monohydrate.

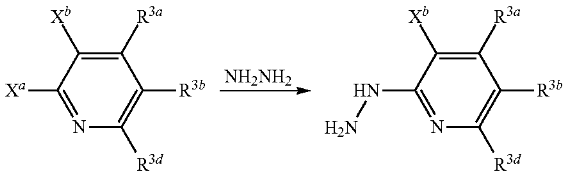

(M-3) (M-25)

[wherein the symbols are the same as defined above.]

The reaction can be carried out according to the Reference Process 19.

Reference Process 21

The compound (M-28) can be prepared by reacting the compound (M-5) with hydrazine monohydrate.

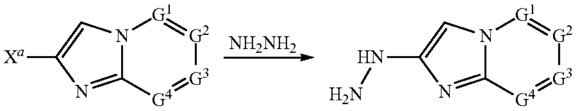

(M-5) (M-28)

[wherein the symbols are the same as defined above.]

The reaction can be carried out according to the Reference Process 19.

Reference Process 22

A compound represented by formula (M-1A) can be prepared by reacting a compound represented by formula (M-31) (hereinafter, referred to as compound (M-31)) with a compound represented by formula (M-32) (hereinafter, referred to as compound (M-32)).

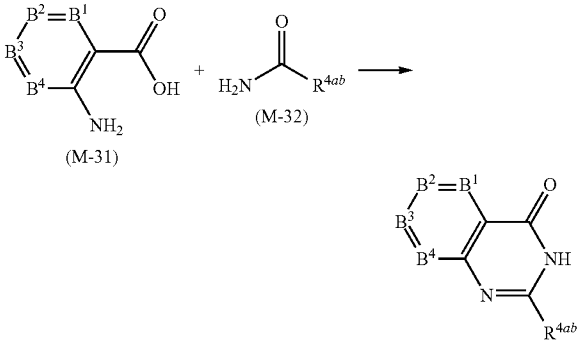

(M-31) (M-32) (M-1A)

[wherein the symbols are the same as defined above.]

The reaction can be carried out according to the method described in, for example, European Journal of Medicinal Chemistry, 2012, 50, 264.

The compound (M-31) and the compound (M-32) are commercially available compounds, or can be prepared according to a well-known method.

Reference Process 23

A compound represented by formula (M-1B) can be prepared according to the below-mentioned scheme.

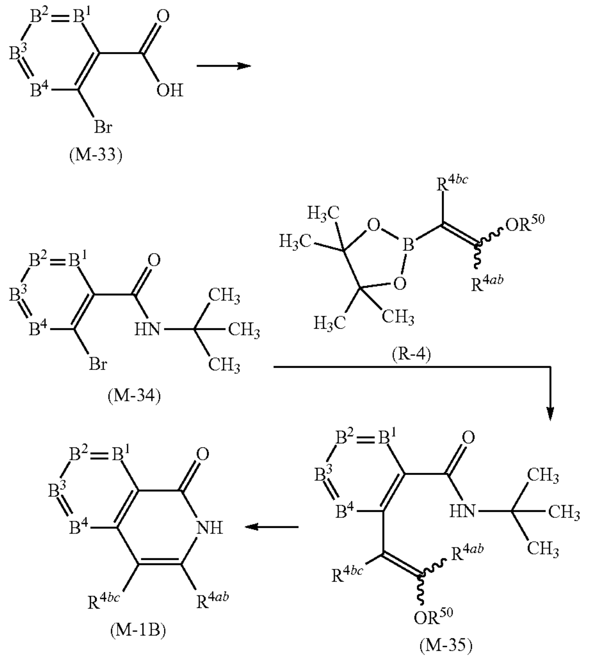

(M-33) (M-34) (R-4) (M-1B) (M-35)

[wherein $R^{4bc}$ represents a C1-C6 chain hydrocarbon group optionally having one or more halogen atoms, a C3-C7 cycloalkyl group optionally having one or more halogen atoms, or a hydrogen atom, and the other symbols are the same as defined above.

The reaction can be carried out according to the method described in, for example, European Journal of Organic Chemistry, 2016, 4171.

A compound represented by formula (M-33) and a compound represented by formula (M-34) are commercially available compounds, or can be prepared according to a well-known method.

Reference Process 24

A compound represented by formula (M-1C) can be prepared by reacting a compound represented by formula (M-36) (hereinafter, referred to as compound (M-36)) with hydrazine monohydrate.

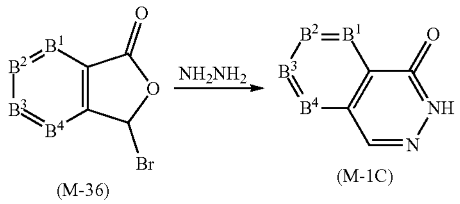

(M-36) (M-1C)

[wherein the symbols are the same as defined above.]

The reaction can be carried out according to the method described in, for example, WO 2011/159854.

The compound (M-36) can be prepared according to the method described in, for example, Bioorganic & Medicinal Chemistry, 2013, 23, 1063.

The present compound or the present compound X may be mixed or combined with one or more kinds of ingredients selected from a group consisting of the following Group (a), Group (b), Group (c), and Group (d) (hereinafter, referred to as Present ingredient).

The above-mentioned mixing or combining represents a use of the Present compound or the present compound X and the Present ingredient at same time, separately or at certain intervals.

When the Present compound or the present compound X and the present ingredient are used at the same time, the Present compound or the present compound X and the Present ingredient may be contained in separate formulations respectively or may be contained in the same one formulation.

One aspect of the present invention is a composition comprising one or more ingredients selected from Group (a) or Group (b) as well as the Present compound.

One aspect of the present invention is a composition comprising one or more ingredients selected from a group consisting of the following Group (a), Group (b), Group (c), and Group (d) as well as the Present compound X (hereinafter, referred to as Composition A).

Group (a) is a group consisting of each active ingredient as Acetylcholinesterase inhibitors (for example, carbamate insecticides, or organophosphorus insecticides), GABA-gated chloride channel blockers (for example, phenylpyrazol insecticides), Sodium channel modulators (for example, pyrethroid insecticides), Nicotinic acetylcholine receptor competitive modulators (for example, neonicotinoid insecticides), Nicotinic acetylcholine receptor allosteric modulators, Glutamatergic chlorine ion channel allosteric modulators (for example, macrolide insecticides), Juvenile hormone mimic, Multisite inhibitors, chordotonal organ TRPV channel modulators, Mites growth inhibitors, Mitochondria ATP biosynthetic enzyme inhibitors, Uncouplers of oxidative phosphorylation, Nicotinic acetylcholine receptor channel blocker (for example, Nereistoxin insecticides), Chitin synthesis inhibitors, Molting inhibitors, Ecdysone receptor agonist, Octopamine receptor agonist, Inhibitors of Mitochondrial electron transport system complex I, II, III and IV, Voltage-dependent sodium channel blockers, Acetyl CoA carboxylase inhibitor, Ryanodine receptor modulator (for example, Diamide insecticides), Chordotonal organ modulators, Microbial pesticides; and the other insecticidal, miticidal or nematicidal active ingredients.

These ingredients are classified as a class based on the action mechanism of IRAC.

Group (b) is a group consisting of

Nucleic acid synthesis inhibitors (for example, Phenylamide fungicides, or Acylamino acid fungicides), cell division and cytoskeleton inhibitors (for example, MBC fungicides), Respiratory inhibitors (for example, QoI fungicides or QiI fungicides), Amino acid synthesis and protein synthesis inhibitors (for example, anilinopyridine fungicides), Signal transduction inhibitors, Lipid synthesis and membrane synthesis inhibitors, sterol biosynthesis inhibitors (for example, DMI fungicides such as triazole), cell wall synthesis inhibitors, Melanin synthesis inhibitors, Plant defense inducers, Other action point contact active fungicides, Microbial fungicides, and the other fungicidal ingredients. These are classified as a class based on the action mechanism of FRAC.

Group (c) is a plant growth modulating ingredient group (including Mycorrhizal fungi, and Root nodule bacteria).

Group (d) is a repellent ingredient group.

Examples of the combination of the Present ingredient and the Present compound X are described below. For example, alanycarb+SX represents a combination of alanycarb and SX.

The symbol of "SX" represents any one of the Present compound X selected from the Compound Class $SX_1$ to the Compound Class $SX_{2332}$. Also, all of the below-mentioned present active ingredient are known ingredients, and are commercially available or may be produced by the known method. If the present ingredient is a bacterium, it is available from the bacterial authority depository. The numerical number in bracket represents a CAS RN (Register Trademark).

Combination of the Present ingredient of the above Group (a) and the Present compound:

abamectin+SX, acephate+SX, acequinocyl+SX, acetamiprid+SX, acetoprole+SX, acrinathrin+SX, acynonapyr+SX, afidopyropen+SX, afoxolaner+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, ainphos-methyl+SX, axocyclotin+SX, bark of *Celastrus angulatus*+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+SX, calcium phosphide+SX, carbaryl+SX, carbofuran+SX, carbosulfan+SX, cartap hydrochloride+SX, cartap+SX, chinomethionat+SX, chlorantraniliprole+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, concanamycin A+SX, coumaphos+SX, cryolite+SX, cyanophos+SX, cyantraniliprole+SX, cycloniliprole+SX, cycloprothrin+SX, cycloxaprid+SX, cyenopyrafen+SX, cyflumetofen+SX, cyfluthrin+SX, cyhalodiamide+SX, cyhalothrin+SX, cyhexatin+SX, cypermethrin+SX, cyphenothrin+SX, cyromazine+SX, dazomet+SX, deltamethrin+SX, demeton-S-methyl+SX, diafenthiuron+SX, diazinon+SX, dichlorvos+SX, dicloromezotiaz+SX, dicofol+SX, dicrotophos+SX, diflovidazin+SX, diflubenzuron+SX, dimefluthrin+SX, dimethoate+SX, dimethylvinphos+SX, dimpropyridaz+SX, dinotefuran+SX, disodium octaborate+SX, disulfoton+SX, DNOC (2-methyl-4,6-dinitrophenol)+SX, doramectin+SX, dried leaves of Dryopteris filix-mas+SX, emamectin-benzoate+SX, empenthrin+SX, endosulfan+SX, EPN(O-ethyl O-(4-nitrophenyl)phenylphosphonothioate)+SX, epsilon-metofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, extract of *Artemisia absinthium*+SX, extract of *Cassia nigricans*+SX, extract of *Clitoria ternatea*+SX, extract of *Symphytum officinale*+SX, extracts or simulated blend of *Chenopodium ambrosioides*+SX, extract of *Tanacetum vulgare*+SX, extract of *Urtica dioica*+SX, extract of *Viscum album*+SX, famphur+SX, fenamiphos+SX, fenazaquin+SX, fenbutatin oxide+SX, fenitrothion+SX, fenobucarb+SX, fenoxycarb+SX, fenpropathrin+SX, fenpyroximate+SX, fenthion+SX, fenvalerate+SX, fipronil+SX, flometoquin+SX, flonicamid+SX, fluacrypyrim+SX, fluazaindolizine+SX, fluazuron+SX, flubendiamide+SX, flucycloxuron+SX, flucythrinate+SX, fluensulfone+SX, flufenoprox+SX, flufenoxuron+SX, flufiprole+SX, flumethrin+SX, flupyradifurone+SX, flupyrimin+SX, fluralaner+SX, fluvalinate+SX, fluxametamide+SX, formetanate+SX, fosthiazate+SX, furamethrin+SX, furathiocarb+SX, gamma-cyhalothrin+SX, GS-omega/kappa HXTX-Hvla peptide+SX, halfenprox+SX, halofenozide+SX, heptafluthrin+SX, heptenophos+SX, hexaflumuron+SX, hexythiazox+SX, potassium salt of hop beta acid+SX, hydramethylnon+SX, hydroprene+SX, imicyafos+SX, imidacloprid+SX, imidaclothiz+SX, imiprothrin+SX, indoxacarb+SX, isocycloseram+SX, isofenphos+SX, isoprocarb+SX, isopropyl-O-(methoxyaminothiophosphoryl) salicylate+SX, isoxathion+SX, ivermectin+SX, kadethrin+SX, kappa-tefluthrin+SX, kappa-bifenthrin+SX, kinoprene+SX, lambda-cyhalothrin+SX, lenoremycin+SX, lepimectin+SX, lime sulfur+SX, lotilaner+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methomyl+SX, methoprene+SX, methoxychlor+SX, methoxyfenozide+SX, methyl bromide+SX, metofluthrin+SX, metolcarb+SX, metoxadiazone+SX, mevinphos+SX, milbemectin+SX, milbemycin oxime+SX, momfluorothrin+SX, monocrotophos+SX, moxidectin+SX, naled+SX, neem oil+SX, nicotine+SX, nicotine-sulfate+SX, nitenpyram+SX, novaluron+SX, noviflumuron+SX, oil of the seeds of *Chenopodium anthelminticum*+SX, omethoate+SX, oxamyl+SX, oxazosulfyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, prallethrin+SX, profenofos+SX, profluthrin+SX, propargite+SX, propetamphos+SX, propoxur+SX, propylene glycol alginate+SX, prothiofos+SX, pyflubumide+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, ryanodine+SX, sarolaner+SX, selamectin+SX, sigma-cypermethrin+SX, silafluofen+SX, sodium borate+SX, sodium metaborate+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, tefluthrin+SX, temephos+SX, terbufos+SX, terpene constituents of the extract of *Chenopodium ambrosioides* near *ambrosioides*+SX, tetrachlorantraniliprole+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultap-disodium+SX, thiosultap-monosodium+SX, tioxazafen+SX, tolfenpyrad+SX, tralomethrin+SX, transfluthrin+SX, triazamate+SX, triazophos+SX, trichlorfon+SX, b triflumezopyrim+SX, triflumuron+SX, trimethacarb+SX, tyclopyrazoflor+SX, vamidothion+SX, wood extract of *Quassia amara*+SX, XMC (3,5-dimethylphenyl N-methylcarbamate)+SX, xylylcarb+SX, zeta-cypermethrin+SX, zinc phosphide+SX, N-[3-chloro-1-(pyridin-3-yl)-1H-pyrazol-4-yl]-N-ethyl-3-(3,3,3-trifluoropropanesulfinyl)propanamide (1477923-37-7)+SX, 4-[5-(3,5-dichlorophenyl)-5-(trifluoromethyl)-4,5-dihydro-1,2-oxazol-3-yl]-2-methyl-N-(1-oxothietan-3-yl)benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl)propanamide (1118626-57-5)+SX, N-[2-bromo-6-chloro-4-(1,1,1,2,3,3,3-heptafluoropropan-2-yl)phenyl]-3-{ethyl[(pyridin-4-yl)carbonyl]amino}-2-methoxybenzamide (1429513-53-0)+SX, N-[2-bromo-6-chloro-4-(1,1,1,2,3,3,3-heptafluoropropan-2-yl)phenyl]-3-[ethyl(4-cyanobenzoyl)amino]-2-methoxybenzamide (1609007-65-9)+SX, N-[2-bromo-6-(difluoromethoxy)-4-(1,1,1,2,3,3,3-heptafluoropropan-2-yl)phenyl]-3-{methyl[(pyridin-4-yl)carbonyl]amino}-2-methoxybenzamide (1630969-78-6)+SX, 1-{2-fluoro-4-methyl-5-[(2,2,2-trifluoroethyl)sulfanyl]phenyl}-3-(trifluoromethyl)-1H-1,2,4-triazol-5-amine (885026-50-6)+SX, BT crop protein Cry1Ab+SX, BT crop protein Cry1Ac+SX, BT crop protein Cry1Fa+SX, BT crop protein Cry1A105+SX, BT crop protein Cry2Ab+SX, BT crop protein Vip3A+SX, BT crop protein Cry3A+SX, BT crop protein Cry3Ab+SX, BT crop protein Cry3Bb+SX, BT crop protein Cry34AB1/Cry35AB1+SX, *Adoxophyes orana* granulosis virus strain BV-0001+SX, *Anticarsia gemmatalis* mNPV+SX, *Autographa californica* mNPV+SX, *Cydia pomonella* GV strain V15+SX, *Cydia pomonella* GV strain V22+SX, *Cryptophlebia leucotreta* GV+SX, *Dendrolimus punctatus* cypovirus+SX, *Helicoverpa armigera* NPV strain BV-0003+SX, *Helicoverpa zea* NPV+SX, *Lymantria dispar* NPV+SX, *Mamestra brassicae* NPV+SX, *Mamestra configurata* NPV+SX, Neodiprion *abietis* NPV+SX, Neodiprion *lecontei* NPV+SX, Neodiprion *sertifer* NPV+SX, *Nosema locustae*+SX, *Orgyia pseudotsugata* NPV+SX, *Pieris rapae* GV+SX, *Plodia interpunctella* GV+SX, *Spodoptera exigua* mNPV+SX, *Spodoptera littoralis* mNPV+SX, *Spodoptera litura* NPV+SX, *Arthrobotrys dactyloides*+SX, *Bacillus firmus* strain GB126+SX, *Bacillus firmus* strain I-1582+SX, *Bacillus megaterium*+SX, *Bacillus* sp. strain AQ175+SX, *Bacillus* sp. strain AQ177+SX, *Bacillus* sp. strain AQ178+SX, *Bacillus sphaericus* strain 2362+SX, *Bacillus sphaericus* strain ABTS1743+SX, *Bacillus sphaericus* Serotype strain H5a5b+SX, *Bacillus thuringiensis* strain AQ52+SX, *Bacillus thuringiensis* strain BD #32+SX, *Bacillus thuringiensis* strain CR37 1+SX, *Bacillus thuringiensis* subsp. *aizawai* strain ABTS-1857+SX, *Bacillus thuringiensis* subsp. *aizawai* strain AM65-52+SX, *Bacillus thuringiensis* subsp. *aizawai* strain GC-91+SX, *Bacillus thuringiensis* subsp. *aizawai* Serotype strain H-7+SX, *Bacillus thuringiensis* subsp. *kurstaki* strain ABTS351+SX, *Bacillus thuringiensis* subsp. *kurstaki* strain BMP123+SX, *Bacillus thuringiensis* subsp. *kurstaki* strain EG234+SX, *Bacillus thuringiensis* subsp. *kurstaki* strain EG7841+SX, *Bacillus thuringiensis* subsp. *kurstaki* strain EVB113-19+SX, *Bacillus thuringiensis* subsp. *kurstaki* strain F810+SX, *Bacillus thuringiensis* subsp. *kurstaki* strain HD-1+SX, *Bacillus thuringiensis* subsp. *kurstaki* strain PB54+SX, *Bacillus thuringiensis* subsp. *kurstaki* strain SA11+SX, *Bacillus thuringiensis* subsp. *kurstaki* strain SA12+SX, *Bacillus thuringiensis* subsp. *tenebriosis* strain NB176+SX, *Bacillus thuringiensis* subsp. *Thuringiensis* strain MPPL002+SX, *Bacillus thuringiensis* subsp. *morrisoni*+SX, *Bacillus thuringiensis* var. *colmeri*+SX, *Bacillus thuringiensis* var. *darmstadiensis* strain 24-91+SX, *Bacillus thuringiensis* var. *dendrolimus*+SX, *Bacillus thuringiensis* var. *galleriae*+SX, *Bacillus thuringiensis* var. *israelensis* strain BMP144+SX, *Bacillus thuringiensis* var. *israelensis* serotype strain H-14+SX, *Bacillus thuringiensis* var. *japonensis* strain buibui+SX, *Bacillus thuringiensis* var. *san diego* strain M-7+SX, *Bacillus thuringiensis* vaR7216+SX, *Bacillus thuringiensis* var. *aegypti*+SX, *Bacillus thuringiensis* var. T36+SX, *Beauveria bassiana* strain ANT-03+SX, *Beauveria bassiana* strain ATCC74040+SX, *Beauveria bassiana* strain GHA+SX, *Beauveria brongniartii*+SX, *Burkholderia rinojensis* strain A396+SX, *Chromobacterium subtsugae* strain PRAA4-1T+SX, *Dactyllela ellipsospora*+SX, *Dectylaria thaumasia*+SX, *Hirsutella minnesotensis*+SX, *Hirsutella rhossiliensis*+SX, *Hirsutella thompsonii*+SX, *Lagenidium giganteum*+SX, *Lecanicillium lecanii* strain KV01+SX, *Lecanicillium lecanii* conidia of strain DAOM198499+SX, *Lecanicillium lecanii* conidia of strain DAOM216596+SX, *Lecanicillium muscarium* strain Ve6+SX, *Metarhizium anisopliae* strain F52+SX, *Metarhizium anisopliae* var. *acridum*+SX, *Metarhizium anisopliae* var. *anisopliae* BIPESCO 5/F52+SX, *Metarhizium flavoviride*+SX, *Monacrosporium phymatopagum*+SX, *Paecilomyces fumosoroseus* Apopka strain 97+SX, *Paecilomyces lilacinus* strain 251+SX, *Paecilomyces tenuipes* strain T1+SX, *Paenibacillus popilliae*+SX, *Pasteuria nishizawae* strain Pn1+SX, *Pasteuria penetrans*+SX, *Pasteuria usgae*+SX, *Pasteuria thoynei*+SX, *Serratia entomophila*+SX, *Verticillium chlamydosporium*+SX, *Verticillium lecani* strain NCIM1312+SX, 2-chloro-4-fluoro-5-{[5-(trifluoromethylthio)pentyl]oxy} phenyl 2,2,2-trifluoroethyl sulfoxide (1472050-04-6)+SX, 4-chloro-5-[2,2-difluoro-2-(3,4,5-trifluorophenyl)ethoxy]-2-methylphenyl 2,2,2-trifluoroethyl sulfoxide (1632218-00-8)+SX, 4-fluoro-5-[2,2-difluoro-2-(3,4,5-trifluorophenyl)ethoxy]-2-methylphenyl 2,2,2-trifluoroethyl sulfoxide (1632217-98-1)+SX, 2-({2-fluoro-4-methyl-5-[(2,2,2-trifluoroethyl)sulfinyl]phenyl} imino)-3-(2,2,2-trifluoroethyl)-1,3-thiazolidin-4-one (1445683-71-5)+SX, (1Z)-2-(4-tert-butylphenyl)-2-cyano-1-(1-ethyl-3-methyl-1H-pyrazol-5-yl)ethenyl 2,2-dimethylpropanoate (1253429-01-4)+SX, N-[(1S,2S)-2-(2,4-dichlorophenyl)cyclobutyl]-2-(trifluoromethyl)pyridine-3-carboxamide (1644251-74-0)+SX, (3R)-3-(2-chlorothiazol-5-yl)-8-methyl-7-oxo-6-phenyl-2,3-dihydrothiazolo[3,2-a]pyrimidin-4-ium-5-olate (2249718-27-0)+SX.

Combination of the Present ingredient of the above Group (b) and the Present compound X:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper sulfate+SX, benalaxyl+SX, benalaxyl-M+SX, benodanil+SX, benomyl+SX, benthiavalicarb+SX, benthivalicarb-isopropyl+SX, benzovindiflupyr+SX, binapacryl+SX, biphenyl+SX, bitertanol+SX, bixafen+SX, blasticidin-S+SX, Bordeaux mixture+SX, boscalid+SX, bromothalonil+SX, bromuconazole+SX, bupirimate+SX, captafol+SX, captan+SX, carbendazim+SX, carboxin+SX, carpropamid+SX, chinomethionat+SX, chitin+SX, chloroneb+SX, chlorothalonil+SX, chlozolinate+SX, colletochlorin B+SX, copper(II) acetate+SX, copper(II) hydroxide+SX, copper oxychloride+SX, copper(II) sulfate+SX, coumoxystrobin+SX, cyazofamid+SX, cyflufenamid+SX, cymoxanil+SX, cyproconazole+SX, cyprodinil+SX, dichlobentiazox+SX, dichlofluanid+SX, diclocymet+SX, diclomezine+SX, dicloran+SX, diethofencarb+SX, difenoconazole+SX, diflumetorim+SX, imethachlone+SX, dimethirimol+SX, dimethomorph+SX, dimoxystrobin+SX, diniconazole+SX, diniconazole-M+SX, dinocap+SX, dipotassium hydrogenphosphite+SX, dipymetitrone+SX, dithianon+SX, dodecylbenzenesulphonic acid bisethylenediamine copper(II) salt+SX, dodemorph+SX, dodine+SX, edifenphos+SX, enoxastrobin+SX, epoxiconazole+SX, etaconazole+SX, ethaboxam+SX, ethirimol+SX, etridiazole+SX, extract from *Melaleuca alternifolia*+SX, extract from *Reynoutria sachalinensis*+SX, extract from the cotyledons of lupine plantlets ("BLAD")+SX, extract of *Allium sativum*+SX, extract of *Equisetum arvense*+SX, extract of *Tropaeolum majus*+SX, famoxadone+SX, fenamidone+SX, fenaminstrobin+SX, fenarimol+SX, fenbuconazole+SX, fenfuram+SX, fenhexamid+SX, fenoxanil+SX, fenpiclonil+SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, florylpicoxamid+SX, fluazinam+SX, fludioxonil+SX, flufenoxystrobin+SX, fluindapyr+SX, flumorph+SX, fluopicolide+SX, fluopyram+SX, fluopimomide+SX, fluoroimide+SX, fluoxapiprolin+SX, fluoxastrobin+SX, fluquinconazole+SX, flusilazole+SX, flusulfamide+SX, flutianil+SX, flutolanil+SX, flutriafol+SX, fluxapyroxad+SX, folpet+SX, fosetyl+SX, fosetyl-aluminium+SX, fuberidazole+SX, furalaxyl+SX, furametpyr+SX, guazatine+SX, hexaconazole+SX, hymexazole+SX, imazalil+SX, imibenconazole+SX, iminoctadine+SX, iminoctadine triacetate+SX, inpyrfluxam+SX, iodocarb+SX, ipconazole+SX, ipfentrifluconazole+SX, ipflufenoquin+SX, iprobenfos+SX, iprodione+SX, iprovalicarb+SX, isofetamid+SX, isoflucypram+SX, isoprothiolane+SX, isopyrazam+SX, isotianil+SX, kasugamycin+SX, kresoxim-methyl+SX, laminarin+SX, leaves and bark of *Quercus*+SX, mancozeb+SX, mandestrobin+SX, mandipropamid+SX, maneb+SX, mefentrifluconazole+SX, mepanipyrim+SX, mepronil+SX, meptyldinocap+SX, metalaxyl+SX, metalaxyl-M+SX, metconazole+SX, methasulfocarb+SX, metiram+SX, metominostrobin+SX, metrafenone+SX, metyltetraprole+SX, mineral oils+SX, myclobutanil+SX, naftifine+SX, nuarimol+SX, octhilinone+SX, ofurace+SX, orysastrobin+SX, oxadixyl+SX, oxathiapiprolin+SX, oxine-copper+SX, oxolinic acid+SX, oxpoconazole+SX, oxpoconaZole fumarate+SX, oxycarboxin+SX, oxytetracycline+SX, pefurazoate+SX, penconazole+SX, pencycuron+SX, penflufen+SX, penthiopyrad+SX, phenamacril+SX, phosphorous acid+SX, phthalide+SX, picarbutrazox+SX, picoxystrobin+SX, piperalin+SX, polyoxins+SX, potassium hydrogencarbonate+SX, potassium dihydrogenphosphite+SX, probenazole+SX, prochloraz+SX, procymidone+SX, propamidine+SX, propamocarb+SX, propiconazole+SX, propineb+SX, proquinazid+SX, prothiocarb+SX, prothioconazole+SX, pydiflumetofen+SX, pyraclostrobin+SX, pyrametostrobin+SX, pyraoxystrobin+SX, pyrapropoyne+SX, pyraziflumid+SX, pyrazophos+SX, pyribencarb+SX, pyributicarb+SX, pyridachlometyl+SX, pyrifenox+SX, pyrimethanil+SX, pyrimorph+SX, pyriofenone+SX, pyrisoxazole+SX, pyroquilon+SX, *Quillaja* extract+SX, quinconazole+SX, quinofumelin+SX, quinoxyfen+SX, quintozene+SX, Saponins of *Chenopodium quinoa*+SX, sedaxane+SX, silthiofam+SX, simeconazole+SX, sodium hydrogencarbonate+SX, spiroxamine+SX, streptomycin+SX, sulfur+SX, tebuconazole+SX, tebufloquin+SX, teclofthalam+SX, tecnazene+SX, terbinafine+SX, tetraconazole+SX, thiabendazole+SX, thifluzamide+SX, thiophanate+SX, thiophanate-methyl+SX, thiram+SX, thymol+SX, tiadinil+SX, tolclofos-methyl+SX, tolfenpyrad+SX, tolprocarb+SX, tolylfluanid+SX, triadimefon+SX, triadimenol+SX, triazoxide+SX, triclopyricarb+SX, tricyclazole+SX, tridemorph+SX, trifloxystrobin+SX, triflumizole+SX, triforine+SX, triticonazole+SX, validamycin+SX, valifenalate+SX, vinclozolin+SX, yellow mustard powder+SX, zinc thiazole+SX, zineb+SX, ziram+SX, zoxamide+SX, N'-[4-({3-[(4-chlorophenyl)methyl]-1,2,4-thiadiazol-5-yl}oxy)-2,5-dimethylphenyl]-N-ethyl-N-methylmethanimidamide (1202781-91-6)+SX, 4-(2-bromo-4-fluorophenyl)-N-(2-chloro-6-fluorophenyl)-1,3-dimethyl-1H-pyrazol-5-amine (1362477-26-6)+SX, 2-[6-(3-fluoro-4-methoxyphenyl)-5-methylpyridin-2-yl]quinazoline (1257056-97-5)+SX, 5-fluoro-2-[(4-methylphenyl)methoxy]pyrimidin-4-amine (1174376-25-0)+SX, 5-fluoro-4-imino-3-methyl-1-tosyl-3,4-dihydropyrimidin-2(1H)-one (1616664-98-2)+SX, N'-(2,5-dimethyl-4-phenoxyphenyl)-N-ethyl-N-methylmethanimidamide (1052688-31-9)+SX, N'-{4-[(4,5-dichlorothiazol-2-yl)oxy]-2,5-dimethylphenyl}-N-ethyl-N-methylmethanimidamide (929908-57-6)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridin-2-amine (1446247-98-8)+SX, 5-(4-chlorobenzyl)-2-(chloromethyl)-2-methyl-1-(1H-1,2,4-triazol-1-ylmethyl)cyclopentan-1-ol (1394057-11-4)+SX, (1R, 2S, 5S)-5-(4-chlorobenzyl)-2-(chloromethyl)-2-methyl-1-(1H-1,2,4-triazol-1-ylmethyl)cyclopentan-1-ol (1801930-06-2)+SX, (1S, 2R, 5R)-5-(4-chlorobenzyl)-2-(chloromethyl)-2-methyl-1-(1H-1,2,4-triazol-1-ylmethyl)cyclopentan-1-ol (1801930-07-3)+SX, 2-(chloromethyl)-5-(4-fluorobenzyl)-2-methyl-1-(1H-1,2,4-triazol-1-ylmethyl)cyclopentan-1-ol (1394057-13-6)+SX, (1R, 2S, 5S)-2-(chloromethyl)-5-(4-fluorobenzyl)-2-methyl-1-(1H-1,2,4-triazol-1-ylmethyl) cyclopentan-1-ol (1801930-08-4)+SX, (1S, 2R, 5R)-2-(chloromethyl)-5-(4-fluorobenzyl)-2-methyl-1-(1H-1, 2,4-triazol-1-ylmethyl)cyclopentan-1-ol (1801930-09-5)+SX, methyl 3-[(4-chlorophenyl)methyl]-2-hydroxy-1-methyl-2-(1H-1,2,4-triazol-1-ylmethyl)cyclopentan-1-carboxylate (1791398-02-1)+SX, methyl ({2-methyl-5-[1-(4-methoxy-2-methylphenyl)-1H-pyrazol-3-yl]phenyl} methyl)carbamate (1605879-98-8)+SX, 2-(difluoromethyl)-N-[1,1,3-trimethyl-2,3-dihydro-1H-inden-4-yl]pyridine-3-carboxamide (1616239-21-4)+SX, 2-(difluoromethyl)-N-[3-ethyl-1,1-dimethyl-2,3-dihydro-1H-inden-4-yl]pyridine-3-carboxamide (1847460-02-9)+SX, 2-(difluoromethyl)-N-[3-propyl- 1,1-dimethyl-2,3-dihydro-1H-inden-4-yl]pyridine-3-carboxamide (1847460-05-2)+SX, (2E,3Z)-5-{[1-(4-chlorophenyl)-1H-pyrazol-3-yl]oxy}-2-(methoxyimino)-N,3-dimethylpent-3-enamide (1445331-27-0)+SX, *Agrobacterium radiobactor* strain K1026+SX, *Agrobacterium radiobactor* strain K84+SX, *Bacillus amyloliquefaciens* (Aveo(Trade mark) EZ Nematicide)+SX, *Bacillus amyloliquefaciens* strain AT332+SX, *Bacillus amyloliquefaciens* strain B3+SX, *Bacillus amyloliquefaciens* strain D747+SX, *Bacillus amyloliquefaciens* strain DB101+SX, *Bacillus amyloliquefaciens* strain DB102+SX, *Bacillus amyloliquefaciens* strain GB03+SX, *Bacillus amyloliquefaciens* strain FZB24+SX, *Bacillus amyloliquefaciens* strain FZB42+SX, *Bacillus amyloliquefaciens* strain IN937a+SX, *Bacillus amyloliquefaciens* strain MBI600+SX, *Bacillus amyloliquefaciens* strain QST713+SX, *Bacillus amyloliquefaciens* isolate strain B246+SX, *Bacillus amyloliquefaciens* strain F727+SX, *Bacillus amyloliquefaciens* subsp. *plantarum* strain D747+SX, *Bacillus licheniformis* strain HB2+SX, *Bacillus licheniformis* strain SB3086+SX, *Bacillus pumilus* strain AQ717+SX, *Bacillus pumilus* strain BUF-33+SX, *Bacillus pumilus* strain GB34+SX, *Bacillus pumilus* strain QST2808+SX, *Bacillus simplex* strain CGF2856+SX, *Bacillus subtilis* strain AQ153+SX, *Bacillus subtilis* strain AQ743+SX, *Bacillus subtilis* strain BU1814+SX, *Bacillus subtilis* strain D747+SX, *Bacillus subtilis* strain DB101+SX, *Bacillus subtilis* strain FZB24+SX, *Bacillus subtilis* strain GB03+SX, *Bacillus subtilis* strain HAI0404+SX, *Bacillus subtilis* strain IAB/BS03+SX, *Bacillus subtilis* strain MBI600+SX, *Bacillus subtilis* strain QST30002/AQ30002+SX, *Bacillus subtilis* strain QST30004/AQ30004+SX, *Bacillus subtilis* strain QST713+SX, *Bacillus subtilis* strain QST714+SX, *Bacillus subtilis* var. *Amyloliquefaciens* strain FZB24+SX, *Bacillus subtilis* strain Y1336+SX, *Burkholderia cepacia*+SX, *Burkholderia cepacia* type Wisconsin strain J82+SX, *Burkholderia cepacia* type Wisconsin strain M54+SX, *Candida oleophila* strain O+SX, *Candida saitoana*+SX, *Chaetomium cupreum*+SX, *Clonostachys rosea*+SX, *Coniothyrium minitans* strain CGMCC8325+SX, *Coniothyrium minitans* strain CON/M/91-8+SX, *Cryptococcus albidus*+SX, *Erwinia carotovora* subsp. *carotovora* strain CGE234M403+SX, *Fusarium oxysporum* strain Fo47+SX, *Gliocladium catenulatum* strain J1446+SX, *Paenibacillus polymyxa* strain AC-1+SX, *Paenibacillus polymyxa* strain BS-0105+SX, *Pantoea agglomerans* strain E325+SX, *Phlebiopsis gigantea* strain VRA1992+SX, *Pseudomonas aureofaciens* strain TX-1+SX, *Pseudomonas chlororaphis* strain 63-28+SX, *Pseudomonas chlororaphis* strain AFS009+SX, *Pseudomonas chlororaphis* strain MA342+SX, *Pseudomonas fluorescens* strain 1629RS+SX, *Pseudomonas fluorescens* strain A506+SX, *Pseudomonas fluorescens* strain CL145A+SX, *Pseudomonas fluorescens* strain G7090+SX, *Pseudomonas* sp. strain CAB-02+SX, *Pseudomonas syringae* strain 742RS+SX, *Pseudomonas syringae* strain MA-4+SX, *Pseudozyma flocculosa* strain PF-A22UL+SX, *Pseudomonas rhodesiae* strain HAI-0804+SX, *Pythium oligandrum* strain DV74+SX, *Pythium oligandrum* strain M1+SX, *Streptomyces griseoviridis* strain K61+SX, *Streptomyces lydicus* strain WYCD108US+SX, *Streptomyces lydicus* strain WYEC108+SX, *Talaromyces flavus* strain SAY-Y-94-01+SX, *Talaromyces flavus* strain V117b+SX, *Trichoderma asperellum* strain ICC012+SX, *Trichoderma asperellum* SKT-1+SX, *Trichoderma asperellum* strain T25+SX, *Trichoderma asperellum* strain T34+SX, *Trichoderma asperellum* strain TV1+SX, *Trichoderma atroviride* strain CNCM 1-1237+SX, *Trichoderma atroviride* strain LC52+SX, *Trichoderma atroviride* strain IMI 206040+SX, *Trichoderma atroviride* strain SC1+SX, *Trichoderma atroviride* strain SKT-1+SX, *Trichoderma atroviride* strain T11+SX, *Trichoderma gamsii* strain ICC080+SX, *Trichoderma harzianum* strain 21+SX, *Trichoderma harzianum* strain DB104+SX, *Trichoderma harzianum* strain DSM 14944+SX, *Trichoderma harzianum* strain ESALQ-1303+SX, *Trichoderma harzianum* strain ESALQ-1306+SX, *Trichoderma harzianum* strain IIHR-Th-2+SX, *Trichoderma harzianum* strain ITEM908+SX, *Trichoderma harzianum* strain kd+SX, *Trichoderma harzianum* strain MC1+SX, *Trichoderma harzianum* strain SF+SX, *Trichoderma harzianum* strain T22+SX, *Trichoderma harzianum* strain T39+SX, *Trichoderma harzianum* strain T78+SX, *Trichoderma harzianum* strain TH35+SX, *Trichoderma polysporum* strain IMI206039+SX, *Trichoderma stromaticum*+SX, *Trichoderma virens* strain G41+SX, *Trichoderma virens* strain GL-21+SX, *Trichoderma viride*+SX, *Variovorax paradoxus* strain CGF4526+SX, Harpin protein+SX, N'-[5-choro-4-(2-fluorophenoxy)-2-methylphenyl)-N-ethyl-N-methylmethanimidamide (2055589-28-9)+SX, N'-[2-choro-4-(2-fluorophenoxy)-5-methylphenyl)-N-ethyl-N-methylmethanimidamide (2055756-21-1)+SX, N'-[4-(1-hydroxy-1-phenyl-2,2,2-trifluoroethyl)-2-methyl-5-methoxyphenyl)-N-isopropyl-N-methylmethanimidamide (2101814-55-3)+SX, N'-[5-bromo-6-(1-methyl-2-propoxyethoxy)-2-methylpyridin-3-yl)-N-ethyl-N-methylmethanimidamide (1817828-69-5)+SX, 1-(2,4-difluorophenyl)-2-(1H-1,2,4-triazol-1-yl)-1-[1-(4-bromo-2,6-difluorophenoxy)cyclopropyl]ethanol (2019215-86-0)+SX, 1-(2,4-difluorophenyl)-2-(1H-1,2,4-triazol-1-yl)-1-[1-(4-chloro-2,6-difluorophenoxy)cyclopropyl]ethanol (2019215-84-8)+SX, 1-[2-(1-chlorocyclopropyl)-3-(2-fluorophenyl)-2-hydroxypropyl]-1H-imidazole-5-carbonitrile (2018316-13-5)+SX, 1-[2-(1-chlorocyclopropyl)-3-(2,3-difluorophenyl)-2-hydroxypropyl]-1H-imidazole-5-carbonitrile (2018317-25-2)+SX, 4-({6-[2-(2,4-difluorophenyl)-1,1-difluoro-2-hydroxy-3-(1H-1,2,4-triazol-1-yl)propyl]pyridin-3-yl}oxy)benzonitrile (2046300-61-0)+SX, 2-[6-(4-bromophenoxy)-2-(trifluoromethyl)pyridin-3-yl]-1-(1H-1,2,4-triazol-1-yl)propan-2-ol (2082661-43-4)+SX, 2-[6-(4-chlorophenoxy)-2-(trifluoromethyl)pyridin-3-yl]-1-(1H-1,2,4-triazol-1-yl)propan-2-ol (2082660-27-1)+SX, (2E,3Z)-5-{[1-(2,4-dichlorophenyl)-1H-pyrazol-3-yl]oxy}-2-(methoxyimino)-N,3-dimethylpent-3-enamide (1445331-54-3)+SX, 5-chloro-4-({2-[6-(4-chlorophenoxy)pyridin-3-yl]ethyl} amino)-6-methylpyrimidine (1605340-92-8)+SX, N-(1-benzyl-1,3-dimethylbutyl)-8-fluoroquinoline-3-carboxamide (2132414-04-9), N-(1-benzyl-3,3,3-trifluoro-1-methylpropyl)-8-fluoroquinoline-3-carboxamide (2132414-00-5)+SX, 4,4-dimethyl-2-({4-[5-(trifluoromethyl)-1,2,4-oxadiazol-3-yl]phenyl}methyl)isoxaZolidin-3-one (2098918-25-1)+SX, 5,5-dimethyl-2-({4-[5-(trifluoromethyl)-1,2,4-oxadiazol-3-yl]phenyl}methyl)isoxazolidin-3-one (2098918-26-2)+SX.

Combination of the Present ingredient of the above Group (c) and the Present compound X:

1-methylcyclopropene+SX, 1,3-diphenylurea+SX, 2,3,5-triiodobenzoic acid+SX, IAA ((1H-indol-3-yl)acetic acid)+SX, IBA (4-(1H-indol-3-yl)butyric acid)+SX, MCPA (2-(4-chloro-2-methylphenoxy) acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, ancymidol+SX, butralin+SX, calcium carbonate+SX, calcium chloride+SX, calcium formate+SX, calcium peroxide+SX, calcium polysulfide+SX, calcium sulfate+SX, chlormequat-chloride+SX, chlorpropham+SX, choline chloride+SX, cloprop+SX, cyanamide+SX, cyclanilide+SX, daminozide+SX, decan-1-ol+SX, dichlorprop+SX, dikegulac+SX, dimethipin+SX, diquat+SX, ethephon+SX, ethychlozate+SX, flumetralin+SX, flurprimidol+SX, forchlorfenuron+SX, formononetin+SX, Gibberellin A+SX, Gibberellin A3+SX, inabenfide+SX, Kinetin+SX, lipochitooligosaccharide SP104+SX, maleic hydrazide+SX, mefluidide+SX, mepiquat-chloride+SX, oxidized glutathione+SX, pacrobutrazol+SX, pendimethalin+SX, prohexandione-calcium+SX, prohydrojasmon+SX, pyraflufen-ethyl+SX, sintofen+SX, sodium 1-naphthaleneacetate+SX, sodium cyanate+SX, streptmycin+SX, thidiazuron+SX, triapenthenol+SX, Tribufos+SX, trinexapac-ethyl+SX, uniconazole-P+SX, 2-(naphthalen-1-yl)acetamide+SX, [4-oxo-4-(2-phenylethyl)amino]butyric acid+SX, methyl 5-(trifluoromethyl)benzo[b]thiophene-2-carboxylate+SX, 3-[(6-chloro-4-phenylquinazolin-2-yl)amino]-1-propanol+SX, *Claroideoglomus etunicatum*+SX, *Claroideoglomus claroideum*+SX, *Funneliformis mosseae*+SX, *Gigaspora margarita*+SX, *Gigaspora rosea*+SX, *Glomus aggregatum*+SX, *Glomus deserticola*+SX, *Glomus monosporum*+SX, *Paraglomus brasillianum*+SX, *Rhizophagus clarus*+SX, *Rhizophagus intraradices* RTI-801+SX, *Rhizophagus irregularis* DAOM 197198+SX, *Azorhizobium caulinodans*+SX, *Azospirillum amazonense*+SX, *Azospirillum brasilense* XOH+SX, *Azospirillum brasilense* Ab-V5+SX, *Azospirillum brasilense* Ab-V6+SX, *Azospirillum caulinodans*+SX, *Azospirillum halopraeferens*+SX, *Azospirillum irakense*+SX, *Azospirillum lipoferum*+SX, *Bradyrhizobium elkanii* SEMIA 587+SX, *Bradyrhizobium elkanii* SEMIA 5019+SX, *Bradyrhizobium japonicum* TA11+SX, *Bradyrhizobium japonicum* USDA110+SX, *Bradyrhizobium liaoningense*+SX, *Bradyrhizobium lupini*+SX, *Delftia acidovorans* RAY209+SX, *Mesorhizobium ciceri*+SX, *Mesorhizobium huakii*+SX, *Mesorhizobium loti*+SX, *Rhizobium etli*+SX, *Rhizobium galegae*+SX, *Rhizobium leguminosarum* bv. *Phaseoli*+SX, *Rhizobium leguminosarum* bv. *Trifolii*+SX, *Rhizobium leguminosarum* bv. *Viciae*+SX, *Rhizobium trifolii*+SX, *Rhizobium tropici*+SX, *Sinorhizobium fredii*+SX, *Sinorhizobium meliloti*+SX, Zucchini Yellow Mosaik Virus weak strain+SX.

Combination of the Present ingredient of the above Group (d) and the Present compound X:

anthraquinone+SX, deet+SX, icaridin+SX.

The ratio of the Present compound X to the Present ingredient includes, but not limited thereto, as a ratio by weight (the Present compound X:the Present ingredient) 1,000:1 to 1:1,000, 500:1 to 1:500, 100:1 to 1:100, 50:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, and 1:50, and the others.

Examples of the pest on which the Present compound X has control efficacies include harmful arthropods such as harmful insects, harmful mites, harmful nematodes, and harmful mollusks. Specific examples of the pest include, but are not limited to, the followings.

Hemiptera Pests:

from the family Delphacidae, for example, small brown planthopper (*Laodelphax striatella*), brown planthopper (*Nilaparvata lugens*), white-backed planthopper (*Sogatella furcifera*), corn planthopper (*Peregrinus maidis*), cereal leafhopper (*Javesella pellucida*), sugarcane leafhopper (*Perkinsiella saccharicida*), and *Tagosodes orizicolus*; from the family Cicadellidae, for example, green rice leafhopper (*Nephotettix cincticeps*), green paddy leafhopper (*Nephotettix virescens*), rice leafhopper (*Nephotettix nigropictus*), zigzag-striped leafhopper (*Recilia dorsalis*), tea green leafhopper (*Empoasca onukii*), potato leafhopper (*Empoasca fabae*), corn leafhopper (*Dalbulus maidis*), and rice leafhopper (*Cofana spectra*);

from the family Cercopidae, for example, *Mahanarva posticata*, and *Mahanarva fimbriolata;* from the family Aphididae, for example, bean aphid (*Aphis fabae*), soybean aphid (*Aphis glycines*), cotton aphid (*Aphis gossypii*), green apple aphid (*Aphis pomi*), apple aphid (*Aphis spiraecola*), green peach aphid (*Myzus persicae*), leaf-curling plum aphid (*Brachycaudus helichrysi*), cabbage aphid (*Brevicoryne brassicae*), rosy apple aphid (*Dysaphis plantaginea*), false cabbage aphid (*Lipaphis erysimi*), potato aphid (*Macrosiphum euphorbiae*), foxglove aphid (*Aulacorthum solani*), lettuce aphid (*Nasonovia ribisnigri*), grain aphid (*Rhopalosiphum padi*), corn aphid (*Rhopalosiphum maidis*), brown citrus aphid (*Toxoptera citricida*), mealy plum aphid (*Hyalopterus pruni*), cane aphid (*Melanaphis sacchari*), black rice root aphid (*Tetraneura nigriabdominalis*), sugarcane cottony aphid (*Ceratovacuna lanigera*), and apple woolly aphid (*Eriosoma lanigerum*);

from the family Phylloxeridae, for example, grapevine phylloxera (*Daktulosphaira vitifoliae*), Pecan phylloxera (*Phylloxera devastatrix*), Pecan leaf phylloxera (*Phylloxera notabilis*), and Southern pecan leaf phylloxera (*Phylloxera russellae*);

from the family Adelgidae, for example, hemlock woolly aphid (*Adelges tsugae*), balsam woolly aphid (*Adelges piceae*), and *Aphrastasia pectinatae;* from the family Pentatomidae, for example, black rice bug (*Scotinophara lurida*), Malayan rice black bug (*Scotinophara coarctata*), common green stink bug (*Nezara antennata*), white-spotted spined bug (*Eysarcoris aeneus*), lewis spined bug (*Eysarcoris lewisi*), white-spotted bug (*Eysarcoris ventralis*), *Eysarcoris annamita*, brown marmorated stink bug (*Halyomorpha halys*), green plant bug (*Nezara viridula*), brown stink bug (*Euschistus heros*), red banded stink bug (*Piezodorus guildinii*), *Oebalus pugnax*, and *Dichelops melacanthus;* from the family Cydnidae, for example, Burrower brown bug (*Scaptocoris castanea*);

from the family Alydidae, for example, bean bug (*Riptortus pedestris*), corbett rice bug (*Leptocorisa chinensis*), and rice bug (*Leptocorisa acuta*);

from the family Coreidae, for example, *Cletus punctiger*, and Australian leaf-footed bug (*Leptoglossus australis*);

from the family Lygaeidae, for example, oriental chinch bug (*Caverelius saccharivorus*), seed bug (*Togo hemipterus*), and chinch bug (*Blissus leucopterus*);

from the family Miridae, for example, rice leaf bug (*Trigonotylus caelestialium*), sorghum plant bug (*Stenotus rubrovittatus*), wheat leaf bug (*Stenodema calcarata*), and American tarnished plant bug (*Lygus lineolaris*);

from the family Aleyrodidae, for example, greenhouse whitefly (*Trialeurodes vaporariorum*), tobacco whitefly (*Bemisia tabaci*), citrus whitefly (*Dialeurodes citri*), citrus spiny whitefly (*Aleurocanthus spiniferus*), tea spiny whitefly (*Aleurocanthus camelliae*), and *Pealius euryae;* from the family Diaspididae, for example, *Abgrallaspis cyanophylli*, red scale (*Aonidiella aurantii*), San Jose scale (*Diaspidiotus perniciosus*), white peach scale (*Pseudaulacaspis pentagona*), arrowhead scale (*Unaspis yanonensis*), and citrus snow scale (*Unaspis citri*);

from the family Coccidae, for example, pink wax scale (*Ceroplastes rubens*);

from the family Margarodidae, for example, fluted scale (*Icerya purchasi*) and seychelles fluted scale (*Icerya seychellarum*);

from the family Pseudococcidae, for example, solanum mealybug (*Phenacoccus solani*), cotton mealybug (*Phenacoccus solenopsis*), Japanese mealybug (*Planococcus kraunhiae*), white peach scale (*Pseudococcus comstocki*), citrus mealybug (*Planococcus citri*), currant mealybug (*Pseudococcus calceolariae*), long-tailed mealybug (*Pseudococcus longispinus*), and tuttle mealybug (*Brevennia rehi*); from the family Psyllidae, for example, citrus psylla (*Diaphorina citri*), two-spotted citrus psyllid (*Trioza erytreae*), pear sucker (*Cacopsylla pyrisuga*), *Cacopsylla chinensis*, potato psyllid (*Bactericera cockerelli*), and Pear *psylla* (*Cacopsylla pyricola*);

from the family Tingidae, for example, sycamore lace bug (*Corythucha ciliata*), aster tingid (*Corythucha marmorata*), Japanese pear lace bug (*Stephanitis nashi*), and azalea lace bug (*Stephanitis pyrioides*);

from the family Cimicidae, for example, common bed bug (*Cimex lectularius*);

from the family Cicadidae, for example, Giant Cicada (*Quesada gigas*);

from *Triatoma* spp., for example, *Triatoma infestans*; and the others.

Lepidoptera Pests:

from the family Crambidae, for example, rice stem borer (*Chilo suppressalis*), Darkheaded stem borer (*Chilo polychrysus*), white stem borer (*Scirpophaga innotata*), yellow paddy borer (*Scirpophaga incertulas*), *Rupela albina*, rice leaf roller (*Cnaphalocrocis medinalis*), *Marasmia patnalis*, rice leaf roller (*Marasmia exigua*), cotton leaf roller (*Notarcha derogata*), corn borer (*Ostrinia furnacalis*), European corn borer (*Ostrinia nubilalis*), cabbage webworm (*Hellula undalis*), grape leafroller (*Herpetogramma luctuosale*), bluegrass webworm (*Pediasia teterrellus*), rice case-worm (*Nymphula depunctalis*), and Sugarcane borer (*Diatraea saccharalis*);

from the family Pyralidae, for example, lesser cornstalk borer (*Elasmopalpus lignosellus*) mealworm moth (*Plodia interpunctella*), and persimmon bark borer (*Euzophera batangensis*);

from the family Noctuidae, for example, cotton worm (*Spodoptera litura*), beet armyworm (*Spodoptera exigua*), rice armyworm (*Mythimna separata*), cabbage moth (*Mamestra brassicae*), pink borer (*Sesamia inferens*), grass armyworm (*Spodoptera mauritia*), green rice caterpillar (*Naranga aenescens*), *Spodoptera frugiperda*, true armyworm (*Spodoptera exempta*), black cutworm (*Agrotis ipsilon*), beet worm (*Autographa nigrisigna*), rice looper (*Plusia festucae*), soybean looper (*Chrysodeixis includens*), *Trichoplusia* spp., *Heliothis* spp. (such as tobacco budworm (*Heliothis virescens*)), *Helicoverpa* spp. (such as tobacco budworm (*Helicoverpa armigera*) and, corn earworm (*Helicoverpa zea*)), velvetbean caterpillar (*Anticarsia gemmatalis*), cotton leafworm (*Alabama argillacea*), and hop vine borer (*Hydraecia immanis*);

from the family Pieridae, for example, common cabbage worm (*Pieris rapae*);

from the family Tortricidae, for example, oriental fruit moth (*Grapholita molesta*), *Grapholita dimorpha*, soybean moth (*Leguminivora glycinivorella*), *Matsumuraeses azukivora*, summer fruit tortrix (*Adoxophyes orana fasciata*), smaller tea tortrix (*Adoxophyes honmai*), Japanese tea tortrix (*Homona magnanima*), apple tortrix (*Archips fuscocupreanus*), codling moth (*Cydia pomonella*), sugarcane shoot borer (*Tetramoera schistaceana*), bean shoot borer (*Epinotia aporema*), and citrus fruit borer (*Ecdytolopha aurantiana*);

from the family Gracillariidae, for example, tea leaf roller (*Caloptilia theivora*), and Asiatic apple leaf miner (*Phyllonorycter ringoniella*);

from the family Carposinidae, for example, peach fruit moth (*Carposina sasakii*);

from the family Lyonetiidae, for example, Coffee leaf miner (*Leucoptera coffeella*), peach leaf miner (*Lyonetia clerkella*), and *Lyonetia prunifoliella;* from the family Lymantriidae, for example, *Lymantria* spp. (such as gypsy moth (*Lymantria dispar*)) and, *Euproctis* spp. (such as tea lymantriid (*Euproctis pseudoconspersa*)); from the family Plutellidae, for example, diamondback moth (*Plutella xylostella*);

from the family Gelechiidae, for example, peach worm (*Anarsia lineatella*), sweetpotato leaf folder (*Helcystogramma triannulella*), pink bollworm (*Pectinophora gossypiella*), potato moth (*Phthorimaea operculella*), and *Tuta absoluta;* from the family Arctiidae, for example, American white moth (*Hyphantria cunea*);

from the family Castniidae, for example, giant sugarcane borer (*Telchin licus*);

from the family Cossidae, for example, *Cossus insularis;* from the family Geometridae, for example, *Ascotis selenaria;* from the family Limacodidae, for example, blue-striped nettle grub (*Parasa lepida*);

from the family Stathmopodidae, for example, persimmon fruit moth (*Stathmopoda masinissa*);

from the family Sphingidae, for example, tobacco hornworm (*Acherontia lachesis*);

from the family Sesiidae, for example, *Nokona feralis*, cherry borer (*Synanthedon hector*), and *Synanthedon tenuis;* from the family Hesperiidae, for example, rice skipper (*Parnara guttata*);

from the family Tineidae, for example, casemaking clothes moth (*Tinea translucens*), and common clothes moth (*Tineola bisselliella*);

and the others.

Thysanoptera Pests:

from the family Thripidae, for example, western flower thrips (*Frankliniella occidentalis*), oriental thrips (*Thrips palmi*), yellow tea thrips (*Scirtothrips dorsalis*), onion thrips (*Thrips tabaci*), eastern flower thrips (*Frankliniella intonsa*), rice thrips (*Stenchaetothrips biformis*), and *Echinothrips americanus;* from the family Phlaeothripidae, for example, aculeated rice thrips (*Haplothrips aculeatus*);

and the others.

Diptera Pests:

from the family Anthomyiidae, for example, seedcorn maggot (*Delia platura*), onion maggot (*Delia antiqua*), and beet leaf miner (*Pegomya cunicularia*);

from the family Ulidiidae, for example, sugarbeet root maggot (*Tetanops myopaeformis*);

from the family Agromyzidae, for example, rice leaf miner (*Agromyza oryzae*), tomato leaf miner (*Liriomyza sativae*), chrysanthemum leaf miner (*Liriomyza trifolii*), and pea leafminer (*Chromatomyia horticola*);

from the family Chloropidae, for example, rice stem maggot (*Chlorops oryzae*);

from the family Tephritidae, for example, melon fly (*Bactrocera cucurbitae*), oriental fruit fly (*Bactrocera dorsalis*), Malaysian fruit fly (*Bactrocera latifrons*), olive fruit fly (*Bactrocera oleae*), Queensland fruit fly (*Bactrocera tryoni*), Mediterranean fruit fly (*Ceratitis capitata*), apple maggot (*Rhagoletis pomonella*), and Japanese cherry fruit fly (*Rhacochlaena japonica*);

from the family Ephydridae, for example, smaller rice leaf miner (*Hydrellia griseola*), whorl maggot (*Hydrellia philippina*), and paddy stem maggot (*Hydrellia sasakii*);

from the family Drosophilidae, for example, cherry drosophila (*Drosophila suzukii*);

from the family Phoridae, for example, *Megaselia spiracularis;* from the family Psychodidae, for example, *Clogmia albipunctata;* from the family Sciaridae, for example, *Bradysia difformis;* from the family Cecidomyiidae, for example, hessian fly (*Mayetiola destructor*) and, paddy gall fly (*Orseolia oryzae*);

from the family Diopsidae, for example, *Diopsis macrophthalma;* from the family Tipulidae, for example, rice crane fly (*Tipula aino*), common cranefly (*Tipula oleracea*), and European cranefly (*Tipula paludosa*);

from the family Culicidae, for example, southern house mosquito (*Culex pipiens pallens*), dengue mosquito (*Aedes aegypti*), Asian tiger mosquito (*Aedes albopictus*), Chinese malaria mosquito (*Anopheles hyracanus sinensis*), *Culex quinquefasciatus, Culex pipiens* molestus Forskal, and brown house mosquito (*Culex quinquefasciatus*);

from the family Simulidae, for example, *Prosimulium yezoensis*, and *Simulium ornatum;* from the family Tabanidae, for example, *Tabanus trigonus;* from the family Muscidae, for example, house fly (*Musca domestica*), false stable fly (*Muscina stabulans*), biting house fly (*Stomoxys calcitrans*), and buffalo fly (*Haematobia irritans*);

from the family Tabanidae, for example, *Tabanus trigonus;* from the family Calliphoridae;

from the family Sarcophagidae;

from the family Chironomidae, for example, *Chironomus plumosus, Chironomus yoshimatsui*, and *Glyptotendipes tokunagai;* from the family Fannidae;

and the others.

Coleoptera Pests:

from the family Chrysomelidae, for example, western corn rootworm (*Diabrotica virgifera virgifera*), southern corn rootworm (*Diabrotica undecimpunctata howardi*), northern corn rootworm (*Diabrotica barberi*), Mexican corn rootworm (*Diabrotica virgifera zeae*), banded cucumber beetle (*Diabrotica balteata*), cucurbit beetle (*Diabrotica speciosa*), bean leaf beetle (*Cerotoma trifurcata*), barley leaf beetle (*Oulema melanopus*), cucurbit leaf beetle (*Aulacophora femoralis*), striped flea beetle (*Phyllotreta striolata*), cabbage flea beetle (*Phyllotreta cruciferae*), western black flea beetle (*Phyllotreta pusilla*), cabbage stem flea beetle (*Psylliodes chrysocephala*), Colorado potato beetle (*Leptinotarsa decemlineata*), rice leaf beetle (*Oulema oryzae*), grape colaspis (*Colaspis brunnea*), corn flea beetle (*Chaetocnema pulicaria*), sweet-potato flea beetle (*Chaetocnema confinis*), potato flea beetle (*Epitrix cucumeris*), rice leaf beetle (*Dicladispa armigera*), southern corn leaf beetle (*Myochrous denticollis*), *Laccoptera quadrimaculata*, and tobacco flea beetle (*Epitrix hirtipennis*);

from the family Carabidae, for example, Seedcorn beetle (*Stenolophus lecontei*), and slender seedcorn beetle (*Clivina impressifrons*);

from the family Scarabaeidae, for example, cupreus chafer (*Anomala cuprea*), soybean beetle (*Anomala rufocuprea*), *Anomala albopilosa*, Japanese beetle (*Popillia japonica*), yellowish elongate chafer (*Heptophylla picea*), European Chafer (*Rhizotrogus majalis*), *Tomarus gibbosus, Holotrichia* spp., *Phyllophaga* spp. (such as June beetle (*Phyllophaga crinita*)), and *Diloboderus* spp. (such as *Diloboderus abderus*);

from the family Curculionidae, for example, coffee bean weevil (*Araecerus coffeae*), sweet-potato weevil (*Cylas formicarius*), West Indian sweet-potato weevil (*Euscepes postfasciatus*), alfalfa weevil (*Hypera postica*), maize wevil (*Sitophilus zeamais*), rice plant weevil (*Echinocnemus squameus*), rice water weevil (*Lissorhoptrus oryzophilus*), *Rhabdoscelus lineaticollis*, boll weevil (*Anthonomus grandis*), nunting billbug (*Sphenophorus venatus*), southern corn billbug (*Sphenophorus callosus*), soybean stalk weevil (*Sternechus subsignatus*), sugarcane weevil (*Sphenophorus levis*), rusty gourd-shaped weevil (*Scepticus griseus*), brown gourd-shaped weevil (*Scepticus uniformis*), Mexican bean weevil (*Zabrotes subfasciatus*), pine beetle (*Tomicus piniperda*), coffee berry borer (*Hypothenemus hampei*), *Aracanthus* spp. (such as *Aracanthus mourei*), and cotton root borer (*Eutinobothrus brasiliensis*);

from the family Tenebrionidae, for example, red meal beetle (*Tribolium castaneum*), and mason beetle (*Tribolium confusum*);

from the family Coccinellidae, for example, twenty-eight-spotted ladybird (*Epilachna vigintioctopunctata*);

from the family Bostrychidae, for example, common powder-post beetle (*Lyctus brunneus*);

from the family Ptinidae;

from the family Cerambycidae, for example, citrus long-horned beetle (*Anoplophora malasiaca*) and, *Migdolus fryanus;* from the family Elateridae, for example, *Melanotus okinawensis*, barley wireworm (*Agriotes fuscicollis*), *Melanotus legatus, Anchastus* spp., *Conoderus* spp., *Ctenicera* spp., *Limonius* spp., and *Aeolus* spp.;

from the family Staphylinidae, for example, *Paederus fuscipes;* from the family Dermestidae, for example, varied carpet beetle (*Anthrenus verbasci*) and, hide beetle (*Dermestes maculates*);

from the family Anobiidae, for example, tobacco beetle (*Lasioderma serricorne*), and biscuit beetle (*Stegobium paniceum*);

and the others.

Orthoptera Pests:

from the family Acrididae, for example, oriental migratory locust (*Locusta migratoria*), Moroccan locust (*Dociostaurus maroccanus*), Australian plague locust (*Chortoicetes terminifera*), red locust (*Nomadacris septemfasciata*), brown locust (*Locustana pardalina*), tree locust (*Anacridium melanorhodon*), Italian locust (*Calliptamus italicus*), differential grasshopper (*Melanoplus differentialis*), two-striped grasshopper (*Melanoplus bivittatus*), migratory grasshopper (*Melanoplus sanguinipes*), red-legged grasshopper (*Melanoplus femurrubrum*), clear-winged grasshopper (*Camnula pellucida*), desert locust (*Schistocerca gregaria*), Yellow-winged locust (*Gastrimargus musicus*), spur-throated locust (*Austracris guttulosa*), Japanese grasshopper (*Oxya yezoensis*), rice grasshopper (*Oxya japonica*), and Bombay locust (*Patanga succincta*);

from the family Gryllotalpidae, for example, oriental mole cricket (*Gryllotalpa orientalis*);

from the family Gryllidae, for example, house cricket (*Acheta domestica*), and emma field cricket (*Teleogryllus emma*);

from the family Tettigoniidae, for example, mormon cricket (*Anabrus simplex*);

and the others.

Hymenoptera Pests:

from the family Tenthredinidae, for example, beet sawfly (*Athalia rosae*), and nippon cabbage sawfly (*Athalia japonica*);

from the family Formicidae, for example, *Solenopsis* spp. (such as red imported fire ant (*Solenopsis invicta*) and, tropical fire ant (*Solenopsis geminata*)), *Atta* spp. (such as brown leaf-cutting ant (*Atta capiguara*)), *Acromyrmex* spp., *Paraponera clavata*, black house ant (*Ochetellus glaber*), little red ant (*Monomorium pharaonis*), Argentine ant (*Linepithema humile*), *Formica japonica, Pristomyrmex punctutus, Pheidole noda*, big-headed ant (*Pheidole megacephala*), *Camponotus* spp. (such as *Camponotus japonicus*, and *Camponotus obscuripes*), *Pogonomyrmex* spp. (such as western harvester ant (*Pogonomyrmex occidentalis*)), *Wasmania* spp. (such as *Wasmania auropunctata*), and long-legged ant (*Anoplolepis gracilipes*);

from the family Vespidae, for example, Asian giant hornet (*Vespa mandarinia japonica*), *Vespa simillima, Vespa analis fabriciusi*, Asian hornet (*Vespa velutina*), and *Polistes jokahamae;* from the family Siricidae, for example, pine wood wasp (*Urocerus gigas*);

from the family Bethylidae;

and the others.

Blattodea Pests:

from the family Blattellidae, for example, German cockroach (*Blattella germanica*);

from the family Blattidae, for example, smoky-brown cockroach (*Periplaneta fuliginosa*), American cockroach (*Periplaneta americana*), brown cockroach (*Periplaneta brunnea*), and black cockroach (*Blatta orientalis*);

from the family Termitidae, for example, Japanese termite (*Reticulitermes speratus*), Formosan termite (*Coptotermes formosanus*), western drywood termite (*Incisitermes minor*), *Cryptotermes domesticus, Odontotermes formosanus, Neotermes koshunensis, Glyptotermes satsumensis, Glyptotermes nakajimai, Glyptotermes fuscus, Hodotermopsis sjostedti, Coptotermes guangzhouensis, Reticulitermes amamianus, Reticulitermes miyatakei, Reticulitermes kanmonensis, Nasutitermes takasagoensis, Pericapritermes nitobei, Sinocapritermes mushae*, and *Cornitermes cumulans*; and the others.

Siphonaptera Pests:

for example, cat flea (*Ctenocephalides felis*), dog flea (*Ctenocephalides canis*), human flea (*Pulex irritans*), oriental rat flea (*Xenopsylla cheopis*), chigoe flea (*Tunga penetrans*), chicken flea (*Echidnophaga gallinacea*), and European rat flea (*Nosopsyllus fasciatus*);

and the others.

Anoplura Pests:

for example, pig louse (*Haematopinus suis*), short-nosed cattle louse (*Haematopinus eurysternus*), sheep biting louse (*Dalmalinia ovis*), *Linognathus seypsus, Pediculus humanis, Pediculuc humanus corporis, Pediculus humanus humanus*, and *Phthirus pubis;* and the others.

Mallophagida Pests:

for example, *Bovicola* spp. (such as cattle biting louse (*Dalmalinia bovis*) and, sheep biting louse (*Dalmalinia ovis*)), *Trichodestes* spp. (such as dog biting louse (*Trichodectes canis*)), *Felicola* spp. (such as cat louse (*Felicola subrostrata*)), *Lipeurus* spp. (such as chicken wing louse (*Lipeurus caponis*)), and Menoponidae family (such as *Trimenopon* spp. and *Menopon* spp.);

and the others.

Acari Pests:

from the family Tetranychidae, for example, common red spider mite (*Tetranychus urticae*), kanzawa spider mite (*Tetranychus kanzawai*), red spider mite (*Tetranychus evansi*), citrus red mite (*Panonychus citri*), fruit-tree red spider mite (*Panonychus ulmi*), and *Oligonychus* spp.;

from the family Eriophyidae, for example, Japanese citrus rust mite (*Aculops pelekassi*), *Phyllocoptruta citri*, tomato mite (*Aculops lycopersici*), purple mite (*Calacarus carinatus*), tea rust mite (*Acaphylla theavagrans*), *Eriophyes chibaensis*, apple bud mite (*Aculus schlechtendali*), *Aceria diospyri, Aceria tosichella*, and *Shevtchenkella* sp.;

from the family Tarsonemidae, for example, broad mite (*Polyphagotarsonemus latus*);

from the family Tenuipalpidae, for example, *Brevipalpus phoenicis;* from the family Tuckerellidae;

from the family Ixodidae, for example, *Haemaphysalis longicornis, Haemaphysalis flava, Dermacentor taiwanensis*, American dog tick (*Dermacentor variabilis*), *Dermacentor andersoni, Ixodes ovatus, Ixodes persulcatus, Ixodes ricinus*, black-legged tick (*Ixodes scapularis*), lone star tick (*Amblyomma americanum*), *Amblyomma maculatum*, cattle tick (*Boophilus microplus*), *Boophilus annulatus*, and brown dog tick (*Rhipicephalus sanguineus*);

from the family Acaridae, for example, cereal mite (*Tyrophagus putrescentiae*), and grassland mite (*Tyrophagus similis*);

from the family Pyroglyphidae, for example, American house dust mite (*Dermatophagoides farinae*), and European house dust mite (*Dermatophagoides pteronyssinus*);

from the family Cheyletidae, for example, *Cheyletus eruditus, Cheyletus malaccensis, Cheyletus moorei*, and *Cheyletiella yasguri;* from the family Sarcoptidae, for example, ear mange mite (*Otodectes cynotis*), and itch mite (*Sarcoptes scabiei*);

from the family Demodicidae, for example, dog follicle mite (*Demodex canis*);

from the family Listrophoridae;

from the family Haplochthoniidae;

from the family Macronyssidae, for example, tropical rat mite (*Ornithonyssus bacoti*), and feather mite (*Ornithonyssus sylviarum*);

from the family Dermanyssidae, for example, bird mite (*Dermanyssus gallinae*);

from the family Trombiculidae, for example, *Leptotrombidium akamushi;* and the others.

Araneae Pests:

from the family Eutichuridae, for example, *Cheiracanthium japonicum;* from the family Theridiidae, for example, red-back spider (*Latrodectus hasseltii*);

and the others.

Polydesmida:

from the family Paradoxosomatidae, for example, flat-backed millipede (*Oxidus gracilis*), and *Nedyopus tambanus;* and the others.

Isopoda:

from the family Armadillidiidae, for example, common pill bug (*Armadillidium vulgare*);

and the others.

Chilopoda Pests:

from the family Scutigeridae, for example, *Thereuonema hilgendorfi;* from the family Scolopendridae, for example, giant tropical centipede (*Scolopendra subspinipes*);

from the family Ethopolidae, for example, *Bothropolys rugosus;* and the others.

Gastropoda:

from the family Limacidae, for example, tree slug (*Limax marginatus*), and garden tawny slug (*Limax flavus*);

from the family Philomycidae, for example, *Meghimatium bilineatum;* from the family Ampullariidae, for example, golden apple snail (*Pomacea canaliculata*);

from the family Lymnaeidae, for example, *Austropeplea ollula;* and the others.

Nematoda Pests:

from the family Aphelenchoididae, for example, rice white-tip nematode (*Aphelenchoides besseyi*);

from the family Pratylenchidae, for example, root lesion nematode (*Pratylenchus coffeae*), *Pratylenchus brachyurus*, California meadow nematode (*Pratylenchus neglectus*), and *Radopholus similis;* from the family Heteroderidae, for example, javanese root-knot nematode (*Meloidogyne javanica*), southern root-knot nematode (*Meloidogyne incognita*), northern root-knot nematode (*Meloidogyne hapla*), soybean cyst nematode (*Heterodera glycines*), potato cyst nematode (*Globodera rostochiensis*), and white potato cyst nematode (*Globodera pallida*);

from the family Hoplolaimidae, for example, *Rotylenchulus reniformis;* from the family Anguinidae, for example, strawberry bud nematode (*Nothotylenchus acris*), and stem nematode (*Ditylenchus dipsaci*);

from the family Tylenchulidae, for example, citrus nematode (*Tylenchulus semipenetrans*);

from the family Longidoridae, for example, dagger nematode (*Xiphinema index*);

from the family Trichodoridae;

from the family Parasitaphelenchidae, for example, pine wilt disease (*Bursaphelenchus xylophilus*);

and the others.

As a target, the harmful arthropods such as harmful insects, harmful mites, harmful mollusks, and harmful nematodes may be the harmful arthropods such as harmful insects, harmful mites, harmful mollusks, and harmful nematodes, each of which has a reduced agent-sensitivity to or a developed agent-resistance to an insecticide, a miticide, a molluscicide, and a nematocide, respectively.

The method for controlling harmful arthropods of the present invention is carried out by applying an effective amount of the present compound, the present compound X, or the composition A to a harmful arthropod directly and/or a habitat thereof (for example, plant bodies, soil, an interior of a house, animal bodies). Examples of the method for controlling harmful arthropods of the present invention include foliage treatment, soil treatment, root treatment, shower treatment, smoking treatment, water surface treatment and seed treatment.

The present compound, the present compound X, or the composition A is usually mixed with an inert carrier such as solid carrier, liquid carrier or gaseous carrier, and if necessary, adding surfactants and the other auxiliary agents for formulation, to formulate into emulsifiable concentrates, oil solutions, dust formulations, granules, wettable powders, water dispersible granules, flowables, dry flowables, microcapsules, aerosols, poison baits, resin formulations, shampoo formulations, paste-like formulations, foams, carbon dioxide formulations, and tablets and the others. Such formulations may be processed into mosquito repellent coils, electric mosquito repellent mats, liquid mosquito formulations, smoking agents, fumigants, sheet formulations, spot-on formulations or formulations for oral treatment. These formulations comprise usually 0.0001 to 95% by weight of the present compound, the present compound A or the composition A.

Examples of the solid carrier to be used in the formulation include fine powders or granules of clays (for example, kaolin clay, diatomaceous earth, bentonite, or acid white clay), dry silica, wet silica, talcs, ceramics, other inorganic minerals (for example, sericite, quartz, sulfur, active carbon, or calcium carbonate) or chemical fertilizers (for example, ammonium sulfate, ammonium phosphate, ammonium nitrate, urea, or ammonium chloride) and the others; as well as synthetic resins (for example, polyester resins such as polypropylene, polyacrylonitrile, polymethyl methacrylate or polyethylene terephthalate; nylon resins (for example, nylon-6, nylon-11, or nylon-66); polyamide resins; polyvinyl chloride, polyvinylidene chloride, vinyl chloride-propylene copolymers, and the others).

Examples of the liquid carriers include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile, or isobutyronitrile); ethers (for example, diisopropyl etheR14-dioxane, 1,2-dimethoxyethane, diethyleneglycol dimethyl ether, diethylene glycol monomethyl ether, propylene glycol monomethyl ether, dipropylene glycol monomethyl ether, or 3-methoxy-3-methyl-1-butanol); amides (for example, DMF, or N,N-dimethylacetamide); sulfoxides (for example, dimethyl sulfoxide); propylene carbonate; and vegetable oils (for example, soybean oil or cottonseed oil).

Examples of gaseous carrier include fluorocarbon, butane gas, liquefied petroleum gas (LPG), dimethyl ether, and carbon dioxide gas.

Examples of the surfactants include nonionic surfactants such as polyoxyethylenated alkyl ethers, polyoxyethylenated alkyl aryl ethers, and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), acidic isopropyl phosphate, 2,6-di-tert-butyl-4-methylphenol, and a mixture of 2-tert-butyl-4-methoxyphenol and 3-tert-butyl-4-methoxyphenol.

Examples of base material of the resin formulation include polyvinyl chloride polymers, polyurethane and the others, and a plasticizer such as phthalate esters (for example, dimethyl phthalate, dioctyl phthalate), adipic acid esters and stearic acid may be added to these base materials, if necessary. The resin formulation can be prepared by mixing the compound of the present invention with the above-mentioned base material, kneading the mixture, followed by molding it by injection molding, extrusion molding or pressure molding and the like. The resultant resin formulation can be subjected to further molding or cutting procedure and the like, if necessary, to be processed into shapes such as a plate, film, tape, net or string shape. These resin formulations can be processed into animal collars, animal ear tags, sheet products, trap strings, gardening supports and other products.

Examples of a base material for the poison baits include bait ingredients such as grain powder, vegetable oil, saccharide and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, insect attraction fragrances such as cheese flavor, onion flavor and peanut oil.

The plants as used herein include entire plant, foliages, flowers, ears, fruits, stems, branches, tree canopies, seeds, vegetative reproductive organs, and seedlings.

The vegetative reproductive organs represent a part of plant which have the ability to grow when the part is separated from the body and placed in soil, among the roots, stems, leaves and the like of the plant. Examples of the vegetative reproductive organs include tuberous root, creeping root, bulb, corm or solid bulb, tuber, rhizome, stolon, rhizophore, cane cuttings, propagule, and vine cutting. Here the stolon is also called runner, propagule is also called bulbils, which is divided into broad bud and bulblets. The vines represent shoots (generic name for leaves and stems) of sweet potato and Japanese yam. Discoid stem, corm, tuber, rhizome, stem fragments, rhizophore and tuberous root are also collectively referred to bulbs. For example, though a cultivation of potato begins by planting tubers in soil, the tubers used are generally called seed potatoes.

Examples of a method of controlling harmful arthropods by applying an effective amount of the present compound, the present compound X, or the composition A to soil include a method of applying an effective amount of the present compound, the present compound X, or the composition A to soil before planting plants or after planting plants, a method of applying an effective amount of the present compound, the present compound X, or the composition A to a root part of a crop to be protected from damage such as ingestion by harmful arthropods, and a method of controlling harmful arthropods which ingest plants by permeating and transferring an effective amount of the present compound, the present compound X or the composition A from roots and the like into the interior of the plant. More specific examples of the method for controlling harmful arthropods include planting hole treatment (spraying into planting holes, soil mixing after planting hole treatment), plant foot treatment (plant foot spraying, soil mixing after plant foot treatment, irrigation at plant foot, plant foot treatment at a later seeding raising stage), planting furrow treatment (planting furrow spraying, soil mixing after planting furrow treatment), planting row treatment (planting row spraying, soil mixing after planting row treatment, planting row spraying at a growing stage), planting row treatment at the time of sowing (planting row spraying at the time of sowing, soil mixing after planting row treatment at the time of sowing), broadcast treatment (overall soil surface spraying, soil mixing after broadcast treatment), side-article treatment, treatment of water surface (application to water surface, application to water surface after flooding), other soil spraying treatment (spraying of a granular formulation on leaves at a growing stage, spraying under a canopy or around a tree stem, spraying on the soil surface, mixing with surface soil, spraying into seed holes, spraying on the ground surfaces of furrows, spraying between plants), other irrigation treatment (soil irrigation, irrigation at a seedling raising stage, drug solution injection treatment, irrigation of a plant part just above the ground, drug solution drip irrigation, chemigation), seedling raising box treatment (spraying into a seedling raising box, irrigation of a seedling raising box, flooding into a seedling raising box with drug solution), seedling raising tray treatment (spraying on a seedling raising tray, irrigation of a seedling raising tray, flooding into a seedling raising tray with drug solution), seedbed treatment (spraying on a seedbed, irrigation of a seedbed, spraying on a lowland rice nursery, immersion of seedlings), seedbed soil incorporation treatment (mixing with seedbed soil, mixing with seedbed soil before sowing, spraying at sowing before covering with soils, spraying at sowing after covering with soils, mixing with covering soil, and other treatment (mixing with culture soil, plowing under, mixing with surface soil, mixing with soil at the place where raindrops fall from a canopy, treatment at a planting position, spraying of a granule formulation on flower clusters, mixing with a paste fertilizer).

As used herein, seeds or vegetative reproductive organs carrying the present compound, the present compound X or the composition A means seeds or vegetative reproductive organs in the state where the present compound, the present compound X or the composition A is adhered to a surface of the seeds or the vegetative reproductive organ. Also, the present compound, the present compound X, or the composition A which are may be adhered on the surface of the seeds or the vegetative reproductive organ may be permeated from the surface to the interior of the plant.

Also, when the composition A is adhered on the surface of the seeds or the vegetative reproductive organs, a layer consisting of single active ingredient may be multiply overlapped, a plural of the active ingredients may be mixed to form a single layer, a layer consisting of the single active ingredient and a layer consisting of the plural of the active ingredients may be multiply overlapped, or a layer consisting of the plural of the active ingredients may be multiply overlapped.

The seeds or vegetative reproductive organs used for the seed treatment may be used as itself, or any materials other than the present compound, the present compound A, or the composition A may be adhered before or after being treated with the present compound, the present compound A or the composition A.

Examples of the application to seeds (or seed treatments) include an application of the present compound X or the composition A X to seeds or vegetative reproductive organs, and specific examples thereof include spraying treatment in which a suspension of the present compound X or the composition A is sprayed onto seed surface or the vegetative reproductive organ surface in the form of mist; smearing treatment in which the present compound X or the composition A is coated a surface of seeds or the vegetative reproductive organ; a soaking treatment in which the seeds are soaked into the solution of the present compound X or the composition A for a certain time; and a method for coating the seeds or the vegetative reproductive organ with a carrier containing the present compound X or the composition A (film coating treatment, pellet coating treatment). Examples of the above-described vegetative reproductive organ include particularly seed potato.

When the composition A is applied to seeds or vegetative reproductive organs, the composition A may be also applied to seeds or vegetative reproductive organs as a single formulation, or the composition A may be applied to seeds or vegetative reproductive organs as a divided plural of formulations by a plurality of times. Examples of the method in which the composition A is applied as a divided plural of formulations by a plurality of times include, for example, a method in which the formulations comprising as an active component the present compound X only are applied, and seeds or vegetative reproductive organs are air dried, followed by applying the formulations comprising the present ingredient: and a method in which the formulations comprising as an active component the present compound X and the present ingredients are applied, and seeds or vegetative reproductive organs are air dried, followed by applying the formulations comprising the present ingredients other than the already-applied present ingredients, are included.

As used herein, seeds or vegetative reproductive organs carrying the present compound X or the composition A means seeds or vegetative reproductive organs in the state where the present compound X or the composition A is adhered to a surface of the seeds or the vegetative reproductive organ. The above-described seeds or vegetative reproductive organs carrying the present compound X or the composition A may be adhered by any other materials that are different from the present compound X or the composition A before or after being adhered the present compound X or the composition A to the seeds or vegetative reproductive organs.

Also, when the composition A is adhered in a form of layer(s) to a surface of seeds or vegetative reproductive organ, the layer(s) is/are composed of one layer or a plural of layers. Also, when a plural layers are formed, each of the layer may be composed of a layer comprising one or more active ingredients, or a combination of a layer comprising one or more active ingredients and a layer not comprising an active ingredient.

Seeds or vegetative reproductive organs carrying the present compound X or the composition A can be obtained, for example, by applying the formulations comprising the present compound X or the composition A by the above-described application method to seeds to seeds or vegetative reproductive organs.

When the present compound, the present compound A or the composition A is applied for harmful arthropods control in agricultural fields, the application dose thereof is usually within a range of 1 to 10,000 g g of the present compound or the present compound X per 10,000 $m^2$. In the case of being applied to seeds or vegetative reproductive organs, the dose of application dose thereof is usually within a range of 0.001 to 100 g of the present compound X per 1 Kg of seeds. When the present compound, the present compound X, or the composition A is formulated into an emulsifiable concentrate, a wettable powder or a flowable etc., they are usually applied by diluting them with water so as to make an effective concentration of the active ingredients 0.01 to 10,000 ppm, and the dust formulation or the granular formulation, etc., is usually applied as itself without diluting them.

Also, the resin preparation which is processed into a sheet or a string may be applied by winding a plant with a sheet or a string of the resin preparation, putting a string of the resin preparation around a crop so that the plant is surrounded by the string, or laying a sheet of the resin preparation on the soil surface near the root of a plant.

When the present compound, the present compound A or the composition A is used to control harmful arthropods that live inside a house, the application dose as an amount of the present compound or the present compound X is usually within a range from 0.01 to 1,000 mg per 1 $m^2$ of an area to be treated, in the case of using it on a planar area. In the case of using it spatially, the application dose as an amount of the present compound or the present compound X is usually within a range from 0.01 to 500 mg per 1 $m^3$ of the space to be treated. When the present compound, the present compound X or the composition A is formulated into emulsifiable concentrates, wettable powders, flowables or the others, such formulations are usually applied after diluting it with water in such a way that a concentration of the active ingredient is within a range from 0.1 to 10,000 ppm. In the case of being formulated into oil solutions, aerosols, smoking agents, poison baits and the others, such formulations are used as itself without diluting it.

When the present compound, the present compound X or the composition is used for controlling external parasites of livestock such as cows, horses, pigs, sheep, goats and chickens and small animals such as dogs, cats, rats and mice, the composition of the present invention may be applied to the animals by a known method in the veterinary field. Specifically, when systemic control is intended, the composition of the present invention is administered to the animals as a tablet, a mixture with feed or a suppository, or by injection (including intramuscular, subcutaneous, intravenous and intraperitoneal injections). On the other hand, when non-systemic control is intended, the composition of the present invention is applied to the animals by means of spraying of the oil solution or aqueous solution, pour-on or spot-on treatment, or washing of the animal with a shampoo formulation, or by putting a collar or ear tag made of the resin formulations to the animal. In the case of being administered to an animal body, the dose of the compound of the present compound or the present compound X is usually within a range from 0.1 to 1,000 mg per 1 kg of an animal body weight.

Also, the composition of the present compound, the present compound X or the composition A may be used as an agent for controlling harmful arthropods in agricultural lands such as paddy fields, fields, turfs, and orchards. Examples of the plants to be applied include the followings.

corn, rice, wheat, barley, rye, oat, sorghum, cotton, soybean, peanut, buckwheat, beet, rapeseed, sunflower, sugar cane, tobacco, solanaceous vegetables (for example, eggplant, tomato, pimento, pepper, or potato), cucurbitaceous vegetables (for example, cucumber, pumpkin, zucchini, water melon, or melon), cruciferous vegetables (for example, Japanese radish, white turnip, horseradish, kohlrabi, Chinese cabbage, cabbage, leaf mustard, broccoli, or cauliflower), asteraceous vegetables (for example, burdock, crown daisy, artichoke, or lettuce), liliaceous vegetables (for example, green onion, onion, garlic, or asparagus), ammiaceous vegetables (for example, carrot, parsley, celery, or parsnip), chenopodiaceous vegetables (for example, spinach, or Swiss chard), lamiaceous vegetables (for example, *Perilla frutescens*, mint, or basil), strawberry, sweet potato, *Dioscorea japonica, colocasia,* pomaceous fruits (for example, apple, pear, Japanese pear, Chinese quince, or quince), stone fleshy fruits (for example, peach, plum, nectarine, *Prunus mume*, cherry fruit, apricot, or prune), citrus fruits (for example, Citrus unshiu, orange, lemon, lime, or grapefruit), nuts (for example, chestnut, walnuts, hazelnuts, almond, pistachio, cashew nuts, or macadamia nuts), berry fruits (for example, blueberry, cranberry, blackberry or raspberry), grape, kaki persimmon, olive, Japanese plum, banana, coffee, date palm, coconuts, tea, mulberry, ornamental foliage plants, woodland plants, lawns, pastures.

The above-mentioned plants are not particularly limited as long as they are commonly cultivated varieties. The above-mentioned plants may include plants which can be produced by a natural mating, plants which is developed by a mutation, F1 hybrid plants, and genetically modified crops. Examples of the genetically modified crops include plants which is imparted with resistance to herbicides including HPPD (that is, 4-hydroxyphenylpyruvate dioxygenase) inhibitors such as isoxaflutole; ALS (that is, acetoacetate synthase) inhibitors such as imazethapyr and thifensulfuron methyl; EPSP (that is, 5-enolpyruvoylshikimate-3-phosphate synthase) inhibitors; glutamine synthetase inhibitors; PPO (that is, protoporphyrinogen oxidase) inhibitors; bromoxynil; dicamba, and the like; plants which have become capable of synthesizing selective toxins and the like (for example, genus *Bacillus* such as *Bacillus thuringiensis*); and the plants being capable of synthesizing a gene segment that match partially an endogenous gene derived from a harmful insect and also imparting with specific insecticidal activity by inducing a gene silencing (RNAi; RNA interference) in a target harmful insect.

EXAMPLES

Hereinafter, the present invention is explained in more detail by using Preparation examples, Reference preparation examples, and Test examples, however, the present invention should not be limited to these examples.

As used herein, "Me" represents a methyl group, "Et" represents an ethyl group, "Pr" represents a propyl group, "i-Pr" represents an isopropyl group, "c-Pr" represents a cyclopropyl group, "c-Bu" represents a cyclobutyl group, "c-Pen" represents a cyclopentyl group, "c-Hex" represents a cyclohexyl group, "Ph" represents a phenyl group, "Py2" represents a 2-pyridyl group, "Py3" represents a 3-pyridyl group, "Py4" represents a 4-pyridyl group, "Bn" represents benzyl group. "Boc" represents a tert-butoxycarbonyl group. When c-Pr, c-Bu, c-Pen, c-Hex, Ph, Py2, Py3, and Py4 have a substituent, the substituent is written with its substituted position before the symbol. For example, "1-CN-c-Pr" represents a 1-cyanocyclopropyl group, "3,4-$F_2$-Ph" represents a 3,4-difluorophenyl group, "4-$CF_3$-Py2" represents a 4-(trifluoromethyl)-2-pyridyl, and "5-$OCH_2CF_2CF_3$-Py2" represents a 5-(2,2,3,3,3-pentafluoropropoxy)-2-pyridyl group.

Herein, when "present compound X" is referred to, it encompasses "present compound" unless otherwise specified. Also herein, when "present compound P" is referred to, it encompasses "present compound N" unless otherwise specified.

Firstly, examples of the present compound X and process intermediate compound thereof are described.

Reference Preparation Example 1

A mixture of 4-(trifluoromethyl)anthranilic acid 3.00 g and formamide 6 mL was stirred at 140° C. for 11 hours. The resulting mixture was stood to cool to room temperature, and water was added thereto, and the mixture was filtered. The obtained solids were dried under reduced pressure to obtain the intermediate compound 1 represented by the following formula 2.90 g.

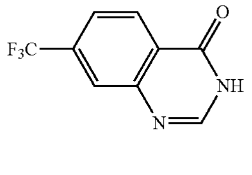 [SMILES: O=c1[nH]cnc2cc(C(F)(F)F)ccc12]

Intermediate compound 1: $^1$H-NMR ($CDCl_3$) δ: 10.46 (1H, br s), 8.43 (1H, d), 8.14 (1H, s), 8.05 (1H, d), 7.75 (1H, dd).

Reference Preparation Example 2

To a mixture of 4-(trifluoromethyl)antranilic acid 3.00 g and THF 22 mL was added dropwise a mixture of triphosgene 1.52 g and THE 15 mL under ice-cooling. The resulting mixture was stirred at room temperature for 4 hours. Water was added to the resulting mixture, and the mixture was extracted with ethyl acetate. The resulting organic layer was dried over anhydrous sodium sulfate, and concentrated under reduced pressure to obtain the intermediate compound 2 represented by the following formula 3.30 g.

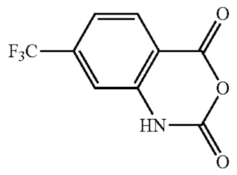

Intermediate compound 2: $^1$H-NMR (DMSO-$D_6$) δ: 11.98 (1H, br s), 8.10 (1H, d), 7.54 (1H, d), 7.37 (1H, s).

Reference Preparation Example 3

To a mixture of 6-bromo-3-(ethylthio)imidazo[1,2-a]pyridin-2-amine 300 mg (prepared as described in WO/2018052136) and THF 4 mL was added dropwise a solution of potassium bis(trimethylsilyl)amide (1 mol/L THF solution) 2.2 mL at −78° C. under nitrogen atmosphere, and the mixture was stirred for 30 minutes. A mixture of the intermediate compound 2 and THF 4 mL was added to the resulting mixture, and the mixture was stirred at room temperature for 30 minutes. Saturated aqueous ammonium chloride solution was added to the resulting mixture, and the mixture was extracted with ethyl acetate. The resulting mixture was dried over anhydrous sodium sulfate, and concentrated under reduced pressure. Hexane was added to the resulting residue, and the obtained solids were filtered. The filtered substances were washed with hexane to obtain the intermediate compound 3 represented by the following formula 491 mg.

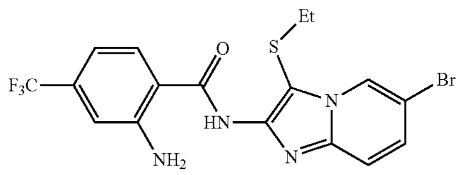 [SMILES: CCSc1c(NC(=O)c2ccc(C(F)(F)F)cc2N)nc2ccc(Br)cn12]

Intermediate compound 3-1: $^1$H-NMR ($CDCl_3$) δ: 8.54 (1H, dd), 8.35 (1H, s), 7.67 (1H, d), 7.60 (1H, dd), 7.41 (1H, dd), 7.00 (1H, s), 6.98 (1H, d), 5.95 (2H, br s), 2.75 (2H, q), 1.27 (3H, t).

The compounds which were prepared according to the Reference Preparation Example 3 and their physical property values were shown below.

A compound represented by formula (B-1):

(B-1)

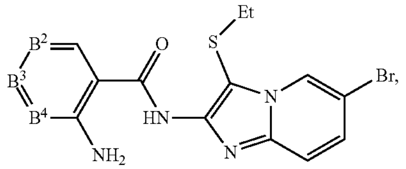

wherein a combination of $B^2$, $B^3$ and $B^4$ represents any combination indicated in [Table B1].

[Table B1]

| Intermediate compound | $B^2$ | $B^3$ | $B^2$ |
|---|---|---|---|
| 3-2 | $CCF_3$ | CH | CH |
| 3-3 | CH | CH | $CCF_3$ |
| 3-4 | CH | $CCF_3$ | N |
| 3-5 | CH | CCl | CH |
| 3-6 | CH | CI | CH |
| 3-7 | $COCF_3$ | CH | CH |

Intermediate compound 3-2: $^1$H-NMR ($CDCl_3$) δ: 8.53-8.53 (1H, m), 8.33 (1H, s), 7.80 (1H, s), 7.57 (1H, d), 7.50 (1H, dd), 7.39 (1H, dd), 6.78 (1H, d), 6.14 (2H, s), 2.74 (2H, q), 1.26 (3H, t).

Intermediate compound 3-3: $^1$H-NMR ($CDCl_3$) δ: 8.51 (1H, dd), 8.25 (1H, br s), 7.73 (1H, d), 7.62 (1H, d), 7.57 (1H, dd), 7.38 (1H, dd), 6.77 (1H, t), 6.39 (2H, br s), 2.72 (2H, q), 1.24 (3H, t).

Intermediate compound 3-4: $^1$H-NMR ($CDCl_3$) δ: 8.52 (1H, d), 8.35 (1H, br s), 7.98 (1H, d), 7.56 (1H, d), 7.40 (1H, dd), 7.03 (1H, d), 6.69 (2H, br s), 2.73 (2H, q), 1.24 (3H, t).

Intermediate compound 3-5: $^1$H-NMR ($CDCl_3$) δ: 8.50 (1H, dd), 8.29 (1H, s), 7.56 (1H, dd), 7.47 (1H, d), 7.37 (1H, dd), 6.73 (1H, d), 6.68 (1H, dd), 5.87 (2H, s), 2.71 (2H, q), 1.23 (3H, t).

Intermediate compound 3-6: $^1$H-NMR ($CDCl_3$) δ: 8.49 (1H, d), 8.28 (1H, br s), 7.56 (1H, d), 7.36 (1H, dd), 7.23 (1H, d), 7.13 (1H, d), 7.04 (1H, dd), 5.79 (2H, br s), 2.71 (2H, q), 1.22 (3H, t).

Intermediate compound 3-7: $^1$H-NMR ($CDCl_3$) δ: 8.51 (1H, s), 8.26 (1H, s), 7.56 (1H, d), 7.39-7.36 (2H, m), 7.18 (1H, d), 6.72 (1H, d), 5.77 (2H, s), 2.73 (2H, q), 1.24 (3H, t).

Reference Preparation Example 4

To a mixture of 6-bromo-imidazo[1,2-a]pyridin-2-amine 0.47 g (prepared as described in WO2012/173412) and THF 5 mL was added dropwise a solution of potassium bis (trimethylsilyl)amide (1 mol/L THF solution) 4.4 mL at −78° C. under nitrogen atmosphere, and the mixture was stirred for 30 minutes. A mixture of the intermediate compound 2 0.61 g and THF 5 mL was added to the resulting mixture, and the mixture was stirred at room temperature for 30 minutes. Saturated aqueous ammonium chloride solution was added to the resulting mixture, and the mixture was extracted with ethyl acetate. The resulting organic layer was dried over anhydrous sodium sulfate, and concentrated under reduced pressure. Hexane was added to the resulting residue, and the obtained solids were filtered. The filtered substances were washed with hexane to obtain the intermediate compound 4 represented by the following formula 0.66 g.

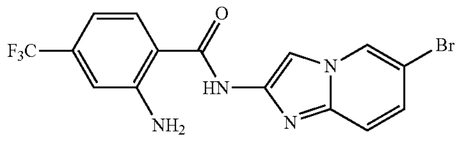

Intermediate compound 4: $^{1}$H-NMR (DMSO-$D_6$) δ: 11.20 (1H, s), 8.95 (1H, dd), 8.29 (1H, s), 7.94 (1H, d), 7.46 (1H, d), 7.36 (1H, dd), 7.11 (1H, d), 6.82 (1H, d), 6.81 (2H, br s).

Reference Preparation Example 5

A mixture of the intermediate compound 4 0.66 g and triethyl orthoformate 20 mL was stirred at 100° C. for 4 hours. Triethyl orthoformate 10 mL was added to the resulting mixture, and the mixture was stirred at 100° C. for 2 hours. The resulting mixture was stood to cool to room temperature, and concentrated under reduced pressure. The obtained solids were washed with hexane to obtain the intermediate compound represented by the following formula 0.54 g.

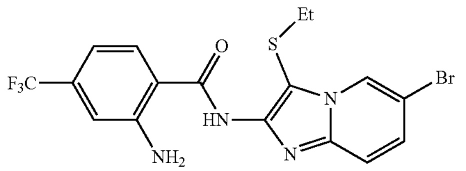 [SMILES: CCSc1c(NC(=O)c2ccc(C(F)(F)F)cc2N)nc2ccc(Br)cn12]

Intermediate compound 5: $^{1}$H-NMR ($CDCl_3$) δ: 9.50 (1H, s), 8.53-8.52 (1H, m), 8.54 (1H, d), 8.36 (1H, dd), 8.10 (1H, d), 7.77 (1H, dd), 7.53 (1H, d), 7.38 (1H, dd).

Reference Preparation Example 6

To a mixture of the intermediate compound 5 0.54 g and DMF 26 mL was added N-iodosuccinimide 0.44 g under ice-cooling, and the mixture was stirred at room temperature for 10 hours. N-iodosuccinimide 0.30 g was added to the resulting mixture under ice-cooling, and the mixture was stirred at room temperature for 6 hours. Water was added to the resulting mixture, and the obtained solids were dissolved in chloroform, and washed with saturated aqueous sodium thiosulfate solution. The resulting organic layer was dried over anhydrous sodium sulfate, and concentrated under reduced pressure to obtain the intermediate compound 6 represented by the following formula 0.32 g.

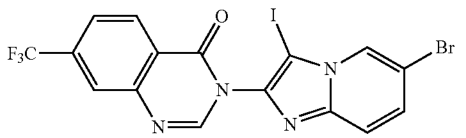 [SMILES: O=c1c2ccc(C(F)(F)F)cc2ncn1-c1nc2ccc(Br)cn2c1I]

Intermediate compound 6: $^{1}$H-NMR ($CDCl_3$) δ: 8.53 (1H, d), 8.37 (1H, d), 8.26 (1H, s), 8.10-8.07 (1H, m), 7.79 (1H, dd), 7.57 (1H, d), 7.47 (1H, dd).

Reference Preparation Example 7

To a mixture of 3-(trifluoromethylthio)aniline 5.00 g and toluene 150 mL was added N-bromosuccinimide 4.83 g at room temperature, and the mixture was stirred at room temperature for 1 hour. Water was added to the resulting mixture, and the mixture was extracted with ethyl acetate. The resulting organic layer was dried over anhydrous sodium sulfate, and concentrated udder reduced pressure. The resulting residue was subjected to a silica gel column chromatography to obtain the intermediate compound 7-1 represented by the following formula 2.99 g.

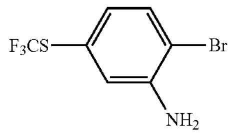

Intermediate compound 7-1: $^{1}$H-NMR ($CDCl_3$) δ: 7.44 (1H, d), 7.03 (1H, d), 6.87 (1H, dd), 4.23 (2H, s).

Reference Preparation Example 8

The intermediate compound 7-2 was obtained by using 4-(trifluoromethylthio)aniline in place of 3-(trifluoromethylthio)aniline according to the method described in the Reference Preparation Example 7.

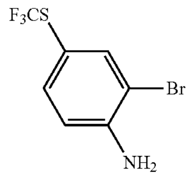

Intermediate compound 7-2: $^{1}$H-NMR ($CDCl_3$) δ: 7.71 (1H, d), 7.37 (1H, dd), 6.75 (1H, d), 4.41 (2H, s).

Reference Preparation Example 9

A mixture of the intermediate compound 7-1 2.99 g, di-tert-butyl dicarbonate 2.88 g, and THF 22 mL was stirred at 70° C. for 4 hours. Water was added to the resulting mixture, and the mixture was extracted with ethyl acetate. The resulting mixture was dried over anhydrous sodium sulfate, and concentrated under reduced pressure. The resulting residue was subjected to a silica gel column chromatography to the intermediate compound 8-1 represented by the following formula 4.64 g.

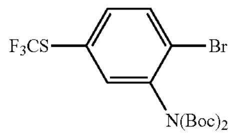

Intermediate compound 8-1: $^{1}$H-NMR ($CDCl_3$) δ: 7.68 (1H, d), 7.53 (1H, d), 1.46 (1H, dd), 1.39 (18H, s).

Reference Preparation Example 10

The intermediate compound 8-2 was obtained by using the intermediate compound 7-2 in place of the intermediate compound 7-1 according to the method described in the Reference Preparation Example 9.

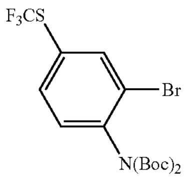

Intermediate compound 8-2: $^{1}$H-NMR ($CDCl_3$) δ: 7.92 (1H, d), 7.61 (1H, dd), 7.28 (1H, d), 1.39 (18H, s).

Reference Preparation Example 11

To a mixture of the intermediate compound 8-1 2.0 g and THF 42 ml was added dropwise butyl lithium 3 mL at −78° C. under nitrogen atmosphere, and the mixture was stirred for 15 minutes. Saturated aqueous ammonium chloride solution was added to the resulting mixture, and the mixture was extracted with ethyl acetate. The resulting organic layer was dried over anhydrous sodium sulfate, and concentrated under reduced pressure. The resulting residue was subjected to a silica gel column chromatography to obtain the intermediate compound 9-1 represented by the following formula 0.93 g.

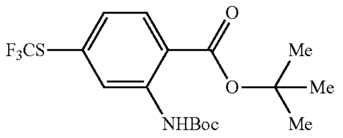

Intermediate compound 9-1: $^{1}$H-NMR ($CDCl_3$) δ: 10.36 (1H, s), 8.77 (1H, s), 7.96 (1H, d), 7.22 (1H, d), 1.61 (9H, s), 1.54 (9H, s).

Reference Preparation Example 12

The intermediate compound 9-2 was obtained by using the intermediate compound 8-2 in place of the intermediate compound 8-1 according to the method described in the Reference Preparation Example 11.

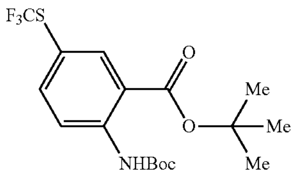

Intermediate compound 9-2: $^{1}$H-NMR ($CDCl_3$) δ: 10.50 (1H, s), 8.53 (1H, d), 8.20 (1H, d), 7.71 (1H, dd), 1.62 (9H, s), 1.54 (9H, s).

Reference Preparation Example 13

A mixture of the intermediate compound 9-1 0.93 g, trifluoroacetic acid 6 mL, and chloroform 23 ml was stirred at room temperature for 20 hours. The resulting mixture was concentrated, and the obtained solids were washed with hexane to obtain the intermediate compound 10-1 represented by the following formula 0.57 g.

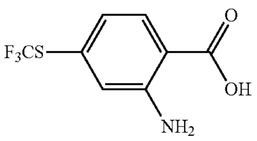

Intermediate compound 10-1: $^{1}$H-NMR ($CDCl_3$) δ: 7.93 (1H, d), 6.96 (1H, s), 6.89 (1H, d).

Reference Preparation Example 14

The intermediate compound 10-2 was obtained by using the intermediate compound 9-2 in place of the intermediate compound 9-1 according to the method described in the Reference Preparation Example 13.

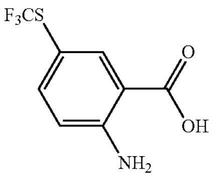

Intermediate compound 10-2: $^{1}$H-NMR ($CDCl_3$) δ: 8.23 (1H, d), 7.53 (1H, dd), 6.70 (1H, d).

Reference Preparation Example 15

To a mixture of 2-fluoro-4-iodobenzoic acid 3.00 g and chloroform 28 mL were added oxalyl chloride 2.2 mL and DMF 0.1 ml successively at room temperature, and the mixture was stirred at room temperature for 1 hour. The resulting mixture was concentrated and the mixture was dissolved in THF 28 mL and to the resulting mixture were added dropwise benzyl alcohol 1.8 mL and triethylamine 4.7 mL successively under ice-cooling, and the mixture was stirred at room temperature for 1 hour. Saturated aqueous sodium bicarbonate solution was added to the resulting mixture, and the mixture was extracted with ethyl acetate. The resulting mixture was dried over anhydrous sodium sulfate, and concentrated under reduced pressure. The resulting residue was subjected to a silica gel column chromatography to obtain the intermediate compound 11 represented by the following formula 3.78 g.

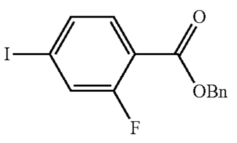 [SMILES: O=C(OCc1ccccc1)c1ccc(I)cc1F]

Intermediate compound 11: $^{1}$H-NMR ($CDCl_3$) δ: 7.68-7.64 (1H, m), 7.57-7.54 (2H, m), 7.45-7.44 (2H, m), 7.41-7.33 (3H, m), 5.37 (2H, s).

Reference Preparation Example 16

A mixture of the intermediate compound 11 2.45 g, potassium fluoride 0.76 g, copper(I) iodide 3.14 g, trimethyl (pentafluoroethyl)silane 2.4 mL and DMF 15 mL was stirred at 80° C. under microwave irradiation for 6 hours. Saturated aqueous ammonium solution and MTBE were added successively to the resulting mixture, and the mixture was filtered through Celite (registered trademark). The resulting filtrates were extracted with MTBE. The resulting organic layer was dried over anhydrous sodium sulfate, and concentrated under reduced pressure. The resulting residue was subjected to a silica gel column chromatography to obtain the intermediate compound 12 represented by the following formula 1.97 g.

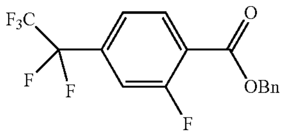 [SMILES: O=C(OCc1ccccc1)c1ccc(C(F)(F)C(F)(F)F)cc1F]

Intermediate compound 12: $^1$H-NMR ($CDCl_3$) δ: 8.11-8.09 (1H, m), 7.47-7.33 (7H, m), 5.39 (2H, s).

Reference Preparation Example 17

To a mixture of the intermediate compound 12 0.80 g and DMSO 5 ml was added sodium azide 194 mg at room temperature, and the mixture was stirred at 80° C. for 1 hour. Sodium azide 75 mg was added to the resulting mixture at room temperature, and the mixture was stirred at 80° C. for 3 hours. The resulting mixture was cooled under ice-cooling, and water was added thereto, and the mixture was extracted with MTBE. The resulting organic layer was dried over anhydrous sodium sulfate, and concentrated under reduced pressure. The resulting residue was subjected to a silica gel column chromatography to obtain the intermediate compound 13 represented by the following formula 13 0.85 g.

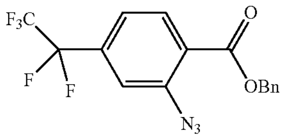 [SMILES: [N-]=[N+]=Nc1cc(C(F)(F)C(F)(F)F)ccc1C(=O)OCc1ccccc1]

Intermediate compound 13: $^1$H-NMR ($CDCl_3$) δ: 7.98 (1H, d), 7.47-7.31 (7H, m), 5.38 (2H, s).

Reference Preparation Example 18

A mixture of the intermediate compound 13 0.85 g, 10% palladium carbon 0.21 g, and methanol 5 mL was stirred for 8 hours under hydrogen atmosphere. The resulting mixture was filtered through Celite (registered trademark), and the filtrates were concentrated under reduced pressure to obtain the intermediate compound 14 represented by the following formula 0.64 g.

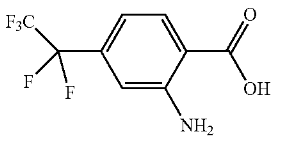

Intermediate compound 14: $^1$H-NMR ($CDCl_3$) δ: 8.01 (1H, d), 6.89 (1H, s), 6.85 (1H, d).

Reference Preparation Example 19

The intermediate compound 15 was obtained by using 2-amino-5-iodobenzoic acid in place of the intermediate compound 7-1 according to the method described in the Reference Preparation Example 9.

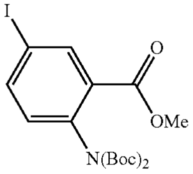

Intermediate compound 15: $^1$H-NMR ($CDCl_3$) δ: 8.32 (1H, d), 7.84 (1H, dd), 6.93 (1H, d), 3.87 (3H, s), 1.38 (18H, s).

Reference Preparation Example 20

The intermediate compound 16 was obtained by using the intermediate compound 15 in place of the intermediate compound 11 according to the method described in the Reference Preparation Example 16.

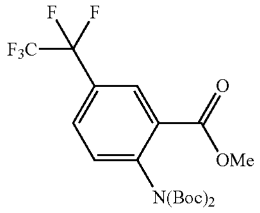

Intermediate compound 16: $^1$H-NMR ($CDCl_3$) δ: 8.25 (1H, s), 7.76 (1H, d), 7.37 (1H, d), 3.90 (3H, s), 1.38 (18H, s).

Reference Preparation Example 21

To a mixture of the intermediate compound 16 2.44 g and ethanol 13 ml was added dropwise 15% aqueous sodium hydroxide solution under ice-cooling. The resulting mixture was stirred at room temperature for 6 hours, and concentrated under reduced pressure, and neutralized with 2N hydrochloric acid. The resulting mixture was extracted with ethyl acetate, and the resulting organic layer was dried over anhydrous sodium sulfate, and concentrated under reduced pressure to obtain the intermediate compound 17 represented by the following formula 1.80 g.

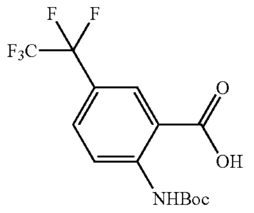 [SMILES: CC(C)(C)OC(=O)Nc1ccc(C(F)(F)C(F)(F)F)cc1C(=O)O]

Intermediate compound 17: $^1$H-NMR (DMSO-$D_6$) δ: 8.13 (1H, s), 7.94-7.93 (1H, m), 7.62-7.61 (1H, m), 7.53 (1H, d), 1.48 (9H, s).

Reference Preparation Example 22

The intermediate compound 18 was obtained by using the intermediate compound 17 in place of the intermediate compound 9-1 according to the method described in the Reference Preparation Example 13.

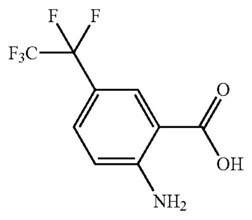 [SMILES: Nc1ccc(C(F)(F)C(F)(F)F)cc1C(=O)O]

Intermediate compound 18: $^1$H-NMR (DMSO-D) δ: 7.91 (1H, d), 7.45 (1H, dd), 6.92 (1H, d).

Reference Preparation Example 23

To a mixture of ethyl imidazo[1,2-a]pyridine-2-carboxylate 5.66 g and DMF 40 mL was added N-chlorosuccinimide 4.37 g under ice-cooling, and the mixture was stirred at 60° C. for 6 hours. Water was added to the resulting mixture, and the precipitated out solids were filtered. The obtained solids were washed with water, and dried under reduced pressure to obtain the intermediate compound 19-1 represented by the following formula 6.60 g.

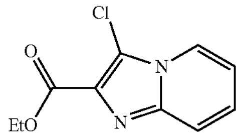 [SMILES: CCOC(=O)c1nc2ccccn2c1Cl]

Intermediate compound 19-1: $^1$H-NMR ($CDCl_3$) δ: 8.16-8.15 (1H, m), 7.71-7.69 (1H, m), 7.36-7.31 (1H, m), 7.05-7.01 (1H, m), 4.50 (2H, q), 1.47 (3H, t).

The compounds which were prepared according to the Reference Preparation Example 23 and their physical property values were shown below.

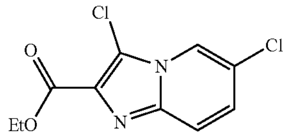

Intermediate compound 19-2: $^1$H-NMR ($CDCl_3$) δ: 8.19 (1H, d), 7.65 (1H, d), 7.29 (1H, dd), 4.49 (2H, q), 1.46 (3H, t).

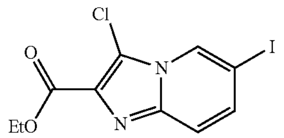

Intermediate compound 1 19-3: $^1$H-NMR ($CDCl_3$) δ: 8.41 (1H, dd), 7.51-7.45 (2H, m), 4.49 (2H, q), 1.46 (3H, t).

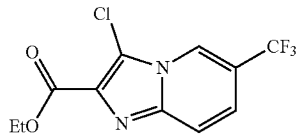 [SMILES: CCOC(=O)c1nc2ccc(C(F)(F)F)cn2c1Cl]

Intermediate compound 1 19-4: $^1$H-NMR ($CDCl_3$) δ: 8.52 (1H, dd), 7.82 (1H, dd), 7.47 (1H, dd), 4.52 (2H, q), 1.48 (3H, t).

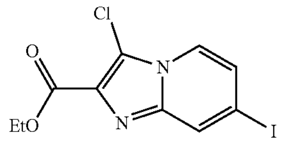 [SMILES: CCOC(=O)c1nc2cc(I)ccn2c1Cl]

Intermediate compound 19-5: $^1$H-NMR ($CDCl_3$) δ: 8.10 (1H, dd), 7.89 (1H, dd), 7.25 (1H, dd), 4.49 (2H, q), 1.46 (3H, t).

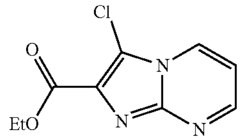 [SMILES: CCOC(=O)c1nc2ncccn2c1Cl]

Intermediate compound 19-6: $^1$H-NMR ($CDCl_3$) δ: 8.74 (1H, dd), 8.47 (1H, dd), 7.10 (1H, dd), 4.51 (2H, q), 1.47 (3H, t).

Reference Preparation Example 24

To a mixture of the intermediate compound 19-1 6.60 g, cesium carbonate 24.2 g and DMF 45 ml was added ethanethiol 2.4 mL at room temperature, and the mixture was stirred for 4 hours. Water was added to the resulting mixture, and the precipitated out solids were filtered. The obtained solids were washed with water and dried under reduced pressure to obtain the intermediate compound 20-1 represented by the following formula 6.76 g.

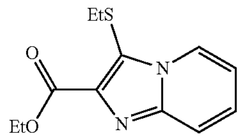

Intermediate compound 20-1: $^1$H-NMR ($CDCl_3$) δ: 8.57-8.55 (1H, m), 7.73-7.70 (1H, m), 7.36-7.32 (1H, m), 7.01-6.98 (1H, m), 4.51 (2H, q), 2.94 (2H, q), 1.48 (3H, t), 1.19 (3H, t).

The compounds which were prepared according to the Reference Preparation Example 24 and their physical property values were shown below.

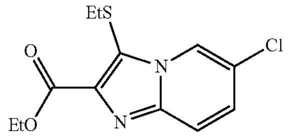

Intermediate compound 20-2: $^1$H-NMR ($CDCl_3$) δ: 8.59 (1H, s), 7.66 (1H, d), 7.30 (1H, d), 4.50 (2H, q), 2.95 (2H, q), 1.47 (3H, t), 1.21 (3H, t).

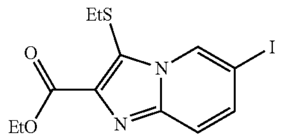

Intermediate compound 20-3: $^1$H-NMR ($CDCl_3$) δ: 8.80 (1H, dd), 7.52-7.48 (2H, m), 4.50 (2H, q), 2.95 (2H, q), 1.47 (3H, t), 1.21 (3H, t).

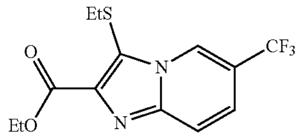

Intermediate compound 20-4: $^1$H-NMR ($CDCl_3$) δ: 8.92 (1H, s), 7.82 (1H, d), 7.47 (1H, d), 4.52 (2H, q), 2.99 (2H, q), 1.48 (3H, t), 1.22 (3H, t).

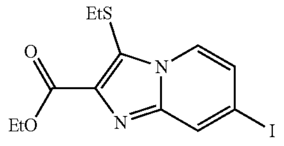

Intermediate compound 20-5: $^1$H-NMR ($CDCl_3$) δ: 8.29 (1H, dd), 8.12 (1H, dd), 7.22 (1H, dd), 4.50 (2H, q), 2.93 (2H, q), 1.47 (3H, t), 1.18 (3H, t).

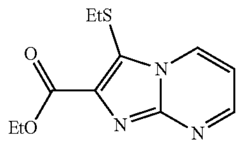

Intermediate compound 20-6: $^1$H-NMR ($CDCl_3$) δ: 8.84 (1H, dd), 8.73 (1H, dd), 7.06 (1H, dd), 4.51 (2H, q), 2.97 (2H, q), 1.47 (3H, t), 1.19 (3H, t).

Reference Preparation Example 25

The intermediate compound 21-1 was obtained by using the intermediate compound 20-1 in place of the intermediate compound 16 according to the method described in the Reference Preparation Example 21.

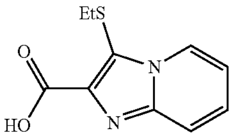

Intermediate compound 21-1: $^1$H-NMR (DMSO-$D_6$) δ: 8.67-8.65 (1H, m), 7.71-7.69 (1H, m), 7.49-7.45 (1H, m), 7.18-7.14 (1H, m), 2.87 (2H, q), 1.05 (3H, t).

The compounds which were prepared according to the Reference Preparation Example 25 and their physical property values were shown below.

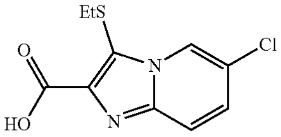

Intermediate compound 21-2: $^1$H-NMR ($CDCl_3$) δ: 8.74 (1H, s), 7.76 (1H, d), 7.52 (1H, d), 2.89 (2H, q), 1.07 (3H, t).

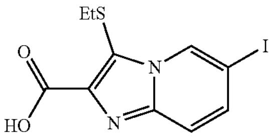

Intermediate compound 21-3: $^1$H-NMR (DMSO-$D_6$) δ: 8.77 (1H, dd), 7.61 (1H, dd), 7.50 (1H, dd), 2.86 (2H, q), 1.03 (3H, t).

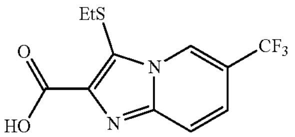

Intermediate compound 21-4: $^1$H-NMR (DMSO-$D_6$) δ: 8.89 (1H, s), 7.82 (1H, d), 7.62 (1H, d), 2.92 (2H, q), 1.03 (3H, t).

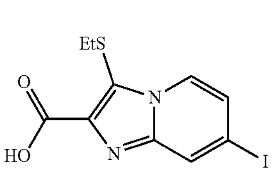

Intermediate compound 21-5: $^1$H-NMR (DMSO-$D_6$) δ: 8.40 (1H, dd), 8.15-8.13 (1H, m), 7.34 (1H, dd), 2.85 (2H, q), 1.01 (3H, t).

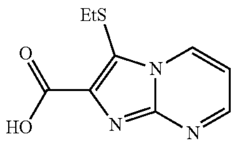

Intermediate compound 21-6: $^{1}$H-NMR (DMSO-$D_6$) δ: 9.46 (1H, dd), 8.66 (1H, dd), 7.26 (1H, dd), 3.23 (2H, q), 1.37 (3H, t).

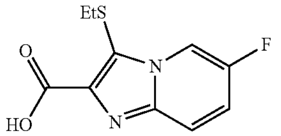

Intermediate compound 44: $^{1}$H-NMR ($CDCl_3$) δ: 8.51-8.50 (1H, m), 8.18-8.15 (1H, m), 7.39-7.33 (1H, m), 3.01 (2H, q), 1.23 (3H, t).

Reference Preparation Example 26

To a mixture of the intermediate compound 21-1 5.45 g, triethylamine 8.5 mL, and tert-butyl alcohol 50 mL was added diphenyl phosphoryladize 9.2 mL, and the mixture was stirred at 90° C. for 5 hours. The resulting mixture was concentrated, and saturated aqueous sodium bicarbonate solution was added thereto, and the mixture was extracted with ethyl acetate. The resulting organic layer was dried over anhydrous sodium sulfate, and concentrated under reduced pressure. The resulting residue was subjected to a silica gel column chromatography to obtain the intermediate compound 22-1 represented by the following formula 4.96 g.

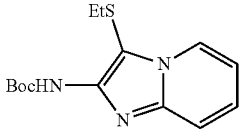

Intermediate compound 22-1: $^{1}$H-NMR ($CDCl_3$) δ: 8.34-8.32 (1H, m), 7.63-7.61 (1H, m), 7.25-7.23 (1H, m), 7.00 (1H, s), 6.92-6.88 (1H, m), 2.64 (2H, q), 1.54 (9H, s), 1.19 (3H, t).

The compounds which were prepared according to the Reference Preparation Example 26 and their physical property values were shown below.

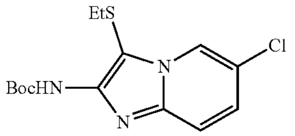

Intermediate compound 22-2: $^{1}$H-NMR ($CDCl_3$) δ: 8.34 (1H, dd), 7.56 (1H, dd), 7.20 (1H, dd), 7.02 (1H, s), 2.66 (2H, q), 1.55 (9H, s), 1.21 (3H, t).

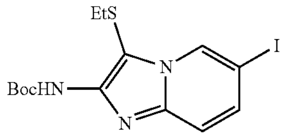

Intermediate compound 22-3: $^{1}$H-NMR ($CDCl_3$) δ: 8.54 (1H, dd), 7.44-7.39 (2H, m), 7.01 (1H, s), 2.65 (2H, q), 1.55 (9H, s), 1.20 (3H, t).

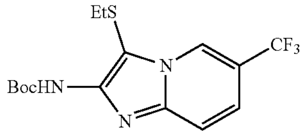

Intermediate compound 22-4: $^{1}$H-NMR ($CDCl_3$) δ: 8.67 (1H, s), 7.72 (1H, d), 7.41 (1H, d), 7.08 (1H, s), 2.69 (2H, q), 1.57 (9H, s), 1.22 (3H, t).

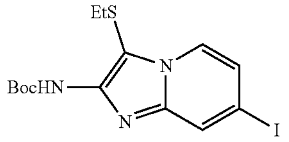

Intermediate compound 22-5: $^{1}$H-NMR ($CDCl_3$) δ: 8.07 (1H, d), 8.01 (1H, s), 7.15 (1H, d), 6.99 (1H, s), 2.64 (2H, q), 1.56 (9H, s), 1.19 (3H, t).

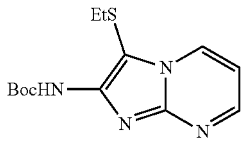

Intermediate compound 22-6: $^{1}$H-NMR ($CDCl_3$) δ: 8.50 (1H, dd), 8.15 (1H, dd), 6.89 (1H, dd), 6.30 (1H, s), 3.22 (2H, q), 1.53 (9H, s), 1.36 (3H, t).

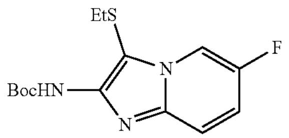

Intermediate compound 22-7: $^{1}$H-NMR ($CDCl_3$) δ: 8.26-8.25 (1H, m), 7.60-7.58 (1H, m), 7.16-7.14 (1H, m), 7.00 (1H, s), 2.65 (2H, q), 1.55 (9H, s), 1.20 (3H, t).

Reference Preparation Example 27

A mixture of the intermediate compound 22-1 4.96 g and 4 mol/L hydrogen chloride in 1,4-dioxane solution 40 mL was stirred at room temperature for 10 hours. The resulting mixture was concentrated, and water was added thereto, and the mixture was neutralized with 10 N aqueous sodium hydroxide solution. The resulting mixture was extracted with chloroform, and the resulting organic layer was dried over anhydrous sodium sulfate, and concentrated under reduced pressure to obtain the intermediate compound 23-1 represented by the following formula 3.20 g.

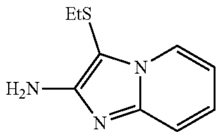

Intermediate compound 23-1: $^{1}$H-NMR ($CDCl_3$) δ: 8.25-8.23 (1H, m), 7.35-7.33 (1H, m), 7.19-7.15 (1H, m), 6.82-6.79 (1H, m), 4.30 (2H, s), 2.60 (2H, q), 1.20 (3H, t).

The compounds which were prepared according to the Reference Preparation Example 27 and their physical property values were shown below.

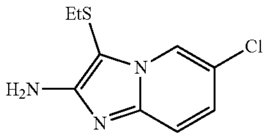

Intermediate compound 23-2: $^{1}$H-NMR (DMSO-$D_6$) δ: 8.34 (1H, dd), 7.26 (1H, dd), 7.20 (1H, dd), 5.57 (2H, s), 2.61 (2H, q), 1.09 (3H, t).

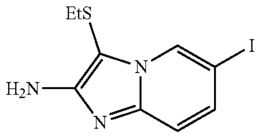

Intermediate compound 23-3: $^{1}$H-NMR ($CDCl_3$) δ: 8.43 (1H, dd), 7.34 (1H, dd), 7.13 (1H, dd), 4.31 (2H, s), 2.61 (2H, q), 1.21 (3H, t).

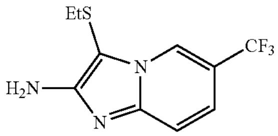

Intermediate compound 23-4: $^{1}$H-NMR ($CDCl_3$) δ: 8.56 (1H, dd), 7.41 (1H, dd), 7.32 (1H, dd), 4.43 (2H, s), 2.64 (2H, q), 1.23 (3H, t).

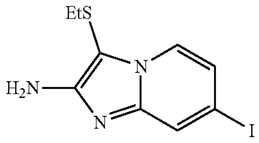

Intermediate compound 23-5: $^{1}$H-NMR ($CDCl_3$) δ: 7.97 (1H, dd), 7.71 (1H, dd), 7.05 (1H, dd), 4.32 (2H, s), 2.59 (2H, q), 1.19 (3H, t).

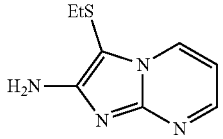

Intermediate compound 23-6: $^{1}$H-NMR (DMSO-$D_6$) δ: 8.44 (1H, dd), 8.27 (1H, dd), 6.93 (1H, dd), 5.23 (2H, s), 2.87 (2H, q), 1.18 (3H, t).

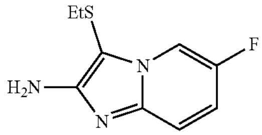

Intermediate compound 23-7: $^{1}$H-NMR ($CDCl_3$) δ: 8.17-8.17 (1H, m), 7.31-7.27 (1H, m), 7.08-7.04 (1H, m), 4.29 (2H, s), 2.61 (2H, q), 1.22 (3H, t).

Reference Preparation Example 28

A mixture of 6-bromo-3-(ethylthio)imidazo[1,2-b]pyridine-2-amine 1.00 g, which was prepared according to the method described in WO 2018/052136, trimethylboroxin 507 mg, [1,1'-bis(diphenylphosphino)ferrocene]dichloropalladium(II) dichloromethane complex 340 mg, potassium carbonate 1.52 g, and 1,4-dioxane 36 ml was stirred at 100° C. for 8 hours. The resulting mixture was stood to cool to room temperature, and water was then added thereto, and the mixture was extracted with ethyl acetate. The resulting organic layer was dried over anhydrous sodium sulfate, and concentrated under reduced pressure. The resulting residue was subjected to a silica gel column chromatography to obtain the intermediate compound 24 represented by the following formula 0.19 g.

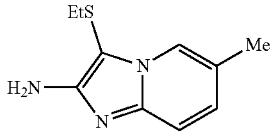

Intermediate compound 24: $^{1}$H-NMR ($CDCl_3$) δ: 8.03-8.02 (1H, m), 7.26-7.23 (1H, m), 7.02 (1H, dd), 4.22 (2H, s), 2.59 (2H, q), 2.34 (3H, s), 1.21 (3H, t).

Reference Preparation Example 29

To a mixture of 2-amino-5-bromopyrimidine 50.0 g and pyridine 280 mL was added dropwise a mixture of p-toluenesulfonyl chloride 164 g and pyridine 280 mL over 40 minutes at room temperature. The resulting mixture was stirred at 80° C. for 15 hours, and stood to cool to room temperature, and water was added thereto. The precipitated out solids were filtered. The obtained solids were washed with water and ethanol successively, and dried under reduced pressure to obtain the intermediate compound 25-1 represented by the following formula 70.6 g.

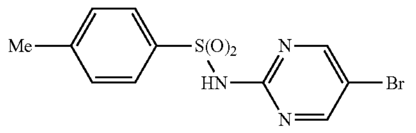

Intermediate compound 25-1: $^1$H-NMR ($CDCl_3$) δ: 9.69 (1H, s), 8.58 (2H, s), 7.99 (2H, d), 7.31 (2H, d), 2.42 (3H, s).

Reference Preparation Example 30

The intermediate compound 25-2 was obtained by using 2-amino-5-iodopyrimidine in place of 2-amino-5-bromopyrimidie according to the method described in Reference Preparation Example 29.

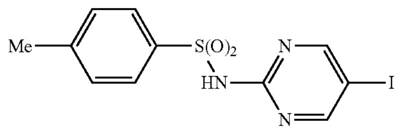

Intermediate compound 25-2: $^1$H-NMR ($CDCl_3$) δ: 9.56 (1H, s), 8.68 (2H, s), 7.99 (2H, d), 7.31 (2H, d), 2.42 (3H, s).

Reference Preparation Example 31

To a mixture of the intermediate compound 25-1 60.8 g and DMF 370 mL was added dropwise diisopropylethylamine 39 mL at room temperature, and the mixture was stirred for 50 minutes. 2-Iodoacetoamide 41.1 g was added to the resulting mixture, and the mixture was stirred at room temperature for 8.5 hours. Water was added to the resulting mixture, and the precipitated out solids were filtered. The obtained solids were washed with water and dried under reduced pressure.

The obtained solids were dissolved in chloroform 500 mL, and trifluoroacetic anhydride 500 ml was added thereto, and the mixture was stirred at 40° C. for 6 hours. The resulting mixture was concentrated under reduced pressure, and ethyl acetate and saturated aqueous sodium bicarbonate solution were added successively to the resulting residue, and the mixture was extracted with ethyl acetate. The resulting organic layer was dried over anhydrous sodium sulfate, and concentrated under reduced pressure to obtain the intermediate compound 26-1 represented by the following formula 16.4 g.

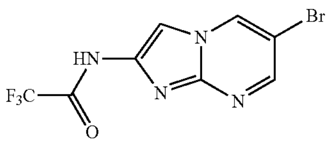 [SMILES: O=C(Nc1cn2cc(Br)cnc2n1)C(F)(F)F]

Intermediate compound 26-1: $^1$H-NMR (DMSO-$D_6$) δ: 12.76 (1H, s), 9.33 (1H, d), 8.56 (1H, d), 8.17 (1H, s).

Reference Preparation Example 32

The intermediate compound 26-2 was obtained by using the intermediate compound 25-2 in place of the intermediate compound 25-1 according to the method described in Reference Preparation Example 31.

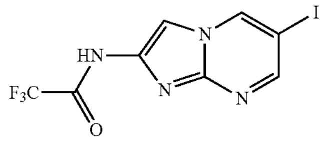 [SMILES: O=C(Nc1cn2cc(I)cnc2n1)C(F)(F)F]

Intermediate compound 26-2: $^1$H-NMR (DMSO-$D_6$) δ: 12.73 (1H, s), 9.35 (1H, d), 8.60 (1H, d), 8.13 (1H, s).

Reference Preparation Example 33

To a mixture of the intermediate compound 26-1 8.20 g and NMP 88 mL were added diethyl disulfide 6.5 ml and iodine 12.1 g successively at room temperature, and the mixture was stirred at 110° C. for 2.5 hours. The resulting mixture was stood to cool to room temperature, and ethyl acetate, water and saturated aqueous sodium thiosulfate solution were added successively thereto, and the mixture was extracted with ethyl acetate. The resulting organic layer was dried over anhydrous sodium sulfate, and concentrated under reduced pressure. The resulting residue was subjected to a silica gel column chromatography to obtain the intermediate compound 27-1 represented by the following formula 3.84 g.

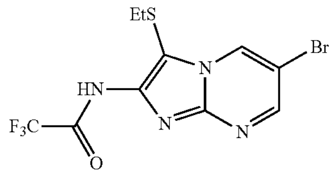

Intermediate compound 27-1: $^1$H-NMR ($CDCl_3$) δ: 8.81 (1H, d), 8.63 (1H, d), 2.82 (2H, q), 1.25 (3H, t).

Reference Preparation Example 34

The intermediate compound 27-2 was obtained by using the intermediate compound 26-2 in place of the intermediate compound 26-1 according to the method described in the Reference Preparation Example 33.

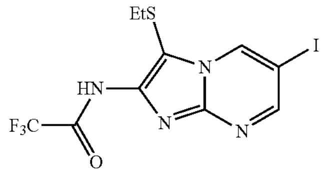

Intermediate compound 27-2: $^1$H-NMR ($CDCl_3$) δ: 8.90 (1H, d), 8.69 (1H, d), 2.84-2.81 (2H, m), 1.25 (3H, t).

Reference Preparation Example 35

A mixture of the intermediate compound 27-1 3.84 g, potassium carbonate 7.19 g, water 100 mL and methanol 200 mL was stirred at 80° C. for 1 hour. The resulting mixture was concentrated, and water was added thereto, and the precipitated out solids were filtered. The obtained solids were died under reduced pressure to obtain the intermediate compound 28-1 represented by the following formula 2.00 g.

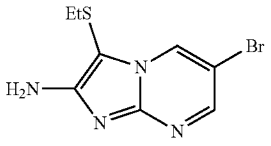

Intermediate compound 2-81: $^1$H-NMR ($CDCl_3$) δ: 8.52 (1H, d), 8.34 (1H, d), 4.60 (2H, s), 2.63 (2H, q), 1.23 (3H, t).

Reference Preparation Example 36

The intermediate compound 28-2 was obtained by using the intermediate compound 27-2 in place of the intermediate compound 27-1 according to the method described in the Reference Preparation Example 35.

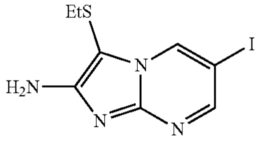

Intermediate compound 28-2: $^1$H-NMR (DMSO-$D_6$) δ: 8.75 (1H, d), 8.33 (1H, d), 6.02 (2H, s), 2.64 (2H, d), 1.09 (3H, t).

Reference Preparation Example 37

To a mixture of chloroacetic acid 9.49 g and water 15 ml was added triethylamine 16.7 ml at 0° C. over 30 minutes. 2-Amino-5-(trifluoromethyl)pyridine 16.1 g was added to the resulting mixture and the mixture was stirred under reflux for 2 hours. The resulting mixture was stood to cool to room temperature, and the precipitated out solids were filtered. The obtained solids were washed with water, and dried reduced pressure to obtain the intermediate compound 29-1 represented by the following formula 11.0 g.

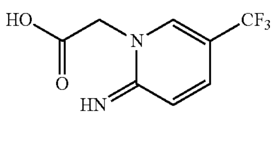 [SMILES: N=c1ccc(C(F)(F)F)cn1CC(=O)O]

Intermediate compound 29-1: LCMS: 219 $[M-H]^-$, RT=0.42 minutes

The compound which was prepared according to the Reference Preparation Example 37 and its physical property value was shown below.

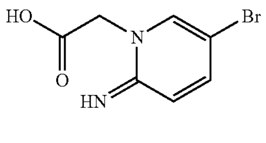 [SMILES: N=c1ccc(Br)cn1CC(=O)O]

Intermediate compound 29-2: LCMS: 229 $[M-H]^-$, RT=0.34 minutes

Reference Preparation Example 38

A mixture of the crude product of the intermediate compound 29-1 13.21 g, which was prepared according to the Reference Preparation Example 37, phosphorus oxychloride 18 mL, and toluene 150 mL was stirred under reflux for 6 hours. The resulting mixture was added dropwise to aqueous solution of sodium hydroxide, and the mixture was extracted with toluene. The resulting organic layer was dried over anhydrous sodium sulfate, and concentrated under reduced pressure to obtain the intermediate compound 30-1 represented by the following formula 13.2 g.

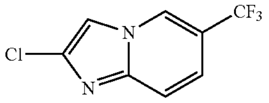 [SMILES: FC(F)(F)c1ccc2nc(Cl)cn2c1]

Intermediate compound 30-1: $^1$H-NMR ($CDCl_3$) δ: 8.44 (1H, s), 7.65 (1H, d), 7.62 (1H, s), 7.38 (1H, d).

Reference Preparation Example 39

To a mixture of the intermediate compound 30-1 15.44 g and DMF 75 mL was added N-iodosuccinimide 17.32 g under ice-cooling, and the mixture was stirred at 70° C. for 5 hours. An aqueous solution of sodium thiosulfate was added to the resulting mixture, and the precipitated out solids were collected by filtration. The obtained solids were washed with water and dried under reduced pressure to obtain the intermediate compound 31-1 represented by the following formula 18.0 g.

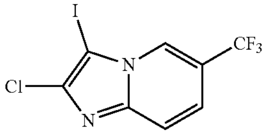 [SMILES: FC(F)(F)c1ccc2nc(Cl)c(I)n2c1]

Intermediate compound 31-1: $^1$H-NMR ($CDCl_3$) δ: 8.41 (1H, s), 7.65 (1H, d), 7.44 (1H, d).

The compound which was prepared according to the Reference Preparation Example 39 and its physical property value was shown below.

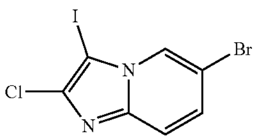 [SMILES: Clc1nc2ccc(Br)cn2c1I]

Intermediate compound 31-2: $^1$H-NMR ($CDCl_3$) δ: 8.20 (1H, s), 7.43 (1H, d), 7.35 (1H, d).

Reference Preparation Example 40

A mixture of the intermediate compound 31-1 18.0 g, 1,4-dioxane 140 mL, tris(dibenzylideneacetone)dipalladium (0) 2.38 g, Xantphos 3.01 g, diisopropylethylamine 27.2 mL and ethanethiol 3.75 mL was stirred under reflux for 3 hours. The resulting mixture was cooled to room temperature, and concentrated under reduced pressure. The residue was subjected to a silica gel column chromatography to obtain the intermediate compound 32-1 represented by the following formula 13.39 g.

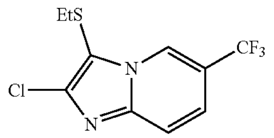

Intermediate compound 32-1: $^{1}$H-NMR ($CDCl_3$) δ: 8.74 (1H, s), 7.67 (1H, d), 7.48 (1H, d), 2.78 (2H, d), 1.24 (3H, t).

The compounds which were prepared according to the Reference Preparation Example 40 and their physical property values were shown below.

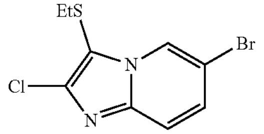

Intermediate compound 32-2: $^{1}$H-NMR ($CDCl_3$) δ: 8.51 (1H, s), 7.46 (1H, d), 7.38 (1H, d), 2.73 (2H, d), 1.23 (3H, t).

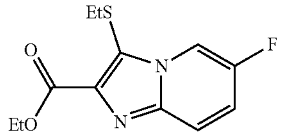

Intermediate compound 32-3: $^{1}$H-NMR ($CDCl_3$) δ: 8.49-8.48 (1H, m), 7.10 (1H, dd), 7.29-7.24 (1H, m), 4.50 (2H, q), 2.95 (2H, q), 1.47 (3H, t), 1.20 (3H, t).

Reference Preparation Example 41

To a mixture of the intermediate compound 32-2 2.66 g and chloroform 10 mL was added mCPBA (purity 70%, 30 water content) 5.16 g under ice-cooling, and the mixture was stirred at room temperature for 2 hours. Saturated aqueous solution of sodium hydrogen carbonate and aqueous solution of sodium thiosulfate were added successively to the resulting mixture, and the mixture was extracted with ethyl acetate. The resulting organic layer was dried over anhydrous sodium sulfate, and concentrated under reduced pressure. The resulting residue was subjected to a silica gel column chromatography to obtain the intermediate compound 33-1 represented by the following formula 1.79 g.

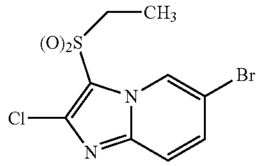

Intermediate compound 33-1: $^{1}$H-NMR ($CDCl_3$) δ: 9.15 (1H, s), 7.60 (1H, d), 7.57 (1H, d), 3.36 (2H, q), 1.36 (3H, t).

The compound which was prepared according to the Reference Preparation Example 41 and its physical property value was shown below.

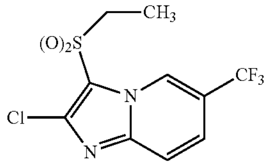

Intermediate compound 33-2: $^{1}$H-NMR ($CDCl_3$) δ: 9.39 (1H, s), 7.81 (1H, d), 7.67 (1H, d), 3.39 (2H, q), 1.37 (3H, t).

Reference Preparation Example 42

To a mixture of the intermediate compound 33-1 324 mg, trans-N,N'-dimethylcyclohexane-1,2-diamine 0.32 mL, sodium iodide 225 mg, copper(I) iodide 190 mg, and toluene 4 ml was stirred at 120° C. for 21 hours. The resulting mixture was cooled to room temperature, and then filtered. Water was added to the resulting filtrate, and the mixture was extracted with chloroform. The resulting organic layer was dried over anhydrous sodium sulfate, and concentrated under reduced pressure. The resulting residue was subjected to a silica gel column chromatography to obtain the intermediate compound 34 represented by the following formula 70 mg.

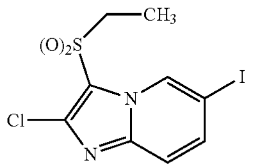

Intermediate compound 34: $^{1}$H-NMR ($CDCl_3$) δ: 9.23 (1H, s), 7.70 (1H, d), 7.46 (1H, d), 3.35 (2H, m), 1.35 (3H, t).

Reference Preparation Example 43

A mixture of the intermediate compound 33-2 936 mg, cesium fluoride 4.56 g and DMSO 10 mL was stirred at 95° C. for 2 hours. The resulting mixture was cooled to room temperature, and ethyl acetate and water were then added successively to the resulting mixture, and the mixture was filtered through Celite (Registered Trademark). The resulting filtrates were separated with a separatory funnel, and the resulting organic layer was dried over anhydrous sodium sulfate, and concentrated under reduced pressure. The resulting residue was subjected to silica gel column chromatography to obtain a crude product of the intermediate compound 35-1 represented by the following formula (containing 22% of the intermediate compound 27) 330 mg.

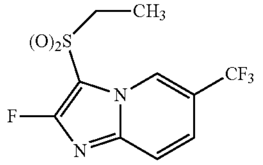

Intermediate compound 35-1: LCMS: 297 $[M+H]^-$, RT=1.76 minutes

The compounds which were prepared according to the Reference Preparation Example 43 and their physical property values were shown below.

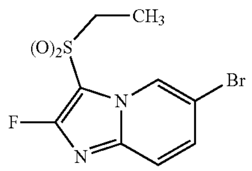

Intermediate compound 35-2: LCMS: 307 $[M+H]^-$, RT=1.64 minutes

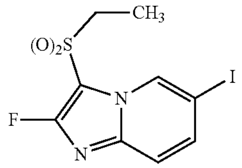

Intermediate compound 35-3: LCMS: 355 $[M+H]^-$, RT=1.72 minutes

Reference Preparation Example 44

To a mixture of 2-aminobenzaldehyde 12.1 g and DMF 100 mL was added N-iodosuccinimide 22.5 g portion wise at room temperature, and the mixture was stirred at room temperature for 4 hours. Aqueous solution of sodium bicarbonate and aqueous solution of sodium thiosulfate were added to the resulting mixture successively under ice-cooling, and the precipitated out solids were filtered. The obtained solids were washed with water, and dried under reduced pressure to obtain the intermediate compound 36-1 represented by the following formula 23.6 g.

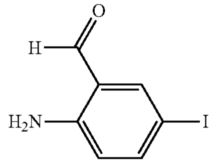

Intermediate compound 36-1: $^{1}$H-NMR ($CDCl_3$) 9.79 (1H, s), 7.75 (1H, d), 7.52 (1H, dd), 6.47 (1H, d), 6.15 (2H, s).

Reference Preparation Example 45

The intermediate compound 36-2 was obtained by using N-bromosuccinimide in place of N-iodosuccinimide according to the method described in the Reference Preparation Example 44.

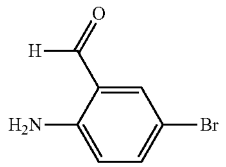

Intermediate compound 36-2: $^{1}$H-NMR ($CDCl_3$) δ: 9.80 (1H, s), 7.58 (1H, d), 7.37 (1H, dd), 6.57 (1H, d), 6.15 (2H, s).

Reference Preparation Example 46

To a mixture of 2-(ethansulfonyl)acetic acid 15.23 g, DMF 0.1 mL and chloroform 60 mL was added dropwise oxalyl chloride 12.9 mL under ice-cooling. The resulting mixture was stirred at room temperature for 1 hour, and then concentrated under reduced pressure. The resulting residue was dissolved in acetonitrile 20 mL, and the resulting mixture was added dropwise to a mixture of the intermediate compound 36-1 23.6 g and acetonitrile 100 mL under ice-cooling. The resulting mixture was stirred at room temperature for 4 hours, and concentrated under reduced pressure. The resulting residue was dissolved in acetonitrile 100 mL, and triethylamine 19.9 mL was added dropwise thereto under ice-cooling, and the mixture was stirred at room temperature for 1 hour. Water was added to the resulting mixture under ice-cooling. The precipitated out solids were filtered, and the obtained solids were washed with water. The obtained solids were washed with a solution of MTBE:ethyl acetate=1:1, and concentrated under reduced pressure to obtain the intermediate compound 37-1 represented by the following formula 13.12 g.

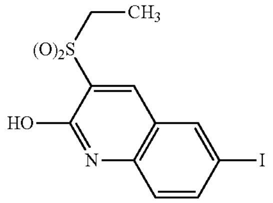

Intermediate compound 37-1: $^{1}$H-NMR (DMSO-$D_6$) δ: 8.69 (1H, s), 8.43 (1H, d), 7.97 (1H, dd), 7.20 (1H, d), 3.51 (2H, q), 1.15 (3H, t).

Reference Preparation Example 47

The intermediate compound 37-2 was obtained by using the intermediate compound 36-2 in place of the intermediate compound 36-1 according to the method described in the Reference Preparation Example 46.

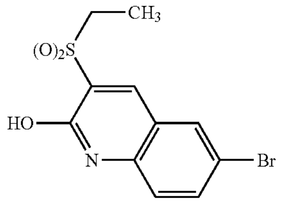

Intermediate compound 37-2: $^{1}$H-NMR (DMSO-$D_6$) δ: 8.71 (1H, s), 8.28 (1H, d), 7.84 (1H, dd), 7.34 (1H, d), 3.52 (2H, q), 1.15 (3H, t).

Reference Preparation Example 48

To a mixture of the intermediate compound 37-1 13.1 g and toluene 100 mL was added phosphorus oxychloride 16.9 mL, and the mixture was stirred at 110° C. for 11 hours. The resulting mixture was concentrated, and the obtained solids were washed with water, and then washed with a mixed solvents of MTBE:hexane=1:4, and concentrated under reduced pressure to obtain the intermediate compound 38-1 13.35 g.

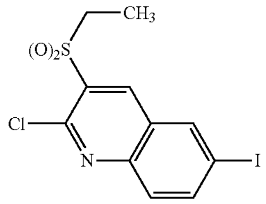

Intermediate compound 38-1: $^1$H-NMR ($CDCl_3$) δ: 8.88 (1H, s), 8.40 (1H, d), 8.17 (1H, dd), 7.83 (1H, d), 3.58 (2H, q), 1.33 (3H, t).

Reference Preparation Example 49

The intermediate compound 38-2 was obtained by using the intermediate compound 37-2 in place of the intermediate compound 37-1 according to the method described in the Reference Preparation Example 48.

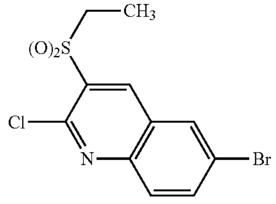

Intermediate compound 38-2: $^1$H-NMR ($CDCl_3$) δ: 8.91 (1H, s), 8.17 (1H, d), 8.01-7.98 (2H, m), 3.59 (2H, q), 1.34 (3H, t).

Reference Preparation Example 50

A mixture of the intermediate compound 38-1 5.0 g and DMSO 30 mL was added cesium fluoride 3.63 g at room temperature, and the mixture was stirred at 50° C. for 4 hours. Iced water was added to the resulting mixture, and the precipitated out solids were filtered. The obtained solids were washed with water and hexane successively, and dried under reduced pressure to obtain the intermediate compound 39-1 represented by the following formula 4.83 g.

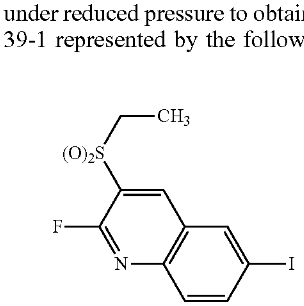

Intermediate compound 39-1: $^1$H-NMR ($CDCl_3$) δ: 8.82 (1H, s), 8.40 (1H, d), 8.15 (1H, dd), 7.76 (1H, d), 3.44 (2H, q), 1.36 (3H, t).

Reference Preparation Example 50-1

The intermediate compound 39-2 was obtained by using the intermediate compound 38-2 in place of the intermediate compound 36-1 according to the method described in the Reference Preparation Example 50.

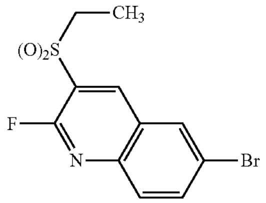

Intermediate compound 39-2: $^1$H-NMR ($CDCl_3$) δ: 8.85 (1H, s), 8.18 (1H, d), 8.00 (1H, dd), 7.91 (1H, d), 3.45 (2H, q), 1.36 (3H, t).

Reference Preparation Example 51

The intermediate compound 40-1 was obtained by using the intermediate compound 10-1 in place of 4-(trifluoroethyl)antranilic acid according to the method described in the Reference Preparation Example 2.

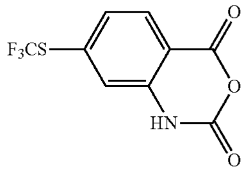

intermediate compound 40-1: $^1$H-NMR (DMSO-$D_6$) δ: 11.90 (1H, s), 8.03 (1H, d), 7.50 (1H, dd), 7.42 (1H, d).

The compounds which were prepared according to the Reference Preparation Example 51 and their physical property values were shown below.

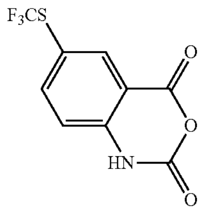

Intermediate compound 40-2: $^1$H-NMR (DMSO-$D_6$) δ: 12.06 (1H, s), 8.15 (1H, d), 8.03 (1H, dd), 7.28 (1H, d).

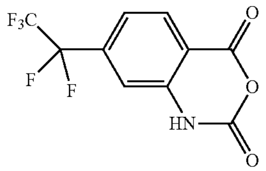 [SMILES: O=c1[nH]c2cc(C(F)(F)C(F)(F)F)ccc2c(=O)o1]

Intermediate compound 40-3: $^1$H-NMR ($DMSO-D_6$) δ: 11.96 (1H, s), 8.15 (1H, d), 7.53 (1H, d), 7.39 (1H, s).

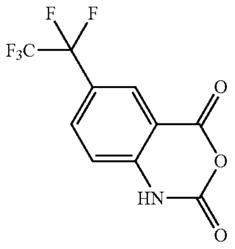 [SMILES: O=c1[nH]c2ccc(C(F)(F)C(F)(F)F)cc2c(=O)o1]

Intermediate compound 40-4: $^1$H-NMR ($DMSO-D_6$) δ: 12.14 (1H, s), 8.08 (1H, d), 8.04 (1H, dd), 7.37 (1H, d).

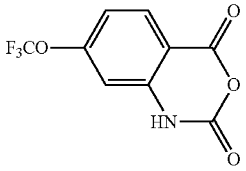 [SMILES: O=c1[nH]c2cc(OC(F)(F)F)ccc2c(=O)o1]

Intermediate compound 40-5: $^1$H-NMR ($DMSO-D_6$) δ: 11.88 (1H, s), 8.05 (1H, d), 7.21 (1H, dd), 7.04 (1H, d).

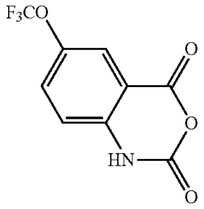

Intermediate compound 40-6: $^1$H-NMR ($DMSO-D_6$) δ: 9.92 (1H, s), 5.83 (1H, d), 5.80-5.77 (1H, m), 5.26 (1H, d).

Reference Preparation Example 52

The intermediate compound 41-1 was obtained by using the intermediate compound 23-1 in place of 6-bromo-3-(ethylthio)imidazo[1,2-a]pyridine-2-amine according to the method described in the Reference Preparation Example 3.

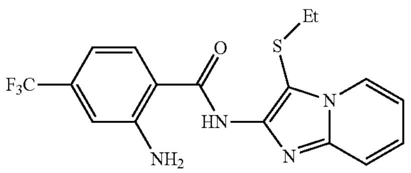 [SMILES: CCSc1c(NC(=O)c2ccc(C(F)(F)F)cc2N)nc2ccccn12]

Intermediate compound 41-1: $^1$H-NMR ($CDCl_3$) δ: 8.40-8.39 (2H, m), 7.67 (1H, s), 7.65 (1H, s), 7.34-7.29 (1H, m), 6.99-6.92 (3H, m), 5.91 (2H, s), 2.70 (2H, q), 1.22 (3H, t).

The compounds which were prepared according to the Reference Preparation Example 52 and their physical property values were shown below.

A compound represented by formula (C-1):

(C-1)

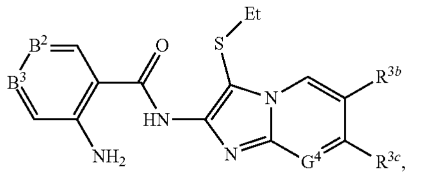

wherein a combination of $B^2$, $B^3$, $G^4$, $R^{3b}$ and $R^{3c}$ represents any combinations indicated in [Table C-1].

TABLE C-1

| Intermediate compound | $B^2$ | $B^3$ | $G^4$ | $R^{3b}$ | $R^{3c}$ |
|---|---|---|---|---|---|
| 41-2 | CH | $CCF_3$ | CH | F | H |
| 41-3 | CH | $CCF_3$ | CH | Cl | H |
| 41-4 | CH | $CCF_3$ | CH | I | H |
| 41-5 | CH | $CCF_3$ | CH | $CF_3$ | H |
| 41-6 | CH | $CCF_3$ | CH | Me | H |
| 41-7 | CH | $CCF_3$ | CH | H | I |
| 41-8 | $CCF_3$ | CH | CH | H | H |
| 41-9 | $CCF_3$ | CH | CH | Cl | H |
| 41-10 | $CCF_3$ | CH | CH | I | H |
| 41-11 | $CCF_3$ | CH | CH | $CF_3$ | H |
| 41-12 | $CCF_3$ | CH | CH | H | I |
| 41-13 | $CCF_3$ | CH | CH | H | $CF_3$ |
| 41-14 | CH | $CSCF_3$ | CH | I | H |
| 41-15 | $CSCF_3$ | CH | CH | I | H |
| 41-16 | $COCF_3$ | CH | CH | H | H |
| 41-17 | CH | $COCF_3$ | CH | I | H |
| 41-18 | $COCF_3$ | CH | CH | I | H |
| 41-19 | CH | $CC_2F_5$ | CH | I | H |
| 41-20 | $CC_2F_5$ | CH | CH | I | H |
| 41-21 | CH | $CCF_3$ | N | Br | H |
| 41-22 | $CCF_3$ | CH | N | Br | H |
| 41-23 | CH | $CCF_3$ | N | I | H |
| 41-24 | $CCF_3$ | CH | N | I | H |
| 41-25 | $COCF_3$ | CH | N | Br | H |
| 41-26 | $COCF_3$ | CH | N | I | H |
| 41-27 | $COCF_3$ | CH | N | H | H |

Intermediate compound 41-2: $^1$H-NMR ($CDCl_3$) δ: 8.34-8.31 (2H, m), 7.66-7.64 (2H, m), 7.25-7.20 (1H, m), 6.98-6.93 (2H, m), 5.92 (2H, s), 2.72 (2H, q), 1.23 (3H, t).

Intermediate compound 41-3: $^1$H-NMR ($CDCl_3$) δ: 8.41-8.40 (1H, m), 8.29 (1H, s), 7.64-7.62 (2H, m), 7.30-7.28 (1H, m), 6.96-6.92 (2H, m), 5.92 (2H, s), 2.72 (2H, q), 1.23 (3H, t).

Intermediate compound 41-4: $^1$H-NMR ($CDCl_3$) δ: 8.62-8.60 (1H, m), 8.35 (1H, s), 7.64 (1H, d), 7.50 (1H, dd), 7.47-7.44 (1H, m), 6.98-6.95 (1H, m), 6.95-6.93 (1H, m), 5.92 (2H, s), 2.72 (2H, q), 1.24 (3H, t).

Intermediate compound 41-5: $^1$H-NMR ($CDCl_3$) δ: 8.88-8.87 (1H, m), 8.52 (1H, d), 8.22 (1H, s), 8.09 (1H, s), 7.83 (1H, d), 7.79 (1H, dd), 7.59 (1H, dd), 2.80 (2H, q), 1.20 (3H, t).

Intermediate compound 41-6: $^1$H-NMR ($DMSO-D_E$) δ: 10.31 (1H, s), 8.39-8.38 (1H, m), 7.89 (1H, d), 7.52-7.51 (1H, m), 7.27 (1H, dd), 7.11-7.10 (1H, m), 6.85 (1H, dd), 6.75 (2H, s), 2.72 (2H, q), 2.38 (3H, s), 1.07 (3H, t).

Intermediate compound 41-7: $^1$H-NMR ($CDCl_3$) δ: 8.60 (1H, s), 8.18 (1H, dd), 8.07-8.06 (1H, m), 7.86-7.84 (1H, m), 7.50 (1H, dd), 7.25-7.23 (1H, m), 6.78 (1H, d), 6.14 (2H, s), 2.74 (2H, q), 1.25 (3H, t).

Intermediate compound 41-8: $^1$H-NMR ($CDCl_3$) δ: 8.41-8.40 (1H, m), 8.31 (1H, s), 7.82-7.79 (1H, m), 7.67 (1H, d), 7.48 (1H, dd), 7.34-7.30 (1H, m), 6.98-6.96 (1H, m), 6.77 (1H, d), 6.12 (2H, s), 2.72 (2H, q), 1.26 (3H, t).

Intermediate compound 41-9: $^1$H-NMR ($CDCl_3$) δ: 8.43-8.41 (1H, m), 8.28 (1H, s), 7.80-7.77 (1H, m), 7.61 (1H, d), 7.49 (1H, dd), 7.30-7.27 (1H, m), 6.77 (1H, d), 6.12 (2H, s), 2.73 (2H, q), 1.26 (3H, t).

Intermediate compound 41-10: $^1$H-NMR ($CDCl_3$) δ: 8.64-8.61 (1H, m), 8.46-8.43 (1H, m), 7.81 (1H, s), 7.50-7.48 (3H, m), 6.77 (1H, d), 6.13 (2H, s), 2.74 (2H, q), 1.26 (3H, t).

Intermediate compound 41-11: $^1$H-NMR ($CDCl_3$) δ: 8.74 (1H, s), 8.46 (1H, s), 7.80 (1H, s), 7.76 (1H, d), 7.50-7.45 (2H, m), 6.77 (1H, d), 6.14 (2H, s), 2.76 (2H, q), 1.26 (3H, t).

Intermediate compound 41-12: $^1$H-NMR ($CDCl_3$) δ: 8.39 (1H, s), 8.14-8.12 (1H, m), 8.06-8.05 (1H, m), 7.65 (1H, d), 7.21 (1H, dd), 6.95-6.93 (2H, m), 5.91 (2H, s), 2.70 (2H, q), 1.21 (3H, t).

Intermediate compound 41-13: $^1$H-NMR ($CDCl_3$) δ: 8.50 (1H, d), 8.48 (1H, s), 7.95 (1H, s), 7.82-7.79 (1H, m), 7.48 (1H, dd), 7.14 (1H, dd), 6.76 (1H, d), 6.13 (2H, s), 2.75 (2H, q), 1.25 (3H, t).

Intermediate compound 41-14: $^1$H-NMR ($CDCl_3$) δ: 8.61-8.60 (1H, m), 8.42 (1H, s), 7.56 (1H, d), 7.50-7.44 (2H, m), 7.00 (1H, s), 6.95 (1H, d), 5.87 (2H, s), 2.72 (2H, q), 1.23 (3H, t).

Intermediate compound 41-15: $^1$H-NMR ($CDCl_3$) δ: 8.60 (1H, s), 8.37 (1H, s), 7.80 (1H, s), 7.47-7.42 (3H, m), 6.71 (1H, d), 6.09 (2H, s), 2.72 (2H, q), 1.25 (3H, t).

Intermediate compound 41-16: $^1$H-NMR ($CDCl_3$) δ: 8.41-8.39 (1H, m), 8.27 (1H, s), 7.67 (1H, d), 7.42-7.41 (1H, m), 7.34-7.29 (1H, m), 7.18-7.15 (1H, m), 6.98-6.94 (1H, m), 6.72 (1H, d), 5.77 (2H, s), 2.71 (2H, q), 1.23 (3H, t).

Intermediate compound 41-17: $^1$H-NMR ($CDCl_3$) δ: 8.61-8.60 (1H, m), 8.28 (1H, s), 7.56 (1H, d), 7.50-7.44 (2H, m), 6.57-6.54 (2H, m), 5.96 (2H, s), 2.71 (2H, q), 1.23 (3H, t).

Intermediate compound 41-18: $^1$H-NMR ($CDCl_3$) δ: 8.62-8.61 (1H, m), 8.30 (1H, s), 7.49-7.45 (2H, m), 7.40-7.39 (1H, m), 7.19-7.16 (1H, m), 6.72 (1H, d), 5.78 (2H, s), 2.72 (2H, q), 1.24 (3H, t).

Intermediate compound 41-19: $^1$H-NMR ($CDCl_3$) δ: 8.61-8.60 (1H, m), 8.32 (1H, s), 7.64 (1H, d), 7.50-7.45 (2H, m), 6.94-6.91 (2H, m), 5.92 (2H, s), 2.72 (2H, q), 1.24 (3H, t).

Intermediate compound 41-20: $^1$H-NMR ($CDCl_3$) δ: 8.62 (1H, s), 8.27 (1H, s), 7.73 (1H, s), 7.51-7.45 (3H, m), 6.79 (1H, d), 6.14 (2H, s), 2.72 (2H, q), 1.25 (3H, t).

Intermediate compound 41-21: $^1$H-NMR ($CDCl_3$) δ: 8.90 (1H, s), 8.80 (1H, d), 8.59 (1H, d), 7.79 (1H, d), 6.96-6.90 (2H, m), 5.90 (2H, s), 2.80 (2H, q), 1.23 (3H, t).

Intermediate compound 41-22: $^1$H-NMR ($CDCl_3$) δ: 8.80 (1H, d), 8.58 (1H, d), 8.51 (1H, s), 7.84 (1H, s), 7.49 (1H, d), 6.77 (1H, d), 6.10 (2H, s), 2.80 (2H, q), 1.26 (3H, t).

Intermediate compound 41-23: $^1$H-NMR ($CDCl_3$) δ: 8.93 (1H, s), 8.88 (1H, d), 8.66 (1H, d), 7.82 (1H, d), 6.95 (1H, s), 6.91 (1H, d), 5.90 (2H, s), 2.79 (2H, q), 1.27 (3H, t).

Intermediate compound 41-24: $^1$H-NMR ($CDCl_3$) δ: 8.89 (1H, d), 8.66 (1H, d), 8.45 (1H, s), 7.83 (1H, s), 7.49 (1H, d), 6.77 (1H, d), 6.10 (2H, s), 2.79 (2H, q), 1.26 (3H, t).

Intermediate compound 41-25: $^1$H-NMR ($CDCl_3$) δ: 8.79 (1H, d), 8.65 (1H, s), 8.57 (1H, d), 7.51 (1H, s), 7.17 (1H, d), 6.71 (1H, d), 5.77 (2H, s), 2.79 (2H, q), 1.25 (3H, t).

Intermediate compound 41-26: $^1$H-NMR ($CDCl_3$) δ: 8.88 (1H, d), 8.68 (1H, s), 8.65 (1H, d), 7.51 (1H, s), 7.17 (1H, d), 6.71 (1H, d), 5.78 (2H, s), 2.79 (2H, q), 1.26 (3H, t).

Intermediate compound 41-27: $^1$H-NMR ($CDCl_3$) δ: 8.54 (1H, dd), 8.12 (1H, dd), 7.78 (1H, s), 7.49 (1H, s), 7.31-7.21 (1H, m), 6.91 (1H, dd), 6.76 (1H, d), 5.72 (2H, s), 3.25 (2H, q), 1.38 (3H, t).

Reference Preparation Example 53

The intermediate compound 42 was obtained by using ethyl 6-fluoroimidazo[1,2-a]pyridine-2-carboxylate in place of the intermediate compound 5 according to the method described in the Reference Preparation Example 6.

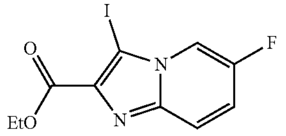 [SMILES: CCOC(=O)c1nc2ccc(F)cn2c1I]

Intermediate compound 42: $^1$H-NMR ($CDCl_3$) δ: 8.24-8.23 (1H, m), 7.71-7.68 (1H, m), 7.28-7.25 (1H, m), 4.50 (2H, q), 1.48 (3H, t).

Reference Preparation Example 54

A mixture of the intermediate compound 35-2 1.00 g, hydrazine monohydrate 0.48 mL and ethanol 5 mL was stirred at 80° C. for 15 minutes. The resulting mixture was stood to cool to room temperature, and water was added thereto, and the resulting solids were filtered, and washed with water, and dried under reduced pressure to obtain the intermediate compound 43 represented by the following formula 0.73 g.

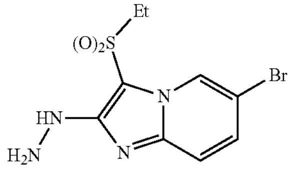

Intermediate compound 43: $^1$H-NMR ($CDCl_3$) δ: 8.69 (1H, dd), 7.46 (1H, dd), 7.36 (1H, dd), 6.74 (1H, s), 3.98 (2H, s), 3.19 (2H, q), 1.32 (3H, t).

Preparation Example 1

To a mixture of the intermediate 1 0.50 g, 3-(ethanesulfonyl)-2-fluoropyridine 0.49 g and NMP 5 mL was added sodium hydride (60%, dispersion in mineral oil) 103 mg under nitrogen atmosphere, and the mixture was stirred at 110° C. for 1 hour. The resulting mixture was stood to cool to room temperature, and water was added thereto, and the mixture was filtered. The obtained solids were washed with water, and dried under reduced pressure to obtain the present compound 1-1 represented by the following formula 0.54 g.

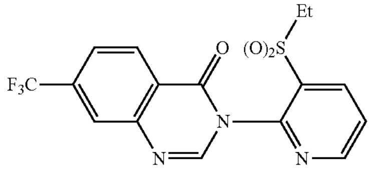

Present compound 1-1: $^1$H-NMR ($CDCl_3$) δ: 8.94-8.93 (1H, m), 8.54-8.52 (1H, m), 8.45 (1H, d), 8.13 (1H, s), 8.11 (1H, s), 7.80-7.77 (2H, m), 3.36-3.34 (2H, m), 1.34 (3H, t).

Preparation Example 2

The present compound 1-2 was obtained by using 5-cyclopropyl-3-(ethanesulfonyl)-2-fluoropyridine in place of 3-(ethanesulfonyl)-2-fluoropyridine according to the Preparation Example 1.

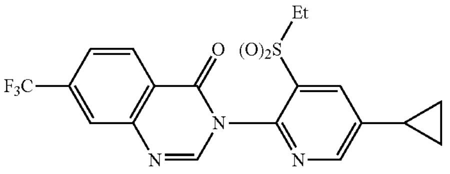

Present compound 1-2: $^1$H-NMR ($CDCl_3$) δ: 8.65 (1H, d), 8.44 (1H, d), 8.09 (1H, d), 8.08 (1H, s), 8.05 (1H, d), 7.76 (1H, dd), 3.30-3.28 (2H, m), 2.14-2.09 (1H, m), 1.31 (3H, t), 1.29-1.24 (2H, m), 0.98-0.92 (2H, m).

Preparation Example 3

A mixture of the intermediate compound 3-1 491 mg and triethyl orthoformate 11 mL was stirred at 100° C. for 1 hour. The resulting mixture was stood to cool to room temperature and concentrated. The obtained solids were washed with hexane to obtain the present compound 2-1 represented by the following formula 447 mg.

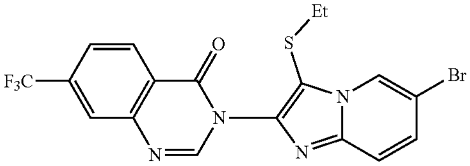 [SMILES: CCSc1c(-n2cnc3cc(C(F)(F)F)ccc3c2=O)nc2ccc(Br)cn12]

Present compound 2-1: $^1$H-NMR ($CDCl_3$) δ: 8.65 (1H, dd), 8.51 (1H, d), 8.20 (1H, s), 8.08 (1H, d), 7.77 (1H, dd), 7.61 (1H, dd), 7.50 (1H, dd), 2.77 (2H, q), 1.18 (3H, t).

Preparation Example 4

The compounds which were prepared according to the Preparation Example 3 and their physical property values were shown below.

A compound represented by formula (A-1):

(A-1)

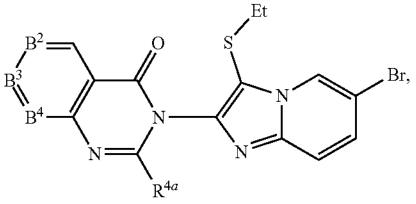

wherein a combination of $R^{4a}$, $B^2$, $B^3$ and $B^4$ represents any combinations indicated in [Table A-1].

TABLE A-1

| Present compound | $R^{4a}$ | $B^2$ | $B^3$ | $B^4$ |
|---|---|---|---|---|
| 2-2 | H | $CCF_3$ | CH | CH |
| 2-3 | H | CH | CH | $CCF_3$ |
| 2-4 | H | CH | $CCF_3$ | N |
| 2-5 | H | CH | CCl | CH |
| 2-6 | H | CH | CI | CH |
| 2-7 | H | $COCF_3$ | CH | CH |

Present compound 2-2: $^1$H-NMR ($CDCl_3$) δ: 8.69-8.67 (1H, m), 8.65-8.64 (1H, m), 8.22 (1H, s), 8.03 (1H, dd), 7.92-7.90 (1H, m), 7.61 (1H, dd), 7.52-7.49 (1H, m), 2.78 (2H, q), 1.19 (3H, t).

Present compound 2-3: $^1$H-NMR ($CDCl_3$) δ: 8.64 (1H, d), 8.60 (1H, d), 8.25 (1H, s), 8.15 (1H, d), 7.63 (1H, t), 7.61 (1H, d), 7.50 (1H, dd), 2.77 (2H, q), 1.19 (3H, t).

Present compound 2-4: $^1$H-NMR ($CDCl_3$) δ: 8.93 (1H, d), 8.66 (1H, d), 8.46 (1H, s), 7.89 (1H, d), 7.63 (1H, d), 7.53 (1H, dd), 2.77 (2H, q), 1.19 (3H, t).

Present compound 2-5: $^1$H-NMR ($CDCl_3$) δ: 8.65-8.63 (1H, m), 8.32 (1H, d), 8.14 (1H, s), 7.79 (1H, d), 7.60 (1H, dd), 7.52 (1H, dd), 7.49 (1H, dd), 2.76 (2H, q), 1.18 (3H, t,).

Present compound 2-6: $^1$H-NMR ($CDCl_3$) δ: 8.64 (1H, dd), 8.21 (1H, d), 8.11 (1H, s), 8.06 (1H, d), 7.88 (1H, dd), 7.60 (1H, dd), 7.49 (1H, dd), 2.75 (2H, q), 1.17 (3H, t).

Present compound 2-7: $^1$H-NMR ($CDCl_3$) δ: 8.67-8.64 (1H, m), 8.23-8.20 (1H, m), 8.16 (1H, s), 7.87-7.85 (1H, m), 7.67-7.59 (2H, m), 7.51-7.49 (1H, m), 2.77 (2H, q,), 1.19 (3H, t).

A compound represented by formula (A-1-2):

(A-1-2)

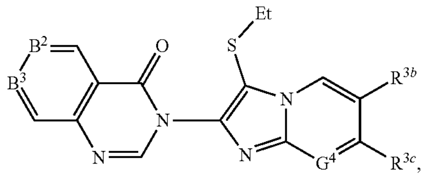

wherein a combination of $B^2$, $B^3$, $G^4$, $R^{3b}$ and $R^{3c}$ represents any combinations indicated in [Table A-1-2].

TABLE A-1-2

| Present compound | $B^2$ | $B^3$ | $G^4$ | $R^{3b}$ | $R^{3c}$ |
|---|---|---|---|---|---|
| 2-8 | CH | $CCF_3$ | CH | H | H |
| 2-9 | CH | $CCF_3$ | CH | F | H |
| 2-10 | CH | $CCF_3$ | CH | Cl | H |
| 2-11 | CH | $CCF_3$ | CH | I | H |
| 2-12 | CH | $CCF_3$ | CH | $CF_3$ | H |
| 2-13 | CH | $CCF_3$ | CH | Me | H |
| 2-14 | CH | $CCF_3$ | CH | H | I |
| 2-16 | $CCF_3$ | CH | CH | H | H |
| 2-17 | $CCF_3$ | CH | CH | Cl | H |
| 2-18 | $CCF_3$ | CH | CH | I | H |
| 2-19 | $CCF_3$ | CH | CH | $CF_3$ | H |
| 2-20 | $CCF_3$ | CH | CH | H | I |
| 2-21 | $CCF_3$ | CH | CH | H | $CF_3$ |
| 2-22 | CH | $CSCF_3$ | CH | I | H |
| 2-23 | $CSCF_3$ | CH | CH | I | H |
| 2-24 | $COCF_3$ | CH | CH | H | H |
| 2-25 | CH | $COCF_3$ | CH | I | H |
| 2-26 | $COCF_3$ | CH | CH | I | H |
| 2-27 | CH | $CC_2F_5$ | CH | I | H |
| 2-28 | $CC_2F_5$ | CH | CH | I | H |

TABLE A-1-2-continued

| Present compound | $B^2$ | $B^3$ | $G^4$ | $R^{3b}$ | $R^{3c}$ |
|---|---|---|---|---|---|
| 2-29 | CH | $CCF_3$ | N | Br | H |
| 2-30 | $CCF_3$ | CH | N | Br | H |
| 2-31 | CH | $CCF_3$ | N | I | H |
| 2-32 | $CCF_3$ | CH | N | I | H |
| 2-33 | $COCF_3$ | CH | N | Br | H |
| 2-34 | $COCF_3$ | CH | N | I | H |
| 2-37 | $COCF_3$ | CH | N | H | H |

Present compound 2-8: $^1$H-NMR ($CDCl_3$) δ: 8.53-8.52 (2H, m), 8.23 (1H, s), 8.08 (1H, s), 7.77 (1H, dd), 7.73-7.70 (1H, m), 7.45-7.43 (1H, m), 7.10-7.09 (1H, m), 2.75 (2H, q,) 1.17 (3H, t,).

Present compound 2-9: $^1$H NMR ($CDCl_3$) δ: 8.51 (1H, d), 8.46-8.45 (1H, m), 8.21 (1H, s), 8.08-8.08 (1H, m), 7.77 (1H, dd), 7.72-7.68 (1H, m), 7.39-7.34 (1H, m), 2.76 (2H, q), 1.18 (3H, t).

Present compound 2-10: $^1$H NMR ($CDCl_3$) δ: 8.56-8.53 (1H, m), 8.51 (1H, d), 8.20 (1H, s), 8.08 (1H, s), 7.79-7.77 (1H, m), 7.68-7.65 (1H, m), 7.41 (1H, dd), 2.77 (2H, q), 1.18 (3H, t).

Present compound 2-11: $^1$H-NMR ($CDCl_3$) δ: 8.75-8.74 (1H, m), 8.51 (1H, d), 8.20 (1H, s), 8.08 (1H, s), 7.77 (1H, dd), 7.61 (1H, dd), 7.50 (1H, dd), 2.76 (2H, q), 1.18 (3H, dd).

Present compound 2-12: $^1$H-NMR ($CDCl_3$) δ: 8.89-8.87 (1H, m), 8.51 (1H, d), 8.21 (1H, s), 8.10-8.08 (1H, m), 7.83 (1H, d), 7.79 (1H, dd), 7.59 (1H, dd), 2.80 (2H, q), 1.20 (3H, t).

Present compound 2-13: $^1$H-NMR ($CDCl_3$) δ: 8.51 (1H, d), 8.30-8.28 (1H, m), 8.21 (1H, s), 8.07 (1H, s), 7.76 (1H, dd), 7.61 (1H, d), 7.28 (1H, dd), 2.73 (2H, q), 2.45 (3H, s), 1.17 (3H, t).

Present compound 2-14: $^1$H-NMR ($CDCl_3$) δ: 8.51 (1H, d), 8.26 (1H, dd), 8.20 (1H, s), 8.12-8.11 (1H, m), 8.08 (1H, s), 7.77 (1H, dd), 7.33 (1H, dd), 2.74 (2H, q), 1.17 (3H, t).

Present compound 2-16: $^1$H-NMR ($CDCl_3$) δ: 8.69-8.68 (1H, m), 8.54-8.52 (1H, m), 8.25 (1H, s), 8.03 (1H, dd), 7.91 (1H, d), 7.71 (1H, d), 7.45-7.43 (1H, m), 7.10-7.09 (1H, m), 2.76 (2H, q), 1.18 (3H, t).

Present compound 2-17: $^1$H-NMR ($CDCl_3$) δ: 8.69-8.67 (1H, m), 8.56-8.55 (1H, m), 8.22 (1H, s), 8.03 (1H, dd), 7.92-7.90 (1H, m), 7.66 (1H, dd), 7.41 (1H, dd), 2.78 (2H, q), 1.19 (3H, t).

Present compound 2-18: $^1$H-NMR ($CDCl_3$) δ: 8.76-8.74 (1H, m), 8.69-8.67 (1H, m), 8.22 (1H, s), 8.03 (1H, dd), 7.91 (1H, d), 7.62 (1H, dd), 7.50 (1H, d), 2.77 (2H, q), 1.19 (3H, t).

Present compound 2-19: $^1$H-NMR ($CDCl_3$) δ: 8.89-8.87 (1H, m), 8.69-8.68 (1H, m), 8.24 (1H, s), 8.04 (1H, dd), 7.93 (1H, d), 7.83 (1H, d), 7.59 (1H, dd), 2.81 (2H, q), 1.21 (3H, t).

Present compound 2-20: $^1$H-NMR ($CDCl_3$) δ: 8.69-8.66 (1H, m), 8.27-8.25 (1H, m), 8.22 (1H, s), 8.13-8.12 (1H, m), 8.03 (1H, dd), 7.92-7.90 (1H, m), 7.33 (1H, dd), 2.76 (2H, q), 1.18 (3H, t).

Present compound 2-21: $^1$H-NMR ($CDCl_3$) δ: 8.69-8.68 (1H, m), 8.65 (1H, d), 8.24 (1H, s), 8.05-8.04 (2H, m), 7.93 (1H, d), 7.28-7.26 (1H, m), 2.81 (2H, q), 1.20 (3H, t).

Present compound 2-22: $^1$H-NMR ($CDCl_3$) δ: 8.76-8.74 (1H, m), 8.41 (1H, d), 8.17 (1H, s), 8.09 (1H, d), 7.77 (1H, dd), 7.61 (1H, dd), 7.49 (1H, dd), 2.76 (2H, q), 1.19 (3H, t).

Present compound 2-23: $^1$H-NMR ($CDCl_3$) δ: 8.76-8.74 (1H, m), 8.68 (1H, d), 8.20 (1H, s), 8.05 (1H, dd), 7.84 (1H, d), 7.61 (1H, dd), 7.49 (1H, dd), 2.78 (2H, q), 1.19 (3H, t).

Present compound 2-24: $^1$H-NMR ($CDCl_3$) δ: 8.54-8.52 (1H, m), 8.23-8.21 (1H, m), 8.18 (1H, s), 7.85 (1H, d), 7.72-7.70 (1H, m), 7.66 (1H, dd), 7.46-7.41 (1H, m), 7.10-7.08 (1H, m), 2.76 (2H, q), 1.18 (3H, t).

Present compound 2-25: $^1$H-NMR ($CDCl_3$) δ: 8.76-8.74 (1H, m), 8.43 (1H, d), 8.16 (1H, s), 7.62-7.59 (2H, m), 7.49 (1H, dd), 7.39-7.37 (1H, m), 2.76 (2H, q), 1.18 (3H, t).

Present compound 2-26: $^1$H-NMR ($CDCl_3$) δ: 8.76-8.74 (1H, m), 8.22-8.20 (1H, m), 8.14 (1H, s), 7.85 (1H, d), 7.66 (1H, dd), 7.61 (1H, dd), 7.49 (1H, d), 2.77 (2H, q), 1.19 (3H, t).

Present compound 2-27: $^1$H-NMR ($CDCl_3$) δ: 8.76-8.74 (1H, m), 8.52 (1H, d), 8.20 (1H, s), 8.08-8.07 (1H, m), 7.76-7.74 (1H, m), 7.61 (1H, dd), 7.50 (1H, dd), 2.76 (2H, q), 1.18 (3H, t).

Present compound 2-28: $^1$H-NMR ($CDCl_3$) δ: 8.77-8.75 (1H, m), 8.66-8.65 (1H, m), 8.23 (1H, s), 8.00 (1H, dd), 7.92 (1H, d), 7.61 (1H, dd), 7.50 (1H, d), 2.78 (2H, q), 1.19 (3H, t).

Present compound 2-29: $^1$H-NMR ($CDCl_3$) δ: 8.90 (1H, d), 8.73 (1H, d), 8.51 (1H, d), 8.28 (1H, s), 8.10-8.07 (1H, m), 7.79 (1H, dd), 2.82 (2H, q), 1.21 (3H, t).

Present compound 2-30: $^1$H-NMR ($CDCl_3$) δ: 8.91 (1H, d), 8.73 (1H, d), 8.70-8.69 (1H, m), 8.31 (1H, s), 8.04 (1H, dd), 7.92 (1H, d), 2.84 (2H, q), 1.22 (3H, t).

Present compound 2-31: $^1$H-NMR ($CDCl_3$) δ: 9.00 (1H, d), 8.81 (1H, d), 8.51 (1H, d,), 8.28 (1H, s), 8.10-8.07 (1H, m), 7.78 (1H, dd), 2.81 (2H, q), 1.20 (3H, t).

Present compound 2-32: $^1$H-NMR ($CDCl_3$) δ: 9.00 (1H, d), 8.81 (1H, d), 8.69-8.68 (1H, m), 8.31 (1H, s), 8.04 (1H, dd), 7.92 (1H, d), 2.83 (2H, q), 1.21 (3H, t).

Present compound 2-33: $^1$H-NMR ($CDCl_3$) δ: 8.90 (1H, d), 8.73 (1H, d), 8.23 (1H, s), 8.22-8.21 (1H, m), 7.86 (1H, d), 7.68-7.65 (1H, m), 2.83 (2H, q), 1.22 (3H, t).

Present compound 2-34: $^1$H-NMR ($CDCl_3$) δ: 9.00 (1H, d), 8.80 (1H, d), 8.23 (1H, s), 8.22-8.21 (1H, m), 7.86 (1H, d), 7.67-7.66 (1H, m), 2.83 (2H, q), 1.21 (3H, t).

Present compound 2-37: $^1$H-NMR ($CDCl_3$) δ: 8.65 (1H, dd), 8.19 (1H, d), 8.08 (1H, s), 7.97 (1H, dd), 7.91 (1H, d), 7.72 (1H, dd), 6.98 (1H, dd), 3.30 (2H, q), 1.38 (3H, t).

Preparation Example 4-1

To a mixture of 7-(trifluoromethyl)-3-(ethylthio)-imidazo [1,2-a]pyridine-2-amine 310 mg which was prepared according to the method described in WO 2016/129684, and THF 2 mL was added dropwise a solution of potassium bis(trimethylsilyl)amide (1 mol/L THF solution) 2.2 mL at −78° C. under nitrogen atmosphere, and the mixture was stirred for 30 minutes. The intermediate compound 2 350 mg was added to the resulting mixture, and the mixture was stirred at room temperature for 30 minutes. Saturated aqueous ammonium chloride solution was added to the resulting mixture, and the mixture was extracted with ethyl acetate. The resulting organic layer was dried over anhydrous sodium sulfate, and dried reduced pressure. Triethyl orthoformate 13 mL was added to the resulting residue, and the mixture was stirred at 100° C. for 1 hour. The resulting mixture was stood to cool to room temperature, and concentrated. The obtained solids were washed with hexane to obtain the present compound 2-15 represented by the following formula 525 mg.

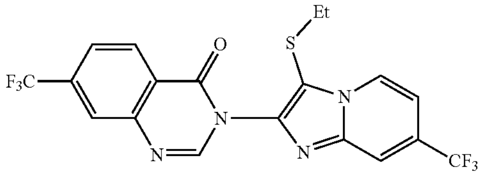 [SMILES: CCSc1c(-n2cnc3cc(C(F)(F)F)ccc3c2=O)nc2cc(C(F)(F)F)ccn12]

Present compound 2-15: $^1$H-NMR ($CDCl_3$) δ: 8.65 (1H, d), 8.51 (1H, d), 8.22 (1H, s), 8.09 (1H, s), 8.03-8.02 (1H, m), 7.79 (1H, dd), 7.27 (1H, dd), 2.79 (2H, q), 1.19 (3H, t,).

The compounds which were prepared according to the Preparation Example 4-1 and their physical property values were shown below.

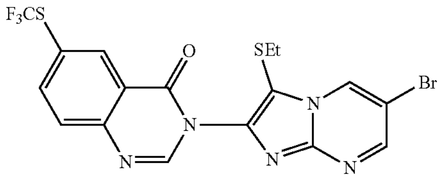

Present compound 2-35: $^1$H-NMR ($CDCl_3$) δ: 8.90 (1H, d), 8.73 (1H, d), 8.69 (1H, d), 8.29 (1H, s), 8.06 (1H, dd), 7.85 (1H, d), 2.84 (2H, q), 1.22 (3H, t).

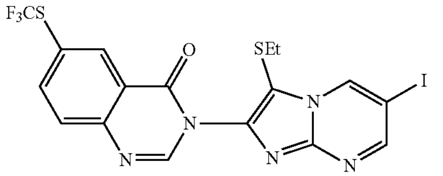

Present compound 2-36: $^1$H-NMR ($CDCl_3$) δ: 9.00 (1H, d), 8.80 (1H, d), 8.69 (1H, d), 8.28 (1H, s), 8.06 (1H, dd), 7.85 (1H, d), 2.83 (2H, q), 1.23 (3H, d).

Preparation Example 5

To a mixture of the present compound 2-1 252 mg and chloroform 11 mL was added mCPBA (purity 70%, 30% water content) 296 mg under ice-cooling, and the mixture was stirred under ice-cooling for 8 hours. Saturated aqueous solution of sodium hydrogen carbonate and an aqueous solution of sodium thiosulfate were added to the resulting mixture successively, and the mixture was extracted with chloroform. The resulting organic layer was dried over anhydrous sodium sulfate, and concentrated under reduced pressure. The resulting residue was subjected to a silica gel column chromatography (hexane:ethyl acetate=1:2) to obtain the present compound 3-1 178 mg.

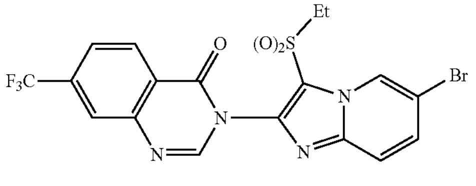

Present compound 3-1: $^1$H-NMR ($CDCl_3$) δ: 9.06 (1H, dd), 8.47 (1H, d), 8.26 (1H, s), 8.09 (1H, d), 7.78 (1H, dd), 7.73 (1H, dd), 7.68 (1H, dd), 3.56 (2H, q), 1.46 (3H, t).

Preparation Example 6

The compounds which were prepared according to the Preparation Example 5 and their physical property values were shown below.

A compound represented by formula (A-2):

(A-2)

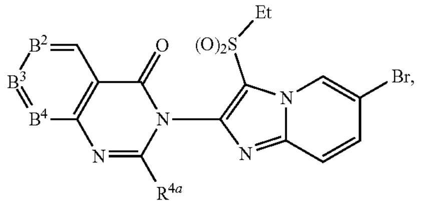

wherein the combination of $R^{4a}$, $B^2$, $B^3$ and $B^4$ represents any combinations indicated in [Table A-2].

TABLE A-2

| Present compound | $R^{4a}$ | $B^2$ | $B^3$ | $B^4$ |
|---|---|---|---|---|
| 3-2 | H | $CCF_3$ | CH | CH |
| 3-3 | H | CH | CH | $CCF_3$ |
| 3-4 | H | CH | $CCF_3$ | N |
| 3-5 | H | CH | CHl | CH |
| 3-6 | H | CH | CI | CH |
| 3-7 | H | $COCF_3$ | CH | CH |

Present compound 3-2: $^1$H-NMR ($CDCl_3$) δ: 9.06-9.05 (1H, m), 8.64-8.63 (1H, m), 8.28 (1H, s), 8.04 (1H, dd), 7.93-7.91 (1H, m), 7.73 (1H, dd), 7.69 (1H, dd), 3.59 (2H, q), 1.47 (3H, t).

Present compound 3-3: $^1$H-NMR ($CDCl_3$) δ: 9.06 (1H, dd), 8.55 (1H, dd), 8.31 (1H, s), 8.16 (1H, dd), 7.73 (1H, dd), 7.68 (1H, dd), 7.64 (1H, t), 3.58 (2H, q), 1.46 (3H, t).

Present compound 3-4: $^1$H-NMR ($CDCl_3$) δ: 9.04 (1H, dd), 8.88 (1H, d), 8.52 (1H, s), 7.88 (1H, d), 7.74 (1H, dd), 7.70 (1H, dd), 3.56 (2H, q), 1.47 (3H, t).

Present compound 3-5: $^1$H-NMR ($CDCl_3$) δ: 9.05 (1H, dd), 8.27 (1H, d), 8.19 (1H, s), 7.80 (1H, d), 7.72 (1H, dd), 7.67 (1H, dd), 7.52 (1H, dd), 3.56 (2H, q), 1.45 (3H, t).

Present compound 3-6: $^1$H-NMR ($CDCl_3$) δ: 9.05 (1H, dd), 8.22 (1H, d), 8.17 (1H, s), 8.01 (1H, d), 7.88 (1H, dd), 7.72 (1H, dd), 7.67 (1H, dd), 3.56 (2H, q), 1.44 (3H, t).

Present compound 3-7: $^1$H-NMR ($CDCl_3$) δ: 9.07-9.05 (1H, m), 8.20 (1H, s), 8.17-8.1b (1H, m), 7.86 (1H, d), 7.72 (1H, dd), 7.68-7.66 (2H, m), 3.58 (2H, q), 1.46 (3H, t).

A compound represented by formula (A-2-2):

(A-2-2)

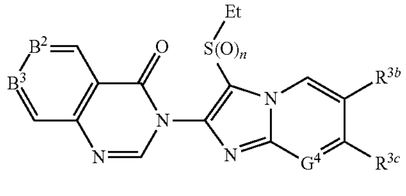

wherein the combination of n, $B^2$, $B^3$, $G^4$, $R^{3b}$ and $R^{3c}$ represents any combinations indicated in [Table A-2-2].

TABLE A-2-2

| Present compound | n | $B^2$ | $B^3$ | $G^4$ | $R^{3b}$ | $R^{3c}$ |
|---|---|---|---|---|---|---|
| 3-8 | 2 | CH | $CCF_3$ | CH | H | H |
| 3-9 | 2 | CH | $CCF_3$ | CH | F | H |
| 3-10 | 2 | CH | $CCF_3$ | CH | Cl | H |
| 3-11 | 1 | CH | $CCF_3$ | CH | I | H |
| 3-12 | 2 | CH | $CCF_3$ | CH | I | H |
| 3-13 | 2 | CH | $CCF_3$ | CH | $CF_3$ | H |
| 3-14 | 2 | CH | $CCF_3$ | CH | Me | H |
| 3-15 | 2 | CH | $CCF_3$ | CH | H | I |
| 3-16 | 2 | CH | $CCF_3$ | CH | H | $CF_3$ |
| 3-17 | 2 | $CCF_3$ | CH | CH | H | H |
| 3-18 | 2 | $CCF_3$ | CH | CH | Cl | H |
| 3-19 | 1 | $CCF_3$ | CH | CH | I | H |
| 3-20 | 2 | $CCF_3$ | CH | CH | I | H |
| 3-21 | 2 | $CCF_3$ | CH | CH | $CF_3$ | H |
| 3-22 | 2 | $CCF_3$ | CH | CH | H | I |
| 3-23 | 2 | $CCF_3$ | CH | CH | H | $CF_3$ |
| 3-24 | 2 | CH | $CSCF_3$ | CH | I | H |
| 3-25 | 2 | $CSCF_3$ | CH | CH | I | H |
| 3-26 | 2 | $COCF_3$ | CH | CH | H | H |
| 3-27 | 2 | CH | $COCF_3$ | CH | I | H |
| 3-28 | 2 | $COCF_3$ | CH | CH | I | H |
| 3-29 | 2 | CH | $CC_2F_5$ | CH | I | H |
| 3-30 | 2 | $CC_2F_5$ | CH | CH | I | H |
| 3-31 | 2 | CH | $CCF_3$ | N | Br | H |
| 3-32 | 2 | $CCF_3$ | CH | N | Br | H |
| 3-33 | 2 | CH | $CCF_3$ | N | I | H |
| 3-34 | 2 | $CCF_3$ | CH | N | I | H |
| 3-35 | 2 | $COCF_3$ | CH | N | Br | H |
| 3-36 | 2 | $COCF_3$ | CH | N | I | H |
| 3-37 | 2 | $CSCF_3$ | CH | N | Br | H |
| 3-38 | 2 | $CSCF_3$ | CH | N | I | H |
| 3-39 | 2 | $COCF_3$ | CH | N | H | H |

Present compound 3-8: $^1$H-NMR ($CDCl_3$) δ: 8.93 (1H, d), 8.47 (1H, d), 8.28 (1H, s), 8.08 (1H, s), 7.85-7.83 (1H, m), 7.77 (1H, dd), 7.64-7.61 (1H, m), 7.24-7.22 (1H, m), 3.57-3.52 (2H, m), 1.44 (3H, t).

Present compound 3-9: $^1$H-NMR ($CDCl_3$) δ: 8.91-8.90 (1H, m), 8.47 (1H, d), 8.26 (1H, s), 8.09 (1H, s), 7.83 (1H, dd), 7.79-7.77 (1H, m), 7.56-7.51 (1H, m), 3.56 (2H, q), 1.45 (3H, t).

Present compound 3-10: $^1$H-NMR ($CDCl_3$) δ: 8.97 (1H, dd), 8.47 (1H, d), 8.26 (1H, s), 8.09-8.08 (1H, m), 7.80-7.77 (2H, m), 7.59 (1H, dd), 3.56 (2H, q), 1.46 (3H, t).

Present compound 3-11: $^1$H-NMR ($CDCl_3$) δ: 9.28 (1H, dd), 8.58 (1H, s), 8.45 (1H, d), 8.09 (1H, s), 7.78 (1H, dd), 7.69 (1H, dd), 7.55 (1H, dd), 3.71-3.61 (2H, m), 1.60 (3H, t).

Present compound 3-12: $^1$H-NMR ($CDCl_3$) δ: 9.14-9.13 (1H, m), 8.46 (1H, d), 8.25 (1H, s), 8.10-8.07 (1H, m), 7.80-7.77 (2H, m), 7.61 (1H, dd), 3.56 (2H, q), 1.45 (3H, t).

Present compound 3-13: $^1$H-NMR ($CDCl_3$) δ: 9.30-9.27 (1H, m), 8.47 (1H, d), 8.28 (1H, s), 8.10 (1H, s), 7.96 (1H, d), 7.80-7.75 (2H, m), 3.61 (2H, q), 1.47 (3H, t).

Present compound 3-14: $^1$H-NMR ($CDCl_3$) δ: 8.69-8.67 (1H, m), 8.47 (1H, d), 8.26 (1H, s), 8.08 (1H, s), 7.77 (1H, dd), 7.72 (1H, d), 7.46 (1H, dd), 3.52 (2H, q), 2.48 (3H, s), 1.44 (3H, t).

Present compound 3-15: $^1$H-NMR ($CDCl_3$) δ: 8.65 (1H, dd), 8.47-8.45 (1H, m), 8.26-8.24 (2H, m), 8.09-8.07 (1H, m), 7.78 (1H, dd), 7.46 (1H, dd), 3.58-3.53 (2H, m), 1.43 (3H, t).

Present compound 3-16: $^1$H-NMR ($CDCl_3$) δ: 9.07 (1H, d), 8.47 (1H, d), 8.28 (1H, s), 8.16-8.13 (1H, m), 8.10 (1H, s), 7.79 (1H, dd), 7.39 (1H, dd), 3.63-3.59 (2H, m), 1.47 (3H, t).

Present compound 3-17: $^1$H-NMR ($CDCl_3$) δ: 8.95-8.93 (1H, m), 8.65-8.64 (1H, m), 8.31 (1H, s), 8.04 (1H, dd), 7.93 (1H, d), 7.86-7.83 (1H, m), 7.64-7.62 (1H, m), 7.24-7.23 (1H, m), 3.60-3.56 (2H, m), 1.46 (3H, t).

Present compound 3-18: $^1$H-NMR ($CDCl_3$) δ: 8.97 (1H, dd), 8.64 (1H, d), 8.28 (1H, s), 8.04 (1H, dd), 7.92 (1H, d), 7.78 (1H, dd), 7.59 (1H, dd), 3.59 (2H, q), 1.47 (3H, t).

Present compound 3-19: $^1$H-NMR ($CDCl_3$) δ: 9.28 (1H, dd), 8.62 (1H, d), 8.60 (1H, s), 8.05 (1H, dd), 7.93 (1H, d), 7.69 (1H, dd), 7.55 (1H, dd), 3.72-3.63 (2H, m), 1.62 (3H, t).

Present compound 3-20: $^1$H-NMR ($CDCl_3$) δ: 9.14 (1H, dd), 8.63 (1H, d), 8.28 (1H, s), 8.04 (1H, dd), 7.92 (1H, d), 7.80 (1H, dd), 7.61 (1H, dd), 3.58 (2H, q), 1.47 (3H, t).

Present compound 3-21: $^1$H-NMR ($CDCl_3$) δ: 9.29-9.27 (1H, m), 8.66-8.63 (1H, m), 8.30 (1H, s), 8.05 (1H, dd), 7.98-7.92 (2H, m), 7.77 (1H, dd), 3.64 (2H, q), 1.49 (3H, t).

Present compound 3-22: $^1$H-NMR ($CDCl_3$) δ: 8.65 (1H, dd), 8.64-8.62 (1H, m), 8.27 (1H, s), 8.26-8.25 (1H, m), 8.04 (1H, dd), 7.92 (1H, d), 7.46 (1H, dd), 3.58-3.56 (2H, m), 1.45 (3H, t).

Present compound 3-23: $^1$H-NMR ($CDCl_3$) δ: 9.08-9.06 (1H, m), 8.65-8.63 (1H, m), 8.30 (1H, s), 8.15-8.13 (1H, m), 8.05 (1H, dd), 7.93 (1H, d), 7.39 (1H, dd), 3.64-3.60 (2H, m), 1.48 (3H, t).

Present compound 3-24: $^1$H-NMR ($CDCl_3$) δ: 9.14 (1H, dd), 8.37 (1H, d), 8.23 (1H, s), 8.10 (1H, d), 7.80-7.76 (2H, m), 7.60 (1H, dd), 3.56 (2H, q), 1.45 (3H, t).

Present compound 3-25: $^1$H-NMR ($CDCl_3$) δ: 9.15-9.14 (1H, m), 8.63 (1H, d), 8.25 (1H, s), 8.05 (1H, dd), 7.84 (1H, d), 7.79 (1H, dd), 7.60 (1H, dd), 3.57 (2H, q), 1.46 (3H, t).

Present compound 3-26: $^1$H-NMR ($CDCl_3$) δ: 8.94-8.93 (1H, m), 8.23 (1H, s), 8.18-8.17 (1H, m), 7.86 (1H, d), 7.84-7.82 (1H, m), 7.66 (1H, dd), 7.64-7.59 (1H, m), 7.23-7.21 (1H, m), 3.59-3.55 (2H, m), 1.45 (3H, t).

Present compound 3-27: $^1$H-NMR ($CDCl_3$) δ: 9.15-9.13 (1H, m), 8.38 (1H, d), 8.21 (1H, s), 7.79 (1H, dd), 7.64-7.62 (1H, m), 7.60 (1H, dd), 7.38 (1H, dd), 3.56 (2H, q), 1.45 (3H, t).

Present compound 3-28: $^1$H-NMR ($CDCl_3$) δ: 9.14 (1H, dd), 8.20 (1H, s), 8.17-8.15 (1H, m), 7.85 (1H, d), 7.79 (1H, dd), 7.67-7.65 (1H, m), 7.60 (1H, dd), 3.57 (2H, q), 1.46 (3H, t).

Present compound 3-29: $^1$H-NMR ($CDCl_3$) δ: 9.15-9.13 (1H, m), 8.47 (1H, d), 8.26 (1H, d), 8.07 (1H, s), 7.81-7.78 (1H, m), 7.76-7.74 (1H, m), 7.61 (1H, d), 3.56 (2H, q), 1.47-1.44 (3H, m).

Present compound 3-30: $^1$H-NMR ($CDCl_3$) δ: 9.14 (1H, dd), 8.61 (1H, d), 8.28 (1H, s), 8.01 (1H, dd), 7.93 (1H, d), 7.80 (1H, dd), 7.61 (1H, dd), 3.58 (2H, q), 1.47 (3H, t).

Present compound 3-31: $^1$H-NMR ($CDCl_3$) δ: 9.33 (1H, d), 8.88 (1H, d), 8.47 (1H, d), 8.35 (1H, s), 8.10-8.09 (1H, m), 7.79 (1H, dd), 3.67 (2H, q), 1.49 (3H, t).

Present compound 3-32: $^1$H-NMR ($CDCl_3$) δ: 9.33 (1H, d), 8.88 (1H, d), 8.65-8.63 (1H, m), 8.37 (1H, s), 8.05 (1H, dd), 7.93 (1H, d), 3.69 (2H, q), 1.51 (3H, t).

Present compound 3-33: $^1$H-NMR ($CDCl_3$) δ: 9.41 (1H, d), 8.95 (1H, d), 8.47 (1H, d), 8.35 (1H, s), 8.10-8.08 (1H, m), 7.79 (1H, dd), 3.67 (2H, q), 1.49 (3H, t).

Present compound 3-34: $^1$H-NMR ($CDCl_3$) δ: 9.41 (1H, d), 8.95 (1H, d), 8.64-8.63 (1H, m), 8.37 (1H, s), 8.05 (1H, dd), 7.93 (1H, d), 3.69 (2H, q), 1.50 (3H, t).

Present compound 3-35: $^1$H-NMR ($CDCl_3$) δ: 9.33 (1H, d), 8.87 (1H, d), 8.30 (1H, s), 8.17-8.16 (1H, m), 7.87 (1H, d), 7.69-7.67 (1H, m), 3.69 (2H, q), 1.50 (3H, t).

Present compound 3-36: $^1$H-NMR ($CDCl_3$) δ: 9.41 (1H, d), 8.95 (1H, d), 8.29 (1H, s), 8.17-8.16 (1H, m), 7.86 (1H, d), 7.68-7.67 (1H, m), 3.68 (2H, q), 1.49 (3H, t).

Present compound 3-37: $^1$H-NMR ($CDCl_3$) δ: 9.33 (1H, d), 8.88 (1H, d), 8.64 (1H, d), 8.35 (1H, s), 8.07 (1H, dd), 7.86 (1H, d), 3.69 (2H, q), 1.50 (3H, t).

Present compound 3-38: $^1$H-NMR ($CDCl_3$) δ: 9.41 (1H, d), 8.95 (1H, d), 8.64 (1H, d), 8.35 (1H, s), 8.06 (1H, dd), 7.85 (1H, d), 3.68 (2H, q), 1.50 (3H, t).

Present compound 3-39: $^1$H-NMR ($CDCl_3$) δ: 8.91 (1H, dd), 8.18 (1H, s), 8.16-8.12 (2H, m), 7.92 (1H, d), 7.73 (1H, d), 7.18 (1H, dd), 3.60-3.39 (2H, m), 1.33 (3H, t).

Preparation Example 7

A mixture of the intermediate compound 6 318 mg, 1,4-dioxane 12 mL, tris(dibenzylideneacetone)dipalladium (0) 55 mg, and Xantphos 69 mg, diisopropylethylamine 0.31 mL, and ethanethiol 0.043 ml was stirred at 50° C. for 2 hours. The resulting mixture was stood to cool to room temperature, and ethanethiol 0.021 mL was added thereto, and the mixture was stirred at 50° C. for 2 hours. The resulting mixture was stood to cool to room temperature, and ethanethiol 0.021 mL was added thereto, and the mixture was stirred at 50° C. for 1.5 hours, and the resulting mixture was then stood to cool to room temperature, and water was added thereto, and the mixture was extracted with ethyl acetate. The resulting organic layer was dried over anhydrous sodium sulfate, and concentrated under reduced pressure. The resulting residue was subjected to a silica gel column chromatography (hexane:ethyl acetate: 1:1) to obtain the present compound 2-1 191 mg.

Preparation Example 8

To a mixture of the intermediate compound 3-1 300 mg and acetonitrile 4.4 mL were added sodium sulfite 135 mg and iodine 166 mg, and the mixture was stirred at room temperature for 4 hours. Water was added to the resulting mixture, and the mixture was extracted with ethyl acetate. The resulting organic layer was dried over anhydrous sodium sulfate, and concentrated under reduced pressure. The resulting residue was subjected to a silica gel column chromatography (hexane:ethyl acetate=1:1) to obtain the present compound 4-1 represented by the following formula 174 mg.

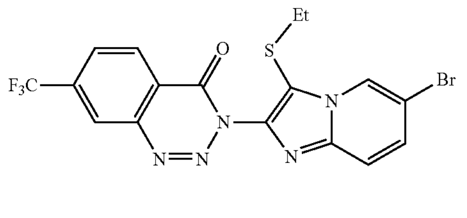 [SMILES: CCSc1c(-n2nnc3cc(C(F)(F)F)ccc3c2=O)nc2ccc(Br)cn12]

Present compound 4-1: $^1$H-NMR ($CDCl_3$) δ: 8.67 (1H, dd), 8.60 (1H, d), 8.56-8.53 (1H, m), 8.09 (1H, dd), 7.64 (1H, dd), 7.50 (1H, dd), 2.78 (2H, q), 1.20 (3H, t).

Preparation Example 9

The present compound 4-2 represented by the following formula was obtained by using the intermediate compound 3-2 in place of the intermediate compound 3-1 according to the method described in the Preparation Example 8.

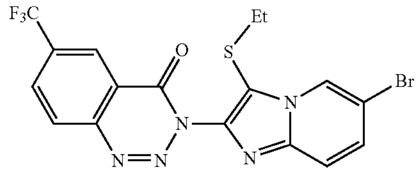 [SMILES: CCSc1c(-n2nnc3ccc(C(F)(F)F)cc3c2=O)nc2ccc(Br)cn12]

Present compound 4-2: $^1$H-NMR ($CDCl_3$) δ: 8.75-8.74 (1H, m), 8.67 (1H, d), 8.41 (1H, d), 8.24 (1H, dd), 7.65 (1H, d), 7.50 (1H, dd), 2.78 (2H, q), 1.20 (3H, t).

Preparation Example 10

The present compound represented by the following formula 5-1 was obtained by using the present compound 4-1 in place of the present compound 2-1 according to the method described in the Preparation Example 5.

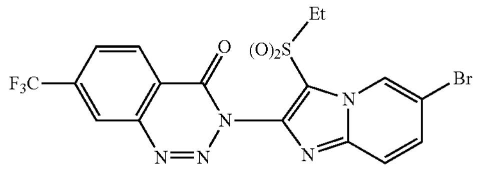

Present compound 5-1: $^1$H-NMR ($CDCl_3$) δ: 9.07 (1H, dd), 8.58 (1H, d), 8.56-8.53 (1H, m), 8.09 (1H, dd), 7.78 (1H, dd), 7.69 (1H, dd), 3.48 (2H, q), 1.44 (3H, t).

Preparation Example 11

The present compound 5-2 represented by the following formula was obtained by using the present compound 4-2 in place of the present compound 2-1 according to the method described in the Preparation Example 5.

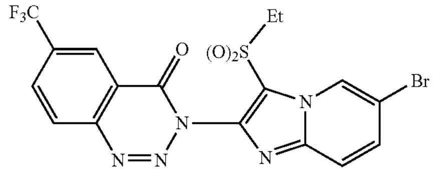

Present compound 5-2: $^1$H-NMR ($CDCl_3$) δ: 9.07-9.06 (1H, m), 8.72-8.71 (1H, m), 8.41 (1H, d), 8.25 (1H, dd), 7.78 (1H, dd), 7.69 (1H, dd), 3.49 (2H, q), 1.45 (3H, t).

Preparation Example 12

The present compound 6-1 represented by the following formula was obtained by using 6-(trifluoromethyl)isoquinoline-1(2H)-one in place of the intermediate compound 1 and using the intermediate compound 35-2 in place of 3-(ethanesulfonyl)-2-fluoropyridine.

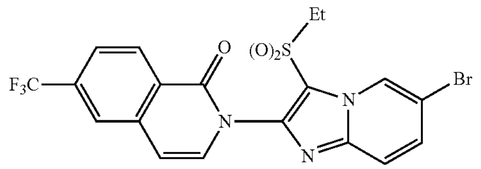

Present compound 6-1: $^1$H-NMR ($CDCl_3$) δ: 9.07 (1H, dd), 8.55 (1H, d), 7.87-7.84 (1H, m), 7.73 (1H, dd), 7.69 (1H, dd), 7.64 (1H, dd), 7.37 (1H, d), 6.69 (1H, d), 3.63 (2H, q), 1.46 (3H, t).

Preparation Example 13

The compounds which were prepared according to the Preparation Example 12 and their physical property values were shown below.

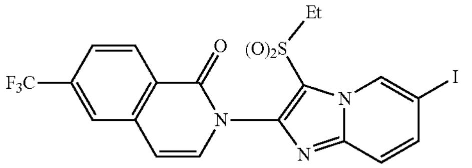

Present compound 6-2: $^1$H-NMR ($CDCl_3$) δ: 9.15 (1H, dd), 8.55 (1H, d), 7.87-7.84 (1H, m), 7.76-7.73 (2H, m), 7.57 (1H, dd), 7.36 (1H, d), 6.69 (1H, d), 3.62 (2H, q), 1.46 (3H, t).

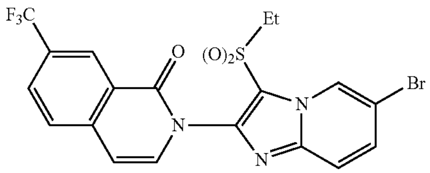

Present compound 6-3: $^1$H-NMR ($CDCl_3$) δ: 9.06 (1H, dd), 8.73-8.70 (1H, m), 7.90 (1H, dd), 7.71-7.67 (2H, m), 7.64 (1H, dd), 7.39 (1H, d), 6.68 (1H, d), 3.68-3.62 (2H, m), 1.48 (3H, t).

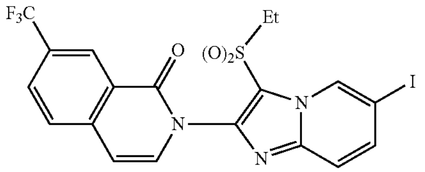

Present compound 6-4: $^1$H-NMR ($CDCl_3$) δ: 9.16-9.15 (1H, m), 8.72-8.70 (1H, m), 7.91-7.89 (1H, m), 7.75 (1H, dd), 7.69 (1H, d), 7.58-7.55 (1H, m), 7.39 (1H, d), 6.68 (1H, d), 3.68-3.61 (2H, q), 1.47 (3H, t).

Preparation Example 14

The present compound 6-5 represented by the following formula was obtained by using the intermediate compound 38-2 in place of 3-(ethanesulfonyl)-2-fluoropyridine.

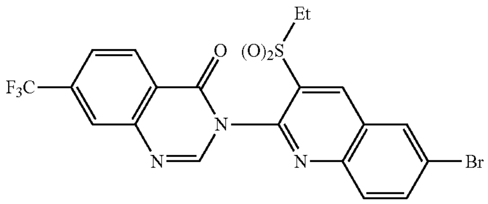

Present compound 6-5: $^1$H-NMR ($CDCl_3$) δ: 8.97 (1H, s), 8.46 (1H, d), 8.31-8.30 (1H, m), 8.20 (1H, s), 8.14-8.13 (1H, m), 8.10-8.09 (2H, m), 7.79 (1H, dd), 3.48-3.34 (2H, m), 1.37 (3H, t).

Preparation Example 15

The present compound 6-6 represented by the following formula was obtained by using the intermediate compound 38-1 in place of 3-(ethanesulfonyl)-2-fluoropyridine.

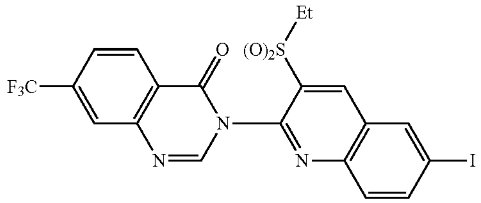

Present compound 6-6: $^1$H-NMR ($CDCl_3$) δ: 8.94 (1H, s), 8.54 (1H, d), 8.46 (1H, d), 8.25 (1H, dd), 8.19 (1H, s), 8.14-8.12 (1H, m), 7.94 (1H, d), 7.79 (1H, dd), 3.47-3.33 (2H, m), 1.36 (3H, t).

Preparation Example 16

A mixture of the present compound 3-1 0.18 g, cyclopropyl boronic acid 92 mg, [1,1'-bix(diphenylphosphino)ferrocene]dichloropalladium (II) dichloromethane adduct 52 mg, tripotassium phosphate 377 mg, toluene 2.5 mL, and water 0.7 mL was stirred at 100° C. for 6 hours. The resulting mixture was stood to cool to room temperature, and water was added thereto, and the mixture was extracted with ethyl acetate. The resulting organic layer was dried over anhydrous sodium sulfate, and concentrated under reduced pressure. The resulting residue was subjected to a silica gel column chromatography (ethyl acetate:hexane: 2:1) to obtain the present compound 7-1 represented by the following formula 90 mg.

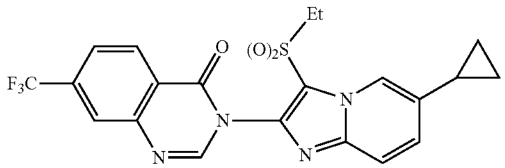

Present compound 7-1: $^1$H-NMR ($CDCl_3$) δ: 8.69 (1H, dd), 8.46 (1H, d), 8.25 (1H, s), 8.09-8.06 (1H, m), 7.76 (1H, dd), 7.71 (1H, dd), 7.29 (1H, dd), 3.52 (2H, q), 2.07-1.99 (1H, m), 1.44 (3H, t), 1.13-1.10 (2H, m), 0.82-0.77 (2H, m).

Preparation Example 17

The compounds which were prepared according to the Preparation Example 16 and their physical property values were shown below.

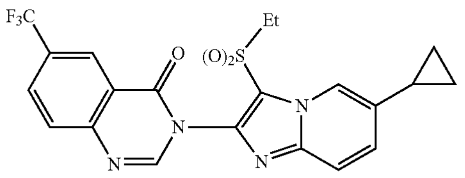

Present compound 7-2: $^1$H-NMR ($CDCl_3$) δ: 8.70-8.69 (1H, m), 8.64-8.62 (1H, m), 8.27 (1H, s), 8.02 (1H, dd), 7.91 (1H, d), 7.71 (1H, dd), 7.29 (1H, dd), 3.57-3.52 (2H, m), 2.05-2.03 (1H, m), 1.45 (3H, t), 1.14-1.09 (2H, m), 0.81-0.78 (2H, m).

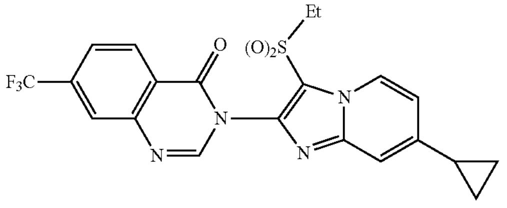

Present compound 7-3: $^1$H-NMR ($CDCl_3$) δ: 8.75 (1H, dd), 8.46 (1H, d), 8.26 (1H, s), 8.09-8.06 (1H, m), 7.76 (1H, dd), 7.46-7.43 (1H, m), 6.88 (1H, dd), 3.54-3.47 (2H, m), 2.07-2.03 (1H, m), 1.41 (3H, t), 1.24-1.19 (2H, m), 0.91-0.87 (2H, m).

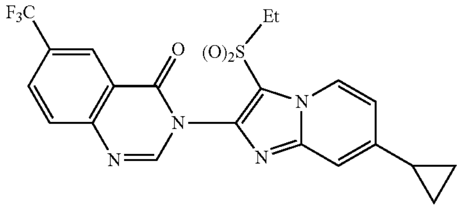

Present compound 7-4: $^1$H-NMR ($CDCl_3$) δ: 8.75 (1H, d), 8.65-8.62 (1H, m), 8.28 (1H, s), 8.02 (1H, dd), 7.91 (1H, d), 7.46-7.44 (1H, m), 6.89 (1H, dd), 3.58-3.48 (2H, m), 2.07-2.02 (1H, m), 1.43 (3H, t), 1.22-1.19 (2H, m), 0.90-0.88 (2H, m).

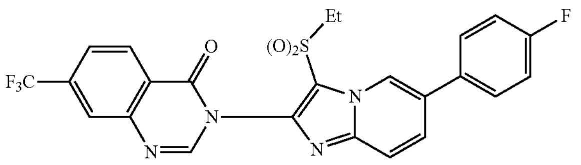

Present compound 7-5: $^1$H-NMR ($CDCl_3$) δ: 9.02 (1H, s), 8.48 (1H, d), 8.29 (1H, s), 8.09 (1H, s), 7.89 (1H, d), 7.81-7.77 (2H, m), 7.60-7.56 (2H, m), 7.25-7.21 (2H, m), 3.57 (2H, q), 1.46 (3H, t).

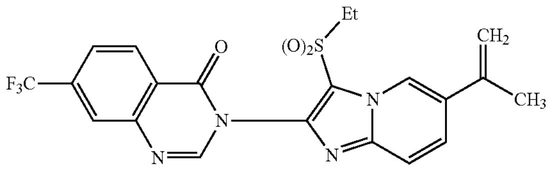

Present compound 7-6: $^1$H-NMR ($CDCl_3$) δ: 8.90 (1H, s), 8.47 (1H, d), 8.27 (1H, s), 8.08 (1H, s), 7.81-7.74 (3H, m), 5.55 (1H, s), 5.34 (1H, s), 3.58-3.52 (2H, m), 2.23 (3H, s), 1.45 (3H, t).

Reference Preparation Example 55

A mixture of the present compound 3-1 2.0 g, bis(pinacolato)diboron 1.1 g, [1,1'-bis(diphenylphosphino)ferrocene]dichloropalladium(II) dichloromethane adduct 0.086 g, potassium acetate 1.17 g, and toluene 20 mL was stirred at 120° C. for 8 hours. The resulting mixture was stood to cool to room temperature, and water was added thereto, and the mixture was extracted with chloroform. The resulting organic layer was dried over anhydrous magnesium sulfate, and dried under reduced pressure to obtain the intermediate compound 47 represented by the following formula 1.9 g.

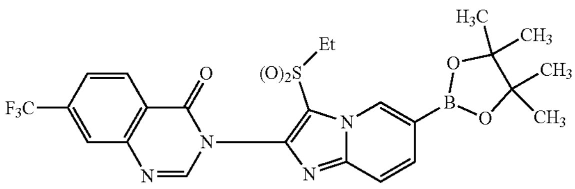

Intermediate compound 47: $^1$H-NMR ($CDCl_3$) δ: 9.17 (1H, s), 8.47 (1H, d), 8.28 (1H, s), 8.08 (1H, s), 7.89 (1H, dd), 7.80-7.75 (2H, m), 3.55 (2H, q), 1.45 (3H, t), 1.38 (12H, s).

Preparation Example 19

A mixture of the intermediate compound 47 300 mg, 2-bromopyridine 130 m,[1,1'-bis(diphenylphosphino)ferrocene]dichloropalladium(II) dichloromethane adduct 8.0 mg, tripotassium phosphate 350 mg, dimethoxyethane 3.0 mL, and water 0.3 mL was stirred at 80° C. for 4 hours. The resulting mixture was stood to cool to room temperature, and water was then added thereto, and the mixture was extracted with ethyl acetate. The resulting organic layer was dried over anhydrous sodium sulfate, and concentrated under reduced pressure. The resulting residue was subjected to a silica gel column chromatography (ethyl acetate:hexane: 4:1) to obtain the present compound 8-1 represented by the following formula 190 mg.

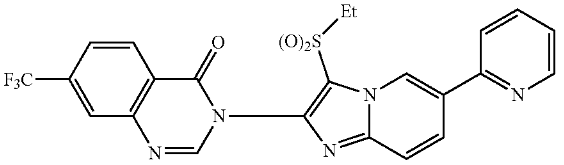

Present compound 8-1: $^{1}$H-NMR ($CDCl_3$) δ: 9.55 (1H, s), 8.77 (1H, d), 8.48 (1H, d), 8.31-8.27 (2H, m), 8.09 (1H, s), 7.93-7.84 (2H, m), 7.82-7.76 (2H, m), 7.40-7.35 (1H, m), 3.60 (2H, q), 1.48 (3H, t).

Preparation Example 20

The present compound 8-2 represented by the following formula was obtained by using 2-bromopyrimidine in place of 2-bromopyridine.

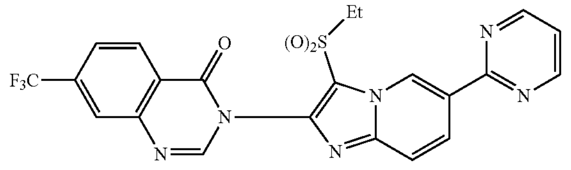

Present compound 8-2: $^{1}$H-NMR ($CDCl_3$) δ: 10.02 (1H, s), 8.87 (2H, d), 8.69 (1H, dd), 8.48 (1H, d), 8.32 (1H, s), 8.10 (1H, s), 7.90 (1H, dd), 7.78 (1H, dd), 7.33 (1H, t), 3.62 (2H, q), 1.50 (3H, t).

Preparation Example 21

To a mixture of the intermediate compound 47 1.1 g, sodium acetate 1.2 g, THF 4 ml and water 2 mL was added 30% hydrogen peroxide aqueous solution 1.1 mL, and the mixture was stirred at 0° C. for 4 hours. Saturated aqueous solution of sodium thiosulfate 20 mL was added to the resulting mixture, and the mixture was stirred for 1 hour. Saturated aqueous solution of sodium hydrogen carbonate was added to the resulting mixture, and the mixture was extracted with chloroform. The resulting organic layer was dried over anhydrous sodium sulfate, and concentrated under reduced pressure to obtain the present compound 9 represented by the following formula 0.63 g.

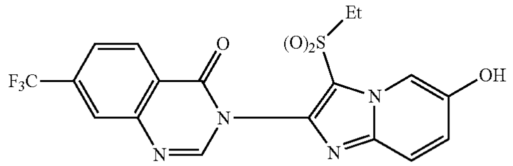

Present compound 9: $^{1}$H-NMR ($CDCl_3$) δ: 8.56-8.47 (2H, m), 8.33-8.27 (1H, m), 8.11 (1H, s), 7.80 (1H, d), 7.71-7.64 (1H, m), 7.40-7.32 (1H, m), 3.50 (2H, q), 1.42 (3H, t).

Preparation Example 22

A mixture of the present compound 9 30 mg, cesium carbonate 443 mg, ethyl p-toluene sulfonate 136 mg, and NMP 3 mL was stirred at 80° C. for 1 hour. Saturated aqueous solution of sodium thiosulfate 20 mL was added to the resulting mixture, and the mixture was stirred for 1 hour. The resulting mixture was stood to cool to room temperature, and water was then added thereto, and the mixture was extracted with ethyl acetate. The resulting organic layer was dried over anhydrous sodium sulfate, and concentrated under reduced pressure. The resulting residue was subjected to a silica gel column chromatography (ethyl acetate: hexane=1:1) to obtain the present compound 10-1 represented by the following formula 100 mg.

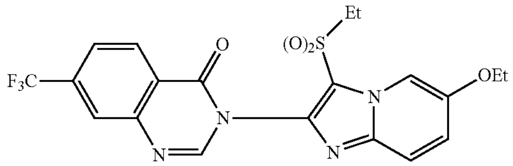

Present compound 10-1: $^{1}$H-NMR ($CDCl_3$) δ: 8.51-8.46 (2H, m), 8.28 (1H, s), 8.11 (1H, s), 7.80 (1H, d), 7.72 (1H, d), 7.41-7.38 (1H, m), 4.14 (2H, q), 3.54 (2H, q), 1.54 (3H, t), 1.46 (3H, t).

Preparation Example 23

To a mixture of the intermediate compound 43 150 mg and ethanol 5 ml were added methyl 2-formyl-5-(trifluoromethyl)benzoate which was prepared by the method described in Tetrahedron Letters, 2018, 59, 1564 164 mg and concentrated hydrochloric acid 18 μL under ice-cooling, and the mixture was stirred for 30 minutes under ice-cooling. The resulting mixture was concentrated under reduced pressure, and toluene 20 mL and para-toluenesulfonic acid 24 mg were added thereto, and the mixture was stirred at 110° C. for 6 hours. The resulting mixture was stood to cool to room temperature, and saturated aqueous solution of hydrogen bicarbonate was added thereto, and the mixture was extracted with ethyl acetate. The resulting organic layer was dried over anhydrous sodium sulfate, and concentrated under reduced pressure. The resulting residue was subjected to a silica gel column chromatography (hexane:ethyl acetate=1:2) to obtain the present compound 11 represented by the following formula 155 mg.

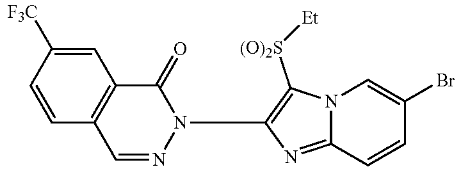

Present compound 11: $^{1}$H-NMR ($CDCl_3$) δ: 9.05 (1H, d), 8.76 (1H, d), 8.40 (1H, s), 8.11 (1H, dd), 7.93 (1H, d), 7.72 (1H, d), 7.63 (1H, dd), 3.58 (2H, q), 1.46 (3H, t).

Preparation Example 24

A mixture of the present compound 3-7 500 mg, pyrazole 73 mg, copper(I) iodide 19 mg, and N,N'-dimethyletylene diamine 19 mg, cesium carbonate 63 mg, and DMF 1 ml was stirred at 150° C. for 9 hours. Water was added to the resulting mixture, and the mixture was extracted with ethyl acetate. The resulting organic layer was dried over anhydrous sodium sulfate and concentrated under reduced pressure. The resulting residue was subjected to a silica gel column chromatography (hexane:ethyl acetate: 1:2) to obtain the present compound 12-1 represented by the following formula 40 mg.

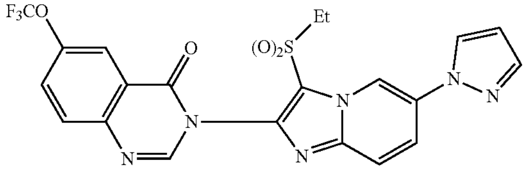

Present compound 12-1: $^{1}$H-NMR ($CDCl_3$) δ: 9.33 (1H, d), 8.24 (1H, s), 8.17 (1H, d), 8.05 (1H, dd), 7.98 (1H, d), 7.91 (1H, d), 7.86 (1H, d), 7.83 (1H, d), 7.67 (1H, dd), 6.60 (1H, t), 3.61 (2H, q), 1.48 (3H, t).

The compound which was prepared according to the Preparation Example 24 and its physical property value was shown below.

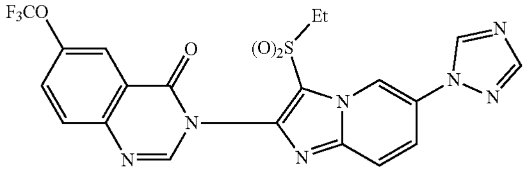

Present compound 12-2: $^{1}$H-NMR ($CDCl_3$) δ: 9.40 (1H, s), 8.68 (1H, s), 8.26 (1H, s), 8.22 (1H, s), 8.18 (1H, d), 7.99-7.96 (2H, m), 7.87 (1H, d), 7.68 (1H, dd), 3.63 (2H, q), 1.49 (3H, t).

Preparation Example 25

A mixture of the present compound 3-7 1.00 g, tert-butyl carbamate 272 mg, 2-dicyclohexylphosphino-2',4',6'-triisopropylbiphenyl 184 mg, palladium(II) acetate 69 mg, cesium carbonate 880 mg, and dioxane 15 ml was stirred at 100° C. under nitrogen atmosphere for 18 hours. Water was added to the resulting mixture at room temperature, and the mixture was extracted with ethyl acetate. The resulting organic layer was washed with saturated brine, dried over anhydrous sodium sulfate, and concentrated under reduced pressure. The resulting residue was subjected to a silica gel column chromatography (ethyl acetate:hexane=1:1) to obtain the present compound 13 represented by the following formula 173 mg.

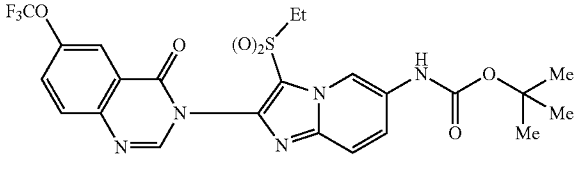

Present compound 13: $^{1}$H-NMR ($CDCl_3$) δ: 9.31 (1H, s), 8.21 (1H, s), 8.17-8.15 (1H, m), 7.85 (1H, d), 7.72-7.70 (1H, m), 7.68-7.63 (2H, m), 6.64 (1H, s), 3.59-3.50 (2H, m), 1.58 (9H, s), 1.46 (3H, t).

Next, examples of the present compound X which was prepared according to any method of the Preparation Examples described in the Examples or the process described herein were described below. Here T1 to T36 represents any group indicated below.

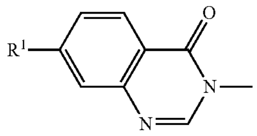

T1

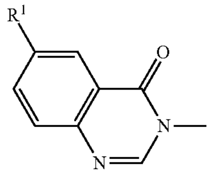

T2

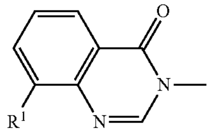

T3

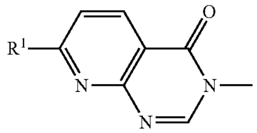

T4

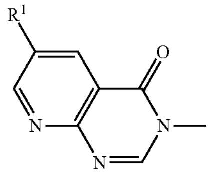

T5

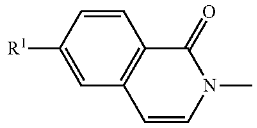

T6

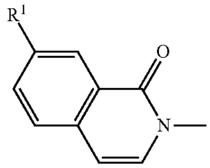

T7

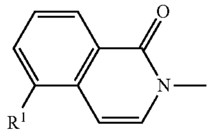

T8

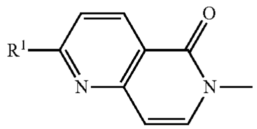

T9

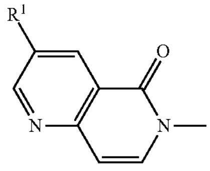

T10

-continued
T11
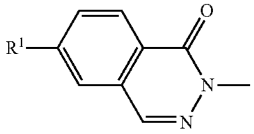
T12
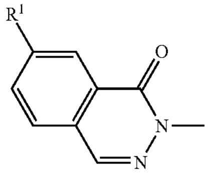
T13
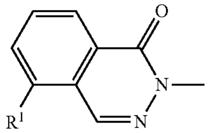
T14
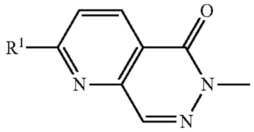
T15
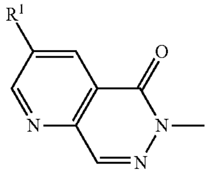
T16
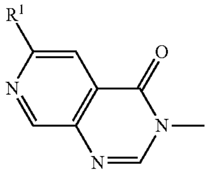
T17
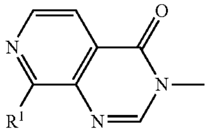
T18
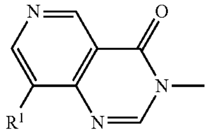
T19
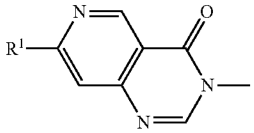
T20
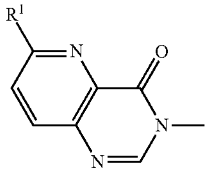
-continued
T21
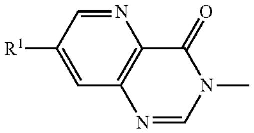
T22
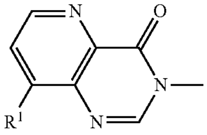
T23
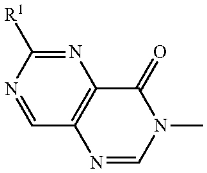
T24
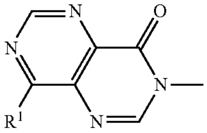
T25
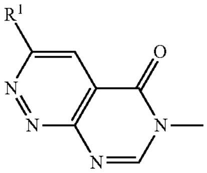
T26
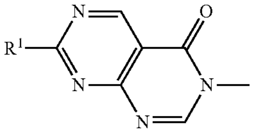
T27
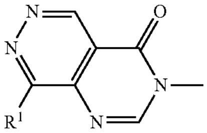
T28
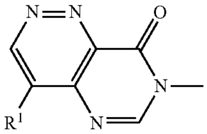
T29
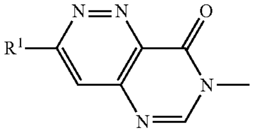
T30
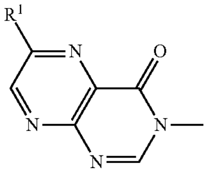

-continued

T31

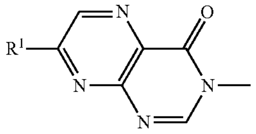

T32

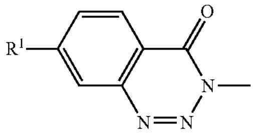

T33

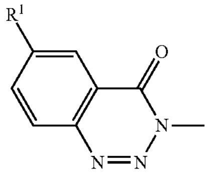

T34

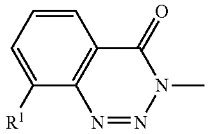

T35

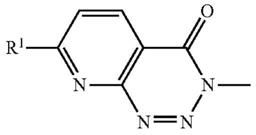

T36

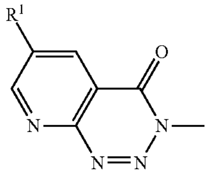

A compound represented by formula (L-1):

(L-1)

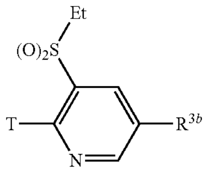

(hereinafter, referred to as compound (L-1)), wherein T represents a group represented by T1, $R^{3b}$ represents a hydrogen atom, and $R^1$ represents any substituents indicated in [Table L1] to [Table L3] (hereinafter, referred to as Compound Class $SX_1$).

TABLE L1

| |
|---|
| $CF_3$ |
| $CHF_2$ |
| $CH_2C_3$ |
| $CF_2CF_3$ |
| $CH_2CF_2CF_3$ |
| $CF_2CF_2CF_3$ |
| $CF_2CF_2CF_2CF_3$ |
| $CF_2CF_2CF_2CF_2CF_3$ |

TABLE L1-continued

| |
|---|
| $CF(CF_3)_2$ |
| $C(Me)_2CN$ |
| $CH_2C(Me)_2CN$ |
| $CH_2CH_2C(Me)_2CN$ |
| c-Pr |
| c-Bu |
| 1-CN-c-Pr |
| $2,2\text{-}F_2\text{-c-Pr}$ |
| Oc-Pr |
| Oc-Bu |
| O(1-CN-c-Pr) |
| $O(2,2\text{-}F_2\text{-c-Pr})$ |

TABLE L2

| |
|---|
| $SCF_3$ |
| $SCH_2CF_3$ |
| $SCF_2CF_3$ |
| $SCH_2CF_2CF_3$ |
| $SCF_2CF_2CF_3$ |
| $SCH_2CF_2CF_2CF_3$ |
| $SCF_2CF_2CF_2CF_3$ |
| $S(O)CF_3$ |
| $S(O)CH_2CF_3$ |
| $S(O)CF_2CF_3$ |
| $S(O)CH_2CF_2CF_3$ |
| $S(O)CF_2CF_2CF_3$ |
| $S(O)CH_2CF_2CF_2CF_3$ |
| $S(O)CF_2CF_2CF_2CF_3$ |
| $S(O)_2CF_3$ |
| $S(O)_2CH_2CF_3$ |
| $S(O)_2CF_2CF_3$ |
| $S(O)_2CH_2CF_2CF_3$ |
| $S(O)_2CF_2CF_2CF_3$ |
| $S(O)_2CH_2CF_2CF_2CF_3$ |
| $S(O)_2CF_2CF_2CF_2CF_3$ |

TABLE L3

| |
|---|
| $OCF_3$ |
| $OCHF_2$ |
| $OCH_2CF_3$ |
| $OCH_2CHF_2$ |
| $OCF_2CF_3$ |
| $OCH(CH_3)CF_3$ |
| $OCH_2CF_2CHF_2$ |
| $OCH_2CF_2CF_3$ |
| $OCF_2CF_2CF_3$ |
| $OCH_2CF_2CHFCF_3$ |
| $OCH_2CF_2CF_2CF_3$ |
| $OCF_2CF_2CF_2CF_3$ |
| $OCH_2CF_2CF_2CF_2CF_3$ |
| $OCH_2C(Me)_2CN$ |
| $OCH_2CH_2C(Me)_2CN$ |
| $OS(O)_2CF_3$ |
| $OS(O)_2CF_2CF_3$ |
| $OS(O)_2CF_2CF_2CF_3$ |
| F |
| Cl |
| Br |
| I |

A compound (L-1) wherein T represents a group represented by T1, $R^{3b}$ represents a chlorine atom, and $R^1$ represents any substituents indicated in [Table L1] to [Table L3] (hereinafter, referred to as Compound Class $SX_2$).

A compound (L-1) wherein T represents a group represented by T1, $R^{3b}$ represents a cyclopropyl group, and $R^1$ represents any substituents indicated in [Table L1] to [Table L3] (hereinafter, referred to as Compound Class $SX_3$).

A compound (L-1) wherein T represents a group represented by T1, $R^{3b}$ represents a 1-cyanocyclopropyl group, and $R^1$ represents any substituents indicated in [Table L1] to [Table L3] (hereinafter, referred to as Compound Class $SX_4$).

A compound (L-1) wherein T represents a group represented by T1, $R^{3b}$ represents $CF_3$, and $R^1$ represents any substituents indicated in [Table L1] to [Table L3] (hereinafter, referred to as Compound Class $SX_5$).

A compound (L-1) wherein T represents a group represented by T2, $R^{3b}$ represents a hydrogen atom, and $R^1$ represents any substituents indicated in [Table L1] to [Table L3] (hereinafter, referred to as Compound Class $SX_6$).

A compound (L-1) wherein T represents a group represented by T2, $R^{3b}$ represents a chlorine atom, and $R^1$ represents any substituents indicated in [Table L1] to [Table L3] (hereinafter, referred to as Compound Class $SX_7$).

A compound (L-1) wherein T represents a group represented by T2, $R^{3b}$ represents a cyclopropyl group, and $R^1$ represents any substituents indicated in [Table L1] to [Table L3] (hereinafter, referred to as Compound Class $SX_8$).

A compound (L-1) wherein T represents a group represented by T2, $R^{3b}$ represents a cyanocyclopropyl group, and $R^1$ represents any substituents indicated in [Table L1] to [Table L3] (hereinafter, referred to as Compound Class $SX_9$).

A compound (L-1) wherein T represents a group represented by T2, $R^{3b}$ represents $CF_3$, and $R^1$ represents any substituents indicated in [Table L1] to [Table L3] (hereinafter, referred to as Compound Class $SX_{10}$).

A compound (L-1) wherein T represents a group represented by T3, $R^{3b}$ represents a hydrogen atom, and $R^1$ represents any substituents indicated in [Table L1] to [Table L3] (hereinafter, referred to as Compound Class $SX_{11}$).

A compound (L-1) wherein T represents a group represented by T3, $R^{3b}$ represents a chlorine atom, and $R^1$ represents any substituents indicated in [Table L1] to [Table L3] (hereinafter, referred to as Compound Class $SX_{12}$).

A compound (L-1) wherein T represents a group represented by T3, $R^{3b}$ represents a cyclopropyl group, and $R^1$ represents any substituents indicated in [Table L1] to [Table L3] (hereinafter, referred to as Compound Class $SX_{13}$).

A compound (L-1) wherein T represents a group represented by T3, $R^{3b}$ represents a 1-cyanocyclopropyl group, and $R^1$ represents any substituents indicated in [Table L1] to [Table L3] (hereinafter, referred to as Compound Class $SX_{14}$).

A compound (L-1) wherein T represents a group represented by T3, $R^{3b}$ represents $CF_3$, and $R^1$ represents any substituents indicated in [Table L1] to [Table L3] (hereinafter, referred to as Compound Class $SX_{15}$).

A compound (L-1) wherein T represents a group represented by T4, $R^{3b}$ represents a hydrogen atom, and $R^1$ represents any substituents indicated in [Table L1] to [Table L3] (hereinafter, referred to as Compound Class $SX_{16}$).

A compound (L-1) wherein T represents a group represented by T4, $R^{3b}$ represents a chlorine atom, and $R^1$ represents any substituents indicated in [Table L1] to [Table L3] (hereinafter, referred to as Compound Class $SX_{17}$).

A compound (L-1) wherein T represents a group represented by T4, $R^{3b}$ represents a cyclopropyl group, and $R^1$ represents any substituents indicated in [Table L1] to [Table L3] (hereinafter, referred to as Compound Class $SX_{18}$).

A compound (L-1) wherein T represents a group represented by T4, $R^{3b}$ represents a 1-cyanocyclopropyl group, and $R^1$ represents any substituents indicated in [Table L1] to [Table L3] (hereinafter, referred to as Compound Class $SX_{19}$).

A compound (L-1) wherein T represents a group represented by T4, $R^{3b}$ represents $CF_3$, and $R^1$ represents any substituents indicated in [Table L1] to [Table L3] (hereinafter, referred to as Compound Class $SX_{20}$).

A compound (L-1) wherein T represents a group represented by T5, $R^{3b}$ represents a hydrogen atom, and $R^1$ represents any substituents indicated in [Table L1] to [Table L3] (hereinafter, referred to as Compound Class $SX_{21}$).

A compound (L-1) wherein T represents a group represented by T5, $R^{3b}$ represents a chlorine atom, and $R^1$ represents any substituents indicated in [Table L1] to [Table L3] (hereinafter, referred to as Compound Class $SX_{22}$).

A compound (L-1) wherein T represents a group represented by T5, $R^{3b}$ represents a cyclopropyl group, and $R^1$ represents any substituents indicated in [Table L1] to [Table L3] (hereinafter, referred to as Compound Class $SX_{23}$).

A compound (L-1) wherein T represents a group represented by T5, $R^{3b}$ represents a 1-cyanocyclopropyl group, and $R^1$ represents any substituents indicated in [Table L1] to [Table L3] (hereinafter, referred to as Compound Class $SX_{24}$).

A compound (L-1) wherein T represents a group represented by T5, $R^{3b}$ represents $CF_3$, and $R^1$ represents any (hereinafter, referred to as Compound Class $SX_{25}$).

A compound (L-1) wherein T represents a group represented by T6, $R^{3b}$ represents a hydrogen atom, and $R^1$ represents any substituents indicated in [Table L1] to [Table L3] (hereinafter, referred to as Compound Class $SX_{26}$).

A compound (L-1) wherein T represents a group represented by T6, $R^{3b}$ represents a chlorine atom, and $R^1$ represents any substituents indicated in [Table L1] to [Table L3] (hereinafter, referred to as Compound Class $SX_{27}$).

A compound (L-1) wherein T represents a group represented by T6, $R^{3b}$ represents a cyclopropyl group, and $R^1$ represents any substituents indicated in [Table L1] to [Table L3] (hereinafter, referred to as Compound Class $SX_{28}$).

A compound (L-1) wherein T represents a group represented by T6, $R^{3b}$ represents a 1-cyanocyclopropyl group, and $R^1$ represents any substituents indicated in [Table L1] to [Table L3] (hereinafter, referred to as Compound Class $SX_{29}$).

A compound (L-1) wherein T represents a group represented by T6, $R^{3b}$ represents $CF_3$, and $R^1$ represents any substituents indicated in [Table L1] to [Table L3] (hereinafter, referred to as Compound Class $SX_{30}$).

A compound (L-1) wherein T represents a group represented by T7, $R^{3b}$ represents a hydrogen atom, and $R^1$ represents any substituents indicated in [Table L1] to [Table L3] (hereinafter, referred to as Compound Class $SX_{31}$).

A compound (L-1) wherein T represents a group represented by T7, $R^{3b}$ represents a chlorine atom, and $R^1$ represents any substituents indicated in [Table L1] to [Table L3] (hereinafter, referred to as Compound Class $SX_{32}$).

A compound (L-1) wherein T represents a group represented by T7, $R^{3b}$ represents a cyclopropyl group, and $R^1$ represents any substituents indicated in [Table L1] to [Table L3] (hereinafter, referred to as Compound Class $SX_{33}$).

A compound (L-1) wherein T represents a group represented by T7, $R^{3b}$ represents a 1-cyanocyclopropyl group, and $R^1$ represents any substituents indicated in [Table L1] to [Table L3] (hereinafter, referred to as Compound Class $SX_{34}$).

A compound (L-1) wherein T represents a group represented by T7, $R^{3b}$ represents $CF_3$, and $R^1$ represents any substituents indicated in [Table L1] to [Table L3] (hereinafter, referred to as Compound Class $SX_{35}$).

A compound (L-1) wherein T represents a group represented by T8, $R^{3b}$ represents a hydrogen atom, and $R^1$ represents any substituents indicated in [Table L1] to [Table L3] (hereinafter, referred to as Compound Class $SX_{36}$).

A compound (L-1) wherein T represents a group represented by T8, $R^{3b}$ represents a chlorine atom, and $R^1$ represents any substituents indicated in [Table L1] to [Table L3] (hereinafter, referred to as Compound Class $SX_{37}$).

A compound (L-1) wherein T represents a group represented by T8, $R^{3b}$ represents a cyclopropyl group, and $R^1$ represents any substituents indicated in [Table L1] to [Table L3] (hereinafter, referred to as Compound Class $SX_{38}$).

A compound (L-1) wherein T represents a group represented by T8, $R^{3b}$ represents a 1-cyanocyclopropyl group, and $R^1$ represents any substituents indicated in [Table L1] to [Table L3] (hereinafter, referred to as Compound Class $SX_{39}$).

A compound (L-1) wherein T represents a group represented by T8, $R^{3b}$ represents $CF_3$, and $R^1$ represents any substituents indicated in [Table L1] to [Table L3] (hereinafter, referred to as Compound Class $SX_{40}$).

A compound (L-1) wherein T represents a group represented by T9, $R^{3b}$ represents a hydrogen atom, and $R^1$ represents any substituents indicated in [Table L1] to [Table L3] (hereinafter, referred to as Compound Class $SX_{41}$).

A compound (L-1) wherein T represents a group represented by T9, $R^{3b}$ represents a chlorine atom, and $R^1$ represents any substituents indicated in [Table L1] to [Table L3] (hereinafter, referred to as Compound Class $SX_{42}$).

A compound (L-1) wherein T represents a group represented by T9, $R^{3b}$ represents a cyclopropyl group, and $R^1$ represents any substituents indicated in [Table L1] to [Table L3] (hereinafter, referred to as Compound Class $SX_{43}$).

A compound (L-1) wherein T represents a group represented by T9, $R^{3b}$ represents a 1-cyanocyclopropyl group, and $R^1$ represents any substituents indicated in [Table L1] to [Table L3] (hereinafter, referred to as Compound Class $SX_{44}$).

A compound (L-1) wherein T represents a group represented by T9, $R^{3b}$ represents $CF_3$, and $R^1$ represents any substituents indicated in [Table L1] to [Table L3] (hereinafter, referred to as Compound Class $SX_{45}$).

A compound (L-1) wherein T represents a group represented by T10, $R^{3b}$ represents a hydrogen atom, and $R^1$ represents any substituents indicated in [Table L1] to [Table L3] (hereinafter, referred to as Compound Class $SX_{46}$).

A compound (L-1) wherein T represents a group represented by T10, $R^{3b}$ represents a chlorine atom, and $R^1$ represents any substituents indicated in [Table L1] to [Table L3] (hereinafter, referred to as Compound Class $SX_{47}$).

A compound (L-1) wherein T represents a group represented by T10, $R^{3b}$ represents a cyclopropyl group, and $R^1$ represents any substituents indicated in [Table L1] to [Table L3] (hereinafter, referred to as Compound Class $SX_{48}$).

A compound (L-1) wherein T represents a group represented by T10, $R^{3b}$ represents a 1-cyanocyclopropyl group, and $R^1$ represents any substituents indicated in [Table L1] to [Table L3] (hereinafter, referred to as Compound Class $SX_{49}$).

A compound (L-1) wherein T represents a group represented by T10, $R^{3b}$ represents $CF_3$, and $R^1$ represents any substituents indicated in [Table L1] to [Table L3] (hereinafter, referred to as Compound Class $SX_{50}$).

A compound (L-1) wherein T represents a group represented by T11, $R^{3b}$ represents a hydrogen atom, and $R^1$ represents any substituents indicated in [Table L1] to [Table L3] (hereinafter, referred to as Compound Class $SX_{51}$).

A compound (L-1) wherein T represents a group represented by T11, $R^{3b}$ represents a chlorine atom, and $R^1$ represents any substituents indicated in [Table L1] to [Table L3] (hereinafter, referred to as Compound Class $SX_{52}$).

A compound (L-1) wherein T represents a group represented by T11, $R^{3b}$ represents a cyclopropyl group, and $R^1$ represents any substituents indicated in [Table L1] to [Table L3] (hereinafter, referred to as Compound Class $SX_{53}$).

A compound (L-1) wherein T represents a group represented by T11, $R^{3b}$ represents a 1-cyanocyclopropyl group, and $R^1$ represents any substituents indicated in [Table L1] to [Table L3] (hereinafter, referred to as Compound Class $SX_{54}$).

A compound (L-1) wherein T represents a group represented by T11, $R^{3b}$ represents $CF_3$, and $R^1$ represents any substituents indicated in [Table L1] to [Table L3] (hereinafter, referred to as Compound Class $SX_{55}$).

A compound (L-1) wherein T represents a group represented by T12, $R^{3b}$ represents a hydrogen atom, and $R^1$ represents any substituents indicated in [Table L1] to [Table L3] (hereinafter, referred to as Compound Class $SX_{56}$).

A compound (L-1) wherein T represents a group represented by T12, $R^{3b}$ represents a chlorine atom, and $R^1$ represents any substituents indicated in [Table L1] to [Table L3] (hereinafter, referred to as Compound Class $SX_{57}$).

A compound (L-1) wherein T represents a group represented by T12, $R^{3b}$ represents a cyclopropyl group, and $R^1$ represents any substituents indicated in [Table L1] to [Table L3] (hereinafter, referred to as Compound Class $SX_{58}$).

A compound (L-1) wherein T represents a group represented by T12, $R^{3b}$ represents a 1-cyanocyclopropyl group, and $R^1$ represents any substituents indicated in [Table L1] to [Table L3] (hereinafter, referred to as Compound Class $SX_{59}$).

A compound (L-1) wherein T represents a group represented by T12, $R^{3b}$ represents $CF_3$, and $R^1$ represents any substituents indicated in [Table L1] to [Table L3] (hereinafter, referred to as Compound Class $SX_{60}$).

A compound (L-1) wherein T represents a group represented by T13, $R^{3b}$ represents a hydrogen atom, and $R^1$ represents any substituents indicated in [Table L1] to [Table L3] (hereinafter, referred to as Compound Class $SX_{62}$).

A compound (L-1) wherein T represents a group represented by T13, $R^{3b}$ represents a chlorine atom, and $R^1$ represents any substituents indicated in [Table L1] to [Table L3] (hereinafter, referred to as Compound Class $SX_{62}$).

A compound (L-1) wherein T represents a group represented by T13, $R^{3b}$ represents a cyclopropyl group, and $R^1$ represents any substituents indicated in [Table L1] to [Table L3] (hereinafter, referred to as Compound Class $SX_{63}$).

A compound (L-1) wherein T represents a group represented by T13, $R^{3b}$ represents a 1-cyanocyclopropyl group, and $R^1$ represents any substituents indicated in [Table L1] to [Table L3] (hereinafter, referred to as Compound Class $SX_{64}$).

A compound (L-1) wherein T represents a group represented by T13, $R^{3b}$ represents $CF_3$, and $R^1$ represents any substituents indicated in [Table L1] to [Table L3] (hereinafter, referred to as Compound Class $SX_{65}$).

A compound (L-1) wherein T represents a group represented by T14, $R^{3b}$ represents a hydrogen atom, and $R^1$ represents any substituents indicated in [Table L1] to [Table L3] (hereinafter, referred to as Compound Class $SX_{66}$).

A compound (L-1) wherein T represents a group represented by T14, $R^{3b}$ represents a chlorine atom, and $R^1$ represents any substituents indicated in [Table L1] to [Table L3] (hereinafter, referred to as Compound Class $SX_{67}$).

A compound (L-1) wherein T represents a group represented by T14, $R^{3b}$ represents a cyclopropyl group, and $R^1$ represents any substituents indicated in [Table L1] to [Table L3] (hereinafter, referred to as Compound Class $SX_{68}$).

A compound (L-1) wherein T represents a group represented by T14, $R^{3b}$ represents a 1-cyanocyclopropyl group, and $R^1$ represents any substituents indicated in [Table L1] to [Table L3] (hereinafter, referred to as Compound Class $SX_{69}$).

A compound (L-1) wherein T represents a group represented by T14, $R^{3b}$ represents $CF_3$, and $R^1$ represents any substituents indicated in [Table L1] to [Table L3] (hereinafter, referred to as Compound Class $SX_{70}$).

A compound (L-1) wherein T represents a group represented by T15, $R^{3b}$ represents a hydrogen atom, and $R^1$ represents any substituents indicated in [Table L1] to [Table L3] (hereinafter, referred to as Compound Class $SX_{71}$).

A compound (L-1) wherein T represents a group represented by T15, $R^{3b}$ represents a chlorine atom, and $R^1$ represents any substituents indicated in [Table L1] to [Table L3] (hereinafter, referred to as Compound Class $SX_{72}$).

A compound (L-1) wherein T represents a group represented by T15, $R^{3b}$ represents a cyclopropyl group, and $R^1$ represents any substituents indicated in [Table L1] to [Table L3] (hereinafter, referred to as Compound Class $SX_{73}$).

A compound (L-1) wherein T represents a group represented by T15, $R^{3b}$ represents a 1-cyanocyclopropyl group, and $R^1$ represents any substituents indicated in [Table L1] to [Table L3] (hereinafter, referred to as Compound Class $SX_{74}$).

A compound (L-1) wherein T represents a group represented by T15, $R^{3b}$ represents $CF_3$, and $R^1$ represents any substituents indicated in [Table L1] to [Table L3] (hereinafter, referred to as Compound Class $SX_{75}$).

A compound represented by formula (L-2):

(L-2)

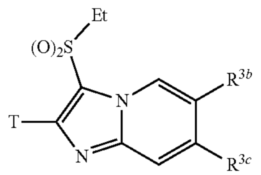

(hereinafter, referred to as compound (L-2)), wherein T represents a group represented by T1, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{76}$).

A compound (L-2) wherein T represents a group represented by T1, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{77}$).

A compound (L-2) wherein T represents a group represented by T1, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{78}$).

A compound (L-2) wherein T represents a group represented by T1, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{79}$).

A compound (L-2) wherein T represents a group represented by T1, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{80}$).

A compound (L-2) wherein T represents a group represented by T1, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{81}$).

A compound (L-2) wherein T represents a group represented by T1, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{82}$).

A compound (L-2) wherein T represents a group represented by T1, $R^{3b}$ represents a hydrogen atom, $R^{3c}$ represents a bromine atom and $R^1$ represents any substituents indicated in [Table L1] to [Table L3] (hereinafter, referred to as Compound Class $SX_{83}$).

A compound (L-2) wherein T represents a group represented by T1, $R^{3b}$ represents a hydrogen atom, $R^{3c}$ represents an iodine atom and $R^1$ represents any substituents indicated in [Table L1] to [Table L3] (hereinafter, referred to as Compound Class $SX_{84}$).

A compound (L-2) wherein T represents a group represented by T2, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{85}$).

A compound (L-2) wherein T represents a group represented by T2, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{86}$).

A compound (L-2) wherein T represents a group represented by T2, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{87}$).

A compound (L-2) wherein T represents a group represented by T2, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{88}$).

A compound (L-2) wherein T represents a group represented by T2, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{89}$).

A compound (L-2) wherein T represents a group represented by T2, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{90}$).

A compound (L-2) wherein T represents a group represented by T2, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{91}$).

A compound (L-2) wherein T represents a group represented by T2, $R^{3b}$ represents a hydrogen atom, $R^{3c}$ represents a bromine atom and $R^1$ represents any substituents indicated in [Table L1] to [Table L3] (hereinafter, referred to as Compound Class $SX_{92}$).

A compound (L-2) wherein T represents a group represented by T2, $R^{3b}$ represents a hydrogen atom, $R^{3c}$ represents an iodine atom and $R^1$ represents any substituents indicated in [Table L1] to [Table L3] (hereinafter, referred to as Compound Class $SX_{93}$).

A compound (L-2) wherein T represents a group represented by T3, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{94}$).

A compound (L-2) wherein T represents a group represented by T3, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{95}$).

A compound (L-2) wherein T represents a group represented by T3, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{96}$).

A compound (L-2) wherein T represents a group represented by T3, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{97}$).

A compound (L-2) wherein T represents a group represented by T3, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{98}$).

A compound (L-2) wherein T represents a group represented by T3, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{99}$).

A compound (L-2) wherein T represents a group represented by T3, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{100}$).

A compound (L-2) wherein T represents a group represented by T3, $R^{3b}$ represents a hydrogen atom, $R^{3c}$ represents a bromine atom and $R^1$ represents any substituents indicated in [Table L1] to [Table L3] (hereinafter, referred to as Compound Class $SX_{101}$).

A compound (L-2) wherein T represents a group represented by T3, $R^{3b}$ represents a hydrogen atom, $R^{3c}$ represents an iodine atom and $R^1$ represents any substituents indicated in [Table L1] to [Table L3] (hereinafter, referred to as Compound Class $SX_{102}$).

A compound (L-2) wherein T represents a group represented by T4, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{103}$).

A compound (L-2) wherein T represents a group represented by T4, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{104}$).

A compound (L-2) wherein T represents a group represented by T4, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{105}$).

A compound (L-2) wherein T represents a group represented by T4, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{106}$).

A compound (L-2) wherein T represents a group represented by T4, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{107}$).

A compound (L-2) wherein T represents a group represented by T4, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{108}$).

A compound (L-2) wherein T represents a group represented by T4, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{109}$).

A compound (L-2) wherein T represents a group represented by T4, $R^{3b}$ represents a hydrogen atom, $R^{3c}$ represents a bromine atom and $R^1$ represents any substituents indicated in [Table L1] to [Table L3] (hereinafter, referred to as Compound Class $SX_{110}$).

A compound (L-2) wherein T represents a group represented by T4, $R^{3b}$ represents a hydrogen atom, $R^{3c}$ represents an iodine atom and $R^1$ represents any substituents indicated in [Table L1] to [Table L3] (hereinafter, referred to as Compound Class $SX_{111}$).

A compound (L-2) wherein T represents a group represented by T5, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{112}$).

A compound (L-2) wherein T represents a group represented by T5, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{113}$).

A compound (L-2) wherein T represents a group represented by T5, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{114}$).

A compound (L-2) wherein T represents a group represented by T5, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{115}$).

A compound (L-2) wherein T represents a group represented by T5, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{116}$).

A compound (L-2) wherein T represents a group represented by T5, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{117}$).

A compound (L-2) wherein T represents a group represented by T5, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{118}$).

A compound (L-2) wherein T represents a group represented by T5, $R^{3b}$ represents a hydrogen atom, $R^{3c}$ represents a bromine atom and $R^1$ represents any substituents indicated in [Table L1] to [Table L3] (hereinafter, referred to as Compound Class $SX_{119}$).

A compound (L-2) wherein T represents a group represented by T5, $R^{3b}$ represents a hydrogen atom, $R^{3c}$ represents an iodine atom and $R^1$ represents any substituents indicated in [Table L1] to [Table L3] (hereinafter, referred to as Compound Class $SX_{120}$).

A compound (L-2) wherein T represents a group represented by T6, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{121}$).

A compound (L-2) wherein T represents a group represented by T6, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{122}$).

A compound (L-2) wherein T represents a group represented by T6, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{123}$).

A compound (L-2) wherein T represents a group represented by T6, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{124}$).

A compound (L-2) wherein T represents a group represented by T6, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{125}$).

A compound (L-2) wherein T represents a group represented by T6, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{126}$).

A compound (L-2) wherein T represents a group represented by T6, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{127}$).

A compound (L-2) wherein T represents a group represented by T6, $R^{3b}$ represents a hydrogen atom, $R^{3c}$ represents a bromine atom and $R^1$ represents any substituents indicated in [Table L1] to [Table L3] (hereinafter, referred to as Compound Class $SX_{128}$).

A compound (L-2) wherein T represents a group represented by T6, $R^{3b}$ represents a hydrogen atom, $R^{3c}$ represents an iodine atom and $R^1$ represents any substituents indicated in [Table L1] to [Table L3] (hereinafter, referred to as Compound Class $SX_{129}$).

A compound (L-2) wherein T represents a group represented by T7, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{130}$).

A compound (L-2) wherein T represents a group represented by T7, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{131}$).

A compound (L-2) wherein T represents a group represented by T7, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{132}$).

A compound (L-2) wherein T represents a group represented by T7, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{133}$).

A compound (L-2) wherein T represents a group represented by T7, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{134}$).

A compound (L-2) wherein T represents a group represented by T7, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{135}$).

A compound (L-2) wherein T represents a group represented by T7, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{136}$).

A compound (L-2) wherein T represents a group represented by T7, $R^{3b}$ represents a hydrogen atom, $R^{3c}$ represents a bromine atom and $R^1$ represents any substituents indicated in [Table L1] to [Table L3] (hereinafter, referred to as Compound Class $SX_{137}$).

A compound (L-2) wherein T represents a group represented by T7, $R^{3b}$ represents a hydrogen atom, $R^{3c}$ represents an iodine atom and $R^1$ represents any substituents indicated in [Table L1] to [Table L3] (hereinafter, referred to as Compound Class $SX_{138}$).

A compound (L-2) wherein T represents a group represented by T8, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{139}$).

A compound (L-2) wherein T represents a group represented by T8, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{140}$).

A compound (L-2) wherein T represents a group represented by T8, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{141}$).

A compound (L-2) wherein T represents a group represented by T8, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{142}$).

A compound (L-2) wherein T represents a group represented by T8, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{143}$).

A compound (L-2) wherein T represents a group represented by T8, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{144}$).

A compound (L-2) wherein T represents a group represented by T8, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{145}$).

A compound (L-2) wherein T represents a group represented by T8, $R^{3b}$ represents a hydrogen atom, $R^{3c}$ represents a bromine atom and $R^1$ represents any substituents indicated in [Table L1] to [Table L3] (hereinafter, referred to as Compound Class $SX_{146}$).

A compound (L-2) wherein T represents a group represented by T8, $R^{3b}$ represents a hydrogen atom, $R^{3c}$ represents an iodine atom and $R^1$ represents any substituents indicated in [Table L1] to [Table L3] (hereinafter, referred to as Compound Class $SX_{147}$).

A compound (L-2) wherein T represents a group represented by T9, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{148}$).

A compound (L-2) wherein T represents a group represented by T9, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{149}$).

A compound (L-2) wherein T represents a group represented by T9, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{150}$).

A compound (L-2) wherein T represents a group represented by T9, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{151}$).

A compound (L-2) wherein T represents a group represented by T9, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{152}$).

A compound (L-2) wherein T represents a group represented by T9, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{153}$).

A compound (L-2) wherein T represents a group represented by T9, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{154}$).

A compound (L-2) wherein T represents a group represented by T9, $R^{3b}$ represents a hydrogen atom, $R^{3c}$ represents a bromine atom and $R^1$ represents any substituents indicated in [Table L1] to [Table L3] (hereinafter, referred to as Compound Class $SX_{155}$).

A compound (L-2) wherein T represents a group represented by T9, $R^{3b}$ represents a hydrogen atom, $R^{3c}$ represents an iodine atom and $R^1$ represents any substituents indicated in [Table L1] to [Table L3] (hereinafter, referred to as Compound Class $SX_{156}$).

A compound (L-2) wherein T represents a group represented by T10, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{157}$).

A compound (L-2) wherein T represents a group represented by T10, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{158}$).

A compound (L-2) wherein T represents a group represented by T10, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{159}$).

A compound (L-2) wherein T represents a group represented by T10, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{160}$).

A compound (L-2) wherein T represents a group represented by T10, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{161}$).

A compound (L-2) wherein T represents a group represented by T10, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{162}$).

A compound (L-2) wherein T represents a group represented by T10, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{163}$).

A compound (L-2) wherein T represents a group represented by T10, $R^{3b}$ represents a hydrogen atom, $R^{3c}$ represents a bromine atom and $R^1$ represents any substituents indicated in [Table L1] to [Table L3] (hereinafter, referred to as Compound Class $SX_{164}$).

A compound (L-2) wherein T represents a group represented by T10, $R^{3b}$ represents a hydrogen atom, $R^{3c}$ represents an iodine atom and $R^1$ represents any substituents indicated in [Table L1] to [Table L3] (hereinafter, referred to as Compound Class $SX_{165}$).

A compound (L-2) wherein T represents a group represented by T11, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{166}$).

A compound (L-2) wherein T represents a group represented by T11, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{167}$).

A compound (L-2) wherein T represents a group represented by T11, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{168}$).

A compound (L-2) wherein T represents a group represented by T11, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{169}$).

A compound (L-2) wherein T represents a group represented by T11, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{170}$).

A compound (L-2) wherein T represents a group represented by T11, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{171}$).

A compound (L-2) wherein T represents a group represented by T11, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{172}$).

A compound (L-2) wherein T represents a group represented by T11, $R^{3b}$ represents a hydrogen atom, $R^{3c}$ represents a bromine atom and $R^1$ represents any substituents indicated in [Table L1] to [Table L3] (hereinafter, referred to as Compound Class $SX_{173}$).

A compound (L-2) wherein T represents a group represented by T11, $R^{3b}$ represents a hydrogen atom, $R^{3c}$ represents an iodine atom and $R^1$ represents any substituents indicated in [Table L1] to [Table L3] (hereinafter, referred to as Compound Class $SX_{174}$).

A compound (L-2) wherein T represents a group represented by T12, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{175}$).

A compound (L-2) wherein T represents a group represented by T12, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{176}$).

A compound (L-2) wherein T represents a group represented by T12, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{177}$).

A compound (L-2) wherein T represents a group represented by T12, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{178}$).

A compound (L-2) wherein T represents a group represented by T12, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{179}$).

A compound (L-2) wherein T represents a group represented by T12, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{180}$).

A compound (L-2) wherein T represents a group represented by T12, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{181}$).

A compound (L-2) wherein T represents a group represented by T12, $R^{3b}$ represents a hydrogen atom, $R^{3c}$ represents a bromine atom and $R^1$ represents any substituents indicated in [Table L1] to [Table L3] (hereinafter, referred to as Compound Class $SX_{182}$).

A compound (L-2) wherein T represents a group represented by T12, $R^{3b}$ represents a hydrogen atom, $R^{3c}$ represents an iodine atom and $R^1$ represents any substituents indicated in [Table L1] to [Table L3] (hereinafter, referred to as Compound Class $SX_{183}$).

A compound (L-2) wherein T represents a group represented by T13, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{184}$).

A compound (L-2) wherein T represents a group represented by T13, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{185}$).

A compound (L-2) wherein T represents a group represented by T13, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{186}$).

A compound (L-2) wherein T represents a group represented by T13, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{187}$).

A compound (L-2) wherein T represents a group represented by T13, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{188}$).

A compound (L-2) wherein T represents a group represented by T13, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{189}$).

A compound (L-2) wherein T represents a group represented by T13, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{190}$).

A compound (L-2) wherein T represents a group represented by T13, $R^{3b}$ represents a hydrogen atom, $R^{3c}$ represents a bromine atom and $R^1$ represents any substituents indicated in [Table L1] to [Table L3] (hereinafter, referred to as Compound Class $SX_{191}$).

A compound (L-2) wherein T represents a group represented by T13, $R^{3b}$ represents a hydrogen atom, $R^{3c}$ represents an iodine atom and $R^1$ represents any substituents indicated in [Table L1] to [Table L3] (hereinafter, referred to as Compound Class $SX_{192}$).

A compound (L-2) wherein T represents a group represented by T14, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{193}$).

A compound (L-2) wherein T represents a group represented by T14, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{194}$).

A compound (L-2) wherein T represents a group represented by T14, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{195}$).

A compound (L-2) wherein T represents a group represented by T14, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{196}$).

A compound (L-2) wherein T represents a group represented by T14, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{197}$).

A compound (L-2) wherein T represents a group represented by T14, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{198}$).

A compound (L-2) wherein T represents a group represented by T14, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{199}$).

A compound (L-2) wherein T represents a group represented by T14, $R^{3b}$ represents a hydrogen atom, $R^{3c}$ represents a bromine atom and $R^1$ represents any substituents indicated in [Table L1] to [Table L3] (hereinafter, referred to as Compound Class $SX_{200}$).

A compound (L-2) wherein T represents a group represented by T14, $R^{3b}$ represents a hydrogen atom, $R^{3c}$ represents an iodine atom and $R^1$ represents any substituents indicated in [Table L1] to [Table L3] (hereinafter, referred to as Compound Class $SX_{201}$).

A compound (L-2) wherein T represents a group represented by T15, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{202}$).

A compound (L-2) wherein T represents a group represented by T15, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{203}$).

A compound (L-2) wherein T represents a group represented by T15, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{204}$).

A compound (L-2) wherein T represents a group represented by T15, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{205}$).

A compound (L-2) wherein T represents a group represented by T15, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{206}$).

A compound (L-2) wherein T represents a group represented by T15, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{207}$).

A compound (L-2) wherein T represents a group represented by T15, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{208}$).

A compound (L-2) wherein T represents a group represented by T15, $R^{3b}$ represents a hydrogen atom, $R^{3c}$ represents a bromine atom and $R^1$ represents any substituents indicated in [Table L1] to [Table L3] (hereinafter, referred to as Compound Class $SX_{209}$).

A compound (L-2) wherein T represents a group represented by T15, $R^{3b}$ represents a hydrogen atom, $R^{3c}$ represents an iodine atom and $R^1$ represents any substituents indicated in [Table L1] to [Table L3] (hereinafter, referred to as Compound Class $SX_{210}$).

A compound (L-2) wherein T represents a group represented by T16, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{211}$).

A compound (L-2) wherein T represents a group represented by T16, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{212}$).

A compound (L-2) wherein T represents a group represented by T16, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{213}$).

A compound (L-2) wherein T represents a group represented by T16, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{214}$).

A compound (L-2) wherein T represents a group represented by T16, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{215}$).

A compound (L-2) wherein T represents a group represented by T16, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{216}$).

A compound (L-2) wherein T represents a group represented by T16, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{217}$).

A compound (L-2) wherein T represents a group represented by T16, $R^{3b}$ represents a hydrogen atom, $R^{3c}$ represents a bromine atom and $R^1$ represents any substituents indicated in [Table L1] to [Table L3] (hereinafter, referred to as Compound Class $SX_{218}$).

A compound (L-2) wherein T represents a group represented by T16, $R^{3b}$ represents a hydrogen atom, $R^{3c}$ represents an iodine atom and $R^1$ represents any substituents indicated in [Table L1] to [Table L3] (hereinafter, referred to as Compound Class $SX_{219}$).

A compound (L-2) wherein T represents a group represented by T17, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{220}$).

A compound (L-2) wherein T represents a group represented by T17, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{221}$).

A compound (L-2) wherein T represents a group represented by T17, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{222}$).

A compound (L-2) wherein T represents a group represented by T17, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{223}$).

A compound (L-2) wherein T represents a group represented by T17, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{224}$).

A compound (L-2) wherein T represents a group represented by T17, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{225}$).

A compound (L-2) wherein T represents a group represented by T17, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{226}$).

A compound (L-2) wherein T represents a group represented by T17, $R^{3b}$ represents a hydrogen atom, $R^{3c}$ represents a bromine atom and $R^1$ represents any substituents indicated in [Table L1] to [Table L3] (hereinafter, referred to as Compound Class $SX_{2277}$).

A compound (L-2) wherein T represents a group represented by T17, $R^{3b}$ represents a hydrogen atom, $R^{3c}$ represents an iodine atom and $R^1$ represents any substituents indicated in [Table L1] to [Table L3] (hereinafter, referred to as Compound Class $SX_{228}$).

A compound (L-2) wherein T represents a group represented by T18, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{229}$).

A compound (L-2) wherein T represents a group represented by T18, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{230}$).

A compound (L-2) wherein T represents a group represented by T18, $R^{3c}$ represents a chlorine atom, $R^{3c}$ represents a hydrogen atom, and $R^1$ represents any substituents indicated in [Table L1] to [Table L3] (hereinafter, referred to as Compound Class $SX_{231}$).

A compound (L-2) wherein T represents a group represented by T18, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{232}$).

A compound (L-2) wherein T represents a group represented by T18, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{233}$).

A compound (L-2) wherein T represents a group represented by T18, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{234}$).

A compound (L-2) wherein T represents a group represented by T18, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{235}$).

A compound (L-2) wherein T represents a group represented by T18, $R^{3b}$ represents a hydrogen atom, $R^{3c}$ represents a bromine atom and $R^1$ represents any substituents indicated in [Table L1] to [Table L3] (hereinafter, referred to as Compound Class $SX_{236}$).

A compound (L-2) wherein T represents a group represented by T18, $R^{3b}$ represents a hydrogen atom, $R^{3c}$ represents an iodine atom and $R^1$ represents any substituents indicated in [Table L1] to [Table L3] (hereinafter, referred to as Compound Class $SX_{237}$).

A compound (L-2) wherein T represents a group represented by T19, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{238}$).

A compound (L-2) wherein T represents a group represented by T19, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{239}$).

A compound (L-2) wherein T represents a group represented by T19, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{240}$).

A compound (L-2) wherein T represents a group represented by T19, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{241}$).

A compound (L-2) wherein T represents a group represented by T19, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{242}$).

A compound (L-2) wherein T represents a group represented by T19, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{243}$).

A compound (L-2) wherein T represents a group represented by T19, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{244}$).

A compound (L-2) wherein T represents a group represented by T19, $R^{3b}$ represents a hydrogen atom, $R^{3c}$ represents a bromine atom and $R^1$ represents any substituents indicated in [Table L1] to [Table L3] (hereinafter, referred to as Compound Class $SX_{245}$).

A compound (L-2) wherein T represents a group represented by T19, $R^{3b}$ represents a hydrogen atom, $R^{3c}$ represents an iodine atom and $R^1$ represents any substituents indicated in [Table L1] to [Table L3] (hereinafter, referred to as Compound Class $SX_{246}$).

A compound (L-2) wherein T represents a group represented by T20, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{247}$).

A compound (L-2) wherein T represents a group represented by T20, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{248}$).

A compound (L-2) wherein T represents a group represented by T20, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{249}$).

A compound (L-2) wherein T represents a group represented by T20, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{250}$).

A compound (L-2) wherein T represents a group represented by T20, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{251}$).

A compound (L-2) wherein T represents a group represented by T20, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{252}$).

A compound (L-2) wherein T represents a group represented by T20, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{253}$).

A compound (L-2) wherein T represents a group represented by T20, $R^{3b}$ represents a hydrogen atom, $R^{3c}$ represents a bromine atom and $R^1$ represents any substituents indicated in [Table L1] to [Table L3] (hereinafter, referred to as Compound Class $SX_{254}$).

A compound (L-2) wherein T represents a group represented by T20, $R^{3b}$ represents a hydrogen atom, $R^{3c}$ represents an iodine atom and $R^1$ represents any substituents indicated in [Table L1] to [Table L3] (hereinafter, referred to as Compound Class $SX_{255}$).

A compound (L-2) wherein T represents a group represented by T21, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{256}$).

A compound (L-2) wherein T represents a group represented by T20, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{257}$).

A compound (L-2) wherein T represents a group represented by T20, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{258}$).

A compound (L-2) wherein T represents a group represented by T20, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{259}$).

A compound (L-2) wherein T represents a group represented by T20, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{260}$).

A compound (L-2) wherein T represents a group represented by T20, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{261}$).

A compound (L-2) wherein T represents a group represented by T20, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{262}$).

A compound (L-2) wherein T represents a group represented by T20, $R^{3b}$ represents a hydrogen atom, $R^{3c}$ represents a bromine atom and $R^1$ represents any substituents indicated in [Table L1] to [Table L3] (hereinafter, referred to as Compound Class $SX_{263}$).

A compound (L-2) wherein T represents a group represented by T20, $R^{3b}$ represents a hydrogen atom, $R^{3c}$ represents an iodine atom and $R^1$ represents any substituents indicated in [Table L1] to [Table L3] (hereinafter, referred to as Compound Class $SX_{264}$).

A compound (L-2) wherein T represents a group represented by T22, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{265}$).

A compound (L-2) wherein T represents a group represented by T22, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{266}$).

A compound (L-2) wherein T represents a group represented by T22, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{267}$).

A compound (L-2) wherein T represents a group represented by T22, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{268}$).

A compound (L-2) wherein T represents a group represented by T22, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{269}$).

A compound (L-2) wherein T represents a group represented by T22, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{270}$).

A compound (L-2) wherein T represents a group represented by T22, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{271}$).

A compound (L-2) wherein T represents a group represented by T22, $R^{3b}$ represents a hydrogen atom, $R^{3c}$ represents a bromine atom and $R^1$ represents any substituents indicated in [Table L1] to [Table L3] (hereinafter, referred to as Compound Class $SX_{272}$).

A compound (L-2) wherein T represents a group represented by T22, $R^{3b}$ represents a hydrogen atom, $R^{3c}$ represents an iodine atom and $R^1$ represents any substituents indicated in [Table L1] to [Table L3] (hereinafter, referred to as Compound Class $SX_{273}$).

A compound (L-2) wherein T represents a group represented by T23, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{274}$).

A compound (L-2) wherein T represents a group represented by T23, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{275}$).

A compound (L-2) wherein T represents a group represented by T23, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{276}$).

A compound (L-2) wherein T represents a group represented by T23, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{277}$).

A compound (L-2) wherein T represents a group represented by T23, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{278}$).

A compound (L-2) wherein T represents a group represented by T23, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{279}$).

A compound (L-2) wherein T represents a group represented by T23, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{280}$).

A compound (L-2) wherein T represents a group represented by T23, $R^{3b}$ represents a hydrogen atom, $R^{3c}$ represents a bromine atom and $R^1$ represents any substituents indicated in [Table L1] to [Table L3] (hereinafter, referred to as Compound Class $SX_{281}$).

A compound (L-2) wherein T represents a group represented by T23, $R^{3b}$ represents a hydrogen atom, $R^{3c}$ represents an iodine atom and $R^1$ represents any substituents indicated in [Table L1] to [Table L3] (hereinafter, referred to as Compound Class $SX_{282}$).

A compound (L-2) wherein T represents a group represented by T24, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{283}$).

A compound (L-2) wherein T represents a group represented by T24, $R^{3b}$ represents $CF_3$, $R^7$ represents a hydrogen atom, and $R^1$ represents any substituents indicated in [Table L1] to [Table L3] (hereinafter, referred to as Compound Class $SX_{284}$).

A compound (L-2) wherein T represents a group represented by T24, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{285}$).

A compound (L-2) wherein T represents a group represented by T24, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{286}$).

A compound (L-2) wherein T represents a group represented by T24, $R^{1b}$ represents an iodine atom, $R^{3c}$ represents a hydrogen atom, and $R^1$ represents any substituents indicated in [Table L1] to [Table L3] (hereinafter, referred to as Compound Class $SX_{287}$).

A compound (L-2) wherein T represents a group represented by T24, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{288}$).

A compound (L-2) wherein T represents a group represented by T24, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{289}$).

A compound (L-2) wherein T represents a group represented by T24, $R^{3b}$ represents a hydrogen atom, $R^{3c}$ represents a bromine atom and $R^1$ represents any substituents indicated in [Table L1] to [Table L3] (hereinafter, referred to as Compound Class $SX_{290}$).

A compound (L-2) wherein T represents a group represented by T24, $R^{3b}$ represents a hydrogen atom, $R^{3c}$ represents an iodine atom and $R^1$ represents any substituents indicated in [Table L1] to [Table L3] (hereinafter, referred to as Compound Class $SX_{291}$).

A compound (L-2) wherein T represents a group represented by T25, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{292}$).

A compound (L-2) wherein T represents a group represented by T25, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{293}$).

A compound (L-2) wherein T represents a group represented by T25, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{294}$).

A compound (L-2) wherein T represents a group represented by T25, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{295}$).

A compound (L-2) wherein T represents a group represented by T25, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{296}$).

A compound (L-2) wherein T represents a group represented by T25, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{297}$).

A compound (L-2) wherein T represents a group represented by T25, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{298}$).

A compound (L-2) wherein T represents a group represented by T25, $R^{3b}$ represents a hydrogen atom, $R^{3c}$ represents a bromine atom and $R^1$ represents any substituents indicated in [Table L1] to [Table L3] (hereinafter, referred to as Compound Class $SX_{299}$).

A compound (L-2) wherein T represents a group represented by T25, $R^{3b}$ represents a hydrogen atom, $R^{3c}$ represents an iodine atom and $R^1$ represents any substituents indicated in [Table L1] to [Table L3] (hereinafter, referred to as Compound Class $SX_{300}$).

A compound (L-2) wherein T represents a group represented by T26, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{301}$).

A compound (L-2) wherein T represents a group represented by T26, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{302}$).

A compound (L-2) wherein T represents a group represented by T26, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{303}$).

A compound (L-2) wherein T represents a group represented by T26, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{304}$).

A compound (L-2) wherein T represents a group represented by T26, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{305}$).

A compound (L-2) wherein T represents a group represented by T26, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{306}$).

A compound (L-2) wherein T represents a group represented by T26, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{307}$).

A compound (L-2) wherein T represents a group represented by T26, $R^{3b}$ represents a hydrogen atom, $R^{3c}$ represents a bromine atom and $R^1$ represents any substituents indicated in [Table L1] to [Table L3] (hereinafter, referred to as Compound Class $SX_{308}$).

A compound (L-2) wherein T represents a group represented by T26, $R^{3b}$ represents a hydrogen atom, $R^{3c}$ represents an iodine atom and $R^1$ represents any substituents indicated in [Table L1] to [Table L3] (hereinafter, referred to as Compound Class $SX_{309}$).

A compound (L-2) wherein T represents a group represented by T27, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{310}$).

A compound (L-2) wherein T represents a group represented by T27, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{311}$).

A compound (L-2) wherein T represents a group represented by T27, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{312}$).

A compound (L-2) wherein T represents a group represented by T27, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{313}$).

A compound (L-2) wherein T represents a group represented by T27, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{314}$).

A compound (L-2) wherein T represents a group represented by T27, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{315}$).

A compound (L-2) wherein T represents a group represented by T27, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{316}$).

A compound (L-2) wherein T represents a group represented by T27, $R^{3b}$ represents a hydrogen atom, $R^{3c}$ represents a bromine atom and $R^1$ represents any substituents indicated in [Table L1] to [Table L3] (hereinafter, referred to as Compound Class $SX_{317}$).

A compound (L-2) wherein T represents a group represented by T27, $R^{3b}$ represents a hydrogen atom, $R^{3c}$ represents an iodine atom and $R^1$ represents any substituents indicated in [Table L1] to [Table L3] (hereinafter, referred to as Compound Class $SX_{318}$).

A compound (L-2) wherein T represents a group represented by T28, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{319}$).

A compound (L-2) wherein T represents a group represented by T28, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{320}$).

A compound (L-2) wherein T represents a group represented by T28, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{321}$).

A compound (L-2) wherein T represents a group represented by T28, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{322}$).

A compound (L-2) wherein T represents a group represented by T28, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{323}$).

A compound (L-2) wherein T represents a group represented by T28, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{324}$).

A compound (L-2) wherein T represents a group represented by T28, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{325}$).

A compound (L-2) wherein T represents a group represented by T28, $R^{3b}$ represents a hydrogen atom, $R^{3c}$ represents a bromine atom and $R^1$ represents any substituents indicated in [Table L1] to [Table L3] (hereinafter, referred to as Compound Class $SX_{326}$).

A compound (L-2) wherein T represents a group represented by T28, $R^{3b}$ represents a hydrogen atom, $R^{3c}$ represents sents an iodine atom and $R^1$ represents any substituents indicated in [Table L1] to [Table L3] (hereinafter, referred to as Compound Class $SX_{327}$).

A compound (L-2) wherein T represents a group represented by T29, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{328}$).

A compound (L-2) wherein T represents a group represented by T29, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{329}$).

A compound (L-2) wherein T represents a group represented by T29, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{330}$).

A compound (L-2) wherein T represents a group represented by T29, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{331}$).

A compound (L-2) wherein T represents a group represented by T29, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{332}$).

A compound (L-2) wherein T represents a group represented by T29, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{333}$).

A compound (L-2) wherein T represents a group represented by T29, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{334}$).

A compound (L-2) wherein T represents a group represented by T29, $R^{3b}$ represents a hydrogen atom, $R^{3c}$ represents a bromine atom and $R^1$ represents any substituents indicated in [Table L1] to [Table L3] (hereinafter, referred to as Compound Class $SX_{335}$).

A compound (L-2) wherein T represents a group represented by T29, $R^{3b}$ represents a hydrogen atom, $R^{3c}$ represents an iodine atom and $R^1$ represents any substituents indicated in [Table L1] to [Table L3] (hereinafter, referred to as Compound Class $SX_{336}$).

A compound (L-2) wherein T represents a group represented by T30, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{337}$).

A compound (L-2) wherein T represents a group represented by T30, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{338}$).

A compound (L-2) wherein T represents a group represented by T30, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{339}$).

A compound (L-2) wherein T represents a group represented by T30, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{340}$).

A compound (L-2) wherein T represents a group represented by T30, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{341}$).

A compound (L-2) wherein T represents a group represented by T30, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{342}$).

A compound (L-2) wherein T represents a group represented by T30, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{343}$).

A compound (L-2) wherein T represents a group represented by T30, $R^{3b}$ represents a hydrogen atom, $R^{3c}$ represents a bromine atom and $R^1$ represents any substituents indicated in [Table L1] to [Table L3] (hereinafter, referred to as Compound Class $SX_{344}$).

A compound (L-2) wherein T represents a group represented by T30, $R^{3b}$ represents a hydrogen atom, $R^{3c}$ represents an iodine atom and $R^1$ represents any substituents indicated in [Table L1] to [Table L3] (hereinafter, referred to as Compound Class $SX_{345}$).

A compound (L-2) wherein T represents a group represented by T31, $R^{3b}$ represents a hydrogen atom, $R^{3c}$ represents a hydrogen atom and $R^1$ represents any substituents indicated in [Table L1] to [Table L3] (hereinafter, referred to as Compound Class $SX_{346}$).

A compound (L-2) wherein T represents a group represented by T31, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{347}$).

A compound (L-2) wherein T represents a group represented by T31, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{348}$).

A compound (L-2) wherein T represents a group represented by T31, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{349}$).

A compound (L-2) wherein T represents a group represented by T31, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{350}$).

A compound (L-2) wherein T represents a group represented by T31, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{351}$).

A compound (L-2) wherein T represents a group represented by T31, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{352}$).

A compound (L-2) wherein T represents a group represented by T31, $R^{3b}$ represents a hydrogen atom, $R^{3c}$ represents sents a bromine atom and $R^1$ represents any substituents indicated in [Table L1] to [Table L3] (hereinafter, referred to as Compound Class $SX_{353}$).

A compound (L-2) wherein T represents a group represented by T31, $R^{3b}$ represents a hydrogen atom, $R^{3c}$ represents an iodine atom and $R^1$ represents any substituents indicated in [Table L1] to [Table L3] (hereinafter, referred to as Compound Class $SX_{354}$).

A compound represented by formula (L-3):

(L-3)

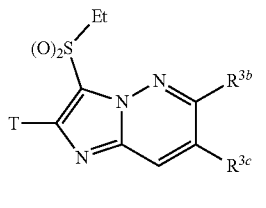

(hereinafter, referred to as compound (L-3)), wherein T represents a group represented by T1, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{355}$).

A compound (L-3) wherein T represents a group represented by T1, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{336}$).

A compound (L-3) wherein T represents a group represented by T1, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{357}$).

A compound (L-3) wherein T represents a group represented by T1, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{358}$).

A compound (L-3) wherein T represents a group represented by T1, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{359}$).

A compound (L-3) wherein T represents a group represented by T1, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{360}$).

A compound (L-3) wherein T represents a group represented by T1, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{361}$).

A compound (L-3) wherein T represents a group represented by T1, $R^{3b}$ represents a hydrogen atom, $R^{3c}$ represents a bromine atom and $R^1$ represents any substituents indicated in [Table L1] to [Table L3] (hereinafter, referred to as Compound Class $SX_{362}$).

A compound (L-3) wherein T represents a group represented by T1, $R^{3b}$ represents a hydrogen atom, $R^{3c}$ represents an iodine atom and $R^1$ represents any substituents indicated in [Table L1] to [Table L3] (hereinafter, referred to as Compound Class $SX_{363}$).

A compound (L-3) wherein T represents a group represented by T2, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{364}$).

A compound (L-3) wherein T represents a group represented by T2, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{365}$).

A compound (L-3) wherein T represents a group represented by T2, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{366}$).

A compound (L-3) wherein T represents a group represented by T2, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{367}$).

A compound (L-3) wherein T represents a group represented by T2, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{368}$).

A compound (L-3) wherein T represents a group represented by T2, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{369}$).

A compound (L-3) wherein T represents a group represented by T2, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{370}$).

A compound (L-3) wherein T represents a group represented by T2, $R^{3b}$ represents a hydrogen atom, $R^{3c}$ represents a bromine atom and $R^1$ represents any substituents indicated in [Table L1] to [Table L3] (hereinafter, referred to as Compound Class $SX_{371}$).

A compound (L-3) wherein T represents a group represented by T2, $R^{3b}$ represents a hydrogen atom, $R^{3c}$ represents an iodine atom and $R^1$ represents any substituents indicated in [Table L1] to [Table L3] (hereinafter, referred to as Compound Class $SX_{372}$).

A compound (L-3) wherein T represents a group represented by T3, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{373}$).

A compound (L-3) wherein T represents a group represented by T3, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{374}$).

A compound (L-3) wherein T represents a group represented by T3, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{375}$).

A compound (L-3) wherein T represents a group represented by T3, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{376}$).

A compound (L-3) wherein T represents a group represented by T3, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{377}$).

A compound (L-3) wherein T represents a group represented by T3, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{378}$).

A compound (L-3) wherein T represents a group represented by T3, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{379}$).

A compound (L-3) wherein T represents a group represented by T3, $R^{3b}$ represents a hydrogen atom, $R^{3c}$ represents a bromine atom and $R^1$ represents any substituents indicated in [Table L1] to [Table L3] (hereinafter, referred to as Compound Class $SX_{380}$).

A compound (L-3) wherein T represents a group represented by T3, $R^{3b}$ represents a hydrogen atom, $R^{3c}$ represents an iodine atom and $R^1$ represents any substituents indicated in [Table L1] to [Table L3] (hereinafter, referred to as Compound Class $SX_{381}$).

A compound (L-3) wherein T represents a group represented by T4, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{382}$).

A compound (L-3) wherein T represents a group represented by T4, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{383}$).

A compound (L-3) wherein T represents a group represented by T4, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{384}$).

A compound (L-3) wherein T represents a group represented by T4, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{385}$).

A compound (L-3) wherein T represents a group represented by T4, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{386}$).

A compound (L-3) wherein T represents a group represented by T4, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{387}$).

A compound (L-3) wherein T represents a group represented by T4, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{388}$).

A compound (L-3) wherein T represents a group represented by T4, $R^{3b}$ represents a hydrogen atom, $R^{3c}$ represents a bromine atom and $R^1$ represents any substituents indicated in [Table L1] to [Table L3] (hereinafter, referred to as Compound Class $SX_{389}$).

A compound (L-3) wherein T represents a group represented by T4, $R^{3b}$ represents a hydrogen atom, $R^{3c}$ represents an iodine atom and $R^1$ represents any substituents indicated in [Table L1] to [Table L3] (hereinafter, referred to as Compound Class $SX_{390}$).

A compound (L-3) wherein T represents a group represented by T5, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{391}$).

A compound (L-3) wherein T represents a group represented by T5, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{392}$).

A compound (L-3) wherein T represents a group represented by T5, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{393}$).

A compound (L-3) wherein T represents a group represented by T5, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{394}$).

A compound (L-3) wherein T represents a group represented by T5, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{395}$).

A compound (L-3) wherein T represents a group represented by T5, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{396}$).

A compound (L-3) wherein T represents a group represented by T5, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{397}$).

A compound (L-3) wherein T represents a group represented by T5, $R^{3b}$ represents a hydrogen atom, $R^{3c}$ represents a bromine atom and $R^1$ represents any substituents indicated in [Table L1] to [Table L3] (hereinafter, referred to as Compound Class $SX_{398}$).

A compound (L-3) wherein T represents a group represented by T5, $R^{3b}$ represents a hydrogen atom, $R^{3c}$ represents an iodine atom and $R^1$ represents any substituents indicated in [Table L1] to [Table L3] (hereinafter, referred to as Compound Class $SX_{399}$).

A compound (L-3) wherein T represents a group represented by T6, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{400}$).

A compound (L-3) wherein T represents a group represented by T6, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{401}$).

A compound (L-3) wherein T represents a group represented by T6, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{402}$).

A compound (L-3) wherein T represents a group represented by T6, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{403}$).

A compound (L-3) wherein T represents a group represented by T6, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{404}$).

A compound (L-3) wherein T represents a group represented by T6, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{405}$).

A compound (L-3) wherein T represents a group represented by T6, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{406}$).

A compound (L-3) wherein T represents a group represented by T6, $R^{3b}$ represents a hydrogen atom, $R^{3c}$ represents a bromine atom and $R^1$ represents any substituents indicated in [Table L1] to [Table L3] (hereinafter, referred to as Compound Class $SX_{407}$).

A compound (L-3) wherein T represents a group represented by T6, $R^{3b}$ represents a hydrogen atom, $R^{3c}$ represents an iodine atom and $R^1$ represents any substituents indicated in [Table L1] to [Table L3] (hereinafter, referred to as Compound Class $SX_{408}$).

A compound (L-3) wherein T represents a group represented by T7, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{409}$).

A compound (L-3) wherein T represents a group represented by T7, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{410}$).

A compound (L-3) wherein T represents a group represented by T7, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{411}$).

A compound (L-3) wherein T represents a group represented by T7, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{412}$).

A compound (L-3) wherein T represents a group represented by T7, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{413}$).

A compound (L-3) wherein T represents a group represented by T7, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{414}$).

A compound (L-3) wherein T represents a group represented by T7, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{415}$).

A compound (L-3) wherein T represents a group represented by T7, $R^{3b}$ represents a hydrogen atom, $R^{3c}$ represents a bromine atom and $R^1$ represents any substituents indicated in [Table L1] to [Table L3] (hereinafter, referred to as Compound Class $SX_{416}$).

A compound (L-3) wherein T represents a group represented by T7, $R^{3b}$ represents a hydrogen atom, $R^{3c}$ represents an iodine atom and $R^1$ represents any substituents indicated in [Table L1] to [Table L3] (hereinafter, referred to as Compound Class $SX_{417}$).

A compound (L-3) wherein T represents a group represented by T8, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{418}$).

A compound (L-3) wherein T represents a group represented by T8, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{419}$).

A compound (L-3) wherein T represents a group represented by T8, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{420}$).

A compound (L-3) wherein T represents a group represented by T8, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{421}$).

A compound (L-3) wherein T represents a group represented by T8, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{422}$).

A compound (L-3) wherein T represents a group represented by T8, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{423}$).

A compound (L-3) wherein T represents a group represented by T8, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{424}$).

A compound (L-3) wherein T represents a group represented by T8, $R^{3b}$ represents a hydrogen atom, $R^{3c}$ represents a bromine atom and $R^1$ represents any substituents indicated in [Table L1] to [Table L3] (hereinafter, referred to as Compound Class $SX_{425}$).

A compound (L-3) wherein T represents a group represented by T8, $R^{3b}$ represents a hydrogen atom, $R^{3c}$ represents an iodine atom and $R^1$ represents any substituents indicated in [Table L1] to [Table L3] (hereinafter, referred to as Compound Class $SX_{426}$).

A compound (L-3) wherein T represents a group represented by T9, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{427}$).

A compound (L-3) wherein T represents a group represented by T9, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{428}$).

A compound (L-3) wherein T represents a group represented by T9, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{429}$).

A compound (L-3) wherein T represents a group represented by T9, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{430}$).

A compound (L-3) wherein T represents a group represented by T9, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{431}$).

A compound (L-3) wherein T represents a group represented by T9, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{432}$).

A compound (L-3) wherein T represents a group represented by T9, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{433}$).

A compound (L-3) wherein T represents a group represented by T9, $R^{3b}$ represents a hydrogen atom, $R^{3c}$ represents a bromine atom and $R^1$ represents any substituents indicated in [Table L1] to [Table L3] (hereinafter, referred to as Compound Class $SX_{434}$).

A compound (L-3) wherein T represents a group represented by T9, $R^{3b}$ represents a hydrogen atom, $R^{3c}$ represents an iodine atom and $R^1$ represents any substituents indicated in [Table L1] to [Table L3] (hereinafter, referred to as Compound Class $SX_{435}$).

A compound (L-3) wherein T represents a group represented by T10, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{436}$).

A compound (L-3) wherein T represents a group represented by T10, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{437}$).

A compound (L-3) wherein T represents a group represented by T10, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{438}$).

A compound (L-3) wherein T represents a group represented by T10, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{439}$).

A compound (L-3) wherein T represents a group represented by T10, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{440}$).

A compound (L-3) wherein T represents a group represented by T10, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{441}$).

A compound (L-3) wherein T represents a group represented by T10, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{442}$).

A compound (L-3) wherein T represents a group represented by T10, $R^{3b}$ represents a hydrogen atom, $R^{3c}$ represents a bromine atom and $R^1$ represents any substituents indicated in [Table L1] to [Table L3] (hereinafter, referred to as Compound Class $SX_{443}$).

A compound (L-3) wherein T represents a group represented by T10, $R^{3b}$ represents a hydrogen atom, $R^{3c}$ represents an iodine atom and $R^1$ represents any substituents indicated in [Table L1] to [Table L3] (hereinafter, referred to as Compound Class $SX_{444}$).

A compound (L-3) wherein T represents a group represented by T11, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{445}$).

A compound (L-3) wherein T represents a group represented by T11, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{446}$).

A compound (L-3) wherein T represents a group represented by T11, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{447}$).

A compound (L-3) wherein T represents a group represented by T11, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{448}$).

A compound (L-3) wherein T represents a group represented by T11, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{449}$).

A compound (L-3) wherein T represents a group represented by T11, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{450}$).

A compound (L-3) wherein T represents a group represented by T11, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{451}$).

A compound (L-3) wherein T represents a group represented by T11, $R^{3b}$ represents a hydrogen atom, $R^{3c}$ represents a bromine atom and $R^1$ represents any substituents indicated in [Table L1] to [Table L3] (hereinafter, referred to as Compound Class $SX_{452}$).

A compound (L-3) wherein T represents a group represented by T11, $R^{3b}$ represents a hydrogen atom, $R^{3c}$ represents an iodine atom and $R^1$ represents any substituents indicated in [Table L1] to [Table L3] (hereinafter, referred to as Compound Class $SX_{453}$).

A compound (L-3) wherein T represents a group represented by T12, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{454}$).

A compound (L-3) wherein T represents a group represented by T12, $R^{3c}$ represents $CF_3$, $R^{3c}$ represents a hydrogen atom, and $R^1$ represents any substituents indicated in [Table L1] to [Table L3] (hereinafter, referred to as Compound Class $SX_{455}$).

A compound (L-3) wherein T represents a group represented by T12, $R^{3c}$ represents a chlorine atom, $R^{3c}$ represents a hydrogen atom, and $R^1$ represents any substituents indicated in [Table L1] to [Table L3] (hereinafter, referred to as Compound Class $SX_{456}$).

A compound (L-3) wherein T represents a group represented by T12, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{457}$).

A compound (L-3) wherein T represents a group represented by T12, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{458}$).

A compound (L-3) wherein T represents a group represented by T12, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{459}$).

A compound (L-3) wherein T represents a group represented by T12, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{460}$).

A compound (L-3) wherein T represents a group represented by T12, $R^{3b}$ represents a hydrogen atom, $R^{3c}$ represents a bromine atom and $R^1$ represents any substituents indicated in [Table L1] to [Table L3] (hereinafter, referred to as Compound Class $SX_{461}$).

A compound (L-3) wherein T represents a group represented by T12, $R^{3b}$ represents a hydrogen atom, $R^{3c}$ represents an iodine atom and $R^1$ represents any substituents indicated in [Table L1] to [Table L3] (hereinafter, referred to as Compound Class $SX_{462}$).

A compound (L-3) wherein T represents a group represented by T13, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{463}$).

A compound (L-3) wherein T represents a group represented by T13, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{464}$).

A compound (L-3) wherein T represents a group represented by T13, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{465}$).

A compound (L-3) wherein T represents a group represented by T13, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{466}$).

A compound (L-3) wherein T represents a group represented by T13, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{467}$).

A compound (L-3) wherein T represents a group represented by T13, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{468}$).

A compound (L-3) wherein T represents a group represented by T13, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{469}$).

A compound (L-3) wherein T represents a group represented by T13, $R^{3b}$ represents a hydrogen atom, $R^{3c}$ represents a bromine atom and $R^1$ represents any substituents indicated in [Table L1] to [Table L3] (hereinafter, referred to as Compound Class $SX_{470}$).

A compound (L-3) wherein T represents a group represented by T13, $R^{3b}$ represents a hydrogen atom, $R^{3c}$ represents an iodine atom and $R^1$ represents any substituents indicated in [Table L1] to [Table L3] (hereinafter, referred to as Compound Class $SX_{471}$).

A compound (L-3) wherein T represents a group represented by T14, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{472}$).

A compound (L-3) wherein T represents a group represented by T14, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{473}$).

A compound (L-3) wherein T represents a group represented by T14, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{474}$).

A compound (L-3) wherein T represents a group represented by T14, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{475}$).

A compound (L-3) wherein T represents a group represented by T14, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{476}$).

A compound (L-3) wherein T represents a group represented by T14, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{477}$).

A compound (L-3) wherein T represents a group represented by T14, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{478}$).

A compound (L-3) wherein T represents a group represented by T14, $R^{3b}$ represents a hydrogen atom, $R^{3c}$ represents a bromine atom and $R^1$ represents any substituents indicated in [Table L1] to [Table L3] (hereinafter, referred to as Compound Class $SX_{479}$).

A compound (L-3) wherein T represents a group represented by T14, $R^{3b}$ represents a hydrogen atom, $R^{3c}$ represents an iodine atom and $R^1$ represents any substituents indicated in [Table L1] to [Table L3] (hereinafter, referred to as Compound Class $SX_{480}$).

A compound (L-3) wherein T represents a group represented by T15, $R^{3b}$ represents a hydrogen atom, $R^{3c}$ represents sents a hydrogen atom, and $R^1$ represents any substituents indicated in [Table L1] to [Table L3] (hereinafter, referred to as Compound Class $SX_{481}$).

A compound (L-3) wherein T represents a group represented by T15, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{482}$).

A compound (L-3) wherein T represents a group represented by T15, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{483}$).

A compound (L-3) wherein T represents a group represented by T15, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{484}$).

A compound (L-3) wherein T represents a group represented by T15, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{485}$).

A compound (L-3) wherein T represents a group represented by T15, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{486}$).

A compound (L-3) wherein T represents a group represented by T15, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{487}$).

A compound (L-3) wherein T represents a group represented by T15, $R^{3b}$ represents a hydrogen atom, $R^{3c}$ represents a bromine atom and $R^1$ represents any substituents indicated in [Table L1] to [Table L3] (hereinafter, referred to as Compound Class $SX_{488}$).

A compound (L-3) wherein T represents a group represented by T15, $R^{3b}$ represents a hydrogen atom, $R^{3c}$ represents an iodine atom and $R^1$ represents any substituents indicated in [Table L1] to [Table L3] (hereinafter, referred to as Compound Class $SX_{489}$).

A compound (L-3) wherein T represents a group represented by T16, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{490}$).

A compound (L-3) wherein T represents a group represented by T16, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{491}$).

A compound (L-3) wherein T represents a group represented by T16, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{492}$).

A compound (L-3) wherein T represents a group represented by T16, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{493}$).

A compound (L-3) wherein T represents a group represented by T16, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{494}$).

A compound (L-3) wherein T represents a group represented by T16, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{495}$).

A compound (L-3) wherein T represents a group represented by T16, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{496}$).

A compound (L-3) wherein T represents a group represented by T16, $R^{3b}$ represents a hydrogen atom, $R^{3c}$ represents a bromine atom and $R^1$ represents any substituents indicated in [Table L1] to [Table L3] (hereinafter, referred to as Compound Class $SX_{497}$).

A compound (L-3) wherein T represents a group represented by T16, $R^{3b}$ represents a hydrogen atom, $R^{3c}$ represents an iodine atom and $R^1$ represents any substituents indicated in [Table L1] to [Table L3] (hereinafter, referred to as Compound Class $SX_{498}$).

A compound (L-3) wherein T represents a group represented by T17, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{499}$).

A compound (L-3) wherein T represents a group represented by T17, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{500}$).

A compound (L-3) wherein T represents a group represented by T17, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{501}$).

A compound (L-3) wherein T represents a group represented by T17, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{502}$).

A compound (L-3) wherein T represents a group represented by T17, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{503}$).

A compound (L-3) wherein T represents a group represented by T17, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{504}$).

A compound (L-3) wherein T represents a group represented by T17, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{505}$).

A compound (L-3) wherein T represents a group represented by T17, $R^{3b}$ represents a hydrogen atom, $R^{3c}$ represents a bromine atom and $R^1$ represents any substituents indicated in [Table L1] to [Table L3] (hereinafter, referred to as Compound Class $SX_{506}$).

A compound (L-3) wherein T represents a group represented by T17, $R^{3b}$ represents a hydrogen atom, $R^{3c}$ represents an iodine atom and $R^1$ represents any substituents indicated in [Table L1] to [Table L3] (hereinafter, referred to as Compound Class $SX_{507}$).

A compound (L-3) wherein T represents a group represented by T18, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{508}$).

A compound (L-3) wherein T represents a group represented by T18, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{509}$).

A compound (L-3) wherein T represents a group represented by T18, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{510}$).

A compound (L-3) wherein T represents a group represented by T18, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{511}$).

A compound (L-3) wherein T represents a group represented by T18, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{512}$).

A compound (L-3) wherein T represents a group represented by T18, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{513}$).

A compound (L-3) wherein T represents a group represented by T18, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{514}$).

A compound (L-3) wherein T represents a group represented by T18, $R^{3b}$ represents a hydrogen atom, $R^{3c}$ represents a bromine atom and $R^1$ represents any substituents indicated in [Table L1] to [Table L3] (hereinafter, referred to as Compound Class $SX_{515}$).

A compound (L-3) wherein T represents a group represented by T18, $R^{3b}$ represents a hydrogen atom, $R^{3c}$ represents an iodine atom and $R^1$ represents any substituents indicated in [Table L1] to [Table L3] (hereinafter, referred to as Compound Class $SX_{516}$).

A compound (L-3) wherein T represents a group represented by T19, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{517}$).

A compound (L-3) wherein T represents a group represented by T19, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{518}$).

A compound (L-3) wherein T represents a group represented by T19, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{519}$).

A compound (L-3) wherein T represents a group represented by T19, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{520}$).

A compound (L-3) wherein T represents a group represented by T19, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{521}$).

A compound (L-3) wherein T represents a group represented by T19, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{522}$).

A compound (L-3) wherein T represents a group represented by T19, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{523}$).

A compound (L-3) wherein T represents a group represented by T19, $R^{3b}$ represents a hydrogen atom, $R^{3c}$ represents a bromine atom and $R^1$ represents any substituents indicated in [Table L1] to [Table L3] (hereinafter, referred to as Compound Class $SX_{524}$).

A compound (L-3) wherein T represents a group represented by T19, $R^{3b}$ represents a hydrogen atom, $R^{3c}$ represents an iodine atom and $R^1$ represents any substituents indicated in [Table L1] to [Table L3] (hereinafter, referred to as Compound Class $SX_{525}$).

A compound (L-3) wherein T represents a group represented by T20, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{526}$).

A compound (L-3) wherein T represents a group represented by T20, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{527}$).

A compound (L-3) wherein T represents a group represented by T20, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{528}$).

A compound (L-3) wherein T represents a group represented by T20, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{529}$).

A compound (L-3) wherein T represents a group represented by T20, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{530}$).

A compound (L-3) wherein T represents a group represented by T20, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{531}$).

A compound (L-3) wherein T represents a group represented by T20, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{532}$).

A compound (L-3) wherein T represents a group represented by T20, $R^{3b}$ represents a hydrogen atom, $R^{3c}$ represents a bromine atom and $R^1$ represents any substituents indicated in [Table L1] to [Table L3] (hereinafter, referred to as Compound Class $SX_{533}$).

A compound (L-3) wherein T represents a group represented by T20, $R^{3b}$ represents a hydrogen atom, $R^{3c}$ represents an iodine atom and $R^1$ represents any substituents indicated in [Table L1] to [Table L3] (hereinafter, referred to as Compound Class $SX_{534}$).

A compound (L-3) wherein T represents a group represented by T21, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{535}$).

A compound (L-3) wherein T represents a group represented by T21, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{536}$).

A compound (L-3) wherein T represents a group represented by T21, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{537}$).

A compound (L-3) wherein T represents a group represented by T21, $R^{3b}$ represents a bromine atom, $R^3$ represents a hydrogen atom, and $R^1$ represents any substituents indicated in [Table L1] to [Table L3] (hereinafter, referred to as Compound Class $SX_{538}$).

A compound (L-3) wherein T represents a group represented by T21, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{539}$).

A compound (L-3) wherein T represents a group represented by T21, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{540}$).

A compound (L-3) wherein T represents a group represented by T21, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{541}$).

A compound (L-3) wherein T represents a group represented by T21, $R^{3b}$ represents a hydrogen atom, $R^{3c}$ represents a bromine atom and $R^1$ represents any substituents indicated in [Table L1] to [Table L3] (hereinafter, referred to as Compound Class $SX_{542}$).

A compound (L-3) wherein T represents a group represented by T21, $R^{3b}$ represents a hydrogen atom, $R^{3c}$ represents an iodine atom and $R^1$ represents any substituents indicated in [Table L1] to [Table L3] (hereinafter, referred to as Compound Class $SX_{543}$).

A compound (L-3) wherein T represents a group represented by T22, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{544}$).

A compound (L-3) wherein T represents a group represented by T22, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{545}$).

A compound (L-3) wherein T represents a group represented by T22, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{546}$).

A compound (L-3) wherein T represents a group represented by T22, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{547}$).

A compound (L-3) wherein T represents a group represented by T22, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{548}$).

A compound (L-3) wherein T represents a group represented by T22, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{549}$).

A compound (L-3) wherein T represents a group represented by T22, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{550}$).

A compound (L-3) wherein T represents a group represented by T22, $R^{3b}$ represents a hydrogen atom, $R^{3c}$ represents a bromine atom and $R^1$ represents any substituents indicated in [Table L1] to [Table L3] (hereinafter, referred to as Compound Class $SX_{551}$).

A compound (L-3) wherein T represents a group represented by T22, $R^{3b}$ represents a hydrogen atom, $R^{3c}$ represents an iodine atom and $R^1$ represents any substituents indicated in [Table L1] to [Table L3] (hereinafter, referred to as Compound Class $SX_{552}$).

A compound (L-3) wherein T represents a group represented by T23, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{553}$).

A compound (L-3) wherein T represents a group represented by T23, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{554}$).

A compound (L-3) wherein T represents a group represented by T23, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{555}$).

A compound (L-3) wherein T represents a group represented by T23, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{556}$).

A compound (L-3) wherein T represents a group represented by T23, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{557}$).

A compound (L-3) wherein T represents a group represented by T23, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{558}$).

A compound (L-3) wherein T represents a group represented by T23, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{559}$).

A compound (L-3) wherein T represents a group represented by T23, $R^{3b}$ represents a hydrogen atom, $R^{3c}$ represents a bromine atom and $R^1$ represents any substituents indicated in [Table L1] to [Table L3] (hereinafter, referred to as Compound Class $SX_{560}$).

A compound (L-3) wherein T represents a group represented by T23, $R^{3b}$ represents a hydrogen atom, $R^{3c}$ represents an iodine atom and $R^1$ represents any substituents indicated in [Table L1] to [Table L3] (hereinafter, referred to as Compound Class $SX_{561}$).

A compound (L-3) wherein T represents a group represented by T24, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{562}$).

A compound (L-3) wherein T represents a group represented by T24, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{563}$).

A compound (L-3) wherein T represents a group represented by T24, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{564}$).

A compound (L-3) wherein T represents a group represented by T24, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{565}$).

A compound (L-3) wherein T represents a group represented by T24, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{566}$).

A compound (L-3) wherein T represents a group represented by T24, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{567}$).

A compound (L-3) wherein T represents a group represented by T24, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{568}$).

A compound (L-3) wherein T represents a group represented by T24, $R^{3b}$ represents a hydrogen atom, $R^{3c}$ represents a bromine atom and $R^1$ represents any substituents indicated in [Table L1] to [Table L3] (hereinafter, referred to as Compound Class $SX_{569}$).

A compound (L-3) wherein T represents a group represented by T24, $R^{3b}$ represents a hydrogen atom, $R^{3c}$ represents an iodine atom and $R^1$ represents any substituents indicated in [Table L1] to [Table L3] (hereinafter, referred to as Compound Class $SX_{570}$).

A compound (L-3) wherein T represents a group represented by T25, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{571}$).

A compound (L-3) wherein T represents a group represented by T25, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{572}$).

A compound (L-3) wherein T represents a group represented by T25, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{573}$).

A compound (L-3) wherein T represents a group represented by T25, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{574}$).

A compound (L-3) wherein T represents a group represented by T25, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{575}$).

A compound (L-3) wherein T represents a group represented by T25, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{576}$).

A compound (L-3) wherein T represents a group represented by T25, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{577}$).

A compound (L-3) wherein T represents a group represented by T25, $R^{3b}$ represents a hydrogen atom, $R^{3c}$ represents a bromine atom and $R^1$ represents any substituents indicated in [Table L1] to [Table L3] (hereinafter, referred to as Compound Class $SX_{578}$).

A compound (L-3) wherein T represents a group represented by T25, $R^{3b}$ represents a hydrogen atom, $R^{3c}$ represents an iodine atom and $R^1$ represents any substituents indicated in [Table L1] to [Table L3] (hereinafter, referred to as Compound Class $SX_{579}$).

A compound (L-3) wherein T represents a group represented by T26, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{580}$).

A compound (L-3) wherein T represents a group represented by T26, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{581}$).

A compound (L-3) wherein T represents a group represented by T26, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{582}$).

A compound (L-3) wherein T represents a group represented by T26, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{583}$).

A compound (L-3) wherein T represents a group represented by T26, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{584}$).

A compound (L-3) wherein T represents a group represented by T26, $R^{3b}$ represents a hydrogen atom, $R^{3c}$ represents sents $CF_3$, and $R^1$ represents any substituents indicated in [Table L1] to [Table L3] (hereinafter, referred to as Compound Class $SX_{585}$).

A compound (L-3) wherein T represents a group represented by T26, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{586}$).

A compound (L-3) wherein T represents a group represented by T26, $R^{3b}$ represents a hydrogen atom, $R^{3c}$ represents a bromine atom and $R^1$ represents any substituents indicated in [Table L1] to [Table L3] (hereinafter, referred to as Compound Class $SX_{587}$).

A compound (L-3) wherein T represents a group represented by T26, $R^{3b}$ represents a hydrogen atom, $R^{3c}$ represents an iodine atom and $R^1$ represents any substituents indicated in [Table L1] to [Table L3] (hereinafter, referred to as Compound Class $SX_{588}$).

A compound (L-3) wherein T represents a group represented by T27, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{589}$).

A compound (L-3) wherein T represents a group represented by T27, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{590}$).

A compound (L-3) wherein T represents a group represented by T27, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{591}$).

A compound (L-3) wherein T represents a group represented by T27, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{592}$).

A compound (L-3) wherein T represents a group represented by T27, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{593}$).

A compound (L-3) wherein T represents a group represented by T27, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{594}$).

A compound (L-3) wherein T represents a group represented by T27, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{595}$).

A compound (L-3) wherein T represents a group represented by T27, $R^{3b}$ represents a hydrogen atom, $R^{3c}$ represents a bromine atom and $R^1$ represents any substituents indicated in [Table L1] to [Table L3] (hereinafter, referred to as Compound Class $SX_{596}$).

A compound (L-3) wherein T represents a group represented by T27, $R^{3b}$ represents a hydrogen atom, $R^{3c}$ represents an iodine atom and $R^1$ represents any substituents indicated in [Table L1] to [Table L3] (hereinafter, referred to as Compound Class $SX_{597}$).

A compound (L-3) wherein T represents a group represented by T28, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{598}$).

A compound (L-3) wherein T represents a group represented by T28, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{599}$).

A compound (L-3) wherein T represents a group represented by T28, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{600}$).

A compound (L-3) wherein T represents a group represented by T28, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{601}$).

A compound (L-3) wherein T represents a group represented by T28, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{602}$).

A compound (L-3) wherein T represents a group represented by T28, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{603}$).

A compound (L-3) wherein T represents a group represented by T28, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{604}$).

A compound (L-3) wherein T represents a group represented by T28, $R^{3b}$ represents a hydrogen atom, $R^{3c}$ represents a bromine atom and $R^1$ represents any substituents indicated in [Table L1] to [Table L3] (hereinafter, referred to as Compound Class $SX_{605}$).

A compound (L-3) wherein T represents a group represented by T28, $R^{3b}$ represents a hydrogen atom, $R^{3c}$ represents an iodine atom and $R^1$ represents any substituents indicated in [Table L1] to [Table L3] (hereinafter, referred to as Compound Class $SX_{606}$).

A compound (L-3) wherein T represents a group represented by T29, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{607}$).

A compound (L-3) wherein T represents a group represented by T29, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{608}$).

A compound (L-3) wherein T represents a group represented by T29, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{609}$).

A compound (L-3) wherein T represents a group represented by T29, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{610}$).

A compound (L-3) wherein T represents a group represented by T29, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{611}$).

A compound (L-3) wherein T represents a group represented by T29, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{612}$).

A compound (L-3) wherein T represents a group represented by T29, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{613}$).

A compound (L-3) wherein T represents a group represented by T29, $R^{3b}$ represents a hydrogen atom, $R^{3c}$ represents a bromine atom and $R^1$ represents any substituents indicated in [Table L1] to [Table L3] (hereinafter, referred to as Compound Class $SX_{614}$).

A compound (L-3) wherein T represents a group represented by T29, $R^{3b}$ represents a hydrogen atom, $R^{3c}$ represents an iodine atom and $R^1$ represents any substituents indicated in [Table L1] to [Table L3] (hereinafter, referred to as Compound Class $SX_{615}$).

A compound (L-3) wherein T represents a group represented by T30, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{616}$).

A compound (L-3) wherein T represents a group represented by T30, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{617}$).

A compound (L-3) wherein T represents a group represented by T30, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{618}$).

A compound (L-3) wherein T represents a group represented by T30, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{619}$).

A compound (L-3) wherein T represents a group represented by T30, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{620}$).

A compound (L-3) wherein T represents a group represented by T30, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{621}$).

A compound (L-3) wherein T represents a group represented by T30, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{622}$).

A compound (L-3) wherein T represents a group represented by T30, $R^{3b}$ represents a hydrogen atom, $R^{3c}$ represents a bromine atom and $R^1$ represents any substituents indicated in [Table L1] to [Table L3] (hereinafter, referred to as Compound Class $SX_{623}$).

A compound (L-3) wherein T represents a group represented by T30, $R^{3b}$ represents a hydrogen atom, $R^{3c}$ represents an iodine atom and $R^1$ represents any substituents indicated in [Table L1] to [Table L3] (hereinafter, referred to as Compound Class $SX_{624}$).

A compound (L-3) wherein T represents a group represented by T31, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{625}$).

A compound (L-3) wherein T represents a group represented by T31, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{626}$).

A compound (L-3) wherein T represents a group represented by T31, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{627}$).

A compound (L-3) wherein T represents a group represented by T31, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{628}$).

A compound (L-3) wherein T represents a group represented by T31, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{629}$).

A compound (L-3) wherein T represents a group represented by T31, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{630}$).

A compound (L-3) wherein T represents a group represented by T31, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{631}$).

A compound (L-3) wherein T represents a group represented by T31, $R^{3b}$ represents a hydrogen atom, $R^{3c}$ represents a bromine atom and $R^1$ represents any substituents indicated in [Table L1] to [Table L3] (hereinafter, referred to as Compound Class $SX_{632}$).

A compound (L-3) wherein T represents a group represented by T31, $R^{3b}$ represents a hydrogen atom, $R^{3c}$ represents an iodine atom and $R^1$ represents any substituents indicated in [Table L1] to [Table L3] (hereinafter, referred to as Compound Class $SX_{633}$).

A compound represented by formula (L-4):

(L-4)

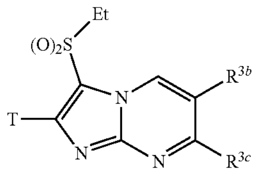

(hereinafter, referred to as compound (L-4)), wherein T represents a group represented by T1, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{634}$).

A compound (L-4) wherein T represents a group represented by T1, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{635}$).

A compound (L-4) wherein T represents a group represented by T1, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{636}$).

A compound (L-4) wherein T represents a group represented by T1, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{637}$).

A compound (L-4) wherein T represents a group represented by T1, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{638}$).

A compound (L-4) wherein T represents a group represented by T1, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{639}$.

A compound (L-4) wherein T represents a group represented by T1, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{640}$).

A compound (L-4) wherein T represents a group represented by T1, $R^{3b}$ represents a hydrogen atom, $R^{3c}$ represents a bromine atom and $R^1$ represents any substituents indicated in [Table L1] to [Table L3] (hereinafter, referred to as Compound Class $SX_{641}$).

A compound (L-4) wherein T represents a group represented by T1, $R^{3b}$ represents a hydrogen atom, $R^{3c}$ represents an iodine atom and $R^1$ represents any substituents indicated in [Table L1] to [Table L3] (hereinafter, referred to as Compound Class $SX_{642}$).

A compound (L-4) wherein T represents a group represented by T2, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{643}$).

A compound (L-4) wherein T represents a group represented by T2, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{644}$).

A compound (L-4) wherein T represents a group represented by T2, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{645}$).

A compound (L-4) wherein T represents a group represented by T2, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{646}$).

A compound (L-4) wherein T represents a group represented by T2, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{647}$).

A compound (L-4) wherein T represents a group represented by T2, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{648}$).

A compound (L-4) wherein T represents a group represented by T2, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{649}$).

A compound (L-4) wherein T represents a group represented by T2, $R^{3b}$ represents a hydrogen atom, $R^{3c}$ represents a bromine atom and $R^1$ represents any substituents indicated in [Table L1] to [Table L3] (hereinafter, referred to as Compound Class $SX_{650}$).

A compound (L-4) wherein T represents a group represented by T2, $R^{3b}$ represents a hydrogen atom, $R^{3c}$ represents an iodine atom and $R^1$ represents any substituents indicated in [Table L1] to [Table L3] (hereinafter, referred to as Compound Class $SX_{651}$).

A compound (L-4) wherein T represents a group represented by T3, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{652}$).

A compound (L-4) wherein T represents a group represented by T3, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{653}$).

A compound (L-4) wherein T represents a group represented by T3, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{654}$).

A compound (L-4) wherein T represents a group represented by T3, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{655}$).

A compound (L-4) wherein T represents a group represented by T3, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{656}$).

A compound (L-4) wherein T represents a group represented by T3, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{657}$).

A compound (L-4) wherein T represents a group represented by T3, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{658}$).

A compound (L-4) wherein T represents a group represented by T3, $R^{3b}$ represents a hydrogen atom, $R^{3c}$ represents a bromine atom and $R^1$ represents any substituents indicated in [Table L1] to [Table L3] (hereinafter, referred to as Compound Class $SX_{659}$).

A compound (L-4) wherein T represents a group represented by T3, $R^{3b}$ represents a hydrogen atom, $R^{3c}$ represents an iodine atom and $R^1$ represents any substituents indicated in [Table L1] to [Table L3] (hereinafter, referred to as Compound Class $SX_{660}$).

A compound (L-4) wherein T represents a group represented by T4, $R^{3b}$ represents a hydrogen atom, $R^{3c}$ represents sents a hydrogen atom, and $R^1$ represents any substituents indicated in [Table L1] to [Table L3] (hereinafter, referred to as Compound Class $SX_{661}$).

A compound (L-4) wherein T represents a group represented by T4, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{662}$).

A compound (L-4) wherein T represents a group represented by T4, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{663}$).

A compound (L-4) wherein T represents a group represented by T4, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{664}$).

A compound (L-4) wherein T represents a group represented by T4, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{665}$).

A compound (L-4) wherein T represents a group represented by T4, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{666}$).

A compound (L-4) wherein T represents a group represented by T4, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{667}$).

A compound (L-4) wherein T represents a group represented by T4, $R^{3b}$ represents a hydrogen atom, $R^{3c}$ represents a bromine atom and $R^1$ represents any substituents indicated in [Table L1] to [Table L3] (hereinafter, referred to as Compound Class $SX_{668}$).

A compound (L-4) wherein T represents a group represented by T4, $R^{3b}$ represents a hydrogen atom, $R^{3c}$ represents an iodine atom and $R^1$ represents any substituents indicated in [Table L1] to [Table L3] (hereinafter, referred to as Compound Class $SX_{669}$).

A compound (L-4) wherein T represents a group represented by T5, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{670}$).

A compound (L-4) wherein T represents a group represented by T5, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{671}$).

A compound (L-4) wherein T represents a group represented by T5, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{672}$).

A compound (L-4) wherein T represents a group represented by T5, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{673}$).

A compound (L-4) wherein T represents a group represented by T5, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{674}$).

A compound (L-4) wherein T represents a group represented by T5, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{675}$).

A compound (L-4) wherein T represents a group represented by T5, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{676}$).

A compound (L-4) wherein T represents a group represented by T5, $R^{3b}$ represents a hydrogen atom, $R^{3c}$ represents a bromine atom and $R^1$ represents any substituents indicated in [Table L1] to [Table L3] (hereinafter, referred to as Compound Class $SX_{677}$).

A compound (L-4) wherein T represents a group represented by T5, $R^{3b}$ represents a hydrogen atom, $R^{3c}$ represents an iodine atom and $R^1$ represents any substituents indicated in [Table L1] to [Table L3] (hereinafter, referred to as Compound Class $SX_{678}$).

A compound (L-4) wherein T represents a group represented by T6, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{679}$).

A compound (L-4) wherein T represents a group represented by T6, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{680}$).

A compound (L-4) wherein T represents a group represented by T6, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{681}$).

A compound (L-4) wherein T represents a group represented by T6, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{682}$).

A compound (L-4) wherein T represents a group represented by T6, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{683}$).

A compound (L-4) wherein T represents a group represented by T6, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{684}$).

A compound (L-4) wherein T represents a group represented by T6, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{685}$).

A compound (L-4) wherein T represents a group represented by T6, $R^{3b}$ represents a hydrogen atom, $R^{3c}$ represents a bromine atom and $R^1$ represents any substituents indicated in [Table L1] to [Table L3] (hereinafter, referred to as Compound Class $SX_{686}$).

A compound (L-4) wherein T represents a group represented by T6, $R^{3b}$ represents a hydrogen atom, $R^{3c}$ represents an iodine atom and $R^1$ represents any substituents indicated in [Table L1] to [Table L3] (hereinafter, referred to as Compound Class $SX_{687}$).

A compound (L-4) wherein T represents a group represented by T7, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{688}$).

A compound (L-4) wherein T represents a group represented by T7, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{689}$).

A compound (L-4) wherein T represents a group represented by T7, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{690}$).

A compound (L-4) wherein T represents a group represented by T7, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{691}$).

A compound (L-4) wherein T represents a group represented by T7, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{692}$).

A compound (L-4) wherein T represents a group represented by T7, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{692}$).

A compound (L-4) wherein T represents a group represented by T7, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{693}$).

A compound (L-4) wherein T represents a group represented by T7, $R^{3b}$ represents a hydrogen atom, $R^{3c}$ represents a bromine atom and $R^1$ represents any substituents indicated in [Table L1] to [Table L3] (hereinafter, referred to as Compound Class $SX_{694}$).

A compound (L-4) wherein T represents a group represented by T7, $R^{3b}$ represents a hydrogen atom, $R^{3c}$ represents an iodine atom and $R^1$ represents any substituents indicated in [Table L1] to [Table L3] (hereinafter, referred to as Compound Class $SX_{695}$).

A compound (L-4) wherein T represents a group represented by T8, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{696}$).

A compound (L-4) wherein T represents a group represented by T8, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{697}$).

A compound (L-4) wherein T represents a group represented by T8, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{699}$).

A compound (L-4) wherein T represents a group represented by T8, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{700}$).

A compound (L-4) wherein T represents a group represented by T8, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{701}$).

A compound (L-4) wherein T represents a group represented by T8, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{702}$).

A compound (L-4) wherein T represents a group represented by T8, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{703}$).

A compound (L-4) wherein T represents a group represented by T8, $R^{3b}$ represents a hydrogen atom, $R^{3c}$ represents a bromine atom and $R^1$ represents any substituents indicated in [Table L1] to [Table L3] (hereinafter, referred to as Compound Class $SX_{704}$).

A compound (L-4) wherein T represents a group represented by T8, $R^{3b}$ represents a hydrogen atom, $R^{3c}$ represents an iodine atom and $R^1$ represents any substituents indicated in [Table L1] to [Table L3] (hereinafter, referred to as Compound Class $SX_{705}$).

A compound (L-4) wherein T represents a group represented by T9, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{706}$).

A compound (L-4) wherein T represents a group represented by T9, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{707}$).

A compound (L-4) wherein T represents a group represented by T9, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{708}$).

A compound (L-4) wherein T represents a group represented by T9, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{709}$).

A compound (L-4) wherein T represents a group represented by T7, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{710}$).

A compound (L-4) wherein T represents a group represented by T9, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{711}$).

A compound (L-4) wherein T represents a group represented by T9, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{712}$).

A compound (L-4) wherein T represents a group represented by T9, $R^{3b}$ represents a hydrogen atom, $R^{3c}$ represents a bromine atom and $R^1$ represents any substituents indicated in [Table L1] to [Table L3] (hereinafter, referred to as Compound Class $SX_{713}$).

A compound (L-4) wherein T represents a group represented by T9, $R^{3b}$ represents a hydrogen atom, $R^{3c}$ represents an iodine atom and $R^1$ represents any substituents indicated in [Table L1] to [Table L3] (hereinafter, referred to as Compound Class $SX_{714}$).

A compound (L-4) wherein T represents a group represented by T10, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{715}$).

A compound (L-4) wherein T represents a group represented by T10, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{716}$).

A compound (L-4) wherein T represents a group represented by T10, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{717}$).

A compound (L-4) wherein T represents a group represented by T10, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{718}$).

A compound (L-4) wherein T represents a group represented by T10, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{719}$).

A compound (L-4) wherein T represents a group represented by T10, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{720}$).

A compound (L-4) wherein T represents a group represented by T10, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{721}$).

A compound (L-4) wherein T represents a group represented by T10, $R^{3b}$ represents a hydrogen atom, $R^{3c}$ represents a bromine atom and $R^1$ represents any substituents indicated in [Table L1] to [Table L3] (hereinafter, referred to as Compound Class $SX_{722}$).

A compound (L-4) wherein T represents a group represented by T10, $R^{3b}$ represents a hydrogen atom, $R^{3c}$ represents an iodine atom and $R^1$ represents any substituents indicated in [Table L1] to [Table L3] (hereinafter, referred to as Compound Class $SX_{723}$).

A compound (L-4) wherein T represents a group represented by T11, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{724}$).

A compound (L-4) wherein T represents a group represented by T11, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{725}$).

A compound (L-4) wherein T represents a group represented by T11, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{726}$).

A compound (L-4) wherein T represents a group represented by T11, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{727}$).

A compound (L-4) wherein T represents a group represented by T11, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{728}$).

A compound (L-4) wherein T represents a group represented by T11, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{729}$).

A compound (L-4) wherein T represents a group represented by T11, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{730}$).

A compound (L-4) wherein T represents a group represented by T11, $R^{3b}$ represents a hydrogen atom, $R^{3c}$ represents a bromine atom and $R^1$ represents any substituents indicated in [Table L1] to [Table L3] (hereinafter, referred to as Compound Class $SX_{731}$).

A compound (L-4) wherein T represents a group represented by T11, $R^{3b}$ represents a hydrogen atom, $R^{3c}$ represents an iodine atom and $R^1$ represents any substituents indicated in [Table L1] to [Table L3] (hereinafter, referred to as Compound Class $SX_{732}$).

A compound (L-4) wherein T represents a group represented by T12, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{733}$).

A compound (L-4) wherein T represents a group represented by T12, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{734}$).

A compound (L-4) wherein T represents a group represented by T12, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{735}$).

A compound (L-4) wherein T represents a group represented by T12, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{736}$).

A compound (L-4) wherein T represents a group represented by T12, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{737}$).

A compound (L-4) wherein T represents a group represented by T12, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{738}$).

A compound (L-4) wherein T represents a group represented by T12, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{739}$).

A compound (L-4) wherein T represents a group represented by T12, $R^{3b}$ represents a hydrogen atom, $R^{3c}$ represents a bromine atom and $R^1$ represents any substituents indicated in [Table L1] to [Table L3] (hereinafter, referred to as Compound Class $SX_{740}$).

A compound (L-4) wherein T represents a group represented by T12, $R^{3b}$ represents a hydrogen atom, $R^{3c}$ represents an iodine atom and $R^1$ represents any substituents indicated in [Table L1] to [Table L3] (hereinafter, referred to as Compound Class $SX_{741}$).

A compound (L-4) wherein T represents a group represented by T13, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{742}$).

A compound (L-4) wherein T represents a group represented by T13, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{743}$).

A compound (L-4) wherein T represents a group represented by T13, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{744}$).

A compound (L-4) wherein T represents a group represented by T13, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{745}$).

A compound (L-4) wherein T represents a group represented by T13, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{746}$).

A compound (L-4) wherein T represents a group represented by T13, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{747}$).

A compound (L-4) wherein T represents a group represented by T13, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{748}$).

A compound (L-4) wherein T represents a group represented by T13, $R^{3b}$ represents a hydrogen atom, $R^{3c}$ represents a bromine atom and $R^1$ represents any substituents indicated in [Table L1] to [Table L3] (hereinafter, referred to as Compound Class $SX_{749}$).

A compound (L-4) wherein T represents a group represented by T13, $R^{3b}$ represents a hydrogen atom, $R^{3c}$ represents an iodine atom and $R^1$ represents any substituents indicated in [Table L1] to [Table L3] (hereinafter, referred to as Compound Class $SX_{750}$).

A compound (L-4) wherein T represents a group represented by T14, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{751}$).

A compound (L-4) wherein T represents a group represented by T14, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{752}$).

A compound (L-4) wherein T represents a group represented by T14, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{753}$).

A compound (L-4) wherein T represents a group represented by T14, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{754}$).

A compound (L-4) wherein T represents a group represented by T14, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{755}$).

A compound (L-4) wherein T represents a group represented by T14, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{756}$).

A compound (L-4) wherein T represents a group represented by T14, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{757}$).

A compound (L-4) wherein T represents a group represented by T14, $R^{3b}$ represents a hydrogen atom, $R^{3c}$ represents a bromine atom and $R^1$ represents any substituents indicated in [Table L1] to [Table L3] (hereinafter, referred to as Compound Class $SX_{758}$).

A compound (L-4) wherein T represents a group represented by T14, $R^{3b}$ represents a hydrogen atom, $R^{3c}$ represents an iodine atom and $R^1$ represents any substituents indicated in [Table L1] to [Table L3] (hereinafter, referred to as Compound Class $SX_{759}$.

A compound (L-4) wherein T represents a group represented by T15, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{760}$).

A compound (L-4) wherein T represents a group represented by T15, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{761}$).

A compound (L-4) wherein T represents a group represented by T15, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{762}$).

A compound (L-4) wherein T represents a group represented by T15, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{763}$).

A compound (L-4) wherein T represents a group represented by T15, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{764}$).

A compound (L-4) wherein T represents a group represented by T15, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{765}$).

A compound (L-4) wherein T represents a group represented by T15, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{766}$).

A compound (L-4) wherein T represents a group represented by T15, $R^{3b}$ represents a hydrogen atom, $R^{3c}$ represents a bromine atom and $R^1$ represents any substituents indicated in [Table L1] to [Table L3] (hereinafter, referred to as Compound Class $SX_{767}$).

A compound (L-4) wherein T represents a group represented by T15, $R^{3b}$ represents a hydrogen atom, $R^{3c}$ represents an iodine atom and $R^1$ represents any substituents indicated in [Table L1] to [Table L3] (hereinafter, referred to as Compound Class $SX_{768}$).

A compound (L-4) wherein T represents a group represented by T16, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{769}$).

A compound (L-4) wherein T represents a group represented by T16, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{770}$).

A compound (L-4) wherein T represents a group represented by T16, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{771}$).

A compound (L-4) wherein T represents a group represented by T16, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{772}$).

A compound (L-4) wherein T represents a group represented by T16, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{773}$).

A compound (L-4) wherein T represents a group represented by T16, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{774}$).

A compound (L-4) wherein T represents a group represented by T16, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{775}$).

A compound (L-4) wherein T represents a group represented by T16, $R^{3b}$ represents a hydrogen atom, $R^{3c}$ represents a bromine atom and $R^1$ represents any substituents indicated in [Table L1] to [Table L3] (hereinafter, referred to as Compound Class $SX_{776}$).

A compound (L-4) wherein T represents a group represented by T16, $R^{3b}$ represents a hydrogen atom, $R^{3c}$ represents an iodine atom and $R^1$ represents any substituents indicated in [Table L1] to [Table L3] (hereinafter, referred to as Compound Class $SX_{777}$).

A compound (L-4) wherein T represents a group represented by T17, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{778}$).

A compound (L-4) wherein T represents a group represented by T17, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{779}$).

A compound (L-4) wherein T represents a group represented by T17, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{780}$).

A compound (L-4) wherein T represents a group represented by T17, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{781}$).

A compound (L-4) wherein T represents a group represented by T17, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{782}$).

A compound (L-4) wherein T represents a group represented by T17, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{783}$).

A compound (L-4) wherein T represents a group represented by T17, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{784}$).

A compound (L-4) wherein T represents a group represented by T17, $R^{3b}$ represents a hydrogen atom, $R^{3c}$ represents a bromine atom and $R^1$ represents any substituents indicated in [Table L1] to [Table L3] (hereinafter, referred to as Compound Class $SX_{785}$).

A compound (L-4) wherein T represents a group represented by T17, $R^{3b}$ represents a hydrogen atom, $R^{3c}$ represents an iodine atom and $R^1$ represents any substituents indicated in [Table L1] to [Table L3] (hereinafter, referred to as Compound Class $SX_{786}$).

A compound (L-4) wherein T represents a group represented by T18, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{787}$).

A compound (L-4) wherein T represents a group represented by T18, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{788}$).

A compound (L-4) wherein T represents a group represented by T18, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{789}$).

A compound (L-4) wherein T represents a group represented by T18, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{790}$).

A compound (L-4) wherein T represents a group represented by T18, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{791}$).

A compound (L-4) wherein T represents a group represented by T18, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{792}$).

A compound (L-4) wherein T represents a group represented by T18, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{793}$).

A compound (L-4) wherein T represents a group represented by T18, $R^{3b}$ represents a hydrogen atom, $R^{3c}$ represents a bromine atom and $R^1$ represents any substituents indicated in [Table L1] to [Table L3] (hereinafter, referred to as Compound Class $SX_{794}$).

A compound (L-4) wherein T represents a group represented by T18, $R^{3b}$ represents a hydrogen atom, $R^{3c}$ represents an iodine atom and $R^1$ represents any substituents indicated in [Table L1] to [Table L3] (hereinafter, referred to as Compound Class $SX_{795}$).

A compound (L-4) wherein T represents a group represented by T19, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{796}$).

A compound (L-4) wherein T represents a group represented by T19, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{797}$).

A compound (L-4) wherein T represents a group represented by T19, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{798}$).

A compound (L-4) wherein T represents a group represented by T19, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{799}$).

A compound (L-4) wherein T represents a group represented by T19, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{800}$).

A compound (L-4) wherein T represents a group represented by T19, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{801}$).

A compound (L-4) wherein T represents a group represented by T19, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{802}$).

A compound (L-4) wherein T represents a group represented by T19, $R^{3b}$ represents a hydrogen atom, $R^{3c}$ represents a bromine atom and $R^1$ represents any substituents indicated in [Table L1] to [Table L3] (hereinafter, referred to as Compound Class $SX_{803}$).

A compound (L-4) wherein T represents a group represented by T19, $R^{3b}$ represents a hydrogen atom, $R^{3c}$ represents an iodine atom and $R^1$ represents any substituents indicated in [Table L1] to [Table L3] (hereinafter, referred to as Compound Class $SX_{804}$).

A compound (L-4) wherein T represents a group represented by T20, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{805}$).

A compound (L-4) wherein T represents a group represented by T20, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{806}$).

A compound (L-4) wherein T represents a group represented by T20, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{807}$).

A compound (L-4) wherein T represents a group represented by T20, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{808}$).

A compound (L-4) wherein T represents a group represented by T20, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{809}$).

A compound (L-4) wherein T represents a group represented by T20, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{810}$).

A compound (L-4) wherein T represents a group represented by T20, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{811}$).

A compound (L-4) wherein T represents a group represented by T20, $R^{3b}$ represents a hydrogen atom, $R^{3c}$ represents a bromine atom and $R^1$ represents any substituents indicated in [Table L1] to [Table L3] (hereinafter, referred to as Compound Class $SX_{812}$).

A compound (L-4) wherein T represents a group represented by T20, $R^{3b}$ represents a hydrogen atom, $R^{3c}$ represents an iodine atom and $R^1$ represents any substituents indicated in [Table L1] to [Table L3] (hereinafter, referred to as Compound Class $SX_{813}$).

A compound (L-4) wherein T represents a group represented by T21, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{814}$).

A compound (L-4) wherein T represents a group represented by T21, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{815}$).

A compound (L-4) wherein T represents a group represented by T21, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{816}$).

A compound (L-4) wherein T represents a group represented by T21, $R^{3b}$ represents a bromine atom, $R^{3c}$ represents sents a hydrogen atom, and $R^1$ represents any substituents indicated in [Table L1] to [Table L3] (hereinafter, referred to as Compound Class $SX_{817}$).

A compound (L-4) wherein T represents a group represented by T21, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{818}$).

A compound (L-4) wherein T represents a group represented by T21, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{819}$).

A compound (L-4) wherein T represents a group represented by T21, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{820}$).

A compound (L-4) wherein T represents a group represented by T21, $R^{3b}$ represents a hydrogen atom, $R^{3c}$ represents a bromine atom and $R^1$ represents any substituents indicated in [Table L1] to [Table L3] (hereinafter, referred to as Compound Class $SX_{821}$).

A compound (L-4) wherein T represents a group represented by T21, $R^{3b}$ represents a hydrogen atom, $R^{3c}$ represents an iodine atom and $R^1$ represents any substituents indicated in [Table L1] to [Table L3] (hereinafter, referred to as Compound Class $SX_{822}$).

A compound (L-4) wherein T represents a group represented by T22, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{823}$).

A compound (L-4) wherein T represents a group represented by T22, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{824}$).

A compound (L-4) wherein T represents a group represented by T22, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{825}$).

A compound (L-4) wherein T represents a group represented by T22, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{826}$).

A compound (L-4) wherein T represents a group represented by T22, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{827}$).

A compound (L-4) wherein T represents a group represented by T22, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{828}$).

A compound (L-4) wherein T represents a group represented by T22, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{829}$).

A compound (L-4) wherein T represents a group represented by T22, $R^{3b}$ represents a hydrogen atom, $R^{3c}$ represents a bromine atom and $R^1$ represents any substituents indicated in [Table L1] to [Table L3] (hereinafter, referred to as Compound Class $SX_{830}$).

A compound (L-4) wherein T represents a group represented by T22, $R^{3b}$ represents a hydrogen atom, $R^{3c}$ represents an iodine atom and $R^1$ represents any substituents indicated in [Table L1] to [Table L3] (hereinafter, referred to as Compound Class $SX_{831}$).

A compound (L-4) wherein T represents a group represented by T23, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{832}$).

A compound (L-4) wherein T represents a group represented by T23, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{833}$).

A compound (L-4) wherein T represents a group represented by T23, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{834}$).

A compound (L-4) wherein T represents a group represented by T23, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{835}$).

A compound (L-4) wherein T represents a group represented by T23, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{836}$).

A compound (L-4) wherein T represents a group represented by T23, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{837}$).

A compound (L-4) wherein T represents a group represented by T23, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{838}$).

A compound (L-4) wherein T represents a group represented by T23, $R^{3b}$ represents a hydrogen atom, $R^{3c}$ represents a bromine atom and $R^1$ represents any substituents indicated in [Table L1] to [Table L3] (hereinafter, referred to as Compound Class $SX_{839}$).

A compound (L-4) wherein T represents a group represented by T23, $R^{3b}$ represents a hydrogen atom, $R^{3c}$ represents an iodine atom and $R^1$ represents any substituents indicated in [Table L1] to [Table L3] (hereinafter, referred to as Compound Class $SX_{840}$).

A compound (L-4) wherein T represents a group represented by T24, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{841}$).

A compound (L-4) wherein T represents a group represented by T24, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{842}$).

A compound (L-4) wherein T represents a group represented by T24, $R^{3b}$ represents a chlorine atom, $R^{3c}$ represents sents a hydrogen atom, and $R^1$ represents any substituents indicated in [Table L1] to [Table L3] (hereinafter, referred to as Compound Class $SX_{843}$).

A compound (L-4) wherein T represents a group represented by T24, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{844}$).

A compound (L-4) wherein T represents a group represented by T24, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{845}$).

A compound (L-4) wherein T represents a group represented by T24, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{846}$).

A compound (L-4) wherein T represents a group represented by T24, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{847}$).

A compound (L-4) wherein T represents a group represented by T24, $R^{3b}$ represents a hydrogen atom, $R^{3c}$ represents a bromine atom and $R^1$ represents any substituents indicated in [Table L1] to [Table L3] (hereinafter, referred to as Compound Class $SX_{848}$).

A compound (L-4) wherein T represents a group represented by T24, $R^{3b}$ represents a hydrogen atom, $R^{3c}$ represents an iodine atom and $R^1$ represents any substituents indicated in [Table L1] to [Table L3] (hereinafter, referred to as Compound Class $SX_{849}$).

A compound (L-4) wherein T represents a group represented by T25, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{850}$).

A compound (L-4) wherein T represents a group represented by T25, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{851}$).

A compound (L-4) wherein T represents a group represented by T25, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{852}$).

A compound (L-4) wherein T represents a group represented by T25, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{853}$).

A compound (L-4) wherein T represents a group represented by T25, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{854}$).

A compound (L-4) wherein T represents a group represented by T25, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{855}$).

A compound (L-4) wherein T represents a group represented by T25, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{856}$).

A compound (L-4) wherein T represents a group represented by T25, $R^{3b}$ represents a hydrogen atom, $R^{3c}$ represents a bromine atom and $R^1$ represents any substituents indicated in [Table L1] to [Table L3] (hereinafter, referred to as Compound Class $SX_{857}$).

A compound (L-4) wherein T represents a group represented by T25, $R^{3b}$ represents a hydrogen atom, $R^{3c}$ represents an iodine atom and $R^1$ represents any substituents indicated in [Table L1] to [Table L3] (hereinafter, referred to as Compound Class $SX_{858}$).

A compound (L-4) wherein T represents a group represented by T26, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{859}$).

A compound (L-4) wherein T represents a group represented by T26, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{860}$).

A compound (L-4) wherein T represents a group represented by T26, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{861}$).

A compound (L-4) wherein T represents a group represented by T26, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{862}$).

A compound (L-4) wherein T represents a group represented by T26, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{863}$).

A compound (L-4) wherein T represents a group represented by T26, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{864}$).

A compound (L-4) wherein T represents a group represented by T26, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{865}$).

A compound (L-4) wherein T represents a group represented by T26, $R^{3b}$ represents a hydrogen atom, $R^{3c}$ represents a bromine atom and $R^1$ represents any substituents indicated in [Table L1] to [Table L3] (hereinafter, referred to as Compound Class $SX_{866}$).

A compound (L-4) wherein T represents a group represented by T26, $R^{3b}$ represents a hydrogen atom, $R^{3c}$ represents an iodine atom and $R^1$ represents any substituents indicated in [Table L1] to [Table L3] (hereinafter, referred to as Compound Class $SX_{867}$).

A compound (L-4) wherein T represents a group represented by T27, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{868}$).

A compound (L-4) wherein T represents a group represented by T27, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{869}$).

A compound (L-4) wherein T represents a group represented by T27, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{870}$).

A compound (L-4) wherein T represents a group represented by T27, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{871}$).

A compound (L-4) wherein T represents a group represented by T27, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{872}$).

A compound (L-4) wherein T represents a group represented by T27, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{873}$).

A compound (L-4) wherein T represents a group represented by T27, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{874}$).

A compound (L-4) wherein T represents a group represented by T27, $R^{3b}$ represents a hydrogen atom, $R^{3c}$ represents a bromine atom and $R^1$ represents any substituents indicated in [Table L1] to [Table L3] (hereinafter, referred to as Compound Class $SX_{875}$).

A compound (L-4) wherein T represents a group represented by T27, $R^{3b}$ represents a hydrogen atom, $R^{3c}$ represents an iodine atom and $R^1$ represents any substituents indicated in [Table L1] to [Table L3] (hereinafter, referred to as Compound Class $SX_{876}$).

A compound (L-4) wherein T represents a group represented by T28, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{877}$).

A compound (L-4) wherein T represents a group represented by T28, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{878}$).

A compound (L-4) wherein T represents a group represented by T28, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{879}$).

A compound (L-4) wherein T represents a group represented by T28, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{880}$).

A compound (L-4) wherein T represents a group represented by T28, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{881}$).

A compound (L-4) wherein T represents a group represented by T28, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{882}$).

A compound (L-4) wherein T represents a group represented by T28, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{883}$).

A compound (L-4) wherein T represents a group represented by T28, $R^{3b}$ represents a hydrogen atom, $R^{3c}$ represents a bromine atom and $R^1$ represents any substituents indicated in [Table L1] to [Table L3] (hereinafter, referred to as Compound Class $SX_{884}$).

A compound (L-4) wherein T represents a group represented by T28, $R^{3b}$ represents a hydrogen atom, $R^{3c}$ represents an iodine atom and $R^1$ represents any substituents indicated in [Table L1] to [Table L3] (hereinafter, referred to as Compound Class $SX_{885}$).

A compound (L-4) wherein T represents a group represented by T29, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{886}$).

A compound (L-4) wherein T represents a group represented by T29, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{887}$).

A compound (L-4) wherein T represents a group represented by T29, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{888}$).

A compound (L-4) wherein T represents a group represented by T29, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{889}$).

A compound (L-4) wherein T represents a group represented by T29, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{890}$).

A compound (L-4) wherein T represents a group represented by T29, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{891}$).

A compound (L-4) wherein T represents a group represented by T29, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{892}$).

A compound (L-4) wherein T represents a group represented by T29, $R^{3b}$ represents a hydrogen atom, $R^{3c}$ represents a bromine atom and $R^1$ represents any substituents indicated in [Table L1] to [Table L3] (hereinafter, referred to as Compound Class $SX_{893}$).

A compound (L-4) wherein T represents a group represented by T29, $R^{3b}$ represents a hydrogen atom, $R^{3c}$ represents an iodine atom and $R^1$ represents any substituents indicated in [Table L1] to [Table L3] (hereinafter, referred to as Compound Class $SX_{894}$).

A compound (L-4) wherein T represents a group represented by T30, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{895}$).

A compound (L-4) wherein T represents a group represented by T30, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{896}$).

A compound (L-4) wherein T represents a group represented by T30, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{897}$).

A compound (L-4) wherein T represents a group represented by T30, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{898}$).

A compound (L-4) wherein T represents a group represented by T30, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{899}$).

A compound (L-4) wherein T represents a group represented by T30, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{900}$).

A compound (L-4) wherein T represents a group represented by T30, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{901}$).

A compound (L-4) wherein T represents a group represented by T30, $R^{3b}$ represents a hydrogen atom, $R^{3c}$ represents a bromine atom and $R^1$ represents any substituents indicated in [Table L1] to [Table L3] (hereinafter, referred to as Compound Class $SX_{902}$).

A compound (L-4) wherein T represents a group represented by T30, $R^{3b}$ represents a hydrogen atom, $R^{3c}$ represents an iodine atom and $R^1$ represents any substituents indicated in [Table L1] to [Table L3] (hereinafter, referred to as Compound Class $SX_{903}$).

A compound (L-4) wherein T represents a group represented by T31, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{904}$).

A compound (L-4) wherein T represents a group represented by T31, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{905}$).

A compound (L-4) wherein T represents a group represented by T31, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{906}$).

A compound (L-4) wherein T represents a group represented by T31, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{907}$).

A compound (L-4) wherein T represents a group represented by T31, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{908}$).

A compound (L-4) wherein T represents a group represented by T31, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{909}$).

A compound (L-4) wherein T represents a group represented by T31, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{910}$).

A compound (L-4) wherein T represents a group represented by T31, $R^{3b}$ represents a hydrogen atom, $R^{3c}$ represents a bromine atom and $R^1$ represents any substituents indicated in [Table L1] to [Table L3] (hereinafter, referred to as Compound Class $SX_{911}$).

A compound (L-4) wherein T represents a group represented by T31, $R^{3b}$ represents a hydrogen atom, $R^{3c}$ represents an iodine atom and $R^1$ represents any substituents indicated in [Table L1] to [Table L3] (hereinafter, referred to as Compound Class $SX_{912}$).

A compound represented by formula (L-5):

(L-5)

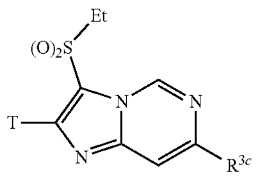

(hereinafter, referred to as compound (L-5)), wherein T represents a group represented by T1, $R^{3c}$ represents a hydrogen atom, and $R^1$ represents any substituents indicated in [Table L1] to [Table L3] (hereinafter, referred to as Compound Class $SX_{913}$).

A compound (L-5) wherein T represents a group represented by T1, $R^{3c}$ represents $CF_3$, and $R^1$ represents any substituents indicated in [Table L1] to [Table L3] (hereinafter, referred to as Compound Class $SX_{914}$).

A compound (L-5) wherein T represents a group represented by T1, $R^{3c}$ represents a chlorine atom, and $R^1$ represents any substituents indicated in [Table L1] to [Table L3] (hereinafter, referred to as Compound Class $SX_{915}$).

A compound (L-5) wherein T represents a group represented by T1, $R^{3c}$ represents a bromine atom, and $R^1$ represents any substituents indicated in [Table L1] to [Table L3] (hereinafter, referred to as Compound Class $SX_{916}$).

A compound (L-5) wherein T represents a group represented by T1, $R^{3c}$ represents an iodine atom, and $R^1$ represents any substituents indicated in [Table L1] to [Table L3] (hereinafter, referred to as Compound Class $SX_{917}$).

A compound (L-5) wherein T represents a group represented by T2, $R^{3c}$ represents a hydrogen atom, and $R^1$ represents any substituents indicated in [Table L1] to [Table L3] (hereinafter, referred to as Compound Class $SX_{918}$).

A compound (L-5) wherein T represents a group represented by T2, $R^{3c}$ represents $CF_3$, and $R^1$ represents any substituents indicated in [Table L1] to [Table L3] (hereinafter, referred to as Compound Class $SX_{919}$).

A compound (L-5) wherein T represents a group represented by T2, $R^{3c}$ represents a chlorine atom, and $R^1$ represents any substituents indicated in [Table L1] to [Table L3] (hereinafter, referred to as Compound Class $SX_{920}$).

A compound (L-5) wherein T represents a group represented by T2, $R^{3c}$ represents a bromine atom, and $R^1$ represents any substituents indicated in [Table L1] to [Table L3] (hereinafter, referred to as Compound Class $SX_{921}$).

A compound (L-5) wherein T represents a group represented by T2, $R^{3c}$ represents an iodine atom, and $R^1$ represents any substituents indicated in [Table L1] to [Table L3] (hereinafter, referred to as Compound Class $SX_{922}$).

A compound (L-5) wherein T represents a group represented by T3, $R^{3c}$ represents a hydrogen atom, and $R^1$ represents any substituents indicated in [Table L1] to [Table L3] (hereinafter, referred to as Compound Class $SX_{923}$).

A compound (L-5) wherein T represents a group represented by T3, $R^{3c}$ represents $CF_3$, and $R^1$ represents any substituents indicated in [Table L1] to [Table L3] (hereinafter, referred to as Compound Class $SX_{924}$).

A compound (L-5) wherein T represents a group represented by T3, $R^{3c}$ represents a chlorine atom, and $R^1$ represents any substituents indicated in [Table L1] to [Table L3] (hereinafter, referred to as Compound Class $SX_{925}$).

A compound (L-5) wherein T represents a group represented by T3, $R^{3c}$ represents a bromine atom, and $R^1$ represents any substituents indicated in [Table L1] to [Table L3] (hereinafter, referred to as Compound Class $SX_{926}$).

A compound (L-5) wherein T represents a group represented by T3, $R^{3c}$ represents an iodine atom, and $R^1$ represents any substituents indicated in [Table L1] to [Table L3] (hereinafter, referred to as Compound Class $SX_{927}$).

A compound (L-5) wherein T represents a group represented by T4, $R^{3c}$ represents a hydrogen atom, and $R^1$ represents any substituents indicated in [Table L1] to [Table L3] (hereinafter, referred to as Compound Class $SX_{928}$).

A compound (L-5) wherein T represents a group represented by T4, $R^{3c}$ represents $CF_3$, and $R^1$ represents any substituents indicated in [Table L1] to [Table L3] (hereinafter, referred to as Compound Class $SX_{929}$).

A compound (L-5) wherein T represents a group represented by T4, $R^{3c}$ represents a chlorine atom, and $R^1$ represents any substituents indicated in [Table L1] to [Table L3] (hereinafter, referred to as Compound Class $SX_{930}$).

A compound (L-5) wherein T represents a group represented by T4, $R^{3c}$ represents a bromine atom, and $R^1$ represents any substituents indicated in [Table L1] to [Table L3] (hereinafter, referred to as Compound Class $SX_{931}$).

A compound (L-5) wherein T represents a group represented by T4, $R^{3c}$ represents an iodine atom, and $R^1$ represents any substituents indicated in [Table L1] to [Table L3] (hereinafter, referred to as Compound Class $SX_{932}$).

A compound (L-5) wherein T represents a group represented by T5, $R^{3c}$ represents a hydrogen atom, and $R^1$ represents any substituents indicated in [Table L1] to [Table L3] (hereinafter, referred to as Compound Class $SX_{933}$).

A compound (L-5) wherein T represents a group represented by T5, $R^{3c}$ represents $CF_3$, and $R^1$ represents any substituents indicated in [Table L1] to [Table L3] (hereinafter, referred to as Compound Class $SX_{934}$).

A compound (L-5) wherein T represents a group represented by T5, $R^{3c}$ represents a chlorine atom, and $R^1$ represents any substituents indicated in [Table L1] to [Table L3] (hereinafter, referred to as Compound Class $SX_{935}$).

A compound (L-5) wherein T represents a group represented by T5, $R^{3c}$ represents a bromine atom, and $R^1$ represents any substituents indicated in [Table L1] to [Table L3] (hereinafter, referred to as Compound Class $SX_{936}$).

A compound (L-5) wherein T represents a group represented by T5, $R^{3c}$ represents an iodine atom, and $R^1$ represents any substituents indicated in [Table L1] to [Table L3] (hereinafter, referred to as Compound Class $SX_{937}$).

A compound (L-5) wherein T represents a group represented by T6, $R^{3c}$ represents a hydrogen atom, and $R^1$ represents any substitutions indicted in [Table L1] to [Table L3] (hereinafter, referred to as Compound Class $SX_{938}$).

A compound (L-5) wherein T represents a group represented by T6, $R^{3c}$ represents $CF_3$, and $R^1$ represents any substituents indicated in [Table L1] to [Table L3] (hereinafter, referred to as Compound Class $SX_{939}$).

A compound (L-5) wherein T represents a group represented by T6, $R^{3c}$ represents a chlorine atom, and $R^1$ represents any substituents indicated in [Table L1] to [Table L3] (hereinafter, referred to as Compound Class $SX_{940}$).

A compound (L-5) wherein T represents a group represented by T6, $R^{3c}$ represents a bromine atom, and $R^1$ represents any substituents indicated in [Table L1] to [Table L3] (hereinafter, referred to as Compound Class $SX_{941}$).

A compound (L-5) wherein T represents a group represented by T6, $R^{3c}$ represents an iodine atom, and $R^1$ represents any substituents indicated in [Table L1] to [Table L3] (hereinafter, referred to as Compound Class $SX_{942}$).

A compound (L-5) wherein T represents a group represented by T7, $R^{3c}$ represents a hydrogen atom, and $R^1$ represents any substituents indicated in [Table L1] to [Table L3] (hereinafter, referred to as Compound Class $SX_{943}$).

A compound (L-5) wherein T represents a group represented by T7, $R^{3c}$ represents $CF_3$, and $R^1$ represents any substituents indicated in [Table L1] to [Table L3] (hereinafter, referred to as Compound Class $SX_{944}$).

A compound (L-5) wherein T represents a group represented by T7, $R^{3c}$ represents a chlorine atom, and $R^1$ represents any substituents indicated in [Table L1] to [Table L3] (hereinafter, referred to as Compound Class $SX_{945}$).

A compound (L-5) wherein T represents a group represented by T7, $R^{3c}$ represents a bromine atom, and $R^1$ represents any substituents indicated in [Table L1] to [Table L3] (hereinafter, referred to as Compound Class $SX_{946}$).

A compound (L-5) wherein T represents a group represented by T7, $R^{3c}$ represents an iodine atom, and $R^1$ represents any substituents indicated in [Table L1] to [Table L3] (hereinafter, referred to as Compound Class $SX_{947}$).

A compound (L-5) wherein T represents a group represented by T8, $R^{3c}$ represents a hydrogen atom, and $R^1$ represents any substituents indicated in [Table L1] to [Table L3] (hereinafter, referred to as Compound Class $SX_{948}$).

A compound (L-5) wherein T represents a group represented by T8, $R^{3c}$ represents $CF_3$, and $R^1$ represents any substituents indicated in [Table L1] to [Table L3] (hereinafter, referred to as Compound Class $SX_{949}$).

A compound (L-5) wherein T represents a group represented by T8, $R^{3c}$ represents a chlorine atom, and $R^1$ represents any substituents indicated in [Table L1] to [Table L3] (hereinafter, referred to as Compound Class $SX_{950}$).

A compound (L-5) wherein T represents a group represented by T8, $R^{3c}$ represents a bromine atom, and $R^1$ represents any substituents indicated in [Table L1] to [Table L3] (hereinafter, referred to as Compound Class $SX_{951}$).

A compound (L-5) wherein T represents a group represented by T8, $R^{3c}$ represents an iodine atom, and $R^1$ represents any substituents indicated in [Table L1] to [Table L3] (hereinafter, referred to as Compound Class $SX_{952}$).

A compound (L-5) wherein T represents a group represented by T9, $R^{3c}$ represents a hydrogen atom, and $R^1$ represents any substituents indicated in [Table L1] to [Table L3] (hereinafter, referred to as Compound Class $SX_{953}$).

A compound (L-5) wherein T represents a group represented by T9, $R^{3c}$ represents $CF_3$, and $R^1$ represents any substituents indicated in [Table L1] to [Table L3] (hereinafter, referred to as Compound Class $SX_{954}$).

A compound (L-5) wherein T represents a group represented by T9, $R^{3c}$ represents a chlorine atom, and $R^1$ represents any substituents indicated in [Table L1] to [Table L3] (hereinafter, referred to as Compound Class $SX_{955}$).

A compound (L-5) wherein T represents a group represented by T9, $R^{3c}$ represents a bromine atom, and $R^1$ represents any substituents indicated in [Table L1] to [Table L3] (hereinafter, referred to as Compound Class $SX_{956}$).

A compound (L-5) wherein T represents a group represented by T9, $R^{3c}$ represents an iodine atom, and $R^1$ represents any substituents indicated in [Table L1] to [Table L3] (hereinafter, referred to as Compound Class $SX_{957}$).

A compound (L-5) wherein T represents a group represented by T10, $R^{3c}$ represents a hydrogen atom, and $R^1$ represents any substituents indicated in [Table L1] to [Table L3] (hereinafter, referred to as Compound Class $SX_{958}$).

A compound (L-5) wherein T represents a group represented by T10, $R^{3c}$ represents $CF_3$, and $R^1$ represents any substituents indicated in [Table L1] to [Table L3] (hereinafter, referred to as Compound Class $SX_{959}$).

A compound (L-5) wherein T represents a group represented by T10, $R^{3c}$ represents a chlorine atom, and $R^1$ represents any substituents indicated in [Table L1] to [Table L3] (hereinafter, referred to as Compound Class $SX_{960}$).

A compound (L-5) wherein T represents a group represented by T10, $R^{3c}$ represents a bromine atom, and $R^1$ represents any substituents indicated in [Table L1] to [Table L3] (hereinafter, referred to as Compound Class $SX_{961}$).

A compound (L-5) wherein T represents a group represented by T10, $R^{3c}$ represents an iodine atom, and $R^1$ represents any substituents indicated in [Table L1] to [Table L3] (hereinafter, referred to as Compound Class $SX_{962}$).

A compound (L-5) wherein T represents a group represented by T11, $R^{3c}$ represents a hydrogen atom, and $R^1$ represents any substituents indicated in [Table L1] and [Table L3] (hereinafter, referred to as Compound Class $SX_{963}$).

A compound (L-5) wherein T represents a group represented by T11, $R^{3c}$ represents $CF_3$, and $R^1$ represents any substituents indicated in [Table L1] to [Table L3] (hereinafter, referred to as Compound Class $SX_{964}$).

A compound (L-5) wherein T represents a group represented by T11, $R^{3c}$ represents a chlorine atom, and $R^1$ represents any substituents indicated in [Table L1] to [Table L3] (hereinafter, referred to as Compound Class $SX_{965}$).

A compound (L-5) wherein T represents a group represented by T11, $R^{3c}$ represents a bromine atom, and $R^1$ represents any substituents indicated in [Table L1] to [Table L3] (hereinafter, referred to as Compound Class $SX_{966}$).

A compound (L-5) wherein T represents a group represented by T11, $R^{3c}$ represents an iodine atom, and $R^1$ represents any substituents indicated in [Table L1] to [Table L3] (hereinafter, referred to as Compound Class $SX_{967}$).

A compound (L-5) wherein T represents a group represented by T12, $R^{3c}$ represents a hydrogen atom, and $R^1$ represents any substituents indicated in [Table L1] to [Table L3] (hereinafter, referred to as Compound Class $SX_{968}$).

A compound (L-5) wherein T represents a group represented by T12, $R^{3c}$ represents $CF_3$, and $R^1$ represents any substituents indicated in [Table L1] to [Table L3] (hereinafter, referred to as Compound Class $SX_{969}$).

A compound (L-5) wherein T represents a group represented by T12, $R^{3c}$ represents a chlorine atom, and $R^1$ represents any substituents indicated in [Table L1] to [Table L3] (hereinafter, referred to as Compound Class $SX_{970}$).

A compound (L-5) wherein T represents a group represented by T12, $R^{3c}$ represents a bromine atom, and $R^1$ represents any substituents indicated in [Table L1] to [Table L3] (hereinafter, referred to as Compound Class $SX_{971}$).

A compound (L-5) wherein T represents a group represented by T12, $R^{3c}$ represents an iodine atom, and $R^1$ represents any substituents indicated in [Table L1] to [Table L3] (hereinafter, referred to as Compound Class $SX_{972}$).

A compound (L-5) wherein T represents a group represented by T13, $R^{3c}$ represents a hydrogen atom, and $R^1$ represents any substituents indicated in [Table L1] to [Table L3] (hereinafter, referred to as Compound Class $SX_{973}$).

A compound (L-5) wherein T represents a group represented by T13, $R^{3c}$ represents $CF_3$, and $R^1$ represents any substituents indicated in [Table L1] to [Table L3] (hereinafter, referred to as Compound Class $SX_{974}$).

A compound (L-5) wherein T represents a group represented by T13, $R^{3c}$ represents a chlorine atom, and $R^1$ represents any substituents indicated in [Table L1] to [Table L3] (hereinafter, referred to as Compound Class $SX_{975}$).

A compound (L-5) wherein T represents a group represented by T13, $R^{3c}$ represents a bromine atom, and $R^1$ represents any substituents indicated in [Table L1] to [Table L3] (hereinafter, referred to as Compound Class $SX_{976}$).

A compound (L-5) wherein T represents a group represented by T13, $R^{3c}$ represents an iodine atom, and $R^1$ represents any substituents indicated in [Table L1] to [Table L3] (hereinafter, referred to as Compound Class $SX_{977}$).

A compound (L-5) wherein T represents a group represented by T14, $R^{3c}$ represents a hydrogen atom, and $R^1$ represents any substituents indicated in [Table L1] to [Table L3] (hereinafter, referred to as Compound Class $SX_{978}$).

A compound (L-5) wherein T represents a group represented by T14, $R^{3c}$ represents $CF_3$, and $R^1$ represents any substituents indicated in [Table L1] to [Table L3] (hereinafter, referred to as Compound Class $SX_{979}$).

A compound (L-5) wherein T represents a group represented by T14, $R^{3c}$ represents a chlorine atom, and $R^1$ represents any substituents indicated in [Table L1] to [Table L3] (hereinafter, referred to as Compound Class $SX_{980}$).

A compound (L-5) wherein T represents a group represented by T14, $R^{3c}$ represents a bromine atom, and $R^1$ represents any substituents indicated in [Table L1] to [Table L3] (hereinafter, referred to as Compound Class $SX_{981}$).

A compound (L-5) wherein T represents a group represented by T14, $R^{3c}$ represents an iodine atom, and $R^1$ represents any substituents indicated in [Table L1] and [Table L3] (hereinafter, referred to as Compound Class $SX_{982}$).

A compound (L-5) wherein T represents a group represented by T15, $R^{3c}$ represents a hydrogen atom, and $R^1$ represents any substituents indicated in [Table L1] to [Table L3] (hereinafter, referred to as Compound Class $SX_{983}$).

A compound (L-5) wherein T represents a group represented by T15, $R^{3c}$ represents $CF_3$, and $R^1$ represents any substituents indicated in [Table L1] to [Table L3] (hereinafter, referred to as Compound Class $SX_{984}$).

A compound (L-5) wherein T represents a group represented by T15, $R^{3c}$ represents a chlorine atom, and $R^1$ represents any substituents indicated in [Table L1] to [Table L3] (hereinafter, referred to as Compound Class $SX_{985}$).

A compound (L-5) wherein T represents a group represented by T15, $R^{3c}$ represents a bromine atom, and $R^1$ represents any substituents indicated in [Table L1] to [Table L3] (hereinafter, referred to as Compound Class $SX_{986}$).

A compound (L-5) wherein T represents a group represented by T15, $R^{3c}$ represents an iodine atom, and $R^1$ represents any substituents indicated in [Table L1] to [Table L3] (hereinafter, referred to as Compound Class $SX_{987}$).

A compound (L-5) wherein T represents a group represented by T16, $R^{3c}$ represents a hydrogen atom, and $R^1$ represents any substituents indicated in [Table L1] and [Table L3] (hereinafter, referred to as Compound Class $SX_{988}$).

A compound (L-5) wherein T represents a group represented by T16, $R^{3c}$ represents $CF_3$, and $R^1$ represents any substituents indicated in [Table L1] to [Table L3] (hereinafter, referred to as Compound Class $SX_{989}$).

A compound (L-5) wherein T represents a group represented by T16, $R^{3c}$ represents a chlorine atom, and $R^1$ represents any substituents indicated in [Table L1] to [Table L3] (hereinafter, referred to as Compound Class $SX_{990}$).

A compound (L-5) wherein T represents a group represented by T16, $R^{3c}$ represents a bromine atom, and $R^1$ represents any substituents indicated in [Table L1] to [Table L3] (hereinafter, referred to as Compound Class $SX_{991}$).

A compound (L-5) wherein T represents a group represented by T16, $R^{3c}$ represents an iodine atom, and $R^1$ represents any substituents indicated in [Table L1] to [Table L3] (hereinafter, referred to as Compound Class $SX_{992}$).

A compound (L-5) wherein T represents a group represented by T17, $R^{3c}$ represents a hydrogen atom, and $R^1$ represents any substituents indicated in [Table L1] to [Table L3] (hereinafter, referred to as Compound Class $SX_{993}$).

A compound (L-5) wherein T represents a group represented by T17, $R^{3c}$ represents $CF_3$, and $R^1$ represents any substituents indicated in [Table L1] to [Table L3] (hereinafter, referred to as Compound Class $SX_{994}$).

A compound (L-5) wherein T represents a group represented by T17, $R^{3c}$ represents a chlorine atom, and $R^1$ represents any substituents indicated in [Table L1] to [Table L3] (hereinafter, referred to as Compound Class $SX_{995}$).

A compound (L-5) wherein T represents a group represented by T17, $R^{3c}$ represents a bromine atom, and $R^1$ represents any substituents indicated in [Table L1] to [Table L3] (hereinafter, referred to as Compound Class $SX_{996}$).

A compound (L-5) wherein T represents a group represented by T17, $R^{3c}$ represents an iodine atom, and $R^1$ represents any substituents indicated in [Table L1] to [Table L3] (hereinafter, referred to as Compound Class $SX_{997}$).

A compound (L-5) wherein T represents a group represented by T18, $R^{3c}$ represents a hydrogen atom, and $R^1$ represents any substituents indicated in [Table L1] to [Table L3] (hereinafter, referred to as Compound Class $SX_{998}$).

A compound (L-5) wherein T represents a group represented by T18, $R^{3c}$ represents $CF_3$, and $R^1$ represents any substituents indicated in [Table L1] to [Table L3] (hereinafter, referred to as Compound Class $SX_{999}$).

A compound (L-5) wherein T represents a group represented by T18, $R^{3c}$ represents a chlorine atom, and $R^1$ represents any substituents indicated in [Table L1] to [Table L3] (hereinafter, referred to as Compound Class $SX_{1000}$).

A compound (L-5) wherein T represents a group represented by T18, $R^{3c}$ represents a bromine atom, and $R^1$ represents any substituents indicated in [Table L1] to [Table L3] (hereinafter, referred to as Compound Class $SX_{1001}$).

A compound (L-5) wherein T represents a group represented by T18, $R^{3c}$ represents an iodine atom, and $R^1$ represents any substituents indicated in [Table L1] to [Table L3] (hereinafter, referred to as Compound Class $SX_{1002}$).

A compound (L-5) wherein T represents a group represented by T19, $R^{3c}$ represents a hydrogen atom, and $R^1$ represents any substituents indicated in [Table L1] to [Table L3] (hereinafter, referred to as Compound Class $SX_{1003}$).

A compound (L-5) wherein T represents a group represented by T19, $R^{3c}$ represents $CF_3$, and $R^1$ represents any substituents indicated in [Table L1] to [Table L3] (hereinafter, referred to as Compound Class $SX_{1004}$).

A compound (L-5) wherein T represents a group represented by T19, $R^{3c}$ represents a chlorine atom, and $R^1$ represents any substituents indicated in [Table L1] to [Table L3] (hereinafter, referred to as Compound Class $SX_{1005}$).

A compound (L-5) wherein T represents a group represented by T19, $R^{3c}$ represents a bromine atom, and $R^1$ represents any substituents indicated in [Table L1] to [Table L3] (hereinafter, referred to as Compound Class $SX_{1006}$).

A compound (L-5) wherein T represents a group represented by T19, $R^{3c}$ represents an iodine atom, and $R^1$ represents any substituents indicated in [Table L1] and [Table L3] (hereinafter, referred to as Compound Class $SX_{1007}$).

A compound (L-5) wherein T represents a group represented by T20, $R^{3c}$ represents a hydrogen atom, and $R^1$ represents any substituents indicated in [Table L1] to [Table L3] (hereinafter, referred to as Compound Class $SX_{1008}$).

A compound (L-5) wherein T represents a group represented by T20, $R^{3c}$ represents $CF_3$, and $R^1$ represents any substituents indicated in [Table L1] to [Table L3] (hereinafter, referred to as Compound Class $SX_{1009}$).

A compound (L-5) wherein T represents a group represented by T20, $R^{3c}$ represents a chlorine atom, and $R^1$ represents any substituents indicated in [Table L1] to [Table L3] (hereinafter, referred to as Compound Class $SX_{1010}$).

A compound (L-5) wherein T represents a group represented by T20, $R^{3c}$ represents a bromine atom, and $R^1$ represents any substituents indicated in [Table L1] to [Table L3] (hereinafter, referred to as Compound Class $SX_{1011}$).

A compound (L-5) wherein T represents a group represented by T20, $R^{3c}$ represents an iodine atom, and $R^1$ represents any substituents indicated in [Table L1] to [Table L3] (hereinafter, referred to as Compound Class $SX_{1012}$).

A compound (L-5) wherein T represents a group represented by T21, $R^{3c}$ represents a hydrogen atom, and $R^1$ represents any substituents indicated in [Table L1] and [Table L3] (hereinafter, referred to as Compound Class $SX_{1013}$).

A compound (L-5) wherein T represents a group represented by T21, $R^{3c}$ represents $CF_3$, and $R^1$ represents any substituents indicated in [Table L1] to [Table L3] (hereinafter, referred to as Compound Class $SX_{1014}$).

A compound (L-5) wherein T represents a group represented by T21, $R^{3c}$ represents a chlorine atom, and $R^1$ represents any substituents indicated in [Table L1] to [Table L3] (hereinafter, referred to as Compound Class $SX_{1015}$).

A compound (L-5) wherein T represents a group represented by T21, $R^{3c}$ represents a bromine atom, and $R^1$ represents any substituents indicated in [Table L1] to [Table L3] (hereinafter, referred to as Compound Class $SX_{1016}$).

A compound (L-5) wherein T represents a group represented by T21, $R^{3c}$ represents an iodine atom, and $R^1$ represents any substituents indicated in [Table L1] to [Table L3] (hereinafter, referred to as Compound Class $SX_{1017}$).

A compound (L-5) wherein T represents a group represented by T22, $R^{3c}$ represents a hydrogen atom, and $R^1$ represents any substituents indicated in [Table L1] to [Table L3] (hereinafter, referred to as Compound Class $SX_{1018}$).

A compound (L-5) wherein T represents a group represented by T22, $R^{3c}$ represents $CF_3$, and $R^1$ represents any substituents indicated in [Table L1] to [Table L3] (hereinafter, referred to as Compound Class $SX_{1019}$).

A compound (L-5) wherein T represents a group represented by T22, $R^{3c}$ represents a chlorine atom, and $R^1$ represents any substituents indicated in [Table L1] to [Table L3] (hereinafter, referred to as Compound Class $SX_{1020}$).

A compound (L-5) wherein T represents a group represented by T22, $R^{3c}$ represents a bromine atom, and $R^1$ represents any substituents indicated in [Table L1] to [Table L3] (hereinafter, referred to as Compound Class $SX_{1021}$).

A compound (L-5) wherein T represents a group represented by T22, $R^{3c}$ represents an iodine atom, and $R^1$ represents any substituents indicated in [Table L1] to [Table L3] (hereinafter, referred to as Compound Class $SX_{1022}$).

A compound (L-5) wherein T represents a group represented by T23, $R^{3c}$ represents a hydrogen atom, and $R^1$ represents any substituents indicated in [Table L1] to [Table L3] (hereinafter, referred to as Compound Class $SX_{1023}$).

A compound (L-5) wherein T represents a group represented by T23, $R^{3c}$ represents $CF_3$, and $R^1$ represents any substituents indicated in [Table L1] to [Table L3] (hereinafter, referred to as Compound Class $SX_{1024}$).

A compound (L-5) wherein T represents a group represented by T23, $R^{3c}$ represents a chlorine atom, and $R^1$ represents any substituents indicated in [Table L1] to [Table L3] (hereinafter, referred to as Compound Class $SX_{1025}$).

A compound (L-5) wherein T represents a group represented by T23, $R^{3c}$ represents a bromine atom, and $R^1$ represents any substituents indicated in [Table L1] to [Table L3] (hereinafter, referred to as Compound Class $SX_{1026}$).

A compound (L-5) wherein T represents a group represented by T23, $R^{3c}$ represents an iodine atom, and $R^1$ represents any substituents indicated in [Table L1] to [Table L3] (hereinafter, referred to as Compound Class $SX_{1027}$).

A compound (L-5) wherein T represents a group represented by T24, $R^{3c}$ represents a hydrogen atom, and $R^1$ represents any substituents indicated in [Table L1] to [Table L3] (hereinafter, referred to as Compound Class $SX_{1028}$).

A compound (L-5) wherein T represents a group represented by T24, $R^{3c}$ represents $CF_3$, and $R^1$ represents any substituents indicated in [Table L1] to [Table L3] (hereinafter, referred to as Compound Class $SX_{1029}$).

A compound (L-5) wherein T represents a group represented by T24, $R^{3c}$ represents a chlorine atom, and $R^1$ represents any substituents indicated in [Table L1] to [Table L3] (hereinafter, referred to as Compound Class $SX_{1030}$).

A compound (L-5) wherein T represents a group represented by T24, $R^{3c}$ represents a bromine atom, and $R^1$ represents any substituents indicated in [Table L1] to [Table L3] (hereinafter, referred to as Compound Class $SX_{1031}$).

A compound (L-5) wherein T represents a group represented by T24, $R^{3c}$ represents an iodine atom, and $R^1$ represents any substituents indicated in [Table L1] and [Table L3] (hereinafter, referred to as Compound Class $SX_{1032}$).

A compound (L-5) wherein T represents a group represented by T25, $R^{3c}$ represents a hydrogen atom, and $R^1$ represents any substituents indicated in [Table L1] to [Table L3] (hereinafter, referred to as Compound Class $SX_{1033}$).

A compound (L-5) wherein T represents a group represented by T25, $R^{3c}$ represents $CF_3$, and $R^1$ represents any substituents indicated in [Table L1] to [Table L3] (hereinafter, referred to as Compound Class $SX_{1034}$).

A compound (L-5) wherein T represents a group represented by T25, $R^{3c}$ represents a chlorine atom, and $R^1$ represents any substituents indicated in [Table L1] to [Table L3] (hereinafter, referred to as Compound Class $SX_{1035}$).

A compound (L-5) wherein T represents a group represented by T25, $R^{3c}$ represents a bromine atom, and $R^1$ represents any substituents indicated in [Table L1] to [Table L3] (hereinafter, referred to as Compound Class $SX_{1036}$).

A compound (L-5) wherein T represents a group represented by T25, $R^{3c}$ represents an iodine atom, and $R^1$ represents any substituents indicated in [Table L1] to [Table L3] (hereinafter, referred to as Compound Class $SX_{1037}$).

A compound (L-5) wherein T represents a group represented by T26, $R^{3c}$ represents a hydrogen atom, and $R^1$ represents any substituents indicated in [Table L1] and [Table L3] (hereinafter, referred to as Compound Class $SX_{1038}$).

A compound (L-5) wherein T represents a group represented by T26, $R^{3c}$ represents $CF_3$, and $R^1$ represents any substituents indicated in [Table L1] to [Table L3] (hereinafter, referred to as Compound Class $SX_{1039}$).

A compound (L-5) wherein T represents a group represented by T26, $R^{3c}$ represents a chlorine atom, and $R^1$ represents any substituents indicated in [Table L1] to [Table L3] (hereinafter, referred to as Compound Class $SX_{1040}$).

A compound (L-5) wherein T represents a group represented by T26, $R^{3c}$ represents a bromine atom, and $R^1$ represents any substituents indicated in [Table L1] to [Table L3] (hereinafter, referred to as Compound Class $SX_{1041}$).

A compound (L-5) wherein T represents a group represented by T26, $R^{3c}$ represents an iodine atom, and $R^1$ represents any substituents indicated in [Table L1] to [Table L3] (hereinafter, referred to as Compound Class $SX_{1042}$).

A compound (L-5) wherein T represents a group represented by T27, $R^{3c}$ represents a hydrogen atom, and $R^1$ represents any substituents indicated in [Table L1] to [Table L3] (hereinafter, referred to as Compound Class $SX_{1043}$).

A compound (L-5) wherein T represents a group represented by T27, $R^{3c}$ represents $CF_3$, and $R^1$ represents any substituents indicated in [Table L1] to [Table L3] (hereinafter, referred to as Compound Class $SX_{1044}$).

A compound (L-5) wherein T represents a group represented by T27, $R^{3c}$ represents a chlorine atom, and $R^1$ represents any substituents indicated in [Table L1] to [Table L3] (hereinafter, referred to as Compound Class $SX_{1045}$).

A compound (L-5) wherein T represents a group represented by T27, $R^{3c}$ represents a bromine atom, and $R^1$ represents any substituents indicated in [Table L1] to [Table L3] (hereinafter, referred to as Compound Class $SX_{1046}$).

A compound (L-5) wherein T represents a group represented by T27, $R^{3c}$ represents an iodine atom, and $R^1$ represents any substituents indicated in [Table L1] to [Table L3] (hereinafter, referred to as Compound Class $SX_{1047}$).

A compound (L-5) wherein T represents a group represented by T28, $R^{3c}$ represents a hydrogen atom, and $R^1$ represents any substituents indicated in [Table L1] to [Table L3] (hereinafter, referred to as Compound Class $SX_{1048}$).

A compound (L-5) wherein T represents a group represented by T28, $R^{3c}$ represents $CF_3$, and $R^1$ represents any substituents indicated in [Table L1] to [Table L3] (hereinafter, referred to as Compound Class $SX_{1049}$).

A compound (L-5) wherein T represents a group represented by T28, $R^{3c}$ represents a chlorine atom, and $R^1$ represents any substituents indicated in [Table L1] to [Table L3] (hereinafter, referred to as Compound Class $SX_{1050}$).

A compound (L-5) wherein T represents a group represented by T28, $R^{3c}$ represents a bromine atom, and $R^1$ represents any substituents indicated in [Table L1] to [Table L3] (hereinafter, referred to as Compound Class $SX_{1051}$).

A compound (L-5) wherein T represents a group represented by T28, $R^{3c}$ represents an iodine atom, and $R^1$ represents any substituents indicated in [Table L1] to [Table L3] (hereinafter, referred to as Compound Class $SX_{1052}$).

A compound (L-5) wherein T represents a group represented by T29, $R^{3c}$ represents a hydrogen atom, and $R^1$ represents any substituents indicated in [Table L1] to [Table L3] (hereinafter, referred to as Compound Class $SX_{1053}$).

A compound (L-5) wherein T represents a group represented by T29, $R^{3c}$ represents $CF_3$, and $R^1$ represents any substituents indicated in [Table L1] to [Table L3] (hereinafter, referred to as Compound Class $SX_{1054}$).

A compound (L-5) wherein T represents a group represented by T29, $R^{3c}$ represents a chlorine atom, and $R^1$ represents any substituents indicated in [Table L1] to [Table L3] (hereinafter, referred to as Compound Class $SX_{1055}$).

A compound (L-5) wherein T represents a group represented by T29, $R^{3c}$ represents a bromine atom, and $R^1$ represents any substituents indicated in [Table L1] to [Table L3] (hereinafter, referred to as Compound Class $SX_{1056}$).

A compound (L-5) wherein T represents a group represented by T29, $R^{3c}$ represents an iodine atom, and $R^1$ represents any substituents indicated in [Table L1] and [Table L3] (hereinafter, referred to as Compound Class $SX_{1057}$).

A compound (L-5) wherein T represents a group represented by T30, $R^{3c}$ represents a hydrogen atom, and $R^1$ represents any substituents indicated in [Table L1] to [Table L3] (hereinafter, referred to as Compound Class $SX_{1058}$).

A compound (L-5) wherein T represents a group represented by T30, $R^{3c}$ represents $CF_3$, and $R^1$ represents any substituents indicated in [Table L1] to [Table L3] (hereinafter, referred to as Compound Class $SX_{1059}$).

A compound (L-5) wherein T represents a group represented by T30, $R^{3c}$ represents a chlorine atom, and $R^1$ represents any substituents indicated in [Table L1] to [Table L3] (hereinafter, referred to as Compound Class $SX_{1060}$).

A compound (L-5) wherein T represents a group represented by T30, $R^{3c}$ represents a bromine atom, and $R^1$ represents any substituents indicated in [Table L1] to [Table L3] (hereinafter, referred to as Compound Class $SX_{1061}$).

A compound (L-5) wherein T represents a group represented by T30, $R^{3c}$ represents an iodine atom, and $R^1$ represents any substituents indicated in [Table L1] to [Table L3] (hereinafter, referred to as Compound Class $SX_{1062}$).

A compound (L-5) wherein T represents a group represented by T31, $R^{3c}$ represents a hydrogen atom, and $R^1$ represents any substituents indicated in [Table L1] and [Table L3] (hereinafter, referred to as Compound Class $SX_{1063}$).

A compound (L-5) wherein T represents a group represented by T31, $R^{3c}$ represents $CF_3$, and $R^1$ represents any substituents indicated in [Table L1] to [Table L3] (hereinafter, referred to as Compound Class $SX_{1064}$).

A compound (L-5) wherein T represents a group represented by T31, $R^{3c}$ represents a chlorine atom, and $R^1$ represents any substituents indicated in [Table L1] to [Table L3] (hereinafter, referred to as Compound Class $SX_{1065}$).

A compound (L-5) wherein T represents a group represented by T31, $R^{3c}$ represents a bromine atom, and $R^1$ represents any substituents indicated in [Table L1] to [Table L3] (hereinafter, referred to as Compound Class $SX_{1066}$).

A compound (L-5) wherein T represents a group represented by T31, $R^{3c}$ represents an iodine atom, and $R^1$ represents any substituents indicated in [Table L1] to [Table L3] (hereinafter, referred to as Compound Class $SX_{1067}$).

A compound represented by formula (L-6):

(L-6)

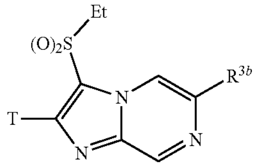

(hereinafter, referred to as compound (L-6)), wherein T represents a group represented by T1, $R^{3b}$ represents a hydrogen atom, and $R^1$ represents any substituents indicated in [Table L1] to [Table L3] (hereinafter, referred to as Compound Class $SX_{1068}$).

A compound (L-6) wherein T represents a group represented by T1, $R^{3b}$ represents $CF_3$, and $R^1$ represents any substituents indicated in [Table L1] to [Table L3] (hereinafter, referred to as Compound Class $SX_{1069}$).

A compound (L-6) wherein T represents a group represented by T1, $R^{3b}$ represents a chlorine atom, and $R^1$ represents any substituents indicated in [Table L1] to [Table L3] (hereinafter, referred to as Compound Class $SX_{1070}$).

A compound (L-6) wherein T represents a group represented by T1, $R^{3b}$ represents a bromine atom, and $R^1$ represents any substituents indicated in [Table L1] to [Table L3] (hereinafter, referred to as Compound Class $SX_{1071}$).

A compound (L-6) wherein T represents a group represented by T1, $R^{3b}$ represents an iodine atom, and $R^1$ represents any substituents indicated in [Table L1] to [Table L3] (hereinafter, referred to as Compound Class $SX_{1072}$).

A compound (L-6), wherein T represents a group represented by T2, $R^{3b}$ represents a hydrogen atom, and $R^1$ represents any substituents indicated in [Table L1] to [Table L3] (hereinafter, referred to as Compound Class $SX_{1073}$).

A compound (L-6) wherein T represents a group represented by T2, $R^{3b}$ represents $CF_3$, and $R^1$ represents any represents any substituents indicated in [Table L1] and [Table L3] (hereinafter, referred to as Compound Class $SX_{1074}$).

A compound (L-6) wherein T represents a group represented by T2, $R^{3b}$ represents a chlorine atom, and $R^1$ represents any substituents indicated in [Table L1] to [Table L3] (hereinafter, referred to as Compound Class $SX_{1075}$).

A compound (L-6) wherein T represents a group represented by T2, $R^{3b}$ represents a bromine atom, and $R^1$ represents any substituents indicated in [Table L1] to [Table L3] (hereinafter, referred to as Compound Class $SX_{1076}$).

A compound (L-6) wherein T represents a group represented by T2, $R^{3b}$ represents an iodine atom, and $R^1$ represents any substituents indicated in [Table L1] to [Table L3] (hereinafter, referred to as Compound Class $SX_{1077}$).

A compound (L-6), wherein T represents a group represented by T3, $R^{3b}$ represents a hydrogen atom, and $R^1$ represents any substituents indicated in [Table L1] to [Table L3] (hereinafter, referred to as Compound Class $SX_{1078}$).

A compound (L-6) wherein T represents a group represented by T3, $R^{3b}$ represents $CF_3$, and $R^1$ represents any substituents indicated in [Table L1] to [Table L3] (hereinafter, referred to as Compound Class $SX_{1079}$).

A compound (L-6) wherein T represents a group represented by T3, $R^{3b}$ represents a chlorine atom, and $R^1$ represents any substituents indicated in [Table L1] and [Table L3] (hereinafter, referred to as Compound Class $SX_{1080}$).

A compound (L-6) wherein T represents a group represented by T3, $R^{3b}$ represents a bromine atom, and $R^1$ represents any substituents indicated in [Table L1] to [Table L3] (hereinafter, referred to as Compound Class $SX_{1081}$).

A compound (L-6) wherein T represents a group represented by T3, $R^{3b}$ represents an iodine atom, and $R^1$ represents any substituents indicated in [Table L1] to [Table L3] (hereinafter, referred to as Compound Class $SX_{1082}$). A compound (L-6), wherein T represents a group represented by T4, $R^{3b}$ represents a hydrogen atom, and $R^1$ represents any substituents indicated in [Table L1] to [Table L3] (hereinafter, referred to as Compound Class $SX_{1083}$).

A compound (L-6) wherein T represents a group represented by T4, $R^{3b}$ represents $CF_3$, and $R^1$ represents any substituents indicated in [Table L1] to [Table L3] (hereinafter, referred to as Compound Class $SX_{1084}$).

A compound (L-6) wherein T represents a group represented by T4, $R^{3b}$ represents a chlorine atom, and $R^1$ represents any substituents indicated in [Table L1] to [Table L3] (hereinafter, referred to as Compound Class $SX_{1085}$).

A compound (L-6) wherein T represents a group represented by T4, $R^{3b}$ represents a bromine atom, and $R^1$ represents any substituents indicated in [Table L1] to [Table L3] (hereinafter, referred to as Compound Class $SX_{1086}$).

A compound (L-6) wherein T represents a group represented by T4, $R^{3b}$ represents an iodine atom, and $R^1$ represents any substituents indicated in [Table L1] to [Table L3] (hereinafter, referred to as Compound Class $SX_{1087}$).

A compound (L-6), wherein T represents a group represented by T5, $R^{3b}$ represents a hydrogen atom, and $R^1$ represents any substituents indicated in [Table L1] to [Table L3] (hereinafter, referred to as Compound Class $SX_{1088}$).

A compound (L-6) wherein T represents a group represented by T5, $R^{3b}$ represents $CF_3$, and $R^1$ represents any substituents indicated in [Table L1] to [Table L3] (hereinafter, referred to as Compound Class $SX_{1089}$).

A compound (L-6) wherein T represents a group represented by T5, $R^{3b}$ represents a chlorine atom, and $R^1$ represents any substituents indicated in [Table L1] to [Table L3] (hereinafter, referred to as Compound Class $SX_{1090}$).

A compound (L-6) wherein T represents a group represented by T5, $R^{3b}$ represents a bromine atom, and $R^1$ represents any substituents indicated in [Table L1] to [Table L3] (hereinafter, referred to as Compound Class $SX_{1091}$).

A compound (L-6) wherein T represents a group represented by T5, $R^{3b}$ represents an iodine atom, and $R^1$ represents any substituents indicated in [Table L1] to [Table L3] (hereinafter, referred to as Compound Class $SX_{1092}$).

A compound (L-6), wherein T represents a group represented by T6, $R^{3b}$ represents a hydrogen atom, and $R^1$ represents any substituents indicated in [Table L1] to [Table L3] (hereinafter, referred to as Compound Class $SX_{1093}$).

A compound (L-6) wherein T represents a group represented by T6, $R^{3b}$ represents $CF_3$, and $R^1$ represents any substituents indicated in [Table L1] to [Table L3] (hereinafter, referred to as Compound Class $SX_{1094}$).

A compound (L-6) wherein T represents a group represented by T6, $R^{3b}$ represents a chlorine atom, and $R^1$ represents any substituents indicated in [Table L1] to [Table L3] (hereinafter, referred to as Compound Class $SX_{1095}$).

A compound (L-6) wherein T represents a group represented by T6, $R^{3b}$ represents a bromine atom, and $R^1$ represents any substituents indicated in [Table L1] to [Table L3] (hereinafter, referred to as Compound Class $SX_{1096}$).

A compound (L-6) wherein T represents a group represented by T6, $R^{3b}$ represents an iodine atom, and $R^1$ represents any substituents indicated in [Table L1] to [Table L3] (hereinafter, referred to as Compound Class $SX_{1097}$).

A compound (L-6), wherein T represents a group represented by T7, $R^{3b}$ represents a hydrogen atom, and $R^1$ represents any substituents indicated in [Table L1] to [Table L3] (hereinafter, referred to as Compound Class $SX_{1098}$).

A compound (L-6) wherein T represents a group represented by T7, $R^{3b}$ represents $CF_3$, and $R^1$ represents any represents any substituents indicated in [Table L1] and [Table L3] (hereinafter, referred to as Compound Class $SX_{1089}$).

A compound (L-6) wherein T represents a group represented by T7, $R^{3b}$ represents a chlorine atom, and $R^1$ represents any substituents indicated in [Table L1] to [Table L3] (hereinafter, referred to as Compound Class $SX_{1100}$).

A compound (L-6) wherein T represents a group represented by T7, $R^{3b}$ represents a bromine atom, and $R^1$ represents any substituents indicated in [Table L1] to [Table L3] (hereinafter, referred to as Compound Class $SX_{1101}$).

A compound (L-6) wherein T represents a group represented by T7, $R^{3b}$ represents an iodine atom, and $R^1$ represents any substituents indicated in [Table L1] to [Table L3] (hereinafter, referred to as Compound Class $SX_{1102}$).

A compound (L-6), wherein T represents a group represented by T8, $R^{3b}$ represents a hydrogen atom, and $R^1$ represents any substituents indicated in [Table L1] to [Table L3] (hereinafter, referred to as Compound Class $SX_{1103}$).

A compound (L-6) wherein T represents a group represented by T8, $R^{3b}$ represents $CF_3$, and $R^1$ represents any substituents indicated in [Table L1] to [Table L3] (hereinafter, referred to as Compound Class $SX_{1104}$).

A compound (L-6) wherein T represents a group represented by T8, $R^{3b}$ represents a chlorine atom, and $R^1$ represents any substituents indicated in [Table L1] and [Table L3] (hereinafter, referred to as Compound Class $SX_{1105}$).

A compound (L-6) wherein T represents a group represented by T8, $R^{3b}$ represents a bromine atom, and $R^1$ represents any substituents indicated in [Table L1] to [Table L3] (hereinafter, referred to as Compound Class $SX_{1106}$).

A compound (L-6) wherein T represents a group represented by T8, $R^{3b}$ represents an iodine atom, and $R^1$ represents any substituents indicated in [Table L1] to [Table L3] (hereinafter, referred to as Compound Class $SX_{1107}$).

A compound (L-6), wherein T represents a group represented by T9, $R^{3b}$ represents a hydrogen atom, and $R^1$ represents any substituents indicated in [Table L1] to [Table L3] (hereinafter, referred to as Compound Class $SX_{1108}$).

A compound (L-6) wherein T represents a group represented by T9, $R^{3b}$ represents $CF_3$, and $R^1$ represents any substituents indicated in [Table L1] to [Table L3] (hereinafter, referred to as Compound Class $SX_{1109}$).

A compound (L-6) wherein T represents a group represented by T9, $R^{3b}$ represents a chlorine atom, and $R^1$ represents any substituents indicated in [Table L1] to [Table L3] (hereinafter, referred to as Compound Class $SX_{1110}$).

A compound (L-6) wherein T represents a group represented by T9, $R^{3b}$ represents a bromine atom, and $R^1$ represents any substituents indicated in [Table L1] to [Table L3] (hereinafter, referred to as Compound Class $SX_{1111}$).

A compound (L-6) wherein T represents a group represented by T9, $R^{3b}$ represents an iodine atom, and $R^1$ represents any substituents indicated in [Table L1] to [Table L3] (hereinafter, referred to as Compound Class $SX_{1112}$).

A compound (L-6), wherein T represents a group represented by T10, $R^{3b}$ represents a hydrogen atom, and $R^1$ represents any substituents indicated in [Table L1] to [Table L3] (hereinafter, referred to as Compound Class $SX_{1113}$).

A compound (L-6) wherein T represents a group represented by T10, $R^{3b}$ represents $CF_3$, and $R^1$ represents any substituents indicated in [Table L1] to [Table L3] (hereinafter, referred to as Compound Class $SX_{1114}$).

A compound (L-6) wherein T represents a group represented by T10, $R^{3b}$ represents a chlorine atom, and $R^1$ represents any substituents indicated in [Table L1] to [Table L3] (hereinafter, referred to as Compound Class $SX_{1115}$).

A compound (L-6) wherein T represents a group represented by T10, $R^{3b}$ represents a bromine atom, and $R^1$ represents any substituents indicated in [Table L1] to [Table L3] (hereinafter, referred to as Compound Class $SX_{1116}$).

A compound (L-6) wherein T represents a group represented by T10, $R^{3b}$ represents an iodine atom, and $R^1$ represents any substituents indicated in [Table L1] to [Table L3] (hereinafter, referred to as Compound Class $SX_{1117}$).

A compound (L-6), wherein T represents a group represented by T11, $R^{3b}$ represents a hydrogen atom, and $R^1$ represents any substituents indicated in [Table L1] to [Table L3] (hereinafter, referred to as Compound Class $SX_{1118}$).

A compound (L-6) wherein T represents a group represented by T11, $R^{3b}$ represents $CF_3$, and $R^1$ represents any substituents indicated in [Table L1] to [Table L3] (hereinafter, referred to as Compound Class $SX_{1119}$).

A compound (L-6) wherein T represents a group represented by T11, $R^{3b}$ represents a chlorine atom, and $R^1$ represents any substituents indicated in [Table L1] to [Table L3] (hereinafter, referred to as Compound Class $SX_{1120}$).

A compound (L-6) wherein T represents a group represented by T11, $R^{3b}$ represents a bromine atom, and $R^1$ represents any substituents indicated in [Table L1] to [Table L3] (hereinafter, referred to as Compound Class $SX_{1121}$).

A compound (L-6) wherein T represents a group represented by T11, $R^{3b}$ represents an iodine atom, and $R^1$ represents any substituents indicated in [Table L1] to [Table L3] (hereinafter, referred to as Compound Class $SX_{1122}$).

A compound (L-6), wherein T represents a group represented by T12, $R^{3b}$ represents a hydrogen atom, and $R^1$ represents any substituents indicated in [Table L1] to [Table L3] (hereinafter, referred to as Compound Class $SX_{1123}$).

A compound (L-6) wherein T represents a group represented by T12, $R^{3b}$ represents $CF_3$, and $R^1$ represents any represents any substituents indicated in [Table L1] and [Table L3] (hereinafter, referred to as Compound Class $SX_{1124}$).

A compound (L-6) wherein T represents a group represented by T12, $R^{3b}$ represents a chlorine atom, and $R^1$ represents any substituents indicated in [Table L1] to [Table L3] (hereinafter, referred to as Compound Class $SX_{1125}$).

A compound (L-6) wherein T represents a group represented by T12, $R^{3b}$ represents a bromine atom, and $R^1$ represents any substituents indicated in [Table L1] to [Table L3] (hereinafter, referred to as Compound Class $SX_{1126}$).

A compound (L-6) wherein T represents a group represented by T12, $R^{3b}$ represents an iodine atom, and $R^1$ represents any substituents indicated in [Table L1] to [Table L3] (hereinafter, referred to as Compound Class $SX_{1127}$).

A compound (L-6), wherein T represents a group represented by T13, $R^{3b}$ represents a hydrogen atom, and $R^1$ represents any substituents indicated in [Table L1] to [Table L3] (hereinafter, referred to as Compound Class $SX_{1128}$).

A compound (L-6) wherein T represents a group represented by T13, $R^{3b}$ represents $CF_3$, and $R^1$ represents any substituents indicated in [Table L1] to [Table L3] (hereinafter, referred to as Compound Class $SX_{1129}$).

A compound (L-6) wherein T represents a group represented by T13, $R^{3b}$ represents a chlorine atom, and $R^1$ represents any substituents indicated in [Table L1] and [Table L3] (hereinafter, referred to as Compound Class $SX_{1130}$).

A compound (L-6) wherein T represents a group represented by T13, $R^{3b}$ represents a bromine atom, and $R^1$ represents any substituents indicated in [Table L1] to [Table L3] (hereinafter, referred to as Compound Class $SX_{1131}$).

A compound (L-6) wherein T represents a group represented by T13, $R^{3b}$ represents an iodine atom, and $R^1$ represents any substituents indicated in [Table L1] to [Table L3] (hereinafter, referred to as Compound Class $SX_{1132}$).

A compound (L-6), wherein T represents a group represented by T14, $R^{3b}$ represents a hydrogen atom, and $R^1$ represents any substituents indicated in [Table L1] to [Table L3] (hereinafter, referred to as Compound Class $SX_{1133}$).

A compound (L-6) wherein T represents a group represented by T14, $R^{3b}$ represents $CF_3$, and $R^1$ represents any substituents indicated in [Table L1] to [Table L3] (hereinafter, referred to as Compound Class $SX_{1134}$).

A compound (L-6) wherein T represents a group represented by T14, $R^{3b}$ represents a chlorine atom, and $R^1$ represents any substituents indicated in [Table L1] to [Table L3] (hereinafter, referred to as Compound Class $SX_{1135}$).

A compound (L-6) wherein T represents a group represented by T14, $R^{3b}$ represents a bromine atom, and $R^1$ represents any substituents indicated in [Table L1] to [Table L3] (hereinafter, referred to as Compound Class $SX_{1136}$).

A compound (L-6) wherein T represents a group represented by T14, $R^{3b}$ represents an iodine atom, and $R^1$ represents any substituents indicated in [Table L1] to [Table L3] (hereinafter, referred to as Compound Class $SX_{1137}$).

A compound (L-6), wherein T represents a group represented by T15, $R^{3b}$ represents a hydrogen atom, and $R^1$ represents any substituents indicated in [Table L1] to [Table L3] (hereinafter, referred to as Compound Class $SX_{1138}$).

A compound (L-6) wherein T represents a group represented by T15, $R^{3b}$ represents $CF_3$, and $R^1$ represents any substituents indicated in [Table L1] to [Table L3] (hereinafter, referred to as Compound Class $SX_{1139}$).

A compound (L-6) wherein T represents a group represented by T15, $R^{3b}$ represents a chlorine atom, and $R^1$ represents any substituents indicated in [Table L1] to [Table L3] (hereinafter, referred to as Compound Class $SX_{1140}$).

A compound (L-6) wherein T represents a group represented by T15, $R^{3b}$ represents a bromine atom, and $R^1$ represents any substituents indicated in [Table L1] to [Table L3] (hereinafter, referred to as Compound Class $SX_{1141}$).

A compound (L-6) wherein T represents a group represented by T15, $R^{3b}$ represents an iodine atom, and $R^1$ represents any substituents indicated in [Table L1] to [Table L3] (hereinafter, referred to as Compound Class $SX_{1142}$).

A compound (L-6), wherein T represents a group represented by T16, $R^{3b}$ represents a hydrogen atom, and $R^1$ represents any substituents indicated in [Table L1] to [Table L3] (hereinafter, referred to as Compound Class $SX_{1143}$).

A compound (L-6) wherein T represents a group represented by T16, $R^{3b}$ represents $CF_3$, and $R^1$ represents any substituents indicated in [Table L1] to [Table L3] (hereinafter, referred to as Compound Class $SX_{1144}$).

A compound (L-6) wherein T represents a group represented by T16, $R^{3b}$ represents a chlorine atom, and $R^1$ represents any substituents indicated in [Table L1] to [Table L3] (hereinafter, referred to as Compound Class $SX_{1145}$).

A compound (L-6) wherein T represents a group represented by T16, $R^{3b}$ represents a bromine atom, and $R^1$ represents any substituents indicated in [Table L1] to [Table L3] (hereinafter, referred to as Compound Class $SX_{1146}$).

A compound (L-6) wherein T represents a group represented by T16, $R^{3b}$ represents an iodine atom, and $R^1$ represents any substituents indicated in [Table L1] to [Table L3] (hereinafter, referred to as Compound Class $SX_{1147}$).

A compound (L-6), wherein T represents a group represented by T17, $R^{3b}$ represents a hydrogen atom, and $R^1$ represents any substituents indicated in [Table L1] to [Table L3] (hereinafter, referred to as Compound Class $SX_{1148}$).

A compound (L-6) wherein T represents a group represented by T17, $R^{3b}$ represents $CF_3$, and $R^1$ represents any represents any substituents indicated in [Table L1] and [Table L3] (hereinafter, referred to as Compound Class $SX_{1149}$).

A compound (L-6) wherein T represents a group represented by T17, $R^{3b}$ represents a chlorine atom, and $R^1$ represents any substituents indicated in [Table L1] to [Table L3] (hereinafter, referred to as Compound Class $SX_{1150}$).

A compound (L-6) wherein T represents a group represented by T17, $R^{3b}$ represents a bromine atom, and $R^1$ represents any substituents indicated in [Table L1] to [Table L3] (hereinafter, referred to as Compound Class $SX_{1151}$).

A compound (L-6) wherein T represents a group represented by T17, $R^{3b}$ represents an iodine atom, and $R^1$ represents any substituents indicated in [Table L1] to [Table L3] (hereinafter, referred to as Compound Class $SX_{1152}$).

A compound (L-6), wherein T represents a group represented by T18, $R^{3b}$ represents a hydrogen atom, and $R^1$ represents any substituents indicated in [Table L1] to [Table L3] (hereinafter, referred to as Compound Class $SX_{1153}$).

A compound (L-6) wherein T represents a group represented by T18, $R^{3b}$ represents $CF_3$, and $R^1$ represents any substituents indicated in [Table L1] to [Table L3] (hereinafter, referred to as Compound Class $SX_{1154}$).

A compound (L-6) wherein T represents a group represented by T18, $R^{3b}$ represents a chlorine atom, and $R^1$ represents any substituents indicated in [Table L1] and [Table L3] (hereinafter, referred to as Compound Class $SX_{1155}$).

A compound (L-6) wherein T represents a group represented by T18, $R^{3b}$ represents a bromine atom, and $R^1$ represents any substituents indicated in [Table L1] to [Table L3] (hereinafter, referred to as Compound Class $SX_{1156}$).

A compound (L-6) wherein T represents a group represented by T18, $R^{3b}$ represents an iodine atom, and $R^1$ represents any substituents indicated in [Table L1] to [Table L3] (hereinafter, referred to as Compound Class $SX_{1157}$).

A compound (L-6), wherein T represents a group represented by T19, $R^{3b}$ represents a hydrogen atom, and $R^1$ represents any substituents indicated in [Table L1] to [Table L3] (hereinafter, referred to as Compound Class $SX_{1158}$).

A compound (L-6) wherein T represents a group represented by T19, $R^{3b}$ represents $CF_3$, and $R^1$ represents any substituents indicated in [Table L1] to [Table L3] (hereinafter, referred to as Compound Class $SX_{1159}$).

A compound (L-6) wherein T represents a group represented by T19, $R^{3b}$ represents a chlorine atom, and $R^1$ represents any substituents indicated in [Table L1] to [Table L3] (hereinafter, referred to as Compound Class $SX_{1160}$).

A compound (L-6) wherein T represents a group represented by T19, $R^{3b}$ represents a bromine atom, and $R^1$ represents any substituents indicated in [Table L1] to [Table L3] (hereinafter, referred to as Compound Class $SX_{1161}$).

A compound (L-6) wherein T represents a group represented by T19, $R^{3b}$ represents an iodine atom, and $R^1$ represents any substituents indicated in [Table L1] to [Table L3] (hereinafter, referred to as Compound Class $SX_{1162}$).

A compound (L-6), wherein T represents a group represented by T20, $R^{3b}$ represents a hydrogen atom, and $R^1$ represents any substituents indicated in [Table L1] to [Table L3] (hereinafter, referred to as Compound Class $SX_{1163}$).

A compound (L-6) wherein T represents a group represented by T20, $R^{3b}$ represents $CF_3$, and $R^1$ represents any substituents indicated in [Table L1] to [Table L3] (hereinafter, referred to as Compound Class $SX_{1164}$).

A compound (L-6) wherein T represents a group represented by T20, $R^{3b}$ represents a chlorine atom, and $R^1$ represents any substituents indicated in [Table L1] to [Table L3] (hereinafter, referred to as Compound Class $SX_{1165}$).

A compound (L-6) wherein T represents a group represented by T20, $R^{3b}$ represents a bromine atom, and $R^1$ represents any substituents indicated in [Table L1] to [Table L3] (hereinafter, referred to as Compound Class $SX_{1166}$).

A compound (L-6) wherein T represents a group represented by T20, $R^{3b}$ represents an iodine atom, and $R^1$ represents any substituents indicated in [Table L1] to [Table L3] (hereinafter, referred to as Compound Class $SX_{1167}$).

A compound (L-6), wherein T represents a group represented by T21, $R^{3b}$ represents a hydrogen atom, and $R^1$ represents any substituents indicated in [Table L1] to [Table L3] (hereinafter, referred to as Compound Class $SX_{1168}$).

A compound (L-6) wherein T represents a group represented by T21, $R^{3b}$ represents $CF_3$, and $R^1$ represents any substituents indicated in [Table L1] to [Table L3] (hereinafter, referred to as Compound Class $SX_{1169}$).

A compound (L-6) wherein T represents a group represented by T21, $R^{3b}$ represents a chlorine atom, and $R^1$ represents any substituents indicated in [Table L1] to [Table L3] (hereinafter, referred to as Compound Class $SX_{1170}$).

A compound (L-6) wherein T represents a group represented by T21, $R^{3b}$ represents a bromine atom, and $R^1$ represents any substituents indicated in [Table L1] to [Table L3] (hereinafter, referred to as Compound Class $SX_{1171}$).

A compound (L-6) wherein T represents a group represented by T21, $R^{3b}$ represents an iodine atom, and $R^1$ represents any substituents indicated in [Table L1] to [Table L3] (hereinafter, referred to as Compound Class $SX_{1172}$).

A compound (L-6), wherein T represents a group represented by T22, $R^{3b}$ represents a hydrogen atom, and $R^1$ represents any substituents indicated in [Table L1] to [Table L3] (hereinafter, referred to as Compound Class $SX_{1173}$).

A compound (L-6) wherein T represents a group represented by T22, $R^{3b}$ represents $CF_3$, and $R^1$ represents any represents any substituents indicated in [Table L1] and [Table L3] (hereinafter, referred to as Compound Class $SX_{1174}$).

A compound (L-6) wherein T represents a group represented by T22, $R^{3b}$ represents a chlorine atom, and $R^1$ represents any substituents indicated in [Table L1] to [Table L3] (hereinafter, referred to as Compound Class $SX_{1175}$).

A compound (L-6) wherein T represents a group represented by T22, $R^{3b}$ represents a bromine atom, and $R^1$ represents any substituents indicated in [Table L1] to [Table L3] (hereinafter, referred to as Compound Class $SX_{1176}$).

A compound (L-6) wherein T represents a group represented by T22, $R^{3b}$ represents an iodine atom, and $R^1$ represents any substituents indicated in [Table L1] to [Table L3] (hereinafter, referred to as Compound Class $SX_{1177}$).

A compound (L-6), wherein T represents a group represented by T23, $R^{3b}$ represents a hydrogen atom, and $R^1$ represents any substituents indicated in [Table L1] to [Table L3] (hereinafter, referred to as Compound Class $SX_{1178}$).

A compound (L-6) wherein T represents a group represented by T23, $R^{3b}$ represents $CF_3$, and $R^1$ represents any substituents indicated in [Table L1] to [Table L3] (hereinafter, referred to as Compound Class $SX_{1179}$).

A compound (L-6) wherein T represents a group represented by T23, $R^{3b}$ represents a chlorine atom, and $R^1$ represents any substituents indicated in [Table L1] and [Table L3] (hereinafter, referred to as Compound Class $SX_{1180}$).

A compound (L-6) wherein T represents a group represented by T23, $R^{3b}$ represents a bromine atom, and $R^1$ represents any substituents indicated in [Table L1] to [Table L3] (hereinafter, referred to as Compound Class $SX_{1181}$).

A compound (L-6) wherein T represents a group represented by T23, $R^{3b}$ represents an iodine atom, and $R^1$ represents any substituents indicated in [Table L1] to [Table L3] (hereinafter, referred to as Compound Class $SX_{1182}$).

A compound (L-6), wherein T represents a group represented by T24, $R^{3b}$ represents a hydrogen atom, and $R^1$ represents any substituents indicated in [Table L1] to [Table L3] (hereinafter, referred to as Compound Class $SX_{1183}$).

A compound (L-6) wherein T represents a group represented by T24, $R^{3b}$ represents $CF_3$, and $R^1$ represents any substituents indicated in [Table L1] to [Table L3] (hereinafter, referred to as Compound Class $SX_{1184}$).

A compound (L-6) wherein T represents a group represented by T24, $R^{3b}$ represents a chlorine atom, and $R^1$ represents any substituents indicated in [Table L1] to [Table L3] (hereinafter, referred to as Compound Class $SX_{1185}$).

A compound (L-6) wherein T represents a group represented by T24, $R^{3b}$ represents a bromine atom, and $R^1$ represents any substituents indicated in [Table L1] to [Table L3] (hereinafter, referred to as Compound Class $SX_{1186}$).

A compound (L-6) wherein T represents a group represented by T24, $R^{3b}$ represents an iodine atom, and $R^1$ represents any substituents indicated in [Table L1] to [Table L3] (hereinafter, referred to as Compound Class $SX_{1187}$).

A compound (L-6), wherein T represents a group represented by T25, $R^{3b}$ represents a hydrogen atom, and $R^1$ represents any substituents indicated in [Table L1] to [Table L3] (hereinafter, referred to as Compound Class $SX_{1188}$).

A compound (L-6) wherein T represents a group represented by T25, $R^{3b}$ represents $CF_3$, and $R^1$ represents any substituents indicated in [Table L1] to [Table L3] (hereinafter, referred to as Compound Class $SX_{1189}$).

A compound (L-6) wherein T represents a group represented by T25, $R^{3b}$ represents a chlorine atom, and $R^1$ represents any substituents indicated in [Table L1] to [Table L3] (hereinafter, referred to as Compound Class $SX_{1190}$).

A compound (L-6) wherein T represents a group represented by T25, $R^{3b}$ represents a bromine atom, and $R^1$ represents any substituents indicated in [Table L1] to [Table L3] (hereinafter, referred to as Compound Class $SX_{1191}$).

A compound (L-6) wherein T represents a group represented by T25, $R^{3b}$ represents an iodine atom, and $R^1$ represents any substituents indicated in [Table L1] to [Table L3] (hereinafter, referred to as Compound Class $SX_{1192}$).

A compound (L-6), wherein T represents a group represented by T26, $R^{3b}$ represents a hydrogen atom, and $R^1$ represents any substituents indicated in [Table L1] to [Table L3] (hereinafter, referred to as Compound Class $SX_{1193}$).

A compound (L-6) wherein T represents a group represented by T26, $R^{3b}$ represents $CF_3$, and $R^1$ represents any substituents indicated in [Table L1] to [Table L3] (hereinafter, referred to as Compound Class $SX_{1194}$).

A compound (L-6) wherein T represents a group represented by T26, $R^{3b}$ represents a chlorine atom, and $R^1$ represents any substituents indicated in [Table L1] to [Table L3] (hereinafter, referred to as Compound Class $SX_{1195}$).

A compound (L-6) wherein T represents a group represented by T26, $R^{3b}$ represents a bromine atom, and $R^1$ represents any substituents indicated in [Table L1] to [Table L3] (hereinafter, referred to as Compound Class $SX_{1196}$).

A compound (L-6) wherein T represents a group represented by T26, $R^{3b}$ represents an iodine atom, and $R^1$ represents any substituents indicated in [Table L1] to [Table L3] (hereinafter, referred to as Compound Class $SX_{1197}$).

A compound (L-6), wherein T represents a group represented by T27, $R^{3b}$ represents a hydrogen atom, and $R^1$ represents any substituents indicated in [Table L1] to [Table L3] (hereinafter, referred to as Compound Class $SX_{1198}$).

A compound (L-6) wherein T represents a group represented by T27, $R^{3b}$ represents $CF_3$, and $R^1$ represents any substituents indicated in [Table L1] and [Table L3] (hereinafter, referred to as Compound Class $SX_{1199}$).

A compound (L-6) wherein T represents a group represented by T27, $R^{3b}$ represents a chlorine atom, and $R^1$ represents any substituents indicated in [Table L1] to [Table L3] (hereinafter, referred to as Compound Class $SX_{1200}$).

A compound (L-6) wherein T represents a group represented by T27, $R^{3b}$ represents a bromine atom, and $R^1$ represents any substituents indicated in [Table L1] to [Table L3] (hereinafter, referred to as Compound Class $SX_{1201}$).

A compound (L-6) wherein T represents a group represented by T27, $R^{3b}$ represents an iodine atom, and $R^1$ represents any substituents indicated in [Table L1] to [Table L3] (hereinafter, referred to as Compound Class $SX_{1202}$).

A compound (L-6), wherein T represents a group represented by T28, $R^{3b}$ represents a hydrogen atom, and $R^1$ represents any substituents indicated in [Table L1] to [Table L3] (hereinafter, referred to as Compound Class $SX_{1203}$).

A compound (L-6) wherein T represents a group represented by T28, $R^{3b}$ represents $CF_3$, and $R^1$ represents any substituents indicated in [Table L1] to [Table L3] (hereinafter, referred to as Compound Class $SX_{1204}$).

A compound (L-6) wherein T represents a group represented by T28, $R^{3b}$ represents a chlorine atom, and $R^1$ represents any substituents indicated in [Table L1] and [Table L3] (hereinafter, referred to as Compound Class $SX_{1205}$).

A compound (L-6) wherein T represents a group represented by T28, $R^{3b}$ represents a bromine atom, and $R^1$ represents any substituents indicated in [Table L1] to [Table L3] (hereinafter, referred to as Compound Class $SX_{1206}$).

A compound (L-6) wherein T represents a group represented by T28, $R^{3b}$ represents an iodine atom, and $R^1$ represents any substituents indicated in [Table L1] to [Table L3] (hereinafter, referred to as Compound Class $SX_{1207}$).

A compound (L-6), wherein T represents a group represented by T29, $R^{3b}$ represents a hydrogen atom, and $R^1$ represents any substituents indicated in [Table L1] to [Table L3] (hereinafter, referred to as Compound Class $SX_{1208}$).

A compound (L-6) wherein T represents a group represented by T29, $R^{3b}$ represents $CF_3$, and $R^1$ represents any substituents indicated in [Table L1] to [Table L3] (hereinafter, referred to as Compound Class $SX_{1209}$).

A compound (L-6) wherein T represents a group represented by T29, $R^{3b}$ represents a chlorine atom, and $R^1$ represents any substituents indicated in [Table L1] to [Table L3] (hereinafter, referred to as Compound Class $SX_{1210}$).

A compound (L-6) wherein T represents a group represented by T29, $R^{3b}$ represents a bromine atom, and $R^1$ represents any substituents indicated in [Table L1] to [Table L3] (hereinafter, referred to as Compound Class $SX_{1211}$).

A compound (L-6) wherein T represents a group represented by T29, $R^{3b}$ represents an iodine atom, and $R^1$ represents any substituents indicated in [Table L1] to [Table L3] (hereinafter, referred to as Compound Class $SX_{1212}$).

A compound (L-6), wherein T represents a group represented by T30, $R^{3b}$ represents a hydrogen atom, and $R^1$ represents any substituents indicated in [Table L1] to [Table L3] (hereinafter, referred to as Compound Class $SX_{1213}$).

A compound (L-6) wherein T represents a group represented by T30, $R^{3b}$ represents $CF_3$, and $R^1$ represents any substituents indicated in [Table L1] to [Table L3] (hereinafter, referred to as Compound Class $SX_{1214}$).

A compound (L-6) wherein T represents a group represented by T30, $R^{3b}$ represents a chlorine atom, and $R^1$ represents any substituents indicated in [Table L1] to [Table L3] (hereinafter, referred to as Compound Class $SX_{1215}$).

A compound (L-6) wherein T represents a group represented by T30, $R^{3b}$ represents a bromine atom, and $R^1$ represents any substituents indicated in [Table L1] to [Table L3] (hereinafter, referred to as Compound Class $SX_{1216}$).

A compound (L-6) wherein T represents a group represented by T30, $R^{3b}$ represents an iodine atom, and $R^1$ represents any substituents indicated in [Table L1] to [Table L3] (hereinafter, referred to as Compound Class $SX_{1217}$).

A compound (L-6), wherein T represents a group represented by T31, $R^{3b}$ represents a hydrogen atom, and $R^1$ represents any substituents indicated in [Table L1] to [Table L3] (hereinafter, referred to as Compound Class $SX_{1218}$).

A compound (L-6) wherein T represents a group represented by T31, $R^{3b}$ represents $CF_3$, and $R^1$ represents any substituents indicated in [Table L1] to [Table L3] (hereinafter, referred to as Compound Class $SX_{1219}$).

A compound (L-6) wherein T represents a group represented by T31, $R^{3b}$ represents a chlorine atom, and $R^1$ represents any substituents indicated in [Table L1] to [Table L3] (hereinafter, referred to as Compound Class $SX_{1220}$).

A compound (L-6) wherein T represents a group represented by T31, $R^{3b}$ represents a bromine atom, and $R^1$ represents any substituents indicated in [Table L1] to [Table L3] (hereinafter, referred to as Compound Class $SX_{1221}$).

A compound (L-6) wherein T represents a group represented by T31, $R^{3b}$ represents an iodine atom, and $R^1$ represents any substituents indicated in [Table L1] to [Table L3] (hereinafter, referred to as Compound Class $SX_{1222}$).

A compound (L-1) wherein T represents a group represented by T1, $R^1$ represents $CF_3$, and $R^{3b}$ represents any substituents indicated in [Table L4] to [Table L12] (hereinafter, referred to as Compound Class $SX_{1223}$).

TABLE L4

| |
|---|
| F |
| Br |
| I |
| Me |
| Et |
| Pr |
| i-Pr |
| $CHF_2$ |
| $CH{=}CH_2$ |
| $CMe{=}CH_2$ |
| c-Pr |
| c-Bu |
| c-Pen |
| c-Hex |
| 1-F-c-Pr |
| 2,2-$F_2$-c-Pr |
| 1-CN-c-Pr |
| 1-CN-c-Bu |
| 1-CN-c-Pen |
| 1-CN-c-Hex |
| CHO |
| C(O)Me |
| C(O)c-Pr |
| C(O)OEt |
| C(O)NHc-Pr |
| CH=N—OH |
| CH=N—OMe |
| CH=N—OEt |
| CH=N—$OCH_2CF_3$ |
| CMe=N—OH |
| CMe=N—OMe |
| CMe=N—OEt |
| CMe=N—$OCH_2CF_3$ |
| $C(NH_2)$=N—$OCH_2CF_3$ |
| $NO_2$ |
| CN |

TABLE L5

| |
|---|
| Ph |
| 3-F—Ph |
| 4-F—Ph |
| 3-Cl—Ph |
| 4-Cl—Ph |
| 3-$CF_3$—Ph |
| 4-$CF_3$—Ph |
| 3-$NMe_2$—Ph |
| 4-$NMe_2$—Ph |
| 3-CN—Ph |
| 4-CN—Ph |
| 4-C(O)$NMe_2$—Ph |
| 4-NHC(O)Me—Ph |
| 3,4-$F_2$—Ph |
| 3,5-$F_2$—Ph |
| 2,4-$F_2$—Ph |
| 3,4,5-$F_3$—Ph |
| 3,4-$Cl_2$—Ph |
| 3,5-$Cl_2$—Ph |
| 3,5-$Cl_2$-4-F—Ph |
| OPh |
| O-2-F—Ph |
| O-3-$CF_3$—Ph |
| O-4-$CF_3$—Ph |
| $NH_2$ |
| $NHCH_2CF_3$ |
| NHc-Pr |
| NH(1-CN-c-Pr) |
| NHOMe |
| $NMe_2$ |
| NHC(O)Me |
| NHC(O)c-Pr |
| NMeC(O)c-Pr |
| SEt |
| S(O)Et |
| $S(O)_2Et$ |

TABLE L6

| |
|---|
| Py2 |
| 4-F—Py2 |
| 5-F—Py2 |
| 4-Cl—Py2 |
| 5-Cl—Py2 |
| 4-$CF_3$—Py2 |
| 5-$CF_3$—Py2 |
| 6-$CF_3$—Py2 |
| 3-Me—Py2 |
| 4-Me—Py2 |
| 5-Me—Py2 |
| 6-Me—Py2 |
| 4-CN—Py2 |
| 5-CN—Py2 |
| 5-$OCH_2CF_2CF_3$—Py2 |
| 3,5-$F_2$—Py2 |
| Py3 |
| 6-$CF_3$—Py3 |

TABLE L6-continued
| |
|---|
| 5-$CF_3$—Py3 |
| 6-F—Py3 |
| 6-Cl—Py3 |
| Py4 |
| OPy2 |
| OPy3 |
| OPy4 |
| O-5-$CF_3$—Py2 |
| O-6-$CF_3$—Py2 |
| OMe |
| OEt |
| OPr |
| Oi-Pr |
| Oc-Pr |
| $OCMe_2CN$ |
| $CMe_2CN$ |
| $CMeCN_2$ |
| $CH_2CMe_2CN$ |
TABLE L7
| |
|---|
| 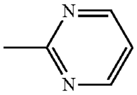 |
| 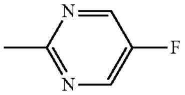 |
| 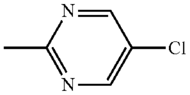 |
| 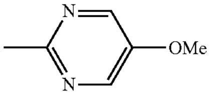 |
| 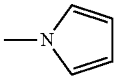 |
| 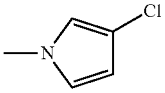 |
| 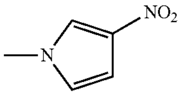 |
| 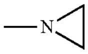 |
| 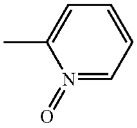 |
| 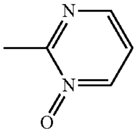 |
TABLE L8
| |
|---|
| 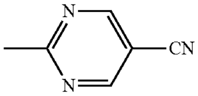 |
| 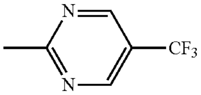 |
| 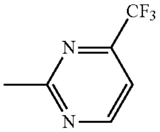 |
| 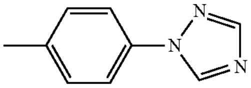 |
| 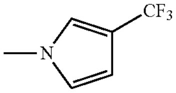 |
| 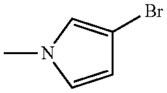 |
| 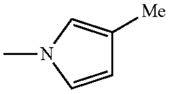 |
| 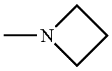 |
| 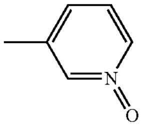 |
| 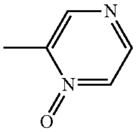 |
TABLE L9
| |
|---|
| 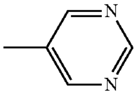 |
| 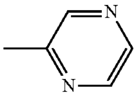 |
| 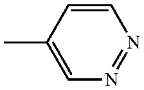 |

TABLE L9-continued
| |
|---|
| 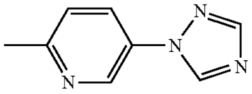 |
| 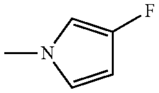 |
| 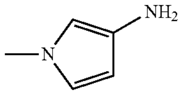 |
| 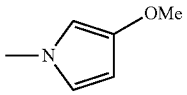 |
| 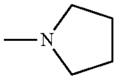 |
| 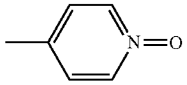 |
| 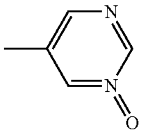 |
TABLE L10
| |
|---|
| 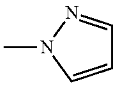 |
| 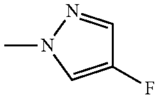 |
| 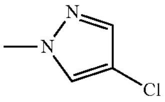 |
| 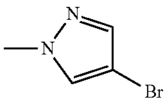 |
| 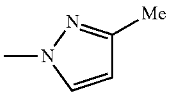 |
| 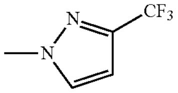 |
| 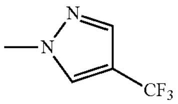 |
TABLE L10-continued
| |
|---|
| 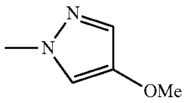 |
| 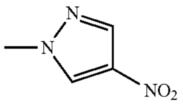 |
| 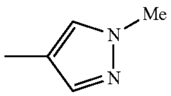 |
TABLE L11
| |
|---|
| 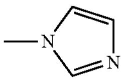 |
| 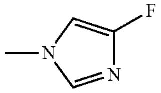 |
| 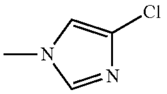 |
| 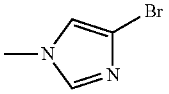 |
| 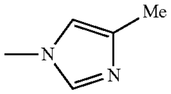 |
| 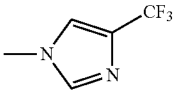 |
| 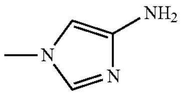 |
| 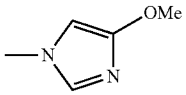 |
| 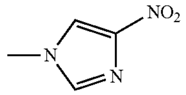 |
| 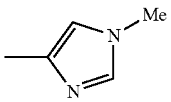 |

TABLE L12

| |
|---|
| 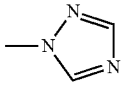 |
| 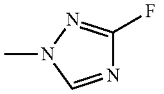 |
| 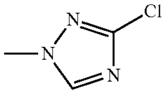 |
| 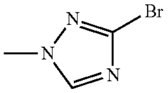 |
| 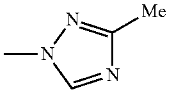 |
| 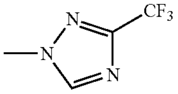 |
| 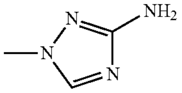 |
| 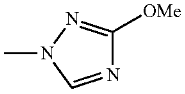 |
| 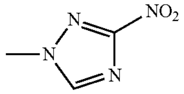 |
| 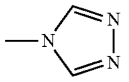 |

A compound (L-1) wherein T represents a group represented by T1, $R^1$ represents $C_2F_5$, and $R^{3b}$ represents any substituents indicated in [Table L4] to [Table L12] (hereinafter, referred to as Compound Class $SX_{1224}$).

A compound (L-1) wherein T represents a group represented by T1, $R^1$ represents $SCF_3$, and $R^{3b}$ represents any substituents indicated in [Table L4] to [Table L12] (hereinafter, referred to as Compound Class $SX_{1225}$).

A compound (L-1) wherein T represents a group represented by T1, $R^1$ represents $S(O)CF_3$, and $R^{3b}$ represents any substituents indicated in [Table L4] to [Table L12] (hereinafter, referred to as Compound Class $SX_{1226}$).

A compound (L-1) wherein T represents a group represented by T1, $R^1$ represents $S(O)_2CF_3$, and $R^{3b}$ represents any substituents indicated in [Table L4] to [Table L12] (hereinafter, referred to as Compound Class $SX_{1227}$).

A compound (L-1) wherein T represents a group represented by T2, $R^1$ represents $CF_3$, and $R^{3b}$ represents any substituents indicated in [Table L4] to [Table L12] (hereinafter, referred to as Compound Class $SX_{1228}$).

A compound (L-1) wherein T represents a group represented by T2, $R^1$ represents $C_2F_5$, and $R^{3b}$ represents any substituents indicated in [Table L4] to [Table L12] (hereinafter, referred to as Compound Class $SX_{1229}$).

A compound (L-1) wherein T represents a group represented by T2, $R^1$ represents $SCF_3$, and $R^{3b}$ represents any substituents indicated in [Table L4] to [Table L12] (hereinafter, referred to as Compound Class $SX_{1230}$).

A compound (L-1) wherein T represents a group represented by T2, $R^1$ represents $S(O)CF_3$, and $R^{3b}$ represents any substituents indicated in [Table L4] to [Table L12] (hereinafter, referred to as Compound Class $SX_{1231}$).

A compound (L-1) wherein T represents a group represented by T2, $R^1$ represents $S(O)_2CF_3$, and $R^{3b}$ represents any substituents indicated in [Table L4] to [Table L12] (hereinafter, referred to as Compound Class $SX_{1232}$).

A compound (L-1) wherein T represents a group represented by T3, $R^1$ represents $CF_3$, and $R^{3b}$ represents any substituents indicated in [Table L4] to [Table L12] (hereinafter, referred to as Compound Class $SX_{1233}$).

A compound (L-1) wherein T represents a group represented by T3, $R^1$ represents $C_2F_5$, and $R^{3b}$ represents any substituents indicated in [Table L4] to [Table L12] (hereinafter, referred to as Compound Class $SX_{1234}$).

A compound (L-1) wherein T represents a group represented by T3, $R^1$ represents $SCF_3$, and $R^{3b}$ represents any substituents indicated in [Table L4] to [Table L12] (hereinafter, referred to as Compound Class $SX_{1235}$).

A compound (L-1) wherein T represents a group represented by T3, $R^1$ represents $S(O)CF_3$, and $R^{3b}$ represents any substituents indicated in [Table L4] to [Table L12] (hereinafter, referred to as Compound Class $SX_{1236}$).

A compound (L-1) wherein T represents a group represented by T3, $R^1$ represents $S(O)_2CF_3$, and $R^{3b}$ represents any substituents indicated in [Table L4] to [Table L12] (hereinafter, referred to as Compound Class $SX_{1237}$).

A compound (L-1) wherein T represents a group represented by T6, $R^1$ represents $CF_3$, and $R^{3b}$ represents any substituents indicated in [Table L4] to [Table L12] (hereinafter, referred to as Compound Class $SX_{1238}$).

A compound (L-1) wherein T represents a group represented by T6, $R^1$ represents $C_2F_5$, and $R^{3b}$ represents any substituents indicated in [Table L4] to [Table L12] (hereinafter, referred to as Compound Class $SX_{1239}$).

A compound (L-1) wherein T represents a group represented by T6, $R^1$ represents $SCF_3$, and $R^{3b}$ represents any substituents indicated in [Table L4] to [Table L12] (hereinafter, referred to as Compound Class $SX_{1240}$).

A compound (L-1) wherein T represents a group represented by T6, $R^1$ represents $S(O)CF_3$, and $R^{3b}$ represents any substituents indicated in [Table L4] to [Table L12] (hereinafter, referred to as Compound Class $SX_{1241}$).

A compound (L-1) wherein T represents a group represented by T6, $R^1$ represents $S(O)_2CF_3$, and $R^{3b}$ represents any substituents indicated in [Table L4] to [Table L12] (hereinafter, referred to as Compound Class $SX_{1242}$).

A compound (L-1) wherein T represents a group represented by T7, $R^1$ represents $CF_3$, and $R^{3b}$ represents any substituents indicated in [Table L4] to [Table L12] (hereinafter, referred to as Compound Class $SX_{1243}$).

A compound (L-1) wherein T represents a group represented by T7, $R^1$ represents $C_2F_5$, and $R^{3b}$ represents any substituents indicated in [Table L4] to [Table L12] (hereinafter, referred to as Compound Class $SX_{1244}$).

A compound (L-1) wherein T represents a group represented by T7, $R^1$ represents $SCF_3$, and $R^{3b}$ represents any substituents indicated in [Table L4] to [Table L12] (hereinafter, referred to as Compound Class $SX_{1245}$).

A compound (L-1) wherein T represents a group represented by T7, $R^1$ represents $S(O)CF_3$, and $R^{3b}$ represents any substituents indicated in [Table L4] to [Table L12] (hereinafter, referred to as Compound Class $SX_{1246}$).

A compound (L-1) wherein T represents a group represented by T7, $R^1$ represents $S(O)_2CF_3$, and $R^{3b}$ represents any substituents indicated in [Table L4] to [Table L12] (hereinafter, referred to as Compound Class $SX_{1247}$).

A compound (L-1) wherein T represents a group represented by T8, $R^1$ represents $CF_3$, and $R^{3b}$ represents any substituents indicated in [Table L4] to [Table L12] (hereinafter, referred to as Compound Class $SX_{1248}$).

A compound (L-1) wherein T represents a group represented by T8, $R^1$ represents $C_2F_5$, and $R^{3b}$ represents any substituents indicated in [Table L4] to [Table L12] (hereinafter, referred to as Compound Class $SX_{1249}$).

A compound (L-1) wherein T represents a group represented by T8, $R^1$ represents $SCF_3$, and $R^{3b}$ represents any substituents indicated in [Table L4] to [Table L12] (hereinafter, referred to as Compound Class $SX_{1250}$).

A compound (L-1) wherein T represents a group represented by T8, $R^1$ represents $S(O)CF_3$, and $R^{3b}$ represents any substituents indicated in [Table L4] to [Table L12] (hereinafter, referred to as Compound Class $SX_{1251}$).

A compound (L-1) wherein T represents a group represented by T8, $R^1$ represents $S(O)_2CF_3$, and $R^{3b}$ represents any substituents indicated in [Table L4] to [Table L12] (hereinafter, referred to as Compound Class $SX_{1252}$).

A compound (L-1) wherein T represents a group represented by T11, $R^1$ represents $CF_3$, and $R^{3b}$ represents any substituents indicated in [Table L4] to [Table L12] (hereinafter, referred to as Compound Class $SX_{1253}$).

A compound (L-1) wherein T represents a group represented by T11, $R^1$ represents $C_2F_5$, and $R^{3b}$ represents any substituents indicated in [Table L4] to [Table L12] (hereinafter, referred to as Compound Class $SX_{1254}$).

A compound (L-1) wherein T represents a group represented by T11, $R^1$ represents $SCF_3$, and $R^{3b}$ represents any substituents indicated in [Table L4] to [Table L12] (hereinafter, referred to as Compound Class $SX_{1255}$).

A compound (L-1) wherein T represents a group represented by T11, $R^1$ represents $S(O)CF_3$, and $R^{3b}$ represents any substituents indicated in [Table L4] to [Table L12] (hereinafter, referred to as Compound Class $SX_{1256}$).

A compound (L-1) wherein T represents a group represented by T11, $R^1$ represents $S(O)_2CF_3$, and $R^{3b}$ represents any substituents indicated in [Table L4] to [Table L12] (hereinafter, referred to as Compound Class $SX_{1257}$).

A compound (L-1) wherein T represents a group represented by T12, $R^1$ represents $CF_3$, and $R^{3b}$ represents any substituents indicated in [Table L4] to [Table L12] (hereinafter, referred to as Compound Class $SX_{1258}$).

A compound (L-1) wherein T represents a group represented by T12, $R^1$ represents $C_2F_5$, and $R^{3b}$ represents any substituents indicated in [Table L4] to [Table L12] (hereinafter, referred to as Compound Class $SX_{1259}$).

A compound (L-1) wherein T represents a group represented by T12, $R^1$ represents $SCF_3$, and $R^{3b}$ represents any substituents indicated in [Table L4] to [Table L12] (hereinafter, referred to as Compound Class $SX_{1260}$).

A compound (L-1) wherein T represents a group represented by T12, $R^1$ represents $S(O)CF_3$, and $R^{3b}$ represents any substituents indicated in [Table L4] to [Table L12] (hereinafter, referred to as Compound Class $SX_{1261}$).

A compound (L-1) wherein T represents a group represented by T12, $R^1$ represents $S(O)_2CF_3$, and $R^{3b}$ represents any substituents indicated in [Table L4] to [Table L12] (hereinafter, referred to as Compound Class $SX_{1262}$).

A compound (L-1) wherein T represents a group represented by T13, $R^1$ represents $CF_3$, and $R^{3b}$ represents any substituents indicated in [Table L4] to [Table L12] (hereinafter, referred to as Compound Class $SX_{1263}$).

A compound (L-1) wherein T represents a group represented by T13, $R^1$ represents $C_2F_5$, and $R^{3b}$ represents any substituents indicated in [Table L4] to [Table L12] (hereinafter, referred to as Compound Class $SX_{1264}$).

A compound (L-1) wherein T represents a group represented by T13, $R^1$ represents $SCF_3$, and $R^{3b}$ represents any substituents indicated in [Table L4] to [Table L12] (hereinafter, referred to as Compound Class $SX_{1265}$).

A compound (L-1) wherein T represents a group represented by T13, $R^1$ represents $S(O)CF_3$, and $R^{3b}$ represents any substituents indicated in [Table L4] to [Table L12] (hereinafter, referred to as Compound Class $SX_{1266}$).

A compound (L-1) wherein T represents a group represented by T13, $R^1$ represents $S(O)_2CF_3$, and $R^{3b}$ represents any substituents indicated in [Table L4] to [Table L12] (hereinafter, referred to as Compound Class $SX_{1267}$).

A compound (L-2) wherein T represents a group represented by T1, $R^1$ represents $CF_3$, $R^{3b}$ represents a hydrogen atom, and $R^{3b}$ represents any substituents indicated in [Table L4] to [Table L12] (hereinafter, referred to as Compound Class $SX_{1268}$).

A compound (L-2) wherein T represents a group represented by T1, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1269}$).

A compound (L-2) wherein T represents a group represented by T1, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1270}$).

A compound (L-2) wherein T represents a group represented by T1, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1271}$).

A compound (L-2) wherein T represents a group represented by T1, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1272}$).

A compound (L-2) wherein T represents a group represented by T1, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1273}$).

A compound (L-2) wherein T represents a group represented by T1, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1274}$).

A compound (L-2) wherein T represents a group represented by T1, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1275}$).

A compound (L-2) wherein T represents a group represented by T1, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1276}$).

A compound (L-2) wherein T represents a group represented by T1, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1277}$).

A compound (L-2) wherein T represents a group represented by T2, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1278}$).

A compound (L-2) wherein T represents a group represented by T2, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1279}$).

A compound (L-2) wherein T represents a group represented by T2, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1280}$).

A compound (L-2) wherein T represents a group represented by T2, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1281}$).

A compound (L-2) wherein T represents a group represented by T2, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1282}$).

A compound (L-2) wherein T represents a group represented by T2, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1283}$).

A compound (L-2) wherein T represents a group represented by T2, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1284}$).

A compound (L-2) wherein T represents a group represented by T2, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1285}$).

A compound (L-2) wherein T represents a group represented by T2, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1286}$).

A compound (L-2) wherein T represents a group represented by T2, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1287}$).

A compound (L-2) wherein T represents a group represented by T3, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1288}$).

A compound (L-2) wherein T represents a group represented by T3, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1289}$).

A compound (L-2) wherein T represents a group represented by T3, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1290}$).

A compound (L-2) wherein T represents a group represented by T3, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1291}$).

A compound (L-2) wherein T represents a group represented by T3, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1292}$).

A compound (L-2) wherein T represents a group represented by T3, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1293}$).

A compound (L-2) wherein T represents a group represented by T3, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1294}$).

A compound (L-2) wherein T represents a group represented by T3, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1295}$).

A compound (L-2) wherein T represents a group represented by T3, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1296}$).

A compound (L-2) wherein T represents a group represented by T3, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1297}$).

A compound (L-2) wherein T represents a group represented by T6, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1298}$).

A compound (L-2) wherein T represents a group represented by T6, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1299}$).

A compound (L-2) wherein T represents a group represented by T6, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1300}$).

A compound (L-2) wherein T represents a group represented by T6, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1301}$).

A compound (L-2) wherein T represents a group represented by T6, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1302}$).

A compound (L-2) wherein T represents a group represented by T6, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1303}$).

A compound (L-2) wherein T represents a group represented by T6, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1304}$).

A compound (L-2) wherein T represents a group represented by T6, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1305}$).

A compound (L-2) wherein T represents a group represented by T6, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1306}$).

A compound (L-2) wherein T represents a group represented by T6, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1307}$).

A compound (L-2) wherein T represents a group represented by T7, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1308}$).

A compound (L-2) wherein T represents a group represented by T7, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1309}$).

A compound (L-2) wherein T represents a group represented by T7, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1310}$).

A compound (L-2) wherein T represents a group represented by T7, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1311}$).

A compound (L-2) wherein T represents a group represented by T7, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1312}$).

A compound (L-2) wherein T represents a group represented by T7, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1313}$).

A compound (L-2) wherein T represents a group represented by T7, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1314}$).

A compound (L-2) wherein T represents a group represented by T7, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1315}$).

A compound (L-2) wherein T represents a group represented by T7, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1316}$).

A compound (L-2) wherein T represents a group represented by T7, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1317}$).

A compound (L-2) wherein T represents a group represented by T8, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1318}$).

A compound (L-2) wherein T represents a group represented by T8, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1319}$).

A compound (L-2) wherein T represents a group represented by T8, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1320}$).

A compound (L-2) wherein T represents a group represented by T8, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1321}$).

A compound (L-2) wherein T represents a group represented by T8, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1322}$).

A compound (L-2) wherein T represents a group represented by T8, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1323}$).

A compound (L-2) wherein T represents a group represented by T8, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1324}$).

A compound (L-2) wherein T represents a group represented by T8, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1325}$).

A compound (L-2) wherein T represents a group represented by T8, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1326}$).

A compound (L-2) wherein T represents a group represented by T8, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1327}$).

A compound (L-2) wherein T represents a group represented by T11, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1328}$).

A compound (L-2) wherein T represents a group represented by T11, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1329}$).

A compound (L-2) wherein T represents a group represented by T11, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1330}$).

A compound (L-2) wherein T represents a group represented by T11, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1331}$).

A compound (L-2) wherein T represents a group represented by T11, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1332}$).

A compound (L-2) wherein T represents a group represented by T11, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1333}$).

A compound (L-2) wherein T represents a group represented by T11, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1334}$).

A compound (L-2) wherein T represents a group represented by T11, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1335}$).

A compound (L-2) wherein T represents a group represented by T11, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1336}$).

A compound (L-2) wherein T represents a group represented by T11, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1337}$).

A compound (L-2) wherein T represents a group represented by T12, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1338}$).

A compound (L-2) wherein T represents a group represented by T12, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1339}$).

A compound (L-2) wherein T represents a group represented by T12, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1340}$).

A compound (L-2) wherein T represents a group represented by T12, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1341}$).

A compound (L-2) wherein T represents a group represented by T12, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1342}$).

A compound (L-2) wherein T represents a group represented by T12, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1343}$).

A compound (L-2) wherein T represents a group represented by T12, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1344}$).

A compound (L-2) wherein T represents a group represented by T12, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1345}$).

A compound (L-2) wherein T represents a group represented by T12, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1346}$).

A compound (L-2) wherein T represents a group represented by T12, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1347}$).

A compound (L-2) wherein T represents a group represented by T13, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1348}$).

A compound (L-2) wherein T represents a group represented by T13, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1349}$).

A compound (L-2) wherein T represents a group represented by T13, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1350}$).

A compound (L-2) wherein T represents a group represented by T13, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1351}$).

A compound (L-2) wherein T represents a group represented by T13, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1352}$).

A compound (L-2) wherein T represents a group represented by T13, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1353}$).

A compound (L-2) wherein T represents a group represented by T13, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1354}$).

A compound (L-2) wherein T represents a group represented by T13, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1355}$).

A compound (L-2) wherein T represents a group represented by T13, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1356}$).

A compound (L-2) wherein T represents a group represented by T13, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1357}$).

A compound (L-3) wherein T represents a group represented by T1, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1358}$).

A compound (L-3) wherein T represents a group represented by T1, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1359}$).

A compound (L-3) wherein T represents a group represented by T1, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1360}$).

A compound (L-3) wherein T represents a group represented by T1, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1361}$).

A compound (L-3) wherein T represents a group represented by T1, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1362}$).

A compound (L-3) wherein T represents a group represented by T1, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1363}$).

A compound (L-3) wherein T represents a group represented by T1, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1364}$).

A compound (L-3) wherein T represents a group represented by T1, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1365}$).

A compound (L-3) wherein T represents a group represented by T1, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1366}$).

A compound (L-3) wherein T represents a group represented by T1, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1367}$).

A compound (L-3) wherein T represents a group represented by T2, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1368}$).

A compound (L-3) wherein T represents a group represented by T2, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1369}$).

A compound (L-3) wherein T represents a group represented by T2, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1370}$).

A compound (L-3) wherein T represents a group represented by T2, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1371}$).

A compound (L-3) wherein T represents a group represented by T2, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1372}$).

A compound (L-3) wherein T represents a group represented by T2, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1373}$).

A compound (L-3) wherein T represents a group represented by T2, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1374}$).

A compound (L-3) wherein T represents a group represented by T2, $R^1$ represents $SCF_3$, $R^{3b}$ represents a hydrogen atom, and $R^{3b}$ represents any substituents indicated in [Table L4] to [Table L12] (hereinafter, referred to as Compound Class $SX_{1375}$).

A compound (L-3) wherein T represents a group represented by T2, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1376}$).

A compound (L-3) wherein T represents a group represented by T2, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1377}$).

A compound (L-3) wherein T represents a group represented by T3, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1778}$).

A compound (L-3) wherein T represents a group represented by T3, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1379}$).

A compound (L-3) wherein T represents a group represented by T3, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1380}$).

A compound (L-3) wherein T represents a group represented by T3, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1381}$).

A compound (L-3) wherein T represents a group represented by T3, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1382}$).

A compound (L-3) wherein T represents a group represented by T3, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1383}$).

A compound (L-3) wherein T represents a group represented by T3, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1384}$).

A compound (L-3) wherein T represents a group represented by T3, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1385}$).

A compound (L-3) wherein T represents a group represented by T3, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1386}$).

A compound (L-3) wherein T represents a group represented by T3, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1387}$).

A compound (L-3) wherein T represents a group represented by T6, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1388}$).

A compound (L-3) wherein T represents a group represented by T6, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1389}$).

A compound (L-3) wherein T represents a group represented by T6, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1390}$).

A compound (L-3) wherein T represents a group represented by T6, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1391}$).

A compound (L-3) wherein T represents a group represented by T6, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1392}$).

A compound (L-3) wherein T represents a group represented by T6, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1393}$).

A compound (L-3) wherein T represents a group represented by T6, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1394}$).

A compound (L-3) wherein T represents a group represented by T6, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1395}$).

A compound (L-3) wherein T represents a group represented by T6, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1396}$).

A compound (L-3) wherein T represents a group represented by T6, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1397}$).

A compound (L-3) wherein T represents a group represented by T7, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1398}$).

A compound (L-3) wherein T represents a group represented by T7, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1399}$).

A compound (L-3) wherein T represents a group represented by T7, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1400}$).

A compound (L-3) wherein T represents a group represented by T7, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1401}$).

A compound (L-3) wherein T represents a group represented by T7, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1402}$).

A compound (L-3) wherein T represents a group represented by T7, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1403}$).

A compound (L-3) wherein T represents a group represented by T7, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1404}$).

A compound (L-3) wherein T represents a group represented by T7, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1405}$).

A compound (L-3) wherein T represents a group represented by T7, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1046}$).

A compound (L-3) wherein T represents a group represented by T7, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1407}$).

A compound (L-3) wherein T represents a group represented by T8, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1408}$).

A compound (L-3) wherein T represents a group represented by T8, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1409}$).

A compound (L-3) wherein T represents a group represented by T8, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1410}$).

A compound (L-3) wherein T represents a group represented by T8, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1411}$).

A compound (L-3) wherein T represents a group represented by T8, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1412}$).

A compound (L-3) wherein T represents a group represented by T8, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1413}$).

A compound (L-3) wherein T represents a group represented by T8, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1414}$).

A compound (L-3) wherein T represents a group represented by T8, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1415}$).

A compound (L-3) wherein T represents a group represented by T8, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1416}$).

A compound (L-3) wherein T represents a group represented by T8, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1417}$).

A compound (L-3) wherein T represents a group represented by T11, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1418}$).

A compound (L-3) wherein T represents a group represented by T11, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1419}$).

A compound (L-3) wherein T represents a group represented by T11, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1420}$).

A compound (L-3) wherein T represents a group represented by T11, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1421}$).

A compound (L-3) wherein T represents a group represented by T11, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1422}$).

A compound (L-3) wherein T represents a group represented by T11, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1423}$).

A compound (L-3) wherein T represents a group represented by T11, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1424}$).

A compound (L-3) wherein T represents a group represented by T11, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1425}$).

A compound (L-3) wherein T represents a group represented by T11, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1426}$).

A compound (L-3) wherein T represents a group represented by T11, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1427}$).

A compound (L-3) wherein T represents a group represented by T12, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1428}$).

A compound (L-3) wherein T represents a group represented by T12, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1429}$).

A compound (L-3) wherein T represents a group represented by T12, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1430}$).

A compound (L-3) wherein T represents a group represented by T12, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1431}$).

A compound (L-3) wherein T represents a group represented by T12, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1432}$).

A compound (L-3) wherein T represents a group represented by T12, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1433}$).

A compound (L-3) wherein T represents a group represented by T12, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1434}$).

A compound (L-3) wherein T represents a group represented by T12, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1435}$).

A compound (L-3) wherein T represents a group represented by T12, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1436}$).

A compound (L-3) wherein T represents a group represented by T12, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1437}$).

A compound (L-3) wherein T represents a group represented by T13, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1438}$).

A compound (L-3) wherein T represents a group represented by T13, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1439}$).

A compound (L-3) wherein T represents a group represented by T13, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1440}$).

A compound (L-3) wherein T represents a group represented by T13, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1441}$).

A compound (L-3) wherein T represents a group represented by T13, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1442}$).

A compound (L-3) wherein T represents a group represented by T13, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1443}$).

A compound (L-3) wherein T represents a group represented by T13, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1444}$).

A compound (L-3) wherein T represents a group represented by T13, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1445}$).

A compound (L-3) wherein T represents a group represented by T13, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1446}$).

A compound (L-3) wherein T represents a group represented by T13, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1447}$).

A compound (L-4) wherein T represents a group represented by T1, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1448}$).

A compound (L-4) wherein T represents a group represented by T1, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1449}$).

A compound (L-4) wherein T represents a group represented by T1, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1450}$).

A compound (L-4) wherein T represents a group represented by T1, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1451}$).

A compound (L-4) wherein T represents a group represented by T1, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1452}$).

A compound (L-4) wherein T represents a group represented by T1, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1453}$).

A compound (L-4) wherein T represents a group represented by T1, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1454}$).

A compound (L-4) wherein T represents a group represented by T1, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1445}$).

A compound (L-4) wherein T represents a group represented by T1, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1456}$).

A compound (L-4) wherein T represents a group represented by T1, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1457}$).

A compound (L-4) wherein T represents a group represented by T2, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1458}$).

A compound (L-4) wherein T represents a group represented by T2, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1459}$).

A compound (L-4) wherein T represents a group represented by T2, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1460}$).

A compound (L-4) wherein T represents a group represented by T2, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1461}$).

A compound (L-4) wherein T represents a group represented by T2, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1462}$).

A compound (L-4) wherein T represents a group represented by T2, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1463}$).

A compound (L-4) wherein T represents a group represented by T2, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1464}$).

A compound (L-4) wherein T represents a group represented by T2, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1465}$).

A compound (L-4) wherein T represents a group represented by T2, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1466}$).

A compound (L-4) wherein T represents a group represented by T2, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1467}$).

A compound (L-4) wherein T represents a group represented by T3, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1468}$).

A compound (L-4) wherein T represents a group represented by T3, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1469}$).

A compound (L-4) wherein T represents a group represented by T3, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1470}$).

A compound (L-4) wherein T represents a group represented by T3, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1471}$).

A compound (L-4) wherein T represents a group represented by T3, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1472}$).

A compound (L-4) wherein T represents a group represented by T3, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1473}$).

A compound (L-4) wherein T represents a group represented by T3, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1474}$).

A compound (L-4) wherein T represents a group represented by T3, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1475}$).

A compound (L-4) wherein T represents a group represented by T3, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1476}$).

A compound (L-4) wherein T represents a group represented by T3, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1477}$).

A compound (L-4) wherein T represents a group represented by T6, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1478}$).

A compound (L-4) wherein T represents a group represented by T6, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1479}$).

A compound (L-4) wherein T represents a group represented by T6, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1480}$).

A compound (L-4) wherein T represents a group represented by T6, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1481}$).

A compound (L-4) wherein T represents a group represented by T6, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1482}$).

A compound (L-4) wherein T represents a group represented by T6, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1483}$).

A compound (L-4) wherein T represents a group represented by T6, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1484}$).

A compound (L-4) wherein T represents a group represented by T6, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1485}$).

A compound (L-4) wherein T represents a group represented by T6, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1486}$).

A compound (L-4) wherein T represents a group represented by T6, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1487}$).

A compound (L-4) wherein T represents a group represented by T7, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1488}$).

A compound (L-4) wherein T represents a group represented by T7, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1489}$).

A compound (L-4) wherein T represents a group represented by T7, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1490}$).

A compound (L-4) wherein T represents a group represented by T7, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1491}$).

A compound (L-4) wherein T represents a group represented by T7, $R^1$ represents $S(O)_2CF_3$, $R^c$ represents a hydrogen atom, and $R^{3b}$ represents any substituents indicated in [Table L4] to [Table L12] (hereinafter, referred to as Compound Class $SX_{1492}$).

A compound (L-4) wherein T represents a group represented by T7, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1493}$).

A compound (L-4) wherein T represents a group represented by T7, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1494}$).

A compound (L-4) wherein T represents a group represented by T7, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1495}$).

A compound (L-4) wherein T represents a group represented by T7, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1496}$).

A compound (L-4) wherein T represents a group represented by T7, $R^1$ represents $S(O)_2CF_3$, $R^{3c}$ represents a hydrogen atom, and $R^{3c}$ represents any substituents indicated in [Table L4] to [Table L12] (hereinafter, referred to as Compound Class $SX_{1497}$).

A compound (L-4) wherein T represents a group represented by T8, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1498}$).

A compound (L-4) wherein T represents a group represented by T8, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1499}$).

A compound (L-4) wherein T represents a group represented by T8, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1500}$).

A compound (L-4) wherein T represents a group represented by T8, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1501}$).

A compound (L-4) wherein T represents a group represented by T8, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1502}$).

A compound (L-4) wherein T represents a group represented by TB, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1503}$).

A compound (L-4) wherein T represents a group represented by T8, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1504}$).

A compound (L-4) wherein T represents a group represented by T8, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1505}$).

A compound (L-4) wherein T represents a group represented by T8, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1506}$).

A compound (L-4) wherein T represents a group represented by T8, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1507}$).

A compound (L-4) wherein T represents a group represented by T11, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1508}$).

A compound (L-4) wherein T represents a group represented by T11, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1509}$).

A compound (L-4) wherein T represents a group represented by T11, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1510}$).

A compound (L-4) wherein T represents a group represented by T11, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1511}$).

A compound (L-4) wherein T represents a group represented by T11, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1512}$).

A compound (L-4) wherein T represents a group represented by T11, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1513}$).

A compound (L-4) wherein T represents a group represented by T11, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1514}$).

A compound (L-4) wherein T represents a group represented by T11, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1515}$).

A compound (L-4) wherein T represents a group represented by T11, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1516}$).

A compound (L-4) wherein T represents a group represented by T11, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1517}$).

A compound (L-4) wherein T represents a group represented by T12, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1518}$).

A compound (L-4) wherein T represents a group represented by T12, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1519}$).

A compound (L-4) wherein T represents a group represented by T12, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1520}$).

A compound (L-4) wherein T represents a group represented by T12, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1521}$).

A compound (L-4) wherein T represents a group represented by T12, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1522}$).

A compound (L-4) wherein T represents a group represented by T12, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1523}$).

A compound (L-4) wherein T represents a group represented by T12, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1524}$).

A compound (L-4) wherein T represents a group represented by T12, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1525}$).

A compound (L-4) wherein T represents a group represented by T12, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1526}$).

A compound (L-4) wherein T represents a group represented by T12, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1527}$).

A compound (L-4) wherein T represents a group represented by T13, $R^1$ represents $CF_3$, $R^{3c}$ represents a hydrogen atom, and $R^{3b}$ represents any substituents indicated in [Table L4] to [Table L12] (hereinafter, referred to as Compound Class $SX_{1528}$).

A compound (L-4) wherein T represents a group represented by T13, $R^1$ represents $C_2F_5$, $R^{3c}$ represents a hydrogen atom, and $R^{3b}$ represents any substituents indicated in [Table L4] to [Table L12] (hereinafter, referred to as Compound Class $SX_{1529}$).

A compound (L-4) wherein T represents a group represented by T13, $R^1$ represents $SCF_3$, $R^{3c}$ represents a hydrogen atom, and $R^{3b}$ represents any substituents indicated in [Table L4] to [Table L12] (hereinafter, referred to as Compound Class $SX_{1530}$).

A compound (L-4) wherein T represents a group represented by T13, $R^1$ represents $S(O)CF_3$, $R^{3c}$ represents a hydrogen atom, and $R^{3b}$ represents any substituents indicated in [Table L4] to [Table L12] (hereinafter, referred to as Compound Class $SX_{1531}$).

A compound (L-4) wherein T represents a group represented by T13, $R^1$ represents $S(O)_2CF_3$, $R^{3c}$ represents a hydrogen atom, and $R^{3b}$ represents any substituents indicated in [Table L4] to [Table L12] (hereinafter, referred to as Compound Class $SX_{1532}$).

A compound (L-4) wherein T represents a group represented by T13, $R^1$ represents $CF_3$, $R^{3b}$ represents a hydrogen atom, and $R^{3c}$ represents any substituents indicated in [Table L4] to [Table L12] (hereinafter, referred to as Compound Class $SX_{1533}$).

A compound (L-4) wherein T represents a group represented by T13, $R^1$ represents $C_2F_5$, $R^{3b}$ represents a hydrogen atom, and $R^{3c}$ represents any substituents indicated in [Table L4] to [Table L12] (hereinafter, referred to as Compound Class $SX_{1534}$).

A compound (L-4) wherein T represents a group represented by T13, $R^1$ represents $SCF_3$, $R^{3b}$ represents a hydrogen atom, and $R^{3c}$ represents any substituents indicated in [Table L4] to [Table L12] (hereinafter, referred to as Compound Class $SX_{1535}$).

A compound (L-4) wherein T represents a group represented by T13, $R^1$ represents $S(O)CF_3$, $R^{3b}$ represents a hydrogen atom, and $R^{3c}$ represents any substituents indicated in [Table L4] to [Table L12] (hereinafter, referred to as Compound Class $SX_{1536}$).

A compound (L-4) wherein T represents a group represented by T13, $R^1$ represents $S(O)_2CF_3$, $R^{3b}$ represents a hydrogen atom, and $R^{3c}$ represents any substituents indicated in [Table L4] to [Table L12] (hereinafter, referred to as Compound Class $SX_{1537}$).

A compound (L-5) wherein T represents a group represented by T1, $R^1$ represents $CF_3$, and $R^{3c}$ represents any substituents indicated in [Table L4] to [Table L12] (hereinafter, referred to as Compound Class $SX_{1538}$).

A compound (L-5) wherein T represents a group represented by T1, $R^1$ represents $C_2F_5$, and $R^{3c}$ represents any substituents indicated in [Table L4] to [Table L12] (hereinafter, referred to as Compound Class $SX_{1539}$).

A compound (L-5) wherein T represents a group represented by T1, $R^1$ represents $SCF_3$, and $R^{3c}$ represents any substituents indicated in [Table L4] to [Table L12] (hereinafter, referred to as Compound Class $SX_{1540}$).

A compound (L-5) wherein T represents a group represented by T1, $R^1$ represents $S(O)CF_3$, and $R^{3c}$ represents any substituents indicated in [Table L4] to [Table L12] (hereinafter, referred to as Compound Class $SX_{1541}$).

A compound (L-5) wherein T represents a group represented by T1, $R^1$ represents $S(O)_2CF_3$, and $R^{3c}$ represents any substituents indicated in [Table L4] to [Table L12] (hereinafter, referred to as Compound Class $SX_{1542}$).

A compound (L-5) wherein T represents a group represented by T2, $R^1$ represents $CF_3$, and $R^{3c}$ represents any substituents indicated in [Table L4] to [Table L12] (hereinafter, referred to as Compound Class $SX_{1543}$).

A compound (L-5) wherein T represents a group represented by T2, $R^1$ represents $C_2F_5$, and $R^{3c}$ represents any substituents indicated in [Table L4] to [Table L12] (hereinafter, referred to as Compound Class $SX_{1544}$).

A compound (L-5) wherein T represents a group represented by T2, $R^1$ represents $SCF_3$, and $R^{3c}$ represents any substituents indicated in [Table L4] to [Table L12] (hereinafter, referred to as Compound Class $SX_{1545}$).

A compound (L-5) wherein T represents a group represented by T2, $R^1$ represents $S(O)CF_3$, and $R^{3c}$ represents any substituents indicated in [Table L4] to [Table L12] (hereinafter, referred to as Compound Class $SX_{1546}$).

A compound (L-5) wherein T represents a group represented by T2, $R^1$ represents $S(O)_2CF_3$, and $R^{3c}$ represents any substituents indicated in [Table L4] to [Table L12] (hereinafter, referred to as Compound Class $SX_{1547}$).

A compound (L-5) wherein T represents a group represented by T3, $R^1$ represents $CF_3$, and $R^{3c}$ represents any substituents indicated in [Table L4] to [Table L12] (hereinafter, referred to as Compound Class $SX_{1548}$).

A compound (L-5) wherein T represents a group represented by T3, $R^1$ represents $C_2F_5$, and $R^{3c}$ represents any substituents indicated in [Table L4] to [Table L12] (hereinafter, referred to as Compound Class $SX_{1549}$).

A compound (L-5) wherein T represents a group represented by T3, $R^1$ represents $SCF_3$, and $R^{3c}$ represents any substituents indicated in [Table L4] to [Table L12] (hereinafter, referred to as Compound Class $SX_{1550}$).

A compound (L-5) wherein T represents a group represented by T3, $R^1$ represents $S(O)CF_2$, and $R^{3c}$ represents any substituents indicated in [Table L4] to [Table L12] (hereinafter, referred to as Compound Class $SX_{1551}$).

A compound (L-5) wherein T represents a group represented by T3, $R^1$ represents $S(O)_2CF_3$, and $R^{3c}$ represents any substituents indicated in [Table L4] to [Table L12] (hereinafter, referred to as Compound Class $SX_{1552}$).

A compound (L-5) wherein T represents a group represented by T6, $R^1$ represents $CF_3$, and $R^{3c}$ represents any substituents indicated in [Table L4] to [Table L12] (hereinafter, referred to as Compound Class $SX_{1553}$).

A compound (L-5) wherein T represents a group represented by T6, $R^1$ represents $C_2F_5$, and $R^{3c}$ represents any substituents indicated in [Table L4] to [Table L12] (hereinafter, referred to as Compound Class $SX_{1554}$).

A compound (L-5) wherein T represents a group represented by T6, $R^1$ represents $SCF_3$, and $R^{3c}$ represents any substituents indicated in [Table L4] to [Table L12] (hereinafter, referred to as Compound Class $SX_{1555}$).

A compound (L-5) wherein T represents a group represented by T6, $R^1$ represents $S(O)CF_3$, and $R^{3c}$ represents any substituents indicated in [Table L4] to [Table L12] (hereinafter, referred to as Compound Class $SX_{1556}$).

A compound (L-5) wherein T represents a group represented by T6, $R^1$ represents $S(O)_2CF_3$, and $R^{3c}$ represents any substituents indicated in [Table L4] to [Table L12] (hereinafter, referred to as Compound Class $SX_{1557}$).

A compound (L-5) wherein T represents a group represented by T7, $R^1$ represents $CF_3$, and $R^{3c}$ represents any substituents indicated in [Table L4] to [Table L12] (hereinafter, referred to as Compound Class $SX_{1558}$).

A compound (L-5) wherein T represents a group represented by T7, $R^1$ represents $C_2F_5$, and $R^{1c}$ represents any substituents indicated in [Table L4] to [Table L12] (hereinafter, referred to as Compound Class $SX_{1559}$).

A compound (L-5) wherein T represents a group represented by T7, $R^1$ represents $SCF_3$, and $R^{3c}$ represents any substituents indicated in [Table L4] to [Table L12] (hereinafter, referred to as Compound Class $SX_{1560}$).

A compound (L-5) wherein T represents a group represented by T7, $R^1$ represents $S(O)CF_3$, and $R^{3c}$ represents any substituents indicated in [Table L4] to [Table L12] (hereinafter, referred to as Compound Class $SX_{1561}$).

A compound (L-5) wherein T represents a group represented by T7, $R^1$ represents $S(O)_2CF_3$, and $R^{3c}$ represents any substituents indicated in [Table L4] to [Table L12] (hereinafter, referred to as Compound Class $SX_{1562}$).

A compound (L-5) wherein T represents a group represented by T8, $R^1$ represents $CF_3$, and $R^{3c}$ represents any substituents indicated in [Table L4] to [Table L12] (hereinafter, referred to as Compound Class $SX_{1563}$).

A compound (L-5) wherein T represents a group represented by T8, $R^1$ represents $C_2F_5$, and $R^{3c}$ represents any substituents indicated in [Table L4] to [Table L12] (hereinafter, referred to as Compound Class $SX_{1564}$).

A compound (L-5) wherein T represents a group represented by T8, $R^1$ represents $SCF_3$, and $R^{3c}$ represents any substituents indicated in [Table L4] to [Table L12] (hereinafter, referred to as Compound Class $SX_{1565}$).

A compound (L-5) wherein T represents a group represented by T8, $R^1$ represents $S(O)CF_3$, and $R^{3c}$ represents any substituents indicated in [Table L4] to [Table L12] (hereinafter, referred to as Compound Class $SX_{1566}$).

A compound (L-5) wherein T represents a group represented by T8, $R^1$ represents $S(O)_2CF_3$, and $R^{3c}$ represents any substituents indicated in [Table L4] to [Table L12] (hereinafter, referred to as Compound Class $SX_{1567}$).

A compound (L-5) wherein T represents a group represented by T11, $R^1$ represents $CF_3$, and $R^{3c}$ represents any substituents indicated in [Table L4] to [Table L12] (hereinafter, referred to as Compound Class $SX_{1568}$).

A compound (L-5) wherein T represents a group represented by T11, $R^1$ represents $C_2F_5$, and $R^{3c}$ represents any substituents indicated in [Table L4] to [Table L12] (hereinafter, referred to as Compound Class $SX_{1569}$).

A compound (L-5) wherein T represents a group represented by T11, $R^1$ represents $SCF_3$, and $R^{3c}$ represents any substituents indicated in [Table L4] to [Table L12] (hereinafter, referred to as Compound Class $SX_{1570}$).

A compound (L-5) wherein T represents a group represented by T11, $R^1$ represents $S(O)CF_3$, and $R^{3c}$ represents any substituents indicated in [Table L4] to [Table L12] (hereinafter, referred to as Compound Class $SX_{1571}$).

A compound (L-5) wherein T represents a group represented by T11, $R^1$ represents $S(O)_2CF_3$, and $R^{3c}$ represents any substituents indicated in [Table L4] to [Table L12] (hereinafter, referred to as Compound Class $SX_{1572}$).

A compound (L-5) wherein T represents a group represented by T12, $R^1$ represents $CF_3$, and $R^{3c}$ represents any substituents indicated in [Table L4] to [Table L12] (hereinafter, referred to as Compound Class $SX_{1573}$).

A compound (L-5) wherein T represents a group represented by T12, $R^1$ represents $C_2F_5$, and $R^{3c}$ represents any substituents indicated in [Table L4] to [Table L12] (hereinafter, referred to as Compound Class $SX_{1574}$).

A compound (L-5) wherein T represents a group represented by T12, $R^1$ represents $SCF_3$, and $R^{30}$ represents any substituents indicated in [Table L4] to [Table L12] (hereinafter, referred to as Compound Class $SX_{1575}$).

A compound (L-5) wherein T represents a group represented by T12, $R^1$ represents $S(O)CF_3$, and $R^{3c}$ represents any substituents indicated in [Table L4] to [Table L12] (hereinafter, referred to as Compound Class $SX_{1576}$).

A compound (L-5) wherein T represents a group represented by T12, $R^1$ represents $S(O)_2CF_3$, and $R^{3c}$ represents any substituents indicated in [Table L4] to [Table L12] (hereinafter, referred to as Compound Class $SX_{1577}$).

A compound (L-5) wherein T represents a group represented by T13, $R^1$ represents $CF_3$, and $R^{3c}$ represents any substituents indicated in [Table L4] to [Table L12] (hereinafter, referred to as Compound Class $SX_{1578}$).

A compound (L-5) wherein T represents a group represented by T13, $R^1$ represents $C_2F_5$, and $R^{3c}$ represents any substituents indicated in [Table L4] to [Table L12] (hereinafter, referred to as Compound Class $SX_{1579}$).

A compound (L-5) wherein T represents a group represented by T13, $R^1$ represents $SCF_3$, and $R^{3c}$ represents any substituents indicated in [Table L4] to [Table L12] (hereinafter, referred to as Compound Class $SX_{1580}$).

A compound (L-5) wherein T represents a group represented by T13, $R^1$ represents $S(O)CF_3$, and $R^{3c}$ represents any substituents indicated in [Table L4] to [Table L12] (hereinafter, referred to as Compound Class $SX_{1581}$).

A compound (L-5) wherein T represents a group represented by T13, $R^1$ represents $S(O)_2CF_3$, and $R^{3c}$ represents any substituents indicated in [Table L4] to [Table L12] (hereinafter, referred to as Compound Class $SX_{1582}$).

A compound (L-6) wherein T represents a group represented by T1, $R^1$ represents $CF_3$, and $R^{3c}$ represents any substituents indicated in [Table L4] to [Table L12] (hereinafter, referred to as Compound Class $SX_{1583}$).

A compound (L-6) wherein T represents a group represented by T1, $R^1$ represents $C_2F_5$, and $R^{3b}$ represents any substituents indicated in [Table L4] to [Table L12] (hereinafter, referred to as Compound Class $SX_{1584}$).

A compound (L-6) wherein T represents a group represented by T1, $R^1$ represents $SCF_3$, and $R^{3b}$ represents any substituents indicated in [Table L4] to [Table L12] (hereinafter, referred to as Compound Class $SX_{1585}$).

A compound (L-6) wherein T represents a group represented by T1, $R^1$ represents $S(O)CF_3$, and $R^{3b}$ represents any substituents indicated in [Table L4] to [Table L12] (hereinafter, referred to as Compound Class $SX_{1586}$).

A compound (L-6) wherein T represents a group represented by T1, $R^1$ represents $S(O)_2CF_3$, and $R^{3b}$ represents any substituents indicated in [Table L4] to [Table L12] (hereinafter, referred to as Compound Class $SX_{1587}$).

A compound (L-6) wherein T represents a group represented by T2, $R^1$ represents $CF_3$, and $R^{3b}$ represents any substituents indicated in [Table L4] to [Table L12] (hereinafter, referred to as Compound Class $SX_{1588}$).

A compound (L-6) wherein T represents a group represented by T2, $R^1$ represents $C_2F_5$, and $R^{3b}$ represents any substituents indicated in [Table L4] to [Table L12] (hereinafter, referred to as Compound Class $SX_{1589}$).

A compound (L-6) wherein T represents a group represented by T2, $R^1$ represents $SCF_3$, and $R^{3b}$ represents any substituents indicated in [Table L4] to [Table L12] (hereinafter, referred to as Compound Class $SX_{1590}$).

A compound (L-6) wherein T represents a group represented by T2, $R^1$ represents $S(O)CF_3$, and $R^{3b}$ represents any substituents indicated in [Table L4] to [Table L12] (hereinafter, referred to as Compound Class $SX_{1591}$).

A compound (L-6) wherein T represents a group represented by T2, $R^1$ represents $S(O)_2CF_3$, and $R^{3b}$ represents any substituents indicated in [Table L4] to [Table L12] (hereinafter, referred to as Compound Class $SX_{1592}$).

A compound (L-6) wherein T represents a group represented by T3, $R^1$ represents $CF_3$, and $R^{3b}$ represents any substituents indicated in [Table L4] to [Table L12] (hereinafter, referred to as Compound Class $SX_{1593}$).

A compound (L-6) wherein T represents a group represented by T3, $R^1$ represents $C_2F_5$, and $R^{3b}$ represents any substituents indicated in [Table L4] to [Table L12] (hereinafter, referred to as Compound Class $SX_{1594}$).

A compound (L-6) wherein T represents a group represented by T3, $R^1$ represents $SCF_3$, and $R^{3b}$ represents any substituents indicated in [Table L4] to [Table L12] (hereinafter, referred to as Compound Class $SX_{1595}$).

A compound (L-6) wherein T represents a group represented by T3, $R^1$ represents $S(O)CF_3$, and $R^{3b}$ represents any substituents indicated in [Table L4] to [Table L12] (hereinafter, referred to as Compound Class $SX_{1596}$).

A compound (L-6) wherein T represents a group represented by T3, $R^1$ represents $S(O)_2CF_3$, and $R^{3b}$ represents any substituents indicated in [Table L4] to [Table L12] (hereinafter, referred to as Compound Class $SX_{1597}$).

A compound (L-6) wherein T represents a group represented by T6, $R^1$ represents $CF_3$, and $R^{3b}$ represents any substituents indicated in [Table L4] to [Table L12] (hereinafter, referred to as Compound Class $SX_{1598}$).

A compound (L-6) wherein T represents a group represented by T6, $R^1$ represents $C_2F_5$, and $R^{3b}$ represents any substituents indicated in [Table L4] to [Table L12] (hereinafter, referred to as Compound Class $SX_{1599}$).

A compound (L-6) wherein T represents a group represented by T6, $R^1$ represents $SCF_3$, and $R^{3b}$ represents any substituents indicated in [Table L4] to [Table L12] (hereinafter, referred to as Compound Class $SX_{1600}$).

A compound (L-6) wherein T represents a group represented by T6, $R^1$ represents $S(O)CF_3$, and $R^{3b}$ represents any substituents indicated in [Table L4] to [Table L12] (hereinafter, referred to as Compound Class $SX_{1601}$).

A compound (L-6) wherein T represents a group represented by T6, $R^1$ represents $S(O)_2CF_3$, and $R^{3b}$ represents any substituents indicated in [Table L4] to [Table L12] (hereinafter, referred to as Compound Class $SX_{1602}$).

A compound (L-6) wherein T represents a group represented by T7, $R^1$ represents $CF_3$, and $R^{3b}$ represents any substituents indicated in [Table L4] to [Table L12] (hereinafter, referred to as Compound Class $SX_{1603}$).

A compound (L-6) wherein T represents a group represented by T7, $R^1$ represents $C_2F_5$, and $R^{3b}$ represents any substituents indicated in [Table L4] to [Table L12] (hereinafter, referred to as Compound Class $SX_{1604}$).

A compound (L-6) wherein T represents a group represented by T7, $R^1$ represents $SCF_3$, and $R^{3b}$ represents any substituents indicated in [Table L4] to [Table L12] (hereinafter, referred to as Compound Class $SX_{1605}$).

A compound (L-6) wherein T represents a group represented by T7, $R^1$ represents $S(O)CF_3$, and $R^{3b}$ represents any substituents indicated in [Table L4] to [Table L12] (hereinafter, referred to as Compound Class $SX_{1606}$).

A compound (L-6) wherein T represents a group represented by T7, $R^1$ represents $S(O)_2CF_3$, and $R^{3b}$ represents any substituents indicated in [Table L4] to [Table L12] (hereinafter, referred to as Compound Class $SX_{1607}$).

A compound (L-6) wherein T represents a group represented by T8, $R^1$ represents $CF_3$, and $R^{3b}$ represents any substituents indicated in [Table L4] to [Table L12] (hereinafter, referred to as Compound Class $SX_{1608}$).

A compound (L-6) wherein T represents a group represented by T8, $R^1$ represents $C_2F_5$, and $R^{3b}$ represents any substituents indicated in [Table L4] to [Table L12] (hereinafter, referred to as Compound Class $SX_{1609}$).

A compound (L-6) wherein T represents a group represented by T8, $R^1$ represents $SCF_3$, and $R^{3b}$ represents any substituents indicated in [Table L4] to [Table L12] (hereinafter, referred to as Compound Class $SX_{1610}$).

A compound (L-6) wherein T represents a group represented by T8, $R^1$ represents $S(O)CF_3$, and $R^{3b}$ represents any substituents indicated in [Table L4] to [Table L12] (hereinafter, referred to as Compound Class $SX_{1611}$).

A compound (L-6) wherein T represents a group represented by T8, $R^1$ represents $S(O)_2CF_3$, and $R^{3b}$ represents any substituents indicated in [Table L4] to [Table L12] (hereinafter, referred to as Compound Class $SX_{1612}$).

A compound (L-6) wherein T represents a group represented by T9, $R^1$ represents $CF_3$, and $R^{3b}$ represents any substituents indicated in [Table L4] to [Table L12] (hereinafter, referred to as Compound Class $SX_{1613}$).

A compound (L-6) wherein T represents a group represented by T11, $R^1$ represents $CF_3$, and $R^{3b}$ represents any substituents indicated in [Table L4] to [Table L12] (hereinafter, referred to as Compound Class $SX_{1614}$).

A compound (L-6) wherein T represents a group represented by T11, $R^1$ represents $C_2F_5$, and $R^{3b}$ represents any substituents indicated in [Table L4] to [Table L12] (hereinafter, referred to as Compound Class $SX_{1615}$).

A compound (L-6) wherein T represents a group represented by T11, $R^1$ represents $SCF_3$, and $R^{3b}$ represents any substituents indicated in [Table L4] to [Table L12] (hereinafter, referred to as Compound Class $SX_{1616}$).

A compound (L-6) wherein T represents a group represented by T11, $R^1$ represents $S(O)CF_3$, and $R^{3b}$ represents any substituents indicated in [Table L4] to [Table L12] (hereinafter, referred to as Compound Class $SX_{1617}$).

A compound (L-6) wherein T represents a group represented by T11, $R^1$ represents $S(O)CF_3$, and $R^{3b}$ represents any substituents indicated in [Table L4] to [Table L12] (hereinafter, referred to as Compound Class $SX_{1618}$).

A compound (L-6) wherein T represents a group represented by T12, $R^1$ represents $CF_3$, and $R^{3b}$ represents any substituents indicated in [Table L4] to [Table L12] (hereinafter, referred to as Compound Class $SX_{1619}$).

A compound (L-6) wherein T represents a group represented by T12, $R^1$ represents $C_2F_5$, and $R^{3b}$ represents any substituents indicated in [Table L4] to [Table L12] (hereinafter, referred to as Compound Class $SX_{1620}$).

A compound (L-6) wherein T represents a group represented by T12, $R^1$ represents $SCF_3$, and $R^{3b}$ represents any substituents indicated in [Table L4] to [Table L12] (hereinafter, referred to as Compound Class $SX_{1621}$).

A compound (L-6) wherein T represents a group represented by T12, $R^1$ represents $S(O)_2CF_3$, and $R^{3b}$ represents any substituents indicated in [Table L4] to [Table L12] (hereinafter, referred to as Compound Class $SX_{1622}$).

A compound (L-6) wherein T represents a group represented by T12, $R^1$ represents $S(O)_2CF_3$, and $R^{3b}$ represents any substituents indicated in [Table L4] to [Table L12] (hereinafter, referred to as Compound Class $SX_{1623}$).

A compound (L-6) wherein T represents a group represented by T13, $R^1$ represents $CF_3$, and $R^{3b}$ represents any substituents indicated in [Table L4] to [Table L12] (hereinafter, referred to as Compound Class $SX_{1624}$).

A compound (L-6) wherein T represents a group represented by T13, $R^1$ represents $C_2F_5$, and $R^{3b}$ represents any substituents indicated in [Table L4] to [Table L12] (hereinafter, referred to as Compound Class $SX_{1625}$.

A compound (L-6) wherein T represents a group represented by T13, $R^1$ represents $SCF_3$, and $R^{3b}$ represents any substituents indicated in [Table L4] to [Table L12] (hereinafter, referred to as Compound Class $SX_{1626}$).

A compound (L-6) wherein T represents a group represented by T13, $R^1$ represents $S(O)CF_3$, and $R^{3b}$ represents any substituents indicated in [Table L4] to [Table L12] (hereinafter, referred to as Compound Class $SX_{1627}$).

A compound (L-6) wherein T represents a group represented by T13, $R^1$ represents $S(O)_2CF_3$, and $R^{3b}$ represents any substituents indicated in [Table L4] to [Table L12] (hereinafter, referred to as Compound Class $SX_{1628}$).

A compound represented by formula (L-7):

(L-7)

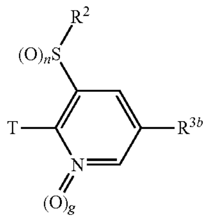

(hereinafter, referred to as compound (L-7), wherein T represents a group represented by T1, $R^1$ represents $CF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1629}$).

A compound (L-7) wherein T represents a group represented by T1, $R^1$ represents $CF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1630}$).

A compound (L-7) wherein T represents a group represented by T1, $R^1$ represents $CF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1631}$).

A compound (L-7) wherein T represents a group represented by T1, $R^1$ represents $CF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1632}$).

A compound (L-7) wherein T represents a group represented by T1, $R^1$ represents $CF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1633}$).

A compound (L-7) wherein T represents a group represented by T1, $R^1$ represents $CF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1634}$).

A compound (L-7) wherein T represents a group represented by T1, $R^1$ represents $CF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1635}$).

A compound (L-7) wherein T represents a group represented by T2, $R^1$ represents $CF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1636}$).

A compound (L-7) wherein T represents a group represented by T2, $R^1$ represents $CF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1637}$).

A compound (L-7) wherein T represents a group represented by T2, $R^1$ represents $CF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1638}$).

A compound (L-7) wherein T represents a group represented by T2, $R^1$ represents $CF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1639}$).

A compound (L-7) wherein T represents a group represented by T2, $R^1$ represents $CF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1640}$).

A compound (L-7) wherein T represents a group represented by T2, $R^1$ represents $CF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1641}$).

A compound (L-7) wherein T represents a group represented by T2, $R^1$ represents $CF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1642}$).

A compound (L-7) wherein T represents a group represented by T3, $R^1$ represents $CF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1643}$).

A compound (L-7) wherein T represents a group represented by T3, $R^1$ represents $CF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1644}$).

A compound (L-7) wherein T represents a group represented by T3, $R^1$ represents $CF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1645}$).

A compound (L-7) wherein T represents a group represented by T3, $R^1$ represents $CF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1646}$).

A compound (L-7) wherein T represents a group represented by T3, $R^1$ represents $CF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1647}$).

A compound (L-7) wherein T represents a group represented by T3, $R^1$ represents $CF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1648}$).

A compound (L-7) wherein T represents a group represented by T3, $R^1$ represents $CF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1649}$).

A compound (L-7) wherein T represents a group represented by T4, $R^1$ represents $CF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1650}$).

A compound (L-7) wherein T represents a group represented by T4, $R^1$ represents $CF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1651}$).

A compound (L-7) wherein T represents a group represented by T4, $R^1$ represents $CF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1652}$).

A compound (L-7) wherein T represents a group represented by T4, $R^1$ represents $CF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1653}$).

A compound (L-7) wherein T represents a group represented by T4, $R^1$ represents $CF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1654}$).

A compound (L-7) wherein T represents a group represented by T4, $R^1$ represents $CF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1655}$).

A compound (L-7) wherein T represents a group represented by T4, $R^1$ represents $CF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1656}$).

A compound (L-7) wherein T represents a group represented by T5, $R^1$ represents $CF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1657}$).

A compound (L-7) wherein T represents a group represented by T5, $R^1$ represents $CF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1658}$).

A compound (L-7) wherein T represents a group represented by T5, $R^1$ represents $CF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1659}$).

A compound (L-7) wherein T represents a group represented by T5, $R^1$ represents $CF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1660}$).

A compound (L-7) wherein T represents a group represented by T5, $R^1$ represents $CF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1661}$).

A compound (L-7) wherein T represents a group represented by T5, $R^1$ represents $CF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1662}$).

A compound (L-7) wherein T represents a group represented by T5, $R^1$ represents $CF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1663}$).

A compound (L-7) wherein T represents a group represented by T1, $R^1$ represents $C_2F_5$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1664}$).

A compound (L-7) wherein T represents a group represented by T1, $R^1$ represents $C_2F_5$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1665}$).

A compound (L-7) wherein T represents a group represented by T1, $R^1$ represents $C_2F_5$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1666}$).

A compound (L-7) wherein T represents a group represented by T1, $R^1$ represents $C_2F_5$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1667}$).

A compound (L-7) wherein T represents a group represented by T1, $R^1$ represents $C_2F_5$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1668}$).

A compound (L-7) wherein T represents a group represented by T1, $R^1$ represents $C_2F_5$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1669}$).

A compound (L-7) wherein T represents a group represented by T1, $R^1$ represents $C_2F_5$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1670}$).

A compound (L-7) wherein T represents a group represented by T2, $R^1$ represents $C_2F_5$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1671}$).

A compound (L-7) wherein T represents a group represented by T2, $R^1$ represents $C_2F_5$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1672}$).

A compound (L-7) wherein T represents a group represented by T2, $R^1$ represents $C_2F_5$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1673}$).

A compound (L-7) wherein T represents a group represented by T2, $R^1$ represents $C_2F_5$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1674}$).

A compound (L-7) wherein T represents a group represented by T2, $R^1$ represents $C_2F_5$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1675}$).

A compound (L-7) wherein T represents a group represented by T2, $R^1$ represents $C_2F_5$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1676}$).

A compound (L-7) wherein T represents a group represented by T2, $R^1$ represents $C_2F_5$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1677}$).

A compound (L-7) wherein T represents a group represented by T3, $R^1$ represents $C_2F_5$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1678}$).

A compound (L-7) wherein T represents a group represented by T3, $R^1$ represents $C_2F_5$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1679}$).

A compound (L-7) wherein T represents a group represented by T3, $R^1$ represents $C_2F_5$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1680}$).

A compound (L-7) wherein T represents a group represented by T3, $R^1$ represents $C_2F_5$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1681}$).

A compound (L-7) wherein T represents a group represented by T3, $R^1$ represents $C_2F_5$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1682}$).

A compound (L-7) wherein T represents a group represented by T3, $R^1$ represents $C_2F_5$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1683}$).

A compound (L-7) wherein T represents a group represented by T3, $R^1$ represents $C_2F_5$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1684}$).

A compound (L-7) wherein T represents a group represented by T4, $R^1$ represents $C_2F_5$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1685}$).

A compound (L-7) wherein T represents a group represented by T4, $R^1$ represents $C_2F_5$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1686}$).

A compound (L-7) wherein T represents a group represented by T4, $R^1$ represents $C_2F_5$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1687}$).

A compound (L-7) wherein T represents a group represented by T4, $R^1$ represents $C_2F_5$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1688}$).

A compound (L-7) wherein T represents a group represented by T4, $R^1$ represents $C_2F_5$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1689}$).

A compound (L-7) wherein T represents a group represented by T4, $R^1$ represents $C_2F_5$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1690}$).

A compound (L-7) wherein T represents a group represented by T4, $R^1$ represents $C_2F_5$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1691}$).

A compound (L-7) wherein T represents a group represented by T5, $R^1$ represents $C_2F_5$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1692}$).

A compound (L-7) wherein T represents a group represented by T5, $R^1$ represents $C_2F_5$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1693}$).

A compound (L-7) wherein T represents a group represented by T5, $R^1$ represents $C_2F_5$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1694}$).

A compound (L-7) wherein T represents a group represented by T5, $R^1$ represents $C_2F_5$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1695}$).

A compound (L-7) wherein T represents a group represented by T5, $R^1$ represents $C_2F_5$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1696}$).

A compound (L-7) wherein T represents a group represented by T5, $R^1$ represents $C_2F_5$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1697}$).

A compound (L-7) wherein T represents a group represented by T5, $R^1$ represents $C_2F_5$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1698}$).

A compound (L-7) wherein T represents a group represented by T1, $R^1$ represents $SCF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1699}$).

A compound (L-7) wherein T represents a group represented by T1, $R^1$ represents $SCF_3$, n is 1, g is 0, $R^2$ represents a methyl group, and $R^{3c}$ represents a hydrogen atom, a chlorine atom, $CF_3$, or any substituents indicated in [Table L4] to [Table L12] (hereinafter, referred to as Compound Class $SX_{1700}$).

A compound (L-7) wherein T represents a group represented by T1, $R^1$ represents $SCF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1701}$).

A compound (L-7) wherein T represents a group represented by T1, $R^1$ represents $SCF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1702}$).

A compound (L-7) wherein T represents a group represented by T1, $R^1$ represents $SCF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1703}$).

A compound (L-7) wherein T represents a group represented by T1, $R^1$ represents $SCF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1704}$).

A compound (L-7) wherein T represents a group represented by T1, $R^1$ represents $SCF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1705}$).

A compound (L-7) wherein T represents a group represented by T2, $R^1$ represents $SCF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1706}$).

A compound (L-7) wherein T represents a group represented by T2, $R^1$ represents $SCF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1707}$).

A compound (L-7) wherein T represents a group represented by T2, $R^1$ represents $SCF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1708}$).

A compound (L-7) wherein T represents a group represented by T2, $R^1$ represents $SCF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1709}$).

A compound (L-7) wherein T represents a group represented by T2, $R^1$ represents $SCF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1710}$).

A compound (L-7) wherein T represents a group represented by T2, $R^1$ represents $SCF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1711}$).

A compound (L-7) wherein T represents a group represented by T2, $R^1$ represents $SCF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1712}$).

A compound (L-7) wherein T represents a group represented by T3, $R^1$ represents $SCF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1713}$).

A compound (L-7) wherein T represents a group represented by T3, $R^1$ represents $SCF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1714}$).

A compound (L-7) wherein T represents a group represented by T3, $R^1$ represents $SCF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1715}$).

A compound (L-7) wherein T represents a group represented by T3, $R^1$ represents $SCF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1716}$).

A compound (L-7) wherein T represents a group represented by T3, $R^1$ represents $SCF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1717}$).

A compound (L-7) wherein T represents a group represented by T3, $R^1$ represents $SCF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1718}$).

A compound (L-7) wherein T represents a group represented by T3, $R^1$ represents $SCF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1719}$).

A compound (L-7) wherein T represents a group represented by T4, $R^1$ represents $SCF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1720}$).

A compound (L-7) wherein T represents a group represented by T4, $R^1$ represents $SCF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1721}$).

A compound (L-7) wherein T represents a group represented by T4, $R^1$ represents $SCF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1722}$).

A compound (L-7) wherein T represents a group represented by T4, $R^1$ represents $SCF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1723}$).

A compound (L-7) wherein T represents a group represented by T4, $R^1$ represents $SCF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1724}$).

A compound (L-7) wherein T represents a group represented by T4, $R^1$ represents $SCF_3$, n is 1, g is 0, $R^2$ represents an ethyl group, and $R^{3c}$ represents a hydrogen atom, a chlorine atom, $CF_3$, or any substituents indicated in [Table L4] to [Table L12] (hereinafter, referred to as Compound Class $SX_{1725}$).

A compound (L-7) wherein T represents a group represented by T4, $R^1$ represents $SCF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1726}$).

A compound (L-7) wherein T represents a group represented by T5, $R^1$ represents $SCF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1727}$).

A compound (L-7) wherein T represents a group represented by T5, $R^1$ represents $SCF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1728}$).

A compound (L-7) wherein T represents a group represented by T5, $R^1$ represents $SCF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1729}$).

A compound (L-7) wherein T represents a group represented by T5, $R^1$ represents $SCF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1730}$).

A compound (L-7) wherein T represents a group represented by T5, $R^1$ represents $SCF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1731}$).

A compound (L-7) wherein T represents a group represented by T5, $R^1$ represents $SCF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1732}$).

A compound (L-7) wherein T represents a group represented by T5, $R^1$ represents $SCF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1733}$).

A compound (L-7) wherein T represents a group represented by T1, $R^1$ represents $S(O)CF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1734}$).

A compound (L-7) wherein T represents a group represented by T1, $R^1$ represents $S(O)CF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1735}$).

A compound (L-7) wherein T represents a group represented by T1, $R^1$ represents $S(O)CF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1736}$).

A compound (L-7) wherein T represents a group represented by T1, $R^1$ represents $S(O)CF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1737}$).

A compound (L-7) wherein T represents a group represented by T1, $R^1$ represents $S(O)CF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1738}$).

A compound (L-7) wherein T represents a group represented by T1, $R^1$ represents $S(O)CF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1739}$).

A compound (L-7) wherein T represents a group represented by T1, $R^1$ represents $S(O)CF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1740}$).

A compound (L-7) wherein T represents a group represented by T2, $R^1$ represents $S(O)CF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1741}$).

A compound (L-7) wherein T represents a group represented by T2, $R^1$ represents $S(O)CF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1742}$).

A compound (L-7) wherein T represents a group represented by T2, $R^1$ represents $S(O)CF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1743}$).

A compound (L-7) wherein T represents a group represented by T2, $R^1$ represents $S(O)CF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1744}$).

A compound (L-7) wherein T represents a group represented by T2, $R^1$ represents $S(O)CF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1745}$).

A compound (L-7) wherein T represents a group represented by T2, $R^1$ represents $S(O)CF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1746}$).

A compound (L-7) wherein T represents a group represented by T2, $R^1$ represents $S(O)CF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1747}$).

A compound (L-7) wherein T represents a group represented by T3, $R^1$ represents $S(O)CF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1748}$).

A compound (L-7) wherein T represents a group represented by T3, $R^1$ represents $S(O)CF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1749}$).

A compound (L-7) wherein T represents a group represented by T3, $R^1$ represents $S(O)CF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1750}$).

A compound (L-7) wherein T represents a group represented by T3, $R^1$ represents $S(O)CF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1751}$).

A compound (L-7) wherein T represents a group represented by T3, $R^1$ represents $S(O)CF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1752}$).

A compound (L-7) wherein T represents a group represented by T3, $R^1$ represents $S(O)CF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1753}$).

A compound (L-7) wherein T represents a group represented by T3, $R^1$ represents $S(O)CF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1754}$).

A compound (L-7) wherein T represents a group represented by T4, $R^1$ represents $S(O)CF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1755}$).

A compound (L-7) wherein T represents a group represented by T4, $R^1$ represents $S(O)CF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1756}$).

A compound (L-7) wherein T represents a group represented by T4, $R^1$ represents $S(O)CF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1757}$).

A compound (L-7) wherein T represents a group represented by T4, $R^1$ represents $S(O)CF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1758}$).

A compound (L-7) wherein T represents a group represented by T4, $R^1$ represents $S(O)CF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1759}$).

A compound (L-7) wherein T represents a group represented by T4, $R^1$ represents $S(O)CF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1760}$).

A compound (L-7) wherein T represents a group represented by T4, $R^1$ represents $S(O)CF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1761}$).

A compound (L-7) wherein T represents a group represented by T5, $R^1$ represents $S(O)CF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1762}$).

A compound (L-7) wherein T represents a group represented by T5, $R^1$ represents $S(O)CF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1763}$).

A compound (L-7) wherein T represents a group represented by T5, $R^1$ represents $S(O)CF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1764}$).

A compound (L-7) wherein T represents a group represented by T5, $R^1$ represents $S(O)CF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1765}$).

A compound (L-7) wherein T represents a group represented by T5, $R^1$ represents $S(O)CF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1766}$).

A compound (L-7) wherein T represents a group represented by T5, $R^1$ represents $S(O)CF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1767}$).

A compound (L-7) wherein T represents a group represented by T5, $R^1$ represents $S(O)CF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1768}$).

A compound (L-7) wherein T represents a group represented by T1, $R^1$ represents $S(O)_2CF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1769}$).

A compound (L-7) wherein T represents a group represented by T1, $R^1$ represents $S(O)_2CF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1770}$).

A compound (L-7) wherein T represents a group represented by T1, $R^1$ represents $S(O)_2CF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1771}$).

A compound (L-7) wherein T represents a group represented by T1, $R^1$ represents $S(O)_2CF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1772}$).

A compound (L-7) wherein T represents a group represented by T1, $R^1$ represents $S(O)_2CF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1773}$).

A compound (L-7) wherein T represents a group represented by T1, $R^1$ represents $S(O)_2CF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1774}$).

A compound (L-7) wherein T represents a group represented by T1, $R^1$ represents $S(O)_2CF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1775}$).

A compound (L-7) wherein T represents a group represented by T2, $R^1$ represents $S(O)_2CF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1776}$).

A compound (L-7) wherein T represents a group represented by T2, $R^1$ represents $S(O)_2CF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1777}$).

A compound (L-7) wherein T represents a group represented by T2, $R^1$ represents $S(O)_2CF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1778}$).

A compound (L-7) wherein T represents a group represented by T2, $R^1$ represents $S(O)_2CF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1779}$).

A compound (L-7) wherein T represents a group represented by T2, $R^1$ represents $S(O)_2CF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1780}$).

A compound (L-7) wherein T represents a group represented by T2, $R^1$ represents $S(O)_2CF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1781}$).

A compound (L-7) wherein T represents a group represented by T2, $R^1$ represents $S(O)_2CF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1782}$).

A compound (L-7) wherein T represents a group represented by T3, $R^1$ represents $S(O)_2CF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1783}$).

A compound (L-7) wherein T represents a group represented by T3, $R^1$ represents $S(O)_2CF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1784}$).

A compound (L-7) wherein T represents a group represented by T3, $R^1$ represents $S(O)_2CF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1785}$).

A compound (L-7) wherein T represents a group represented by T3, $R^1$ represents $S(O)_2CF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1786}$).

A compound (L-7) wherein T represents a group represented by T3, $R^1$ represents $S(O)_2CF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1787}$).

A compound (L-7) wherein T represents a group represented by T3, $R^1$ represents $S(O)_2CF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1788}$).

A compound (L-7) wherein T represents a group represented by T3, $R^1$ represents $S(O)_2CF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1789}$).

A compound (L-7) wherein T represents a group represented by T4, $R^1$ represents $S(O)_2CF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1790}$).

A compound (L-7) wherein T represents a group represented by T4, $R^1$ represents $S(O)_2CF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1791}$).

A compound (L-7) wherein T represents a group represented by T4, $R^1$ represents $S(O)_2CF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1792}$).

A compound (L-7) wherein T represents a group represented by T4, $R^1$ represents $S(O)_2CF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1793}$).

A compound (L-7) wherein T represents a group represented by T4, $R^1$ represents $S(O)_2CF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1794}$).

A compound (L-7) wherein T represents a group represented by T4, $R^1$ represents $S(O)_2CF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1795}$).

A compound (L-7) wherein T represents a group represented by T4, $R^1$ represents $S(O)_2CF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1796}$).

A compound (L-7) wherein T represents a group represented by T5, $R^1$ represents $S(O)_2CF_3$, n is 0, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1797}$).

A compound (L-7) wherein T represents a group represented by T5, $R^1$ represents $S(O)_2CF_3$, n is 1, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1798}$).

A compound (L-7) wherein T represents a group represented by T5, $R^1$ represents $S(O)_2CF_3$, n is 2, g is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1799}$).

A compound (L-7) wherein T represents a group represented by T5, $R^1$ represents $S(O)_2CF_3$, n is 2, g is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1800}$).

A compound (L-7) wherein T represents a group represented by T5, $R^1$ represents $S(O)_2CF_3$, n is 0, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1801}$).

A compound (L-7) wherein T represents a group represented by T5, $R^1$ represents $S(O)_2CF_3$, n is 1, g is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1802}$).

A compound (L-7) wherein T represents a group represented by T5, $R^1$ represents $S(O)_2CF_3$, n is 2, g is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1803}$).

A compound represented by formula (L-8):

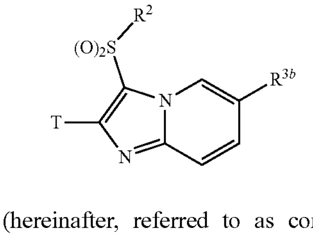

(L-8)

(hereinafter, referred to as compound (L-8), wherein T represents a group represented by T1, $R^1$ represents $CF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1804}$).

A compound (L-8) wherein T represents a group represented by T1, $R^1$ represents $CF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1805}$).

A compound (L-8) wherein T represents a group represented by T1, $R^1$ represents $CF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1806}$).

A compound (L-8) wherein T represents a group represented by T1, $R^1$ represents $CF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1807}$).

A compound (L-8) wherein T represents a group represented by T1, $R^1$ represents $CF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1808}$).

A compound (L-8) wherein T represents a group represented by T2, $R^1$ represents $CF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1809}$).

A compound (L-8) wherein T represents a group represented by T2, $R^1$ represents $CF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1810}$).

A compound (L-8) wherein T represents a group represented by T2, $R^1$ represents $CF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1811}$).

A compound (L-8) wherein T represents a group represented by T2, $R^1$ represents $CF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1812}$).

A compound (L-8) wherein T represents a group represented by T2, $R^1$ represents $CF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1813}$).

A compound (L-8) wherein T represents a group represented by T3, $R^1$ represents $CF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1814}$).

A compound (L-8) wherein T represents a group represented by T3, $R^1$ represents $CF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1815}$).

A compound (L-8) wherein T represents a group represented by T3, $R^1$ represents $CF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1816}$).

A compound (L-8) wherein T represents a group represented by T3, $R^1$ represents $CF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1817}$).

A compound (L-8) wherein T represents a group represented by T3, $R^1$ represents $CF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1818}$).

A compound (L-8) wherein T represents a group represented by T4, $R^1$ represents $CF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1819}$).

A compound (L-8) wherein T represents a group represented by T4, $R^1$ represents $CF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1820}$).

A compound (L-8) wherein T represents a group represented by T4, $R^1$ represents $CF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1821}$).

A compound (L-8) wherein T represents a group represented by T4, $R^1$ represents $CF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1822}$).

A compound (L-8) wherein T represents a group represented by T4, $R^1$ represents $CF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1823}$).

A compound (L-8) wherein T represents a group represented by T5, $R^1$ represents $CF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1824}$).

A compound (L-8) wherein T represents a group represented by T5, $R^1$ represents $CF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1825}$).

A compound (L-8) wherein T represents a group represented by T5, $R^1$ represents $CF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1826}$).

A compound (L-8) wherein T represents a group represented by T5, $R^1$ represents $CF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1827}$).

A compound (L-8) wherein T represents a group represented by T5, $R^1$ represents $CF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1828}$).

A compound (L-8) wherein T represents a group represented by T1, $R^1$ represents $C_2F_5$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1829}$).

A compound (L-8) wherein T represents a group represented by T1, $R^1$ represents $C_2F_5$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1830}$).

A compound (L-8) wherein T represents a group represented by T1, $R^1$ represents $C_2F_5$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1831}$).

A compound (L-8) wherein T represents a group represented by T1, $R^1$ represents $C_2F_5$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1832}$).

A compound (L-8) wherein T represents a group represented by T1, $R^1$ represents $C_2F_5$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1833}$).

A compound (L-8) wherein T represents a group represented by T2, $R^1$ represents $C_2F_5$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1834}$).

A compound (L-8) wherein T represents a group represented by T2, $R^1$ represents $C_2F_5$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1835}$).

A compound (L-8) wherein T represents a group represented by T2, $R^1$ represents $C_2F_5$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1836}$).

A compound (L-8) wherein T represents a group represented by T2, $R^1$ represents $C_2F_5$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1837}$).

A compound (L-8) wherein T represents a group represented by T2, $R^1$ represents $C_2F_5$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1838}$).

A compound (L-8) wherein T represents a group represented by T3, $R^1$ represents $C_2F_5$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1839}$).

A compound (L-8) wherein T represents a group represented by T3, $R^1$ represents $C_2F_5$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1840}$).

A compound (L-8) wherein T represents a group represented by T3, $R^1$ represents $C_2F_5$, n is 2, $R^2$ represents a methyl group, and $R^h$ represents a hydrogen atom, a chlorine atom, $CF_3$, or any substituents indicated in [Table L4] to [Table L12] (hereinafter, referred to as Compound Class $SX_{1841}$).

A compound (L-8) wherein T represents a group represented by T3, $R^1$ represents $C_2F_5$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1842}$).

A compound (L-8) wherein T represents a group represented by T3, $R^1$ represents $C_2F_5$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1843}$).

A compound (L-8) wherein T represents a group represented by T4, $R^1$ represents $C_2F_5$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1844}$).

A compound (L-8) wherein T represents a group represented by T4, $R^1$ represents $C_2F_5$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1845}$).

A compound (L-8) wherein T represents a group represented by T4, $R^1$ represents $C_2F_5$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1846}$).

A compound (L-8) wherein T represents a group represented by T4, $R^1$ represents $C_2F_5$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1847}$).

A compound (L-8) wherein T represents a group represented by T4, $R^1$ represents $C_2F_5$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1848}$).

A compound (L-8) wherein T represents a group represented by T5, $R^1$ represents $C_2F_5$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1849}$).

A compound (L-8) wherein T represents a group represented by T5, $R^1$ represents $C_2F_5$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1850}$).

A compound (L-8) wherein T represents a group represented by T5, $R^1$ represents $C_2F_5$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1851}$).

A compound (L-8) wherein T represents a group represented by T5, $R^1$ represents $C_2F_5$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1852}$).

A compound (L-8) wherein T represents a group represented by T5, $R^1$ represents $C_2F_5$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1853}$).

A compound (L-8) wherein T represents a group represented by T1, $R^1$ represents $SCF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1854}$).

A compound (L-8) wherein T represents a group represented by T1, $R^1$ represents $SCF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1855}$).

A compound (L-8) wherein T represents a group represented by T1, $R^1$ represents $SCF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1856}$).

A compound (L-8) wherein T represents a group represented by T1, $R^1$ represents $SCF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1857}$).

A compound (L-8) wherein T represents a group represented by T1, $R^1$ represents $SCF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1858}$).

A compound (L-8) wherein T represents a group represented by T2, $R^1$ represents $SCF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1859}$).

A compound (L-8) wherein T represents a group represented by T2, $R^1$ represents $SCF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1860}$).

A compound (L-8) wherein T represents a group represented by T2, $R^1$ represents $SCF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1861}$).

A compound (L-8) wherein T represents a group represented by T2, $R^1$ represents $SCF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1862}$).

A compound (L-8) wherein T represents a group represented by T2, $R^1$ represents $SCF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1863}$).

A compound (L-8) wherein T represents a group represented by T3, $R^1$ represents $SCF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1864}$).

A compound (L-8) wherein T represents a group represented by T3, $R^1$ represents $SCF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1865}$).

A compound (L-8) wherein T represents a group represented by T3, $R^1$ represents $SCF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1866}$). A compound (L-8) wherein T represents a group represented by T3, $R^1$ represents $SCF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1867}$).

A compound (L-8) wherein T represents a group represented by T3, $R^1$ represents $SCF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1868}$).

A compound (L-8) wherein T represents a group represented by T4, $R^1$ represents $SCF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1869}$).

A compound (L-8) wherein T represents a group represented by T4, $R^1$ represents $SCF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1870}$).

A compound (L-8) wherein T represents a group represented by T4, $R^1$ represents $SCF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1871}$).

A compound (L-8) wherein T represents a group represented by T4, $R^1$ represents $SCF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1872}$).

A compound (L-8) wherein T represents a group represented by T4, $R^1$ represents $SCF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1873}$).

A compound (L-8) wherein T represents a group represented by T5, $R^1$ represents $SCF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1874}$).

A compound (L-8) wherein T represents a group represented by T5, $R^1$ represents $SCF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1875}$).

A compound (L-8) wherein T represents a group represented by T5, $R^1$ represents $SCF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1876}$).

A compound (L-8) wherein T represents a group represented by T5, $R^1$ represents $SCF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1877}$).

A compound (L-8) wherein T represents a group represented by T5, $R^1$ represents $SCF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1878}$).

A compound (L-8) wherein T represents a group represented by T1, $R^1$ represents $S(O)CF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1879}$).

A compound (L-8) wherein T represents a group represented by T1, $R^1$ represents $S(O)CF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1880}$).

A compound (L-8) wherein T represents a group represented by T1, $R^1$ represents $S(O)CF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1881}$).

A compound (L-8) wherein T represents a group represented by T1, $R^1$ represents $S(O)CF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1882}$).

A compound (L-8) wherein T represents a group represented by T1, $R^1$ represents $S(O)CF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1883}$).

A compound (L-8) wherein T represents a group represented by T2, $R^1$ represents $S(O)CF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1884}$).

A compound (L-8) wherein T represents a group represented by T2, $R^1$ represents $S(O)CF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1885}$).

A compound (L-8) wherein T represents a group represented by T2, $R^1$ represents $S(O)CF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1886}$).

A compound (L-8) wherein T represents a group represented by T2, $R^1$ represents $S(O)CF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1887}$).

A compound (L-8) wherein T represents a group represented by T2, $R^1$ represents $S(O)CF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1888}$).

A compound (L-8) wherein T represents a group represented by T3, $R^1$ represents $S(O)CF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1889}$).

A compound (L-8) wherein T represents a group represented by T3, $R^1$ represents $S(O)CF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1890}$).

A compound (L-8) wherein T represents a group represented by T3, $R^1$ represents $S(O)CF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1891}$).

A compound (L-8) wherein T represents a group represented by T3, $R^1$ represents $S(O)CF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1892}$).

A compound (L-8) wherein T represents a group represented by T3, $R^1$ represents $S(O)CF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1893}$).

A compound (L-8) wherein T represents a group represented by T4, $R^1$ represents $S(O)CF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1894}$).

A compound (L-8) wherein T represents a group represented by T4, $R^1$ represents $S(O)CF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1895}$).

A compound (L-8) wherein T represents a group represented by T4, $R^1$ represents $S(O)CF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1896}$).

A compound (L-8) wherein T represents a group represented by T4, $R^1$ represents $S(O)CF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1897}$).

A compound (L-8) wherein T represents a group represented by T4, $R^1$ represents $S(O)CF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1898}$).

A compound (L-8) wherein T represents a group represented by T5, $R^1$ represents $S(O)CF_3$, n is 0, $R^2$ represents a methyl group, and $R^{3c}$ represents a hydrogen atom, a chlorine atom, $CF_3$, or any substituents indicated in [Table L4] to [Table L12] (hereinafter, referred to as Compound Class $SX_{1899}$).

A compound (L-8) wherein T represents a group represented by T5, $R^1$ represents $S(O)CF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1900}$).

A compound (L-8) wherein T represents a group represented by T5, $R^1$ represents $S(O)CF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1901}$).

A compound (L-8) wherein T represents a group represented by T5, $R^1$ represents $S(O)CF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1902}$).

A compound (L-8) wherein T represents a group represented by T5, $R^1$ represents $S(O)CF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1903}$.

A compound (L-8) wherein T represents a group represented by T1, $R^1$ represents $S(O)_2CF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1904}$.

A compound (L-8) wherein T represents a group represented by T1, $R^1$ represents $S(O)_2CF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1905}$).

A compound (L-8) wherein T represents a group represented by T1, $R^1$ represents $S(O)_2CF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1906}$).

A compound (L-8) wherein T represents a group represented by T1, $R^1$ represents $S(O)_2CF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1907}$).

A compound (L-8) wherein T represents a group represented by T1, $R^1$ represents $S(O)_2CF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1908}$).

A compound (L-8) wherein T represents a group represented by T2, $R^1$ represents $S(O)_2CF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1909}$).

A compound (L-8) wherein T represents a group represented by T2, $R^1$ represents $S(O)_2CF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1910}$).

A compound (L-8) wherein T represents a group represented by T2, $R^1$ represents $S(O)_2CF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1911}$).

A compound (L-8) wherein T represents a group represented by T2, $R^1$ represents $S(O)_2CF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1912}$).

A compound (L-8) wherein T represents a group represented by T2, $R^1$ represents $S(O)_2CF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1913}$).

A compound (L-8) wherein T represents a group represented by T3, $R^1$ represents $S(O) CF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1914}$).

A compound (L-8) wherein T represents a group represented by T3, $R^1$ represents $S(O)_2CF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1915}$).

A compound (L-8) wherein T represents a group represented by T3, $R^1$ represents $S(O)_2CF_3$, n is 2, $R^2$ represents a methyl group, and $R^{3b}$ represents a hydrogen atom, a chlorine atom, $CF_3$, or any substituent indicated in [Table L4] to [Table L12] (hereinafter, referred to as Compound Class $SX_{1916}$).

A compound (L-8) wherein T represents a group represented by T3, $R^1$ represents $S(O)_2CF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1917}$).

A compound (L-8) wherein T represents a group represented by T3, $R^1$ represents $S(O)_2CF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1918}$).

A compound (L-8) wherein T represents a group represented by T4, $R^1$ represents $S(O)_2CF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1919}$).

A compound (L-8) wherein T represents a group represented by T4, $R^1$ represents $S(O)_2CF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1920}$).

A compound (L-8) wherein T represents a group represented by T4, $R^1$ represents $S(O)_2CF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1921}$).

A compound (L-8) wherein T represents a group represented by T4, $R^1$ represents $S(O)_2CF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1922}$).

A compound (L-8) wherein T represents a group represented by T4, $R^1$ represents $S(O)_2CF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1923}$).

A compound (L-8) wherein T represents a group represented by T5, $R^1$ represents $S(O)_2CF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1924}$).

A compound (L-8) wherein T represents a group represented by T5, $R^1$ represents $S(O)_2CF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1925}$).

A compound (L-8) wherein T represents a group represented by T5, $R^1$ represents $S(O)_2CF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{1926}$).

A compound (L-8) wherein T represents a group represented by T5, $R^1$ represents $S(O)_2CF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1927}$).

A compound (L-8) wherein T represents a group represented by T5, $R^1$ represents $S(O)_2CF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{1928}$).

A compound (L-1) wherein T represents a group represented by T32, $R^{3b}$ represents a hydrogen atom, and $R^1$ represents any substituents indicated in [Table L1] to [Table L3] (hereinafter, referred to as Compound Class $SX_{1929}$).

A compound (L-1) wherein T represents a group represented by T32, $R^{3b}$ represents a chlorine atom, and $R^1$ represents any substituents indicated in [Table L1] to [Table L3] (hereinafter, referred to as Compound Class $SX_{1930}$).

A compound (L-1) wherein T represents a group represented by T32, $R^{3b}$ represents a cyclopropyl group, and $R^1$ represents any substituents indicated in [Table L1] to [Table L3] (hereinafter, referred to as Compound Class $SX_{1931}$).

A compound (L-1) wherein T represents a group represented by T32, $R^{3b}$ represents a 1-cyanocyclopropyl group, and $R^1$ represents any substituents indicated in [Table L1] to [Table L3] (hereinafter, referred to as Compound Class $SX_{1932}$).

A compound (L-1) wherein T represents a group represented by T32, $R^{3b}$ represents $CF_3$, and $R^1$ represents any substituents indicated in [Table L1] to [Table L3] (hereinafter, referred to as Compound Class $SX_{1933}$).

A compound (L-1) wherein T represents a group represented by T33, $R^{3b}$ represents a hydrogen atom, and $R^1$ represents any substituents indicated in [Table L1] to [Table L3] (hereinafter, referred to as Compound Class $SX_{1934}$).

A compound (L-1) wherein T represents a group represented by T33, $R^{3b}$ represents a chlorine atom, and $R^1$ represents any substituents indicated in [Table L1] to [Table L3] (hereinafter, referred to as Compound Class $SX_{1935}$).

A compound (L-1) wherein T represents a group represented by T33, $R^{3b}$ represents a cyclopropyl group, and $R^1$ represents any substituents indicated in [Table L1] to [Table L3] (hereinafter, referred to as Compound Class $SX_{1936}$).

A compound (L-1) wherein T represents a group represented by T33, $R^{3b}$ represents a 1-cyanocyclopropyl group, and $R^1$ represents any substituents indicated in [Table L1] to [Table L3] (hereinafter, referred to as Compound Class $SX_{1937}$).

A compound (L-1) wherein T represents a group represented by T33, $R^{3b}$ represents $CF_3$, and $R^1$ represents any substituents indicated in [Table L1] to [Table L3] (hereinafter, referred to as Compound Class $SX_{1938}$).

A compound (L-1) wherein T represents a group represented by T34, $R^{3b}$ represents a hydrogen atom, and $R^1$ represents any substituents indicated in [Table L1] to [Table L3] (hereinafter, referred to as Compound Class $SX_{1939}$).

A compound (L-1) wherein T represents a group represented by T34, $R^{3b}$ represents a chlorine atom, and $R^1$ represents any substituents indicated in [Table L1] to [Table L3] (hereinafter, referred to as Compound Class $SX_{1940}$).

A compound (L-1) wherein T represents a group represented by T34, $R^{3b}$ represents a cyclopropyl group, and $R^1$ represents any substituents indicated in [Table L1] to [Table L3] (hereinafter, referred to as Compound Class $SX_{1941}$).

A compound (L-1) wherein T represents a group represented by T34, $R^{3b}$ represents a 1-cyanocyclopropyl group, and $R^1$ represents any substituents indicated in [Table L1] to [Table L3] (hereinafter, referred to as Compound Class $SX_{1942}$).

A compound (L-1) wherein T represents a group represented by T34, $R^{3b}$ represents $CF_3$, and $R^1$ represents any substituents indicated in [Table L1] to [Table L3] (hereinafter, referred to as Compound Class $SX_{1943}$).

A compound (L-1) wherein T represents a group represented by T35, $R^{3b}$ represents a hydrogen atom, and $R^1$ represents any substituents indicated in [Table L1] to [Table L3] (hereinafter, referred to as Compound Class $SX_{1944}$).

A compound (L-1) wherein T represents a group represented by T35, $R^{3b}$ represents a chlorine atom, and $R^1$ represents any substituents indicated in [Table L1] to [Table L3] (hereinafter, referred to as Compound Class $SX_{1945}$).

A compound (L-1) wherein T represents a group represented by T35, $R^{3b}$ represents a cyclopropyl group, and $R^1$ represents any substituents indicated in [Table L1] to [Table L3] (hereinafter, referred to as Compound Class $SX_{1946}$).

A compound (L-1) wherein T represents a group represented by T35, $R^{3b}$ represents a 1-cyanocyclopropyl group, and $R^1$ represents any substituents indicated in [Table L1] to [Table L3] (hereinafter, referred to as Compound Class $SX_{1947}$).

A compound (L-1) wherein T represents a group represented by T35, $R^{3b}$ represents $CF_3$, and $R^1$ represents any substituents indicated in [Table L1] to [Table L3] (hereinafter, referred to as Compound Class $SX_{1948}$).

A compound (L-1) wherein T represents a group represented by T36, $R^{3b}$ represents a hydrogen atom, and $R^1$ represents any substituents indicated in [Table L1] to [Table L3] (hereinafter, referred to as Compound Class $SX_{1949}$).

A compound (L-1) wherein T represents a group represented by T36, $R^{3b}$ represents a chlorine atom, and $R^1$ represents any substituents indicated in [Table L1] to [Table L3] (hereinafter, referred to as Compound Class $SX_{1950}$).

A compound (L-1) wherein T represents a group represented by T36, $R^{3b}$ represents a cyclopropyl group, and $R^1$ represents any substituents indicated in [Table L1] to [Table L3] (hereinafter, referred to as Compound Class $SX_{1951}$).

A compound (L-1) wherein T represents a group represented by T36, $R^{3b}$ represents a 1-cyanocyclopropyl group, and $R^1$ represents any substituents indicated in [Table L1] to [Table L3] (hereinafter, referred to as Compound Class $SX_{1952}$).

A compound (L-1) wherein T represents a group represented by T36, $R^{3b}$ represents $CF_3$, and $R^1$ represents any substituents indicated in [Table L1] to [Table L3] (hereinafter, referred to as Compound Class $SX_{1953}$).

A compound (L-2) wherein T represents a group represented by T32, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{1954}$).

A compound (L-2) wherein T represents a group represented by T32, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{1955}$).

A compound (L-2) wherein T represents a group represented by T32, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{1956}$).

A compound (L-2) wherein T represents a group represented by T32, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{1957}$).

A compound (L-2) wherein T represents a group represented by T32, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{1958}$).

A compound (L-2) wherein T represents a group represented by T32, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{1959}$).

A compound (L-2) wherein T represents a group represented by T32, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{1960}$).

A compound (L-2) wherein T represents a group represented by T32, $R^{3b}$ represents a hydrogen atom, $R^{3c}$ represents a bromine atom, and $R^1$ represents any substituents indicated in [Table L1] to [Table L3] (hereinafter, referred to as Compound Class $SX_{1961}$).

A compound (L-2) wherein T represents a group represented by T32, $R^{3b}$ represents a hydrogen atom, $R^{3c}$ represents an iodine atom, and $R^1$ represents any substituents indicated in [Table L1] to [Table L3] (hereinafter, referred to as Compound Class $SX_{1962}$).

A compound (L-2) wherein T represents a group represented by T33, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{1963}$).

A compound (L-2) wherein T represents a group represented by T33, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{1964}$).

A compound (L-2) wherein T represents a group represented by T33, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{1965}$).

A compound (L-2) wherein T represents a group represented by T33, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{1966}$).

A compound (L-2) wherein T represents a group represented by T33, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{1967}$).

A compound (L-2) wherein T represents a group represented by T33, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{1968}$).

A compound (L-2) wherein T represents a group represented by T33, $R^{3b}$ represents a hydrogen atom, $R^4$ represents a chlorine atom, and $R^1$ represents any substituents indicated in [Table L1] to [Table L3] (hereinafter, referred to as Compound Class $SX_{1969}$).

A compound (L-2) wherein T represents a group represented by T33, $R^{3b}$ represents a hydrogen atom, $R^{3c}$ represents a bromine atom, and $R^1$ represents any substituents indicated in [Table L1] to [Table L3] (hereinafter, referred to as Compound Class $SX_{1970}$).

A compound (L-2) wherein T represents a group represented by T33, $R^{3b}$ represents a hydrogen atom, $R^{3c}$ represents an iodine atom, and $R^1$ represents any substituents indicated in [Table L1] to [Table L3] (hereinafter, referred to as Compound Class $SX_{1971}$).

A compound (L-2) wherein T represents a group represented by T34, $R^{3b}$ represents a hydrogen atom, $R^{3c}$ represents a hydrogen atom, and $R^1$ represents any (hereinafter, referred to as Compound Class $SX_{1972}$).

A compound (L-2) wherein T represents a group represented by T34, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{1973}$).

A compound (L-2) wherein T represents a group represented by T34, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{1974}$).

A compound (L-2) wherein T represents a group represented by T34, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{1975}$).

A compound (L-2) wherein T represents a group represented by T34, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{1976}$).

A compound (L-2) wherein T represents a group represented by T34, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{1977}$.

A compound (L-2) wherein T represents a group represented by T34, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{1978}$).

A compound (L-2) wherein T represents a group represented by T34, $R^{3b}$ represents a hydrogen atom, $R^{3c}$ represents a bromine atom, and $R^1$ represents any substituents indicated in [Table L1] to [Table L3] (hereinafter, referred to as Compound Class $SX_{1979}$).

A compound (L-2) wherein T represents a group represented by T34, $R^{3b}$ represents a hydrogen atom, $R^{3c}$ represents an iodine atom, and $R^1$ represents any substituents indicated in [Table L1] to [Table L3] (hereinafter, referred to as Compound Class $SX_{1980}$).

A compound (L-2) wherein T represents a group represented by T35, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{1981}$).

A compound (L-2) wherein T represents a group represented by T35, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{1982}$).

A compound (L-2) wherein T represents a group represented by T35, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{1983}$).

A compound (L-2) wherein T represents a group represented by T35, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{1984}$).

A compound (L-2) wherein T represents a group represented by T35, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{1985}$).

A compound (L-2) wherein T represents a group represented by T35, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{1986}$).

A compound (L-2) wherein T represents a group represented by T35, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{1987}$).

A compound (L-2) wherein T represents a group represented by T35, $R^{3b}$ represents a hydrogen atom, $R^{3c}$ represents a bromine atom, and $R^1$ represents any substituents indicated in [Table L1] to [Table L3] (hereinafter, referred to as Compound Class $SX_{1988}$).

A compound (L-2) wherein T represents a group represented by T35, $R^{3b}$ represents a hydrogen atom, $R^{3c}$ represents an iodine atom, and $R^1$ represents any substituents indicated in [Table L1] to [Table L3] (hereinafter, referred to as Compound Class $SX_{1989}$).

A compound (L-2) wherein T represents a group represented by T36, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{1990}$).

A compound (L-2) wherein T represents a group represented by T36, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{1991}$).

A compound (L-2) wherein T represents a group represented by T36, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{1992}$).

A compound (L-2) wherein T represents a group represented by T36, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{1993}$).

A compound (L-2) wherein T represents a group represented by T36, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{1994}$).

A compound (L-2) wherein T represents a group represented by T36, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{1995}$).

A compound (L-2) wherein T represents a group represented by T36, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{1996}$).

A compound (L-2) wherein T represents a group represented by T36, $R^{3b}$ represents a hydrogen atom, $R^{3c}$ represents a bromine atom, and $R^1$ represents any substituents indicated in [Table L1] to [Table L3] (hereinafter, referred to as Compound Class $SX_{1997}$).

A compound (L-2) wherein T represents a group represented by T36, $R^{3b}$ represents a hydrogen atom, $R^{3c}$ represents an iodine atom, and $R^1$ represents any substituents indicated in [Table L1] to [Table L3] (hereinafter, referred to as Compound Class $SX_{1998}$).

A compound (L-3) wherein T represents a group represented by T32, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{1999}$).

A compound (L-3) wherein T represents a group represented by T32, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{2000}$).

A compound (L-3) wherein T represents a group represented by T32, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{2001}$).

A compound (L-3) wherein T represents a group represented by T32, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{2002}$).

A compound (L-3) wherein T represents a group represented by T32, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{2003}$).

A compound (L-3) wherein T represents a group represented by T32, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{2004}$).

A compound (L-3) wherein T represents a group represented by T32, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{2005}$).

A compound (L-3) wherein T represents a group represented by T32, $R^{3b}$ represents a hydrogen atom, $R^{3c}$ represents a bromine atom, and $R^1$ represents any substituents indicated in [Table L1] to [Table L3] (hereinafter, referred to as Compound Class $SX_{2006}$).

A compound (L-3) wherein T represents a group represented by T32, $R^{3b}$ represents a hydrogen atom, $R^{3c}$ represents an iodine atom, and $R^1$ represents any substituents indicated in [Table L1] to [Table L3] (hereinafter, referred to as Compound Class $SX_{2007}$).

A compound (L-3) wherein T represents a group represented by T33, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{2008}$).

A compound (L-3) wherein T represents a group represented by T33, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{2009}$).

A compound (L-3) wherein T represents a group represented by T33, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{2010}$).

A compound (L-3) wherein T represents a group represented by T33, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{2011}$).

A compound (L-3) wherein T represents a group represented by T33, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{2012}$).

A compound (L-3) wherein T represents a group represented by T33, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{2013}$).

A compound (L-3) wherein T represents a group represented by T33, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{2014}$).

A compound (L-3) wherein T represents a group represented by T33, $R^{3b}$ represents a hydrogen atom, $R^{3c}$ represents a bromine atom, and $R^1$ represents any substituents indicated in [Table L1] to [Table L3] (hereinafter, referred to as Compound Class $SX_{2015}$).

A compound (L-3) wherein T represents a group represented by T33, $R^{3b}$ represents a hydrogen atom, $R^{3c}$ represents an iodine atom, and $R^1$ represents any substituents indicated in [Table L1] to [Table L3] (hereinafter, referred to as Compound Class $SX_{2016}$).

A compound (L-3) wherein T represents a group represented by T34, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{2017}$).

A compound (L-3) wherein T represents a group represented by T34, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{2018}$).

A compound (L-3) wherein T represents a group represented by T34, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{2019}$).

A compound (L-3) wherein T represents a group represented by T34, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{2020}$).

A compound (L-3) wherein T represents a group represented by T34, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{2021}$).

A compound (L-3) wherein T represents a group represented by T34, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{2022}$).

A compound (L-3) wherein T represents a group represented by T34, $R^{3b}$ represents a hydrogen atom, $R^{3c}$ representssents a chlorine atom, and $R^1$ represents any substituents indicated in [Table L1] to [Table L3] (hereinafter, referred to as Compound Class $SX_{2023}$).

A compound (L-3) wherein T represents a group represented by T34, $R^{3b}$ represents a hydrogen atom, $R^{3c}$ represents a bromine atom, and $R^1$ represents any substituents indicated in [Table L1] to [Table L3] (hereinafter, referred to as Compound Class $SX_{2024}$).

A compound (L-3) wherein T represents a group represented by T34, $R^{3b}$ represents a hydrogen atom, $R^{3c}$ represents an iodine atom, and $R^1$ represents any substituents indicated in [Table L1] to [Table L3] (hereinafter, referred to as Compound Class $SX_{2025}$).

A compound (L-3) wherein T represents a group represented by T35, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{2026}$).

A compound (L-3) wherein T represents a group represented by T35, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{2027}$).

A compound (L-3) wherein T represents a group represented by T35, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{2028}$).

A compound (L-3) wherein T represents a group represented by T35, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{2029}$).

A compound (L-3) wherein T represents a group represented by T35, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{2030}$).

A compound (L-3) wherein T represents a group represented by T35, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{2031}$).

A compound (L-3) wherein T represents a group represented by T35, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{2032}$).

A compound (L-3) wherein T represents a group represented by T35, $R^{3b}$ represents a hydrogen atom, $R^{3c}$ represents a bromine atom, and $R^1$ represents any substituents indicated in [Table L1] to [Table L3] (hereinafter, referred to as Compound Class $SX_{2033}$).

A compound (L-3) wherein T represents a group represented by T35, $R^{3b}$ represents a hydrogen atom, $R^{3c}$ represents an iodine atom, and $R^1$ represents any substituents indicated in [Table L1] to [Table L3] (hereinafter, referred to as Compound Class $SX_{2034}$).

A compound (L-3) wherein T represents a group represented by T36, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{2035}$).

A compound (L-3) wherein T represents a group represented by T36, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{2036}$).

A compound (L-3) wherein T represents a group represented by T36, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{2037}$).

A compound (L-3) wherein T represents a group represented by T36, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{2038}$).

A compound (L-3) wherein T represents a group represented by T36, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{2039}$).

A compound (L-3) wherein T represents a group represented by T36, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{2040}$).

A compound (L-3) wherein T represents a group represented by T36, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{2041}$).

A compound (L-3) wherein T represents a group represented by T36, $R^{3b}$ represents a hydrogen atom, $R^{3c}$ represents a bromine atom, and $R^1$ represents any substituents indicated in [Table L1] to [Table L3] (hereinafter, referred to as Compound Class $SX_{2042}$).

A compound (L-3) wherein T represents a group represented by T36, $R^{3b}$ represents a hydrogen atom, $R^{3c}$ represents an iodine atom, and $R^1$ represents any substituents indicated in [Table L1] to [Table L3] (hereinafter, referred to as Compound Class $SX_{2043}$).

A compound (L-4) wherein T represents a group represented by T32, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{2045}$).

A compound (L-4) wherein T represents a group represented by T32, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{2043}$).

A compound (L-4) wherein T represents a group represented by T32, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{2047}$).

A compound (L-4) wherein T represents a group represented by T32, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{2048}$).

A compound (L-4) wherein T represents a group represented by T32, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{2049}$).

A compound (L-4) wherein T represents a group represented by T32, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{2050}$).

A compound (L-4) wherein T represents a group represented by T32, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{2051}$).

A compound (L-4) wherein T represents a group represented by T32, $R^{3b}$ represents a hydrogen atom, $R^{3c}$ represents a bromine atom, and $R^1$ represents any substituents indicated in [Table L1] to [Table L3] (hereinafter, referred to as Compound Class $SX_{2052}$).

A compound (L-3) wherein T represents a group represented by T32, $R^{3b}$ represents a hydrogen atom, $R^{3c}$ represents an iodine atom, and $R^1$ represents any substituents indicated in [Table L1] to [Table L3] (hereinafter, referred to as Compound Class $SX_{2053}$).

A compound (L-4) wherein T represents a group represented by T33, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{2054}$).

A compound (L-4) wherein T represents a group represented by T33, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{2055}$).

A compound (L-4) wherein T represents a group represented by T33, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{2056}$).

A compound (L-4) wherein T represents a group represented by T33, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{2057}$).

A compound (L-4) wherein T represents a group represented by T33, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{2058}$).

A compound (L-4) wherein T represents a group represented by T33, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{2059}$).

A compound (L-4) wherein T represents a group represented by T33, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{2060}$).

A compound (L-4) wherein T represents a group represented by T33, $R^{3b}$ represents a hydrogen atom, $R^{3c}$ represents a bromine atom, and $R^1$ represents any substituents indicated in [Table L1] to [Table L3] (hereinafter, referred to as Compound Class $SX_{2061}$).

A compound (L-3) wherein T represents a group represented by T33, $R^{3b}$ represents a hydrogen atom, $R^{3c}$ represents an iodine atom, and $R^1$ represents any substituents indicated in [Table L1] to [Table L3] (hereinafter, referred to as Compound Class $SX_{2062}$).

A compound (L-4) wherein T represents a group represented by T34, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{2063}$).

A compound (L-4) wherein T represents a group represented by T34, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{2064}$).

A compound (L-4) wherein T represents a group represented by T34, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{2065}$).

A compound (L-4) wherein T represents a group represented by T34, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{2066}$).

A compound (L-4) wherein T represents a group represented by T34, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{2067}$).

A compound (L-4) wherein T represents a group represented by T34, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{2068}$).

A compound (L-4) wherein T represents a group represented by T34, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{2069}$).

A compound (L-4) wherein T represents a group represented by T34, $R^{3b}$ represents a hydrogen atom, $R^{3c}$ represents a bromine atom, and $R^1$ represents any substituents indicated in [Table L1] to [Table L3] (hereinafter, referred to as Compound Class $SX_{2070}$).

A compound (L-3) wherein T represents a group represented by T34, $R^{3b}$ represents a hydrogen atom, $R^{3c}$ represents an iodine atom, and $R^1$ represents any substituents indicated in [Table L1] to [Table L3] (hereinafter, referred to as Compound Class $SX_{2071}$).

A compound (L-4) wherein T represents a group represented by T35, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{2072}$).

A compound (L-4) wherein T represents a group represented by T35, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{2073}$).

A compound (L-4) wherein T represents a group represented by T35, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{2074}$).

A compound (L-4) wherein T represents a group represented by T35, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{2075}$).

A compound (L-4) wherein T represents a group represented by T35, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{2076}$).

A compound (L-4) wherein T represents a group represented by T35, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{2077}$).

A compound (L-4) wherein T represents a group represented by T35, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{2078}$).

A compound (L-4) wherein T represents a group represented by T35, $R^{3b}$ represents a hydrogen atom, $R^{3c}$ represents a bromine atom, and $R^1$ represents any substituents indicated in [Table L1] to [Table L3] (hereinafter, referred to as Compound Class $SX_{2079}$).

A compound (L-3) wherein T represents a group represented by T35, $R^{3b}$ represents a hydrogen atom, $R^{3c}$ represents an iodine atom, and $R^1$ represents any substituents indicated in [Table L1] to [Table L3] (hereinafter, referred to as Compound Class $SX_{2080}$).

A compound (L-4) wherein T represents a group represented by T36, $R^{3b}$ represents a hydrogen atom, $R^{3c}$ represents a hydrogen atom, and $R^1$ represents any substituents indicated in [Table L1] to [Table L3] (hereinafter, referred to as Compound Class $SX_{2081}$).

A compound (L-4) wherein T represents a group represented by T36, $R^{3b}$ represents $CF_3$, $R^{3c}$ represents a hydrogen atom, and $R^1$ represents any substituents indicated in [Table L1] to [Table L3] (hereinafter, referred to as Compound Class $SX_{2082}$).

A compound (L-4) wherein T represents a group represented by T36, $R^{3b}$ represents a chlorine atom, $R^{3c}$ represents a hydrogen atom, and $R^1$ represents any substituents indicated in [Table L1] to [Table L3] (hereinafter, referred to as Compound Class $SX_{2083}$).

A compound (L-4) wherein T represents a group represented by T36, $R^{3b}$ represents a bromine atom, $R^{3c}$ represents a hydrogen atom, and $R^1$ represents any substituents indicated in [Table L1] to [Table L3] (hereinafter, referred to as Compound Class $SX_{2084}$).

A compound (L-4) wherein T represents a group represented by T36, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{2085}$).

A compound (L-4) wherein T represents a group represented by T36, $R^{3b}$ represents a hydrogen atom, $R^{3c}$ represents $CF_3$, and $R^1$ represents any substituents indicated in [Table L1] to [Table L3] (hereinafter, referred to as Compound Class $SX_{2086}$).

A compound (L-4) wherein T represents a group represented by T36, $R^{3b}$ represents a hydrogen atom, $R^{3c}$ represents a chlorine atom, and $R^1$ represents any substituents indicated in [Table L1] to [Table L3] (hereinafter, referred to as Compound Class $SX_{2087}$).

A compound (L-4) wherein T represents a group represented by T36, $R^{3b}$ represents a hydrogen atom, $R^{3c}$ represents a bromine atom, and $R^1$ represents any substituents indicated in [Table L1] to [Table L3] (hereinafter, referred to as Compound Class $SX_{2088}$).

A compound (L-3) wherein T represents a group represented by T36, $R^{3b}$ represents a hydrogen atom, $R^{3c}$ represents an iodine atom, and $R^1$ represents any substituents indicated in [Table L1] to [Table L3] (hereinafter, referred to as Compound Class $SX_{2089}$).

A compound (L-5) wherein T represents a group represented by T32, $R^{3c}$ represents a hydrogen atom, and $R^1$ represents any substituents indicated in [Table L1] to [Table L3] (hereinafter, referred to as Compound Class $SX_{2090}$).

A compound (L-5) wherein T represents a group represented by T32, $R^{3c}$ represents $CF_3$, and $R^1$ represents any substituents indicated in [Table L1] to [Table L3] (hereinafter, referred to as Compound Class $SX_{2091}$).

A compound (L-5) wherein T represents a group represented by T32, $R^{3c}$ represents a chlorine atom, and $R^1$ represents any substituents indicated in [Table L1] to [Table L3] (hereinafter, referred to as Compound Class $SX_{2092}$).

A compound (L-5) wherein T represents a group represented by T32, $R^{3c}$ represents a bromine atom, and $R^1$ represents any substituents indicated in [Table L1] to [Table L3] (hereinafter, referred to as Compound Class $SX_{2093}$).

A compound (L-5) wherein T represents a group represented by T32, $R^{3c}$ represents an iodine atom, $R^{3c}$ represents a hydrogen atom, and $R^1$ represents any substituents indicated in [Table L1] to [Table L3] (hereinafter, referred to as Compound Class $SX_{2095}$).

A compound (L-5) wherein T represents a group represented by T33, $R^{3c}$ represents a hydrogen atom, and $R^1$ represents any substituents indicated in [Table L1] to [Table L3] (hereinafter, referred to as Compound Class $SX_{2095}$).

A compound (L-5) wherein T represents a group represented by T33, $R^{3c}$ represents $CF_3$, and $R^1$ represents any substituents indicated in [Table L1] to [Table L3] (hereinafter, referred to as Compound Class $SX_{2096}$).

A compound (L-5) wherein T represents a group represented by T33, $R^{3c}$ represents a chlorine atom, and $R^1$ represents any substituents indicated in [Table L1] to [Table L3] (hereinafter, referred to as Compound Class $SX_{2097}$).

A compound (L-5) wherein T represents a group represented by T33, $R^{3c}$ represents a bromine atom, and $R^1$ represents any substituents indicated in [Table L1] to [Table L3] (hereinafter, referred to as Compound Class $SX_{2098}$).

A compound (L-5) wherein T represents a group represented by T33, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{2099}$).

A compound (L-5) wherein T represents a group represented by T34, $R^{3c}$ represents a hydrogen atom, and $R^1$ represents any substituents indicated in [Table L1] to [Table L3] (hereinafter, referred to as Compound Class $SX_{2100}$).

A compound (L-5) wherein T represents a group represented by T34, $R^{3c}$ represents $CF_3$, and $R^1$ represents any substituents indicated in [Table L1] to [Table L3] (hereinafter, referred to as Compound Class $SX_{2101}$).

A compound (L-5) wherein T represents a group represented by T34, $R^{3c}$ represents a chlorine atom, and $R^1$ represents any substituents indicated in [Table L1] to [Table L3] (hereinafter, referred to as Compound Class $SX_{2102}$).

A compound (L-5) wherein T represents a group represented by T34, $R^{3c}$ represents a bromine atom, and $R^1$ represents any substituents indicated in [Table L1] to [Table L3] (hereinafter, referred to as Compound Class $SX_{2103}$).

A compound (L-5) wherein T represents a group represented by T34, $R^{3c}$ represents an iodine atom, $R^{3c}$ represents a hydrogen atom, and $R^1$ represents any substituents indicated in [Table L1] to [Table L3] (hereinafter, referred to as Compound Class $SX_{2104}$).

A compound (L-5) wherein T represents a group represented by T35, $R^{3c}$ represents a hydrogen atom, and $R^1$ represents any substituents indicated in [Table L1] to [Table L3] (hereinafter, referred to as Compound Class $SX_{2105}$).

A compound (L-5) wherein T represents a group represented by T35, $R^{3c}$ represents $CF_3$, and $R^1$ represents any substituents indicated in [Table L1] to [Table L3] (hereinafter, referred to as Compound Class $SX_{2106}$).

A compound (L-5) wherein T represents a group represented by T35, $R^{3c}$ represents a chlorine atom, and $R^1$ represents any substituents indicated in [Table L1] to [Table L3] (hereinafter, referred to as Compound Class $SX_{2107}$).

A compound (L-5) wherein T represents a group represented by T35, $R^{3c}$ represents a bromine atom, and $R^1$ represents any substituents indicated in [Table L1] to [Table L3] (hereinafter, referred to as Compound Class $SX_{2108}$).

A compound (L-5) wherein T represents a group represented by T35, $R^{3c}$ represents an iodine atom, $R^{3c}$ represents a hydrogen atom, and $R^1$ represents any substituents indicated in [Table L1] to [Table L3] (hereinafter, referred to as Compound Class $SX_{2109}$).

A compound (L-5) wherein T represents a group represented by T36, $R^{3c}$ represents a hydrogen atom, and $R^1$ represents any substituents indicated in [Table L1] to [Table L3] (hereinafter, referred to as Compound Class $SX_{2110}$).

A compound (L-5) wherein T represents a group represented by T36, $R^{3c}$ represents $CF_3$, and $R^1$ represents any substituents indicated in [Table L1] to [Table L3] (hereinafter, referred to as Compound Class $SX_{2111}$).

A compound (L-5) wherein T represents a group represented by T36, $R^{3c}$ represents a chlorine atom, and $R^1$ represents any substituents indicated in [Table L1] to [Table L3] (hereinafter, referred to as Compound Class $SX_{2112}$).

A compound (L-5) wherein T represents a group represented by T36, $R^{3b}$ represents a bromine atom, and $R^1$ represents any substituents indicated in [Table L1] to [Table L3] (hereinafter, referred to as Compound Class $SX_{2113}$).

A compound (L-5) wherein T represents a group represented by T36, $R^{3c}$ represents an iodine atom, $R^{3c}$ represents a hydrogen atom, and $R^1$ represents any substituents indicated in [Table L1] to [Table L3] (hereinafter, referred to as Compound Class $SX_{2114}$).

A compound (L-6) wherein T represents a group represented by T32, $R^{3b}$ represents a hydrogen atom, and $R^1$ represents any substituents indicated in [Table L1] to [Table L3] (hereinafter, referred to as Compound Class $SX_{2115}$).

A compound (L-6) wherein T represents a group represented by T32, $R^{3b}$ represents $CF_3$, and $R^1$ represents any substituents indicated in [Table L1] to [Table L3] (hereinafter, referred to as Compound Class $SX_{2116}$).

A compound (L-6) wherein T represents a group represented by T32, $R^{3b}$ represents a chlorine atom, and $R^1$ represents any substituents indicated in [Table L1] to [Table L3] (hereinafter, referred to as Compound Class $SX_{2117}$).

A compound (L-6) wherein T represents a group represented by T32, $R^{3b}$ represents a bromine atom, and $R^1$ represents any substituents indicated in [Table L1] to [Table L3] (hereinafter, referred to as Compound Class $SX_{2118}$).

A compound (L-6) wherein T represents a group represented by T32, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{2119}$).

A compound (L-6) wherein T represents a group represented by T33, $R^{3b}$ represents a hydrogen atom, and $R^1$ represents any substituents indicated in [Table L1] to [Table L3] (hereinafter, referred to as Compound Class $SX_{2120}$).

A compound (L-6) wherein T represents a group represented by T33, $R^{3b}$ represents $CF_3$, and $R^1$ represents any substituents indicated in [Table L1] to [Table L3] (hereinafter, referred to as Compound Class $SX_{2121}$).

A compound (L-6) wherein T represents a group represented by T33, $R^{3b}$ represents a chlorine atom, and $R^1$ represents any substituents indicated in [Table L1] to [Table L3] (hereinafter, referred to as Compound Class $SX_{2122}$).

A compound (L-6) wherein T represents a group represented by T33, $R^{3b}$ represents a bromine atom, and $R^1$ represents any substituents indicated in [Table L1] to [Table L3] (hereinafter, referred to as Compound Class $SX_{2123}$).

A compound (L-6) wherein T represents a group represented by T33, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{2124}$).

A compound (L-6) wherein T represents a group represented by T34, $R^{3b}$ represents a hydrogen atom, and $R^1$ represents any substituents indicated in [Table L1] to [Table L3] (hereinafter, referred to as Compound Class $SX_{2125}$).

A compound (L-6) wherein T represents a group represented by T34, $R^{3b}$ represents $CF_3$, and $R^1$ represents any substituents indicated in [Table L1] to [Table L3] (hereinafter, referred to as Compound Class $SX_{2126}$).

A compound (L-6) wherein T represents a group represented by T34, $R^{3b}$ represents a chlorine atom, and $R^1$ represents any substituents indicated in [Table L1] to [Table L3] (hereinafter, referred to as Compound Class $SX_{2127}$).

A compound (L-6) wherein T represents a group represented by T34, $R^{3b}$ represents a bromine atom, and $R^1$ represents any substituents indicated in [Table L1] to [Table L3] (hereinafter, referred to as Compound Class $SX_{2128}$).

A compound (L-6) wherein T represents a group represented by T34, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{2129}$).

A compound (L-6) wherein T represents a group represented by T35, $R^{3b}$ represents a hydrogen atom, and $R^1$ represents any substituents indicated in [Table L1] to [Table L3] (hereinafter, referred to as Compound Class $SX_{2130}$).

A compound (L-6) wherein T represents a group represented by T35, $R^{3b}$ represents $CF_3$, and $R^1$ represents any substituents indicated in [Table L1] to [Table L3] (hereinafter, referred to as Compound Class $SX_{2131}$).

A compound (L-6) wherein T represents a group represented by T35, $R^{3b}$ represents a chlorine atom, and $R^1$ represents any substituents indicated in [Table L1] to [Table L3] (hereinafter, referred to as Compound Class $SX_{2132}$).

A compound (L-6) wherein T represents a group represented by T35, $R^{3b}$ represents a bromine atom, and $R^1$ represents any substituents indicated in [Table L1] to [Table L3] (hereinafter, referred to as Compound Class $SX_{2133}$).

A compound (L-6) wherein T represents a group represented by T35, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{2134}$).

A compound (L-6) wherein T represents a group represented by T36, $R^{3b}$ represents a hydrogen atom, and $R^1$ represents any substituents indicated in [Table L1] to [Table L3] (hereinafter, referred to as Compound Class $SX_{2135}$).

A compound (L-6) wherein T represents a group represented by T36, $R^{3b}$ represents $CF_3$, and $R^1$ represents any substituents indicated in [Table L1] to [Table L3] (hereinafter, referred to as Compound Class $SX_{2136}$).

A compound (L-6) wherein T represents a group represented by T36, $R^{3b}$ represents a chlorine atom, and $R^1$ represents any substituents indicated in [Table L1] to [Table L3] (hereinafter, referred to as Compound Class $SX_{2137}$).

A compound (L-6) wherein T represents a group represented by T36, $R^{3b}$ represents a bromine atom, and $R^1$ represents any substituents indicated in [Table L1] to [Table L3] (hereinafter, referred to as Compound Class $SX_{2138}$).

A compound (L-6) wherein T represents a group represented by T36, $R^{3b}$ represents an iodine atom, $R^{3c}$ represents a hydrogen atom, and $R^1$ represents any substituents indicated in [Table L1] to [Table L3] (hereinafter, referred to as Compound Class $SX_{2139}$).

A compound (L-1) wherein T represents a group represented by T32, $R^1$ represents $CF_3$, and $R^{3b}$ represents any substituents indicated in [Table L4] to [Table L12] (hereinafter, referred to as Compound Class $SX_{2140}$).

A compound (L-1) wherein T represents a group represented by T32, $R^1$ represents $C_2F_5$, and $R^{3b}$ represents any substituents indicated in [Table L4] to [Table L12] (hereinafter, referred to as Compound Class $SX_{2141}$).

A compound (L-1) wherein T represents a group represented by T32, $R^1$ represents $OCF_3$, and $R^{3b}$ represents any substituents indicated in [Table L4] to [Table L12] (hereinafter, referred to as Compound Class $SX_{2142}$).

A compound (L-1) wherein T represents a group represented by T32, $R^1$ represents $SCF_3$, and $R^{3b}$ represents any substituents indicated in [Table L4] to [Table L12] (hereinafter, referred to as Compound Class $SX_{2143}$).

A compound (L-1) wherein T represents a group represented by T32, $R^1$ represents $S(O)CF_3$, and $R^{3b}$ represents any substituents indicated in [Table L4] to [Table L12] (hereinafter, referred to as Compound Class $SX_{2144}$).

A compound (L-1) wherein T represents a group represented by T32, $R^1$ represents $S(O)_2CF_3$, and $R^{3b}$ represents any substituents indicated in [Table L4] to [Table L12] (hereinafter, referred to as Compound Class $SX_{2145}$).

A compound (L-1) wherein T represents a group represented by T32, $R^1$ represents a fluorine atom, and $R^{3b}$ represents any substituents indicated in [Table L4] to [Table L12] (hereinafter, referred to as Compound Class $SX_{2146}$).

A compound (L-1) wherein T represents a group represented by T32, $R^1$ represents a chlorine atom, and $R^{3b}$ represents any substituents indicated in [Table L4] to [Table L12] (hereinafter, referred to as Compound Class $SX_{2147}$).

A compound (L-1) wherein T represents a group represented by T32, $R^1$ represents a bromine atom, and $R^{3b}$ represents any substituents indicated in [Table L4] to [Table L12] (hereinafter, referred to as Compound Class $SX_{2148}$).

A compound (L-1) wherein T represents a group represented by T32, $R^1$ represents an iodine atom, and $R^{3b}$ represents any substituents indicated in [Table L4] to [Table L12] (hereinafter, referred to as Compound Class $SX_{2149}$).

A compound (L-1) wherein T represents a group represented by T33, $R^1$ represents $CF_3$, and $R^{3b}$ represents any substituents indicated in [Table L4] to [Table L12] (hereinafter, referred to as Compound Class $SX_{2150}$).

A compound (L-1) wherein T represents a group represented by T33, $R^1$ represents $C_2F_5$, and $R^{3b}$ represents any substituents indicated in [Table L4] to [Table L12] (hereinafter, referred to as Compound Class $SX_{2151}$).

A compound (L-1) wherein T represents a group represented by T33, $R^1$ represents $OCF_3$, and $R^{3b}$ represents any substituents indicated in [Table L4] to [Table L12] (hereinafter, referred to as Compound Class $SX_{2152}$).

A compound (L-1) wherein T represents a group represented by T33, $R^1$ represents $SCF_3$, and $R^{3b}$ represents any substituents indicated in [Table L4] to [Table L12] (hereinafter, referred to as Compound Class $SX_{2153}$).

A compound (L-1) wherein T represents a group represented by T33, $R^1$ represents $S(O)CF_3$, and $R^{3b}$ represents any substituents indicated in [Table L4] to [Table L12] (hereinafter, referred to as Compound Class $SX_{2153-1}$).

A compound (L-1) wherein T represents a group represented by T33, $R^1$ represents $S(O)_2CF_3$, and $R^{3b}$ represents any substituents indicated in [Table L4] to [Table L12] (hereinafter, referred to as Compound Class $SX_{2154}$).

A compound (L-1) wherein T represents a group represented by T33, $R^1$ represents a fluorine atom, and $R^{3b}$ represents any substituents indicated in [Table L4] to [Table L12] (hereinafter, referred to as Compound Class $SX_{2155}$).

A compound (L-1) wherein T represents a group represented by T33, $R^1$ represents a chlorine atom, and $R^{3b}$ represents any substituents indicated in [Table L4] to [Table L12] (hereinafter, referred to as Compound Class $SX_{2156}$).

A compound (L-1) wherein T represents a group represented by T33, $R^1$ represents a bromine atom, and $R^{3b}$ represents any substituents indicated in [Table L4] to [Table L12] (hereinafter, referred to as Compound Class $SX_{2157}$).

A compound (L-1) wherein T represents a group represented by T33, $R^1$ represents an iodine atom, and $R^{3b}$ represents any substituents indicated in [Table L4] to [Table L12] (hereinafter, referred to as Compound Class $SX_{2158}$).

A compound (L-1) wherein T represents a group represented by T34, $R^1$ represents $CF_3$, and $R^{3b}$ represents any substituents indicated in [Table L4] to [Table L12] (hereinafter, referred to as Compound Class $SX_{2159}$).

A compound (L-1) wherein T represents a group represented by T34, $R^1$ represents $C_2F_5$, and $R^{3b}$ represents any substituents indicated in [Table L4] to [Table L12] (hereinafter, referred to as Compound Class $SX_{2160}$).

A compound (L-1) wherein T represents a group represented by T34, $R^1$ represents $OCF_3$, and $R^{3b}$ represents any substituents indicated in [Table L4] to [Table L12] (hereinafter, referred to as Compound Class $SX_{2161}$).

A compound (L-1) wherein T represents a group represented by T34, $R^1$ represents $SCF_3$, and $R^{3b}$ represents any substituents indicated in [Table L4] to [Table L12] (hereinafter, referred to as Compound Class $SX_{2162}$).

A compound (L-1) wherein T represents a group represented by T34, $R^1$ represents $S(O)CF_3$, and $R^{3b}$ represents any substituents indicated in [Table L4] to [Table L12] (hereinafter, referred to as Compound Class $SX_{2163}$).

A compound (L-1) wherein T represents a group represented by T34, $R^1$ represents $S(O)_2CF_3$, and $R^{3b}$ represents any substituents indicated in [Table L4] to [Table L12] (hereinafter, referred to as Compound Class $SX_{2164}$).

A compound (L-1) wherein T represents a group represented by T34, $R^1$ represents a fluorine atom, and $R^{3b}$ represents any substituents indicated in [Table L4] to [Table L12] (hereinafter, referred to as Compound Class $SX_{2165}$).

A compound (L-1) wherein T represents a group represented by T34, $R^1$ represents a chlorine atom, and $R^{3b}$ represents any substituents indicated in [Table L4] to [Table L12] (hereinafter, referred to as Compound Class $SX_{2166}$).

A compound (L-1) wherein T represents a group represented by T34, $R^1$ represents a bromine atom, and $R^{3b}$ represents any substituents indicated in [Table L4] to [Table L12] (hereinafter, referred to as Compound Class $SX_{2167}$).

A compound (L-1) wherein T represents a group represented by T34, $R^1$ represents an iodine atom, and $R^{3b}$ represents any substituents indicated in [Table L4] to [Table L12] (hereinafter, referred to as Compound Class $SX_{2168}$).

A compound (L-1) wherein T represents a group represented by T35, $R^1$ represents $CF_3$, and $R^{3b}$ represents any substituents indicated in [Table L4] to [Table L12] (hereinafter, referred to as Compound Class $SX_{2169}$).

A compound (L-1) wherein T represents a group represented by T35, $R^1$ represents $C_2F_5$, and $R^{3b}$ represents any substituents indicated in [Table L4] to [Table L12] (hereinafter, referred to as Compound Class $SX_{2170}$).

A compound (L-1) wherein T represents a group represented by T35, $R^1$ represents $OCF_3$, and $R^{3b}$ represents any substituents indicated in [Table L4] to [Table L12] (hereinafter, referred to as Compound Class $SX_{2171}$).

A compound (L-1) wherein T represents a group represented by T35, $R^1$ represents $SCF_3$, and $R^{3b}$ represents any substituents indicated in [Table L4] to [Table L12] (hereinafter, referred to as Compound Class $SX_{2172}$).

A compound (L-1) wherein T represents a group represented by T35, $R^1$ represents $S(O)CF_3$, and $R^{3b}$ represents any substituents indicated in [Table L4] to [Table L12] (hereinafter, referred to as Compound Class $SX_{2173}$).

A compound (L-1) wherein T represents a group represented by T35, $R^1$ represents $S(O)_2CF_3$, and $R^{3b}$ represents any substituents indicated in [Table L4] to [Table L12] (hereinafter, referred to as Compound Class $SX_{2174}$).

A compound (L-1) wherein T represents a group represented by T35, $R^1$ represents a fluorine atom, and $R^{3b}$ represents any substituents indicated in [Table L4] to [Table L12] (hereinafter, referred to as Compound Class $SX_{2175}$).

A compound (L-1) wherein T represents a group represented by T35, $R^1$ represents a chlorine atom, and $R^{3b}$ represents any substituents indicated in [Table L4] to [Table L12] (hereinafter, referred to as Compound Class $SX_{2176}$).

A compound (L-1) wherein T represents a group represented by T35, $R^1$ represents a bromine atom, and $R^{3b}$ represents any substituents indicated in [Table L4] to [Table L12] (hereinafter, referred to as Compound Class $SX_{2177}$).

A compound (L-1) wherein T represents a group represented by T35, $R^1$ represents an iodine atom, and $R^{3b}$ represents any substituents indicated in [Table L4] to [Table L12] (hereinafter, referred to as Compound Class $SX_{2178}$).

A compound (L-1) wherein T represents a group represented by T36, $R^1$ represents $CF_3$, and $R^{3b}$ represents any substituents indicated in [Table L4] to [Table L12] (hereinafter, referred to as Compound Class $SX_{2179}$).

A compound (L-1) wherein T represents a group represented by T36, $R^1$ represents $C_2F_5$, and $R^{3b}$ represents any substituents indicated in [Table L4] to [Table L12] (hereinafter, referred to as Compound Class $SX_{2180}$).

A compound (L-1) wherein T represents a group represented by T36, $R^1$ represents $OCF_3$, and $R^{3b}$ represents any substituents indicated in [Table L4] to [Table L12] (hereinafter, referred to as Compound Class $SX_{2181}$).

A compound (L-1) wherein T represents a group represented by T36, $R^1$ represents $SCF_3$, and $R^{3b}$ represents any substituents indicated in [Table L4] to [Table L12] (hereinafter, referred to as Compound Class $SX_{2182}$).

A compound (L-1) wherein T represents a group represented by T36, $R^1$ represents $S(O)CF_3$, and $R^{3b}$ represents any substituents indicated in [Table L4] to [Table L12] (hereinafter, referred to as Compound Class $SX_{2183}$).

A compound (L-1) wherein T represents a group represented by T36, $R^1$ represents $S(O)_2CF_3$, and $R^{3b}$ represents any substituents indicated in [Table L4] to [Table L12] (hereinafter, referred to as Compound Class $SX_{2184}$).

A compound (L-1) wherein T represents a group represented by T36, $R^1$ represents a fluorine atom, and $R^{3b}$ represents any substituents indicated in [Table L4] to [Table L12] (hereinafter, referred to as Compound Class $SX_{2185}$).

A compound (L-1) wherein T represents a group represented by T36, $R^1$ represents a chlorine atom, and $R^{3b}$ represents any substituents indicated in [Table L4] to [Table L12] (hereinafter, referred to as Compound Class $SX_{2186}$).

A compound (L-1) wherein T represents a group represented by T36, $R^1$ represents a bromine atom, and $R^{3b}$ represents any substituents indicated in [Table L4] to [Table L12] (hereinafter, referred to as Compound Class $SX_{2187}$).

A compound (L-1) wherein T represents a group represented by T36, $R^1$ represents an iodine atom, and $R^{3b}$ represents any substituents indicated in [Table L4] to [Table L12] (hereinafter, referred to as Compound Class $SX_{2188}$).

A compound (L-2) wherein T represents a group represented by T32, $R^1$ represents $CF_3$, and $R^{3b}$ represents any substituents indicated in [Table L4] to [Table L12] (hereinafter, referred to as Compound Class $SX_{2189}$).

A compound (L-2) wherein T represents a group represented by T32, $R^1$ represents $C_2F_5$, and $R^{3b}$ represents any substituents indicated in [Table L4] to [Table L12] (hereinafter, referred to as Compound Class $SX_{2190}$).

A compound (L-2) wherein T represents a group represented by T32, $R^1$ represents $OCF_3$, and $R^{3b}$ represents any substituents indicated in [Table L4] to [Table L12] (hereinafter, referred to as Compound Class $SX_{2191}$).

A compound (L-2) wherein T represents a group represented by T32, $R^1$ represents $SCF_3$, and $R^{3b}$ represents any substituents indicated in [Table L4] to [Table L12] (hereinafter, referred to as Compound Class $SX_{2192}$).

A compound (L-2) wherein T represents a group represented by T32, $R^1$ represents $S(O)CF_3$, and $R^{3b}$ represents any substituents indicated in [Table L4] to [Table L12] (hereinafter, referred to as Compound Class $SX_{2193}$).

A compound (L-2) wherein T represents a group represented by T32, $R^1$ represents $S(O)_2CF_3$, and $R^{3b}$ represents any substituents indicated in [Table L4] to [Table L12] (hereinafter, referred to as Compound Class $SX_{2194}$).

A compound (L-2) wherein T represents a group represented by T32, $R^1$ represents a fluorine atom, and $R^{3b}$ represents any substituents indicated in [Table L4] to [Table L12] (hereinafter, referred to as Compound Class $SX_{2195}$).

A compound (L-2) wherein T represents a group represented by T32, $R^1$ represents a chlorine atom, and $R^{3b}$ represents any substituents indicated in [Table L4] to [Table L12] (hereinafter, referred to as Compound Class $SX_{2196}$).

A compound (L-2) wherein T represents a group represented by T32, $R^1$ represents a bromine atom, and $R^{3b}$ represents any substituents indicated in [Table L4] to [Table L12] (hereinafter, referred to as Compound Class $SX_{2197}$).

A compound (L-2) wherein T represents a group represented by T32, $R^1$ represents an iodine atom, and $R^{3b}$ represents any substituents indicated in [Table L4] to [Table L12] (hereinafter, referred to as Compound Class $SX_{2198}$).

A compound (L-2) wherein T represents a group represented by T33, $R^1$ represents $CF_3$, and $R^{3b}$ represents any substituents indicated in [Table L4] to [Table L12] (hereinafter, referred to as Compound Class $SX_{2199}$).

A compound (L-2) wherein T represents a group represented by T33, $R^1$ represents $C_2F_5$, and $R^{3b}$ represents any substituents indicated in [Table L4] to [Table L12] (hereinafter, referred to as Compound Class $SX_{2200}$).

A compound (L-2) wherein T represents a group represented by T33, $R^1$ represents $OCF_3$, and $R^{3b}$ represents any substituents indicated in [Table L4] to [Table L12] (hereinafter, referred to as Compound Class $SX_{2201}$).

A compound (L-2) wherein T represents a group represented by T33, $R^1$ represents $SCF_3$, and $R^{3b}$ represents any substituents indicated in [Table L4] to [Table L12] (hereinafter, referred to as Compound Class $SX_{2202}$).

A compound (L-2) wherein T represents a group represented by T33, $R^1$ represents $S(O)CF_3$, and $R^{3b}$ represents any substituents indicated in [Table L4] to [Table L12] (hereinafter, referred to as Compound Class $SX_{2203}$).

A compound (L-2) wherein T represents a group represented by T33, $R^1$ represents $S(O)_2CF_3$, and $R^{3b}$ represents any substituents indicated in [Table L4] to [Table L12] (hereinafter, referred to as Compound Class $SX_{2204}$).

A compound (L-2) wherein T represents a group represented by T33, $R^1$ represents a fluorine atom, and $R^{3b}$ represents any substituents indicated in [Table L4] to [Table L12] (hereinafter, referred to as Compound Class $SX_{2205}$).

A compound (L-2) wherein T represents a group represented by T33, $R^1$ represents a chlorine atom, and $R^{3b}$ represents any substituents indicated in [Table L4] to [Table L12] (hereinafter, referred to as Compound Class $SX_{2206}$).

A compound (L-2) wherein T represents a group represented by T33, $R^1$ represents a bromine atom, and $R^{3b}$ represents any substituents indicated in [Table L4] to [Table L12] (hereinafter, referred to as Compound Class $SX_{2207}$).

A compound (L-2) wherein T represents a group represented by T33, $R^1$ represents an iodine atom, and $R^{3b}$ represents any substituents indicated in [Table L4] to [Table L12] (hereinafter, referred to as Compound Class $SX_{2208}$).

A compound (L-2) wherein T represents a group represented by T34, $R^1$ represents $CF_3$, and $R^{3b}$ represents any substituents indicated in [Table L4] to [Table L12] (hereinafter, referred to as Compound Class $SX_{2209}$).

A compound (L-2) wherein T represents a group represented by T34, $R^1$ represents $C_2F_5$, and $R^{3b}$ represents any substituents indicated in [Table L4] to [Table L12] (hereinafter, referred to as Compound Class $SX_{2210}$).

A compound (L-2) wherein T represents a group represented by T34, $R^1$ represents $OCF_3$, and $R^{3b}$ represents any substituents indicated in [Table L4] to [Table L12] (hereinafter, referred to as Compound Class $SX_{2211}$).

A compound (L-2) wherein T represents a group represented by T34, $R^1$ represents $SCF_3$, and $R^{3b}$ represents any substituents indicated in [Table L4] to [Table L12] (hereinafter, referred to as Compound Class $SX_{2212}$).

A compound (L-2) wherein T represents a group represented by T34, $R^1$ represents $S(O)CF_3$, and $R^{3b}$ represents any substituents indicated in [Table L4] to [Table L12] (hereinafter, referred to as Compound Class $SX_{2213}$).

A compound (L-2) wherein T represents a group represented by T34, $R^1$ represents $S(O)_2CF_3$, and $R^{3b}$ represents any substituents indicated in [Table L4] to [Table L12] (hereinafter, referred to as Compound Class $SX_{2214}$).

A compound (L-2) wherein T represents a group represented by T34, $R^1$ represents a fluorine atom, and $R^{3b}$ represents any substituents indicated in [Table L4] to [Table L12] (hereinafter, referred to as Compound Class $SX_{2215}$).

A compound (L-2) wherein T represents a group represented by T34, $R^1$ represents a chlorine atom, and $R^{3b}$ represents any substituents indicated in [Table L4] to [Table L12] (hereinafter, referred to as Compound Class $SX_{2216}$).

A compound (L-2) wherein T represents a group represented by T34, $R^1$ represents a bromine atom, and $R^{3b}$ represents any substituents indicated in [Table L4] to [Table L12] (hereinafter, referred to as Compound Class $SX_{2217}$).

A compound (L-2) wherein T represents a group represented by T34, $R^1$ represents an iodine atom, and $R^{3b}$ represents any substituents indicated in [Table L4] to [Table L12] (hereinafter, referred to as Compound Class $SX_{2218}$).

A compound (L-2) wherein T represents a group represented by T35, $R^1$ represents $CF_3$, and $R^{3b}$ represents any substituents indicated in [Table L4] to [Table L12](hereinafter, referred to as Compound Class $SX_{2219}$).

A compound (L-2) wherein T represents a group represented by T35, $R^1$ represents $C_2F_5$, and $R^{3b}$ represents any substituents indicated in [Table L4] to [Table L12] (hereinafter, referred to as Compound Class $SX_{2220}$).

A compound (L-2) wherein T represents a group represented by T35, $R^1$ represents $OCF_3$, and $R^{3b}$ represents any substituents indicated in [Table L4] to [Table L12] (hereinafter, referred to as Compound Class $SX_{2221}$).

A compound (L-2) wherein T represents a group represented by T35, $R^1$ represents $SCF_3$, and $R^{3b}$ represents any substituents indicated in [Table L4] to [Table L12] (hereinafter, referred to as Compound Class $SX_{2222}$).

A compound (L-2) wherein T represents a group represented by T35, $R^1$ represents $S(O)CF_3$, and $R^{3b}$ represents any substituents indicated in [Table L4] to [Table L12] (hereinafter, referred to as Compound Class $SX_{2223}$).

A compound (L-2) wherein T represents a group represented by T35, $R^1$ represents $S(O)_2CF_3$, and $R^{3b}$ represents any substituents indicated in [Table L4] to [Table L12] (hereinafter, referred to as Compound Class $SX_{2224}$).

A compound (L-2) wherein T represents a group represented by T35, $R^1$ represents a fluorine atom, and $R^{3b}$ represents any substituents indicated in [Table L4] to [Table L12] (hereinafter, referred to as Compound Class $SX_{2225}$).

A compound (L-2) wherein T represents a group represented by T35, $R^1$ represents a chlorine atom, and $R^{3b}$ represents any substituents indicated in [Table L4] to [Table L12] (hereinafter, referred to as Compound Class $SX_{2226}$).

A compound (L-2) wherein T represents a group represented by T35, $R^1$ represents a bromine atom, and $R^{3b}$ represents any substituents indicated in [Table L4] to [Table L12] (hereinafter, referred to as Compound Class $SX_{2227}$).

A compound (L-2) wherein T represents a group represented by T36, $R^1$ represents an iodine atom, and $R^{3b}$ represents any substituents indicated in [Table L4] to [Table L12] (hereinafter, referred to as Compound Class $SX_{2228}$.

A compound (L-2) wherein T represents a group represented by T36, $R^1$ represents $CF_3$, and $R^{3b}$ represents any substituents indicated in [Table L4] to [Table L12] (hereinafter, referred to as Compound Class $SX_{2229}$).

A compound (L-2) wherein T represents a group represented by T36, $R^1$ represents $C_2F_5$, and $R^{3b}$ represents any substituents indicated in [Table L4] to [Table L12] (hereinafter, referred to as Compound Class $SX_{2230}$).

A compound (L-2) wherein T represents a group represented by T36, $R^1$ represents $OCF_3$, and $R^{3b}$ represents any substituents indicated in [Table L4] to [Table L12] (hereinafter, referred to as Compound Class $SX_{2231}$).

A compound (L-2) wherein T represents a group represented by T36, $R^1$ represents $SCF_3$, and $R^{3b}$ represents any substituents indicated in [Table L4] to [Table L12] (hereinafter, referred to as Compound Class $SX_{2232}$).

A compound (L-2) wherein T represents a group represented by T36, $R^1$ represents $S(O)CF_3$, and $R^{3b}$ represents any substituents indicated in [Table L4] to [Table L12] (hereinafter, referred to as Compound Class $SX_{2233}$).

A compound (L-2) wherein T represents a group represented by T36, $R^1$ represents $S(O)_2CF_3$, and $R^{3b}$ represents any substituents indicated in [Table L4] to [Table L12] (hereinafter, referred to as Compound Class $SX_{2234}$).

A compound (L-2) wherein T represents a group represented by T36, $R^1$ represents a fluorine atom, and $R^{3b}$ represents any substituents indicated in [Table L4] to [Table L12] (hereinafter, referred to as Compound Class $SX_{2235}$).

A compound (L-2) wherein T represents a group represented by T36, $R^1$ represents a chlorine atom, and $R^{3b}$ represents any substituents indicated in [Table L4] to [Table L12] (hereinafter, referred to as Compound Class $SX_{2236}$).

A compound (L-2) wherein T represents a group represented by T36, $R^1$ represents a bromine atom, and $R^{3b}$ represents any substituents indicated in [Table L4] to [Table L12] (hereinafter, referred to as Compound Class $SX_{2237}$).

A compound (L-2) wherein T represents a group represented by T36, $R^1$ represents an iodine atom, and $R^{3b}$ represents any substituents indicated in [Table L4] to [Table L12] (hereinafter, referred to as Compound Class $SX_{2238}$).

A compound (L-3) wherein T represents a group represented by T32, $R^1$ represents $CF_3$, and $R^{3b}$ represents any substituents indicated in [Table L4] to [Table L12] (hereinafter, referred to as Compound Class $SX_{2239}$).

A compound (L-3) wherein T represents a group represented by T32, $R^1$ represents $C_2F_5$, and $R^{3b}$ represents any substituents indicated in [Table L4] to [Table L12] (hereinafter, referred to as Compound Class $SX_{2240}$).

A compound (L-3) wherein T represents a group represented by T32, $R^1$ represents $OCF_3$, and $R^{3b}$ represents any substituents indicated in [Table L4] to [Table L12] (hereinafter, referred to as Compound Class $SX_{2241}$).

A compound (L-3) wherein T represents a group represented by T32, $R^1$ represents $SCF_3$, and $R^{3b}$ represents any substituents indicated in [Table L4] to [Table L12] (hereinafter, referred to as Compound Class $SX_{2242}$).

A compound (L-3) wherein T represents a group represented by T32, $R^1$ represents $S(O)CF_3$, and $R^{3b}$ represents any substituents indicated in [Table L4] to [Table L12] (hereinafter, referred to as Compound Class $SX_{2243}$).

A compound (L-3) wherein T represents a group represented by T32, $R^1$ represents $S(O)_2CF_3$, and $R^{3b}$ represents any substituents indicated in [Table L4] to [Table L12] (hereinafter, referred to as Compound Class $SX_{2244}$).

A compound (L-3) wherein T represents a group represented by T32, $R^1$ represents a fluorine atom, and $R^{3b}$ represents any substituents indicated in [Table L4] to [Table L12] (hereinafter, referred to as Compound Class $SX_{2245}$).

A compound (L-3) wherein T represents a group represented by T32, $R^1$ represents a chlorine atom, and $R^{3b}$ represents any substituents indicated in [Table L4] to [Table L12] (hereinafter, referred to as Compound Class $SX_{2246}$).

A compound (L-3) wherein T represents a group represented by T32, $R^1$ represents a bromine atom, and $R^{3b}$ represents any substituents indicated in [Table L4] to [Table L12] (hereinafter, referred to as Compound Class $SX_{2247}$).

A compound (L-3) wherein T represents a group represented by T32, $R^1$ represents an iodine atom, and $R^{3b}$ represents any substituents indicated in [Table L4] to [Table L12] (hereinafter, referred to as Compound Class $SX_{2248}$).

A compound (L-3) wherein T represents a group represented by T33, $R^1$ represents $CF_3$, and $R^{3b}$ represents any substituents indicated in [Table L4] to [Table L12] (hereinafter, referred to as Compound Class $SX_{2249}$).

A compound (L-3) wherein T represents a group represented by T33, $R^1$ represents $C_2F_5$, and $R^{3b}$ represents any substituents indicated in [Table L4] to [Table L12] (hereinafter, referred to as Compound Class $SX_{2250}$).

A compound (L-3) wherein T represents a group represented by T33, $R^1$ represents $OCF_3$, and $R^{3b}$ represents any substituents indicated in [Table L4] to [Table L12] (hereinafter, referred to as Compound Class $SX_{2251}$).

A compound (L-3) wherein T represents a group represented by T33, $R^1$ represents $SCF_3$, and $R^{3b}$ represents any substituents indicated in [Table L4] to [Table L12] (hereinafter, referred to as Compound Class $SX_{2252}$).

A compound (L-3) wherein T represents a group represented by T33, $R^1$ represents $S(O)CF_3$, and $R^{3b}$ represents any substituents indicated in [Table L4] to [Table L12] (hereinafter, referred to as Compound Class $SX_{2253}$).

A compound (L-3) wherein T represents a group represented by T33, $R^1$ represents $S(O)—CF_3$, and $R^{3b}$ represents any substituents indicated in [Table L4] to [Table L12] (hereinafter, referred to as Compound Class $SX_{2254}$).

A compound (L-3) wherein T represents a group represented by T33, $R^1$ represents a fluorine atom, and $R^{3b}$ represents any substituents indicated in [Table L4] to [Table L12] (hereinafter, referred to as Compound Class $SX_{2255}$).

A compound (L-3) wherein T represents a group represented by T33, $R^1$ represents a chlorine atom, and $R^{3b}$ represents any substituents indicated in [Table L4] to [Table L12] (hereinafter, referred to as Compound Class $SX_{2256}$).

A compound (L-3) wherein T represents a group represented by T33, $R^1$ represents a bromine atom, and $R^{2b}$ represents any substituents indicated in [Table L4] to [Table L12] (hereinafter, referred to as Compound Class $SX_{2257}$).

A compound (L-3) wherein T represents a group represented by T33, $R^1$ represents an iodine atom, and $R^{3b}$ represents any substituents indicated in [Table L4] to [Table L12] (hereinafter, referred to as Compound Class $SX_{2258}$).

A compound (L-3) wherein T represents a group represented by T34, $R^1$ represents $CF_3$, and $R^{3b}$ represents any substituents indicated in [Table L4] to [Table L12] (hereinafter, referred to as Compound Class $SX_{2259}$).

A compound (L-3) wherein T represents a group represented by T35, $R^1$ represents $C_2F_5$, and $R^{3b}$ represents any substituents indicated in [Table L4] to [Table L12] (hereinafter, referred to as Compound Class $SX_{2260}$).

A compound (L-3) wherein T represents a group represented by T34, $R^1$ represents $OCF_3$, and $R^{3b}$ represents any substituents indicated in [Table L4] to [Table L12] (hereinafter, referred to as Compound Class $SX_{2261}$).

A compound (L-3) wherein T represents a group represented by T34, $R^1$ represents $SCF_3$, and $R^{3b}$ represents any substituents indicated in [Table L4] to [Table L12] (hereinafter, referred to as Compound Class $SX_{2262}$).

A compound (L-3) wherein T represents a group represented by T34, $R^1$ represents $S(O)CF_3$, and $R^{3b}$ represents any substituents indicated in [Table L4] to [Table L12] (hereinafter, referred to as Compound Class $SX_{2263}$).

A compound (L-3) wherein T represents a group represented by T34, $R^1$ represents $S(O)_2CF_3$, and $R^{3b}$ represents any substituents indicated in [Table L4] to [Table L12] (hereinafter, referred to as Compound Class $SX_{2264}$).

A compound (L-3) wherein T represents a group represented by T34, $R^1$ represents a fluorine atom, and $R^{3b}$ represents any substituents indicated in [Table L4] to [Table L12] (hereinafter, referred to as Compound Class $SX_{2265}$).

A compound (L-3) wherein T represents a group represented by T34, $R^1$ represents a chlorine atom, and $R^{3b}$ represents any substituents indicated in [Table L4] to [Table L12] (hereinafter, referred to as Compound Class $SX_{2266}$).

A compound (L-3) wherein T represents a group represented by T34, $R^1$ represents a bromine atom, and $R^{3b}$ represents any substituents indicated in [Table L4] to [Table L12] (hereinafter, referred to as Compound Class $SX_{2267}$).

A compound (L-3) wherein T represents a group represented by T34, $R^1$ represents an iodine atom, and $R^{3b}$ represents any substituents indicated in [Table L4] to [Table L12] (hereinafter, referred to as Compound Class $SX_{2268}$).

A compound (L-3) wherein T represents a group represented by T35, $R^1$ represents $CF_3$, and $R^{3b}$ represents any substituents indicated in [Table L4] to [Table L12] (hereinafter, referred to as Compound Class $SX_{2269}$).

A compound (L-3) wherein T represents a group represented by T35, $R^1$ represents $C_2F_5$, and $R^{3b}$ represents any substituents indicated in [Table L4] to [Table L12] (hereinafter, referred to as Compound Class $SX_{2270}$).

A compound (L-3) wherein T represents a group represented by T35, $R^1$ represents $OCF_3$, and $R^{3b}$ represents any substituents indicated in [Table L4] to [Table L12] (hereinafter, referred to as Compound Class $SX_{2271}$).

A compound (L-3) wherein T represents a group represented by T35, $R^1$ represents $SCF_3$, and $R^{3b}$ represents any substituents indicated in [Table L4] to [Table L12] (hereinafter, referred to as Compound Class $SX_{2272}$).

A compound (L-3) wherein T represents a group represented by T35, $R^1$ represents $S(O)CF_3$, and $R^{3b}$ represents any substituents indicated in [Table L4] to [Table L12] (hereinafter, referred to as Compound Class $SX_{2273}$).

A compound (L-3) wherein T represents a group represented by T35, $R^1$ represents $S(O)_2CF_3$, and $R^{3b}$ represents any substituents indicated in [Table L4] to [Table L12] (hereinafter, referred to as Compound Class $SX_{2274}$).

A compound (L-3) wherein T represents a group represented by T35, $R^1$ represents a fluorine atom, and $R^{3b}$ represents any substituents indicated in [Table L4] to [Table L12] (hereinafter, referred to as Compound Class $SX_{2275}$).

A compound (L-3) wherein T represents a group represented by T35, $R^1$ represents a chlorine atom, and $R^{3b}$ represents any substituents indicated in [Table L4] to [Table L12] (hereinafter, referred to as Compound Class $SX_{2276}$).

A compound (L-3) wherein T represents a group represented by T35, $R^1$ represents a bromine atom, and $R^{3b}$ represents any substituents indicated in [Table L4] to [Table L12] (hereinafter, referred to as Compound Class $SX_{2277}$).

A compound (L-3) wherein T represents a group represented by T35, $R^1$ represents an iodine atom, and $R^{3b}$ represents any substituents indicated in [Table L4] to [Table L12] (hereinafter, referred to as Compound Class $SX_{2278}$).

A compound (L-3) wherein T represents a group represented by T36, $R^1$ represents $CF_3$, and $R^{3b}$ represents any substituents indicated in [Table L4] to [Table L12] (hereinafter, referred to as Compound Class $SX_{2279}$).

A compound (L-3) wherein T represents a group represented by T36, $R^1$ represents $C_2F_5$, and $R^{3b}$ represents any substituents indicated in [Table L4] to [Table L12] (hereinafter, referred to as Compound Class $SX_{2280}$).

A compound (L-3) wherein T represents a group represented by T36, $R^1$ represents $OCF_3$, and $R^{3b}$ represents any substituents indicated in [Table L4] to [Table L12] (hereinafter, referred to as Compound Class $SX_{2281}$).

A compound (L-3) wherein T represents a group represented by T36, $R^1$ represents $SCF_3$, and $R^{3b}$ represents any substituents indicated in [Table L4] to [Table L12] (hereinafter, referred to as Compound Class $SX_{2282}$).

A compound (L-3) wherein T represents a group represented by T36, $R^1$ represents $S(O)CF_3$, and $R^{3b}$ represents any substituents indicated in [Table L4] to [Table L12] (hereinafter, referred to as Compound Class $SX_{2283}$).

A compound (L-3) wherein T represents a group represented by T36, $R^1$ represents $S(O)_2CF_3$, and $R^{3b}$ represents any substituents indicated in [Table L4] to [Table L12] (hereinafter, referred to as Compound Class $SX_{2284}$).

A compound (L-3) wherein T represents a group represented by T36, $R^1$ represents a fluorine atom, and $R^{3b}$ represents any substituents indicated in [Table L4] to [Table L12] (hereinafter, referred to as Compound Class $SX_{2285}$).

A compound (L-3) wherein T represents a group represented by T36, $R^1$ represents a chlorine atom, and $R^{3b}$ represents any substituents indicated in [Table L4] to [Table L12] (hereinafter, referred to as Compound Class $SX_{2286}$).

A compound (L-3) wherein T represents a group represented by T36, $R^1$ represents a bromine atom, and $R^{3b}$ represents any substituents indicated in [Table L4] to [Table L12] (hereinafter, referred to as Compound Class $SX_{2287}$).

A compound (L-3) wherein T represents a group represented by T36, $R^1$ represents an iodine atom, and $R^{3b}$ represents any substituents indicated in [Table L4] to [Table L12] (hereinafter, referred to as Compound Class $SX_{2288}$).

A compound (L-4) wherein T represents a group represented by T32, $R^1$ represents $CF_3$, and $R^{3b}$ represents any substituents indicated in [Table L4] to [Table L12] (hereinafter, referred to as Compound Class $SX_{2289}$).

A compound (L-4) wherein T represents a group represented by T32, $R^1$ represents $C_2F_5$, and $R^{3b}$ represents any substituents indicated in [Table L4] to [Table L12] (hereinafter, referred to as Compound Class $SX_{2290}$).

A compound (L-4) wherein T represents a group represented by T32, $R^1$ represents $OCF_3$, and $R^{3b}$ represents any substituents indicated in [Table L4] to [Table L12] (hereinafter, referred to as Compound Class $SX_{2291}$).

A compound (L-4) wherein T represents a group represented by T32, $R^1$ represents $SCF_3$, and $R^{3b}$ represents any substituents indicated in [Table L4] to [Table L12] (hereinafter, referred to as Compound Class $SX_{2292}$).

A compound (L-4) wherein T represents a group represented by T32, $R^1$ represents $S(O)CF_3$, and $R^{3b}$ represents any substituents indicated in [Table L4] to [Table L12] (hereinafter, referred to as Compound Class $SX_{2293}$).

A compound (L-4) wherein T represents a group represented by T32, $R^1$ represents $S(O)_2CF_3$, and $R^{3b}$ represents any substituents indicated in [Table L4] to [Table L12] (hereinafter, referred to as Compound Class $SX_{2294}$).

A compound (L-4) wherein T represents a group represented by T32, $R^1$ represents a fluorine atom, and $R^{3b}$ represents any substituents indicated in [Table L4] to [Table L12] (hereinafter, referred to as Compound Class $SX_{2295}$).

A compound (L-4) wherein T represents a group represented by T32, $R^1$ represents a chlorine atom, and $R^{3b}$ represents any substituents indicated in [Table L4] to [Table L12] (hereinafter, referred to as Compound Class $SX_{2296}$).

A compound (L-4) wherein T represents a group represented by T32, $R^1$ represents a bromine atom, and $R^{3b}$ represents any substituents indicated in [Table L4] to [Table L12] (hereinafter, referred to as Compound Class $SX_{2297}$).

A compound (L-4) wherein T represents a group represented by T32, $R^1$ represents an iodine atom, and $R^{3b}$ represents any substituents indicated in [Table L4] to [Table L12] (hereinafter, referred to as Compound Class $SX_{2298}$).

A compound (L-4) wherein T represents a group represented by T33, $R^1$ represents $CF_3$, and $R^{3b}$, represents any substituents indicated in [Table L4] to [Table L12] (hereinafter, referred to as Compound Class $SX_{2299}$).

A compound (L-4) wherein T represents a group represented by T33, $R^1$ represents $C_2F_5$, and $R^{3b}$ represents any substituents indicated in [Table L4] to [Table L12] (hereinafter, referred to as Compound Class $SX_{2300}$).

A compound (L-4) wherein T represents a group represented by T33, $R^1$ represents $OCF_3$, and $R^{3b}$ represents any substituents indicated in [Table L4] to [Table L12] (hereinafter, referred to as Compound Class $SX_{2301}$).

A compound (L-4) wherein T represents a group represented by T33, $R^1$ represents $SCF_3$, and $R^{3b}$ represents any substituents indicated in [Table L4] to [Table L12] (hereinafter, referred to as Compound Class $SX_{2302}$).

A compound (L-4) wherein T represents a group represented by T33, $R^1$ represents $S(O)CF_3$, and $R^{3b}$ represents any substituents indicated in [Table L4] to [Table L12] (hereinafter, referred to as Compound Class $SX_{2303}$).

A compound (L-4) wherein T represents a group represented by T33, $R^1$ represents $S(O)_2CF_3$, and $R^{3b}$ represents any substituents indicated in [Table L4] to [Table L12] (hereinafter, referred to as Compound Class $SX_{2304}$).

A compound (L-4) wherein T represents a group represented by T33, $R^1$ represents a fluorine atom, and $R^{3b}$ represents any substituents indicated in [Table L4] to [Table L12] (hereinafter, referred to as Compound Class $SX_{2305}$).

A compound (L-4) wherein T represents a group represented by T33, $R^1$ represents a chlorine atom, and $R^{3b}$ represents any substituents indicated in [Table L4] to [Table L12] (hereinafter, referred to as Compound Class $SX_{2306}$).

A compound (L-4) wherein T represents a group represented by T33, $R^1$ represents a bromine atom, and $R^{3b}$ represents any substituents indicated in [Table L4] to [Table L12] (hereinafter, referred to as Compound Class $SX_{2307}$).

A compound (L-4) wherein T represents a group represented by T33, $R^1$ represents an iodine atom, and $R^{3b}$ represents any substituents indicated in [Table L4] to [Table L12] (hereinafter, referred to as Compound Class $SX_{2308}$).

A compound (L-4) wherein T represents a group represented by T34, $R^1$ represents $CF_3$, and $R^{3b}$ represents any substituents indicated in [Table L4] to [Table L12] (hereinafter, referred to as Compound Class $SX_{2309}$).

A compound (L-4) wherein T represents a group represented by T34, $R^1$ represents $C_2F_5$, and $R^{3b}$ represents any substituents indicated in [Table L4] to [Table L12] (hereinafter, referred to as Compound Class $SX_{2310}$).

A compound (L-4) wherein T represents a group represented by T34, $R^1$ represents $OCF_3$, and $R^{3b}$ represents any substituents indicated in [Table L4] to [Table L12] (hereinafter, referred to as Compound Class $SX_{2311}$).

A compound (L-4) wherein T represents a group represented by T34, $R^1$ represents $SCF_3$, and $R^{3b}$ represents any substituents indicated in [Table L4] to [Table L12] (hereinafter, referred to as Compound Class $SX_{2312}$).

A compound (L-4) wherein T represents a group represented by T34, $R^1$ represents $S(O)CF_3$, and $R^{3b}$ represents any substituents indicated in [Table L4] to [Table L12] (hereinafter, referred to as Compound Class $SX_{2313}$).

A compound (L-4) wherein T represents a group represented by T34, $R^1$ represents $S(O)_2CF_3$, and $R^{3b}$ represents any substituents indicated in [Table L4] to [Table L12] (hereinafter, referred to as Compound Class $SX_{2314}$).

A compound (L-4) wherein T represents a group represented by T34, $R^1$ represents a fluorine atom, and $R^{3b}$ represents any substituents indicated in [Table L4] to [Table L12] (hereinafter, referred to as Compound Class $SX_{2315}$).

A compound (L-4) wherein T represents a group represented by T34, $R^1$ represents a chlorine atom, and $R^{3b}$ represents any substituents indicated in [Table L4] to [Table L12] (hereinafter, referred to as Compound Class $SX_{2316}$).

A compound (L-4) wherein T represents a group represented by T34, $R^1$ represents a bromine atom, and $R^{3b}$ represents any substituents indicated in [Table L4] to [Table L12] (hereinafter, referred to as Compound Class $SX_{2317}$).

A compound (L-4) wherein T represents a group represented by T34, $R^1$ represents an iodine atom, and $R^{3b}$ represents any substituents indicated in [Table L4] to [Table L12] (hereinafter, referred to as Compound Class $SX_{2318}$).

A compound (L-4) wherein T represents a group represented by T35, $R^1$ represents $CF_3$, and $R^{3b}$ represents any substituents indicated in [Table L4] to [Table L12] (hereinafter, referred to as Compound Class $SX_{2319}$).

A compound (L-4) wherein T represents a group represented by T35, $R^1$ represents $C_2F_5$, and $R^{3b}$ represents any substituents indicated in [Table L4] to [Table L12] (hereinafter, referred to as Compound Class $SX_{2320}$).

A compound (L-4) wherein T represents a group represented by T35, $R^1$ represents $OCF_3$, and $R^{3b}$ represents any substituents indicated in [Table L4] to [Table L12] (hereinafter, referred to as Compound Class $SX_{2321}$).

A compound (L-4) wherein T represents a group represented by T35, $R^1$ represents $SCF_3$, and $R^{3b}$ represents any substituents indicated in [Table L4] to [Table L12] (hereinafter, referred to as Compound Class $SX_{2322}$).

A compound (L-4) wherein T represents a group represented by T35, $R^1$ represents $S(O)CF_3$, and $R^{3b}$ represents any substituents indicated in [Table L4] to [Table L12] (hereinafter, referred to as Compound Class $SX_{2323}$).

A compound (L-4) wherein T represents a group represented by T35, $R^1$ represents $S(O)_2CF_3$, and $R^{3b}$ represents any substituents indicated in [Table L4] to [Table L12] (hereinafter, referred to as Compound Class $SX_{2324}$).

A compound (L-4) wherein T represents a group represented by T35, $R^1$ represents a fluorine atom, and $R^{3b}$ represents any substituents indicated in [Table L4] to [Table L12] (hereinafter, referred to as Compound Class $SX_{2325}$).

A compound (L-4) wherein T represents a group represented by T35, $R^1$ represents a chlorine atom, and $R^{3b}$ represents any substituents indicated in [Table L4] to [Table L12] (hereinafter, referred to as Compound Class $SX_{2326}$).

A compound (L-4) wherein T represents a group represented by T35, $R^1$ represents a bromine atom, and $R^{3b}$ represents any substituents indicated in [Table L4] to [Table L12] (hereinafter, referred to as Compound Class $SX_{2327}$).

A compound (L-4) wherein T represents a group represented by T35, $R^1$ represents an iodine atom, and $R^{3b}$ represents any substituents indicated in [Table L4] to [Table L12] (hereinafter, referred to as Compound Class $SX_{2328}$).

A compound (L-4) wherein T represents a group represented by T36, $R^1$ represents $CF_3$, and $R^{3b}$ represents any substituents indicated in [Table L4] to [Table L12] (hereinafter, referred to as Compound Class $SX_{2329}$).

A compound (L-4) wherein T represents a group represented by T36, $R^1$ represents $C_2F_5$, and $R^{3b}$ represents any substituents indicated in [Table L4] to [Table L12] (hereinafter, referred to as Compound Class $SX_{2330}$).

A compound (L-4) wherein T represents a group represented by T36, $R^1$ represents $OCF_3$, and $R^{3b}$ represents any substituents indicated in [Table L4] to [Table L12](hereinafter, referred to as Compound Class $SX_{2331}$).

A compound (L-4) wherein T represents a group represented by T36, $R^1$ represents $SCF_3$, and $R^{3b}$ represents any substituents indicated in [Table L4] to [Table L12] (hereinafter, referred to as Compound Class $SX_{2332}$).

A compound (L-4) wherein T represents a group represented by T36, $R^1$ represents $S(O)CF_3$, and $R^{3b}$ represents any substituents indicated in [Table L4] to [Table L12] (hereinafter, referred to as Compound Class $SX_{2333}$).

A compound (L-4) wherein T represents a group represented by T36, $R^1$ represents $S(O)_2CF_3$, and $R^{3b}$ represents any substituents indicated in [Table L4] to [Table L12] (hereinafter, referred to as Compound Class $SX_{2334}$).

A compound (L-4) wherein T represents a group represented by T36, $R^1$ represents a fluorine atom, and $R^{3b}$ represents any substituents indicated in [Table L4] to [Table L12] (hereinafter, referred to as Compound Class $SX_{2335}$).

A compound (L-4) wherein T represents a group represented by T36, $R^1$ represents a chlorine atom, and $R^{3b}$ represents any substituents indicated in [Table L4] to [Table L12] (hereinafter, referred to as Compound Class $SX_{2336}$).

A compound (L-4) wherein T represents a group represented by T36, $R^1$ represents a bromine atom, and $R^{3b}$ represents any substituents indicated in [Table L4] to [Table L12] (hereinafter, referred to as Compound Class $SX_{2337}$).

A compound (L-4) wherein T represents a group represented by T36, $R^1$ represents an iodine atom, and $R^{3b}$ represents any substituents indicated in [Table L4] to [Table L12] (hereinafter, referred to as Compound Class $SX_{2338}$).

A compound (L-5) wherein T represents a group represented by T32, $R^1$ represents $CF_3$, and $R^{3b}$ represents any substituents indicated in [Table L4] to [Table L12] (hereinafter, referred to as Compound Class $SX_{2339}$).

A compound (L-5) wherein T represents a group represented by T32, $R^1$ represents $C_2F_5$, and $R^{3b}$ represents any substituents indicated in [Table L4] to [Table L12] (hereinafter, referred to as Compound Class $SX_{2340}$).

A compound (L-5) wherein T represents a group represented by T32, $R^1$ represents $OCF_3$, and $R^{3b}$ represents any substituents indicated in [Table L4] to [Table L12] (hereinafter, referred to as Compound Class $SX_{2341}$).

A compound (L-5) wherein T represents a group represented by T32, $R^1$ represents $SCF_3$, and $R^{3b}$ represents any substituents indicated in [Table L4] to [Table L12] (hereinafter, referred to as Compound Class $SX_{2342}$).

A compound (L-5) wherein T represents a group represented by T32, $R^1$ represents $S(O)CF_3$, and $R^{3b}$ represents any substituents indicated in [Table L4] to [Table L12] (hereinafter, referred to as Compound Class $SX_{2343}$).

A compound (L-5) wherein T represents a group represented by T32, $R^1$ represents $S(O)_2CF_3$, and $R^{3b}$ represents any substituents indicated in [Table L4] to [Table L12] (hereinafter, referred to as Compound Class $SX_{2344}$).

A compound (L-5) wherein T represents a group represented by T32, $R^1$ represents a fluorine atom, and $R^{3b}$ represents any substituents indicated in [Table L4] to [Table L12] (hereinafter, referred to as Compound Class $SX_{2345}$).

A compound (L-5) wherein T represents a group represented by T32, $R^1$ represents a chlorine atom, and $R^{3b}$ represents any substituents indicated in [Table L4] to [Table L12] (hereinafter, referred to as Compound Class $SX_{2346}$).

A compound (L-5) wherein T represents a group represented by T32, $R^1$ represents a bromine atom, and $R^{3b}$ represents any substituents indicated in [Table L4] to [Table L12] (hereinafter, referred to as Compound Class $SX_{2347}$).

A compound (L-5) wherein T represents a group represented by T32, $R^1$ represents an iodine atom, and $R^{3b}$ represents any substituents indicated in [Table L4] to [Table L12] (hereinafter, referred to as Compound Class $SX_{2348}$).

A compound (L-5) wherein T represents a group represented by T33, $R^1$ represents $CF_3$, and $R^{3b}$ represents any substituents indicated in [Table L4] to [Table L12] (hereinafter, referred to as Compound Class $SX_{2349}$).

A compound (L-5) wherein T represents a group represented by T33, $R^1$ represents $C_2F_5$, and $R^{3b}$ represents any substituents indicated in [Table L4] to [Table L12] (hereinafter, referred to as Compound Class $SX_{2350}$).

A compound (L-5) wherein T represents a group represented by T33, $R^1$ represents $OCF_3$, and $R^{3b}$ represents any substituents indicated in [Table L4] to [Table L12] (hereinafter, referred to as Compound Class $SX_{2351}$).

A compound (L-5) wherein T represents a group represented by T33, $R^1$ represents $SCF_3$, and $R^{3b}$ represents any substituents indicated in [Table L4] to [Table L12] (hereinafter, referred to as Compound Class $SX_{2352}$).

A compound (L-5) wherein T represents a group represented by T33, $R^1$ represents $S(O)CF_3$, and $R^{3b}$ represents any substituents indicated in [Table L4] to [Table L12] (hereinafter, referred to as Compound Class $SX_{2353}$).

A compound (L-5) wherein T represents a group represented by T33, $R^1$ represents $S(O)_2CF_3$, and $R^{3b}$ represents any substituents indicated in [Table L4] to [Table L12] (hereinafter, referred to as Compound Class $SX_{2354}$).

A compound (L-5) wherein T represents a group represented by T33, $R^1$ represents a fluorine atom, and $R^{3b}$ represents any substituents indicated in [Table L4] to [Table L12] (hereinafter, referred to as Compound Class $SX_{2355}$).

A compound (L-5) wherein T represents a group represented by T33, $R^1$ represents a chlorine atom, and $R^{3b}$ represents any substituents indicated in [Table L4] to [Table L12] (hereinafter, referred to as Compound Class $SX_{2356}$).

A compound (L-5) wherein T represents a group represented by T33, $R^1$ represents a bromine atom, and $R^{3b}$ represents any substituents indicated in [Table L4] to [Table L12] (hereinafter, referred to as Compound Class $SX_{2357}$).

A compound (L-5) wherein T represents a group represented by T33, $R^1$ represents an iodine atom, and $R^{3b}$ represents any substituents indicated in [Table L4] to [Table L12] (hereinafter, referred to as Compound Class $SX_{2358}$).

A compound (L-5) wherein T represents a group represented by T34, $R^1$ represents $CF_3$, and $R^{3b}$ represents any substituents indicated in [Table L4] to [Table L12] (hereinafter, referred to as Compound Class $SX_{2359}$).

A compound (L-5) wherein T represents a group represented by T34, $R^1$ represents $C_2F_5$, and $R^{3b}$ represents any substituents indicated in [Table L4] to [Table L12] (hereinafter, referred to as Compound Class $SX_{2360}$).

A compound (L-5) wherein T represents a group represented by T34, $R^1$ represents $OCF_3$, and $R^{3b}$ represents any substituents indicated in [Table L4] to [Table L12] (hereinafter, referred to as Compound Class $SX_{2361}$).

A compound (L-5) wherein T represents a group represented by T34, $R^1$ represents $SCF_3$, and $R^{3b}$ represents any substituents indicated in [Table L4] to [Table L12](hereinafter, referred to as Compound Class $SX_{2362}$).

A compound (L-5) wherein T represents a group represented by T34, $R^1$ represents $S(O)CF_3$, and $R^{3b}$ represents any substituents indicated in [Table L4] to [Table L12] (hereinafter, referred to as Compound Class $SX_{2363}$).

A compound (L-5) wherein T represents a group represented by T34, $R^1$ represents $S(O)_2CF_3$, and $R^{3b}$ represents any substituents indicated in [Table L4] to [Table L12] (hereinafter, referred to as Compound Class $SX_{2364}$).

A compound (L-5) wherein T represents a group represented by T34, $R^1$ represents a fluorine atom, and $R^{3b}$ represents any substituents indicated in [Table L4] to [Table L12] (hereinafter, referred to as Compound Class $SX_{2365}$).

A compound (L-5) wherein T represents a group represented by T34, $R^1$ represents a chlorine atom, and $R^{3b}$ represents any substituents indicated in [Table L4] to [Table L12] (hereinafter, referred to as Compound Class $SX_{2366}$).

A compound (L-5) wherein T represents a group represented by T34, $R^1$ represents a bromine atom, and $R^{3b}$ represents any substituents indicated in [Table L4] to [Table L12] (hereinafter, referred to as Compound Class $SX_{2367}$).

A compound (L-5) wherein T represents a group represented by T34, $R^1$ represents an iodine atom, and $R^{3b}$ represents any substituents indicated in [Table L4] to [Table L12] (hereinafter, referred to as Compound Class $SX_{2368}$).

A compound (L-5) wherein T represents a group represented by T35, $R^1$ represents $CF_3$, and $R^{3b}$ represents any substituents indicated in [Table L4] to [Table L12] (hereinafter, referred to as Compound Class $SX_{2369}$).

A compound (L-5) wherein T represents a group represented by T35, $R^1$ represents $C_2F_5$, and $R^{3b}$ represents any substituents indicated in [Table L4] to [Table L12] (hereinafter, referred to as Compound Class $SX_{2370}$).

A compound (L-5) wherein T represents a group represented by T35, $R^1$ represents $OCF_3$, and $R^{3b}$ represents any substituents indicated in [Table L4] to [Table L12] (hereinafter, referred to as Compound Class $SX_{2371}$).

A compound (L-5) wherein T represents a group represented by T35, $R^1$ represents $SCF_3$, and $R^{3b}$ represents any substituents indicated in [Table L4] to [Table L12] (hereinafter, referred to as Compound Class $SX_{2372}$).

A compound (L-5) wherein T represents a group represented by T35, $R^1$ represents $S(O)CF_3$, and $R^{3b}$ represents any substituents indicated in [Table L4] to [Table L12] (hereinafter, referred to as Compound Class $SX_{2373}$).

A compound (L-5) wherein T represents a group represented by T35, $R^1$ represents $S(O)_2CF_3$, and $R^{3b}$ represents any substituents indicated in [Table L4] to [Table L12] (hereinafter, referred to as Compound Class $SX_{2374}$).

A compound (L-5) wherein T represents a group represented by T35, $R^1$ represents a fluorine atom, and $R^{3b}$ represents any substituents indicated in [Table L4] to [Table L12] (hereinafter, referred to as Compound Class $SX_{2375}$).

A compound (L-5) wherein T represents a group represented by T35, $R^1$ represents a chlorine atom, and $R^{3b}$ represents any substituents indicated in [Table L4] to [Table L12] (hereinafter, referred to as Compound Class $SX_{2376}$).

A compound (L-5) wherein T represents a group represented by T35, $R^1$ represents a bromine atom, and $R^{3b}$ represents any substituents indicated in [Table L4] to [Table L12] (hereinafter, referred to as Compound Class $SX_{2377}$).

A compound (L-5) wherein T represents a group represented by T35, $R^1$ represents an iodine atom, and $R^{3b}$ represents any substituents indicated in [Table L4] to [Table L12] (hereinafter, referred to as Compound Class $SX_{2378}$).

A compound (L-5) wherein T represents a group represented by T36, $R^1$ represents $CF_3$, and $R^{3b}$ represents any substituents indicated in [Table L4] to [Table L12] (hereinafter, referred to as Compound Class $SX_{2379}$).

A compound (L-5) wherein T represents a group represented by T36, $R^1$ represents $C_2F_5$, and $R^{3b}$ represents any substituents indicated in [Table L4] to [Table L12] (hereinafter, referred to as Compound Class $SX_{2380}$).

A compound (L-5) wherein T represents a group represented by T36, $R^1$ represents $OCF_3$, and $R^{3b}$ represents any substituents indicated in [Table L4] to [Table L12] (hereinafter, referred to as Compound Class $SX_{2381}$).

A compound (L-5) wherein T represents a group represented by T36, $R^1$ represents $SCF_3$, and $R^{3b}$ represents any substituents indicated in [Table L4] to [Table L12] (hereinafter, referred to as Compound Class $SX_{2382}$).

A compound (L-5) wherein T represents a group represented by T36, $R^1$ represents $S(O)CF_3$, and $R^{3b}$ represents any substituents indicated in [Table L4] to [Table L12] (hereinafter, referred to as Compound Class $SX_{2383}$).

A compound (L-5) wherein T represents a group represented by T36, $R^1$ represents $S(O)_2CF_3$, and $R^{3b}$ represents any substituents indicated in [Table L4] to [Table L12] (hereinafter, referred to as Compound Class $SX_{2384}$).

A compound (L-5) wherein T represents a group represented by T36, $R^1$ represents a fluorine atom, and $R^{3b}$ represents any substituents indicated in [Table L4] to [Table L12] (hereinafter, referred to as Compound Class $SX_{2385}$).

A compound (L-5) wherein T represents a group represented by T34, $R^1$ represents a chlorine atom, and $R^{3b}$ represents any substituents indicated in [Table L4] to [Table L12] (hereinafter, referred to as Compound Class $SX_{2386}$).

A compound (L-5) wherein T represents a group represented by T36, $R^1$ represents a bromine atom, and $R^{3b}$ represents any substituents indicated in [Table L4] to [Table L12] (hereinafter, referred to as Compound Class $SX_{2387}$).

A compound (L-5) wherein T represents a group represented by T36, $R^1$ represents an iodine atom, and $R^{3b}$ represents any substituents indicated in [Table L4] to [Table L12] (hereinafter, referred to as Compound Class $SX_{2388}$).

A compound (L-6) wherein T represents a group represented by T32, $R^1$ represents $CF_3$, and $R^{3b}$ represents any substituents indicated in [Table L4] to [Table L12] (hereinafter, referred to as Compound Class $SX_{2389}$).

A compound (L-6) wherein T represents a group represented by T32, $R^1$ represents $C_2F_5$, and $R^{3b}$ represents any substituents indicated in [Table L4] to [Table L12] (hereinafter, referred to as Compound Class $SX_{2390}$).

A compound (L-6) wherein T represents a group represented by T32, $R^1$ represents $OCF_3$, and $R^{3b}$ represents any substituents indicated in [Table L4] to [Table L12] (hereinafter, referred to as Compound Class $SX_{2391}$).

A compound (L-6) wherein T represents a group represented by T32, $R^1$ represents $SCF_3$, and $R^{3b}$ represents any substituents indicated in [Table L4] to [Table L12] (hereinafter, referred to as Compound Class $SX_{2392}$).

A compound (L-6) wherein T represents a group represented by T32 $R^1$ represents $S(O)CF_3$, and $R^{3b}$ represents any substituents indicated in [Table L4] to [Table L12] (hereinafter, referred to as Compound Class $SX_{2393}$).

A compound (L-6) wherein T represents a group represented by T32, $R^1$ represents $S(O)_2CF_3$, and $R^{3b}$ represents any substituents indicated in [Table L4] to [Table L12] (hereinafter, referred to as Compound Class $SX_{2394}$).

A compound (L-6) wherein T represents a group represented by T32, $R^1$ represents a fluorine atom, and $R^{3b}$ represents any substituents indicated in [Table L4] to [Table L12] (hereinafter, referred to as Compound Class $SX_{2395}$).

A compound (L-6) wherein T represents a group represented by T32, $R^1$ represents a chlorine atom, and $R^{3b}$ represents any substituents indicated in [Table L4] to [Table L12] (hereinafter, referred to as Compound Class $SX_{2396}$).

A compound (L-6) wherein T represents a group represented by T32, $R^1$ represents a bromine atom, and $R^{3b}$ represents any substituents indicated in [Table L4] to [Table L12] (hereinafter, referred to as Compound Class $SX_{2397}$).

A compound (L-6) wherein T represents a group represented by T32, $R^1$ represents an iodine atom, and $R^{3b}$ represents any substituents indicated in [Table L4] to [Table L12] (hereinafter, referred to as Compound Class $SX_{2398}$).

A compound (L-6) wherein T represents a group represented by T33, $R^1$ represents $CF_3$, and $R^{3b}$ represents any substituents indicated in [Table L4] to [Table L12] (hereinafter, referred to as Compound Class $SX_{2399}$).

A compound (L-6) wherein T represents a group represented by T33, $R^1$ represents $C_2F_5$, and $R^{3b}$ represents any substituents indicated in [Table L4] to [Table L12] (hereinafter, referred to as Compound Class $SX_{2400}$).

A compound (L-6) wherein T represents a group represented by T33, $R^1$ represents $OCF_3$, and $R^{3b}$ represents any substituents indicated in [Table L4] to [Table L12] (hereinafter, referred to as Compound Class $SX_{2401}$).

A compound (L-6) wherein T represents a group represented by T33, $R^1$ represents $SCF_3$, and $R^{3b}$ represents any substituents indicated in [Table L4] to [Table L12] (hereinafter, referred to as Compound Class $SX_{2402}$).

A compound (L-6) wherein T represents a group represented by T33 $R^1$ represents $S(O)CF_3$, and $R^{3b}$ represents any substituents indicated in [Table L4] to [Table L12] (hereinafter, referred to as Compound Class $SX_{2403}$).

A compound (L-6) wherein T represents a group represented by T33, $R^1$ represents $S(O)_2CF_3$, and $R^{3b}$ represents any substituents indicated in [Table L4] to [Table L12] (hereinafter, referred to as Compound Class $SX_{2404}$).

A compound (L-6) wherein T represents a group represented by T33, $R^1$ represents a fluorine atom, and $R^{3b}$ represents any substituents indicated in [Table L4] to [Table L12] (hereinafter, referred to as Compound Class $SX_{2405}$).

A compound (L-6) wherein T represents a group represented by T33, $R^1$ represents a chlorine atom, and $R^{3b}$ represents any substituents indicated in [Table L4] to [Table L12] (hereinafter, referred to as Compound Class $SX_{2406}$).

A compound (L-6) wherein T represents a group represented by T33, $R^1$ represents a bromine atom, and $R^{3b}$ represents any substituents indicated in [Table L4] to [Table L12] (hereinafter, referred to as Compound Class $SX_{2407}$).

A compound (L-6) wherein T represents a group represented by T33, $R^1$ represents an iodine atom, and $R^{3b}$ represents any substituents indicated in [Table L4] to [Table L12] (hereinafter, referred to as Compound Class $SX_{2408}$).

A compound (L-6) wherein T represents a group represented by T34, $R^1$ represents $CF_3$, and $R^{3b}$ represents any substituents indicated in [Table L4] to [Table L12] (hereinafter, referred to as Compound Class $SX_{2409}$).

A compound (L-6) wherein T represents a group represented by T34, $R^1$ represents $C_2F_5$, and $R^{3b}$ represents any substituents indicated in [Table L4] to [Table L12] (hereinafter, referred to as Compound Class $SX_{2410}$).

A compound (L-6) wherein T represents a group represented by T34, $R^1$ represents $OCF_3$, and $R^{3b}$ represents any substituents indicated in [Table L4] to [Table L12] (hereinafter, referred to as Compound Class $SX_{2411}$).

A compound (L-6) wherein T represents a group represented by T34, $R^1$ represents $SCF_3$, and $R^{3b}$ represents any substituents indicated in [Table L4] to [Table L12] (hereinafter, referred to as Compound Class $SX_{2412}$).

A compound (L-6) wherein T represents a group represented by T34 $R^1$ represents $S(O)CF_3$, and $R^{3b}$ represents any substituents indicated in [Table L4] to [Table L12] (hereinafter, referred to as Compound Class $SX_{2413}$).

A compound (L-6) wherein T represents a group represented by T34, $R^1$ represents $S(O)_2CF_3$, and $R^{3b}$ represents any substituents indicated in [Table L4] to [Table L12] (hereinafter, referred to as Compound Class $SX_{2414}$).

A compound (L-6) wherein T represents a group represented by T34, $R^1$ represents a fluorine atom, and $R^{3b}$ represents any substituents indicated in [Table L4] to [Table L12] (hereinafter, referred to as Compound Class $SX_{2415}$).

A compound (L-6) wherein T represents a group represented by T34, $R^1$ represents a chlorine atom, and $R^{3b}$ represents any substituents indicated in [Table L4] to [Table L12] (hereinafter, referred to as Compound Class $SX_{2416}$).

A compound (L-6) wherein T represents a group represented by T34, $R^1$ represents a bromine atom, and $R^{3b}$ represents any substituents indicated in [Table L4] to [Table L12] (hereinafter, referred to as Compound Class $SX_{2417}$).

A compound (L-6) wherein T represents a group represented by T34, $R^1$ represents an iodine atom, and $R^{3b}$ represents any substituents indicated in [Table L1] to [Table L12] (hereinafter, referred to as Compound Class $SX_{2418}$).

A compound (L-6) wherein T represents a group represented by T35, $R^1$ represents $CF_3$, and $R^{3b}$ represents any substituents indicated in [Table L4] to [Table L12] (hereinafter, referred to as Compound Class $SX_{2419}$).

A compound (L-6) wherein T represents a group represented by T35, $R^1$ represents $C_2F_5$, and $R^{3b}$ represents any substituents indicated in [Table L4] to [Table L12] (hereinafter, referred to as Compound Class $SX_{2420}$).

A compound (L-6) wherein T represents a group represented by T35, $R^1$ represents $OCF_3$, and $R^{3b}$ represents any substituents indicated in [Table L4] to [Table L12] (hereinafter, referred to as Compound Class $SX_{2421}$).

A compound (L-6) wherein T represents a group represented by T35, $R^1$ represents $SCF_3$, and $R^{3b}$ represents any substituents indicated in [Table L4] to [Table L12] (hereinafter, referred to as Compound Class $SX_{2422}$).

A compound (L-6) wherein T represents a group represented by T35, $R^1$ represents $S(O)CF_3$, and $R^{3b}$ represents any substituents indicated in [Table L4] to [Table L12] (hereinafter, referred to as Compound Class $SX_{2423}$).

A compound (L-6) wherein T represents a group represented by T35, $R^1$ represents $S(O)_2CF_3$, and $R^{3b}$ represents any substituents indicated in [Table L4] to [Table L12] (hereinafter, referred to as Compound Class $SX_{2424}$).

A compound (L-6) wherein T represents a group represented by T35, $R^1$ represents a fluorine atom, and $R^{3b}$ represents any substituents indicated in [Table L4] to [Table L12] (hereinafter, referred to as Compound Class $SX_{2425}$).

A compound (L-6) wherein T represents a group represented by T35, $R^1$ represents a chlorine atom, and $R^{3b}$ represents any substituents indicated in [Table L4] to [Table L12] (hereinafter, referred to as Compound Class $SX_{2426}$).

A compound (L-6) wherein T represents a group represented by T35, $R^1$ represents a bromine atom, and $R^{3b}$ represents any substituents indicated in [Table L4] to [Table L12] (hereinafter, referred to as Compound Class $SX_{2427}$).

A compound (L-6) wherein T represents a group represented by T35, $R^1$ represents an iodine atom, and $R^{3b}$ represents any substituents indicated in [Table L4] to [Table L12] (hereinafter, referred to as Compound Class $SX_{2428}$).

A compound (L-6) wherein T represents a group represented by T36, $R^1$ represents $CF_3$, and $R^{3b}$ represents any substituents indicated in [Table L4] to [Table L12] (hereinafter, referred to as Compound Class $SX_{2429}$).

A compound (L-6) wherein T represents a group represented by T36, $R^1$ represents $C_2F_5$, and $R^{3b}$ represents any substituents indicated in [Table L4] to [Table L12] (hereinafter, referred to as Compound Class $SX_{2430}$).

A compound (L-6) wherein T represents a group represented by T36, $R^1$ represents $OCF_3$, and $R^{3b}$ represents any substituents indicated in [Table L4] to [Table L12] (hereinafter, referred to as Compound Class $SX_{2431}$).

A compound (L-6) wherein T represents a group represented by T36, $R^1$ represents $SCF_3$, and $R^{3b}$ represents any substituents indicated in [Table L4] to [Table L12] (hereinafter, referred to as Compound Class $SX_{2432}$).

A compound (L-6) wherein T represents a group represented by T36, $R^1$ represents $S(O)CF_3$, and $R^{3b}$ represents any substituents indicated in [Table L4] to [Table L12] (hereinafter, referred to as Compound Class $SX_{2433}$).

A compound (L-6) wherein T represents a group represented by T36, $R^1$ represents $S(O)_2CF_3$, and $R^{3b}$ represents any substituents indicated in [Table L4] to [Table L12] (hereinafter, referred to as Compound Class $SX_{2434}$).

A compound (L-6) wherein T represents a group represented by T36, $R^1$ represents a fluorine atom, and $R^{3b}$ represents any substituents indicated in [Table L4] to [Table L12] (hereinafter, referred to as Compound Class $SX_{2435}$).

A compound (L-6) wherein T represents a group represented by T36, $R^1$ represents a chlorine atom, and $R^{3b}$ represents any substituents indicated in [Table L4] to [Table L12] (hereinafter, referred to as Compound Class $SX_{2436}$).

A compound (L-6) wherein T represents a group represented by T36, $R^1$ represents a bromine atom, and $R^{3b}$ represents any substituents indicated in [Table L4] to [Table L12] (hereinafter, referred to as Compound Class $SX_{2437}$).

A compound (L-6) wherein T represents a group represented by T36, $R^1$ represents an iodine atom, and $R^{3b}$ represents any substituents indicated in [Table L4] to [Table L12] (hereinafter, referred to as Compound Class $SX_{2438}$).

A compound (L-1) wherein T represents a group represented by T1, $R^1$ represents $OCF_3$, and $R^{3b}$ represents any substituents indicated in [Table L4] to [Table L12] (hereinafter, referred to as Compound Class $SX_{2439}$).

A compound (L-1) wherein T represents a group represented by T1, $R^1$ represents a fluorine atom, and $R^{3b}$ represents any substituents indicated in [Table L4] to [Table L12] (hereinafter, referred to as Compound Class $SX_{2440}$).

A compound (L-1) wherein T represents a group represented by T1, $R^1$ represents a chlorine atom, and $R^{3b}$ represents any substituents indicated in [Table L4] to [Table L12] (hereinafter, referred to as Compound Class $SX_{2441}$).

A compound (L-1) wherein T represents a group represented by T1, $R^1$ represents a bromine atom, and $R^{3b}$ represents any substituents indicated in [Table L4] to [Table L12] (hereinafter, referred to as Compound Class $SX_{2442}$).

A compound (L-1) wherein T represents a group represented by T1, $R^1$ represents an iodine atom, and $R^{3b}$ represents any substituents indicated in [Table L4] to [Table L12] (hereinafter, referred to as Compound Class $SX_{2443}$).

A compound (L-1) wherein T represents a group represented by T2, $R^1$ represents $OCF_3$, and $R^{3b}$ represents any substituents indicated in [Table L4] to [Table L12] (hereinafter, referred to as Compound Class $SX_{2444}$).

A compound (L-1) wherein T represents a group represented by T2, $R^1$ represents a fluorine atom, and $R^{3b}$ represents any substituents indicated in [Table L4] to [Table L12] (hereinafter, referred to as Compound Class $SX_{2445}$).

A compound (L-1) wherein T represents a group represented by T2, $R^1$ represents a chlorine atom, and $R^{3b}$ represents any substituents indicated in [Table L4] to [Table L12] (hereinafter, referred to as Compound Class $SX_{2446}$).

A compound (L-1) wherein T represents a group represented by T2, $R^1$ represents a bromine atom, and $R^{3b}$ represents any substituents indicated in [Table L4] to [Table L12] (hereinafter, referred to as Compound Class $SX_{2447}$).

A compound (L-1) wherein T represents a group represented by T2, $R^1$ represents an iodine atom, and $R^{3b}$ represents any substituents indicated in [Table L4] to [Table L12] (hereinafter, referred to as Compound Class $SX_{2448}$).

A compound (L-1) wherein T represents a group represented by T3, $R^1$ represents $OCF_3$, and $R^{3b}$ represents any substituents indicated in [Table L4] to [Table L12] (hereinafter, referred to as Compound Class $SX_{2449}$).

A compound (L-1) wherein T represents a group represented by T3, $R^1$ represents a fluorine atom, and $R^{3b}$ represents any substituents indicated in [Table L4] to [Table L12] (hereinafter, referred to as Compound Class $SX_{2450}$).

A compound (L-1) wherein T represents a group represented by T3, $R^1$ represents a chlorine atom, and $R^{3b}$ represents any substituents indicated in [Table L4] to [Table L12] (hereinafter, referred to as Compound Class $SX_{2451}$).

A compound (L-1) wherein T represents a group represented by T3, $R^1$ represents a bromine atom, and $R^{3b}$ represents any substituents indicated in [Table L4] to [Table L12] (hereinafter, referred to as Compound Class $SX_{2452}$).

A compound (L-1) wherein T represents a group represented by T3, $R^1$ represents an iodine atom, and $R^{3b}$ represents any substituents indicated in [Table L4] to [Table L12] (hereinafter, referred to as Compound Class $SX_{2453}$).

A compound (L-1) wherein T represents a group represented by T6, $R^1$ represents $OCF_3$, and $R^{3b}$ represents any substituents indicated in [Table L4] to [Table L12] (hereinafter, referred to as Compound Class $SX_{2454}$).

A compound (L-1) wherein T represents a group represented by T6, $R^1$ represents a fluorine atom, and $R^{3b}$ represents any substituents indicated in [Table L4] to [Table L12] (hereinafter, referred to as Compound Class $SX_{2455}$).

A compound (L-1) wherein T represents a group represented by T6, $R^1$ represents a chlorine atom, and $R^{3b}$ represents any substituents indicated in [Table L4] to [Table L12] (hereinafter, referred to as Compound Class $SX_{2456}$).

A compound (L-1) wherein T represents a group represented by T6, $R^1$ represents a bromine atom, and $R^{3b}$ represents any substituents indicated in [Table L4] to [Table L12] (hereinafter, referred to as Compound Class $SX_{2457}$).

A compound (L-1) wherein T represents a group represented by T6, $R^1$ represents an iodine atom, and $R^{3b}$ represents any substituents indicated in [Table L4] to [Table L12] (hereinafter, referred to as Compound Class $SX_{2458}$).

A compound (L-1) wherein T represents a group represented by T7, $R^1$ represents $OCF_3$, and $R^{3b}$ represents any substituents indicated in [Table L4] to [Table L12] (hereinafter, referred to as Compound Class $SX_{2459}$).

A compound (L-1) wherein T represents a group represented by T7, $R^1$ represents a fluorine atom, and $R^{3b}$ represents any substituents indicated in [Table L4] to [Table L12] (hereinafter, referred to as Compound Class $SX_{2460}$).

A compound (L-1) wherein T represents a group represented by T7, $R^1$ represents a chlorine atom, and $R^{3b}$ represents any substituents indicated in [Table L4] to [Table L12] (hereinafter, referred to as Compound Class $SX_{2461}$).

A compound (L-1) wherein T represents a group represented by T7, $R^1$ represents a bromine atom, and $R^{3b}$ represents any substituents indicated in [Table L4] to [Table L12] (hereinafter, referred to as Compound Class $SX_{2462}$).

A compound (L-1) wherein T represents a group represented by T7, $R^1$ represents an iodine atom, and $R^{3b}$ represents any substituents indicated in [Table L4] to [Table L12] (hereinafter, referred to as Compound Class $SX_{2463}$).

A compound (L-1) wherein T represents a group represented by T8, $R^1$ represents $OCF_3$, and $R^{3b}$ represents any substituents indicated in [Table L4] to [Table L12] (hereinafter, referred to as Compound Class $SX_{2464}$).

A compound (L-1) wherein T represents a group represented by T8, $R^1$ represents a fluorine atom, and $R^{3b}$ represents any substituents indicated in [Table L4] to [Table L12] (hereinafter, referred to as Compound Class $SX_{2465}$).

A compound (L-1) wherein T represents a group represented by T8, $R^1$ represents a chlorine atom, and $R^{3b}$ represents any substituents indicated in [Table L4] to [Table L12] (hereinafter, referred to as Compound Class $SX_{2466}$).

A compound (L-1) wherein T represents a group represented by T8, $R^1$ represents a bromine atom, and $R^{3b}$ represents any substituents indicated in [Table L4] to [Table L12] (hereinafter, referred to as Compound Class $SX_{2467}$).

A compound (L-1) wherein T represents a group represented by T8, $R^1$ represents an iodine atom, and $R^{3b}$ represents any substituents indicated in [Table L4] to [Table L12] (hereinafter, referred to as Compound Class $SX_{2468}$).

A compound (L-1) wherein T represents a group represented by T11, $R^1$ represents $OCF_3$, and $R^{3b}$ represents any substituents indicated in [Table L4] to [Table L12] (hereinafter, referred to as Compound Class $SX_{2469}$).

A compound (L-1) wherein T represents a group represented by T11, $R^1$ represents a fluorine atom, and $R^{3b}$ represents any substituents indicated in [Table L4] to [Table L12] (hereinafter, referred to as Compound Class $SX_{2470}$).

A compound (L-1) wherein T represents a group represented by T11, $R^1$ represents a chlorine atom, and $R^{3b}$ represents any substituents indicated in [Table L4] to [Table L12] (hereinafter, referred to as Compound Class $SX_{2471}$).

A compound (L-1) wherein T represents a group represented by T11, $R^1$ represents a bromine atom, and $R^{3b}$ represents any substituents indicated in [Table L4] to [Table L12] (hereinafter, referred to as Compound Class $SX_{2472}$).

A compound (L-1) wherein T represents a group represented by T11, $R^1$ represents an iodine atom, and $R^{3b}$ represents any substituents indicated in [Table L4] to [Table L12] (hereinafter, referred to as Compound Class $SX_{2473}$).

A compound (L-1) wherein T represents a group represented by T12, $R^1$ represents $OCF_3$, and $R^{3b}$ represents any substituents indicated in [Table L4] to [Table L12] (hereinafter, referred to as Compound Class $SX_{2474}$).

A compound (L-1) wherein T represents a group represented by T11, $R^1$ represents a fluorine atom, and $R^{3b}$ represents any substituents indicated in [Table L4] to [Table L12] (hereinafter, referred to as Compound Class $SX_{2475}$).

A compound (L-1) wherein T represents a group represented by T11, $R^1$ represents a chlorine atom, and $R^{3b}$ represents any substituents indicated in [Table L4] to [Table L12] (hereinafter, referred to as Compound Class $SX_{2476}$).

A compound (L-1) wherein T represents a group represented by T11, $R^1$ represents a bromine atom, and $R^{3b}$ represents any substituents indicated in [Table L4] to [Table L12] (hereinafter, referred to as Compound Class $SX_{2477}$).

A compound (L-1) wherein T represents a group represented by T11, $R^1$ represents an iodine atom, and $R^{3b}$ represents any substituents indicated in [Table L4] to [Table L12] (hereinafter, referred to as Compound Class $SX_{2478}$).

A compound (L-1) wherein T represents a group represented by T13, $R^1$ represents $OCF_3$, and $R^{3b}$ represents any substituents indicated in [Table L4] to [Table L12] (hereinafter, referred to as Compound Class $SX_{2479}$).

A compound (L-1) wherein T represents a group represented by T13, $R^1$ represents a fluorine atom, and $R^{3b}$ represents any substituents indicated in [Table L1] to [Table L12] (hereinafter, referred to as Compound Class $SX_{2480}$).

A compound (L-1) wherein T represents a group represented by T13, $R^1$ represents a chlorine atom, and $R^{3b}$ represents any substituents indicated in [Table L4] to [Table L12] (hereinafter, referred to as Compound Class $SX_{2481}$).

A compound (L-1) wherein T represents a group represented by T13, $R^1$ represents a bromine atom, and $R^{3b}$ represents any substituents indicated in [Table L4] to [Table L12] (hereinafter, referred to as Compound Class $SX_{2482}$).

A compound (L-1) wherein T represents a group represented by T13, $R^1$ represents an iodine atom, and $R^{3b}$ represents any substituents indicated in [Table L4] to [Table L12] (hereinafter, referred to as Compound Class $SX_{2483}$).

A compound (L-2) wherein T represents a group represented by T1, $R^1$ represents $OCF_3$, and $R^{3b}$ represents any substituents indicated in [Table L4] to [Table L12] (hereinafter, referred to as Compound Class $SX_{2484}$).

A compound (L-2) wherein T represents a group represented by T1, $R^1$ represents a fluorine atom, and $R^{3b}$ represents any substituents indicated in [Table L4] to [Table L12] (hereinafter, referred to as Compound Class $SX_{2485}$).

A compound (L-2) wherein T represents a group represented by T1, $R^1$ represents a chlorine atom, and $R^{3b}$ represents any substituents indicated in [Table L4] to [Table L12] (hereinafter, referred to as Compound Class $SX_{2486}$).

A compound (L-2) wherein T represents a group represented by T1, $R^1$ represents a bromine atom, and $R^{3b}$ represents any substituents indicated in [Table L4] to [Table L12] (hereinafter, referred to as Compound Class $SX_{2487}$).

A compound (L-2) wherein T represents a group represented by T1, $R^1$ represents an iodine atom, and $R^{3b}$ represents any substituents indicated in [Table L4] to [Table L12] (hereinafter, referred to as Compound Class $SX_{2487}$).

A compound (L-2) wherein T represents a group represented by T2, $R^1$ represents $OCF_3$, and $R^{3b}$ represents any substituents indicated in [Table L4] to [Table L12] (hereinafter, referred to as Compound Class $SX_{2489}$).

A compound (L-2) wherein T represents a group represented by T2, $R^1$ represents a fluorine atom, and $R^{3b}$ represents any substituents indicated in [Table L4] to [Table L12] (hereinafter, referred to as Compound Class $SX_{2490}$).

A compound (L-2) wherein T represents a group represented by T2, $R^1$ represents a chlorine atom, and $R^{3b}$ represents any substituents indicated in [Table L4] to [Table L12] (hereinafter, referred to as Compound Class $SX_{2491}$).

A compound (L-2) wherein T represents a group represented by T2, $R^1$ represents a bromine atom, and $R^{3b}$ represents any substituents indicated in [Table L4] to [Table L12] (hereinafter, referred to as Compound Class $SX_{2492}$).

A compound (L-2) wherein T represents a group represented by T2, $R^1$ represents an iodine atom, and $R^{3b}$ represents any substituents indicated in [Table L4] to [Table L12] (hereinafter, referred to as Compound Class $SX_{2493}$).

A compound (L-2) wherein T represents a group represented by T3, $R^1$ represents $OCF_3$, and $R^{3b}$ represents any substituents indicated in [Table L4] to [Table L12] (hereinafter, referred to as Compound Class $SX_{2494}$).

A compound (L-2) wherein T represents a group represented by T3, $R^1$ represents a fluorine atom, and $R^{3b}$ represents any substituents indicated in [Table L4] to [Table L12] (hereinafter, referred to as Compound Class $SX_{2495}$).

A compound (L-2) wherein T represents a group represented by T3, $R^1$ represents a chlorine atom, and $R^{3b}$ represents any substituents indicated in [Table L4] to [Table L12] (hereinafter, referred to as Compound Class $SX_{2496}$).

A compound (L-2) wherein T represents a group represented by T3, $R^1$ represents a bromine atom, and $R^{3b}$ represents any substituents indicated in [Table L4] to [Table L12] (hereinafter, referred to as Compound Class $SX_{2497}$).

A compound (L-2) wherein T represents a group represented by T3, $R^1$ represents an iodine atom, and $R^{3b}$ represents any substituents indicated in [Table L4] to [Table L12] (hereinafter, referred to as Compound Class $SX_{2498}$).

A compound (L-2) wherein T represents a group represented by T6, $R^1$ represents $OCF_3$, and $R^{3b}$ represents any substituents indicated in [Table L4] to [Table L12] (hereinafter, referred to as Compound Class $SX_{2499}$).

A compound (L-2) wherein T represents a group represented by T6, $R^1$ represents a fluorine atom, and $R^{3b}$ represents any substituents indicated in [Table L4] to [Table L12] (hereinafter, referred to as Compound Class $SX_{2500}$).

A compound (L-2) wherein T represents a group represented by T6, $R^1$ represents a chlorine atom, and $R^{3b}$ represents any substituents indicated in [Table L4] to [Table L12] (hereinafter, referred to as Compound Class $SX_{2501}$).

A compound (L-2) wherein T represents a group represented by T6, $R^1$ represents a bromine atom, and $R^{3b}$ represents any substituents indicated in [Table L4] to [Table L12] (hereinafter, referred to as Compound Class $SX_{2502}$).

A compound (L-2) wherein T represents a group represented by T6, $R^1$ represents an iodine atom, and $R^{3b}$ represents any substituents indicated in [Table L4] to [Table L12] (hereinafter, referred to as Compound Class $SX_{2503}$).

A compound (L-2) wherein T represents a group represented by T7, $R^1$ represents $OCF_3$, and $R^{3b}$ represents any substituents indicated in [Table L4] to [Table L12] (hereinafter, referred to as Compound Class $SX_{2504}$).

A compound (L-2) wherein T represents a group represented by T7, $R^1$ represents a fluorine atom, and $R^{3b}$ represents any substituents indicated in [Table L4] to [Table L12] (hereinafter, referred to as Compound Class $SX_{2505}$).

A compound (L-2) wherein T represents a group represented by T7, $R^1$ represents a chlorine atom, and $R^{3b}$ represents any substituents indicated in [Table L4] to [Table L12] (hereinafter, referred to as Compound Class $SX_{2506}$).

A compound (L-2) wherein T represents a group represented by T7, $R^1$ represents a bromine atom, and $R^{3b}$ represents any substituents indicated in [Table L4] to [Table L12] (hereinafter, referred to as Compound Class $SX_{2507}$).

A compound (L-2) wherein T represents a group represented by T7, $R^1$ represents an iodine atom, and $R^{3b}$ represents any substituents indicated in [Table L4] to [Table L12] (hereinafter, referred to as Compound Class $SX_{2508}$).

A compound (L-2) wherein T represents a group represented by T8, $R^1$ represents $OCF_3$, and $R^{3b}$ represents any substituents indicated in [Table L4] to [Table L12] (hereinafter, referred to as Compound Class $SX_{2509}$).

A compound (L-2) wherein T represents a group represented by T8, $R^1$ represents a fluorine atom, and $R^{3b}$ represents any substituents indicated in [Table L4] to [Table L12] (hereinafter, referred to as Compound Class $SX_{2510}$).

A compound (L-2) wherein T represents a group represented by T8, $R^1$ represents a chlorine atom, and $R^{3b}$ represents any substituents indicated in [Table L4] to [Table L12] (hereinafter, referred to as Compound Class $SX_{2511}$).

A compound (L-2) wherein T represents a group represented by T8, $R^1$ represents a bromine atom, and $R^{3b}$ represents any substituents indicated in [Table L4] to [Table L12] (hereinafter, referred to as Compound Class $SX_{2512}$).

A compound (L-2) wherein T represents a group represented by T8, $R^1$ represents an iodine atom, and $R^{3b}$ represents any substituents indicated in [Table L4] to [Table L12] (hereinafter, referred to as Compound Class $SX_{2513}$).

A compound (L-2) wherein T represents a group represented by T11, $R^1$ represents $OCF_3$, and $R^{3b}$ represents any substituents indicated in [Table L4] to [Table L12] (hereinafter, referred to as Compound Class $SX_{2514}$).

A compound (L-2) wherein T represents a group represented by T11, $R^1$ represents a fluorine atom, and $R^{3b}$ represents any substituents indicated in [Table L4] to [Table L12] (hereinafter, referred to as Compound Class $SX_{2515}$).

A compound (L-2) wherein T represents a group represented by T11, $R^1$ represents a chlorine atom, and $R^{3b}$ represents any substituents indicated in [Table L4] to [Table L12] (hereinafter, referred to as Compound Class $SX_{2516}$).

A compound (L-2) wherein T represents a group represented by T11, $R^1$ represents a bromine atom, and $R^{3b}$ represents any substituents indicated in [Table L4] to [Table L12] (hereinafter, referred to as Compound Class $SX_{2517}$).

A compound (L-2) wherein T represents a group represented by T11, $R^1$ represents an iodine atom, and $R^{3b}$ represents any substituents indicated in [Table L4] to [Table L12] (hereinafter, referred to as Compound Class $SX_{2518}$).

A compound (L-2) wherein T represents a group represented by T12, $R^1$ represents $OCF_3$, and $R^{3b}$ represents any substituents indicated in [Table L4] to [Table L12] (hereinafter, referred to as Compound Class $SX_{2519}$).

A compound (L-2) wherein T represents a group represented by T12, $R^1$ represents a fluorine atom, and $R^{3b}$ represents any substituents indicated in [Table L4] to [Table L12] (hereinafter, referred to as Compound Class $SX_{2520}$).

A compound (L-2) wherein T represents a group represented by T12, $R^1$ represents a chlorine atom, and $R^{3b}$ represents any substituents indicated in [Table L4] to [Table L12] (hereinafter, referred to as Compound Class $SX_{2521}$).

A compound (L-2) wherein T represents a group represented by T12, $R^1$ represents a bromine atom, and $R^{3b}$ represents any substituents indicated in [Table L4] to [Table L12] (hereinafter, referred to as Compound Class $SX_{2522}$).

A compound (L-2) wherein T represents a group represented by T12, $R^1$ represents an iodine atom, and $R^{3b}$ represents any substituents indicated in [Table L4] to [Table L12] (hereinafter, referred to as Compound Class $SX_{2523}$).

A compound (L-2) wherein T represents a group represented by T13, $R^1$ represents $OCF_3$, and $R^{3b}$ represents any substituents indicated in [Table L4] to [Table L12] (hereinafter, referred to as Compound Class $SX_{2524}$).

A compound (L-2) wherein T represents a group represented by T13, $R^1$ represents a fluorine atom, and $R^{3b}$ represents any substituents indicated in [Table L4] to [Table L12] (hereinafter, referred to as Compound Class $SX_{2525}$).

A compound (L-2) wherein T represents a group represented by T13, $R^1$ represents a chlorine atom, and $R^{3b}$ represents any substituents indicated in [Table L4] to [Table L12] (hereinafter, referred to as Compound Class $SX_{2526}$).

A compound (L-2) wherein T represents a group represented by T13, $R^1$ represents a bromine atom, and $R^{3b}$ represents any substituents indicated in [Table L4] to [Table L12] (hereinafter, referred to as Compound Class $SX_{2527}$).

A compound (L-2) wherein T represents a group represented by T13, $R^1$ represents an iodine atom, and $R^{3b}$ represents any substituents indicated in [Table L4] to [Table L12] (hereinafter, referred to as Compound Class $SX_{2528}$).

A compound (L-3) wherein T represents a group represented by T1, $R^1$ represents $OCF_3$, and $R^{3b}$ represents any substituents indicated in [Table L4] to [Table L12] (hereinafter, referred to as Compound Class $SX_{2529}$).

A compound (L-3) wherein T represents a group represented by T1, $R^1$ represents a fluorine atom, and $R^{3b}$ represents any substituents indicated in [Table L4] to [Table L12] (hereinafter, referred to as Compound Class $SX_{2530}$).

A compound (L-3) wherein T represents a group represented by T1, $R^1$ represents a chlorine atom, and $R^{3b}$ represents any substituents indicated in [Table L4] to [Table L12] (hereinafter, referred to as Compound Class $SX_{2531}$).

A compound (L-3) wherein T represents a group represented by T1, $R^1$ represents a bromine atom, and $R^{3b}$ represents any substituents indicated in [Table L4] to [Table L12] (hereinafter, referred to as Compound Class $SX_{2532}$).

A compound (L-3) wherein T represents a group represented by T1, $R^1$ represents an iodine atom, and $R^{3b}$ represents any substituents indicated in [Table L4] to [Table L12] (hereinafter, referred to as Compound Class $SX_{2533}$).

A compound (L-3) wherein T represents a group represented by T2, $R^1$ represents $OCF_3$, and $R^{3b}$ represents any substituents indicated in [Table L4] to [Table L12] (hereinafter, referred to as Compound Class $SX_{2534}$).

A compound (L-3) wherein T represents a group represented by T2, $R^1$ represents a fluorine atom, and $R^{3b}$ represents any substituents indicated in [Table L4] to [Table L12] (hereinafter, referred to as Compound Class $SX_{2535}$).

A compound (L-3) wherein T represents a group represented by T2, $R^1$ represents a chlorine atom, and $R^{3b}$ represents any substituents indicated in [Table L4] to [Table L12] (hereinafter, referred to as Compound Class $SX_{2536}$).

A compound (L-3) wherein T represents a group represented by T2, $R^1$ represents a bromine atom, and $R^{3b}$ represents any substituents indicated in [Table L4] to [Table L12] (hereinafter, referred to as Compound Class $SX_{2537}$).

A compound (L-3) wherein T represents a group represented by T2, $R^1$ represents an iodine atom, and $R^{3b}$ represents any substituents indicated in [Table L4] to [Table L12] (hereinafter, referred to as Compound Class $SX_{2538}$).

A compound (L-3) wherein T represents a group represented by T3, $R^1$ represents $OCF_3$, and $R^{3b}$ represents any substituents indicated in [Table L4] to [Table L12] (hereinafter, referred to as Compound Class $SX_{2539}$).

A compound (L-3) wherein T represents a group represented by T3, $R^1$ represents a fluorine atom, and $R^{3b}$ represents any substituents indicated in [Table L4] to [Table L12] (hereinafter, referred to as Compound Class $SX_{2540}$).

A compound (L-3) wherein T represents a group represented by T3, $R^1$ represents a chlorine atom, and $R^{3b}$ represents any substituents indicated in [Table L4] to [Table L12] (hereinafter, referred to as Compound Class $SX_{2541}$).

A compound (L-3) wherein T represents a group represented by T3, $R^1$ represents a bromine atom, and $R^{3b}$ represents any substituents indicated in [Table L4] to [Table L12] (hereinafter, referred to as Compound Class $SX_{2542}$).

A compound (L-3) wherein T represents a group represented by T3, $R^1$ represents an iodine atom, and $R^{3b}$ represents any substituents indicated in [Table L4] to [Table L12] (hereinafter, referred to as Compound Class $SX_{2543}$).

A compound (L-3) wherein T represents a group represented by T6, $R^1$ represents $OCF_3$, and $R^{3b}$ represents any substituents indicated in [Table L4] to [Table L12] (hereinafter, referred to as Compound Class $SX_{2544}$).

A compound (L-3) wherein T represents a group represented by T6, $R^1$ represents a fluorine atom, and $R^{3b}$ represents any substituents indicated in [Table L4] to [Table L12] (hereinafter, referred to as Compound Class $SX_{2545}$).

A compound (L-3) wherein T represents a group represented by T6, $R^1$ represents a chlorine atom, and $R^{3b}$ represents any substituents indicated in [Table L4] to [Table L12] (hereinafter, referred to as Compound Class $SX_{2546}$).

A compound (L-3) wherein T represents a group represented by T6, $R^1$ represents a bromine atom, and $R^{3b}$ represents any substituents indicated in [Table L4] to [Table L12] (hereinafter, referred to as Compound Class $SX_{2547}$).

A compound (L-3) wherein T represents a group represented by T6, $R^1$ represents an iodine atom, and $R^{3b}$ represents any substituents indicated in [Table L4] to [Table L12] (hereinafter, referred to as Compound Class $SX_{2548}$).

A compound (L-3) wherein T represents a group represented by T7, $R^1$ represents $OCF_3$, and $R^{3b}$ represents any substituents indicated in [Table L4] to [Table L12] (hereinafter, referred to as Compound Class $SX_{2549}$).

A compound (L-3) wherein T represents a group represented by T7, $R^1$ represents a fluorine atom, and $R^{3b}$ represents any substituents indicated in [Table L4] to [Table L12] (hereinafter, referred to as Compound Class $SX_{2550}$).

A compound (L-3) wherein T represents a group represented by T7, $R^1$ represents a chlorine atom, and $R^{3b}$ represents any substituents indicated in [Table L4] to [Table L12] (hereinafter, referred to as Compound Class $SX_{2551}$).

A compound (L-3) wherein T represents a group represented by T7, $R^1$ represents a bromine atom, and $R^{3b}$ represents any substituents indicated in [Table L4] to [Table L12] (hereinafter, referred to as Compound Class $SX_{2552}$).

A compound (L-3) wherein T represents a group represented by T7, $R^1$ represents an iodine atom, and $R^{3b}$ represents any substituents indicated in [Table L4] to [Table L12] (hereinafter, referred to as Compound Class $SX_{2553}$).

A compound (L-3) wherein T represents a group represented by T8, $R^1$ represents $OCF_3$, and $R^{3b}$ represents any substituents indicated in [Table L4] to [Table L12] (hereinafter, referred to as Compound Class $SX_{2554}$).

A compound (L-3) wherein T represents a group represented by T8, $R^1$ represents a fluorine atom, and $R^{3b}$ represents any substituents indicated in [Table L4] to [Table L12] (hereinafter, referred to as Compound Class $SX_{2555}$).

A compound (L-3) wherein T represents a group represented by T8, $R^1$ represents a chlorine atom, and $R^{3b}$ represents any substituents indicated in [Table L4] to [Table L12] (hereinafter, referred to as Compound Class $SX_{2556}$).

A compound (L-3) wherein T represents a group represented by T8, $R^1$ represents a bromine atom, and $R^{3b}$ represents any substituents indicated in [Table L4] to [Table L12] (hereinafter, referred to as Compound Class $SX_{2557}$).

A compound (L-3) wherein T represents a group represented by T8, $R^1$ represents an iodine atom, and $R^{3b}$ represents any substituents indicated in [Table L4] to [Table L12] (hereinafter, referred to as Compound Class $SX_{2558}$).

A compound (L-3) wherein T represents a group represented by T11, $R^1$ represents $OCF_3$, and $R^{3b}$ represents any substituents indicated in [Table L4] to [Table L12] (hereinafter, referred to as Compound Class $SX_{2559}$).

A compound (L-3) wherein T represents a group represented by T11, $R^1$ represents a fluorine atom, and $R^{3b}$ represents any substituents indicated in [Table L4] to [Table L12] (hereinafter, referred to as Compound Class $SX_{2560}$).

A compound (L-3) wherein T represents a group represented by T11, $R^1$ represents a chlorine atom, and $R^{3b}$ represents any substituents indicated in [Table L4] to [Table L12] (hereinafter, referred to as Compound Class $SX_{2561}$).

A compound (L-3) wherein T represents a group represented by T11, $R^1$ represents a bromine atom, and $R^{3b}$ represents any substituents indicated in [Table L4] to [Table L12] (hereinafter, referred to as Compound Class $SX_{2562}$).

A compound (L-3) wherein T represents a group represented by T11, $R^1$ represents an iodine atom, and $R^{3b}$ represents any substituents indicated in [Table L4] to [Table L12] (hereinafter, referred to as Compound Class $SX_{2563}$).

A compound (L-3) wherein T represents a group represented by T12, $R^1$ represents $OCF_3$, and $R^{3b}$ represents any substituents indicated in [Table L4] to [Table L12] (hereinafter, referred to as Compound Class $SX_{2564}$).

A compound (L-3) wherein T represents a group represented by T12, $R^1$ represents a fluorine atom, and $R^{3b}$ represents any substituents indicated in [Table L4] to [Table L12] (hereinafter, referred to as Compound Class $SX_{2565}$).

A compound (L-3) wherein T represents a group represented by T12, $R^1$ represents a chlorine atom, and $R^{3b}$ represents any substituents indicated in [Table L4] to [Table L12] (hereinafter, referred to as Compound Class $SX_{2566}$).

A compound (L-3) wherein T represents a group represented by T12, $R^1$ represents a bromine atom, and $R^{3b}$ represents any substituents indicated in [Table L4] to [Table L12] (hereinafter, referred to as Compound Class $SX_{2567}$).

A compound (L-3) wherein T represents a group represented by T12, $R^1$ represents an iodine atom, and $R^{3b}$ represents any substituents indicated in [Table L4] to [Table L12] (hereinafter, referred to as Compound Class $SX_{2568}$).

A compound (L-3) wherein T represents a group represented by T13, $R^1$ represents $OCF_3$, and $R^{3b}$ represents any substituents indicated in [Table L4] to [Table L12] (hereinafter, referred to as Compound Class $SX_{2569}$).

A compound (L-3) wherein T represents a group represented by T13, $R^1$ represents a fluorine atom, and $R^{3b}$ represents any substituents indicated in [Table L4] to [Table L12] (hereinafter, referred to as Compound Class $SX_{2570}$).

A compound (L-3) wherein T represents a group represented by T13, $R^1$ represents a chlorine atom, and $R^{3b}$ represents any substituents indicated in [Table L4] to [Table L12] (hereinafter, referred to as Compound Class $SX_{2571}$).

A compound (L-3) wherein T represents a group represented by T13, $R^1$ represents a bromine atom, and $R^{3b}$ represents any substituents indicated in [Table L4] to [Table L12] (hereinafter, referred to as Compound Class $SX_{2572}$).

A compound (L-3) wherein T represents a group represented by T13, $R^1$ represents an iodine atom, and $R^{3b}$ represents any substituents indicated in [Table L4] to [Table L12] (hereinafter, referred to as Compound Class $SX_{2573}$.

A compound (L-4) wherein T represents a group represented by T1, $R^1$ represents $OCF_3$, and $R^{3b}$ represents any substituents indicated in [Table L4] to [Table L12] (hereinafter, referred to as Compound Class $SX_{2574}$).

A compound (L-4) wherein T represents a group represented by T1, $R^1$ represents a fluorine atom, and $R^{3b}$ represents any substituents indicated in [Table L4] to [Table L12] (hereinafter, referred to as Compound Class $SX_{2575}$).

A compound (L-4) wherein T represents a group represented by T1, $R^1$ represents a chlorine atom, and $R^{3b}$ represents any substituents indicated in [Table L4] to [Table L12] (hereinafter, referred to as Compound Class $SX_{2576}$).

A compound (L-4) wherein T represents a group represented by T1, $R^1$ represents a bromine atom, and $R^{3b}$ represents any substituents indicated in [Table L4] to [Table L12] (hereinafter, referred to as Compound Class $SX_{2577}$).

A compound (L-4) wherein T represents a group represented by T1, $R^1$ represents an iodine atom, and $R^{3b}$ represents any substituents indicated in [Table L4] to [Table L12] (hereinafter, referred to as Compound Class $SX_{2578}$).

A compound (L-4) wherein T represents a group represented by T2, $R^1$ represents $OCF_3$, and $R^{3b}$ represents any substituents indicated in [Table L4] to [Table L12] (hereinafter, referred to as Compound Class $SX_{2579}$).

A compound (L-4) wherein T represents a group represented by T2, $R^1$ represents a fluorine atom, and $R^{3b}$ represents any substituents indicated in [Table L4] to [Table L12] (hereinafter, referred to as Compound Class $SX_{2580}$).

A compound (L-4) wherein T represents a group represented by T2, $R^1$ represents a chlorine atom, and $R^{3b}$ represents any substituents indicated in [Table L4] to [Table L12] (hereinafter, referred to as Compound Class $SX_{2581}$).

A compound (L-4) wherein T represents a group represented by T2, $R^1$ represents a bromine atom, and $R^{3b}$ represents any substituents indicated in [Table L4] to [Table L12] (hereinafter, referred to as Compound Class $SX_{2582}$).

A compound (L-4) wherein T represents a group represented by T2, $R^1$ represents an iodine atom, and $R^{3b}$ represents any substituents indicated in [Table L4] to [Table L12] (hereinafter, referred to as Compound Class $SX_{2583}$).

A compound (L-4) wherein T represents a group represented by T3, $R^1$ represents $OCF_3$, and $R^{3b}$ represents any substituents indicated in [Table L4] to [Table L12] (hereinafter, referred to as Compound Class $SX_{2584}$).

A compound (L-4) wherein T represents a group represented by T3, $R^1$ represents a fluorine atom, and $R^{3b}$ represents any substituents indicated in [Table L4] to [Table L12] (hereinafter, referred to as Compound Class $SX_{2585}$).

A compound (L-4) wherein T represents a group represented by T3, $R^1$ represents a chlorine atom, and $R^{3b}$ represents any substituents indicated in [Table L4] to [Table L12] (hereinafter, referred to as Compound Class $SX_{2586}$).

A compound (L-4) wherein T represents a group represented by T3, $R^1$ represents a bromine atom, and $R^{3b}$ represents any substituents indicated in [Table L4] to [Table L12] (hereinafter, referred to as Compound Class $SX_{2587}$).

A compound (L-4) wherein T represents a group represented by T3, $R^1$ represents an iodine atom, and $R^{3b}$ represents any substituents indicated in [Table L4] to [Table L12] (hereinafter, referred to as Compound Class $SX_{2588}$).

A compound (L-4) wherein T represents a group represented by T6, $R^1$ represents $OCF_3$, and $R^{3b}$ represents any substituents indicated in [Table L4] to [Table L12] (hereinafter, referred to as Compound Class $SX_{2589}$).

A compound (L-4) wherein T represents a group represented by T6, $R^1$ represents a fluorine atom, and $R^{3b}$ represents any substituents indicated in [Table L4] to [Table L12] (hereinafter, referred to as Compound Class $SX_{2590}$).

A compound (L-4) wherein T represents a group represented by T6, $R^1$ represents a chlorine atom, and $R^{3b}$ represents any substituents indicated in [Table L4] to [Table L12] (hereinafter, referred to as Compound Class $SX_{2591}$).

A compound (L-4) wherein T represents a group represented by T6, $R^1$ represents a bromine atom, and $R^{3b}$ represents any substituents indicated in [Table L4] to [Table L12] (hereinafter, referred to as Compound Class $SX_{2592}$).

A compound (L-4) wherein T represents a group represented by T6, $R^1$ represents an iodine atom, and $R^{3b}$ represents any substituents indicated in [Table L4] to [Table L12] (hereinafter, referred to as Compound Class $SX_{2593}$).

A compound (L-4) wherein T represents a group represented by T7, $R^1$ represents $OCF_3$, and $R^{3b}$ represents any substituents indicated in [Table L4] to [Table L12] (hereinafter, referred to as Compound Class $SX_{2594}$).

A compound (L-4) wherein T represents a group represented by T7, $R^1$ represents a fluorine atom, and $R^{3b}$ represents any substituents indicated in [Table L4] to [Table L12] (hereinafter, referred to as Compound Class $SX_{2595}$).

A compound (L-4) wherein T represents a group represented by T7, $R^1$ represents a chlorine atom, and $R^{3b}$ represents any substituents indicated in [Table L4] to [Table L12] (hereinafter, referred to as Compound Class $SX_{2596}$).

A compound (L-4) wherein T represents a group represented by T7, $R^1$ represents a bromine atom, and $R^{3b}$ represents any substituents indicated in [Table L4] to [Table L12] (hereinafter, referred to as Compound Class $SX_{2597}$).

A compound (L-4) wherein T represents a group represented by T7, $R^1$ represents an iodine atom, and $R^{3b}$ represents any substituents indicated in [Table L4] to [Table L12] (hereinafter, referred to as Compound Class $SX_{2598}$).

A compound (L-4) wherein T represents a group represented by T8, $R^1$ represents $OCF_3$, and $R^{3b}$ represents any substituents indicated in [Table L4] to [Table L12] (hereinafter, referred to as Compound Class $SX_{2599}$).

A compound (L-4) wherein T represents a group represented by T8, $R^1$ represents a fluorine atom, and $R^{3b}$ represents any substituents indicated in [Table L4] to [Table L12] (hereinafter, referred to as Compound Class $SX_{2600}$).

A compound (L-4) wherein T represents a group represented by T8, $R^1$ represents a chlorine atom, and $R^{3b}$ represents any substituents indicated in [Table L4] to [Table L12] (hereinafter, referred to as Compound Class $SX_{2601}$).

A compound (L-4) wherein T represents a group represented by T8, $R^1$ represents a bromine atom, and $R^{3b}$ represents any substituents indicated in [Table L4] to [Table L12] (hereinafter, referred to as Compound Class $SX_{2602}$).

A compound (L-4) wherein T represents a group represented by T8, $R^1$ represents an iodine atom, and $R^{3b}$ represents any substituents indicated in [Table L4] to [Table L12] (hereinafter, referred to as Compound Class $SX_{2603}$).

A compound (L-4) wherein T represents a group represented by T11, $R^1$ represents $OCF_3$, and $R^{3b}$ represents any substituents indicated in [Table L4] to [Table L12] (hereinafter, referred to as Compound Class $SX_{2604}$).

A compound (L-4) wherein T represents a group represented by T11, $R^1$ represents a fluorine atom, and $R^{3b}$ represents any substituents indicated in [Table L4] to [Table L12] (hereinafter, referred to as Compound Class $SX_{2605}$).

A compound (L-4) wherein T represents a group represented by T11, $R^1$ represents a chlorine atom, and $R^{3b}$ represents any substituents indicated in [Table L4] to [Table L12] (hereinafter, referred to as Compound Class $SX_{2606}$).

A compound (L-4) wherein T represents a group represented by T11, $R^1$ represents a bromine atom, and $R^{3b}$ represents any substituents indicated in [Table L4] to [Table L12] (hereinafter, referred to as Compound Class $SX_{2607}$).

A compound (L-4) wherein T represents a group represented by T11, $R^1$ represents an iodine atom, and $R^{3b}$ represents any substituents indicated in [Table L4] to [Table L12] (hereinafter, referred to as Compound Class $SX_{2608}$).

A compound (L-4) wherein T represents a group represented by T12, $R^1$ represents $OCF_3$, and $R^{3b}$ represents any substituents indicated in [Table L4] to [Table L12] (hereinafter, referred to as Compound Class $SX_{2609}$).

A compound (L-4) wherein T represents a group represented by T12, $R^1$ represents a fluorine atom, and $R^{3b}$ represents any substituents indicated in [Table L4] to [Table L12] (hereinafter, referred to as Compound Class $SX_{2610}$).

A compound (L-4) wherein T represents a group represented by T12, $R^1$ represents a chlorine atom, and $R^{3b}$ represents any substituents indicated in [Table L4] to [Table L12] (hereinafter, referred to as Compound Class $SX_{2611}$).

A compound (L-4) wherein T represents a group represented by T12, $R^1$ represents a bromine atom, and $R^{3b}$ represents any substituents indicated in [Table L4] to [Table L12] (hereinafter, referred to as Compound Class $SX_{2612}$).

A compound (L-4) wherein T represents a group represented by T12, $R^1$ represents an iodine atom, and $R^{3b}$ represents any substituents indicated in [Table L4] to [Table L12] (hereinafter, referred to as Compound Class $SX_{2613}$).

A compound (L-4) wherein T represents a group represented by T13, $R^1$ represents $OCF_3$, and $R^{3b}$ represents any substituents indicated in [Table L4] to [Table L12] (hereinafter, referred to as Compound Class $SX_{2614}$).

A compound (L-4) wherein T represents a group represented by T13, $R^1$ represents a fluorine atom, and $R^{3b}$ represents any substituents indicated in [Table L4] to [Table L12] (hereinafter, referred to as Compound Class $SX_{2615}$).

A compound (L-4) wherein T represents a group represented by T13, $R^1$ represents a chlorine atom, and $R^{3b}$ represents any substituents indicated in [Table L4] to [Table L12] (hereinafter, referred to as Compound Class $SX_{2616}$).

A compound (L-4) wherein T represents a group represented by T13, $R^1$ represents a bromine atom, and $R^{3b}$ represents any substituents indicated in [Table L4] to [Table L12] (hereinafter, referred to as Compound Class $SX_{2617}$).

A compound (L-4) wherein T represents a group represented by T13, $R^1$ represents an iodine atom, and $R^{3b}$ represents any substituents indicated in [Table L4] to [Table L12] (hereinafter, referred to as Compound Class $SX_{2618}$).

A compound (L-5) wherein T represents a group represented by T1, $R^1$ represents $OCF_3$, and $R^{3b}$ represents any substituents indicated in [Table L4] to [Table L12] (hereinafter, referred to as Compound Class $SX_{2619}$).

A compound (L-5) wherein T represents a group represented by T1, $R^1$ represents a fluorine atom, and $R^{3b}$ represents any substituents indicated in [Table L4] to [Table L12] (hereinafter, referred to as Compound Class $SX_{2620}$).

A compound (L-5) wherein T represents a group represented by T1, $R^1$ represents a chlorine atom, and $R^{3b}$ represents any substituents indicated in [Table L4] to [Table L12] (hereinafter, referred to as Compound Class $SX_{2621}$).

A compound (L-5) wherein T represents a group represented by T1, $R^1$ represents a bromine atom, and $R^{3b}$ represents any substituents indicated in [Table L4] to [Table L12] (hereinafter, referred to as Compound Class $SX_{2622}$).

A compound (L-5) wherein T represents a group represented by T1, $R^1$ represents an iodine atom, and $R^{3b}$ represents any substituents indicated in [Table L4] to [Table L12] (hereinafter, referred to as Compound Class $SX_{2623}$).

A compound (L-5) wherein T represents a group represented by T2, $R^1$ represents $OCF_3$, and $R^{3b}$ represents any substituents indicated in [Table L4] to [Table L12] (hereinafter, referred to as Compound Class $SX_{2624}$).

A compound (L-5) wherein T represents a group represented by T2, $R^1$ represents a fluorine atom, and $R^{3b}$ represents any substituents indicated in [Table L4] to [Table L12] (hereinafter, referred to as Compound Class $SX_{2625}$).

A compound (L-5) wherein T represents a group represented by T2, $R^1$ represents a chlorine atom, and $R^{3b}$ represents any substituents indicated in [Table L4] to [Table L12] (hereinafter, referred to as Compound Class $SX_{2626}$).

A compound (L-5) wherein T represents a group represented by T2, $R^1$ represents a bromine atom, and $R^{3b}$ represents any substituents indicated in [Table L4] to [Table L12] (hereinafter, referred to as Compound Class $SX_{2627}$).

A compound (L-5) wherein T represents a group represented by T2, $R^1$ represents an iodine atom, and $R^{3b}$ represents any substituents indicated in [Table L4] to [Table L12] (hereinafter, referred to as Compound Class $SX_{2628}$).

A compound (L-5) wherein T represents a group represented by T3, $R^1$ represents $OCF_3$, and $R^{3b}$ represents any substituents indicated in [Table L4] to [Table L12] (hereinafter, referred to as Compound Class $SX_{2629}$).

A compound (L-5) wherein T represents a group represented by T3, $R^1$ represents a fluorine atom, and $R^{3b}$ represents any substituents indicated in [Table L4] to [Table L12] (hereinafter, referred to as Compound Class $SX_{2630}$).

A compound (L-5) wherein T represents a group represented by T3, $R^1$ represents a chlorine atom, and $R^{3b}$ represents any substituents indicated in [Table L4] to [Table L12] (hereinafter, referred to as Compound Class $SX_{2631}$).

A compound (L-5) wherein T represents a group represented by T3, $R^1$ represents a bromine atom, and $R^{3b}$ represents any substituents indicated in [Table L4] to [Table L12] (hereinafter, referred to as Compound Class $SX_{2632}$).

A compound (L-5) wherein T represents a group represented by T3, $R^1$ represents an iodine atom, and $R^{3b}$ represents any substituents indicated in [Table L4] to [Table L12] (hereinafter, referred to as Compound Class $SX_{2633}$).

A compound (L-5) wherein T represents a group represented by T6, $R^1$ represents $OCF_3$, and $R^{3b}$ represents any substituents indicated in [Table L4] to [Table L12] (hereinafter, referred to as Compound Class $SX_{2634}$).

A compound (L-5) wherein T represents a group represented by T6, $R^1$ represents a fluorine atom, and $R^{3b}$ represents any substituents indicated in [Table L4] to [Table L12] (hereinafter, referred to as Compound Class $SX_{2635}$).

A compound (L-5) wherein T represents a group represented by T6, $R^1$ represents a chlorine atom, and $R^{3b}$ represents any substituents indicated in [Table L4] to [Table L12] (hereinafter, referred to as Compound Class $SX_{2636}$).

A compound (L-5) wherein T represents a group represented by T6, $R^1$ represents a bromine atom, and $R^{3b}$ represents any substituents indicated in [Table L4] to [Table L12] (hereinafter, referred to as Compound Class $SX_{2637}$).

A compound (L-5) wherein T represents a group represented by T6, $R^1$ represents an iodine atom, and $R^{3b}$ represents any substituents indicated in [Table L4] to [Table L12] (hereinafter, referred to as Compound Class $SX_{2638}$).

A compound (L-5) wherein T represents a group represented by T7, $R^1$ represents $OCF_3$, and $R^{3b}$ represents any substituents indicated in [Table L4] to [Table L12] (hereinafter, referred to as Compound Class $SX_{2639}$).

A compound (L-5) wherein T represents a group represented by T7, $R^1$ represents a fluorine atom, and $R^{3b}$ represents any substituents indicated in [Table L4] to [Table L12] (hereinafter, referred to as Compound Class $SX_{2640}$).

A compound (L-5) wherein T represents a group represented by T7, $R^1$ represents a chlorine atom, and $R^{3b}$ represents any substituents indicated in [Table L4] to [Table L12] (hereinafter, referred to as Compound Class $SX_{2641}$).

A compound (L-5) wherein T represents a group represented by T7, $R^1$ represents a bromine atom, and $R^{3b}$ represents any substituents indicated in [Table L4] to [Table L12] (hereinafter, referred to as Compound Class $SX_{2642}$).

A compound (L-5) wherein T represents a group represented by T7, $R^1$ represents an iodine atom, and $R^{3b}$ represents any substituents indicated in [Table L4] to [Table L12] (hereinafter, referred to as Compound Class $SX_{2643}$).

A compound (L-5) wherein T represents a group represented by T8, $R^1$ represents $OCF_3$, and $R^{3b}$ represents any substituents indicated in [Table L4] to [Table L12] (hereinafter, referred to as Compound Class $SX_{2644}$).

A compound (L-5) wherein T represents a group represented by T8, $R^1$ represents a fluorine atom, and $R^{3b}$ represents any substituents indicated in [Table L4] to [Table L12] (hereinafter, referred to as Compound Class $SX_{2645}$).

A compound (L-5) wherein T represents a group represented by T8, $R^1$ represents a chlorine atom, and $R^{3b}$ represents any substituents indicated in [Table L4] to [Table L12] (hereinafter, referred to as Compound Class $SX_{2646}$).

A compound (L-5) wherein T represents a group represented by T8, $R^1$ represents a bromine atom, and $R^{3b}$ represents any substituents indicated in [Table L4] to [Table L12] (hereinafter, referred to as Compound Class $SX_{2647}$).

A compound (L-5) wherein T represents a group represented by T8, $R^1$ represents an iodine atom, and $R^{3b}$ represents any substituents indicated in [Table L4] to [Table L12] (hereinafter, referred to as Compound Class $SX_{2648}$).

A compound (L-5) wherein T represents a group represented by T11, $R^1$ represents $OCF_3$, and $R^{3b}$ represents any substituents indicated in [Table L4] to [Table L12] (hereinafter, referred to as Compound Class $SX_{2649}$).

A compound (L-5) wherein T represents a group represented by T11, $R^1$ represents a fluorine atom, and $R^{3b}$ represents any substituents indicated in [Table L4] to [Table L12] (hereinafter, referred to as Compound Class $SX_{2650}$).

A compound (L-5) wherein T represents a group represented by T11, $R^1$ represents a chlorine atom, and $R^{3b}$ represents any substituents indicated in [Table L4] to [Table L12] (hereinafter, referred to as Compound Class $SX_{2651}$).

A compound (L-5) wherein T represents a group represented by T11, $R^1$ represents a bromine atom, and $R^{3b}$ represents any substituents indicated in [Table L4] to [Table L12] (hereinafter, referred to as Compound Class $SX_{2652}$).

A compound (L-5) wherein T represents a group represented by T11, $R^1$ represents an iodine atom, and $R^{3b}$ represents any substituents indicated in [Table L4] to [Table L12] (hereinafter, referred to as Compound Class $SX_{2653}$).

A compound (L-5) wherein T represents a group represented by T12, $R^1$ represents $OCF_3$, and $R^{3b}$ represents any substituents indicated in [Table L4] to [Table L12](hereinafter, referred to as Compound Class $SX_{2654}$).

A compound (L-5) wherein T represents a group represented by T12, $R^1$ represents a fluorine atom, and $R^{3b}$ represents any substituents indicated in [Table L4] to [Table L12] (hereinafter, referred to as Compound Class $SX_{2655}$).

A compound (L-5) wherein T represents a group represented by T12, $R^1$ represents a chlorine atom, and $R^{3b}$ represents any substituents indicated in [Table L4] to [Table L12] (hereinafter, referred to as Compound Class $SX_{2656}$).

A compound (L-5) wherein T represents a group represented by T12, $R^1$ represents a bromine atom, and $R^{3b}$ represents any substituents indicated in [Table L4] to [Table L12] (hereinafter, referred to as Compound Class $SX_{2657}$).

A compound (L-5) wherein T represents a group represented by T12, $R^1$ represents an iodine atom, and $R^{3b}$ represents any substituents indicated in [Table L4] to [Table L12] (hereinafter, referred to as Compound Class $SX_{2658}$).

A compound (L-5) wherein T represents a group represented by T13, $R^1$ represents $OCF_3$, and $R^{3b}$ represents any substituents indicated in [Table L4] to [Table L12] (hereinafter, referred to as Compound Class $SX_{2659}$).

A compound (L-5) wherein T represents a group represented by T13, $R^1$ represents a fluorine atom, and $R^{3b}$ represents any substituents indicated in [Table L4] to [Table L12] (hereinafter, referred to as Compound Class $SX_{2660}$).

A compound (L-5) wherein T represents a group represented by T13, $R^1$ represents a chlorine atom, and $R^{3b}$ represents any substituents indicated in [Table L4] to [Table L12] (hereinafter, referred to as Compound Class $SX_{2661}$).

A compound (L-5) wherein T represents a group represented by T13, $R^1$ represents a bromine atom, and $R^{3b}$ represents any substituents indicated in [Table L4] to [Table L12] (hereinafter, referred to as Compound Class $SX_{2662}$).

A compound (L-5) wherein T represents a group represented by T13, $R^1$ represents an iodine atom, and $R^{3b}$ represents any substituents indicated in [Table L4] to [Table L12] (hereinafter, referred to as Compound Class $SX_{2663}$).

A compound (L-6) wherein T represents a group represented by T1, $R^1$ represents $OCF_3$, and $R^{3b}$ represents any substituents indicated in [Table L4] to [Table L12] (hereinafter, referred to as Compound Class $SX_{2664}$).

A compound (L-6) wherein T represents a group represented by T1, $R^1$ represents a fluorine atom, and $R^{3b}$ represents any substituents indicated in [Table L4] to [Table L12] (hereinafter, referred to as Compound Class $SX_{2665}$).

A compound (L-6) wherein T represents a group represented by T1, $R^1$ represents a chlorine atom, and $R^{3b}$ represents any substituents indicated in [Table L4] to [Table L12] (hereinafter, referred to as Compound Class $SX_{2666}$).

A compound (L-6) wherein T represents a group represented by T1, $R^1$ represents a bromine atom, and $R^{3b}$ represents any substituents indicated in [Table L4] to [Table L12] (hereinafter, referred to as Compound Class $SX_{2667}$).

A compound (L-6) wherein T represents a group represented by T1, $R^1$ represents an iodine atom, and $R^{3b}$ represents any substituents indicated in [Table L4] to [Table L12] (hereinafter, referred to as Compound Class $SX_{2668}$).

A compound (L-6) wherein T represents a group represented by T2, $R^1$ represents $OCF_3$, and $R^{3b}$ represents any substituents indicated in [Table L4] to [Table L12] (hereinafter, referred to as Compound Class $SX_{2669}$).

A compound (L-6) wherein T represents a group represented by T2, $R^1$ represents a fluorine atom, and $R^{3b}$ represents any substituents indicated in [Table L4] to [Table L12] (hereinafter, referred to as Compound Class $SX_{2670}$).

A compound (L-6) wherein T represents a group represented by T2, $R^1$ represents a chlorine atom, and $R^{3b}$ represents any substituents indicated in [Table L4] to [Table L12] (hereinafter, referred to as Compound Class $SX_{2671}$).

A compound (L-6) wherein T represents a group represented by T2, $R^1$ represents a bromine atom, and $R^{3b}$ represents any substituents indicated in [Table L4] to [Table L12] (hereinafter, referred to as Compound Class $SX_{2672}$).

A compound (L-6) wherein T represents a group represented by T2, $R^1$ represents an iodine atom, and $R^{3b}$ represents any substituents indicated in [Table L4] to [Table L12] (hereinafter, referred to as Compound Class $SX_{2673}$).

A compound (L-6) wherein T represents a group represented by T3, $R^1$ represents $OCF_3$, and $R^{3b}$ represents any substituents indicated in [Table L4] to [Table L12] (hereinafter, referred to as Compound Class $SX_{2674}$).

A compound (L-6) wherein T represents a group represented by T3, $R^1$ represents a fluorine atom, and $R^{3b}$ represents any substituents indicated in [Table L4] to [Table L12] (hereinafter, referred to as Compound Class $SX_{2675}$).

A compound (L-6) wherein T represents a group represented by T3, $R^1$ represents a chlorine atom, and $R^{3b}$ represents any substituents indicated in [Table L4] to [Table L12] (hereinafter, referred to as Compound Class $SX_{2676}$).

A compound (L-6) wherein T represents a group represented by T3, $R^1$ represents a bromine atom, and $R^{3b}$ represents any substituents indicated in [Table L4] to [Table L12] (hereinafter, referred to as Compound Class $SX_{2677}$).

A compound (L-6) wherein T represents a group represented by T3, $R^1$ represents an iodine atom, and $R^{3b}$ represents any substituents indicated in [Table L4] to [Table L12] (hereinafter, referred to as Compound Class $SX_{2678}$).

A compound (L-6) wherein T represents a group represented by T6, $R^1$ represents $OCF_3$, and $R^{3b}$ represents any substituents indicated in [Table L4] to [Table L12] (hereinafter, referred to as Compound Class $SX_{2679}$).

A compound (L-6) wherein T represents a group represented by T6, $R^1$ represents a fluorine atom, and $R^{3b}$ represents any substituents indicated in [Table L4] to [Table L12] (hereinafter, referred to as Compound Class $SX_{2680}$).

A compound (L-6) wherein T represents a group represented by T6, $R^1$ represents a chlorine atom, and $R^{3b}$ represents any substituents indicated in [Table L4] to [Table L12] (hereinafter, referred to as Compound Class $SX_{2681}$).

A compound (L-6) wherein T represents a group represented by T6, $R^1$ represents a bromine atom, and $R^{3b}$ represents any substituents indicated in [Table L4] to [Table L12] (hereinafter, referred to as Compound Class $SX_{2682}$).

A compound (L-6) wherein T represents a group represented by T6, $R^1$ represents an iodine atom, and $R^{3b}$ represents any substituents indicated in [Table L4] to [Table L12] (hereinafter, referred to as Compound Class $SX_{2683}$).

A compound (L-6) wherein T represents a group represented by T7, $R^1$ represents $OCF_3$, and $R^{3b}$ represents any substituents indicated in [Table L4] to [Table L12] (hereinafter, referred to as Compound Class $SX_{2684}$).

A compound (L-6) wherein T represents a group represented by T7, $R^1$ represents a fluorine atom, and $R^{3b}$ represents any substituents indicated in [Table L4] to [Table L12] (hereinafter, referred to as Compound Class $SX_{2685}$).

A compound (L-6) wherein T represents a group represented by T7, $R^1$ represents a chlorine atom, and $R^{3b}$ represents any substituents indicated in [Table L4] to [Table L12] (hereinafter, referred to as Compound Class $SX_{2686}$).

A compound (L-6) wherein T represents a group represented by T7, $R^1$ represents a bromine atom, and $R^{3b}$ represents any substituents indicated in [Table L4] to [Table L12] (hereinafter, referred to as Compound Class $SX_{2687}$).

A compound (L-6) wherein T represents a group represented by T7, $R^1$ represents an iodine atom, and $R^{3b}$ represents any substituents indicated in [Table L4] to [Table L12] (hereinafter, referred to as Compound Class $SX_{2688}$).

A compound (L-6) wherein T represents a group represented by T8, $R^1$ represents $OCF_3$, and $R^{3b}$ represents any substituents indicated in [Table L4] to [Table L12] (hereinafter, referred to as Compound Class $SX_{2689}$).

A compound (L-6) wherein T represents a group represented by T8, $R^1$ represents a fluorine atom, and $R^{3b}$ represents any substituents indicated in [Table L4] to [Table L12] (hereinafter, referred to as Compound Class $SX_{2690}$).

A compound (L-6) wherein T represents a group represented by T8, $R^1$ represents a chlorine atom, and $R^{3b}$ represents any substituents indicated in [Table L4] to [Table L12] (hereinafter, referred to as Compound Class $SX_{2691}$).

A compound (L-6) wherein T represents a group represented by T8, $R^1$ represents a bromine atom, and $R^{3b}$ represents any substituents indicated in [Table L4] to [Table L12] (hereinafter, referred to as Compound Class $SX_{2692}$).

A compound (L-6) wherein T represents a group represented by T8, $R^1$ represents an iodine atom, and $R^{3b}$ represents any substituents indicated in [Table L4] to [Table L12] (hereinafter, referred to as Compound Class $SX_{2693}$).

A compound (L-6) wherein T represents a group represented by T11, $R^1$ represents $OCF_3$, and $R^{3b}$ represents any substituents indicated in [Table L4] to [Table L12] (hereinafter, referred to as Compound Class $SX_{2694}$).

A compound (L-6) wherein T represents a group represented by T11, $R^1$ represents a fluorine atom, and $R^{3b}$ represents any substituents indicated in [Table L4] to [Table L12] (hereinafter, referred to as Compound Class $SX_{2695}$).

A compound (L-6) wherein T represents a group represented by T11, $R^1$ represents a chlorine atom, and $R^{3b}$ represents any substituents indicated in [Table L4] to [Table L12] (hereinafter, referred to as Compound Class $SX_{2696}$).

A compound (L-6) wherein T represents a group represented by T11, $R^1$ represents a bromine atom, and $R^{3b}$ represents any substituents indicated in [Table L4] to [Table L12] (hereinafter, referred to as Compound Class $SX_{2697}$).

A compound (L-6) wherein T represents a group represented by T11, $R^1$ represents an iodine atom, and $R^{3b}$ represents any substituents indicated in [Table L4] to [Table L12] (hereinafter, referred to as Compound Class $SX_{2698}$).

A compound (L-6) wherein T represents a group represented by T12, $R^1$ represents $OCF_3$, and $R^{3b}$ represents any substituents indicated in [Table L4] to [Table L12] (hereinafter, referred to as Compound Class $SX_{2699}$).

A compound (L-6) wherein T represents a group represented by T12, $R^1$ represents a fluorine atom, and $R^{3b}$ represents any substituents indicated in [Table L4] to [Table L12] (hereinafter, referred to as Compound Class $SX_{2700}$).

A compound (L-6) wherein T represents a group represented by T12, $R^1$ represents a chlorine atom, and $R^{3b}$ represents any substituents indicated in [Table L4] to [Table L12] (hereinafter, referred to as Compound Class $SX_{2701}$).

A compound (L-6) wherein T represents a group represented by T12, $R^1$ represents a bromine atom, and $R^{3b}$ represents any substituents indicated in [Table L4] to [Table L12] (hereinafter, referred to as Compound Class $SX_{2702}$).

A compound (L-6) wherein T represents a group represented by T12, $R^1$ represents an iodine atom, and $R^{3b}$ represents any substituents indicated in [Table L4] to [Table L12] (hereinafter, referred to as Compound Class $SX_{2703}$).

A compound (L-6) wherein T represents a group represented by T13, $R^1$ represents $OCF_3$, and $R^{3b}$ represents any substituents indicated in [Table L4] to [Table L12] (hereinafter, referred to as Compound Class $SX_{2704}$).

A compound (L-6) wherein T represents a group represented by T13, $R^1$ represents a fluorine atom, and $R^{3b}$ represents any substituents indicated in [Table L4] to [Table L12] (hereinafter, referred to as Compound Class $SX_{2705}$).

A compound (L-6) wherein T represents a group represented by T13, $R^1$ represents a chlorine atom, and $R^{3b}$ represents any substituents indicated in [Table L4] to [Table L12] (hereinafter, referred to as Compound Class $SX_{2706}$).

A compound (L-6) wherein T represents a group represented by T13, $R^1$ represents a bromine atom, and $R^{3b}$ represents any substituents indicated in [Table L4] to [Table L12] (hereinafter, referred to as Compound Class $SX_{2707}$).

A compound (L-6) wherein T represents a group represented by T13, $R^1$ represents an iodine atom, and $R^{3b}$ represents any substituents indicated in [Table L4] to [Table L12] (hereinafter, referred to as Compound Class $SX_{2708}$).

A compound (L-8) wherein T represents a group represented by T1, $R^1$ represents a fluorine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2709-1}$).

A compound (L-8) wherein T represents a group represented by T1, $R^1$ represents a fluorine atom, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2709-2}$).

A compound (L-8) wherein T represents a group represented by T1, $R^1$ represents a fluorine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2710}$).

A compound (L-8) wherein T represents a group represented by T1, $R^1$ represents a fluorine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2711}$).

A compound (L-8) wherein T represents a group represented by T1, $R^1$ represents a fluorine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2712}$).

A compound (L-8) wherein T represents a group represented by T2, $R^1$ represents a fluorine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2713}$).

A compound (L-8) wherein T represents a group represented by T2, $R^1$ represents a fluorine atom, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2714}$).

A compound (L-8) wherein T represents a group represented by T2, $R^1$ represents a fluorine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2715}$).

A compound (L-8) wherein T represents a group represented by T2, $R^1$ represents a fluorine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2716}$).

A compound (L-8) wherein T represents a group represented by T2, $R^1$ represents a fluorine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2717}$).

A compound (L-8) wherein T represents a group represented by T3, $R^1$ represents a fluorine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2718}$).

A compound (L-8) wherein T represents a group represented by T3, $R^1$ represents a fluorine atom, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2719}$).

A compound (L-8) wherein T represents a group represented by T3, $R^1$ represents a fluorine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2720}$).

A compound (L-8) wherein T represents a group represented by T3, $R^1$ represents a fluorine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2721}$).

A compound (L-8) wherein T represents a group represented by T3, $R^1$ represents a fluorine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2722}$).

A compound (L-8) wherein T represents a group represented by T4, $R^1$ represents a fluorine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2723}$).

A compound (L-8) wherein T represents a group represented by T4, $R^1$ represents a fluorine atom, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2724}$).

A compound (L-8) wherein T represents a group represented by T4, $R^1$ represents a fluorine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2725}$).

A compound (L-8) wherein T represents a group represented by T4, $R^1$ represents a fluorine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2726}$).

A compound (L-8) wherein T represents a group represented by T4, $R^1$ represents a fluorine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2727}$).

A compound (L-8) wherein T represents a group represented by T5, $R^1$ represents a fluorine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2728}$).

A compound (L-8) wherein T represents a group represented by T5, $R^1$ represents a fluorine atom, n is 1, $R^2$ represents a methyl group, and $R^{3c}$ represents a hydrogen atom, a chlorine atom, $CF_3$, or any substituents indicated in [Table L4] to [Table L12] (hereinafter, referred to as Compound Class $SX_{2729}$).

A compound (L-8) wherein T represents a group represented by T5, $R^1$ represents a fluorine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2730}$).

A compound (L-8) wherein T represents a group represented by T5, $R^1$ represents a fluorine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2731}$).

A compound (L-8) wherein T represents a group represented by T5, $R^1$ represents a fluorine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2732}$).

A compound (L-8) wherein T represents a group represented by T1, $R^1$ represents a chlorine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2733}$).

A compound (L-8) wherein T represents a group represented by T1, $R^1$ represents a chlorine atom, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2734}$).

A compound (L-8) wherein T represents a group represented by T1, $R^1$ represents a chlorine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2735}$).

A compound (L-8) wherein T represents a group represented by T1, $R^1$ represents a chlorine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2736}$).

A compound (L-8) wherein T represents a group represented by T1, $R^1$ represents a chlorine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2738}$).

A compound (L-8) wherein T represents a group represented by T2, $R^1$ represents a chlorine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2738}$).

A compound (L-8) wherein T represents a group represented by T2, $R^1$ represents a chlorine atom, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2739}$).

A compound (L-8) wherein T represents a group represented by T2, $R^1$ represents a chlorine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2470}$).

A compound (L-8) wherein T represents a group represented by T2, $R^1$ represents a chlorine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2741}$).

A compound (L-8) wherein T represents a group represented by T2, $R^1$ represents a chlorine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2742}$).

A compound (L-8) wherein T represents a group represented by T3, $R^1$ represents a chlorine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2743}$).

A compound (L-8) wherein T represents a group represented by T3, $R^1$ represents a chlorine atom, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2744}$).

A compound (L-8) wherein T represents a group represented by T3, $R^1$ represents a chlorine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2745}$).

A compound (L-8) wherein T represents a group represented by T3, $R^1$ represents a chlorine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2746}$).

A compound (L-8) wherein T represents a group represented by T3, $R^1$ represents a chlorine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2747}$).

A compound (L-8) wherein T represents a group represented by T4, $R^1$ represents a chlorine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2748}$).

A compound (L-8) wherein T represents a group represented by T4, $R^1$ represents a chlorine atom, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2749}$).

A compound (L-8) wherein T represents a group represented by T4, $R^1$ represents a chlorine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2750}$).

A compound (L-8) wherein T represents a group represented by T4, $R^1$ represents a chlorine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2751}$).

A compound (L-8) wherein T represents a group represented by T4, $R^1$ represents a chlorine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2752}$).

A compound (L-8) wherein T represents a group represented by T5, $R^1$ represents a chlorine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2753}$).

A compound (L-8) wherein T represents a group represented by T5, $R^1$ represents a chlorine atom, n is 1, $R^2$ represents a methyl group, and $R^{3c}$ represents a hydrogen atom, a chlorine atom, $CF_3$, or any substituents indicated in [Table L4] to [Table L12] (hereinafter, referred to as Compound Class $SX_{2754}$).

A compound (L-8) wherein T represents a group represented by T5, $R^1$ represents a chlorine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2755}$).

A compound (L-8) wherein T represents a group represented by T5, $R^1$ represents a chlorine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2756}$).

A compound (L-8) wherein T represents a group represented by T5, $R^1$ represents a chlorine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2757}$).

A compound (L-8) wherein T represents a group represented by T1, $R^1$ represents a bromine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2758}$).

A compound (L-8) wherein T represents a group represented by T1, $R^1$ represents a bromine atom, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2759}$).

A compound (L-8) wherein T represents a group represented by T1, $R^1$ represents a bromine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2760}$).

A compound (L-8) wherein T represents a group represented by T1, $R^1$ represents a bromine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2761}$).

A compound (L-8) wherein T represents a group represented by T1, $R^1$ represents a bromine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2762}$).

A compound (L-8) wherein T represents a group represented by T2, $R^1$ represents a bromine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2763}$).

A compound (L-8) wherein T represents a group represented by T2, $R^1$ represents a bromine atom, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2764}$).

A compound (L-8) wherein T represents a group represented by T2, $R^1$ represents a bromine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2765}$).

A compound (L-8) wherein T represents a group represented by T2, $R^1$ represents a bromine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2766}$).

A compound (L-8) wherein T represents a group represented by T2, $R^1$ represents a bromine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2767}$).

A compound (L-8) wherein T represents a group represented by T3, $R^1$ represents a bromine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2768}$).

A compound (L-8) wherein T represents a group represented by T3, $R^1$ represents a bromine atom, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2769}$).

A compound (L-8) wherein T represents a group represented by T3, $R^1$ represents a bromine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2770}$).

A compound (L-8) wherein T represents a group represented by T3, $R^1$ represents a bromine atom, n is 0, $R^2$ represents an ethyl group, and $R^{11}$ represents a hydrogen atom, a chlorine atom, $CF_3$, or any substituents indicated in [Table L4] to [Table L12] (hereinafter, referred to as Compound Class $SX_{2771}$).

A compound (L-8) wherein T represents a group represented by T3, $R^1$ represents a bromine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2772}$).

A compound (L-8) wherein T represents a group represented by T4, $R^1$ represents a bromine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2773}$).

A compound (L-8) wherein T represents a group represented by T4, $R^1$ represents a bromine atom, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2774}$).

A compound (L-8) wherein T represents a group represented by T4, $R^1$ represents a bromine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2775}$).

A compound (L-8) wherein T represents a group represented by T4, $R^1$ represents a bromine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2776}$).

A compound (L-8) wherein T represents a group represented by T4, $R^1$ represents a bromine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2777}$).

A compound (L-8) wherein T represents a group represented by T5, $R^1$ represents a bromine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2778}$).

A compound (L-8) wherein T represents a group represented by T5, $R^1$ represents a bromine atom, n is 1, $R^2$ represents a methyl group, and $R^{3c}$ represents a hydrogen atom, a chlorine atom, $CF_3$, or any substituents indicated in [Table L4] to [Table L12] (hereinafter, referred to as Compound Class $SX_{2779}$).

A compound (L-8) wherein T represents a group represented by T5, $R^1$ represents a bromine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2780}$).

A compound (L-8) wherein T represents a group represented by T5, $R^1$ represents a bromine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2781}$).

A compound (L-8) wherein T represents a group represented by T5, $R^1$ represents a bromine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2782}$).

A compound (L-8) wherein T represents a group represented by T1, $R^1$ represents an iodine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2783}$.

A compound (L-8) wherein T represents a group represented by T1, $R^1$ represents an iodine atom, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2784}$).

A compound (L-8) wherein T represents a group represented by T1, $R^1$ represents an iodine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2785}$).

A compound (L-8) wherein T represents a group represented by T1, $R^1$ represents an iodine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2786}$).

A compound (L-8) wherein T represents a group represented by T1, $R^1$ represents an iodine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2787}$).

A compound (L-8) wherein T represents a group represented by T2, $R^1$ represents an iodine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2788}$).

A compound (L-8) wherein T represents a group represented by T2, $R^1$ represents an iodine atom, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2789}$).

A compound (L-8) wherein T represents a group represented by T2, $R^1$ represents an iodine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2790}$).

A compound (L-8) wherein T represents a group represented by T2, $R^1$ represents an iodine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2791}$).

A compound (L-8) wherein T represents a group represented by T2, $R^1$ represents an iodine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2792}$).

A compound (L-8) wherein T represents a group represented by T3, $R^1$ represents an iodine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2793}$).

A compound (L-8) wherein T represents a group represented by T3, $R^1$ represents an iodine atom, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2794}$).

A compound (L-8) wherein T represents a group represented by T3, $R^1$ represents an iodine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2795}$).

A compound (L-8) wherein T represents a group represented by T3, $R^1$ represents an iodine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2796}$).

A compound (L-8) wherein T represents a group represented by T3, $R^1$ represents an iodine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2797}$).

A compound (L-8) wherein T represents a group represented by T4, $R^1$ represents an iodine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2798}$).

A compound (L-8) wherein T represents a group represented by T4, $R^1$ represents an iodine atom, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2799}$).

A compound (L-8) wherein T represents a group represented by T4, $R^1$ represents an iodine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2800}$).

A compound (L-8) wherein T represents a group represented by T4, $R^1$ represents an iodine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2801}$).

A compound (L-8) wherein T represents a group represented by T4, $R^1$ represents an iodine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2802}$).

A compound (L-8) wherein T represents a group represented by T5, $R^1$ represents an iodine atom, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2803}$).

A compound (L-8) wherein T represents a group represented by T5, $R^1$ represents an iodine atom, n is 1, $R^2$ represents a methyl group, and $R^{3c}$ represents a hydrogen atom, a chlorine atom, $CF_3$, or any substituents indicated in [Table L4] to [Table L12] (hereinafter, referred to as Compound Class $SX_{2804}$).

A compound (L-8) wherein T represents a group represented by T5, $R^1$ represents an iodine atom, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2805}$).

A compound (L-8) wherein T represents a group represented by T5, $R^1$ represents an iodine atom, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2806}$).

A compound (L-8) wherein T represents a group represented by T5, $R^1$ represents an iodine atom, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2807}$).

A compound (L-8) wherein T represents a group represented by T1, $R^1$ represents $OCF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2808}$).

A compound (L-8) wherein T represents a group represented by T1, $R^1$ represents $OCF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2809}$).

A compound (L-8) wherein T represents a group represented by T1, $R^1$ represents $OCF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2810}$).

A compound (L-8) wherein T represents a group represented by T1, $R^1$ represents $OCF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2811}$).

A compound (L-8) wherein T represents a group represented by T1, $R^1$ represents $OCF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2812}$).

A compound (L-8) wherein T represents a group represented by T2, $R^1$ represents $OCF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2813}$).

A compound (L-8) wherein T represents a group represented by T2, $R^1$ represents $OCF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2814}$).

A compound (L-8) wherein T represents a group represented by T2, $R^1$ represents $OCF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2815}$).

A compound (L-8) wherein T represents a group represented by T2, $R^1$ represents $OCF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2816}$).

A compound (L-8) wherein T represents a group represented by T2, $R^1$ represents $OCF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2817}$).

A compound (L-8) wherein T represents a group represented by T3, $R^1$ represents $OCF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2818}$).

A compound (L-8) wherein T represents a group represented by T3, $R^1$ represents $OCF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2819}$).

A compound (L-8) wherein T represents a group represented by T3, $R^1$ represents $OCF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2820}$).

A compound (L-8) wherein T represents a group represented by T3, $R^1$ represents $OCF_3$, n is 0, $R^2$ represents an ethyl group, and $R^h$ represents a hydrogen atom, a chlorine atom, $CF_3$, or any substituents indicated in [Table L4] to [Table L12] (hereinafter, referred to as Compound Class $SX_{2821}$).

A compound (L-8) wherein T represents a group represented by T3, $R^1$ represents $OCF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2822}$).

A compound (L-8) wherein T represents a group represented by T4, $R^1$ represents $OCF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2823}$).

A compound (L-8) wherein T represents a group represented by T4, $R^1$ represents $OCF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2824}$).

A compound (L-8) wherein T represents a group represented by T4, $R^1$ represents $OCF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2825}$).

A compound (L-8) wherein T represents a group represented by T4, $R^1$ represents $OCF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2826}$).

A compound (L-8) wherein T represents a group represented by T4, $R^1$ represents $OCF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2827}$).

A compound (L-8) wherein T represents a group represented by T5, $R^1$ represents $OCF_3$, n is 0, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2828}$).

A compound (L-8) wherein T represents a group represented by T5, $R^1$ represents $OCF_3$, n is 1, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2829}$).

A compound (L-8) wherein T represents a group represented by T5, $R^1$ represents $OCF_3$, n is 2, $R^2$ represents a methyl group, and $R^{3b}$ represents a hydrogen atom, a chlorine atom, $CF_3$, or any substituents indicated in [Table L4] to [Table L12] (hereinafter, referred to as Compound Class $SX_{2830}$).

A compound (L-8) wherein T represents a group represented by T5, $R^1$ represents $OCF_3$, n is 0, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2831}$).

A compound (L-8) wherein T represents a group represented by T3, $R^1$ represents $OCF_3$, n is 1, $R^2$ represents an ethyl group, and $R^{3b}$ represents a hydrogen atom, a chlorine atom, $CF_3$, or any substituents indicated in [Table L4] to [Table L12] (hereinafter, referred to as Compound Class $SX_{2832}$).

Next, examples of the intermediate compound which is prepared according to the Reference Preparation Examples described in the Examples or the Reference Preparation method described herein are described below. Here T37 to T39 are any groups indicated below.

T37

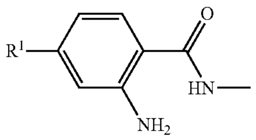

T38

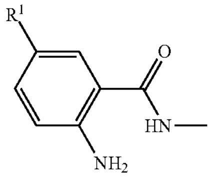

T39

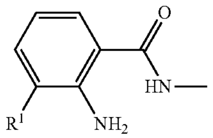

A compound represented by formula (L-9):

(L-9)

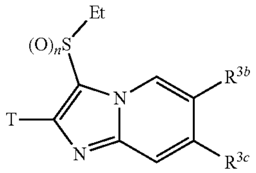

(hereinafter, referred to as Compound (L-9)), wherein n is 0, T represents a group represented by T37, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2833}$).

A compound (L-9) wherein n is 0, T represents a group represented by T37, $R^{3b}$ represents $CF_3$, $R^{3c}$ represents a hydrogen atom, and $R^1$ represents any substituents described in [Table L1] to [Table L3] (hereinafter, referred to as Compound Class $SX_{2834}$).

A compound (L-9) wherein n is 0, T represents a group represented by T37, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2835}$).

A compound (L-9) wherein n is 0, T represents a group represented by T37, $R^{3b}$ represents a bromine atom, $R^{3c}$ represents a hydrogen atom, and $R^1$ represents any substituents described in [Table L1] to [Table L3] (hereinafter, referred to as Compound Class $SX_{2836}$).

A compound (L-9) wherein n is 0, T represents a group represented by T37, $R^{3b}$ represents an iodine atom, $R^{3c}$ represents a hydrogen atom, and $R^1$ represents any substituents described in [Table L1] to [Table L3] (hereinafter, referred to as Compound Class $SX_{2837}$).

A compound (L-9) wherein n is 0, T represents a group represented by T37, $R^{3b}$ represents a hydrogen atom, $R^{3c}$ represents $CF_3$, and $R^1$ represents any substituents described in [Table L1] to [Table L3] (hereinafter, referred to as Compound Class $SX_{2838}$).

A compound (L-9) wherein n is 0, T represents a group represented by T37, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2839}$).

A compound (L-9) wherein n is 0, T represents a group represented by T37, $R^{3b}$ represents a hydrogen atom, $R^{3c}$ represents a bromine atom, and $R^1$ represents any substituents described in [Table L1] to [Table L3] (hereinafter, referred to as Compound Class $SX_{2840}$).

A compound (L-9) wherein n is 1, T represents a group represented by T37, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2841}$).

A compound (L-9) wherein n is 1, T represents a group represented by T37, $R^{3b}$ represents $CF_3$, $R^{3c}$ represents a hydrogen atom, and $R^1$ represents any substituents described in [Table L1] to [Table L3] (hereinafter, referred to as Compound Class $SX_{2842}$).

A compound (L-9) wherein n is 1, T represents a group represented by T37, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2843}$).

A compound (L-9) wherein n is 1, T represents a group represented by T37, $R^{3b}$ represents a bromine atom, $R^{3c}$ represents a hydrogen atom, and $R^1$ represents any substituents described in [Table L1] to [Table L3] (hereinafter, referred to as Compound Class $SX_{2844}$).

A compound (L-9) wherein n is 1, T represents a group represented by T37, $R^{3b}$ represents an iodine atom, $R^{3c}$ represents a hydrogen atom, and $R^1$ represents any substituents described in [Table L1] to [Table L3] (hereinafter, referred to as Compound Class $SX_{2845}$).

A compound (L-9) wherein n is 1, T represents a group represented by T37, $R^{3b}$ represents a hydrogen atom, $R^{3c}$ represents $CF_3$, and $R^1$ represents any substituents described in [Table L1] to [Table L3] (hereinafter, referred to as Compound Class $SX_{2846}$).

A compound (L-9) wherein n is 1, T represents a group represented by T37, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2847}$).

A compound (L-9) wherein n is 1, T represents a group represented by T37, $R^{3b}$ represents a hydrogen atom, $R^{3c}$ represents a bromine atom, and $R^1$ represents any substituents described in [Table L1] to [Table L3] (hereinafter, referred to as Compound Class $SX_{2848}$).

A compound (L-9) wherein n is 2, T represents a group represented by T37, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2849}$).

A compound (L-9) wherein n is 2, T represents a group represented by T37, $R^{3b}$ represents $CF_3$, $R^{3c}$ represents a hydrogen atom, and $R^1$ represents any substituents described in [Table L1] to [Table L3] (hereinafter, referred to as Compound Class $SX_{2850}$).

A compound (L-9) wherein n is 2, T represents a group represented by T37, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2851}$).

A compound (L-9) wherein n is 2, T represents a group represented by T37, $R^{3b}$ represents a bromine atom, $R^{3c}$ represents a hydrogen atom, and $R^1$ represents any substituents described in [Table L1] to [Table L3] (hereinafter, referred to as Compound Class $SX_{2852}$).

A compound (L-9) wherein n is 2, T represents a group represented by T37, $R^{3b}$ represents an iodine atom, $R^{3c}$ represents a hydrogen atom, and $R^1$ represents any substituents described in [Table L1] to [Table L3] (hereinafter, referred to as Compound Class $SX_{2853}$).

A compound (L-9) wherein n is 2, T represents a group represented by T37, $R^{3b}$ represents a hydrogen atom, $R^{3c}$ represents $CF_3$, and $R^1$ represents any substituents described in [Table L1] to [Table L3] (hereinafter, referred to as Compound Class $SX_{2854}$).

A compound (L-9) wherein n is 2, T represents a group represented by T37, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2855}$).

A compound (L-9) wherein n is 2, T represents a group represented by T37, $R^{3b}$ represents a hydrogen atom, $R^{3c}$ represents a bromine atom, and $R^1$ represents any substituents described in [Table L1] to [Table L3] (hereinafter, referred to as Compound Class $SX_{2856}$).

A compound (L-9) wherein n is 0, T represents a group represented by T38, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2857}$).

A compound (L-9) wherein n is 0, T represents a group represented by T38, $R^{3b}$ represents $CF_3$, $R^{3c}$ represents a hydrogen atom, and $R^1$ represents any substituents described in [Table L1] to [Table L3] (hereinafter, referred to as Compound Class $SX_{2858}$).

A compound (L-9) wherein n is 0, T represents a group represented by T38, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2859}$).

A compound (L-9) wherein n is 0, T represents a group represented by T38, $R^{3b}$ represents a bromine atom, $R^{3c}$ represents a hydrogen atom, and $R^1$ represents any substituents described in [Table L1] to [Table L3] (hereinafter, referred to as Compound Class $SX_{2860}$).

A compound (L-9) wherein n is 0, T represents a group represented by T38, $R^{3b}$ represents an iodine atom, $R^{3c}$ represents a hydrogen atom, and $R^1$ represents any substituents described in [Table L1] to [Table L3] (hereinafter, referred to as Compound Class $SX_{2861}$).

A compound (L-9) wherein n is 0, T represents a group represented by T38, $R^{3b}$ represents a hydrogen atom, $R^{3c}$ represents $CF_3$, and $R^1$ represents any substituents described in [Table L1] to [Table L3] (hereinafter, referred to as Compound Class $SX_{2862}$).

A compound (L-9) wherein n is 0, T represents a group represented by T38, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2863}$).

A compound (L-9) wherein n is 0, T represents a group represented by T38, $R^{3b}$ represents a hydrogen atom, $R^{3c}$ represents a bromine atom, and $R^1$ represents any substituents described in [Table L1] to [Table L3] (hereinafter, referred to as Compound Class $SX_{2864}$).

A compound (L-9) wherein n is 1, T represents a group represented by T38, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2865}$).

A compound (L-9) wherein n is 1, T represents a group represented by T38, $R^{3b}$ represents $CF_3$, $R^{3c}$ represents a hydrogen atom, and $R^1$ represents any substituents described in [Table L1] to [Table L3] (hereinafter, referred to as Compound Class $SX_{2866}$).

A compound (L-9) wherein n is 1, T represents a group represented by T38, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2867}$).

A compound (L-9) wherein n is 1, T represents a group represented by T38, $R^{3b}$ represents a bromine atom, $R^{3c}$ represents a hydrogen atom, and $R^1$ represents any substituents described in [Table L1] to [Table L3] (hereinafter, referred to as Compound Class $SX_{2868}$).

A compound (L-9) wherein n is 1, T represents a group represented by T38, $R^{3b}$ represents an iodine atom, $R^{3c}$ represents a hydrogen atom, and $R^1$ represents any substituents described in [Table L1] to [Table L3] (hereinafter, referred to as Compound Class $SX_{2869}$).

A compound (L-9) wherein n is 1, T represents a group represented by T38, $R^{3b}$ represents a hydrogen atom, $R^{3c}$ represents $CF_3$, and $R^1$ represents any substituents described in [Table L1] to [Table L3] (hereinafter, referred to as Compound Class $SX_{2870}$).

A compound (L-9) wherein n is 1, T represents a group represented by T38, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2871}$).

A compound (L-9) wherein n is 1, T represents a group represented by T38, $R^{3b}$ represents a hydrogen atom, $R^{3c}$ represents a bromine atom, and $R^1$ represents any substituents described in [Table L1] to [Table L3] (hereinafter, referred to as Compound Class $SX_{2872}$).

A compound (L-9) wherein n is 2, T represents a group represented by T38, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2873}$).

A compound (L-9) wherein n is 2, T represents a group represented by T38, $R^{3b}$ represents $CF_3$, $R^{3c}$ represents a hydrogen atom, and $R^1$ represents any substituents described in [Table L1] to [Table L3] (hereinafter, referred to as Compound Class $SX_{2874}$).

A compound (L-9) wherein n is 2, T represents a group represented by T38, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2875}$).

A compound (L-9) wherein n is 2, T represents a group represented by T38, $R^{3b}$ represents a bromine atom, $R^{3c}$ represents a hydrogen atom, and $R^1$ represents any substituents described in [Table L1] to [Table L3] (hereinafter, referred to as Compound Class $SX_{2876}$).

A compound (L-9) wherein n is 2, T represents a group represented by T38, $R^{3b}$ represents an iodine atom, $R^{3c}$ represents a hydrogen atom, and $R^1$ represents any substituents described in [Table L1] to [Table L3] (hereinafter, referred to as Compound Class $SX_{2877}$).

A compound (L-9) wherein n is 2, T represents a group represented by T38, $R^{3b}$ represents a hydrogen atom, $R^{3c}$ represents $CF_3$, and $R^1$ represents any substituents described in [Table L1] to [Table L3] (hereinafter, referred to as Compound Class $SX_{2878}$).

A compound (L-9) wherein n is 2, T represents a group represented by T38, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2879}$).

A compound (L-9) wherein n is 2, T represents a group represented by T38, $R^{3b}$ represents a hydrogen atom, $R^{3c}$ represents a bromine atom, and $R^1$ represents any substituents described in [Table L1] to [Table L3] (hereinafter, referred to as Compound Class $SX_{2880}$).

A compound (L-9) wherein n is 0, T represents a group represented by T39, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2881}$).

A compound (L-9) wherein n is 0, T represents a group represented by T39, $R^{3b}$ represents $CF_3$, $R^{3c}$ represents a hydrogen atom, and $R^1$ represents any substituents described in [Table L1] to [Table L3] (hereinafter, referred to as Compound Class $SX_{2882}$).

A compound (L-9) wherein n is 0, T represents a group represented by T39, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2883}$).

A compound (L-9) wherein n is 0, T represents a group represented by T39, $R^{3b}$ represents a bromine atom, $R^{3c}$ represents a hydrogen atom, and $R^1$ represents any substituents described in [Table L1] to [Table L3] (hereinafter, referred to as Compound Class $SX_{2884}$).

A compound (L-9) wherein n is 0, T represents a group represented by T39, $R^{3b}$ represents an iodine atom, $R^{3c}$ represents a hydrogen atom, and $R^1$ represents any substituents described in [Table L1] to [Table L3] (hereinafter, referred to as Compound Class $SX_{2885}$).

A compound (L-9) wherein n is 0, T represents a group represented by T39, $R^{3b}$ represents a hydrogen atom, $R^{3c}$ represents $CF_3$, and $R^1$ represents any substituents described in [Table L1] to [Table L3] (hereinafter, referred to as Compound Class $SX_{2886}$).

A compound (L-9) wherein n is 0, T represents a group represented by T39, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2887}$).

A compound (L-9) wherein n is 0, T represents a group represented by T39, $R^{3b}$ represents a hydrogen atom, $R^{3c}$ represents a bromine atom, and $R^1$ represents any substituents described in [Table L1] to [Table L3] (hereinafter, referred to as Compound Class $SX_{2888}$).

A compound (L-9) wherein n is 1, T represents a group represented by T39, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2889}$).

A compound (L-9) wherein n is 1, T represents a group represented by T39, $R^{3b}$ represents $CF_3$, $R^{3c}$ represents a hydrogen atom, and $R^1$ represents any substituents described in [Table L1] to [Table L3] (hereinafter, referred to as Compound Class $SX_{2890}$).

A compound (L-9) wherein n is 1, T represents a group represented by T39, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2891}$).

A compound (L-9) wherein n is 1, T represents a group represented by T39, $R^{3b}$ represents a bromine atom, $R^{3c}$ represents a hydrogen atom, and $R^1$ represents any substituents described in [Table L1] to [Table L3] (hereinafter, referred to as Compound Class $SX_{2892}$).

A compound (L-9) wherein n is 1, T represents a group represented by T39, $R^{3b}$ represents an iodine atom, $R^{3c}$ represents a hydrogen atom, and $R^1$ represents any substituents described in [Table L1] to [Table L3] (hereinafter, referred to as Compound Class $SX_{2893}$).

A compound (L-9) wherein n is 1, T represents a group represented by T39, $R^{3b}$ represents a hydrogen atom, $R^{3c}$ represents $CF_3$, and $R^1$ represents any substituents described in [Table L1] to [Table L3] (hereinafter, referred to as Compound Class $SX_{2894}$).

A compound (L-9) wherein n is 1, T represents a group represented by T39, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2895}$).

A compound (L-9) wherein n is 1, T represents a group represented by T39, $R^{3b}$ represents a hydrogen atom, $R^{3c}$ represents a bromine atom, and $R^1$ represents any substituents described in [Table L1] to [Table L3] (hereinafter, referred to as Compound Class $SX_{2896}$).

A compound (L-9) wherein n is 2, T represents a group represented by T39, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2897}$).

A compound (L-9) wherein n is 2, T represents a group represented by T39, $R^{3b}$ represents $CF_3$, $R^{3c}$ represents a hydrogen atom, and $R^1$ represents any substituents described in [Table L1] to [Table L3] (hereinafter, referred to as Compound Class $SX_{2898}$).

A compound (L-9) wherein n is 2, T represents a group represented by T39, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2899}$).

A compound (L-9) wherein n is 2, T represents a group represented by T39, $R^{3b}$ represents a bromine atom, $R^{3c}$ represents a hydrogen atom, and $R^1$ represents any substituents described in [Table L1] to [Table L3] (hereinafter, referred to as Compound Class $SX_{2900}$).

A compound (L-9) wherein n is 2, T represents a group represented by T39, $R^{3b}$ represents an iodine atom, $R^{3c}$ represents a hydrogen atom, and $R^1$ represents any substituents described in [Table L1] to [Table L3] (hereinafter, referred to as Compound Class $SX_{2901}$).

A compound (L-9) wherein n is 2, T represents a group represented by T39, $R^{3b}$ represents a hydrogen atom, $R^{3c}$ represents $CF_3$, and $R^1$ represents any substituents described in [Table L1] to [Table L3] (hereinafter, referred to as Compound Class $SX_{2902}$).

A compound (L-9) wherein n is 2, T represents a group represented by T39, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2903}$).

A compound (L-9) wherein n is 2, T represents a group represented by T39, $R^{3b}$ represents a hydrogen atom, $R^{3c}$ represents a bromine atom, and $R^1$ represents any substituents described in [Table L1] to [Table L3] (hereinafter, referred to as Compound Class $SX_{2904}$).

A compound represented by formula (L-10):

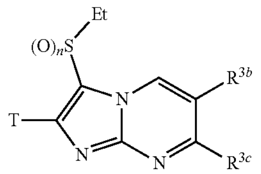

(L-10)

(hereinafter, referred to as Compound (L-10)), wherein n is 0, T represents T37, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2905}$).

A compound (L-10) wherein n is 0, T represents a group represented by T37, $R^{3b}$ represents $CF_3$, $R^{3c}$ represents a hydrogen atom, and $R^1$ represents any substituents described in [Table L1] to [Table L3] (hereinafter, referred to as Compound Class $SX_{2906}$).

A compound (L-10) wherein n is 0, T represents a group represented by T37, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2907}$).

A compound (L-10) wherein n is 0, T represents a group represented by T37, $R^{3b}$ represents a bromine atom, $R^{3c}$ represents a hydrogen atom, and $R^1$ represents any substituents described in [Table L1] to [Table L3] (hereinafter, referred to as Compound Class $SX_{2908}$).

A compound (L-10) wherein n is 0, T represents a group represented by T37, $R^{3b}$ represents an iodine atom, $R^{3c}$ represents a hydrogen atom, and $R^1$ represents any substituents described in [Table L1] to [Table L3] (hereinafter, referred to as Compound Class $SX_{2909}$).

A compound (L-10) wherein n is 0, T represents a group represented by T37, $R^{3b}$ represents a hydrogen atom, $R^{3c}$ represents $CF_3$, and $R^1$ represents any substituents described in [Table L1] to [Table L3] (hereinafter, referred to as Compound Class $SX_{2910}$).

A compound (L-10) wherein n is 0, T represents a group represented by T37, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2911}$).

A compound (L-10) wherein n is 0, T represents a group represented by T37, $R^{3b}$ represents a hydrogen atom, $R^{3c}$ represents a bromine atom, and $R^1$ represents any substituents described in [Table L1] to [Table L3] (hereinafter, referred to as Compound Class $SX_{2912}$).

A compound (L-10) wherein n is 1, T represents a group represented by T37, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2913}$).

A compound (L-10) wherein n is 1, T represents a group represented by T37, $R^{3b}$ represents $CF_3$, $R^{3c}$ represents a hydrogen atom, and $R^1$ represents any substituents described in [Table L1] to [Table L3] (hereinafter, referred to as Compound Class $SX_{2914}$).

A compound (L-10) wherein n is 1, T represents a group represented by T37, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2915}$).

A compound (L-10) wherein n is 1, T represents a group represented by T37, $R^{3b}$ represents a bromine atom, $R^{3c}$ represents a hydrogen atom, and $R^1$ represents any substituents described in [Table L1] to [Table L3] (hereinafter, referred to as Compound Class $SX_{2916}$).

A compound (L-10) wherein n is 1, T represents a group represented by T37, $R^{3b}$ represents an iodine atom, $R^{3c}$ represents a hydrogen atom, and $R^1$ represents any substituents described in [Table L1] to [Table L3] (hereinafter, referred to as Compound Class $SX_{2917}$).

A compound (L-10) wherein n is 1, T represents a group represented by T37, $R^{3b}$ represents a hydrogen atom, $R^{3c}$ represents $CF_3$, and $R^1$ represents any substituents described in [Table L1] to [Table L3] (hereinafter, referred to as Compound Class $SX_{2918}$).

A compound (L-10) wherein n is 1, T represents a group represented by T37, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2919}$).

A compound (L-10) wherein n is 1, T represents a group represented by T37, $R^{3b}$ represents a hydrogen atom, $R^{3c}$ represents a bromine atom, and $R^1$ represents any substituents described in [Table L1] to [Table L3] (hereinafter, referred to as Compound Class $SX_{2920}$).

A compound (L-10) wherein n is 2, T represents a group represented by T37, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2921}$).

A compound (L-10) wherein n is 2, T represents a group represented by T37, $R^{3b}$ represents $CF_3$, $R^{3c}$ represents a hydrogen atom, and $R^1$ represents any substituents described in [Table L1] to [Table L3] (hereinafter, referred to as Compound Class $SX_{2922}$).

A compound (L-10) wherein n is 2, T represents a group represented by T37, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2923}$).

A compound (L-10) wherein n is 2, T represents a group represented by T37, $R^{3b}$ represents a bromine atom, $R^{3c}$ represents a hydrogen atom, and $R^1$ represents any substituents described in [Table L1] to [Table L3] (hereinafter, referred to as Compound Class $SX_{2924}$).

A compound (L-10) wherein n is 2, T represents a group represented by T37, $R^{3b}$ represents an iodine atom, $R^{3c}$ represents a hydrogen atom, and $R^1$ represents any substituents described in [Table L1] to [Table L3] (hereinafter, referred to as Compound Class $SX_{2925}$).

A compound (L-10) wherein n is 2, T represents a group represented by T37, $R^{3b}$ represents a hydrogen atom, $R^{3c}$ represents $CF_3$, and $R^1$ represents any substituents described in [Table L1] to [Table L3] (hereinafter, referred to as Compound Class $SX_{2926}$).

A compound (L-10) wherein n is 2, T represents a group represented by T37, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2927}$).

A compound (L-10) wherein n is 2, T represents a group represented by T37, $R^{3b}$ represents a hydrogen atom, $R^{3c}$ represents a bromine atom, and $R^1$ represents any substituents described in [Table L1] to [Table L3] (hereinafter, referred to as Compound Class $SX_{2928}$).

A compound (L-10) wherein n is 0, T represents a group represented by T38, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2929}$).

A compound (L-10) wherein n is 0, T represents a group represented by T38, $R^{3b}$ represents $CF_3$, $R^{3c}$ represents a hydrogen atom, and $R^1$ represents any substituents described in [Table L1] to [Table L3] (hereinafter, referred to as Compound Class $SX_{2930}$).

A compound (L-10) wherein n is 0, T represents a group represented by T38, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2931}$).

A compound (L-10) wherein n is 0, T represents a group represented by T38, $R^{3b}$ represents a bromine atom, $R^{3c}$ represents a hydrogen atom, and $R^1$ represents any substituents described in [Table L1] to [Table L3] (hereinafter, referred to as Compound Class $SX_{2932}$).

A compound (L-10) wherein n is 0, T represents a group represented by T38, $R^{3b}$ represents an iodine atom, $R^{3c}$ represents a hydrogen atom, and $R^1$ represents any substituents described in [Table L1] to [Table L3] (hereinafter, referred to as Compound Class $SX_{2933}$).

A compound (L-10) wherein n is 0, T represents a group represented by T38, $R^{3b}$ represents a hydrogen atom, $R^{3c}$ represents $CF_3$, and $R^1$ represents any substituents described in [Table L1] to [Table L3] (hereinafter, referred to as Compound Class $SX_{2934}$).

A compound (L-10) wherein n is 0, T represents a group represented by T38, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2935}$).

A compound (L-10) wherein n is 0, T represents a group represented by T38, $R^{3b}$ represents a hydrogen atom, $R^{3c}$ represents a bromine atom, and $R^1$ represents any substituents described in [Table L1] to [Table L3] (hereinafter, referred to as Compound Class $SX_{2936}$).

A compound (L-10) wherein n is 1, T represents a group represented by T38, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2937}$).

A compound (L-10) wherein n is 1, T represents a group represented by T38, $R^{3b}$ represents $CF_3$, $R^{3c}$ represents a hydrogen atom, and $R^1$ represents any substituents described in [Table L1] to [Table L3] (hereinafter, referred to as Compound Class $SX_{2938}$).

A compound (L-10) wherein n is 1, T represents a group represented by T38, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2939}$).

A compound (L-10) wherein n is 1, T represents a group represented by T38, $R^{3b}$ represents a bromine atom, $R^{3c}$ represents a hydrogen atom, and $R^1$ represents any substituents described in [Table L1] to [Table L3] (hereinafter, referred to as Compound Class $SX_{2940}$).

A compound (L-10) wherein n is 1, T represents a group represented by T38, $R^{3b}$ represents an iodine atom, $R^{3c}$ represents a hydrogen atom, and $R^1$ represents any substituents described in [Table L1] to [Table L3] (hereinafter, referred to as Compound Class $SX_{2941}$).

A compound (L-10) wherein n is 1, T represents a group represented by T38, $R^{3b}$ represents a hydrogen atom, $R^{3c}$ represents $CF_3$, and $R^1$ represents any substituents described in [Table L1] to [Table L3] (hereinafter, referred to as Compound Class $SX_{2942}$).

A compound (L-10) wherein n is 1, T represents a group represented by T38, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2943}$).

A compound (L-10) wherein n is 1, T represents a group represented by T38, $R^{3b}$ represents a hydrogen atom, $R^{3c}$ represents a bromine atom, and $R^1$ represents any substituents described in [Table L1] to [Table L3] (hereinafter, referred to as Compound Class $SX_{2944}$).

A compound (L-10) wherein n is 2, T represents a group represented by T38, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2945}$).

A compound (L-10) wherein n is 2, T represents a group represented by T38, $R^{3b}$ represents $CF_3$, $R^{3c}$ represents a hydrogen atom, and $R^1$ represents any substituents described in [Table L1] to [Table L3] (hereinafter, referred to as Compound Class $SX_{2946}$).

A compound (L-10) wherein n is 2, T represents a group represented by T38, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2947}$).

A compound (L-10) wherein n is 2, T represents a group represented by T38, $R^{3b}$ represents a bromine atom, $R^{3c}$ represents a hydrogen atom, and $R^1$ represents any substituents described in [Table L1] to [Table L3] (hereinafter, referred to as Compound Class $SX_{2948}$).

A compound (L-10) wherein n is 2, T represents a group represented by T38, $R^{3b}$ represents an iodine atom, $R^{3c}$ represents a hydrogen atom, and $R^1$ represents any substituents described in [Table L1] to [Table L3] (hereinafter, referred to as Compound Class $SX_{2949}$).

A compound (L-10) wherein n is 2, T represents a group represented by T38, $R^{3b}$ represents a hydrogen atom, $R^{3c}$ represents $CF_3$, and $R^1$ represents any substituents described in [Table L1] to [Table L3] (hereinafter, referred to as Compound Class $SX_{2950}$).

A compound (L-10) wherein n is 2, T represents a group represented by T38, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2951}$).

A compound (L-10) wherein n is 2, T represents a group represented by T38, $R^{3b}$ represents a hydrogen atom, $R^{3c}$ represents a bromine atom, and $R^1$ represents any substituents described in [Table L1] to [Table L3] (hereinafter, referred to as Compound Class $SX_{2952}$).

A compound (L-10) wherein n is 0, T represents a group represented by T39, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2953}$).

A compound (L-10) wherein n is 0, T represents a group represented by T39, $R^{3b}$ represents $CF_3$, $R^{3c}$ represents a hydrogen atom, and $R^1$ represents any substituents described in [Table L1] to [Table L3] (hereinafter, referred to as Compound Class $SX_{2954}$).

A compound (L-10) wherein n is 0, T represents a group represented by T39, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2955}$).

A compound (L-10) wherein n is 0, T represents a group represented by T39, $R^{3b}$ represents a bromine atom, $R^{3c}$ represents a hydrogen atom, and $R^1$ represents any substituents described in [Table L1] to [Table L3] (hereinafter, referred to as Compound Class $SX_{2956}$).

A compound (L-10) wherein n is 0, T represents a group represented by T39, $R^{3b}$ represents an iodine atom, $R^{3c}$ represents a hydrogen atom, and $R^1$ represents any substituents described in [Table L1] to [Table L3] (hereinafter, referred to as Compound Class $SX_{2957}$).

A compound (L-10) wherein n is 0, T represents a group represented by T39, $R^{3b}$ represents a hydrogen atom, $R^{3c}$ represents $CF_3$, and $R^1$ represents any substituents described in [Table L1] to [Table L3] (hereinafter, referred to as Compound Class $SX_{2958}$).

A compound (L-10) wherein n is 0, T represents a group represented by T39, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2959}$).

A compound (L-10) wherein n is 0, T represents a group represented by T39, $R^{3b}$ represents a hydrogen atom, $R^{3c}$ represents a bromine atom, and $R^1$ represents any substituents described in [Table L1] to [Table L3] (hereinafter, referred to as Compound Class $SX_{2960}$).

A compound (L-10) wherein n is 1, T represents a group represented by T39, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2961}$).

A compound (L-10) wherein n is 1, T represents a group represented by T39, $R^{3b}$ represents $CF_3$, $R^{3c}$ represents a hydrogen atom, and $R^1$ represents any substituents described in [Table L1] to [Table L3] (hereinafter, referred to as Compound Class $SX_{2962}$).

A compound (L-10) wherein n is 1, T represents a group represented by T39, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2963}$).

A compound (L-10) wherein n is 1, T represents a group represented by T39, $R^{3b}$ represents a bromine atom, $R^{3c}$ represents a hydrogen atom, and $R^1$ represents any substituents described in [Table L1] to [Table L3] (hereinafter, referred to as Compound Class $SX_{2964}$).

A compound (L-10) wherein n is 1, T represents a group represented by T39, $R^{3b}$ represents an iodine atom, $R^{3c}$ represents a hydrogen atom, and $R^1$ represents any substituents described in [Table L1] to [Table L3] (hereinafter, referred to as Compound Class $SX_{2965}$).

A compound (L-10) wherein n is 1, T represents a group represented by T39, $R^{3b}$ represents a hydrogen atom, $R^{3c}$ represents $CF_3$, and $R^1$ represents any substituents described in [Table L1] to [Table L3] (hereinafter, referred to as Compound Class $SX_{2966}$).

A compound (L-10) wherein n is 1, T represents a group represented by T39, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2967}$).

A compound (L-10) wherein n is 1, T represents a group represented by T39, $R^{3b}$ represents a hydrogen atom, $R^{3c}$ represents a bromine atom, and $R^1$ represents any substituents described in [Table L1] to [Table L3] (hereinafter, referred to as Compound Class $SX_{2968}$).

A compound (L-10) wherein n is 2, T represents a group represented by T39, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{2969}$).

A compound (L-10) wherein n is 2, T represents a group represented by T39, $R^{3b}$ represents $CF_3$, $R^{3c}$ represents a hydrogen atom, and $R^1$ represents any substituents described in [Table L1] to [Table L3] (hereinafter, referred to as Compound Class $SX_{2970}$).

A compound (L-10) wherein n is 2, T represents a group represented by T39, $R^{3b}$ represents a chlorine atom, $R^{3c}$ represents a hydrogen atom, and $R^1$ represents any substituents described in [Table L1] to [Table L3] (hereinafter, referred to as Compound Class $SX_{2971}$).

A compound (L-10) wherein n is 2, T represents a group represented by T39, $R^{3b}$ represents a bromine atom, $R^{3c}$ represents a hydrogen atom, and $R^1$ represents any substituents described in [Table L1] to [Table L3] (hereinafter, referred to as Compound Class $SX_{2972}$).

A compound (L-10) wherein n is 2, T represents a group represented by T39, $R^{3b}$ represents an iodine atom, $R^{3c}$ represents a hydrogen atom, and $R^1$ represents any substituents described in [Table L1] to [Table L3] (hereinafter, referred to as Compound Class $SX_{2973}$).

A compound (L-10) wherein n is 2, T represents a group represented by T39, $R^{3b}$ represents a hydrogen atom, $R^{3c}$ represents $CF_3$, and $R^1$ represents any substituents described in [Table L1] to [Table L3] (hereinafter, referred to as Compound Class $SX_{2974}$).

A compound (L-10) wherein n is 2, T represents a group represented by T39, $R^{3b}$ represents a hydrogen atom, $R^{3c}$ represents a chlorine atom, and $R^1$ represents any substituents described in [Table L1] to [Table L3] (hereinafter, referred to as Compound Class $SX_{2975}$).

A compound (L-10) wherein n is 2, T represents a group represented by T39, $R^{3b}$ represents a hydrogen atom, $R^{3c}$ represents a bromine atom, and $R^1$ represents any substituents described in [Table L1] to [Table L3] (hereinafter, referred to as Compound Class $SX_{2976}$).

A compound (L-9) wherein n is 0, T represents a group represented by T37, $R^1$ represents $CF_3$, $R^{3c}$ represents a hydrogen atom, and $R^{3b}$ represents any substituents described in [Table L4] to [Table L12] (hereinafter, referred to as Compound Class $SX_{2977}$).

A compound (L-9) wherein n is 0, T represents a group represented by T37, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{2978}$).

A compound (L-9) wherein n is 0, T represents a group represented by T37, $R^1$ represents $OCF_3$, $R^{3c}$ represents a hydrogen atom, and $R^{3b}$ represents any substituents described in [Table L4] to [Table L12] (hereinafter, referred to as Compound Class $SX_{2979}$).

A compound (L-9) wherein n is 0, T represents a group represented by T37, $R^1$ represents $SCF_3$, $R^{3c}$ represents a hydrogen atom, and $R^{3b}$ represents any substituents described in [Table L4] to [Table L12] (hereinafter, referred to as Compound Class $SX_{2980}$).

A compound (L-9) wherein n is 0, T represents a group represented by T37, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{2981}$).

A compound (L-9) wherein n is 0, T represents a group represented by T37, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{2982}$).

A compound (L-9) wherein n is 1, T represents a group represented by T37, $R^1$ represents $CF_3$, $R^{3c}$ represents a hydrogen atom, and $R^{3b}$ represents any substituents described in [Table L4] to [Table L12] (hereinafter, referred to as Compound Class $SX_{2983}$).

A compound (L-9) wherein n is 1, T represents a group represented by T37, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{2984}$).

A compound (L-9) wherein n is 1, T represents a group represented by T37, $R^1$ represents $OCF_3$, $R^{3c}$ represents a hydrogen atom, and $R^{3b}$ represents any substituents described in [Table L4] to [Table L12] (hereinafter, referred to as Compound Class $SX_{2985}$).

A compound (L-9) wherein n is 1, T represents a group represented by T37, $R^1$ represents $SCF_3$, $R^{3c}$ represents a hydrogen atom, and $R^{3b}$ represents any substituents described in [Table L4] to [Table L12] (hereinafter, referred to as Compound Class $SX_{2986}$).

A compound (L-9) wherein n is 1, T represents a group represented by T37, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{2987}$).

A compound (L-9) wherein n is 1, T represents a group represented by T37, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{2988}$).

A compound (L-9) wherein n is 2, T represents a group represented by T37, $R^1$ represents $CF_3$, $R^{3c}$ represents a hydrogen atom, and $R^{3b}$ represents any substituents described in [Table L4] to [Table L12] (hereinafter, referred to as Compound Class $SX_{2989}$).

A compound (L-9) wherein n is 2, T represents a group represented by T37, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{2990}$).

A compound (L-9) wherein n is 2, T represents a group represented by T37, $R^1$ represents $OCF_3$, $R^{3c}$ represents a hydrogen atom, and $R^{3b}$ represents any substituents described in [Table L4] to [Table L12] (hereinafter, referred to as Compound Class $SX_{2991}$).

A compound (L-9) wherein n is 2, T represents a group represented by T37, $R^1$ represents $SCF_3$, $R^{3c}$ represents a hydrogen atom, and $R^{3b}$ represents any substituents described in [Table L4] to [Table L12] (hereinafter, referred to as Compound Class $SX_{2992}$).

A compound (L-9) wherein n is 2, T represents a group represented by T37, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{2993}$).

A compound (L-9) wherein n is 2, T represents a group represented by T37, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{2994}$).

A compound (L-9) wherein n is 0, T represents a group represented by T38, $R^1$ represents $CF_3$, $R^{3c}$ represents a hydrogen atom, and $R^{3b}$ represents any substituents described in [Table L4] to [Table L12] (hereinafter, referred to as Compound Class $SX_{2995}$).

A compound (L-9) wherein n is 0, T represents a group represented by T38, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{2996}$).

A compound (L-9) wherein n is 0, T represents a group represented by T38, $R^1$ represents $OCF_3$, $R^{3c}$ represents a hydrogen atom, and $R^{3b}$ represents any substituents described in [Table L4] to [Table L12] (hereinafter, referred to as Compound Class $SX_{2997}$).

A compound (L-9) wherein n is 0, T represents a group represented by T38, $R^1$ represents $SCF_3$, $R^{3c}$ represents a hydrogen atom, and $R^{3b}$ represents any substituents described in [Table L4] to [Table L12] (hereinafter, referred to as Compound Class $SX_{2998}$).

A compound (L-9) wherein n is 0, T represents a group represented by T38, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{2999}$).

A compound (L-9) wherein n is 0, T represents a group represented by T38, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3000}$).

A compound (L-9) wherein n is 1, T represents a group represented by T38, $R^1$ represents $CF_3$, $R^{3c}$ represents a hydrogen atom, and $R^{3b}$ represents any substituents described in [Table L4] to [Table L12] (hereinafter, referred to as Compound Class $SX_{3001}$).

A compound (L-9) wherein n is 1, T represents a group represented by T38, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3002}$).

A compound (L-9) wherein n is 1, T represents a group represented by T38, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3003}$).

A compound (L-9) wherein n is 1, T represents a group represented by T38, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3004}$).

A compound (L-9) wherein n is 1, T represents a group represented by T38, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3005}$).

A compound (L-9) wherein n is 1, T represents a group represented by T38, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3006}$).

A compound (L-9) wherein n is 2, T represents a group represented by T38, $R^1$ represents $CF_3$, $R^{3c}$ represents a hydrogen atom, and $R^{3b}$ represents any substituents described in [Table L4] to [Table L12] (hereinafter, referred to as Compound Class $SX_{3007}$).

A compound (L-9) wherein n is 2, T represents a group represented by T38, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3008}$).

A compound (L-9) wherein n is 2, T represents a group represented by T38, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3009}$).

A compound (L-9) wherein n is 2, T represents a group represented by T38, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3010}$).

A compound (L-9) wherein n is 2, T represents a group represented by T38, $R^1$ represents $S(O)CF_3$, $R^{3b}$ represents a hydrogen atom, and $R^{3b}$ represents any substituents described in [Table L4] to [Table L12] (hereinafter, referred to as Compound Class $SX_{3011}$).

A compound (L-9) wherein n is 2, T represents a group represented by T38, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3012}$).

A compound (L-9) wherein n is 0, T represents a group represented by T39, $R^1$ represents $CF_3$, $R^{3c}$ represents a hydrogen atom, and $R^{3b}$ represents any substituents described in [Table L4] to [Table L12] (hereinafter, referred to as Compound Class $SX_{3013}$).

A compound (L-9) wherein n is 0, T represents a group represented by T39, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3014}$).

A compound (L-9) wherein n is 0, T represents a group represented by T39, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3015}$).

A compound (L-9) wherein n is 0, T represents a group represented by T39, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3016}$).

A compound (L-9) wherein n is 0, T represents a group represented by T39, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3017}$).

A compound (L-9) wherein n is 0, T represents a group represented by T39, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3018}$).

A compound (L-9) wherein n is 1, T represents a group represented by T39, $R^1$ represents $CF_3$, $R^{3c}$ represents a hydrogen atom, and $R^{3b}$ represents any substituents described in [Table L4] to [Table L12] (hereinafter, referred to as Compound Class $SX_{3019}$).

A compound (L-9) wherein n is 1, T represents a group represented by T39, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3020}$).

A compound (L-9) wherein n is 1, T represents a group represented by T39, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3021}$).

A compound (L-9) wherein n is 1, T represents a group represented by T39, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3022}$).

A compound (L-9) wherein n is 1, T represents a group represented by T39, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3023}$).

A compound (L-9) wherein n is 1, T represents a group represented by T39, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3024}$).

A compound (L-9) wherein n is 2, T represents a group represented by T39, $R^1$ represents $CF_3$, $R^{3c}$ represents a hydrogen atom, and $R^{3b}$ represents any substituents described in [Table L4] to [Table L12] (hereinafter, referred to as Compound Class $SX_{3025}$).

A compound (L-9) wherein n is 2, T represents a group represented by T39, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3026}$).

A compound (L-9) wherein n is 2, T represents a group represented by T39, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3027}$).

A compound (L-9) wherein n is 2, T represents a group represented by T39, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3028}$.

A compound (L-9) wherein n is 2, T represents a group represented by T39, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3029}$).

A compound (L-9) wherein n is 2, T represents a group represented by T39, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3030}$).

A compound (L-10) wherein n is 0, T represents a group represented by T37, $R^1$ represents $CF_3$, $R^{3c}$ represents a hydrogen atom, and $R^{3b}$ represents any substituents described in [Table L4] to [Table L12] (hereinafter, referred to as Compound Class $SX_{3031}$).

A compound (L-10) wherein n is 0, T represents a group represented by T37, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3032}$).

A compound (L-10) wherein n is 0, T represents a group represented by T37, $R^1$ represents $OCF_3$, $R^{3c}$ represents a hydrogen atom, and $R^{3b}$ represents any substituents described Compound Class $SX_{3033}$).

A compound (L-10) wherein n is 0, T represents a group represented by T37, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3034}$).

A compound (L-10) wherein n is 0, T represents a group represented by T37, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3035}$).

A compound (L-10) wherein n is 0, T represents a group represented by T37, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3036}$).

A compound (L-10) wherein n is 1, T represents a group represented by T37, $R^1$ represents $CF_3$, $R^{3c}$ represents a hydrogen atom, and $R^{3b}$ represents any substituents described in [Table L4] to [Table L12] (hereinafter, referred to as Compound Class $SX_{3037}$).

A compound (L-10) wherein n is 1, T represents a group represented by T37, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3038}$).

A compound (L-10) wherein n is 1, T represents a group represented by T37, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3039}$).

A compound (L-10) wherein n is 1, T represents a group represented by T37, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3040}$).

A compound (L-10) wherein n is 1, T represents a group represented by T37, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3041}$).

A compound (L-10) wherein n is 1, T represents a group represented by T37, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3042}$).

A compound (L-10) wherein n is 2, T represents a group represented by T37, $R^1$ represents $CF_3$, $R^{3c}$ represents a hydrogen atom, and $R^{3b}$ represents any substituents described in [Table L4] to [Table L12] (hereinafter, referred to as Compound Class $SX_{3043}$).

A compound (L-10) wherein n is 2, T represents a group represented by T37, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3044}$).

A compound (L-10) wherein n is 2, T represents a group represented by T37, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3045}$).

A compound (L-10) wherein n is 2, T represents a group represented by T37, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3046}$).

A compound (L-10) wherein n is 2, T represents a group represented by T37, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3047}$).

A compound (L-10) wherein n is 0, T represents a group represented by T37, $R^1$ represents $S(O)_2CF_3$, $R^{3c}$ represents a hydrogen atom, and $R^{3b}$ represents any substituents described Compound Class $SX_{3048}$).

A compound (L-10) wherein n is 0, T represents a group represented by T38, $R^1$ represents $CF_3$, $R^{3c}$ represents a hydrogen atom, and $R^{3b}$ represents any substituents described in [Table L4] to [Table L12] (hereinafter, referred to as Compound Class $SX_{3049}$).

A compound (L-10) wherein n is 0, T represents a group represented by T38, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3050}$).

A compound (L-10) wherein n is 0, T represents a group represented by T38, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3051}$).

A compound (L-10) wherein n is 0, T represents a group represented by T38, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3052}$).

A compound (L-10) wherein n is 0, T represents a group represented by T38, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3053}$).

A compound (L-10) wherein n is 0, T represents a group represented by T38, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3054}$).

A compound (L-10) wherein n is 1, T represents a group represented by T38, $R^1$ represents $CF_3$, $R^{3c}$ represents a hydrogen atom, and $R^{3b}$ represents any substituents described in [Table L4] to [Table L12] (hereinafter, referred to as Compound Class $SX_{3055}$).

A compound (L-10) wherein n is 1, T represents a group represented by T38, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3056}$).

A compound (L-10) wherein n is 1, T represents a group represented by T38, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3057}$).

A compound (L-10) wherein n is 1, T represents a group represented by T38, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3058}$).

A compound (L-10) wherein n is 1, T represents a group represented by T38, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3059}$).

A compound (L-10) wherein n is 1, T represents a group represented by T38, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3060}$).

A compound (L-10) wherein n is 2, T represents a group represented by T38, $R^1$ represents $CF_3$, $R^{3c}$ represents a hydrogen atom, and $R^{3b}$ represents any substituents described in [Table L4] to [Table L12] (hereinafter, referred to as Compound Class $SX_{3061}$).

A compound (L-10) wherein n is 2, T represents a group represented by T38, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3062}$).

A compound (L-10) wherein n is 2, T represents a group represented by T38, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3063}$).

A compound (L-10) wherein n is 2, T represents a group represented by T38, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3064}$).

A compound (L-10) wherein n is 2, T represents a group represented by T38, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3065}$).

A compound (L-10) wherein n is 2, T represents a group represented by T38, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3066}$).

A compound (L-10) wherein n is 0, T represents a group represented by T39, $R^1$ represents $CF_3$, $R^{3c}$ represents a hydrogen atom, and $R^{3b}$ represents any substituents described in [Table L4] to [Table L12] (hereinafter, referred to as Compound Class $SX_{3067}$).

A compound (L-10) wherein n is 0, T represents a group represented by T39, $R^1$ represents $C_2F_5$, $R^{3c}$ represents a hydrogen atom, and $R^{3b}$ represents any substituents described Compound Class $SX_{3068}$).

A compound (L-10) wherein n is 0, T represents a group represented by T39, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3069}$).

A compound (L-10) wherein n is 0, T represents a group represented by T39, $R^1$ represents $SCF_3$, $R^{3b}$ represents a hydrogen atom, and $R^{3b}$ represents any substituents described in [Table L4] to [Table L12] (hereinafter, referred to as Compound Class $SX_{3070}$).

A compound (L-10) wherein n is 0, T represents a group represented by T39, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3071}$).

A compound (L-10) wherein n is 0, T represents a group represented by T39, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3072}$).

A compound (L-10) wherein n is 1, T represents a group represented by T39, $R^1$ represents $CF_3$, $R^{3c}$ represents a hydrogen atom, and $R^{3b}$ represents any substituents described in [Table L4] to [Table L12] (hereinafter, referred to as Compound Class $SX_{3073}$).

A compound (L-10) wherein n is 1, T represents a group represented by T39, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3074}$).

A compound (L-10) wherein n is 1, T represents a group represented by T39, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3075}$).

A compound (L-10) wherein n is 1 T represents a group represented by T39, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3076}$).

A compound (L-10) wherein n is 1, T represents a group represented by T39, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3077}$).

A compound (L-10) wherein n is 1, T represents a group represented by T39, $R^1$ represents $S(O)_2CF_3$, $R^{3c}$ represents a hydrogen atom, and $R^{3b}$ represents any substituents described in [Table L4] to [Table L12] hereinafter, referred to as Compound Class $SX_{3078}$).

A compound (L-10) wherein n is 2, T represents a group represented by T39, $R^1$ represents $CF_3$, $R^{3c}$ represents a hydrogen atom, and $R^{3b}$ represents any substituents described in [Table L4] to [Table L12] (hereinafter, referred to as Compound Class $SX_{3079}$).

A compound (L-10) wherein n is 2, T represents a group represented by T39, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3080}$).

A compound (L-10) wherein n is 2, T represents a group represented by T39, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3081}$).

A compound (L-10) wherein n is 2, T represents a group represented by T39, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3082}$).

A compound (L-10) wherein n is 2, T represents a group represented by T39, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3083}$).

A compound (L-10) wherein n is 2, T represents a group represented by T39, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3084}$).

A compound represented by formula (L-11):

(L-11)

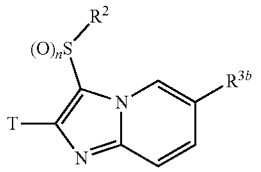

(hereinafter, referred to as Compound (L-11)), wherein T represents a group represented by T37, $R^1$ represents $CF_3$, n is 0, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3085}$).

A compound (L-11) wherein T represents a group represented by T37, $R^1$ represents $CF_3$, n is 1, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3086}$).

A compound (L-11) wherein T represents a group represented by T37, $R^1$ represents $CF_3$, n is 2, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3087}$).

A compound (L-11) wherein T represents a group represented by T38, $R^1$ represents $CF_3$, n is 0, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3088}$).

A compound (L-11) wherein T represents a group represented by T38, $R^1$ represents $CF_3$, n is 1, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3089}$).

A compound (L-11) wherein T represents a group represented by T38, $R^1$ represents $CF_3$, n is 2, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3090}$).

A compound (L-11) wherein T represents a group represented by T39, $R^1$ represents $CF_3$, n is 0, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3091}$).

A compound (L-11) wherein T represents a group represented by T39, $R^1$ represents $CF_3$, n is 1, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3092}$).

A compound (L-11) wherein T represents a group represented by T39, $R^1$ represents $CF_3$, n is 2, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3093}$).

A compound (L-11) wherein T represents a group represented by T37, $R^1$ represents $C_2F_5$, n is 0, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3094}$).

A compound (L-11) wherein T represents a group represented by T37, $R^1$ represents $C_2F_5$, n is 1, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3095}$).

A compound (L-11) wherein T represents a group represented by T37, $R^1$ represents $C_2F_5$, n is 2, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3096}$).

A compound (L-11) wherein T represents a group represented by T38, $R^1$ represents $C_2F_5$, n is 0, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3097}$).

A compound (L-11) wherein T represents a group represented by T38, $R^1$ represents $C_2F_5$, n is 1, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3098}$).

A compound (L-11) wherein T represents a group represented by T38, $R^1$ represents $C_2F_5$, n is 2, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3099}$).

A compound (L-11) wherein T represents a group represented by T39, $R^1$ represents $C_2F_5$, n is 0, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3100}$).

A compound (L-11) wherein T represents a group represented by T39, $R^1$ represents $C_2F_5$, n is 1, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3101}$).

A compound (L-11) wherein T represents a group represented by T39, $R^1$ represents $C_2F_5$, n is 2, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3102}$).

A compound (L-11) wherein T represents a group represented by T37, $R^1$ represents $SCF_3$, n is 0, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3103}$).

A compound (L-11) wherein T represents a group represented by T37, $R^1$ represents $SCF_3$, n is 1, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3104}$).

A compound (L-11) wherein T represents a group represented by T37, $R^1$ represents $SCF_3$, n is 2, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3105}$).

A compound (L-11) wherein T represents a group represented by T38, $R^1$ represents $SCF_3$, n is 0, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3106}$).

A compound (L-11) wherein T represents a group represented by T38, $R^1$ represents $SCF_3$, n is 1, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3107}$).

A compound (L-11) wherein T represents a group represented by T38, $R^1$ represents $SCF_3$, n is 2, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3108}$).

A compound (L-11) wherein T represents a group represented by T39, $R^1$ represents $SCF_3$, n is 0, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3109}$).

A compound (L-11) wherein T represents a group represented by T39, $R^1$ represents $SCF_3$, n is 1, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3110}$).

A compound (L-11) wherein T represents a group represented by T39, $R^1$ represents $SCF_3$, n is 2, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3111}$).

A compound (L-11) wherein T represents a group represented by T37, $R^1$ represents $S(O)CF_3$, n is 0, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3112}$).

A compound (L-11) wherein T represents a group represented by T37, $R^1$ represents $S(O)CF_3$, n is 1, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3113}$).

A compound (L-11) wherein T represents a group represented by T37, $R^1$ represents $S(O)CF_3$, n is 2, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3114}$).

A compound (L-11) wherein T represents a group represented by T38, $R^1$ represents $S(O)CF_3$, n is 0, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3115}$).

A compound (L-11) wherein T represents a group represented by T38, $R^1$ represents $S(O)CF_3$, n is 1, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3116}$).

A compound (L-11) wherein T represents a group represented by T38, $R^1$ represents $S(O)CF_3$, n is 2, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3117}$).

A compound (L-11) wherein T represents a group represented by T39, $R^1$ represents $S(O)CF_3$, n is 0, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3118}$).

A compound (L-11) wherein T represents a group represented by T39, $R^1$ represents $S(O)CF_3$, n is 1, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3119}$).

A compound (L-11) wherein T represents a group represented by T39, $R^1$ represents $S(O)CF_3$, n is 2, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3120}$).

A compound (L-11) wherein T represents a group represented by T37, $R^1$ represents $S(O)_2CF_3$, n is 0, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3121}$).

A compound (L-11) wherein T represents a group represented by T37, $R^1$ represents $S(O)_2CF_3$, n is 1, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3122}$).

A compound (L-11) wherein T represents a group represented by T37, $R^1$ represents $S(O)_2CF_3$, n is 2, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3123}$).

A compound (L-11) wherein T represents a group represented by T38, $R^1$ represents $S(O)_2CF_3$, n is 0, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3124}$).

A compound (L-11) wherein T represents a group represented by T38, $R^1$ represents $S(O)_2CF_3$, n is 1, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3125}$).

A compound (L-11) wherein T represents a group represented by T38, $R^1$ represents $S(O)_2CF_3$, n is 2, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3126}$).

A compound (L-11) wherein T represents a group represented by T39, $R^1$ represents $S(O)_2CF_3$, n is 0, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3127}$).

A compound (L-11) wherein T represents a group represented by T39, $R^1$ represents $S(O)_2CF_3$, n is 1, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3128}$).

A compound (L-11) wherein T represents a group represented by T39, $R^1$ represents $S(O)_2CF_3$, n is 2, $R^2$ represents a methyl group, and $R^{3b}$ represents a hydrogen atom, a chlorine atom, $CF_3$, or any substituents described in [Table L4] to [Table L12] (hereinafter, referred to as Compound Class $SX_{3129}$).

A compound represented by formula (L-12):

(L-12)

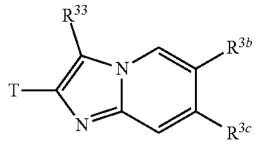

(hereinafter, referred to as Compound (L-12)), wherein $R^{33}$ represents a hydrogen atom, T represents a group represented by T1, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3130}$).

A compound (L-12) wherein $R^{33}$ represents a hydrogen atom, T represents a group represented by T1, $R^{3b}$ represents $CF_3$, $R^{3c}$ represents a hydrogen atom, and $R^1$ represents any substituents described in [Table L1] to [Table L3] (hereinafter, referred to as Compound Class $SX_{3131}$).

A compound (L-12) wherein $R^{33}$ represents a hydrogen atom, T represents a group represented by T1, $R^{3b}$ represents $CF_3$, $R^{3c}$ represents a chlorine atom, and $R^1$ represents any substituents described in [Table L1] to [Table L3] (hereinafter, referred to as Compound Class $SX_{3132}$).

A compound (L-12) wherein $R^{33}$ represents a hydrogen atom, T represents a group represented by T1, $R^{3b}$ represents $CF_3$, $R^{3c}$ represents a bromine atom, and $R^1$ represents any substituents described in [Table L1] to [Table L3] (hereinafter, referred to as Compound Class $SX_{3133}$).

A compound (L-12) wherein $R^{33}$ represents a hydrogen atom, T represents a group represented by T1, $R^{3b}$ represents $CF_3$, $R^{3c}$ represents an iodine atom, and $R^1$ represents any substituents described in [Table L1] to [Table L3] (hereinafter, referred to as Compound Class $SX_{3134}$).

A compound (L-12) wherein $R^{33}$ represents a hydrogen atom, T represents a group represented by T1, $R^{3b}$ represents a hydrogen atom, $R^{3c}$ represents $CF_3$, and $R^1$ represents any substituents described in [Table L1] to [Table L3] (hereinafter, referred to as Compound Class $SX_{3135}$).

A compound (L-12) wherein $R^{33}$ represents a hydrogen atom, T represents a group represented by T1, $R^{3b}$ represents a hydrogen atom, $R^{3c}$ represents a chorine atom, and $R^1$ represents any substituents described in [Table L1] to [Table L3] (hereinafter, referred to as Compound Class $SX_{3136}$).

A compound (L-12) wherein $R^{33}$ represents a hydrogen atom, T represents a group represented by T1, $R^{3b}$ represents a hydrogen atom, $R^{3c}$ represents a bromine atom, and $R^1$ represents any substituents described in [Table L1] to [Table L3] (hereinafter, referred to as Compound Class $SX_{3137}$).

A compound (L-12) wherein $R^{33}$ represents a fluorine atom, T represents a group represented by T1, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3138}$).

A compound (L-12) wherein $R^{33}$ represents a fluorine atom, T represents a group represented by T1, $R^{3b}$ represents $CF_3$, $R^{3c}$ represents a hydrogen atom, and $R^1$ represents any substituents described in [Table L1] to [Table L3] (hereinafter, referred to as Compound Class $SX_{3139}$).

A compound (L-12) wherein $R^{33}$ represents a fluorine atom, T represents a group represented by T1, $R^{3b}$ represents $CF_3$, $R^{3c}$ represents a chlorine atom, and $R^1$ represents any substituents described in [Table L1] to [Table L3] (hereinafter, referred to as Compound Class $SX_{3140}$).

A compound (L-12) wherein $R^{33}$ represents a fluorine atom, T represents a group represented by T1, $R^{3b}$ represents $CF_3$, $R^{3c}$ represents a bromine atom, and $R^1$ represents any substituents described in [Table L1] to [Table L3] (hereinafter, referred to as Compound Class $SX_{3141}$).

A compound (L-12) wherein $R^{33}$ represents a fluorine atom, T represents a group represented by T1, $R^{3b}$ represents $CF_3$, $R^{3c}$ represents an iodine atom, and $R^1$ represents any substituents described in [Table L1] to [Table L3] (hereinafter, referred to as Compound Class $SX_{3142}$).

A compound (L-12) wherein $R^{33}$ represents a fluorine atom, T represents a group represented by T1, $R^{3b}$ represents a hydrogen atom, $R^{3c}$ represents $CF_3$, and $R^1$ represents any substituents described in [Table L1] to [Table L3] (hereinafter, referred to as Compound Class $SX_{3143}$).

A compound (L-12) wherein $R^{33}$ represents a fluorine atom, T represents a group represented by T1, $R^{3b}$ represents a hydrogen atom, $R^{3c}$ represents a chorine atom, and $R^1$ represents any substituents described in [Table L1] to [Table L3] (hereinafter, referred to as Compound Class $SX_{3144}$).

A compound (L-12) wherein $R^{33}$ represents a fluorine atom, T represents a group represented by T1, $R^{3b}$ represents a hydrogen atom, $R^{3c}$ represents a bromine atom, and $R^1$ represents any substituents described in [Table L1] to [Table L3] (hereinafter, referred to as Compound Class $SX_{3145}$).

A compound (L-12) wherein $R^{33}$ represents a chlorine atom, T represents a group represented by T1, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3146}$).

A compound (L-12) wherein $R^{33}$ represents a chlorine atom, T represents a group represented by T1, $R^1$ represents $CF_3$, $R^{3c}$ represents a hydrogen atom, and $R^1$ represents any substituents described in [Table L1] to [Table L3] (hereinafter, referred to as Compound Class $SX_{3147}$).

A compound (L-12) wherein $R^{33}$ represents a chlorine atom, T represents a group represented by T1, $R^{3b}$ represents $CF_3$, $R^{3c}$ represents a chlorine atom, and $R^1$ represents any substituents described in [Table L1] to [Table L3] (hereinafter, referred to as Compound Class $SX_{3148}$).

A compound (L-12) wherein $R^{33}$ represents a chlorine atom, T represents a group represented by T1, $R^{3b}$ represents $CF_3$, $R^{3c}$ represents a bromine atom, and $R^1$ represents any substituents described in [Table L1] to [Table L3] (hereinafter, referred to as Compound Class $SX_{3149}$).

A compound (L-12) wherein $R^{33}$ represents a chlorine atom, T represents a group represented by T1, $R^{3b}$ represents $CF_3$, $R^{3c}$ represents an iodine atom, and $R^1$ represents any substituents described in [Table L1] to [Table L3] (hereinafter, referred to as Compound Class $SX_{3150}$).

A compound (L-12) wherein $R^{33}$ represents a chlorine atom, T represents a group represented by T1, $R^{3b}$ represents a hydrogen atom, $R^{3c}$ represents $CF_3$, and $R^1$ represents any substituents described in [Table L1] to [Table L3] (hereinafter, referred to as Compound Class $SX_{3151}$).

A compound (L-12) wherein $R^{33}$ represents a chlorine atom, T represents a group represented by T1, $R^{3b}$ represents a hydrogen atom, $R^{3c}$ represents a chorine atom, and $R^1$ represents any substituents described in [Table L1] to [Table L3] (hereinafter, referred to as Compound Class $SX_{3152}$).

A compound (L-12) wherein $R^{33}$ represents a chlorine atom, T represents a group represented by T1, $R^{3b}$ represents a hydrogen atom, $R^{3c}$ represents a bromine atom, and $R^1$ represents any substituents described in [Table L1] to [Table L3] (hereinafter, referred to as Compound Class $SX_{3153}$).

A compound (L-12) wherein $R^{33}$ represents a bromine atom, T represents a group represented by T1, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3154}$).

A compound (L-12) wherein $R^{33}$ represents a bromine atom, T represents a group represented by T1, $R^{3b}$ represents $CF_3$, $R^{3c}$ represents a hydrogen atom, and $R^1$ represents any substituents described in [Table L1] to [Table L3] (hereinafter, referred to as Compound Class $SX_{3155}$).

A compound (L-12) wherein $R^{33}$ represents a bromine atom, T represents a group represented by T1, $R^{3b}$ represents $CF_3$, $R^{3c}$ represents a chlorine atom, and $R^1$ represents any substituents described in [Table L1] to [Table L3] (hereinafter, referred to as Compound Class $SX_{3156}$).

A compound (L-12) wherein $R^{33}$ represents a bromine atom, T represents a group represented by T1, $R^{3b}$ represents $CF_3$, $R^{3c}$ represents a bromine atom, and $R^1$ represents any substituents described in [Table L1] to [Table L3] (hereinafter, referred to as Compound Class $SX_{3157}$).

A compound (L-12) wherein $R^{33}$ represents a bromine atom, T represents a group represented by T1, $R^{3b}$ represents $CF_3$, $R^{3c}$ represents an iodine atom, and $R^1$ represents any substituents described in [Table L1] to [Table L3] (hereinafter, referred to as Compound Class $SX_{3158}$).

A compound (L-12) wherein $R^{33}$ represents a bromine atom, T represents a group represented by T1, $R^{3b}$ represents a hydrogen atom, $R^{3c}$ represents $CF_3$, and $R^1$ represents any substituents described in [Table L1] to [Table L3] (hereinafter, referred to as Compound Class $SX_{3159}$).

A compound (L-12) wherein $R^{33}$ represents a bromine atom, T represents a group represented by T1, $R^{3b}$ represents a hydrogen atom, $R^{3c}$ represents a chorine atom, and $R^1$ represents any substituents described in [Table L1] to [Table L3] (hereinafter, referred to as Compound Class $SX_{3160}$).

A compound (L-12) wherein $R^{33}$ represents a bromine atom, T represents a group represented by T1, $R^{3b}$ represents a hydrogen atom, $R^{3c}$ represents a bromine atom, and $R^1$ represents any substituents described in [Table L1] to [Table L3] (hereinafter, referred to as Compound Class $SX_{3161}$).

A compound (L-12) wherein $R^{33}$ represents an iodine atom, T represents a group represented by T1, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3162}$).

A compound (L-12) wherein $R^{33}$ represents an iodine atom, T represents a group represented by T1, $R^{3b}$ represents $CF_3$, $R^{3c}$ represents a hydrogen atom, and $R^1$ represents any substituents described in [Table L1] to [Table L3] (hereinafter, referred to as Compound Class $SX_{3163}$).

A compound (L-12) wherein $R^{33}$ represents an iodine atom, T represents a group represented by T1, $R^{3b}$ represents $CF_3$, $R^{3c}$ represents a chlorine atom, and $R^1$ represents any substituents described in [Table L1] to [Table L3] (hereinafter, referred to as Compound Class $SX_{3164}$).

A compound (L-12) wherein $R^{33}$ represents an iodine atom, T represents a group represented by T1, $R^{3b}$ represents $CF_3$, $R^{3c}$ represents a bromine atom, and $R^1$ represents any substituents described in [Table L1] to [Table L3] (hereinafter, referred to as Compound Class $SX_{3165}$).

A compound (L-12) wherein $R^{33}$ represents an iodine atom, T represents a group represented by T1, $R^{3b}$ represents $CF_3$, $R^{3c}$ represents an iodine atom, and $R^1$ represents any substituents described in [Table L1] to [Table L3] (hereinafter, referred to as Compound Class $SX_{3166}$).

A compound (L-12) wherein $R^{33}$ represents an iodine atom, T represents a group represented by T1, $R^{3b}$ represents a hydrogen atom, $R^{3c}$ represents $CF_3$, and $R^1$ represents any substituents described in [Table L1] to [Table L3] (hereinafter, referred to as Compound Class $SX_{3167}$).

A compound (L-12) wherein $R^{33}$ represents an iodine atom, T represents a group represented by T1, $R^{3b}$ represents a hydrogen atom, $R^{3c}$ represents a chorine atom, and $R^1$ represents any substituents described in [Table L1] to [Table L3] (hereinafter, referred to as Compound Class $SX_{3168}$).

A compound (L-12) wherein $R^{33}$ represents an iodine atom, T represents a group represented by T1, $R^{3b}$ represents a hydrogen atom, $R^{3c}$ represents a bromine atom, and $R^1$ represents any substituents described in [Table L1] to [Table L3] (hereinafter, referred to as Compound Class $SX_{3169}$).

A compound (L-12) wherein $R^{33}$ represents a hydrogen atom, T represents a group represented by T2, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3170}$).

A compound (L-12) wherein $R^{33}$ represents a hydrogen atom, T represents a group represented by T2, $R^{3b}$ represents $CF_3$, $R^{3c}$ represents a hydrogen atom, and $R^1$ represents any substituents described in [Table L1] to [Table L3] (hereinafter, referred to as Compound Class $SX_{3171}$).

A compound (L-12) wherein $R^{33}$ represents a hydrogen atom, T represents a group represented by T2, $R^{3b}$ represents $CF_3$, $R^{3c}$ represents a chlorine atom, and $R^1$ represents any substituents described in [Table L1] to [Table L3] (hereinafter, referred to as Compound Class $SX_{3172}$).

A compound (L-12) wherein $R^{33}$ represents a hydrogen atom, T represents a group represented by T2, $R^{3b}$ represents $CF_3$, $R^{3c}$ represents a bromine atom, and $R^1$ represents any substituents described in [Table L1] to [Table L3] (hereinafter, referred to as Compound Class $SX_{3173}$).

A compound (L-12) wherein $R^{33}$ represents a hydrogen atom, T represents a group represented by T2, $R^{3b}$ represents $CF_3$, $R^{3c}$ represents an iodine atom, and $R^1$ represents any substituents described in [Table L1] to [Table L3] (hereinafter, referred to as Compound Class $SX_{3174}$).

A compound (L-12) wherein $R^{33}$ represents a hydrogen atom, T represents a group represented by T2, $R^{3b}$ represents a hydrogen atom, $R^{3c}$ represents $CF_3$, and $R^1$ represents any substituents described in [Table L1] to [Table L3] (hereinafter, referred to as Compound Class $SX_{3175}$).

A compound (L-12) wherein $R^{33}$ represents a hydrogen atom, T represents a group represented by T2, $R^{3b}$ represents a hydrogen atom, $R^{3c}$ represents a chorine atom, and $R^1$ represents any substituents described in [Table L1] to [Table L3] (hereinafter, referred to as Compound Class $SX_{3176}$).

A compound (L-12) wherein $R^{33}$ represents a hydrogen atom, T represents a group represented by T2, $R^{3b}$ represents a hydrogen atom, $R^{3c}$ represents a bromine atom, and $R^1$ represents any substituents described in [Table L1] to [Table L3] (hereinafter, referred to as Compound Class $SX_{3177}$).

A compound (L-12) wherein $R^{33}$ represents a fluorine atom, T represents a group represented by T2, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3178}$).

A compound (L-12) wherein $R^{33}$ represents a fluorine atom, T represents a group represented by T2, $R^{3b}$ represents $CF_3$, $R^{3c}$ represents a hydrogen atom, and $R^1$ represents any substituents described in [Table L1] to [Table L3] (hereinafter, referred to as Compound Class $SX_{3179}$).

A compound (L-12) wherein $R^{33}$ represents a fluorine atom, T represents a group represented by T2, $R^{3b}$ represents $CF_3$, $R^{3c}$ represents a chlorine atom, and $R^1$ represents any substituents described in [Table L1] to [Table L3] (hereinafter, referred to as Compound Class $SX_{3180}$).

A compound (L-12) wherein $R^{33}$ represents a fluorine atom, T represents a group represented by T2, $R^{3b}$ represents $CF_3$, $R^{3c}$ represents a bromine atom, and $R^1$ represents any substituents described in [Table L1] to [Table L3] (hereinafter, referred to as Compound Class $SX_{3181}$).

A compound (L-12) wherein $R^{33}$ represents a fluorine atom, T represents a group represented by T2, $R^{3b}$ represents $CF_3$, $R^{3c}$ represents an iodine atom, and $R^1$ represents any substituents described in [Table L1] to [Table L3] (hereinafter, referred to as Compound Class $SX_{3182}$).

A compound (L-12) wherein $R^{33}$ represents a fluorine atom, T represents a group represented by T2, $R^{3b}$ represents a hydrogen atom, $R^{3c}$ represents $CF_3$, and $R^1$ represents any substituents described in [Table L1] to [Table L3] (hereinafter, referred to as Compound Class $SX_{3183}$).

A compound (L-12) wherein $R^{33}$ represents a fluorine atom, T represents a group represented by T2, $R^{3b}$ represents a hydrogen atom, $R^{3c}$ represents a chorine atom, and $R^1$ represents any substituents described in [Table L1] to [Table L3] (hereinafter, referred to as Compound Class $SX_{3184}$).

A compound (L-12) wherein $R^{33}$ represents a fluorine atom, T represents a group represented by T2, $R^{3b}$ represents a hydrogen atom, $R^{3c}$ represents a bromine atom, and $R^1$ represents any substituents described in [Table L1] to [Table L3] (hereinafter, referred to as Compound Class $SX_{3185}$).

A compound (L-12) wherein $R^{33}$ represents a chlorine atom, T represents a group represented by T2, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3186}$).

A compound (L-12) wherein $R^{33}$ represents a chlorine atom, T represents a group represented by T2, $R^{3b}$ represents $CF_3$, $R^{3c}$ represents a hydrogen atom, and $R^1$ represents any substituents described in [Table L1] to [Table L3] (hereinafter, referred to as Compound Class $SX_{3187}$).

A compound (L-12) wherein $R^{33}$ represents a chlorine atom, T represents a group represented by T2, $R^{3b}$ represents $CF_3$, $R^{3c}$ represents a chlorine atom, and $R^1$ represents any substituents described in [Table L1] to [Table L3] (hereinafter, referred to as Compound Class $SX_{3187}$).

A compound (L-12) wherein $R^{33}$ represents a chlorine atom, T represents a group represented by T2, $R^{3b}$ represents $CF_3$, $R^{3c}$ represents a bromine atom, and $R^1$ represents any substituents described in [Table L1] to [Table L3] (hereinafter, referred to as Compound Class $SX_{3189}$).

A compound (L-12) wherein $R^{33}$ represents a chlorine atom, T represents a group represented by T2, $R^{3b}$ represents $CF_3$, $R^{3c}$ represents an iodine atom, and $R^1$ represents any substituents described in [Table L1] to [Table L3] (hereinafter, referred to as Compound Class $SX_{3190}$).

A compound (L-12) wherein $R^{33}$ represents a chlorine atom, T represents a group represented by T2, $R^{3b}$ represents a hydrogen atom, $R^{3c}$ represents $CF_3$, and $R^1$ represents any substituents described in [Table L1] to [Table L3] (hereinafter, referred to as Compound Class $SX_{3191}$).

A compound (L-12) wherein $R^{33}$ represents a chlorine atom, T represents a group represented by T2, $R^{3b}$ represents a hydrogen atom, $R^{3c}$ represents a chorine atom, and $R^1$ represents any substituents described in [Table L1] to [Table L3] (hereinafter, referred to as Compound Class $SX_{3192}$).

A compound (L-12) wherein $R^{33}$ represents a chlorine atom, T represents a group represented by T2, $R^{3b}$ represents a hydrogen atom, $R^{3c}$ represents a bromine atom, and $R^1$ represents any substituents described in [Table L1] to [Table L3] (hereinafter, referred to as Compound Class $SX_{3193}$).

A compound (L-12) wherein $R^{33}$ represents a bromine atom, T represents a group represented by T2, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3194}$).

A compound (L-12) wherein $R^{33}$ represents a bromine atom, T represents a group represented by T2, $R^{3b}$ represents $CF_3$, $R^{3c}$ represents a hydrogen atom, and $R^1$ represents any substituents described in [Table L1] to [Table L3] (hereinafter, referred to as Compound Class $SX_{3195}$).

A compound (L-12) wherein $R^{33}$ represents a bromine atom, T represents a group represented by T2, $R^{3b}$ represents $CF_3$, $R^{3c}$ represents a chlorine atom, and $R^1$ represents any substituents described in [Table L1] to [Table L3] (hereinafter, referred to as Compound Class $SX_{3196}$).

A compound (L-12) wherein $R^{33}$ represents a bromine atom, T represents a group represented by T2, $R^{3b}$ represents $CF_3$, $R^{3c}$ represents a bromine atom, and $R^1$ represents any substituents described in [Table L1] to [Table L3] (hereinafter, referred to as Compound Class $SX_{3197}$).

A compound (L-12) wherein $R^{33}$ represents a bromine atom, T represents a group represented by T2, $R^{3b}$ represents $CF_3$, $R^{3c}$ represents an iodine atom, and $R^1$ represents any substituents described in [Table L1] to [Table L3] (hereinafter, referred to as Compound Class $SX_{3198}$).

A compound (L-12) wherein $R^{33}$ represents a bromine atom, T represents a group represented by T2, $R^{3b}$ represents a hydrogen atom, $R^{3c}$ represents $CF_3$, and $R^1$ represents any substituents described in [Table L1] to [Table L3] (hereinafter, referred to as Compound Class $SX_{3199}$).

A compound (L-12) wherein $R^{33}$ represents a bromine atom, T represents a group represented by T2, $R^{3b}$ represents a hydrogen atom, $R^{3c}$ represents a chorine atom, and $R^1$ represents any substituents described in [Table L1] to [Table L3] (hereinafter, referred to as Compound Class $SX_{3200}$).

A compound (L-12) wherein $R^{33}$ represents a bromine atom, T represents a group represented by T2, $R^{3b}$ represents a hydrogen atom, $R^{3c}$ represents a bromine atom, and $R^1$ represents any substituents described in [Table L1] to [Table L3] (hereinafter, referred to as Compound Class $SX_{3201}$).

A compound (L-12) wherein $R^{33}$ represents an iodine atom, T represents a group represented by T2, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3202}$).

A compound (L-12) wherein $R^{33}$ represents an iodine atom, T represents a group represented by T2, $R^{3b}$ represents $CF_3$, $R^{3c}$ represents a hydrogen atom, and $R^1$ represents any substituents described in [Table L1] to [Table L3] (hereinafter, referred to as Compound Class $SX_{3203}$).

A compound (L-12) wherein $R^{33}$ represents an iodine atom, T represents a group represented by T2, $R^{3b}$ represents $CF_3$, $R^{3c}$ represents a chlorine atom, and $R^1$ represents any substituents described in [Table L1] to [Table L3] (hereinafter, referred to as Compound Class $SX_{3204}$).

A compound (L-12) wherein $R^{33}$ represents an iodine atom, T represents a group represented by T2, $R^{3b}$ represents $CF_3$, $R^{3c}$ represents a bromine atom, and $R^1$ represents any substituents described in [Table L1] to [Table L3] (hereinafter, referred to as Compound Class $SX_{3205}$).

A compound (L-12) wherein $R^{33}$ represents an iodine atom, T represents a group represented by T2, $R^{3b}$ represents $CF_3$, $R^{3c}$ represents an iodine atom, and $R^1$ represents any substituents described in [Table L1] to [Table L3] (hereinafter, referred to as Compound Class $SX_{3206}$).

A compound (L-12) wherein $R^{33}$ represents an iodine atom, T represents a group represented by T2, $R^{3b}$ represents a hydrogen atom, $R^{3c}$ represents $CF_3$, and $R^1$ represents any substituents described in [Table L1] to [Table L3] (hereinafter, referred to as Compound Class $SX_{3207}$).

A compound (L-12) wherein $R^{33}$ represents an iodine atom, T represents a group represented by T2, $R^{3b}$ represents a hydrogen atom, $R^{3c}$ represents a chorine atom, and $R^1$ represents any substituents described in [Table L1] to [Table L3] (hereinafter, referred to as Compound Class $SX_{3208}$).

A compound (L-12) wherein $R^{33}$ represents an iodine atom, T represents a group represented by T2, $R^{3b}$ represents a hydrogen atom, $R^{3c}$ represents a bromine atom, and $R^1$ represents any substituents described in [Table L1] to [Table L3] (hereinafter, referred to as Compound Class $SX_{3209}$).

A compound (L-12) wherein $R^{33}$ represents a hydrogen atom, T represents a group represented by T3, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3210}$).

A compound (L-12) wherein $R^{33}$ represents a hydrogen atom, T represents a group represented by T3, $R^{3b}$ represents $CF_3$, $R^{3c}$ represents a hydrogen atom, and $R^1$ represents any substituents described in [Table L1] to [Table L3] (hereinafter, referred to as Compound Class $SX_{3211}$).

A compound (L-12) wherein $R^{33}$ represents a hydrogen atom, T represents a group represented by T3, $R^{3b}$ represents $CF_3$, $R^{3c}$ represents a chlorine atom, and $R^1$ represents any substituents described in [Table L1] to [Table L3] (hereinafter, referred to as Compound Class $SX_{3212}$).

A compound (L-12) wherein $R^{33}$ represents a hydrogen atom, T represents a group represented by T3, $R^{3b}$ represents $CF_3$, $R^{3c}$ represents a bromine atom, and $R^1$ represents any substituents described in [Table L1] to [Table L3] (hereinafter, referred to as Compound Class $SX_{3213}$).

A compound (L-12) wherein $R^{33}$ represents a hydrogen atom, T represents a group represented by T3, $R^{3b}$ represents $CF_3$, $R^{3c}$ represents an iodine atom, and $R^1$ represents any substituents described in [Table L1] to [Table L3] (hereinafter, referred to as Compound Class $SX_{3214}$).

A compound (L-12) wherein $R^{33}$ represents a hydrogen atom, T represents a group represented by T3, $R^{3b}$ represents a hydrogen atom, $R^{3c}$ represents $CF_3$, and $R^1$ represents any substituents described in [Table L1] to [Table L3] (hereinafter, referred to as Compound Class $SX_{3215}$).

A compound (L-12) wherein $R^{33}$ represents a hydrogen atom, T represents a group represented by T3, $R^{3b}$ represents a hydrogen atom, $R^{3c}$ represents a chorine atom, and $R^1$ represents any substituents described in [Table L1] to [Table L3] (hereinafter, referred to as Compound Class $SX_{3216}$).

A compound (L-12) wherein $R^{33}$ represents a hydrogen atom, T represents a group represented by T3, $R^{3b}$ represents a hydrogen atom, $R^{3c}$ represents a bromine atom, and $R^1$ represents any substituents described in [Table L1] to [Table L3] (hereinafter, referred to as Compound Class $SX_{3217}$).

A compound (L-12) wherein $R^{33}$ represents a fluorine atom, T represents a group represented by T3, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3218}$).

A compound (L-12) wherein $R^{33}$ represents a fluorine atom, T represents a group represented by T3, $R^{3b}$ represents $CF_3$, $R^{3c}$ represents a hydrogen atom, and $R^1$ represents any substituents described in [Table L1] to [Table L3] (hereinafter, referred to as Compound Class $SX_{3219}$).

A compound (L-12) wherein $R^{33}$ represents a fluorine atom, T represents a group represented by T3, $R^{3b}$ represents $CF_3$, $R^{3c}$ represents a chlorine atom, and $R^1$ represents any substituents described in [Table L1] to [Table L3] (hereinafter, referred to as Compound Class $SX_{3220}$).

A compound (L-12) wherein $R^{33}$ represents a fluorine atom, T represents a group represented by T3, $R^{3b}$ represents $CF_3$, $R^{3c}$ represents a bromine atom, and $R^1$ represents any substituents described in [Table L1] to [Table L3] (hereinafter, referred to as Compound Class $SX_{3221}$).

A compound (L-12) wherein $R^{33}$ represents a fluorine atom, T represents a group represented by T3, $R^{3b}$ represents $CF_3$, $R^{3c}$ represents an iodine atom, and $R^1$ represents any substituents described in [Table L1] to [Table L3] (hereinafter, referred to as Compound Class $SX_{3222}$).

A compound (L-12) wherein $R^{33}$ represents a fluorine atom, T represents a group represented by T3, $R^{3b}$ represents a hydrogen atom, $R^{3c}$ represents $CF_3$, and $R^1$ represents any substituents described in [Table L1] to [Table L3] (hereinafter, referred to as Compound Class $SX_{3223}$).

A compound (L-12) wherein $R^{33}$ represents a fluorine atom, T represents a group represented by T3, $R^{3b}$ represents a hydrogen atom, $R^{3c}$ represents a chorine atom, and $R^1$ represents any substituents described in [Table L1] to [Table L3] (hereinafter, referred to as Compound Class $SX_{3224}$).

A compound (L-12) wherein $R^{33}$ represents a fluorine atom, T represents a group represented by T3, $R^{3b}$ represents a hydrogen atom, $R^{3c}$ represents a bromine atom, and $R^1$ represents any substituents described in [Table L1] to [Table L3] (hereinafter, referred to as Compound Class $SX_{3225}$).

A compound (L-12) wherein $R^{33}$ represents a chlorine atom, T represents a group represented by T3, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3226}$).

A compound (L-12) wherein $R^{33}$ represents a chlorine atom, T represents a group represented by T3, $R^{3b}$ represents $CF_3$, $R^{3c}$ represents a hydrogen atom, and $R^1$ represents any substituents described in [Table L1] to [Table L3] (hereinafter, referred to as Compound Class $SX_{3227}$).

A compound (L-12) wherein $R^{33}$ represents a chlorine atom, T represents a group represented by T3, $R^{3b}$ represents $CF_3$, $R^{3c}$ represents a chlorine atom, and $R^1$ represents any substituents described in [Table L1] to [Table L3] (hereinafter, referred to as Compound Class $SX_{3228}$).

A compound (L-12) wherein $R^{33}$ represents a chlorine atom, T represents a group represented by T3, $R^{3b}$ represents $CF_3$, $R^{3c}$ represents a bromine atom, and $R^1$ represents any substituents described in [Table L1] to [Table L3] (hereinafter, referred to as Compound Class $SX_{3229}$).

A compound (L-12) wherein $R^{33}$ represents a chlorine atom, T represents a group represented by T3, $R^{3b}$ represents $CF_3$, $R^{3c}$ represents an iodine atom, and $R^1$ represents any substituents described in [Table L1] to [Table L3] (hereinafter, referred to as Compound Class $SX_{3230}$).

A compound (L-12) wherein $R^{33}$ represents a chlorine atom, T represents a group represented by T3, $R^{3b}$ represents a hydrogen atom, $R^{3c}$ represents $CF_3$, and $R^1$ represents any substituents described in [Table L1] to [Table L3] (hereinafter, referred to as Compound Class $SX_{3231}$).

A compound (L-12) wherein $R^{33}$ represents a chlorine atom, T represents a group represented by T3, $R^{3b}$ represents a hydrogen atom, $R^{3c}$ represents a chorine atom, and $R^1$ represents any substituents described in [Table L1] to [Table L3] (hereinafter, referred to as Compound Class $SX_{3232}$).

A compound (L-12) wherein $R^{33}$ represents a chlorine atom, T represents a group represented by T3, $R^{3b}$ represents a hydrogen atom, $R^{3c}$ represents a bromine atom, and $R^1$ represents any substituents described in [Table L1] to [Table L3] (hereinafter, referred to as Compound Class $SX_{3233}$).

A compound (L-12) wherein $R^{33}$ represents a bromine atom, T represents a group represented by T3, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3234}$).

A compound (L-12) wherein $R^{33}$ represents a bromine atom, T represents a group represented by T3, $R^{3b}$ represents $CF_3$, $R^{3c}$ represents a hydrogen atom, and $R^1$ represents any substituents described in [Table L1] to [Table L3] (hereinafter, referred to as Compound Class $SX_{3235}$).

A compound (L-12) wherein $R^{33}$ represents a bromine atom, T represents a group represented by T3, $R^{3b}$ represents $CF_3$, $R^{3c}$ represents a chlorine atom, and $R^1$ represents any substituents described in [Table L1] to [Table L3] (hereinafter, referred to as Compound Class $SX_{3236}$).

A compound (L-12) wherein $R^{33}$ represents a bromine atom, T represents a group represented by T3, $R^{3b}$ represents $CF_3$, $R^{3c}$ represents a bromine atom, and $R^1$ represents any substituents described in [Table L1] to [Table L3] (hereinafter, referred to as Compound Class $SX_{3237}$).

A compound (L-12) wherein $R^{33}$ represents a bromine atom, T represents a group represented by T3, $R^{3b}$ represents $CF_3$, $R^{3c}$ represents an iodine atom, and $R^1$ represents any substituents described in [Table L1] to [Table L3] (hereinafter, referred to as Compound Class $SX_{3238}$).

A compound (L-12) wherein $R^{33}$ represents a bromine atom, T represents a group represented by T3, $R^{3b}$ represents a hydrogen atom, $R^{3c}$ represents $CF_3$, and $R^1$ represents any substituents described in [Table L1] to [Table L3] (hereinafter, referred to as Compound Class $SX_{3239}$).

A compound (L-12) wherein $R^{33}$ represents a bromine atom, T represents a group represented by T3, $R^{3b}$ represents a hydrogen atom, $R^{3c}$ represents a chorine atom, and $R^1$ represents any substituents described in [Table L1] to [Table L3] (hereinafter, referred to as Compound Class $SX_{3240}$).

A compound (L-12) wherein $R^{33}$ represents a bromine atom, T represents a group represented by T3, $R^{3b}$ represents a hydrogen atom, $R^{3c}$ represents a bromine atom, and $R^1$ represents any substituents described in [Table L1] to [Table L3] (hereinafter, referred to as Compound Class $SX_{3241}$).

A compound (L-12) wherein $R^{33}$ represents an iodine atom, T represents a group represented by T3, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3242}$).

A compound (L-12) wherein $R^{33}$ represents an iodine atom, T represents a group represented by T3, $R^{3b}$ represents $CF_3$, $R^{3c}$ represents a hydrogen atom, and $R^1$ represents any substituents described in [Table L1] to [Table L3] (hereinafter, referred to as Compound Class $SX_{3243}$).

A compound (L-12) wherein $R^{33}$ represents an iodine atom, T represents a group represented by T3, $R^{3b}$ represents $CF_3$, $R^{3c}$ represents a chlorine atom, and $R^1$ represents any substituents described in [Table L1] to [Table L3] (hereinafter, referred to as Compound Class $SX_{3244}$).

A compound (L-12) wherein $R^{33}$ represents an iodine atom, T represents a group represented by T3, $R^{3b}$ represents $CF_3$, $R^{3c}$ represents a bromine atom, and $R^1$ represents any substituents described in [Table L1] to [Table L3] (hereinafter, referred to as Compound Class $SX_{3245}$).

A compound (L-12) wherein $R^{33}$ represents an iodine atom, T represents a group represented by T3, $R^{3b}$ represents $CF_3$, $R^{3c}$ represents an iodine atom, and $R^1$ represents any substituents described in [Table L1] to [Table L3] (hereinafter, referred to as Compound Class $SX_{3246}$).

A compound (L-12) wherein $R^{33}$ represents an iodine atom, T represents a group represented by T3, $R^{3b}$ represents a hydrogen atom, $R^{3c}$ represents $CF_3$, and $R^1$ represents any substituents described in [Table L1] to [Table L3] (hereinafter, referred to as Compound Class $SX_{3247}$).

A compound (L-12) wherein $R^{33}$ represents an iodine atom, T represents a group represented by T3, $R^{3b}$ represents a hydrogen atom, $R^{3c}$ represents a chorine atom, and $R^1$ represents any substituents described in [Table L1] to [Table L3] (hereinafter, referred to as Compound Class $SX_{3248}$).

A compound (L-12) wherein $R^{33}$ represents an iodine atom, T represents a group represented by T3, $R^{3b}$ represents a hydrogen atom, $R^{3c}$ represents a bromine atom, and $R^1$ represents any substituents described in [Table L1] to [Table L3] (hereinafter, referred to as Compound Class $SX_{3249}$).

A compound represented by formula (L-13):

(L-13)

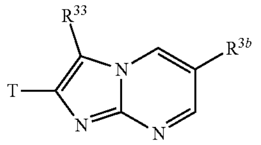

(hereinafter, referred to as Compound (L-13)), wherein $R^{33}$ represents a hydrogen atom, T represents a group represented by T1, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3250}$).

A compound (L-13) wherein $R^{33}$ represents a hydrogen atom, T represents a group represented by T1, $R^{3b}$ represents $CF_3$, $R^{3c}$ represents a hydrogen atom, and $R^1$ represents any substituents described in [Table L1] to [Table L3] (hereinafter, referred to as Compound Class $SX_{3251}$).

A compound (L-13) wherein $R^{33}$ represents a hydrogen atom, T represents a group represented by T1, $R^{3b}$ represents a chlorine atom, $R^{3c}$ represents a hydrogen atom, and $R^1$ represents any substituents described in [Table L1] to [Table L3] (hereinafter, referred to as Compound Class $SX_{3252}$).

A compound (L-13) wherein $R^{33}$ represents a hydrogen atom, T represents a group represented by T1, $R^{3b}$ represents a bromine atom, $R^{3c}$ represents a hydrogen atom, and $R^1$ represents any substituents described in [Table L1] to [Table L3] (hereinafter, referred to as Compound Class $SX_{3253}$).

A compound (L-13) wherein $R^{33}$ represents a hydrogen atom, T represents a group represented by T1, $R^{3b}$ represents an iodine atom, $R^{3c}$ represents a hydrogen atom, and $R^1$ represents any substituents described in [Table L1] to [Table L3] (hereinafter, referred to as Compound Class $SX_{3254}$).

A compound (L-13) wherein $R^{33}$ represents a hydrogen atom, T represents a group represented by T1, $R^{3b}$ represents a hydrogen atom, $R^{3c}$ represents $CF_3$, and $R^1$ represents any substituents described in [Table L1] to [Table L3] (hereinafter, referred to as Compound Class $SX_{3255}$).

A compound (L-13) wherein $R^{33}$ represents a hydrogen atom, T represents a group represented by T1, $R^{3b}$ represents a hydrogen atom, $R^{3c}$ represents a chlorine atom, and $R^1$ represents any substituents described in [Table L1] to [Table L3] (hereinafter, referred to as Compound Class $SX_{3256}$).

A compound (L-13) wherein $R^{33}$ represents a hydrogen atom, T represents a group represented by T1, $R^{3b}$ represents a hydrogen atom, $R^{3c}$ represents a bromine atom, and $R^1$ represents any substituents described in [Table L1] to [Table L3] (hereinafter, referred to as Compound Class $SX_{3257}$).

A compound (L-13) wherein $R^{33}$ represents a fluorine atom, T represents a group represented by T1, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3258}$).

A compound (L-13) wherein $R^{33}$ represents a fluorine atom, T represents a group represented by T1, $R^{3b}$ represents $CF_3$, $R^{3c}$ represents a hydrogen atom, and $R^1$ represents any substituents described in [Table L1] to [Table L3] (hereinafter, referred to as Compound Class $SX_{3259}$).

A compound (L-13) wherein $R^{33}$ represents a fluorine atom, T represents a group represented by T1, $R^{3b}$ represents a chlorine atom, $R^{3c}$ represents a hydrogen atom, and $R^1$ represents any substituents described in [Table L1] to [Table L3] (hereinafter, referred to as Compound Class $SX_{3260}$).

A compound (L-13) wherein $R^{33}$ represents a fluorine atom, T represents a group represented by T1, $R^{3b}$ represents a bromine atom, $R^{3c}$ represents a hydrogen atom, and $R^1$ represents any substituents described in [Table L1] to [Table L3] (hereinafter, referred to as Compound Class $SX_{3261}$).

A compound (L-13) wherein $R^{33}$ represents a fluorine atom, T represents a group represented by T1, $R^{3b}$ represents an iodine atom, $R^{3c}$ represents a hydrogen atom, and $R^1$ represents any substituents described in [Table L1] to [Table L3] (hereinafter, referred to as Compound Class $SX_{3262}$).

A compound (L-13) wherein $R^{33}$ represents a fluorine atom, T represents a group represented by T1, $R^{3b}$ represents a hydrogen atom, $R^{3c}$ represents $CF_3$, and $R^1$ represents any substituents described in [Table L1] to [Table L3] (hereinafter, referred to as Compound Class $SX_{3263}$).

A compound (L-13) wherein $R^{33}$ represents a fluorine atom, T represents a group represented by T1, $R^{3b}$ represents a hydrogen atom, $R^{3c}$ represents a chlorine atom, and $R^1$ represents any substituents described in [Table L1] to [Table L3] (hereinafter, referred to as Compound Class $SX_{3264}$).

A compound (L-13) wherein $R^{33}$ represents a fluorine atom, T represents a group represented by T1, $R^{3b}$ represents a hydrogen atom, $R^{3c}$ represents a bromine atom, and $R^1$ represents any substituents described in [Table L1] to [Table L3] (hereinafter, referred to as Compound Class $SX_{3265}$).

A compound (L-13) wherein $R^{33}$ represents a chlorine atom, T represents a group represented by T1, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3266}$).

A compound (L-13) wherein $R^{33}$ represents a chlorine atom, T represents a group represented by T1, $R^{3b}$ represents $CF_3$, $R^{3c}$ represents a hydrogen atom, and $R^1$ represents any substituents described in [Table L1] to [Table L3] (hereinafter, referred to as Compound Class $SX_{3267}$).

A compound (L-13) wherein $R^{33}$ represents a chlorine atom, T represents a group represented by T1, $R^{3b}$ represents a chlorine atom, $R^{3c}$ represents a hydrogen atom, and $R^1$ represents any substituents described in [Table L1] to [Table L3] (hereinafter, referred to as Compound Class $SX_{3268}$).

A compound (L-13) wherein $R^{33}$ represents a chlorine atom, T represents a group represented by T1, $R^{3b}$ represents a bromine atom, $R^{3c}$ represents a hydrogen atom, and $R^1$ represents any substituents described in [Table L1] to [Table L3] (hereinafter, referred to as Compound Class $SX_{3269}$).

A compound (L-13) wherein $R^{33}$ represents a chlorine atom, T represents a group represented by T1, $R^{3b}$ represents an iodine atom, $R^{3c}$ represents a hydrogen atom, and $R^1$ represents any substituents described in [Table L1] to [Table L3] (hereinafter, referred to as Compound Class $SX_{3270}$).

A compound (L-13) wherein $R^{33}$ represents a chlorine atom, T represents a group represented by T1, $R^{3b}$ represents a hydrogen atom, $R^{3c}$ represents $CF_3$, and $R^1$ represents any substituents described in [Table L1] to [Table L3] (hereinafter, referred to as Compound Class $SX_{3271}$).

A compound (L-13) wherein $R^{33}$ represents a chlorine atom, T represents a group represented by T1, $R^{3b}$ represents a hydrogen atom, $R^{3c}$ represents a chlorine atom, and $R^1$ represents any substituents described in [Table L1] to [Table L3] (hereinafter, referred to as Compound Class $SX_{3272}$).

A compound (L-13) wherein $R^{33}$ represents a chlorine atom, T represents a group represented by T1, $R^{3b}$ represents a hydrogen atom, $R^{3c}$ represents a bromine atom, and $R^1$ represents any substituents described in [Table L1] to [Table L3] (hereinafter, referred to as Compound Class $SX_{3273}$).

A compound (L-13) wherein $R^{33}$ represents a bromine atom, T represents a group represented by T1, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3274}$).

A compound (L-13) wherein $R^{33}$ represents a bromine atom, T represents a group represented by T1, $R^{3b}$ represents $CF_3$, $R^{3c}$ represents a hydrogen atom, and $R^1$ represents any substituents described in [Table L1] to [Table L3] (hereinafter, referred to as Compound Class $SX_{3275}$).

A compound (L-13) wherein $R^{33}$ represents a bromine atom, T represents a group represented by T1, $R^{3b}$ represents a chlorine atom, $R^{3c}$ represents a hydrogen atom, and $R^1$ represents any substituents described in [Table L1] to [Table L3] (hereinafter, referred to as Compound Class $SX_{3276}$).

A compound (L-13) wherein $R^{33}$ represents a bromine atom, T represents a group represented by T1, $R^{3b}$ represents a bromine atom, $R^{3c}$ represents a hydrogen atom, and $R^1$ represents any substituents described in [Table L1] to [Table L3] (hereinafter, referred to as Compound Class $SX_{3277}$).

A compound (L-13) wherein $R^{33}$ represents a bromine atom, T represents a group represented by T1, $R^{3b}$ represents an iodine atom, $R^{3c}$ represents a hydrogen atom, and $R^1$ represents any substituents described in [Table L1] to [Table L3] (hereinafter, referred to as Compound Class $SX_{3278}$).

A compound (L-13) wherein $R^{33}$ represents a bromine atom, T represents a group represented by T1, $R^{3b}$ represents a hydrogen atom, $R^{3c}$ represents $CF_3$, and $R^1$ represents any substituents described in [Table L1] to [Table L3] (hereinafter, referred to as Compound Class $SX_{3279}$).

A compound (L-13) wherein $R^{33}$ represents a bromine atom, T represents a group represented by T1, $R^{3b}$ represents a hydrogen atom, $R^{3c}$ represents a chlorine atom, and $R^1$ represents any substituents described in [Table L1] to [Table L3] (hereinafter, referred to as Compound Class $SX_{3280}$).

A compound (L-13) wherein $R^{33}$ represents a bromine atom, T represents a group represented by T1, $R^{3b}$ represents a hydrogen atom, $R^{3c}$ represents a bromine atom, and $R^1$ represents any substituents described in [Table L1] to [Table L3] (hereinafter, referred to as Compound Class $SX_{3281}$).

A compound (L-13) wherein $R^{33}$ represents an iodine atom, T represents a group represented by T1, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3282}$).

A compound (L-13) wherein $R^{33}$ represents an iodine atom, T represents a group represented by T1, $R^{3b}$ represents $CF_3$, $R^{3c}$ represents a hydrogen atom, and $R^1$ represents any substituents described in [Table L1] to [Table L3] (hereinafter, referred to as Compound Class $SX_{3283}$).

A compound (L-13) wherein $R^{33}$ represents an iodine atom, T represents a group represented by T1, $R^{3b}$ represents a chlorine atom, $R^{3c}$ represents a hydrogen atom, and $R^1$ represents any substituents described in [Table L1] to [Table L3] (hereinafter, referred to as Compound Class $SX_{3284}$).

A compound (L-13) wherein $R^{33}$ represents an iodine atom, T represents a group represented by T1, $R^{3b}$ represents a bromine atom, $R^{3c}$ represents a hydrogen atom, and $R^1$ represents any substituents described in [Table L1] to [Table L3] (hereinafter, referred to as Compound Class $SX_{3285}$).

A compound (L-13) wherein $R^{33}$ represents an iodine atom, T represents a group represented by T1, $R^{3b}$ represents an iodine atom, $R^{3c}$ represents a hydrogen atom, and $R^1$ represents any substituents described in [Table L1] to [Table L3] (hereinafter, referred to as Compound Class $SX_{3286}$).

A compound (L-13) wherein $R^{33}$ represents an iodine atom, T represents a group represented by T1, $R^{3b}$ represents a hydrogen atom, $R^{3c}$ represents $CF_3$, and $R^1$ represents any substituents described in [Table L1] to [Table L3] (hereinafter, referred to as Compound Class $SX_{3287}$).

A compound (L-13) wherein $R^{33}$ represents an iodine atom, T represents a group represented by T1, $R^{3b}$ represents a hydrogen atom, $R^{3c}$ represents a chlorine atom, and $R^1$ represents any substituents described in [Table L1] to [Table L3] (hereinafter, referred to as Compound Class $SX_{3288}$).

A compound (L-13) wherein $R^{33}$ represents an iodine atom, T represents a group represented by T1, $R^{3b}$ represents a hydrogen atom, $R^{3c}$ represents a bromine atom, and $R^1$ represents any substituents described in [Table L1] to [Table L3] (hereinafter, referred to as Compound Class $SX_{3289}$).

A compound (L-13) wherein $R^{33}$ represents a hydrogen atom, T represents a group represented by T2, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3290}$).

A compound (L-13) wherein $R^{33}$ represents a hydrogen atom, T represents a group represented by T2, $R^{3b}$ represents $CF_3$, $R^{3b}$ represents a hydrogen atom, and $R^1$ represents any substituents described in [Table L1] to [Table L3] (hereinafter, referred to as Compound Class $SX_{3291}$).

A compound (L-13) wherein $R^{33}$ represents a hydrogen atom, T represents a group represented by T2, $R^{3b}$ represents a chlorine atom, $R^{3c}$ represents a hydrogen atom, and $R^1$ represents any substituents described in [Table L1] to [Table L3] (hereinafter, referred to as Compound Class $SX_{3292}$).

A compound (L-13) wherein $R^{33}$ represents a hydrogen atom, T represents a group represented by T2, $R^{3b}$ represents a bromine atom, $R^{3c}$ represents a hydrogen atom, and $R^1$ represents any substituents described in [Table L1] to [Table L3] (hereinafter, referred to as Compound Class $SX_{3293}$).

A compound (L-13) wherein $R^{33}$ represents a hydrogen atom, T represents a group represented by T2, $R^{3b}$ represents an iodine atom, $R^{3c}$ represents a hydrogen atom, and $R^1$ represents any substituents described in [Table L1] to [Table L3] (hereinafter, referred to as Compound Class $SX_{3294}$).

A compound (L-13) wherein $R^{33}$ represents a hydrogen atom, T represents a group represented by T2, $R^{3b}$ represents a hydrogen atom, $R^{3c}$ represents $CF_3$, and $R^1$ represents any substituents described in [Table L1] to [Table L3] (hereinafter, referred to as Compound Class $SX_{3295}$).

A compound (L-13) wherein $R^{33}$ represents a hydrogen atom, T represents a group represented by T2, $R^{3b}$ represents a hydrogen atom, $R^{3c}$ represents a chlorine atom, and $R^1$ represents any substituents described in [Table L1] to [Table L3] (hereinafter, referred to as Compound Class $SX_{3296}$).

A compound (L-13) wherein $R^{33}$ represents a hydrogen atom, T represents a group represented by T2, $R^{3b}$ represents a hydrogen atom, $R^{3c}$ represents a bromine atom, and $R^1$ represents any substituents described in [Table L1] to [Table L3] (hereinafter, referred to as Compound Class $SX_{3297}$).

A compound (L-13) wherein $R^{33}$ represents a fluorine atom, T represents a group represented by T2, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3298}$).

A compound (L-13) wherein $R^{33}$ represents a fluorine atom, T represents a group represented by T2, $R^{3b}$ represents $CF_3$, $R^{3c}$ represents a hydrogen atom, and $R^1$ represents any substituents described in [Table L1] to [Table L3] (hereinafter, referred to as Compound Class $SX_{3299}$).

A compound (L-13) wherein $R^{33}$ represents a fluorine atom, T represents a group represented by T2, $R^{3b}$ represents a chlorine atom, $R^{3c}$ represents a hydrogen atom, and $R^1$ represents any substituents described in [Table L1] to [Table L3] (hereinafter, referred to as Compound Class $SX_{3300}$).

A compound (L-13) wherein $R^{33}$ represents a fluorine atom, T represents a group represented by T2, $R^{3b}$ represents a bromine atom, $R^{3c}$ represents a hydrogen atom, and $R^1$ represents any substituents described in [Table L1] to [Table L3] (hereinafter, referred to as Compound Class $SX_{3301}$).

A compound (L-13) wherein $R^{33}$ represents a fluorine atom, T represents a group represented by T2, $R^{3b}$ represents an iodine atom, $R^{3c}$ represents a hydrogen atom, and $R^1$ represents any substituents described in [Table L1] to [Table L3] (hereinafter, referred to as Compound Class $SX_{3302}$).

A compound (L-13) wherein $R^{33}$ represents a fluorine atom, T represents a group represented by T2, $R^{3b}$ represents a hydrogen atom, $R^{3c}$ represents $CF_3$, and $R^1$ represents any substituents described in [Table L1] to [Table L3] (hereinafter, referred to as Compound Class $SX_{3303}$).

A compound (L-13) wherein $R^{33}$ represents a fluorine atom, T represents a group represented by T2, $R^{3b}$ represents a hydrogen atom, $R^{3c}$ represents a chlorine atom, and $R^1$ represents any substituents described in [Table L1] to [Table L3] (hereinafter, referred to as Compound Class $SX_{3304}$).

A compound (L-13) wherein $R^{33}$ represents a fluorine atom, T represents a group represented by T2, $R^{3b}$ represents a hydrogen atom, $R^{3c}$ represents a bromine atom, and $R^1$ represents any substituents described in [Table L1] to [Table L3] (hereinafter, referred to as Compound Class $SX_{3305}$).

A compound (L-13) wherein $R^{33}$ represents a chlorine atom, T represents a group represented by T2, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3306}$).

A compound (L-13) wherein $R^{33}$ represents a chlorine atom, T represents a group represented by T2, $R^{3b}$ represents $CF_3$, $R^{3c}$ represents a hydrogen atom, and $R^1$ represents any substituents described in [Table L1] to [Table L3] (hereinafter, referred to as Compound Class $SX_{3307}$).

A compound (L-13) wherein $R^{33}$ represents a chlorine atom, T represents a group represented by T2, $R^{3b}$ represents a chlorine atom, $R^{3c}$ represents a hydrogen atom, and $R^1$ represents any substituents described in [Table L1] to [Table L3] (hereinafter, referred to as Compound Class $SX_{3308}$).

A compound (L-13) wherein $R^{33}$ represents a chlorine atom, T represents a group represented by T2, $R^{3b}$ represents a bromine atom, $R^{3c}$ represents a hydrogen atom, and $R^1$ represents any substituents described in [Table L1] to [Table L3] (hereinafter, referred to as Compound Class $SX_{3309}$).

A compound (L-13) wherein $R^{33}$ represents a chlorine atom, T represents a group represented by T2, $R^{3b}$ represents an iodine atom, $R^{3c}$ represents a hydrogen atom, and $R^1$ represents any substituents described in [Table L1] to [Table L3] (hereinafter, referred to as Compound Class $SX_{3310}$).

A compound (L-13) wherein $R^{33}$ represents a chlorine atom, T represents a group represented by T2, $R^{3b}$ represents a hydrogen atom, $R^{3c}$ represents $CF_3$, and $R^1$ represents any substituents described in [Table L1] to [Table L3] (hereinafter, referred to as Compound Class $SX_{3311}$).

A compound (L-13) wherein $R^{33}$ represents a chlorine atom, T represents a group represented by T2, $R^{3b}$ represents a hydrogen atom, $R^{3c}$ represents a chlorine atom, and $R^1$ represents any substituents described in [Table L1] to [Table L3] (hereinafter, referred to as Compound Class $SX_{3312}$).

A compound (L-13) wherein $R^{33}$ represents a chlorine atom, T represents a group represented by T2, $R^{3b}$ represents a hydrogen atom, $R^{3c}$ represents a bromine atom, and $R^1$ represents any substituents described in [Table L1] to [Table L3] (hereinafter, referred to as Compound Class $SX_{3313}$).

A compound (L-13) wherein $R^{33}$ represents a bromine atom, T represents a group represented by T2, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3314}$).

A compound (L-13) wherein $R^{33}$ represents a bromine atom, T represents a group represented by T2, $R^{3b}$ represents $CF_3$, $R^{3c}$ represents a hydrogen atom, and $R^1$ represents any substituents described in [Table L1] to [Table L3] (hereinafter, referred to as Compound Class $SX_{3315}$).

A compound (L-13) wherein $R^{33}$ represents a bromine atom, T represents a group represented by T2, $R^{3b}$ represents a chlorine atom, $R^{3c}$ represents a hydrogen atom, and $R^1$ represents any substituents described in [Table L1] to [Table L3] (hereinafter, referred to as Compound Class $SX_{3316}$).

A compound (L-13) wherein $R^{33}$ represents a bromine atom, T represents a group represented by T2, $R^{3b}$ represents a bromine atom, $R^{3c}$ represents a hydrogen atom, and $R^1$ represents any substituents described in [Table L1] to [Table L3] (hereinafter, referred to as Compound Class $SX_{3317}$).

A compound (L-13) wherein $R^{33}$ represents a bromine atom, T represents a group represented by T2, $R^{3b}$ represents an iodine atom, $R^{3c}$ represents a hydrogen atom, and $R^1$ represents any substituents described in [Table L1] to [Table L3] (hereinafter, referred to as Compound Class $SX_{3318}$).

A compound (L-13) wherein $R^{33}$ represents a bromine atom, T represents a group represented by T2, $R^{3b}$ represents a hydrogen atom, $R^{3c}$ represents $CF_3$, and $R^1$ represents any substituents described in [Table L1] to [Table L3] (hereinafter, referred to as Compound Class $SX_{3319}$).

A compound (L-13) wherein $R^{33}$ represents a bromine atom, T represents a group represented by T2, $R^{3b}$ represents a hydrogen atom, $R^{3c}$ represents a chlorine atom, and $R^1$ represents any substituents described in [Table L1] to [Table L3] (hereinafter, referred to as Compound Class $SX_{3320}$).

A compound (L-13) wherein $R^{33}$ represents a bromine atom, T represents a group represented by T2, $R^{3b}$ represents a hydrogen atom, $R^{3c}$ represents a bromine atom, and $R^1$ represents any substituents described in [Table L1] to [Table L3] (hereinafter, referred to as Compound Class $SX_{3321}$).

A compound (L-13) wherein $R^{33}$ represents an iodine atom, T represents a group represented by T2, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3322}$).

A compound (L-13) wherein $R^{33}$ represents an iodine atom, T represents a group represented by T2, $R^{3b}$ represents $CF_3$, $R^{3c}$ represents a hydrogen atom, and $R^1$ represents any substituents described in [Table L1] to [Table L3] (hereinafter, referred to as Compound Class $SX_{3323}$).

A compound (L-13) wherein $R^{33}$ represents an iodine atom, T represents a group represented by T2, $R^{3b}$ represents a chlorine atom, $R^{3c}$ represents a hydrogen atom, and $R^1$ represents any substituents described in [Table L1] to [Table L3] (hereinafter, referred to as Compound Class $SX_{3324}$).

A compound (L-13) wherein $R^{33}$ represents an iodine atom, T represents a group represented by T2, $R^{3b}$ represents a bromine atom, $R^{3c}$ represents a hydrogen atom, and $R^1$ represents any substituents described in [Table L1] to [Table L3] (hereinafter, referred to as Compound Class $SX_{3325}$).

A compound (L-13) wherein $R^{33}$ represents an iodine atom, T represents a group represented by T2, $R^{3b}$ represents an iodine atom, $R^{3c}$ represents a hydrogen atom, and $R^1$ represents any substituents described in [Table L1] to [Table L3] (hereinafter, referred to as Compound Class $SX_{3326}$).

A compound (L-13) wherein $R^{33}$ represents an iodine atom, T represents a group represented by T2, $R^{3b}$ represents a hydrogen atom, $R^{3c}$ represents $CF_3$, and $R^1$ represents any substituents described in [Table L1] to [Table L3] (hereinafter, referred to as Compound Class $SX_{3327}$).

A compound (L-13) wherein $R^{33}$ represents an iodine atom, T represents a group represented by T2, $R^{3b}$ represents a hydrogen atom, $R^{3c}$ represents a chlorine atom, and $R^1$ represents any substituents described in [Table L1] to [Table L3] (hereinafter, referred to as Compound Class $SX_{3328}$).

A compound (L-13) wherein $R^{33}$ represents an iodine atom, T represents a group represented by T2, $R^{3b}$ represents a hydrogen atom, $R^{3c}$ represents a bromine atom, and $R^1$ represents any substituents described in [Table L1] to [Table L3] (hereinafter, referred to as Compound Class $SX_{3329}$).

A compound (L-13) wherein $R^{33}$ represents a hydrogen atom, T represents a group represented by T3, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3330}$).

A compound (L-13) wherein $R^{33}$ represents a hydrogen atom, T represents a group represented by T3, $R^{3b}$ represents $CF_3$, $R^{3b}$ represents a hydrogen atom, and $R^1$ represents any substituents described in [Table L1] to [Table L3] (hereinafter, referred to as Compound Class $SX_{3331}$).

A compound (L-13) wherein $R^{33}$ represents a hydrogen atom, T represents a group represented by T3, $R^{3b}$ represents a chlorine atom, $R^{3c}$ represents a hydrogen atom, and $R^1$ represents any substituents described in [Table L1] to [Table L3] (hereinafter, referred to as Compound Class $SX_{3332}$).

A compound (L-13) wherein $R^{33}$ represents a hydrogen atom, T represents a group represented by T3, $R^{3b}$ represents a bromine atom, $R^{3c}$ represents a hydrogen atom, and $R^1$ represents any substituents described in [Table L1] to [Table L3] (hereinafter, referred to as Compound Class $SX_{3333}$).

A compound (L-13) wherein $R^{33}$ represents a hydrogen atom, T represents a group represented by T3, $R^{3b}$ represents an iodine atom, $R^{3c}$ represents a hydrogen atom, and $R^1$ represents any substituents described in [Table L1] to [Table L3] (hereinafter, referred to as Compound Class $SX_{3334}$).

A compound (L-13) wherein $R^{33}$ represents a hydrogen atom, T represents a group represented by T3, $R^{3b}$ represents a hydrogen atom, $R^{3c}$ represents $CF_3$, and $R^1$ represents any substituents described in [Table L1] to [Table L3] (hereinafter, referred to as Compound Class $SX_{3335}$).

A compound (L-13) wherein $R^{33}$ represents a hydrogen atom, T represents a group represented by T3, $R^{3b}$ represents a hydrogen atom, $R^{3c}$ represents a chlorine atom, and $R^1$ represents any substituents described in [Table L1] to [Table L3] (hereinafter, referred to as Compound Class $SX_{3336}$).

A compound (L-13) wherein $R^{33}$ represents a hydrogen atom, T represents a group represented by T3, $R^{3b}$ represents a hydrogen atom, $R^{3c}$ represents a bromine atom, and $R^1$ represents any substituents described in [Table L1] to [Table L3] (hereinafter, referred to as Compound Class $SX_{3337}$).

A compound (L-13) wherein $R^{33}$ represents a fluorine atom, T represents a group represented by T3, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3338}$).

A compound (L-13) wherein $R^{33}$ represents a fluorine atom, T represents a group represented by T3, $R^{3b}$ represents $CF_3$, $R^{3c}$ represents a hydrogen atom, and $R^1$ represents any substituents described in [Table L1] to [Table L3] (hereinafter, referred to as Compound Class $SX_{3339}$).

A compound (L-13) wherein $R^{33}$ represents a fluorine atom, T represents a group represented by T3, $R^{3b}$ represents a chlorine atom, $R^{3c}$ represents a hydrogen atom, and $R^1$ represents any substituents described in [Table L1] to [Table L3] (hereinafter, referred to as Compound Class $SX_{3340}$).

A compound (L-13) wherein $R^{33}$ represents a fluorine atom, T represents a group represented by T3, $R^{3b}$ represents a bromine atom, $R^{3c}$ represents a hydrogen atom, and $R^1$ represents any substituents described in [Table L1] to [Table L3] (hereinafter, referred to as Compound Class $SX_{3341}$).

A compound (L-13) wherein $R^{33}$ represents a fluorine atom, T represents a group represented by T3, $R^{3b}$ represents an iodine atom, $R^{3c}$ represents a hydrogen atom, and $R^1$ represents any substituents described in [Table L1] to [Table L3] (hereinafter, referred to as Compound Class $SX_{3342}$).

A compound (L-13) wherein $R^{33}$ represents a fluorine atom, T represents a group represented by T3, $R^{3b}$ represents a hydrogen atom, $R^{3c}$ represents $CF_3$, and $R^1$ represents any substituents described in [Table L1] to [Table L3] (hereinafter, referred to as Compound Class $SX_{3343}$).

A compound (L-13) wherein $R^{33}$ represents a fluorine atom, T represents a group represented by T3, $R^{3b}$ represents a hydrogen atom, $R^{3c}$ represents a chlorine atom, and $R^1$ represents any substituents described in [Table L1] to [Table L3] (hereinafter, referred to as Compound Class $SX_{3344}$).

A compound (L-13) wherein $R^{33}$ represents a fluorine atom, T represents a group represented by T3, $R^{3b}$ represents a hydrogen atom, $R^{3c}$ represents a bromine atom, and $R^1$ represents any substituents described in [Table L1] to [Table L3] (hereinafter, referred to as Compound Class $SX_{3345}$).

A compound (L-13) wherein $R^{33}$ represents a chlorine atom, T represents a group represented by T3, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3346}$).

A compound (L-13) wherein $R^{33}$ represents a chlorine atom, T represents a group represented by T3, $R^{3b}$ represents $CF_3$, $R^{3c}$ represents a hydrogen atom, and $R^1$ represents any substituents described in [Table L1] to [Table L3] (hereinafter, referred to as Compound Class $SX_{3347}$).

A compound (L-13) wherein $R^{33}$ represents a chlorine atom, T represents a group represented by T3, $R^{3b}$ represents a chlorine atom, $R^{3c}$ represents a hydrogen atom, and $R^1$ represents any substituents described in [Table L1] to [Table L3] (hereinafter, referred to as Compound Class $SX_{3348}$).

A compound (L-13) wherein $R^{33}$ represents a chlorine atom, T represents a group represented by T3, $R^{3b}$ represents a bromine atom, $R^{3c}$ represents a hydrogen atom, and $R^1$ represents any substituents described in [Table L1] to [Table L3] (hereinafter, referred to as Compound Class $SX_{3349}$).

A compound (L-13) wherein $R^{33}$ represents a chlorine atom, T represents a group represented by T3, $R^{3b}$ represents an iodine atom, $R^{3c}$ represents a hydrogen atom, and $R^1$ represents any substituents described in [Table L1] to [Table L3] (hereinafter, referred to as Compound Class $SX_{3350}$).

A compound (L-13) wherein $R^{33}$ represents a chlorine atom, T represents a group represented by T3, $R^{3b}$ represents a hydrogen atom, $R^{3c}$ represents $CF_3$, and $R^1$ represents any substituents described in [Table L1] to [Table L3] (hereinafter, referred to as Compound Class $SX_{3351}$).

A compound (L-13) wherein $R^{33}$ represents a chlorine atom, T represents a group represented by T3, $R^{3b}$ represents a hydrogen atom, $R^{3c}$ represents a chlorine atom, and $R^1$ represents any substituents described in [Table L1] to [Table L3] (hereinafter, referred to as Compound Class $SX_{3352}$).

A compound (L-13) wherein $R^{33}$ represents a chlorine atom, T represents a group represented by T3, $R^{3b}$ represents a hydrogen atom, $R^{3c}$ represents a bromine atom, and $R^1$ represents any substituents described in [Table L1] to [Table L3] (hereinafter, referred to as Compound Class $SX_{3353}$).

A compound (L-13) wherein $R^{33}$ represents a bromine atom, T represents a group represented by T3, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3354}$).

A compound (L-13) wherein $R^{33}$ represents a bromine atom, T represents a group represented by T3, $R^{3b}$ represents $CF_3$, $R^{3c}$ represents a hydrogen atom, and $R^1$ represents any substituents described in [Table L1] to [Table L3] (hereinafter, referred to as Compound Class $SX_{3355}$).

A compound (L-13) wherein $R^{33}$ represents a bromine atom, T represents a group represented by T3, $R^{3b}$ represents a chlorine atom, $R^{3c}$ represents a hydrogen atom, and $R^1$ represents any substituents described in [Table L1] to [Table L3] (hereinafter, referred to as Compound Class $SX_{3356}$).

A compound (L-13) wherein $R^{33}$ represents a bromine atom, T represents a group represented by T3, $R^{3b}$ represents a bromine atom, $R^{3c}$ represents a hydrogen atom, and $R^1$ represents any substituents described in [Table L1] to [Table L3] (hereinafter, referred to as Compound Class $SX_{3357}$).

A compound (L-13) wherein $R^{33}$ represents a bromine atom, T represents a group represented by T3, $R^{3b}$ represents an iodine atom, $R^{3c}$ represents a hydrogen atom, and $R^1$ represents any substituents described in [Table L1] to [Table L3] (hereinafter, referred to as Compound Class $SX_{3358}$).

A compound (L-13) wherein $R^{33}$ represents a bromine atom, T represents a group represented by T3, $R^{3b}$ represents a hydrogen atom, $R^{3c}$ represents $CF_3$, and $R^1$ represents any substituents described in [Table L1] to [Table L3] (hereinafter, referred to as Compound Class $SX_{3359}$).

A compound (L-13) wherein $R^{33}$ represents a bromine atom, T represents a group represented by T3, $R^{3b}$ represents a hydrogen atom, $R^{3c}$ represents a chlorine atom, and $R^1$ represents any substituents described in [Table L1] to [Table L3] (hereinafter, referred to as Compound Class $SX_{3360}$).

A compound (L-13) wherein $R^{33}$ represents a bromine atom, T represents a group represented by T3, $R^{3b}$ represents a hydrogen atom, $R^{3c}$ represents a bromine atom, and $R^1$ represents any substituents described in [Table L1] to [Table L3] (hereinafter, referred to as Compound Class $SX_{3361}$).

A compound (L-13) wherein $R^{33}$ represents an iodine atom, T represents a group represented by T3, $R^{3b}$ represents a hydrogen atom, $R^{3c}$ represents a hydrogen atom, and $R^1$ represents any substituents described in [Table L1] to [Table L3] (hereinafter, referred to as Compound Class $SX_{3362}$).

A compound (L-13) wherein $R^{33}$ represents an iodine atom, T represents a group represented by T3, $R^{3b}$ represents $CF_3$, $R^{3c}$ represents a hydrogen atom, and $R^1$ represents any substituents described in [Table L1] to [Table L3] (hereinafter, referred to as Compound Class $SX_{3363}$).

A compound (L-13) wherein $R^{33}$ represents an iodine atom, T represents a group represented by T3, $R^{3b}$ represents a chlorine atom, $R^{3c}$ represents a hydrogen atom, and $R^1$ represents any substituents described in [Table L1] to [Table L3] (hereinafter, referred to as Compound Class $SX_{3364}$).

A compound (L-13) wherein $R^{33}$ represents an iodine atom, T represents a group represented by T3, $R^{3b}$ represents a bromine atom, $R^{3c}$ represents a hydrogen atom, and $R^1$ represents any substituents described in [Table L1] to [Table L3] (hereinafter, referred to as Compound Class $SX_{3365}$).

A compound (L-13) wherein $R^{33}$ represents an iodine atom, T represents a group represented by T3, $R^{3b}$ represents an iodine atom, $R^{3c}$ represents a hydrogen atom, and $R^1$ represents any substituents described in [Table L1] to [Table L3] (hereinafter, referred to as Compound Class $SX_{3366}$).

A compound (L-13) wherein $R^{33}$ represents an iodine atom, T represents a group represented by T3, $R^{3b}$ represents a hydrogen atom, $R^{3c}$ represents $CF_3$, and $R^1$ represents any substituents described in [Table L1] to [Table L3] (hereinafter, referred to as Compound Class $SX_{3367}$).

A compound (L-13) wherein $R^{33}$ represents an iodine atom, T represents a group represented by T3, $R^{3b}$ represents a hydrogen atom, $R^{3c}$ represents a chlorine atom, and $R^1$ represents any substituents described in [Table L1] to [Table L3] (hereinafter, referred to as Compound Class $SX_{3368}$).

A compound (L-13) wherein $R^{33}$ represents an iodine atom, T represents a group represented by T3, $R^{3b}$ represents a hydrogen atom, $R^{3c}$ represents a bromine atom, and $R^1$ represents any substituents described in [Table L1] to [Table L3] (hereinafter, referred to as Compound Class $SX_{3369}$).

A compound (L-12) wherein $R^{33}$ represents a hydrogen atom, T represents a group represented by T1, $R^1$ represents $CF_3$, $R^{3c}$ represents a hydrogen atom, and $R^{3b}$ represents any substituents described in [Table L4] to [Table L12] (hereinafter, referred to as Compound Class $SX_{3370}$).

A compound (L-12) wherein $R^{33}$ represents a hydrogen atom, T represents a group represented by T1, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3371}$).

A compound (L-12) wherein $R^{33}$ represents a hydrogen atom, T represents a group represented by T1, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3372}$).

A compound (L-12) wherein $R^{33}$ represents a hydrogen atom, T represents a group represented by T1, $R^1$ represents $SCF_3$, $R^{3b}$ represents a hydrogen atom, and $R^{3b}$ represents any substituents described in [Table L4] to [Table L12] (hereinafter, referred to as Compound Class $SX_{3373}$).

A compound (L-12) wherein $R^{33}$ represents a hydrogen atom, T represents a group represented by T1, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3374}$).

A compound (L-12) wherein $R^{33}$ represents a hydrogen atom, T represents a group represented by T1, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3375}$).

A compound (L-12) wherein $R^{33}$ represents a fluorine atom, T represents a group represented by T1, $R^1$ represents $CF_3$, $R^{3c}$ represents a hydrogen atom, and $R^{3b}$ represents any substituents described in [Table L4] to [Table L12] (hereinafter, referred to as Compound Class $SX_{3376}$).

A compound (L-12) wherein $R^{33}$ represents a fluorine atom, T represents a group represented by T1, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3377}$).

A compound (L-12) wherein $R^{33}$ represents a fluorine atom, T represents a group represented by T1, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3378}$).

A compound (L-12) wherein $R^{33}$ represents a fluorine atom, T represents a group represented by T1, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3379}$).

A compound (L-12) wherein $R^{33}$ represents a fluorine atom, T represents a group represented by T1, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3380}$).

A compound (L-12) wherein $R^{33}$ represents a fluorine atom, T represents a group represented by T1, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3381}$).

A compound (L-12) wherein $R^{33}$ represents a chlorine atom, T represents a group represented by T1, $R^1$ represents $CF_3$, $R^{3c}$ represents a hydrogen atom, and $R^{3b}$ represents any substituents described in [Table L4] to [Table L12] (hereinafter, referred to as Compound Class $SX_{3382}$).

A compound (L-12) wherein $R^{33}$ represents a chlorine atom, T represents a group represented by T1, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3383}$).

A compound (L-12) wherein $R^{33}$ represents a chlorine atom, T represents a group represented by T1, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3384}$).

A compound (L-12) wherein $R^{33}$ represents a chlorine atom, T represents a group represented by T1, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3385}$).

A compound (L-12) wherein $R^{33}$ represents a chlorine atom, T represents a group represented by T1, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3386}$).

A compound (L-12) wherein $R^{33}$ represents a chlorine atom, T represents a group represented by T1, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3387}$).

A compound (L-12) wherein $R^{33}$ represents a bromine atom, T represents a group represented by T1, $R^1$ represents $CF_3$, $R^{3c}$ represents a hydrogen atom, and $R^{3b}$ represents any substituents described in [Table L4] to [Table L12] (hereinafter, referred to as Compound Class $SX_{3388}$).

A compound (L-12) wherein $R^{33}$ represents a bromine atom, T represents a group represented by T1, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3389}$).

A compound (L-12) wherein $R^{33}$ represents a bromine atom, T represents a group represented by T1, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3390}$).

A compound (L-12) wherein $R^{33}$ represents a bromine atom, T represents a group represented by T1, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3391}$).

A compound (L-12) wherein $R^{33}$ represents a bromine atom, T represents a group represented by T1, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3392}$).

A compound (L-12) wherein $R^{33}$ represents a bromine atom, T represents a group represented by T1, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3393}$).

A compound (L-12) wherein $R^{33}$ represents an iodine atom, T represents a group represented by T1, $R^1$ represents $CF_3$, $R^{3c}$ represents a hydrogen atom, and $R^{3b}$ represents any substituents described in [Table L4] to [Table L12] (hereinafter, referred to as Compound Class $SX_{3394}$).

A compound (L-12) wherein $R^{33}$ represents an iodine atom, T represents a group represented by T1, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3395}$).

A compound (L-12) wherein $R^{33}$ represents an iodine atom, T represents a group represented by T1, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3396}$).

A compound (L-12) wherein $R^{33}$ represents an iodine atom, T represents a group represented by T1, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3397}$).

A compound (L-12) wherein $R^{33}$ represents an iodine atom, T represents a group represented by T1, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3398}$).

A compound (L-12) wherein $R^{33}$ represents an iodine atom, T represents a group represented by T1, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3399}$).

A compound (L-12) wherein $R^{33}$ represents a hydrogen atom, T represents a group represented by T2, $R^1$ represents $CF_3$, $R^{3c}$ represents a hydrogen atom, and $R^{3b}$ represents any substituents described in [Table L4] to [Table L12] (hereinafter, referred to as Compound Class $SX_{3400}$).

A compound (L-12) wherein $R^{33}$ represents a hydrogen atom, T represents a group represented by T2, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3401}$).

A compound (L-12) wherein $R^{33}$ represents a hydrogen atom, T represents a group represented by T2, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3402}$).

A compound (L-12) wherein $R^{33}$ represents a hydrogen atom, T represents a group represented by T2, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3403}$).

A compound (L-12) wherein $R^{33}$ represents a hydrogen atom, T represents a group represented by T2, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3404}$).

A compound (L-12) wherein $R^{33}$ represents a hydrogen atom, T represents a group represented by T2, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3405}$.

A compound (L-12) wherein $R^{33}$ represents a fluorine atom, T represents a group represented by T2, $R^1$ represents $CF_3$, $R^{3c}$ represents a hydrogen atom, and $R^{3b}$ represents any substituents described in [Table L4] to [Table L12] (hereinafter, referred to as Compound Class $SX_{3406}$).

A compound (L-12) wherein $R^{33}$ represents a fluorine atom, T represents a group represented by T2, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3407}$).

A compound (L-12) wherein $R^{33}$ represents a fluorine atom, T represents a group represented by T2, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3408}$).

A compound (L-12) wherein $R^{33}$ represents a fluorine atom, T represents a group represented by T2, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3409}$).

A compound (L-12) wherein $R^{33}$ represents a fluorine atom, T represents a group represented by T2, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3410}$).

A compound (L-12) wherein $R^{33}$ represents a fluorine atom, T represents a group represented by T2, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3411}$).

A compound (L-12) wherein $R^{33}$ represents a chlorine atom, T represents a group represented by T2, $R^1$ represents $CF_3$, $R^{3c}$ represents a hydrogen atom, and $R^{3b}$ represents any substituents described in [Table L4] to [Table L12] (hereinafter, referred to as Compound Class $SX_{3412}$).

A compound (L-12) wherein $R^{33}$ represents a chlorine atom, T represents a group represented by T2, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3413}$).

A compound (L-12) wherein $R^{33}$ represents a chlorine atom, T represents a group represented by T2, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3414}$).

A compound (L-12) wherein $R^{33}$ represents a chlorine atom, T represents a group represented by T2, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3415}$.

A compound (L-12) wherein $R^{33}$ represents a chlorine atom, T represents a group represented by T2, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3416}$).

A compound (L-12) wherein $R^{33}$ represents a chlorine atom, T represents a group represented by T2, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3417}$).

A compound (L-12) wherein $R^{33}$ represents a bromine atom, T represents a group represented by T2, $R^1$ represents $CF_3$, $R^{3c}$ represents a hydrogen atom, and $R^{3b}$ represents any substituents described in [Table L4] to [Table L12] (hereinafter, referred to as Compound Class $SX_{3418}$).

A compound (L-12) wherein $R^{33}$ represents a bromine atom, T represents a group represented by T2, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3419}$).

A compound (L-12) wherein $R^{33}$ represents a bromine atom, T represents a group represented by T2, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3420}$).

A compound (L-12) wherein $R^{33}$ represents a bromine atom, T represents a group represented by T2, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3421}$).

A compound (L-12) wherein $R^{33}$ represents a bromine atom, T represents a group represented by T2, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3422}$).

A compound (L-12) wherein $R^{33}$ represents a bromine atom, T represents a group represented by T2, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3423}$).

A compound (L-12) wherein $R^{33}$ represents an iodine atom, T represents a group represented by T2, $R^1$ represents $CF_3$, $R^{3c}$ represents a hydrogen atom, and $R^{3b}$ represents any substituents described in [Table L4] to [Table L12] (hereinafter, referred to as Compound Class $SX_{3424}$).

A compound (L-12) wherein $R^{33}$ represents an iodine atom, T represents a group represented by T2, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3425}$).

A compound (L-12) wherein $R^{33}$ represents an iodine atom, T represents a group represented by T2, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3426}$).

A compound (L-12) wherein $R^{33}$ represents an iodine atom, T represents a group represented by T2, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3427}$).

A compound (L-12) wherein $R^{33}$ represents an iodine atom, T represents a group represented by T2, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3428}$).

A compound (L-12) wherein $R^{33}$ represents an iodine atom, T represents a group represented by T2, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3429}$).

A compound (L-12) wherein $R^{33}$ represents a hydrogen atom, T represents a group represented by T3, $R^1$ represents $CF_3$, $R^{3c}$ represents a hydrogen atom, and $R^{3b}$ represents any substituents described in [Table L4] to [Table L12] (hereinafter, referred to as Compound Class $SX_{3430}$).

A compound (L-12) wherein $R^{33}$ represents a hydrogen atom, T represents a group represented by T3, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3431}$).

A compound (L-12) wherein $R^{33}$ represents a hydrogen atom, T represents a group represented by T3, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3432}$).

A compound (L-12) wherein $R^{33}$ represents a hydrogen atom, T represents a group represented by T3, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3433}$).

A compound (L-12) wherein $R^{33}$ represents a hydrogen atom, T represents a group represented by T3, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3434}$).

A compound (L-12) wherein $R^{33}$ represents a hydrogen atom, T represents a group represented by T3, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3435}$).

A compound (L-12) wherein $R^{33}$ represents a fluorine atom, T represents a group represented by T3, $R^1$ represents $CF_3$, $R^{3c}$ represents a hydrogen atom, and $R^{3b}$ represents any substituents described in [Table L4] to [Table L12] (hereinafter, referred to as Compound Class $SX_{3436}$).

A compound (L-12) wherein $R^{33}$ represents a fluorine atom, T represents a group represented by T3, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3437}$).

A compound (L-12) wherein $R^{33}$ represents a fluorine atom, T represents a group represented by T3, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3438}$).

A compound (L-12) wherein $R^{33}$ represents a fluorine atom, T represents a group represented by T3, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3439}$).

A compound (L-12) wherein $R^{33}$ represents a fluorine atom, T represents a group represented by T3, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3440}$).

A compound (L-12) wherein $R^{33}$ represents a fluorine atom, T represents a group represented by T3, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3441}$).

A compound (L-12) wherein $R^{33}$ represents a chlorine atom, T represents a group represented by T3, $R^1$ represents $CF_3$, $R^{3c}$ represents a hydrogen atom, and $R^{3b}$ represents any substituents described in [Table L4] to [Table L12] (hereinafter, referred to as Compound Class $SX_{3442}$).

A compound (L-12) wherein $R^{33}$ represents a chlorine atom, T represents a group represented by T3, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3443}$).

A compound (L-12) wherein $R^{33}$ represents a chlorine atom, T represents a group represented by T3, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3444}$).

A compound (L-12) wherein $R^{33}$ represents a chlorine atom, T represents a group represented by T3, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3445}$).

A compound (L-12) wherein $R^{33}$ represents a chlorine atom, T represents a group represented by T3, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3446}$).

A compound (L-12) wherein $R^{33}$ represents a chlorine atom, T represents a group represented by T3, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3447}$).

A compound (L-12) wherein $R^{33}$ represents a bromine atom, T represents a group represented by T3, $R^1$ represents $CF_3$, $R^{3c}$ represents a hydrogen atom, and $R^{3b}$ represents any substituents described in [Table L4] to [Table L12] (hereinafter, referred to as Compound Class $SX_{3448}$).

A compound (L-12) wherein $R^{33}$ represents a bromine atom, T represents a group represented by T3, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3449}$).

A compound (L-12) wherein $R^{33}$ represents a bromine atom, T represents a group represented by T3, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3450}$).

A compound (L-12) wherein $R^{33}$ represents a bromine atom, T represents a group represented by T3, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3451}$).

A compound (L-12) wherein $R^{33}$ represents a bromine atom, T represents a group represented by T3, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3452}$).

A compound (L-12) wherein $R^{33}$ represents a bromine atom, T represents a group represented by T3, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3453}$).

A compound (L-12) wherein $R^{33}$ represents an iodine atom, T represents a group represented by T3, $R^1$ represents $CF_3$, $R^{3c}$ represents a hydrogen atom, and $R^{3b}$ represents any substituents described in [Table L4] to [Table L12] (hereinafter, referred to as Compound Class $SX_{3454}$).

A compound (L-12) wherein $R^{33}$ represents an iodine atom, T represents a group represented by T3, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3455}$).

A compound (L-12) wherein $R^{33}$ represents an iodine atom, T represents a group represented by T3, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3456}$).

A compound (L-12) wherein $R^{33}$ represents an iodine atom, T represents a group represented by T3, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3457}$).

A compound (L-12) wherein $R^{33}$ represents an iodine atom, T represents a group represented by T3, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3458}$).

A compound (L-12) wherein $R^{33}$ represents an iodine atom, T represents a group represented by T3, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3459}$).

A compound (L-13) wherein $R^{33}$ represents a hydrogen atom, T represents a group represented by T1, $R^1$ represents $CF_3$, $R^{3c}$ represents a hydrogen atom, and $R^{3b}$ represents any substituents described in [Table L4] to [Table L12] (hereinafter, referred to as Compound Class $SX_{3460}$).

A compound (L-13) wherein $R^{33}$ represents a hydrogen atom, T represents a group represented by T1, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3461}$).

A compound (L-13) wherein $R^{33}$ represents a hydrogen atom, T represents a group represented by T1, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3462}$).

A compound (L-13) wherein $R^{33}$ represents a hydrogen atom, T represents a group represented by T1, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3463}$).

A compound (L-13) wherein $R^{33}$ represents a hydrogen atom, T represents a group represented by T1, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3464}$).

A compound (L-13) wherein $R^{33}$ represents a hydrogen atom, T represents a group represented by T1, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3465}$).

A compound (L-13) wherein $R^{33}$ represents a fluorine atom, T represents a group represented by T1, $R^1$ represents $CF_3$, $R^{3c}$ represents a hydrogen atom, and $R^{3b}$ represents any substituents described in [Table L4] to [Table L12] (hereinafter, referred to as Compound Class $SX_{3466}$).

A compound (L-13) wherein $R^{33}$ represents a fluorine atom, T represents a group represented by T1, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3467}$).

A compound (L-13) wherein $R^{33}$ represents a fluorine atom, T represents a group represented by T1, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3468}$).

A compound (L-13) wherein $R^{33}$ represents a fluorine atom, T represents a group represented by T1, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3469}$).

A compound (L-13) wherein $R^{33}$ represents a fluorine atom, T represents a group represented by T1, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3470}$).

A compound (L-13) wherein $R^{33}$ represents a fluorine atom, T represents a group represented by T1, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3471}$).

A compound (L-13) wherein $R^{33}$ represents a chlorine atom, T represents a group represented by T1, $R^1$ represents $CF_3$, $R^{3c}$ represents a hydrogen atom, and $R^{3b}$ represents any substituents described in [Table L4] to [Table L12] (hereinafter, referred to as Compound Class $SX_{3472}$).

A compound (L-13) wherein $R^{33}$ represents a chlorine atom, T represents a group represented by T1, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3473}$).

A compound (L-13) wherein $R^{33}$ represents a chlorine atom, T represents a group represented by T1, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3474}$).

A compound (L-13) wherein $R^{33}$ represents a chlorine atom, T represents a group represented by T1, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3475}$).

A compound (L-13) wherein $R^{33}$ represents a chlorine atom, T represents a group represented by T1, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3476}$).

A compound (L-13) wherein $R^{33}$ represents a chlorine atom, T represents a group represented by T1, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3477}$).

A compound (L-13) wherein $R^{33}$ represents a bromine atom, T represents a group represented by T1, $R^1$ represents $CF_3$, $R^{3c}$ represents a hydrogen atom, and $R^{3b}$ represents any substituents described in [Table L4] to [Table L12] (hereinafter, referred to as Compound Class $SX_{3478}$).

A compound (L-13) wherein $R^{33}$ represents a bromine atom, T represents a group represented by T1, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3479}$).

A compound (L-13) wherein $R^{33}$ represents a bromine atom, T represents a group represented by T1, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3480}$).

A compound (L-13) wherein $R^{33}$ represents a bromine atom, T represents a group represented by T1, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3481}$).

A compound (L-13) wherein $R^{33}$ represents a bromine atom, T represents a group represented by T1, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3482}$).

A compound (L-13) wherein $R^{33}$ represents a bromine atom, T represents a group represented by T1, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3483}$).

A compound (L-13) wherein $R^{33}$ represents an iodine atom, T represents a group represented by T1, $R^1$ represents $CF_3$, $R^{3c}$ represents a hydrogen atom, and $R^{3b}$ represents any substituents described in [Table L4] to [Table L12] (hereinafter, referred to as Compound Class $SX_{3484}$).

A compound (L-13) wherein $R^{33}$ represents an iodine atom, T represents a group represented by T1, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3485}$).

A compound (L-13) wherein $R^{33}$ represents an iodine atom, T represents a group represented by T1, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3486}$).

A compound (L-13) wherein $R^{33}$ represents an iodine atom, T represents a group represented by T1, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3487}$).

A compound (L-13) wherein $R^{33}$ represents an iodine atom, T represents a group represented by T1, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3488}$).

A compound (L-13) wherein $R^{33}$ represents an iodine atom, T represents a group represented by T1, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3489}$).

A compound (L-13) wherein $R^{33}$ represents a hydrogen atom, T represents a group represented by T2, $R^1$ represents $CF_3$, $R^{3c}$ represents a hydrogen atom, and $R^{3b}$ represents any substituents described in [Table L4] to [Table L12] (hereinafter, referred to as Compound Class $SX_{3490}$).

A compound (L-13) wherein $R^{33}$ represents a hydrogen atom, T represents a group represented by T2, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3491}$).

A compound (L-13) wherein $R^{33}$ represents a hydrogen atom, T represents a group represented by T2, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3492}$).

A compound (L-13) wherein $R^{33}$ represents a hydrogen atom, T represents a group represented by T2, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3493}$).

A compound (L-13) wherein $R^{33}$ represents a hydrogen atom, T represents a group represented by T2, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3494}$).

A compound (L-13) wherein $R^{33}$ represents a hydrogen atom, T represents a group represented by T2, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3495}$.

A compound (L-13) wherein $R^{33}$ represents a fluorine atom, T represents a group represented by T2, $R^1$ represents $CF_3$, $R^{3c}$ represents a hydrogen atom, and $R^{3b}$ represents any substituents described in [Table L4] to [Table L12] (hereinafter, referred to as Compound Class $SX_{3496}$).

A compound (L-13) wherein $R^{33}$ represents a fluorine atom, T represents a group represented by T2, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3497}$).

A compound (L-13) wherein $R^{33}$ represents a fluorine atom, T represents a group represented by T2, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3498}$).

A compound (L-13) wherein $R^{33}$ represents a fluorine atom, T represents a group represented by T2, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3499}$).

A compound (L-13) wherein $R^{33}$ represents a fluorine atom, T represents a group represented by T2, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3500}$).

A compound (L-13) wherein $R^{33}$ represents a fluorine atom, T represents a group represented by T2, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3501}$).

A compound (L-13) wherein $R^{33}$ represents a chlorine atom, T represents a group represented by T2, $R^1$ represents $CF_3$, $R^{3c}$ represents a hydrogen atom, and $R^{3b}$ represents any substituents described in [Table L4] to [Table L12] (hereinafter, referred to as Compound Class $SX_{3502}$).

A compound (L-13) wherein $R^{33}$ represents a chlorine atom, T represents a group represented by T2, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3503}$).

A compound (L-13) wherein $R^{33}$ represents a chlorine atom, T represents a group represented by T2, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3504}$).

A compound (L-13) wherein $R^{33}$ represents a chlorine atom, T represents a group represented by T2, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3505}$).

A compound (L-13) wherein $R^{33}$ represents a chlorine atom, T represents a group represented by T2, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3506}$).

A compound (L-13) wherein $R^{33}$ represents a chlorine atom, T represents a group represented by T2, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3507}$).

A compound (L-13) wherein $R^{33}$ represents a bromine atom, T represents a group represented by T2, $R^1$ represents $CF_3$, $R^{3c}$ represents a hydrogen atom, and $R^{3b}$ represents any substituents described in [Table L4] to [Table L12] (hereinafter, referred to as Compound Class $SX_{3508}$).

A compound (L-13) wherein $R^{33}$ represents a bromine atom, T represents a group represented by T2, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3509}$).

A compound (L-13) wherein $R^{33}$ represents a bromine atom, T represents a group represented by T2, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3510}$).

A compound (L-13) wherein $R^{33}$ represents a bromine atom, T represents a group represented by T2, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3511}$).

A compound (L-13) wherein $R^{33}$ represents a bromine atom, T represents a group represented by T2, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3512}$).

A compound (L-13) wherein $R^{33}$ represents a bromine atom, T represents a group represented by T2, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3513}$).

A compound (L-13) wherein $R^{33}$ represents an iodine atom, T represents a group represented by T2, $R^1$ represents $CF_3$, $R^{3c}$ represents a hydrogen atom, and $R^{3b}$ represents any substituents described in [Table L4] to [Table L12] (hereinafter, referred to as Compound Class $SX_{3514}$).

A compound (L-13) wherein $R^{33}$ represents an iodine atom, T represents a group represented by T2, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3515}$).

A compound (L-13) wherein $R^{33}$ represents an iodine atom, T represents a group represented by T2, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3516}$).

A compound (L-13) wherein $R^{33}$ represents an iodine atom, T represents a group represented by T2, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3517}$).

A compound (L-13) wherein $R^{33}$ represents an iodine atom, T represents a group represented by T2, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3518}$).

A compound (L-13) wherein $R^{33}$ represents an iodine atom, T represents a group represented by T2, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3519}$).

A compound (L-13) wherein $R^{33}$ represents a hydrogen atom, T represents a group represented by T3, $R^1$ represents $CF_3$, $R^{3c}$ represents a hydrogen atom, and $R^{3b}$ represents any substituents described in [Table L4] to [Table L12] (hereinafter, referred to as Compound Class $SX_{3520}$).

A compound (L-13) wherein $R^{33}$ represents a hydrogen atom, T represents a group represented by T3, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3521}$).

A compound (L-13) wherein $R^{33}$ represents a hydrogen atom, T represents a group represented by T3, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3522}$).

A compound (L-13) wherein $R^{33}$ represents a hydrogen atom, T represents a group represented by T3, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3523}$).

A compound (L-13) wherein $R^{33}$ represents a hydrogen atom, T represents a group represented by T3, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3524}$).

A compound (L-13) wherein $R^{33}$ represents a hydrogen atom, T represents a group represented by T3, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3525}$).

A compound (L-13) wherein $R^{33}$ represents a fluorine atom, T represents a group represented by T3, $R^1$ represents $CF_3$, $R^{3c}$ represents a hydrogen atom, and $R^{3b}$ represents any substituents described in [Table L4] to [Table L12] (hereinafter, referred to as Compound Class $SX_{3526}$).

A compound (L-13) wherein $R^{33}$ represents a fluorine atom, T represents a group represented by T3, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3527}$).

A compound (L-13) wherein $R^{33}$ represents a fluorine atom, T represents a group represented by T3, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3528}$).

A compound (L-13) wherein $R^{33}$ represents a fluorine atom, T represents a group represented by T3, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3529}$).

A compound (L-13) wherein $R^{33}$ represents a fluorine atom, T represents a group represented by T3, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3530}$.

A compound (L-13) wherein $R^{33}$ represents a fluorine atom, T represents a group represented by T3, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3531}$).

A compound (L-13) wherein $R^{33}$ represents a chlorine atom, T represents a group represented by T3, $R^1$ represents $CF_3$, $R^{3c}$ represents a hydrogen atom, and $R^{3b}$ represents any substituents described in [Table L4] to [Table L12] (hereinafter, referred to as Compound Class $SX_{3532}$).

A compound (L-13) wherein $R^{33}$ represents a chlorine atom, T represents a group represented by T3, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3533}$).

A compound (L-13) wherein $R^{33}$ represents a chlorine atom, T represents a group represented by T3, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3534}$).

A compound (L-13) wherein $R^{33}$ represents a chlorine atom, T represents a group represented by T3, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3535}$).

A compound (L-13) wherein $R^{33}$ represents a chlorine atom, T represents a group represented by T3, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3536}$).

A compound (L-13) wherein $R^{33}$ represents a chlorine atom, T represents a group represented by T3, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3537}$).

A compound (L-13) wherein $R^{33}$ represents a bromine atom, T represents a group represented by T3, $R^1$ represents $CF_3$, $R^{3c}$ represents a hydrogen atom, and $R^{3b}$ represents any substituents described in [Table L4] to [Table L12] (hereinafter, referred to as Compound Class $SX_{3538}$).

A compound (L-13) wherein $R^{33}$ represents a bromine atom, T represents a group represented by T3, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3539}$).

A compound (L-13) wherein $R^{33}$ represents a bromine atom, T represents a group represented by T3, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3540}$).

A compound (L-13) wherein $R^{33}$ represents a bromine atom, T represents a group represented by T3, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3541}$).

A compound (L-13) wherein $R^{33}$ represents a bromine atom, T represents a group represented by T3, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3542}$).

A compound (L-13) wherein $R^{33}$ represents a bromine atom, T represents a group represented by T3, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3543}$).

A compound (L-13) wherein $R^{33}$ represents an iodine atom, T represents a group represented by T3, $R^1$ represents $CF_3$, $R^{3c}$ represents a hydrogen atom, and $R^{3b}$ represents any substituents described in [Table L4] to [Table L12] (hereinafter, referred to as Compound Class $SX_{3544}$).

A compound (L-13) wherein $R^{33}$ represents an iodine atom, T represents a group represented by T3, $R^1$ represents $C_2F_5$, $R^{3c}$ represents a hydrogen atom, and $R^{3b}$ represents any substituents described in [Table L4] to [Table L12] (hereinafter, referred to as Compound Class $SX_{3545}$).

A compound (L-13) wherein $R^{33}$ represents an iodine atom, T represents a group represented by T3, $R^1$ represents $OCF_3$, $R^{3c}$ represents a hydrogen atom, and $R^{3b}$ represents any substituents described in [Table L4] to [Table L12] (hereinafter, referred to as Compound Class $SX_{3546}$).

A compound (L-13) wherein $R^{33}$ represents an iodine atom, T represents a group represented by T3, $R^1$ represents $SCF_3$, $R^{3c}$ represents a hydrogen atom, and $R^{3b}$ represents any substituents described in [Table L4] to [Table L12] (hereinafter, referred to as Compound Class $SX_{3547}$).

A compound (L-13) wherein $R^{33}$ represents an iodine atom, T represents a group represented by T3, $R^1$ represents $S(O)CF_3$, $R^{3c}$ represents a hydrogen atom, and $R^{3b}$ represents any substituents described in [Table L4] to [Table L12] (hereinafter, referred to as Compound Class $SX_{3548}$).

A compound (L-13) wherein $R^{33}$ represents an iodine atom, T represents a group represented by T3, $R^1$ represents $S(O)_2CF_3$, $R^{3c}$ represents a hydrogen atom, and $R^{3b}$ represents any substituents described in [Table L4] to [Table L12] (hereinafter, referred to as Compound Class $SX_{3549}$).

Next, the Formulation Examples of the present compound X are shown below. The "parts" represents "part by weight". Further, the present compound S represents the compounds described as the compound groups SX1 to SX2832.

Formulation Example 1

Into a mixture of 10 parts of any one of the present compounds S, 35 parts of xylene, and 35 parts of DMF, and then 14 parts of polyoxyethylene styryl phenyl ether and 6 parts of calcium dodecylbenzene sulfonate are added, followed by mixing them to obtain each formulation.

Formulation Example 2

Four (4) parts of sodium lauryl sulfate, 2 parts of calcium lignin sulfonate, 20 parts of wet process silica, and 54 parts of diatomaceous earth are mixed, and further 20 parts of any one of the present compounds S is added thereto, followed by mixing them to obtain each formulation.

Formulation Example 3

To 2 parts of any one of the present compounds S, 1 part of wet process silica, 2 parts of calcium lignin sulfonate, 30 parts of bentonite, and 65 parts of kaolin clay are added, followed by mixing them. To the mixtures is then added an appropriate amount of water, and the mixtures are further stirred, granulated with a granulator, and forced-air dried to obtain each formulation.

Formulation Example 4

Into an appropriate amount of acetone, 1 part of any one of the present compounds S is mixed, and then 5 parts of wet process silica, 0.3 parts of isopropyl acid phosphate, and 93.7 parts of kaolin clay are added, following by mixing them with stirring thoroughly and removal of acetone from the mixture by evaporation to obtain each formulation.

Formulation Example 5

A mixture of 35 parts of polyoxyethylene alkyl ether sulfate ammonium salt and wet process silica (weight ratio of 1:1), 20 parts of any one of the present compounds S, and 45 parts of water are enough mixed to obtain each formulation.

Formulation Example 6

Ten (10) parts of any one of the present compound S, 18 parts of benzyl alcohol 18 parts and 9 parts of DMSO are mixed, and 6.3 parts of GERONOL (registered trademark) TE250, 2.7 parts of Ethylan (registered trademark) NS-500LQ, and 54 parts of solventnaphtha are added thereto, and then mixed to obtain each formulation.

Formulation Example 7

Into a mixture of 5 parts of xylene and 5 parts of trichloroethane, 0.1 parts of any one of the present compounds S are mixed, and the resulting mixture is then mixed with 89.9 parts of kerosene to obtain each solution.

Formulation Example 8

Into 0.5 ml of acetone, 10 mg of any one of the present compounds S is mixed, and the solution is added dropwise to 5 g of a solid feed powder for an animal (solid feed powder for rearing and breeding CE-2, manufactured by CLEA Japan, Inc.), followed by mixing the resulting mixtures uniformly, and then by drying them by evaporation of acetone to obtain each poison bait.

Formulation Example 9

Into an aerosol can, 0.1 parts of any one of the present compounds S and 49.9 parts of Neothiozole (manufactured by Chuo Kasei Co., Ltd.) are placed. After mounting an aerosol valve, 25 parts of dimethyl ether and 25 parts of LPG are filled, followed by shaking and further mounting an actuator to obtain each oily aerosol.

Formulation Example 10

A mixture of 0.6 parts of any one of the present compounds S, 0.01 parts of 2,6-di-tert-butyl-4-methylphenol, 5 parts of xylene, 3.39 parts of kerosene, and 1 part of Rheodol (registered trademark) MO-60 (manufactured by Kao Corporation), and 50 parts of distilled water are filled into an aerosol container, and a valve part of the container is attached. Then, 40 parts of LPG is filled therein through the valve under pressure to obtain each aqueous aerosol.

Formulation Example 11

Zero point one (0.1) g of any one of the present compounds S is mixed into 2 ml of propylene glycol, and the resulting solution is impregnated into a ceramic plate having a size of 4.0 cm×4.0 cm and a thickness of 1.2 cm to obtain each thermal fumigant.

Formulation Example 12

Five (5) parts of any one of the present compounds S, and 95 parts of ethylene-methyl methacrylate copolymer (the ratio of the methyl methacrylate in the copolymer: 10 weight %) are melted and kneaded, and the resulting kneaded product is extruded from an extrusion molding machine to obtain each rod-shaped molded product having a length of 15 cm and a diameter of 3 mm.

Formulation Example 13

Five (5) parts of any one of the present compounds S, and 95 parts of plasticized polyvinyl chloride resin are melted and kneaded, and the resulting kneaded product is extruded from an extrusion molding machine to obtain each rod-shaped molded product having a length of 15 cm and a diameter of 3 mm.

Formulation Example 14

One-hundred (100) mg of any one of the present compounds S, 68.75 mg of lactose, 237.5 mg of corn starch, 43.75 mg of microcrystalline cellulose, 18.75 mg of polyvinylpyrrolidone, 28.75 mg of sodium carboxymethyl starch, and 2.5 mg of magnesium stearate are mixed, and the resulting mixtures are compressed to an appropriate size to obtain each tablet.

Formulation Example 15

Twenty-five (25) mg of any one of the present compounds S, 60 mg of lactose, 25 mg of corn starch, 6 mg of carmellose calcium, and an appropriate amount of 5% aqueous hydroxypropyl methylcellulose solution are mixed, and the resulting mixtures are filled into a hard shell gelatin capsule or a hydroxypropyl methylcellulose capsule to obtain each capsule.

Formulation Example 16

To 100 mg of any one of the present compounds S, 500 mg of fumaric acid, 2000 mg of sodium chloride, 150 mg of methyl paraben, 50 mg of propyl paraben, 25,000 mg of granulated sugar, 13,000 mg of sorbitol (70% solution), 100 mg of Veegum (registered trademark) K (manufactured by Vanderbilt Co.), 35 mg of a perfume, and 500 mg of a coloring agent, distilled water is added so that a final volume is set to be 100 mL, followed by mixing the mixtures to obtain each suspension for oral administration.

Formulation Example 17

Into a mixture of 5 parts of an emulsifier, 3 parts of benzyl alcohol and 30 parts of propylene glycol, 5 parts of any one of the present compounds S is mixed, and phosphate buffer is added thereto so that a pH of the solution is set to be 6.0 to 6.5, and water is added as the rest parts to obtain each solution for oral administration.

Formulation Example 18

To a mixture of 57 parts of fractional distillated palm oil and 3 parts of polysorbate 85, 5 parts of aluminium distearate is added, and heated to disperse it. The resulting mixture is cooled to room temperature, and 25 parts of saccharin is dispersed in an oil vehicle. Ten (10) parts of any one of the present compounds S is divided thereto to obtain each paste for oral administration.

Formulation Example 19

Five (5) parts of any one of the present compounds S is mixed with 95 parts of limestone filler, followed by a wet-granulation of the resulting mixture to obtain each granule for oral administration.

Formulation Example 20

Into 80 parts of diethylene glycol monoethyl ether, 5 parts of any one of the present compounds S is mixed, and 15 parts of propylene carbonate is added thereto, and the resulting mixture is mixed to obtain each spot-on solution.

Formulation Example 21

Into 70 parts of diethylene glycol monoethyl ether, 10 parts of any one of the present compounds S is mixed, and 20 parts of 2-octyldodecanol is added thereto, and the resulting mixture is mixed to obtain each pour-on solution.

Formulation Example 22

To 0.1 parts of any one of the present compounds S, 40 parts of sodium polyoxyethylene laurylether sulfate (25% aqueous solution), 5 parts of lauramidopropyl betaine, 5 parts of coconut fatty acid monoethanolamide, 0.5 parts of carboxy vinyl polymer, and 49.4 parts of purified water are added, and the resulting mixture is enough mixed to obtain each shampoo formulation.

Formulation Example 23

Zero point fifteen (0.15) parts of any one of the present compounds S, 95 parts of animal feed, as well as 4.85 parts of a mixture of dibasic calcium phosphate, diatomaceous earth, Aerosil (registered trademark), and carbonate (or chalk) are enough mixed to obtain each premix for animal feed.

Formulation Example 24

Seven point two (7.2) g of any one of the present compounds S, and 92.8 g of Hosco (registered trademark) S-55 are mixed at 100° C., and the resulting mixture is poured into a suppository mold, followed by performing a cooling solidification to obtain each suppository.

Next, Test Examples are used to show an efficacy of the Present compound X on controlling harmful arthropods.

The following test examples were carried out at 25° C.

Test Method 1

The test compounds is made to a formulation according to a similar method to that described in the Formulation Example 6, and thereto is added water containing 0.03 v/v % of a spreader to prepare a diluted solution containing a prescribed concentration of the test compound.

Cucumber (*Cucumis sativus*) seedling (on the developmental stage of the second true leaf) is planted in a container and approximately 30 cotton aphids (*Aphis gossypii*) (all stages of life) are released onto the leaves of the cucumber. After 1 day, the diluted solutions are sprayed into the seedling in a ratio of 10 mL/seedling. Further, after 5 days, the number of the surviving insects is examined and the controlling value is calculated by the following equation.

$$\text{Controlling value (\%)}=\{1-(Cb\times Tai)/(Cai\times Tb)\}\times 100$$

wherein the symbols in the formula represent the following descriptions.

Cb: Number of the test insects in untreated group;

Cai: Number of the surviving insects at the time of the investigation in untreated group;

Tb: Number of the test insects in treated group;

Tai: Number of the surviving insects at the time of the investigation in treated group;

Here the “untreated group” represents a group where the similar treatment procedure to that of the treated group except not using the test compound is done.

Test Example 1-1

The test was conducted by making the prescribed concentration 500 ppm and using the below-mentioned Present compounds X as a test compound according to the test method 1. As a result of the test, the below-mentioned Present compounds X showed 90% or greater as the controlling value.

Present compound 1-1, 1-2, 2-1, 2-5, 2-7, 2-11, 2-12, 2-15, 2-18, 2-19, 2-21, 2-25, 2-26, 2-36, 3-1, 3-2, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 3-25, 3-26, 3-27, 3-28, 3-29, 3-30, 3-31, 3-32, 3-33, 3-34, 3-35, 3-36, 3-38, 4-2, 5-1, 5-2, 6-1, 6-2, 6-3, 6-4, 6-5, 6-6, 7-1, 7-2, 7-3, 7-4, 7-6, 8-1, 8-2, 9, 11, 12-1, 12-2 and 13

Test Example 1-2

The test was conducted by making the prescribed concentration 200 ppm and using the below-mentioned Present compounds X as a test compound according to the test method 1. As a result of the test, the below-mentioned Present compounds X showed 90% or greater as the controlling value.

Present compound: 1-1, 1-2, 2-1, 2-5, 2-7, 2-11, 2-12, 2-15, 2-18, 2-19, 2-21, 2-25, 2-26, 2-36, 3-1, 3-2, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 3-25, 3-26, 3-27, 3-28, 3-29, 3-30, 3-31, 3-32, 3-33, 3-34, 3-35, 3-36, 3-38, 4-2, 5-1, 5-2, 6-1, 6-2, 6-3, 6-4, 6-5, 6-6, 7-1, 7-2, 7-3, 7-4, 7-6, 8-1, 8-2, 9, 11, 12-1, 12-2, and 13

Test Method 2

The test compounds are made to a formulation according to a similar method to that described in the Formulation Example 6, and thereto is added water containing 0.03 v/v % of a spreader to prepare a diluted solution containing a prescribed concentration of the test compound.

Rice (*Oryza sativa*) seedling (on the developmental stage of the second true leaf) is planted in a container, and the diluted solutions are sprayed into the seedling in a ratio of 10 mL/seedling. Thereafter, 20 3rd instar larvae of brown planthoppers (*Nilaparvata lugens*) are released onto the rice leaves. After 6 days, the morality is calculated by the following equation.

$$\text{Morality } (\%)=\{1-\text{the number of the surviving insects}/20\}\times 100$$

Test Example 2-1

The test was conducted by making the prescribed concentration 500 ppm and using the below-mentioned Present compounds X as a test compound according to the test method 2. As a result of the test, the below-mentioned Present compound X showed 90% or greater as the controlling value.

Present Compound: 7-3

Test Example 2-2

The test was conducted by making the prescribed concentration 200 ppm and using the below-mentioned Present compounds X as a test compound according to the test method 2. As a result of the test, the below-mentioned Present compound X showed 90% or greater as the controlling value.

Present Compound: 7-3

Test Method 3

The test compounds are made to a formulation according to a similar method to that described in the Formulation Example 6, and thereto is added water containing 0.03 v/v % of a spreader to prepare a diluted solution containing a prescribed concentration of the test compound.

Silverleaf whiteflies (*Bemisia tabaci*) are released on tomato (*Lycopersicon esculentum*) seedling that is planted in the container, and then spawn for about 24 hours. The seedling are stored for 8 days, and the larvae of silverleaf whiteflies are hatched from the laid eggs. The diluted solutions are sprayed into the seedling in a ratio of 10 mL/seedling. After 7 days, the number of the surviving insects is examined, and the controlling value is calculated by the following equation.

$$\text{Controlling value } (\%)=\{1-(Cb\times Tai)/(Cai\times Tb)\}\times 100$$

wherein the symbols in the formula represent the following descriptions.

Cb: Number of the insects shortly before the treatment in untreated group;

Cai: Number of the surviving insects at the time of the investigation in untreated group;

Tb: Number of the insects shortly before the treatment in treated group;

Tai: Number of the surviving insects at the time of the investigation in treated group;

Here the "untreated group" represents a group where the similar treatment procedure to that of the treated group except not using the test compound is done.

Test Example 3-1

The test was conducted by making the prescribed concentration 500 ppm and using the below-mentioned Present compounds X as a test compound according to the test method 3. As a result of the test, the below-mentioned Present compound X showed 90% or greater as the controlling value.

Present Compound: 3-28 and 3-30

Test Example 3-2

The test was conducted by making the prescribed concentration 200 ppm and using the below-mentioned Present compounds X as a test compound according to the test method 3. As a result of the test, the below-mentioned Present compound X showed 90% or greater as the controlling value.

Present Compound: 3-28 and 3-30

Test Method 4

Test compounds are made to a formulation according to a similar method to that described in the Formulation example 6, and thereto is added water containing 0.03 v/v % of Shindain (registered trademark) to prepare a diluted solution containing a prescribed concentration of the test compound.

Cabbage (*Brassicae oleracea*) seedling (on the developmental stage of the second to third true leaf) is planted in a cup, and the diluted solutions are sprayed into the seedling at a ratio of 20 mL/seedling. Thereafter, the stem and leaf thereof is cut out and then is installed into a cup that is covered with filter paper on the bed of the cup. Five (5) diamondback moth (*Plutella xylostella*) at the second instar larval stage are released into the cup. After 5 days, the number of the surviving insects is counted, and the mortality of insects is calculated by the following equation.

$$\text{Mortality } (\%)=(1-\text{Number of surviving insects}/5)\times 100$$

Test Example 4-1

The test was conducted by making the prescribed concentration 500 ppm and using the below-mentioned Present compounds X as a test compound according to the test method 4. As a result of the test, the below-mentioned Present compound X showed 80% or greater as the mortality of insects.

Present compound: 1-1, 1-2, 2-1, 2-5, 2-6, 2-11, 2-12, 2-15, 2-18, 2-19, 2-21, 2-25, 2-26, 2-36, 3-1, 3-2, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 3-25, 3-26, 3-27, 3-28, 3-29, 3-30, 3-31, 3-32, 3-33, 3-34, 3-35, 3-36, 3-38, 4-2, 5-1, 5-2, 6-1, 6-2, 6-3, 6-4, 6-5, 6-6, 7-1, 7-2, 7-3, 7-4, 7-5, 7-6, 8-1, 8-2, 9, 11, 12-1, 12-2, and 13

Test Example 4-2

The test was conducted by making the prescribed concentration 200 ppm and using the below-mentioned Present compounds X as a test compound according to the test method 4. As a result of the test, the below-mentioned Present compound X showed 80% or greater as the mortality of insects.

Present compound: 1-1, 1-2, 2-1, 2-5, 2-6, 2-11, 2-12, 2-15, 2-18, 2-19, 2-21, 2-25, 2-26, 2-36, 3-1, 3-2, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 3-25, 3-26, 3-27, 3-28, 3-29, 3-30, 3-31, 3-32, 3-33, 3-34, 3-35, 3-36, 3-38, 4-2, 5-1, 5-2, 6-1, 6-2, 6-3, 6-4, 6-5, 6-6, 7-1, 7-2, 7-3, 7-4, 7-5, 7-6, 8-1, 8-2, 9, 11, 12-1, 12-2, and 13

Test Method 5

Test compounds are made to a formulation according to a similar method to that described in the Formulation example 6, and thereto is added water containing 0.03 v/v % of Shindain (registered trademark) to prepare a diluted solution containing a prescribed concentration of the test compound.

Cabbage (*Brassicae oleracea*) seedling (on the developmental stage of the third to fourth true leaf) is planted in a cup, and the diluted solutions are sprayed into the seedling at a ratio of 20 mL/seedling. Thereafter, 10 cotton worm (*Spodoptera litura*) at the third instar larval stage are released. After 6 days, the number of the surviving insects is counted, and the mortality of insects is calculated by the following equation.

Mortality (%)=(1−Number of surviving insects/10)×100

Test Example 5-1

The test was conducted by making the prescribed concentration 500 ppm and using the below-mentioned Present compounds X as a test compound according to the test method 5. As a result of the test, the below-mentioned Present compound X showed 80% or greater as the mortality of insects.

Present compound: 1-1, 1-2, 2-1, 2-5, 2-11, 2-12, 2-15, 2-18, 2-19, 2-21, 2-25, 2-26, 2-36, 3-1, 3-2, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 3-25, 3-26, 3-27, 3-28, 3-29, 3-30, 3-31, 3-32, 3-33, 3-34, 3-35, 3-36, 4-2, 5-1, 5-2, 6-1, 6-2, 6-3, 6-4, 6-5, 6-6, 7-1, 7-2, 7-3, 7-4, 7-6, 8-1, 8-2, 9, 11, 12-1, 12-2, and 13.

Test Example 5-2

The test was conducted by making the prescribed concentration 200 ppm and using the below-mentioned Present compounds X as a test compound according to the test method 5. As a result of the test, the below-mentioned Present compound X showed 80% or greater as the mortality of insects.

Present compound: 1-1, 1-2, 2-1, 2-5, 2-11, 2-12, 2-15, 2-18, 2-19, 2-21, 2-25, 2-26, 2-36, 3-1, 3-2, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 3-25, 3-26, 3-27, 3-28, 3-29, 3-30, 3-31, 3-32, 3-33, 3-34, 3-35, 3-36, 4-2, 5-1, 5-2, 6-1, 6-2, 6-3, 6-4, 6-5, 6-6, 7-1, 7-2, 7-3, 7-4, 7-6, 8-1, 8-2, 9, 11, 12-1, 12-2 and 13.

Test Method 6

Test compounds are made to a formulation according to a similar method to that described in the Formulation example 5, and thereto is added water to prepare a diluted solution containing a prescribed concentration of the test compound.

A filter paper having a diameter of 5.5 cm in diameter is spread on the bottom of the cup, and then 0.7 ml of the diluted solutions are added dropwise to the filter paper and 30 mg of sucrose is uniformly placed on the filter paper as a bait. Ten (10) housefly (*Musca domestica*) female adults are released into the cup, and the cup is then covered with the lid. After 24 hours, the number of the dead insects is examined, and the mortality of insects is calculated by the following equation.

Mortality (%)=(Number of dead insects/Number of tested insects)×100

Test Example 6

The test was conducted by making the prescribed concentration 500 ppm and using the below-mentioned Present compounds X as a test compound according to the test method 6. As a result of the test, the below-mentioned Present compound X showed 70 t or greater as the mortality of insects.

Present compound: 2-2, 2-6, 2-11, 2-12, 2-15, 3-1, 3-2, 3-6, 3-12, 3-13, 3-20, 3-24, 6-1

Test Method 7

An acetone solution which is adjusted to 800 ppm of the test compound is poured into a container having 20 mL contents, and the test compound is coated uniformly on inner face of the container so as to make 40 $mg/m^2$ thereof, and the container is then allowed to dry.

Into the container, five (5) housefly (*Musca domestica*) female adults are released into the container, and the container is then covered with the lid. After the prescribed time is elapsed, the state of the housefly is examined, and the mortality of insects is calculated by the following equation.

Mortality (%)=(Number of dead insects/Number of tested insects)×100

Test Example 7-1

The test was conducted by making the prescribed elapsed time 1 hour and using the below-mentioned Present compounds X as a test compound according to the test method 7. As a result of the test, the below-mentioned Present compound X showed 80% or greater as the mortality of insects.

Present compound: 2-5, 3-5, 4-2, 6-2, 6-3, 8-1, 8-2

Test Example 7-2

The test is conducted by making the prescribed elapsed time 1 day and using the below-mentioned Present compounds X as a test compound according to the test method 7, and the effect of the test is confirmed.

Test Method 8

Test compounds are made to a formulation according to a similar method to that described in the Formulation example 5, and thereto is added water to prepare a diluted solution containing a prescribed concentration of the test compound.

Into the diluted solution, 30 common house mosquito (*Culex pipiens pallens*) at the last instar larval stage are released, and after 1 day, the state of the house mosquito larvae is examined, and the mortality of insects is calculated by the following equation.

Mortality (%)=(Number of dead insects/Number of tested insects)×100

Test Example 8

The test was conducted by making the prescribed concentration 3.5 ppm and using the below-mentioned Present compounds X as a test compound according to the test method 8. As a result of the test, the below-mentioned Present compound X showed 91% or greater as the mortality of insects.

Present compound: 1-2, 2-1, 2-2, 2-3, 2-5, 2-6, 2-11, 2-12, 2-15, 3-1, 3-2, 3-3, 3-5, 3-6, 3-8, 3-12, 3-13, 3-16, 3-17, 3-20, 3-24, 3-26, 4-2, 5-1, 5-2, 6-1, 6-2, 6-3, 6-5, 6-6, 8-1, 8-2, and 11

Test Method 9

Each 1 mg of the test compounds is dissolved into 50 μL of a mixed solution of polyoxyethylene sorbitan mono-cocoate and acetone (polyoxyethylene sorbitan mono-cocoate:acetone=5:95 (v/v ratio)). Thereto is added water containing 0.03% by volume of Shindain (registered trademark) to prepare a diluted solution containing a prescribed concentration of the test compound.

A young entire seedling of Corns (*Zea mays*) is immersed into the diluted solution for 30 seconds. Thereafter, each two grains of the seedlings are installed in a plastic petri dish (90 mm radius), and 10 Western corn rootworms (*Diabrotica virgifera virgifera*) at the second instar larval stage are released into the dish. After 5 days, the number of the dead insects is counted, and the mortality of insects is calculated by the following equation.

Mortality (%)=(Number of dead insects/10}×100

Test Example 9-1

The test was conducted by making the prescribed concentration 500 ppm and using the below-mentioned Present compounds X as a test compound according to the test method 9. As a result of the test, the below-mentioned Present compound X showed 80% or greater as the mortality of insects.

Present compound X: 1-2, 2-1, 2-11, 2-18, 2-19, 2-21, 2-25, 2-26, 3-1, 3-9, 3-10, 3-11, 3-12, 3-13, 3-15, 3-16, 3-19, 3-20, 3-21, 3-22, 3-23, 3-24, 3-25, 3-27, 3-28, 3-29, 3-30, 4-2, 5-2, 6-1, 6-2, 6-3, 6-4, 6-5, 6-6, 7-2, 7-6, 8-1, 11, 12-1, and 13

Test Example 9-2

The test is conducted by making the prescribed concentration 200 ppm and using the below-mentioned Present compounds X as a test compound according to the test method 9, and the effect of the test is confirmed.

Test Method 10

An acetone solution which is adjusted to 800 ppm of the test compound is poured into a container having 50 mL contents, and the test compound is coated uniformly on inner face of the container so as to make 40 $mg/m^2$ thereof, and the container is then allowed to dry.

Into the container, 5 German cockroach (*Blattella germanica*) male adults are released into the container, and the container is then covered with the lid. After the prescribed time is elapsed, the state of the German cockroach is examined, and the mortality of insects is calculated by the following equation.

Mortality (%)=(Number of dead insects/Number of tested insects)×100

Test Example 10-1

The test is conducted by making the prescribed elapsed time 1 hour and using the below-mentioned Present compounds X as a test compound according to the test method 10, and the effect of the test is confirmed.

Test Example 10-2

The test is conducted by making the prescribed elapsed time 1 day and using the below-mentioned Present compounds X as a test compound according to the test method 10, and the effect of the test is confirmed.

Test Example 10-3

The test is conducted by making the prescribed elapsed time 3 days and using the below-mentioned Present compounds X as a test compound according to the test method 10, and the effect of the test is confirmed.

Test Method 11

An acetone solution which is adjusted to 50 ppm of the test compound is poured into a container having 20 mL contents, and the test compound is coated uniformly on inner face of the container so as to make 2.5 $mg/m^2$ thereof, and the container is then allowed to dry.

Into the container, 5 nymph *Haemaphysalis longicornis* are released into the container, and the container is then covered with the lid. After the prescribed time is elapsed, the state of the *Haemaphysalis longicornis* is examined, and the mortality of insects is calculated by the following equation.

Mortality (%)=(Number of dead insects/Number of tested insects)×100

Test Example 11

The test is conducted by making the prescribed elapsed time 2 days and using the below-mentioned Present compounds X as a test compound according to the test method 11, and the effect of the test is confirmed.

Test Method 12

An acetone solution which is adjusted to 50 ppm of the test compound is poured into a container having 20 mL contents, and the test compound is coated uniformly on inner face of the container so as to make 2.5 $mg/m^2$ thereof, and the container is then allowed to dry.

Into the container, 10 worked ants of *Monomorium pharaonis* are released into the container, and the container is then covered with the lid. After the prescribed time is elapsed, the state of the *Monomorium pharaonis* is examined, and the mortality of insects is calculated by the following equation.

Mortality (%)=(Number of dead insects/Number of tested insects)×100

Test Example 12

The test is conducted by making the prescribed elapsed time 1 hour and using the below-mentioned Present compounds X as a test compound according to the test method 12, and the effect of the test is confirmed.

Test Method 13

Each 1 mg of the present compound X is dissolved into 10 μL of a mixed solution of xylene, DMF, and a surfactant (xylene:DMF:surfactant=4:4:1 (v/v ratio)). Thereto is added water containing 0.02% by volume of a spreader to prepare diluted solution A containing a prescribed concentration of the present compound.

Each 1 mg of the present ingredients is dissolved into 10 μL of a mixed solution of xylene, DMF, and a surfactant (xylene:DMF:surfactant=4:4:1 (v/v ratio)). Thereto is added water containing 0.02% by volume of a spreader to prepare diluted solution B containing a prescribed concentration of the present ingredient.

The diluted solution A is mixed with the diluted solution B to prepare diluted solution C.

Leaf discs of Cucumber (cucumber sativus) cotyledon (length 1.5 cm) are placed in each well of 24-well microplate. Two (2) apterous adults and 8 larvae of cotton aphids (*Aphis gossypii*) per one well are released and the diluted solution C is sprayed at 20 μL per one well. The group is defined as "treated group". A well that is sprayed with 20 μL of water containing 0.02% by volume of a spreader instead of the diluted solution C is defined as "untreated group".

After drying the diluted solution C, the upper microplate is covered with a film sheet. After 5 days, the number of the surviving insects in each well is examined.

The controlling value is calculated by the following equation.

$$\text{Controlling value }(\%)=\{1-(Tai)/(Cai)\}\times 100$$

wherein the symbols in the equation represent the following descriptions.

Cai: Number of the surviving insects at the time of the examination in untreated group;

Tai: Number of the surviving insects at the time of the examination in treated group.

Specific diluted solutions C, which can confirm their effect according to the Test method 13, are described in the following 1) to 5).

1) The diluted solution C comprises the combination recited in List A wherein a concentration of the present compound X is 200 ppm and a concentration of the present ingredient is 2000 ppm. In List A, Comp X represents any one compound selected from the present compound 1-1, 1-2, 2-1, 2-2, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 2-21, 2-22, 2-23, 2-24, 2-25, 2-26, 2-27, 2-28, 2-29, 2-30, 2-31, 2-32, 2-33, 2-34, 2-35, 2-36, 2-37, 3-1, 3-2, 3-3, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 3-25, 3-26, 3-27, 3-28, 3-29, 3-30, 3-31, 3-32, 3-33, 3-34, 3-35, 3-36, 3-37, 3-38, 3-39, 4-1, 4-2, 5-1, 5-2, 6-1, 6-2, 6-3, 6-4, 6-5, 6-6, 7-1, 7-2, 7-3, 7-4, 7-5, 7-6, 8-1, 8-2, 9, 10-1, 11, 12-1, 12-2, and 13.

List A:

Comp X+Clothianidin; Comp X+thiamethoxam; Comp X+imidacloprid; Comp X+thiacloprid; Comp X+flupyradifurone; Comp X+sulfoxaflor; Comp X+triflumezopyrim; Comp X+dicloromezotiaz; Comp X+beta-cyfluthrin; Comp X+tefluthrin; Comp X+fipronil; Comp X+chlorantraniliprole; Comp X+cyantraniliprole; Comp X+tetraniliprole; Comp X+thiodicarb; Comp X+carbofuran; Comp X+fluxametamide; Comp X+afoxolaner; Comp X+fluralaner; Comp X+broflanilide; Comp X+abamectin; Comp X+fluopyram; Comp X+fluensulfone; Comp X+fluazaindolizine; Comp X+tioxazafen; Comp X+flupyrimin; Comp X+Mycorrhizal Fungi; Comp X+*Bradyrhizobium japonicum* TA-li; Comp X+*Bacillus firmus*; Comp X+*Bacillus firmus* I-1582; Comp X+*Bacillus amyloliquefaciens*; Comp X+*Bacillus amyloliquefaciens* FZB42; Comp X+*Pasteuria nishizawae*; Comp X+*Pasteuria nishizawae* Pn1; Comp X+*Pasteuria penetrans*; Comp X+tebuconazole; Comp X+prothioconazole; Comp X+metconazole; Comp X+ipconazole; Comp X+triticonazole; Comp X+difenoconazole; Comp X+imazalil; Comp X+triadimenol; Comp X+tetraconazole; Comp X+flutriafol; Comp X+mandestrobin; Comp X+azoxystrobin; Comp X+pyraclostrobin; Comp X+trifloxystrobin; Comp X+fluoxastrobin; Comp X+picoxystrobin; Comp X+fenamidone; Comp X+metalaxyl; Comp X+metalaxyl-M; Comp X+fludioxonil; Comp X+sedaxane; Comp X+penflufen; Comp X+fluxapyroxad; Comp X+benzovindiflupyr; Comp X+boscalid; Comp X+carboxin; Comp X+penthiopyrad; Comp X+flutolanil; Comp X+captan; Comp X+thiram; Comp X+tolclofos-methyl; Comp X+thiabendazole; Comp X+ethaboxam; Comp X+mancozeb; Comp X+picarbutrazox; Comp X+oxathiapiprolin; Comp X+silthiofam; Comp X+inpyrfluxam.

2) The diluted solution C comprises the combination recited in List A wherein a concentration of the present compound is 200 ppm, and a concentration of the present ingredient is 200 ppm.

3) The diluted solution C comprises the combination recited in List A wherein a concentration of the present compound X is 500 ppm, and a concentration of the present ingredient is 50 ppm.

4) The diluted solution C comprises the combination recited in List A wherein a concentration of the present compound X is 500 ppm, and a concentration of the present ingredient is 5 ppm.

5) The diluted solution C comprises the combination recited in List A wherein a concentration of the present compound X is 500 ppm, and a concentration of the present ingredient is 0.5 ppm.

INDUSTRIAL APPLICABILITY

The present compound X (including the present compound) shows an excellent control effect against a harmful arthropod.

The invention claimed is:

1. A compound represented by formula (I):

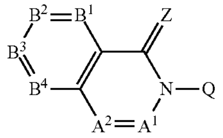

(I)

wherein

Q represents a group represented by formula Q2,

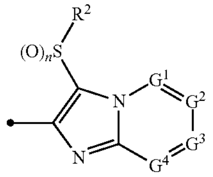

Q2

Z represents an oxygen atom or a sulfur atom, $A^1$ represents $CR^{4a}$, and $A^2$ represents a nitrogen atom, a combination of $B^1$, $B^2$, $B^3$ and $B^4$ represents,

- a combination in which $B^1$ represents a nitrogen atom or $CR^{6a}$, $B^2$ represents $CR^1$, $B^3$ represents a nitrogen atom or $CR^{6c}$, and $B^4$ represents a nitrogen atom or $CR^{6d}$;
- a combination in which $B^1$ represents a nitrogen atom or $CR^{6a}$, $B^2$ represents a nitrogen atom or $CR^{6b}$, $B^3$ represents $CR^1$, and $B^4$ represents a nitrogen atom or $CR^{6d}$;
- a combination in which $B^1$ represents a nitrogen atom or $CR^{6a}$, $B^2$ represents a nitrogen atom or $CR^{6b}$, $B^3$ represents $CR^{6c}$, and $B^4$ represents $CR^1$;
- a combination in which $B^1$ represents a nitrogen atom or $CR^{6a}$, $B^2$ represents $CR^{6b}$, $B^3$ represents a nitrogen atom, and $B^4$ represents $CR^1$; or a combination in which $B^1$ represents $CR^{6a}$, $B^2$ represents a nitrogen atom, $B^3$ represents a nitrogen atom, and $B^4$ represents $CR^1$, $R^1$ represents a C1-C6 chain hydrocarbon group having one or more substituents selected from the group consisting of cyano group and halogen atom, a C3-C4 cycloalkyl group optionally having one or more substituents selected from the group consisting of cyano group and halogen atom, $S(O)_mR^8$, $OR^8$, halogen atom or $OS(O)_mR^8$, m represents 0, 1 or 2, $R^8$ represents a C1-C6 chain hydrocarbon group having one or more substituents selected from the group consisting of cyano group and halogen atom; or a C3-C4 cycloalkyl group optionally having one or more substituents selected from the group consisting of cyano group and halogen atom, $R^{4a}$, $R^{4b}$, $R^{6a}$, $R^{6b}$, $R^{6c}$ and $R^{6d}$ are identical to or different from each other and each represents a C1-C6 chain hydrocarbon group optionally having one or more halogen atoms, a C3-C7 cycloalkyl group optionally having one or more halogen atoms, a C1-C6 alkoxy group optionally having one or more halogen atoms, $NR^9R^{10}$, $C(O)R^7$, $C(O)NR^{19}R^{20}$, $NR^9C(O)R^{18}$, $NR^9C(O)OR^{18}$, $NR^9C(O)NR^{19}R^{20}$, cyano group, halogen atom or a hydrogen atom, $R^9$ and $R^{19}$ are identical to or different from each other and each represents a C1-C6 chain hydrocarbon group optionally having one or more halogen atoms, or a hydrogen atom, $R^{10}$ represents a C1-C6 chain hydrocarbon group optionally having one or more substituents selected from Group F, a C3-C7 cycloalkyl group optionally having one or more substituents selected from Group J, a C3-C7 cycloalkenyl group optionally having one or more substituents selected from Group J, a phenyl group optionally having one or more substituents selected from Group D, a six(6) membered aromatic heterocyclic group optionally having one or more substituents selected from Group D, a hydrogen atom, or $S(O)_2R^{21}$, $R^{21}$ represents a C1-C6 chain hydrocarbon group optionally having one or more halogen atoms, a C3-C7 cycloalkyl group optionally having one or more halogen atoms, or a phenyl group optionally having one or more substituents selected from Group D, $R^7$, $R^{18}$, and $R^{20}$ are identical to or different from each other and each represents a C1-C6 chain hydrocarbon group optionally having one or more substituents selected from Group F, a C3-C7 cycloalkyl group optionally having one or more substituents selected from Group J, or a hydrogen atom, n represents 0, 1 or 2, $R^2$ represents a C1-C6 chain hydrocarbon group optionally having one or more halogen atoms, a cyclopropyl group, or a cyclopropylmethyl group, $G^1$ represents a nitrogen atom or $CR^{3a}$, $G^2$ represents $CR^{3b}$, $G^3$ represents a nitrogen atom or $CR^{3c}$, $G^4$ represents a nitrogen atom or $CR^{3d}$, $R^{3a}$, $R^{3c}$ and $R^{3d}$ are identical to or different from each other and each represents a C1-C6 chain hydrocarbon group optionally having one or more substituents selected from Group B, a C3-C7 cycloalkyl group optionally having one or more substituents selected from Group E, a phenyl group optionally having one or more substituents selected from Group H, a 5 or 6 membered aromatic heterocyclic group optionally having one or more substituents selected from Group H, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{31}R^{32}$, $NR^{24}NR^{11}C(O)NR^{31}R^{32}$, $N{=}CHNR^{31}R^{32}$, $N{=}S(O)_pR^{15}R^{16}$, $C(O)R^{13}$, $C(O)OR^{17}$, $C(O)NR^{31}R^{32}$, $C(O)NR^{11}S(O)_2R^{23}$, $CR^{30}{=}NOR^{17}$, $NR^{11}CR^{24}{=}NOR^{17}$, $S(O)_qR^{23}$, a cyano group, a nitro group, a hydrogen atom, or a halogen atom, $R^{3b}$ represents a halogen atom, p represents 0 or 1, q represents 0 or 1, $R^{30}$ represents a C1-C6 chain hydrocarbon group optionally having one or more halogen atoms, a halogen atom $OR^{35}$, $NR^{36}R^{37}$, or a hydrogen atom, $R^{35}$ represents a C1-C6 chain hydrocarbon group optionally having one or more halogen atoms, $R^{17}$ represents a C1-C6 chain hydrocarbon group optionally having one or more halogen atoms, a phenyl group optionally having one or more substituents selected from Group D, or a hydrogen atom, $R^{11}$, $R^{24}$, $R^{36}$ and $R^{37}$ are identical to or different from each other and each represents a C1-C6 chain hydrocarbon group optionally having one or more halogen atoms, or a hydrogen atom, $R^{12}$ represents a C1-C6 chain hydrocarbon group optionally having one or more substituents selected from Group F, a C3-C7 cycloalkyl group optionally having one or more substituents selected from Group J, a C3-C7 cycloalkenyl group optionally having one or more substituents selected from Group J, a phenyl group optionally having one or more substituents selected from Group D, a 6 membered aromatic heterocyclic group optionally having one or more substituents selected from Group D, a hydrogen atom, or $S(O)_2R^{23}$, $R^{23}$ represents a C1-C6 chain hydrocarbon group optionally having one or more halogen atoms, or a phenyl group optionally having one or more substituents selected from Group D, $R^{11a}$ and $R^{12a}$ combined together with a nitrogen atom to which they are attached represent a 3 to 7 membered nonaromatic heterocyclic group optionally having one or more substituents selected from Group E, $R^{13}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, a 5 or 6 membered aromatic heterocyclic group optionally having one or more substituents selected from Group D, or a hydrogen atom, $R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group {the phenyl moiety in the phenyl C1-C3 alkyl group may have optionally one or more substituents selected from Group D}, $R^{15}$ and $R^{16}$ are identical to or different from each other and each represents a C1-C6 alkyl group optionally having one or more halogen atoms, $R^{31}$ represents a C1-C6 alkyl group optionally having one or more halogen atoms, or a hydrogen atom, $R^{32}$ represents a C1-C6 chain hydrocarbon group optionally having one or more substituents selected from Group F, a C3-C7 cycloalkyl group optionally having one or more substituents selected from Group J, or a hydrogen atom, Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a C1-C6 alkylamino group optionally having one or more halogen atoms, a di(C1-C4 alkyl) amino group optionally having one or more halogen atoms, a C2-C6 alkylcarbonyl group optionally having one or more halogen atoms, a C2-C6 alkoxycarbonyl group optionally having one or more halogen atoms, a C2-C6 alkoxycarbonyloxy group optionally having one or more halogen atoms, an aminocarbonyl group, a C1-C6 alkylaminocarbonyl group optionally having one or more halogen atoms, a di(C1-C4 alkyl)aminocarbonyl group optionally having one or more halogen atoms, a C2-C6 alkoxycarbonylamino group optionally having one or more halogen atoms, a (C2-C6 alkoxycarbonyl)(C1-C6 alkyl) amino group optionally having one or more halogen atoms, a cyano group, an amino group, a nitro group, a hydroxy group, and a halogen atom, Group D: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a C1-C6 alkylamino group optionally having one or more halogen atoms, a di(C1-C4 alkyl)amino group optionally having one or more halogen atoms, a C2-C6 alkylcarbonyl group optionally having one or more halogen atoms, a C2-C6 alkoxycarbonyl group optionally having one or more halogen atoms, a C2-C6 alkoxycarbonyloxy group optionally having one or more halogen atoms, an aminocarbonyl group, a C1-C6 alkylaminocarbonyl group optionally having one or more halogen atoms, a di(C1-C4 alkyl)aminocarbonyl group optionally having one or more halogen atoms, a C2-C6 alkoxycarbonylamino group optionally having one or more halogen atoms, a (C2-C6 alkoxycarbonyl)(C1-C6 alkyl) amino group optionally having one or more halogen atoms, a cyano group, an amino group, a nitro group, a hydroxy group, and a halogen atom, Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylamino group optionally having one or more halogen atoms, a di(C1-C4 alkyl) amino group optionally having one or more halogen atoms, a C2-C6 alkylcarbonyl group optionally having one or more halogen atoms, a C2-C6 alkoxycarbonyl group optionally having one or more halogen atoms, a C2-C6 alkoxycarbonyloxy group optionally having one or more halogen atoms, an aminocarbonyl group, a C1-C6 alkylaminocarbonyl group optionally having one or more halogen atoms, a di(C1-C4 alkyl)aminocarbonyl group optionally having one or more halogen atoms, a C2-C6 alkoxycarbonylamino group optionally having one or more halogen atoms, a (C2-C6 alkoxycarbonyl)(C1-C6 alkyl) amino group optionally having one or more halogen atoms, a cyano group, an amino group, a nitro group, a hydroxy group, an oxo group, and a halogen atom, Group F: a group consisting of a C3-C7 cycloalkyl group optionally having one or more halogen atoms, a phenyl group optionally having one or more substituents selected from Group D, a 5 or 6 membered aromatic heterocyclic group optionally having one or more substituents selected from Group D, a C1-C6 alkoxy group optionally having one or more halogen atoms, a C1-C6 alkylamino group optionally having one or more halogen atoms, a di(C1-C4 alkyl)amino group optionally having one or more halogen atoms, a cyano group, an amino group, a nitro group, a hydroxy group, and a halogen atom, Group H: a group consisting of a C1-C6 chain hydrocarbon group optionally having one or more halogen atoms, a C3-C6 cycloalkyl group optionally having one or more halogen atoms, a phenyl group optionally having one or more substituents selected from Group D, a 5 or 6 membered aromatic heterocyclic group optionally having one or more substituents selected from Group D, a C1-C6 alkoxy group optionally having one or more halogen atoms, a C1-C6 alkylamino group optionally having one or more halogen atoms, a di(C1-C4 alkyl)amino group optionally having one or more halogen atoms, a C2-C6 alkylcarbonyl group optionally having one or more halogen atoms, a C2-C6 alkoxycarbonyl group optionally having one or more halogen atoms, a C2-C6 alkoxycarbonyloxy group optionally having one or more halogen atoms, an aminocarbonyl group, a (C1-C6 alkyl)aminocarbonyl group optionally having one or more halogen atoms, a di(C1-C4 alkyl)aminocarbonyl group optionally having one or more halogen atoms, a C2-C6 alkoxycarbonylamino group optionally having one or more halogen atoms, a (C2-C6 alkoxycarbonyl)(C1-C6 alkyl) amino group optionally having one or more halogen atoms, a cyano group, an amino group, a nitro group, a hydroxy group, and a halogen atom, Group I: a group consisting of a C2-C6 chain hydrocarbon group optionally having one or more halogen atoms, a C3-C6 cycloalkyl group optionally having one or more halogen atoms, a phenyl group optionally having one or more substituents selected from Group D, a 5 or 6 membered aromatic heterocyclic group optionally having one or more substituents selected from Group D, a C2-C6 alkylcarbonyl group optionally having one or more halogen atoms, a C2-C6 alkoxycarbonyl group optionally having one or more halogen atoms, an aminocarbonyl group, a (C1-C6 alkyl)aminocarbonyl group optionally having one or more halogen atoms, and a di(C1-C4 alkyl)aminocarbonyl group optionally having one or more halogen atoms, Group J: a group consisting of a C1-C6 alkyl group optionally having one or more halogen atoms, a C1-C6 alkoxy group optionally having one or more halogen atoms, a C2-C6 alkoxycarbonyl group optionally having one or more halogen atoms, an amino group, a cyano group, and a halogen atom, or N-oxide thereof.

2. The compound according to claim 1 or N-oxide thereof, wherein $R^1$ represents a C1-C6 chain hydrocarbon group having one or more substituents selected from the group consisting of cyano group and halogen atom, a C3-C4 cycloalkyl group optionally having one or more substituents selected from the group consisting of cyano group and halogen atom, $S(O)_mR^8$, $OR^8$, or $OS(O)_2R^8$.

3. The compound according to claim 1 or N-oxide thereof, wherein $R^{3a}$ represents a hydrogen atom, $R^{3c}$ and $R^{3d}$ are identical to or different from each other and each represents a C1-C6 alkyl group, a C2-C6 alkenyl group, a C3-C7 cycloalkyl group {the C1-C6 alkyl group, the C2-C6 alkenyl group, and the C3-C7 cycloalkyl group each may have optionally one or more substituents selected from the group consisting of halogen atom and cyano group}, a phenyl group, a triazolyl group, a pyridyl group, a pyrimidinyl group {the phenyl group, the triazolyl group, the pyridyl group, and the pyrimidinyl group each may have optionally one or more substituents selected from Group J}, $OR^{12}$, $CR^{30}{=}NOR^{17}$, a hydrogen atom.

4. The compound according to claim 1 or N-oxide thereof, wherein $R^{3a}$ and $R^{3d}$ represent a hydrogen atom, and $R^{3c}$ represents a C1-C6 alkyl group optionally having one or more halogen atoms, a cyclopropyl group, a hydrogen atom, or a halogen atom.

5. The compound according to claim 1 or N-oxide thereof, wherein $B^1$ represents CH, a combination of $B^2$, $B^3$ and $B^4$ represents a combination in which $B^2$ represents $CR^1$, $B^3$ represents $CR^{6c}$, and $B^4$ represents $CR^{6d}$; a combination in which $B^2$ represents $CR^{6b}$, $B^3$ represents $CR^1$, and $B^4$ represents $CR^{6d}$; or a combination in which $B^2$ represents $CR^{6b}$, $B^3$ represents $CR^{6c}$, and $B^4$ represents $CR^1$.

6. The compound according to claim 1 or N-oxide thereof, wherein $G^1$ represents a nitrogen atom or CH, $G^3$ represents $CR^{3c}$, and $G^4$ represents a nitrogen atom or CH.

7. The compound according to claim 1 or N-oxide thereof, wherein $G^1$ represents CH, $G^3$ represents $CR^{3c}$, and $G^4$ represents CH.

8. The compound according to claim 1 or N-oxide thereof, wherein $R^1$ represents a C1-C6 alkyl group having one or more substituents selected from a group consisting of halogen atom and cyano group; a cyclopropyl group optionally having one or more substituents selected from the group consisting of cyano group and halogen atom; $S(O)_mR^8$; a halogen atom; or $OR^8$.

9. The compound according to claim 1 or N-oxide thereof, wherein $R^1$ represents a C1-C6 alkyl group having one or more substituents selected from a group consisting of halogen atom and cyano group; a cyclopropyl group optionally having one or more substituents selected from the group consisting of cyano group and halogen atom; $S(O)_mR^8$; or $OR^8$.

10. The compound according to claim 1 or N-oxide thereof, wherein $R^2$ represents an ethyl group.

11. The compound according to claim 1 or N-oxide thereof, wherein Z represents an oxygen atom.

12. A composition for controlling harmful arthropod which comprises the compound of claim 1 or N-oxide thereof.

13. A composition comprising one or more ingredients selected from the group consisting of the following Group (a), Group (b), Group (c), and Group (d), and the compound of claim 1 or N-oxide thereof:

Group (a): a group consisting of insecticidal ingredients, miticidal ingredients, and nematicidal ingredients;

Group (b): fungicidal ingredients,

Group (c): plant growth modulating ingredients; and

Group (d): repellent ingredients.

14. A method for controlling harmful arthropod which comprises applying an effective amount of the compound according to claim 1 or N-oxide thereof.

15. A seed or vegetative reproductive organ carrying an effective amount of the compound according to claim 1 or N-oxide thereof.

16. A compound represented by formula (III):

(III)

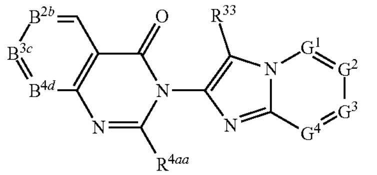

wherein $R^{33}$ represents a hydrogen atom or halogen atom, a combination of $B^{2b}$, $B^{3c}$ and $B^{4d}$ represents a combination in which $B^{2b}$ represents $CR^1$, $B^{3c}$ represents a nitrogen atom or $CR^{6cc}$, and $B^{4d}$ represents a nitrogen atom or $CR^{6dd}$;

a combination in which $B^{2b}$ represents a nitrogen atom or $CR^{6bb}$, $B^{3c}$ represents $CR^1$, and $B^{4d}$ represents a nitrogen atom or $CR^{6dd}$; or a combination in which $B^{2b}$ represents a nitrogen atom or $CR^{6bb}$, $B^{3c}$ represents a nitrogen atom or $CR^{6cc}$, and Bad represents $CR^1$, $R^1$ represents a C1-C6 chain hydrocarbon group having one or more substituents selected from the group consisting of cyano group and halogen atom, a C3-C4 cycloalkyl group optionally having one or more substituents selected from the group consisting of cyano group and halogen atom, $S(O)_mR^8$, $OR^8$, halogen atom or $OS(O)_2R^8$, m represents 0, 1 or 2, $R^8$ represents a C1-C6 chain hydrocarbon group having one or more substituents selected from the group consisting of cyano group and halogen atom; or a C3-C4 cycloalkyl group optionally having one or more substituents selected from the group consisting of cyano group and halogen atom, $R^{4aa}$, $R^{6bb}$, $R^{6cc}$ and $R^{6dd}$ are identical to or different from each other and each represents a C1-C6 chain hydrocarbon group optionally having one or more halogen atoms, halogen atom or a hydrogen atom, $G^1$ represents a nitrogen atom or $CR^{3a}$, $G^2$ represents $CR^{3b}$, $G^3$ represents a nitrogen atom or $CR^{3c}$, $G^4$ represents a nitrogen atom or $CR^{3d}$, $R^{3a}$, $R^{3c}$ and $R^{3d}$ are identical to or different from each other and each represents a C1-C6 chain hydrocarbon group optionally having one or more substituents selected from Group B, a C3-C7 cycloalkyl group optionally having one or more substituents selected from Group E, a phenyl group optionally having one or more substituents selected from Group H, a five(5) or six(6) membered aromatic heterocyclic group optionally having one or more substituents selected from Group H, $OR^{12}$, $NR^{11}R^{12}$, $NR^{11a}R^{12a}$, $NR^{24}NR^{11}R^{12}$, $NR^{24}OR^{11}$, $NR^{11}C(O)R^{13}$, $NR^{24}NR^{11}C(O)R^{13}$, $NR^{11}C(O)OR^{14}$, $NR^{24}NR^{11}C(O)OR^{14}$, $NR^{11}C(O)NR^{31}R^{32}$, $NR^{24}NR^{11}C(O)NR^{31}R^{32}$, $N{=}CHNR^{31}R^{32}$, $N{=}S(O)_pR^{15}R^{16}$, $C(O)R^{13}$, $C(O)R^{17}$, $C(O)NR^{31}R^{32}$, $C(O)NR^{11}S(O)_2R^{23}$, $CR^{30}{=}NOR^{17}$, $NR^{11}CR^{24}{=}NOR^{17}$, $S(O)_qR^{23}$, a cyano group, a nitro group, a hydrogen atom, or a halogen atom, $R^{3b}$ represents a halogen atom, p represents 0 or 1, q represents 0 or 1, $R^{30}$ represents a C1-C6 chain hydrocarbon group optionally having one or more halogen atoms, a halogen atom $OR^{35}$, $NR^{36}R^{37}$, or a hydrogen atom, $R^{35}$ represents a C1-C6 chain hydrocarbon group optionally having one or more halogen atoms, $R^{17}$ represents a C1-C6 chain hydrocarbon group optionally having one or more halogen atoms, a phenyl group optionally having one or more substituents selected from Group D, or a hydrogen atom, $R^{11}$, $R^{24}$, $R^{36}$ and $R^{37}$ are identical to or different from each other and each represents a C1-C6 chain hydrocarbon group optionally having one or more halogen atoms, or a hydrogen atom, $R^{12}$ represents a C1-C6 chain hydrocarbon group optionally having one or more substituents selected from Group F, a C3-C7 cycloalkyl group optionally having one or more substituents selected from Group J, a C3-C7 cycloalkenyl group optionally having one or more substituents selected from Group J, a phenyl group optionally having one or more substituents selected from Group D, a six(6) membered aromatic heterocyclic group optionally having one or more substituents selected from Group D, a hydrogen atom, or $S(O)_2R^{23}$, $R^{23}$ represents a C1-C6 chain hydrocarbon group optionally having one or more halogen atoms, or a phenyl group optionally having one or more substituents selected from Group D, $R^{11a}$ and $R^{12a}$ combined together with a nitrogen atom to which they are attached represent a three(3) to seven(7) membered nonaromatic heterocyclic group optionally having one or more substituents selected from Group E, $R^{13}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, a 5 or 6 membered aromatic heterocyclic group optionally having one or more substituents selected from Group D, or a hydrogen atom, $R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group {the phenyl moiety in the phenyl C1-C3 alkyl group may have optionally one or more substituents selected from Group D}, $R^{15}$ and $R^{16}$ are identical to or different from each other and each represents a C1-C6 alkyl group optionally having one or more halogen atoms, $R^{31}$ represents a C1-C6 alkyl group optionally having one or more halogen atoms, or a hydrogen atom, $R^{32}$ represents a C1-C6 chain hydrocarbon group optionally having one or more substituents selected from Group F, a C3-C7 cycloalkyl group optionally having one or more substituents selected from Group J, or a hydrogen atom, Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a C1-C6 alkylamino group optionally having one or more halogen atoms, a di(C1-C4 alkyl)amino group optionally having one or more halogen atoms, a C2-C6 alkylcarbonyl group optionally having one or more halogen atoms, a C2-C6 alkoxycarbonyl group optionally having one or more halogen atoms, a C2-C6 alkoxycarbonyloxy group optionally having one or more halogen atoms, an aminocarbonyl group, a C1-C6 alkylaminocarbonyl group optionally having one or more halogen atoms, a di(C1-C4 alkyl)aminocarbonyl group optionally having one or more halogen atoms, a C2-C6 alkoxycarbonylamino group optionally having one or more halogen atoms, a (C2-C6 alkoxycarbonyl)(C1-C6 alkyl) amino group optionally having one or more halogen atoms, a cyano group, an amino group, a nitro group, a hydroxy group, and a halogen atom, Group D: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a C1-C6 alkylamino group optionally having one or more halogen atoms, a di(C1-C4 alkyl)amino group optionally having one or more halogen atoms, a C2-C6 alkylcarbonyl group optionally having one or more halogen atoms, a C2-C6 alkoxycarbonyl group optionally having one or more halogen atoms, a C2-C6 alkoxycarbonyloxy group optionally having one or more halogen atoms, an aminocarbonyl group, a C1-C6 alkylaminocarbonyl group optionally having one or more halogen atoms, a di(C1-C4 alkyl)aminocarbonyl group optionally having one or more halogen atoms, a C2-C6 alkoxycarbonylamino group optionally having one or more halogen atoms, a (C2-C6 alkoxycarbonyl)(C1-C6 alkyl) amino group optionally having one or more halogen atoms, a cyano group, an amino group, a nitro group, a hydroxy group, and a halogen atom, Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylamino group optionally having one or more halogen atoms, a di(C1-C4 alkyl) amino group optionally having one or more halogen atoms, a C2-C6 alkylcarbonyl group optionally having one or more halogen atoms, a C2-C6 alkoxycarbonyl group optionally having one or more halogen atoms, a C2-C6 alkoxycarbonyloxy group optionally having one or more halogen atoms, an aminocarbonyl group, a C1-C6 alkylaminocarbonyl group optionally having one or more halogen atoms, a di(C1-C4 alkyl)aminocarbonyl group optionally having one or more halogen atoms, a C2-C6 alkoxycarbonylamino group optionally having one or more halogen atoms, a (C2-C6 alkoxycarbonyl)(C1-C6 alkyl) amino group optionally having one or more halogen atoms, a cyano group, an amino group, a nitro group, a hydroxy group, an oxo group, and a halogen atom, Group F: a group consisting of a C3-C7 cycloalkyl group optionally having one or more halogen atoms, a phenyl group optionally having one or more substituents selected from Group D, a 5 or 6 membered aromatic heterocyclic group optionally having one or more substituents selected from Group D, a C1-C6 alkoxy group optionally having one or more halogen atoms, a C1-C6 alkylamino group optionally having one or more halogen atoms, a di(C1-C4 alkyl)amino group optionally having one or more halogen atoms, a cyano group, an amino group, a nitro group, a hydroxy group, and a halogen atom, Group H: a group consisting of a C1-C6 chain hydrocarbon group optionally having one or more halogen atoms, a C3-C6 cycloalkyl group optionally having one or more halogen atoms, a phenyl group optionally having one or more substituents selected from Group D, a 5 or 6 membered aromatic heterocyclic group optionally having one or more substituents selected from Group D, a C1-C6 alkoxy group optionally having one or more halogen atoms, a C1-C6 alkylamino group optionally having one or more halogen atoms, a di(C1-C4 alkyl)amino group optionally having one or more halogen atoms, a C2-C6 alkylcarbonyl group optionally having one or more halogen atoms, a C2-C6 alkoxycarbonyl group optionally having one or more halogen atoms, a C2-C6 alkoxycarbonyloxy group optionally having one or more halogen atoms, an aminocarbonyl group, a (C1-C6 alkyl)aminocarbonyl group optionally having one or more halogen atoms, a di(C1-C4 alkyl)aminocarbonyl group optionally having one or more halogen atoms, a C2-C6 alkoxycarbonylamino group optionally having one or more halogen atoms, a (C2-C6 alkoxycarbonyl)(C1-C6 alkyl) amino group optionally having one or more halogen atoms, a cyano group, an amino group, a nitro group, a hydroxy group, and a halogen atom.

17. The compound according to claim 16, wherein $R^1$ represents a C1-C6 chain hydrocarbon group having one or more substituents selected from the group consisting of cyano group and halogen atom, a C3-C4 cycloalkyl group optionally having one or more substituents selected from the group consisting of cyano group and halogen atom, $S(O)_mR^8$, $OR^8$, or $OS(O)_2R^8$.

* * * * *